United States Patent
Wolkerstorfer et al.

(10) Patent No.: US 9,045,486 B2
(45) Date of Patent: Jun. 2, 2015

(54) PYRIMIDONE DERIVATIVES AND THEIR USE IN THE TREATMENT, AMELIORATION OR PREVENTION OF A VIRAL DISEASE

(71) Applicants: Savira pharmaceuticals GmbH, Vienna (AT); European Molecular Biology Laboratory, Heidelberg (DE); F. Hoffmann-La Roche AG, Basel (CH)

(72) Inventors: Andrea Wolkerstorfer, Vienna (AT); Oliver Szolar, Vienna (AT); Norbert Handler, Vienna (AT); Helmut Buschmann, Aachen (DE); Stephen Cusack, Seyssinet-Pariset (FR); Mark Smith, Jersey City, NJ (US); Sung-Sau So, Verona, NJ (US); Ronald Charles Hawley, San Francisco, CA (US); Achyutharao Sidduri, Newark, NJ (US); Zhuming Zhang, Hillsborough, NJ (US)

(73) Assignees: Savira pharmaceuticals GmbH, Vienna (AT); European Molecular Biology Laboratory, Heidelberg (DE); F. Hoffman-La Roche AG, Basel (CH)

( * ) Notice: Subject to any disclaimer, the term of this patent is extended or adjusted under 35 U.S.C. 154(b) by 0 days.

(21) Appl. No.: 14/149,284

(22) Filed: Jan. 7, 2014

(65) Prior Publication Data
US 2014/0194431 A1 Jul. 10, 2014

Related U.S. Application Data

(60) Provisional application No. 61/750,017, filed on Jan. 8, 2013.

(51) Int. Cl.
| | | |
|---|---|---|
| *C07D 487/04* | (2006.01) | |
| *C07D 403/04* | (2006.01) | |
| *A61K 31/4985* | (2006.01) | |
| *A61K 31/519* | (2006.01) | |
| *A61P 31/16* | (2006.01) | |
| *A61K 45/06* | (2006.01) | |
| *C07D 471/04* | (2006.01) | |

(52) U.S. Cl.
CPC ............ *C07D 487/04* (2013.01); *A61K 31/519* (2013.01); *A61K 45/06* (2013.01); *C07D 471/04* (2013.01); *C07D 403/04* (2013.01)

(58) Field of Classification Search
CPC . C07D 487/04; A61K 31/4985; A61K 31/519
USPC .......................................... 544/282; 514/249
See application file for complete search history.

(56) References Cited

FOREIGN PATENT DOCUMENTS

| CA | 2812363 A1 | 3/2012 |
|---|---|---|
| WO | WO 2005087766 A1 | 9/2005 |
| WO | WO 2007014352 A2 | 2/2007 |

OTHER PUBLICATIONS

Hayden, F. G., Review in Medical Virology, 14, 17-31,2004.*
Griffiths, P.A. Journal of Virology, 46, 3-8, 2009.*

* cited by examiner

*Primary Examiner* — Venkataraman Balasubramanian
(74) *Attorney, Agent, or Firm* — Bryan Cave LLP

(57) ABSTRACT

The present invention relates to a compound having the general formula (I), optionally in the form of a pharmaceutically acceptable salt, solvate, polymorph, codrug, cocrystal, prodrug, tautomer, racemate, enantiomer, or diastereomer or mixture thereof,

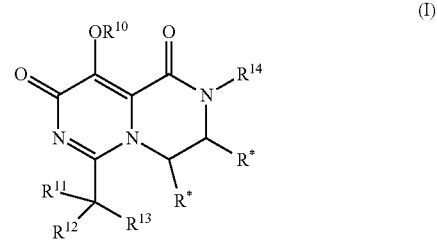

(I)

which are useful in treating, ameloriating or preventing a viral disease. Furthermore, specific combination therapies are disclosed.

13 Claims, No Drawings

PYRIMIDONE DERIVATIVES AND THEIR USE IN THE TREATMENT, AMELIORATION OR PREVENTION OF A VIRAL DISEASE

CROSS-REFERENCE TO RELATED APPLICATIONS

This application claims benefit to U.S. Provisional Application No. 61/750,017, filed Jan. 8, 2013. The contents of the above application are incorporated by reference as if recited in full herein.

FIELD OF THE INVENTION

The present invention relates to a compound having the general formula (I), optionally in the form of a pharmaceutically acceptable salt, solvate, polymorph, codrug, cocrystal, prodrug, tautomer, racemate, enantiomer, or diastereomer or mixture thereof,

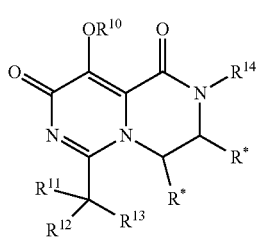

(I)

which is useful in treating, ameloriating or preventing a viral disease. Furthermore, specific combination therapies are disclosed.

BACKGROUND OF THE INVENTION

In recent years the serious threat posed by influenza virus infection to worldwide public health has been highlighted by, firstly, the ongoing level transmission to humans of the highly pathogenic avian influenza A virus H5N1 strain (63% mortality in infected humans, http://www.who.int/csr/disease/avian_influenza/en/) and secondly, the unexpected emergence in 2009 of a novel pandemic influenza virus strain A/H1N1 that has rapidly spread around the entire world (http://www.who.int/csr/disease/swineflu/en/). Whilst the new virus strain is highly contagious but currently generally results in relatively mild illness, the future evolution of this virus is unpredictable. In a much more serious, but highly plausible scenario, H5N1 and related highly pathogenic avian influenza viruses could acquire mutations rendering them more easily transmissible between humans or the new A/H1N1 could become more virulent and only a single point mutation would be enough to confer resistance to oseltamivir (Neumann et al., Nature, 2009 (18; 459(7249) 931-939)); as many seasonal H1N1 strains have recently done (Dharan et al., The Journal of the American Medical Association, 2009 Mar. 11; 301 (10), 1034-1041; Moscona et al., The New England Journal of Medicine, 2009 (March 5; 360(10) pp 953-956)). In this case, the delay in generating and deploying a vaccine (~6 months in the relatively favourable case of A/H1N1 and still not a solved problem for H5N1) could have been catastrophically costly in human lives and societal disruption.

It is widely accepted that to bridge the period before a new vaccine is available and to treat severe cases, as well as to counter the problem of viral resistance, a wider choice of anti-influenza drugs is required. Development of new anti-influenza drugs has therefore a gain become high priority, having been largely abandoned by the major pharmaceutical companies once the neuraminidase inhibitors became available.

An excellent starting point for the development of antiviral medication is structural data of essential viral proteins. Thus, the crystal structure determination of e.g. the influenza virus surface antigen neuraminidase (Von Itzstein, M. et al., (1993), Nature, 363, pp. 418-423) led directly to the development of neuraminidase inhibitors with antiviral activity preventing the release of virus from the cells, however, not the virus production itself. These and their derivatives have subsequently developed into the anti-influenza drugs, zanamivir (Glaxo) and oseltamivir (Roche), which are currently being stockpiled by many countries as a first line of defense against a possible pandemic. However, these medicaments only provide a reduction in the duration of the clinical disease. Alternatively, adamantanes, the other class of licensed anti-influenza drugs (e.g. amantadine and rimantadine) target the viral M2 ion channel protein, which is located in the viral membrane interfering with the uncoating of the virus particle inside the cell. However, they have not been extensively used due to their side effects and the rapid development of resistant virus mutants (Magden, J. et al., (2005), Appl. Microbiol. Biotechnol., 66, pp. 612-621). In addition, more unspecific viral drugs, such as ribavirin, have been shown to work for treatment of influenza and other virus infections (Eriksson, B. et al., (1977), Antimicrob. Agents Chemother., 11, pp. 946-951). However, ribavirin is only approved in a few countries, probably due to severe side effects (Furuta et al., ANTIMICROBIAL AGENTS AND CHEMOTHERAPY, 2005, p. 981-986). Clearly, new antiviral compounds are needed, preferably directed against different targets.

Influenza virus as well as Thogotovirus and isavirus belong to the family of Orthomyxoviridae which, as well as the family of the Bunyaviridae, including the Hantavirus, Nairovirus, Orthobunyavirus, and Phlebovirus, are, amongst others, negative stranded RNA viruses. Their genome is segmented and comes in ribonucleoprotein particles that include the RNA dependent RNA polymerase which carries out (i) the initial copying of the single-stranded negative-sense viral RNA (vRNA) into viral mRNAs (i.e. transcription) and (ii) the vRNA replication. This enzyme, a trimeric complex composed of subunits PA, PB1 and PB2, is central to the life cycle of the virus since it is responsible for the replication and transcription of viral RNA. In previous work the atomic structure of two key domains of the polymerase, the mRNA cap-binding domain in the PB2 subunit (Guilligay et al., Nature Structural & Molecular Biology 2008; May; 15(5): 500-506) and the endonuclease-active site residing within the PA subunit (Dias et al., Nature 2009, 458, 914-918) have been identified and their molecular architecture has been characterized. These two sites are critical for the unique "cap-snatching" mode used to initiate mRNA transcription that is used by the influenza virus and certain other virus families of this genus to generate viral mRNAs. A 5' cap is a modified guanine nucleotide that has been added to the 5' end of a messenger RNA. The 5' cap (also termed an RNA cap or RNA m7G cap) consists of a terminal 7-methylguanosine residue which is linked through a 5'-5'-triphosphate bond to the first transcribed nucleotide. The viral polymerase binds to the 5' RNA cap of cellular mRNA molecules and cleaves the RNA cap together with a stretch of 10 to 15 nucleotides. The capped RNA fragments then serve as primers for the synthesis of viral mRNA (Plotch, S. J. et al., (1981), Cell, 23, pp. 847-858;

Kukkonen, S. K. et al (2005), Arch. Virol., 150, pp. 533-556; Leahy, M. B. et al., (2005), J. Virol., 71, pp. 8347-8351; Noah, D. L. et al., (2005), Adv. Virus Res., 65, pp. 121-145).

The polymerase complex seems to be an appropriate antiviral drug target since it is essential for synthesis of viral mRNA and viral replication and contains several functional active sites likely to be significantly different from those found in host cell proteins (Magden, J. et al., (2005), Appl. Microbiol. Biotechnol., 66, pp. 612-621). Thus, for example, there have been attempts to interfere with the assembly of polymerase subunits by a 25-amino-acid peptide resembling the PA-binding domain within PB1 (Ghanem, A. et al., (2007), J. Virol., 81, pp. 7801-7804). Furthermore, the endonuclease activity of the polymerase has been targeted and a series of 4-substituted 2,4-dioxobutanoic acid compounds has been identified as selective inhibitors of this activity in influenza viruses (Tomassini, J. et al., (1994), Antimicrob. Agents Chemother., 38, pp. 2827-2837). In addition, flutimide, a substituted 2,6-diketopiperazine, identified in extracts of Delitschia confertaspora, a fungal species, has been shown to inhibit the endonuclease of influenza virus (Tomassini, J. et al., (1996), Antimicrob. Agents Chemother., 40, pp. 1189-1193). Moreover, there have been attempts to interfere with viral transcription by nucleoside analogs, such as 2'-deoxy-2'-fluoroguanosine (Tisdale, M. et al., (1995), Antimicrob. Agents Chemother., 39, pp. 2454-2458).

WO 2005/087766 discloses certain pyridopyrazine- and pyrimidopyrazine-dione compounds which are stated to be inhibitors of HIV integrase and inhibitors of HIV replication. The compounds are described as being useful in the prevention and treatment of infection by HIV and in the prevention, delay in the onset, and treatment of AIDS.

WO 2012/039414 describes compounds which are described as having antiviral effects, particularly having growth inhibitory activity on influenza viruses.

EP-A-2 444 400 also discloses compounds which allegedly have antiviral activities, especially inhibiting activity for influenza viruses.

It is an object of the present invention to identify further compounds which are effective against viral diseases and which have improved pharmacological properties.

SUMMARY OF THE INVENTION

Accordingly, in a first embodiment, the present invention provides a compound having the general formula (I).

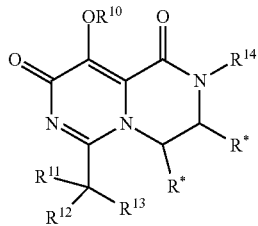

It is understood that throughout the present specification the term "a compound having the general formula (I)" encompasses pharmaceutically acceptable salts, solvates, polymorphs, prodrugs, codrugs, cocrystals, tautomers, racemates, enantiomers, or diastereomers or mixtures thereof unless mentioned otherwise.

A further embodiment of the present invention relates to a pharmaceutical composition comprising a compound having the general formula (I) and optionally one or more pharmaceutically acceptable excipient(s) and/or carrier(s).

The compounds having the general formula (I) are useful for treating, ameliorating or preventing viral diseases.

It has been surprisingly found that the compounds according to the present invention which have the bulky group on the left hand ring have improved properties compared to the compounds disclosed in EP-A-2 444 400. In particular, the interaction with protein could be optimized resulting in better binding properties. Furthermore, shifting of the bulky group should avoid problems due to a chiral center and due to the planarization through shift from sp3 to sp2. In addition, the crucial vector for additional hydrophobic interactions may be stabilized and improved.

DETAILED DESCRIPTION OF THE INVENTION

Before the present invention is described in detail below, it is to be understood that this invention is not limited to the particular methodology, protocols and reagents described herein as these may vary. It is also to be under stood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

DEFINITIONS

The term "alkyl" refers to a saturated straight or branched carbon chain.

The term "cycloalkyl" represents a cyclic version of "alkyl". The term "cycloalkyl" is also meant to include bicyclic, tricyclic and polycyclic versions thereof. Unless specified otherwise, the cycloalkyl group can have 3 to 12 carbon atoms.

"Hal" or "halogen" represents F, Cl, Br and I.

"3- to 7-membered carbo- or heterocyclic ring" refers to a three-, four-, five-, six- or seven-membered ring wherein none, one or more of the carbon atoms in the ring have been replaced by 1 or 2 (for the three-membered ring), 1, 2 or 3 (for the four-membered ring), 1, 2, 3, or 4 (for the five-membered ring) or 1, 2, 3, 4, or 5 (for the six-membered ring) and 1, 2, 3, 4, 5 or 6 (for the seven-membered ring) of the same or different heteroatoms, whereby the heteroatoms are selected from O, N and S.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl or anthracenyl, preferably phenyl.

The term "heteroaryl" preferably refers to a five- or six-membered aromatic ring wherein one or more of the carbon atoms in the ring have been replaced by 1, 2, 3, or 4 (for the five-membered ring) or 1, 2, 3, 4, or 5 (for the six-membered ring) of the same or different heteroatoms, whereby the heteroatoms are selected from O, N and S. Examples of the heteroaryl group include pyrrole, pyrrolidine, oxolane, furan, imidazolidine, imidazole, pyrazole, oxazolidine, oxazole, thiazole, piperidine, pyridine, morpholine, piperazine, and dioxolane.

The term "hydrocarbon group which contains from 5 to 20 carbon atoms and optionally 1 to 4 heteroatoms selected from O, N and S and which contains at least one ring" refers to any group having 5 to 20 carbon atoms and optionally 1 to 4 heteroatoms selected from O, N and 2 as long as the group contains at least one ring. The term is also meant to include bicyclic, tricyclic and polycyclic versions thereof. If more than one ring is present, they can be separate from each other or be annelated. The ring(s) can be either carbocyclic or heterocyclic and can be saturated, unsaturated or aromatic. The carbon atoms and heteroatoms can either all be present in the one or more rings or some of the carbon atoms and/or heteroatoms can be present outside of the ring, e.g., in a linker group (such as —$(CH_2)_p$— with p=1 to 6). Examples of these groups include -(optionally substituted $C_{3-7}$ cycloalkyl), -(optionally substituted aryl) wherein the aryl group can be, for example, phenyl, -(optionally substituted biphenyl), adamantyl, —($C_{3-7}$ cycloalkyl)-aryl as well as the corresponding compounds with a linker.

If a compound or moiety is referred to as being "optionally substituted", it can in each instance include 1 or more of the indicated substituents, whereby the substituents can be the same or different.

The term "pharmaceutically acceptable salt" refers to a salt of a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and a mine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

When the compounds of the present invention are provided in crystalline form, the structure can contain solvent molecules. The solvents are typically pharmaceutically acceptable solvents and include, among others, water (hydrates) or organic solvents. Examples of possible solvates include ethanolates and iso-propanolates.

The term "codrug" refers to two or more therapeutic compounds bonded via a covalent chemical bond. A detailed definition can be found, e.g., in N. Das et al., European Journal of Pharmaceutical Sciences, 41, 2010, 571-588.

The term "cocrystal" refers to a multiple component crystal in which all components are solid under ambient conditions when in their pure form. These components co-exist as a stoichiometric or non-stoichiometric ratio of a target molecule or ion (i.e., compound of the present invention) and one or more neutral molecular cocrystal formers. A detailed discussion can be found, for example, in Ning Shan et al., Drug Discovery Today, 13(9/10), 2008, 440-446 and in D. J. Good et al., Cryst. Growth Des., 9(5), 2009, 2252-2264.

The compounds of the present invention can also be provided in the form of a prodrug, namely a compound which is metabolized in vivo to the active metabolite. Suitable prodrugs are, for instance, esters. Specific examples of suitable groups are given, among others, in US 2007/0072831 in paragraphs [0082] to [0118] under the headings prodrugs and protecting groups. Preferred examples of the prodrug include compounds in which $R^{10}$ is replaced by $P(O)(O)OR^{19}$; $C(O)OR^{19}$; $C(O)R^{19}$; or $C—R^{19}$;

wherein $R^{19}$ is selected from $C_{5-10}$aryl, $C_{1-6}$alkyl-$C_{5-10}$aryl, $C_{1-6}$alkyl, $C_{1-6}$alkyl(—O—$C_{1-6}$alkyl)$_n$ (with n=1 to 30), $C_{1-6}$alkyl-C(O)OR, and $C_{5-10}$aryl-C(O)OR.

The group R is H or $C_{1-6}$ alkyl.

Compounds Having the General Formula (I)

The present invention provides a compound having the general formula (I).

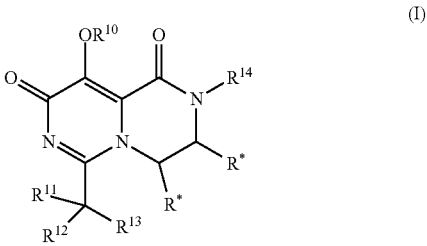

In the appended claims certain provisos are recited. It is understood that any of the compounds which are included in any of the provisos can be excluded, either individually or in combination with other compounds, from one or more of the independent claims having a different category even if it is not currently disclaimed in the independent claim of this category. It is also understood that the disclaimer covers the compounds in the form of their pharmaceutically acceptable salts, solvates, polymorphs, tautomers, racemates, enantiomers, and diastereomers.

The present invention provides a compound having the general formula (I) in which the following definitions apply.

$X^{10}$ is $NR^{15}$, $N(R^{15})C(O)$, $C(O)NR^{15}$, O, C(O), C(O)O, OC(O); $N(R^{15})SO_2$, $SO_2N(R^{15})$, S, SO, or $SO_2$; preferably $X^{10}$ is $N(R^{15})$ or $N(R^{15})SO_2$; more preferably $X^{10}$ is $N(R^{15})SO_2$.

$R^{10}$ is —H, a —$C_{1-6}$ alkyl group or a —C(O)—$C_{1-6}$ alkyl group. In a preferred embodiment $R^{10}$ is —H, or -(optionally substituted $C_{1-6}$ alkyl); more preferably —H.

$R^{11}$ is —H, a —$C_{1-6}$ alkyl group, or a —$C_{1-6}$ alkyl group which is substituted by one or more halogen atoms; preferably $R^{11}$ is —H.

$R^{12}$ is —H, a —$C_{1-6}$ alkyl group, or a —$C_{1-6}$ alkyl group which is substituted by one or more halogen atoms; preferably $R^{12}$ is —H.

In one embodiment $R^{11}$ and $R^{12}$ can be joined together to form a 3- to 7-membered carbo- or heterocyclic ring.

$R^{13}$ is —$R^{16}$, or —$X^{10}$—$R^{16}$. In one embodiment $R^{13}$ is —$R^{16}$. In an alternative embodiment, $R^{13}$ is —$X^{10}$—$R^{16}$.

$R^{14}$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl); preferably $R^{14}$ is —H, -(optionally substituted $C_{1-6}$ alkyl), or -(optionally substituted aryl).

$R^{15}$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl). In a preferred embodiment $R^{15}$ is —H or -(optionally substituted $C_{1-6}$ alkyl).

$R^{16}$ is -(optionally substituted hydrocarbon group which contains from 5 to 20 carbon atoms and optionally 1 to 4 heteroatoms selected from O, N and S and which contains at least one ring). Preferably, the at least one ring is aromatic such as an aryl or heteroaryl ring.

More preferably, $R^{16}$ is a hydrocarbon group which contains from 5 to 20 carbon atoms and optionally 1 to 4 heteroatoms and which contains at least two rings, wherein the hydrocarbon group can be optionally substituted. Even more preferably, at least one of the at least two rings is aromatic such as an aryl or heteroaryl ring. Preferred examples of $R^{16}$ can be selected from the group consisting of

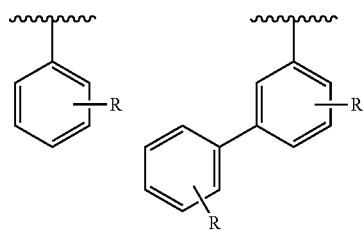

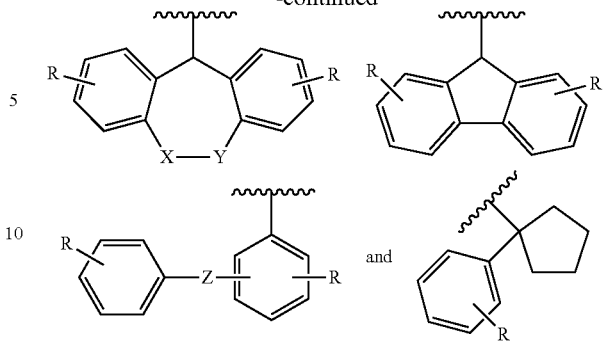

X is absent, $CH_2$, NH, C(O)NH, S or O. Furthermore, Y is $CH_2$.

In an alternative embodiment, X and Y can be joined together to form an annulated, carbo- or heterocylic 3- to 8-membered ring which can be saturated or unsaturated. Specific examples of X—Y include —$CH_2$—, —$CH_2$—$CH_2$—, —O—, and —NH—.

Z is O or S.

R is independently selected from —H, —$C_{1-6}$ alkyl, —$CF_3$, -halogen, —CN, —OH, and —O—$C_{1-6}$ alkyl.

$R^{17}$ is —H, —$C_{1-6}$ alkyl, or —$(CH_2CH_2O)_rH$; preferably $R^{17}$ is —H, or —$C_{1-6}$ alkyl.

$R^{18}$ is —H, or —$C_{1-6}$ alkyl.

R is independently selected from —$C_{1-6}$ alkyl, —C(O)—$C_{1-6}$ alkyl, -Hal, —$CF_3$, —CN, —$COOR^{17}$, —$OR^{17}$, —$(CH_2)_q$ $NR^{17}R^{18}$, —C(O)—$NR^{17}R^{18}$, and —$NR^{17}$—C(O)—$C_{1-6}$ alkyl. Preferably R is -Hal, —$CF_3$, or —CN; more preferably -Hal, or —$CF_3$.

R* is independently selected from —H, —$C_{1-6}$ alkyl, and —$C_{3-7}$ cycloalkyl.

q is 0 to 4.

r is 1 to 3.

The optional substituent of the alkyl group, aryl group, hydrocarbon group and/or cycloalkyl group is selected from the group consisting of one or more substituents R, which includes —$C_{1-6}$ alkyl, —C(O)—$C_{1-6}$ alkyl, -Hal, —$CF_3$, —CN, —$COOR^{17}$, —$OR^{17}$, —$(CH_2)_q NR^{17}R^{18}$, —C(O)—$NR^{17}R^{18}$, and —$NR^{17}$—C(O)—$C_{1-6}$ alkyl. Preferably, the optional substituent of the aryl group, hydrocarbon group and/or cycloalkyl group is -halogen (preferably F), —$OCH_3$ or —CN. Preferably, the optional substituent of the alkyl group is selected from the group consisting of halogen, —CN, —$NR^{18}R^{18}$ (wherein each $R^{18}$ is chosen independently of each other), —OH, and —O—$C_{1-6}$ alkyl. Preferably the substituent of the alkyl group is -halogen, more preferably F.

The present inventors have surprisingly found that the compounds of the present invention which have a bulky moiety $R^{13}$ have improved pharmacological properties compared to corresponding compounds which have a smaller moiety $R^{13}$. Without wishing to be bound by theory it is assumed that the viral polymerase protein has a pocket for binding and that the bulky moiety $R^{13}$ of the compounds of the present invention fills this pocket to a larger extent. It is further assumed that the larger moiety $R^{13}$ is able to provide more hydrophobic interaction with the pocket than smaller moieties such as methyl.

The compounds of the present invention can be administered to a patient in the form of a pharmaceutical composition which can optionally comprise one or more pharmaceutically acceptable excipient(s) and/or carrier(s).

The compounds of the present invention can be administered by various well known routes, including oral, rectal, intragastrical, intracranial and parenteral administration, e.g. intravenous, intramuscular, intranasal, intradermal, subcutaneous, and similar administration routes. Oral, intranasal and parenteral administration are particularly preferred. Depending on the route of administration different pharmaceutical formulations are required and some of those may require that protective coatings are applied to the drug formulation to prevent degradation of a compound of the invention in, for example, the digestive tract.

Thus, preferably, a compound of the invention is formulated as a syrup, an infusion or injection solution, a spray, a tablet, a capsule, a capslet, lozenge, a liposome, a suppository, a plaster, a band-aid, a retard capsule, a powder, or a slow release formulation. Preferably, the diluent is water, a buffer, a buffered salt solution or a salt solution and the carrier preferably is selected from the group consisting of cocoa butter and vitebesole.

Particular preferred pharmaceutical forms for the administration of a compound of the invention are forms suitable for injectionable use and include sterile aqueous solutions or dispersions and sterile powders for the extemporaneous preparation of sterile injectable solutions or dispersions. In all cases the final solution or dispersion form must be sterile and fluid. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils. A compound of the invention can also be formulated into liposomes, in particular for parenteral administration. Liposomes provide the advantage of increased half life in the circulation, if compared to the free drug and a prolonged more even release of the enclosed drug.

Sterilization of infusion or injection solutions can be accomplished by any number of art recognized techniques including but not limited to addition of preservatives like anti-bacterial or anti-fungal agents, e.g. parabene, chlorobutanol, phenol, sorbic acid or thimersal. Further, isotonic agents, such as sugars or salts, in particular sodium chloride, may be incorporated in infusion or injection solutions.

Production of sterile injectable solutions containing one or several of the compounds of the invention is accomplished by incorporating the respective compound in the required amount in the appropriate solvent with various ingredients enumerated above as required followed by sterilization. To obtain a sterile powder the above solutions are vacuum-dried or freeze-dried as necessary. Preferred diluents of the present invention are water, physiological acceptable buffers, physiological acceptable buffer salt solutions or salt solutions. Preferred carriers are cocoa butter and vitebesole. Excipients which can be used with the various pharmaceutical forms of a compound of the invention can be chosen from the following non-limiting list:
a) binders such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;
b) lubricants such as magnesium stearate, talc, calcium stearate, zinc stearate, stearic acid, hydrogenated vegetable oil, leucine, glycerids and sodium stearyl fumarates,
c) disintegrants such as starches, croscarmellose, sodium methyl cellulose, agar, bentonite, alginic acid, carboxymethyl cellulose, polyvinyl pyrrolidone and the like.

In one embodiment the formulation is for oral administration and the formulation comprises one or more or all of the following ingredients: pregelatinized starch, talc, povidone K 30, croscarmellose sodium, sodium stearyl fumarate, gelatin, titanium dioxide, sorbitol, monosodium citrate, xanthan gum, titanium dioxide, flavoring, sodium benzoate and saccharin sodium.

If a compound of the invention is administered intranasally in a preferred embodiment, it may be administered in the form of a dry powder inhaler or an aerosol spray from a pressurized container, pump, spray or nebulizer with the use of a suitable propellant, e.g., dichlorodifluoromethane, trichlorofluoromethane, dichlorotetrafluoroethane, a hydrofluoro-alkane such as 1,1,1,2-tetrafluoroethane (HFA 134A™) or 1,1,1,2,3,3,3-heptafluoropropane (HFA 227EA™), carbon dioxide, or another suitable gas. The pressurized container, pump, spray or nebulizer may contain a solution or suspension of the compound of the invention, e.g., using a mixture of ethanol and the propellant as the solvent, which may additionally contain a lubricant, e.g., sorbitan trioleate.

Other suitable excipients can be found in the Handbook of Pharmaceutical Excipients, published by the American Pharmaceutical Association, which is herein incorporated by reference.

It is to be understood that depending on the severity of the disorder and the particular type which is treatable with one of the compounds of the invention, as well as on the respective patient to be treated, e.g. the general health status of the patient, etc., different doses of the respective compound are required to elicit a therapeutic or prophylactic effect. The determination of the appropriate dose lies within the discretion of the attending physician. It is contemplated that the dosage of a compound of the invention in the therapeutic or prophylactic use of the invention should be in the range of about 0.1 mg to about 1 g of the active ingredient (i.e. compound of the invention) per kg body weight. However, in a preferred use of the present invention a compound of the invention is administered to a subject in need thereof in an amount ranging from 1.0 to 500 mg/kg body weight, preferably ranging from 1 to 200 mg/kg body weight. The duration of therapy with a compound of the invention will vary, depending on the severity of the disease being treated and the condition and idiosyncratic response of each individual patient. In one preferred embodiment of a prophylactic or therapeutic use, from 10 mg to 200 mg of the compound are orally administered to an adult per day, depending on the severity of the disease and/or the degree of exposure to disease carriers.

As is known in the art, the pharmaceutically effective amount of a given composition will also depend on the administration route. In general, the required amount will be higher if the administration is through the gastrointestinal tract, e.g., by suppository, rectal, or by an intragastric probe, and lower if the route of administration is parenteral, e.g., intravenous. Typically, a compound of the invention will be administered in ranges of 50 mg to 1 g/kg body weight, preferably 10 mg to 500 mg/kg body weight, if rectal or intragastric administration is used and in ranges of 1 to 100 mg/kg body weight if parenteral administration is used. For intranasal administration, 1 to 100 mg/kg body weight are envisaged.

If a person is known to be at risk of developing a disease treatable with a compound of the invention, prophylactic administration of the biologically active blood serum or the pharmaceutical composition according to the invention may be possible. In these cases the respective compound of the invention is preferably administered in above outlined preferred and particular preferred doses on a daily basis. Preferably, from 0.1 mg to 1 g/kg body weight once a day, preferably 10 to 200 mg/kg body weight. This administration can be continued until the risk of developing the respective viral disorder has lessened. In most instances, however, a compound of the invention will be administered once a disease/disorder has been diagnosed. In these cases it is preferred that a first dose of a compound of the invention is administered one, two, three or four times daily.

The compounds of the present invention are particularly useful for treating, ameliorating, or preventing viral diseases. The type of viral disease is not particularly limited. Examples of possible viral diseases include, but are not limited to, viral diseases which are caused by Poxyiridae, Herpesviridae, Adenoviridae, Papillomaviridae, Polyomaviridae, Parvoviridae, Hepadnaviridae, Reoviridae, Filoviridae, Paramyxoviridae, Rhabdoviridae, Orthomyxoviridae, Bunyaviridae, Arenaviridae, Coronaviridae, Picornaviridae, Hepeviridae, Caliciviridae, Astroviridae, Togaviridae, Flaviviridae, Deltavirus, Bornaviridae, and prions. Preferably viral diseases which are caused by Herpesviridae, Filoviridae, Paramyxoviridae, Rhabdoviridae, Orthomyxoviridae, Bunyaviridae, Arenaviridae, Coronaviridae, Picornaviridae, Togaviridae, Flaviviridae, more preferably viral diseases which are caused by orthomyxoviridae.

Examples of the various viruses are given in the following table.

| Family | Virus (preferred examples) |
|---|---|
| Poxviridae | Smallpox virus |
| | Molluscum contagiosum virus |
| Herpesviridae | Herpes simplex virus |
| | Varicella zoster virus |
| | Cytomegalovirus |
| | Epstein Barr virus |
| | Kaposi's sarcoma-associated herpesvirus |
| Adenoviridae | Human adenovirus A-F |
| Papillomaviridae | Papillomavirus |
| Polyomaviridae | BK-virus |
| | JC-Virsu |
| Parvoviridae | B19 virus |
| | Adeno associated virus 2/3/5 |
| Hepadnaviridae | Hepatitis B virus |
| Reoviridae | Reovirus 1/2/3 |
| | Rotavirus A/B/C |
| | Colorado tick fever virus |
| Filoviridae | Ebola virus |
| | Marburg virus |
| Paramyxoviridae | Parainfluenza virus 1-4 |
| | Mumps virus |
| | Measles virus |
| | Respiratory syncytial virus |
| | Hendravirus |
| Rhabdoviridae | Vesicular stomatitis virus |
| | Rabies virus |
| | Mokola virus |
| | European bat virus |
| | Duvenhage virus |
| Orthomyxoviridae | Influenza virus types A-C |
| Bunyaviridae | California encephalitis virus |
| | La Crosse virus |
| | Hantaan virus |
| | Puumala virus |
| | Sin Nombre virus |
| | Seoul virus |
| | Crimean-Congo hemorrhagic fever virus |
| | Sakhalin virus |
| | Rift valley virus |
| | Sandfly fever virus |
| | Uukuniemi virus |
| Arenaviridae | Lassa virus |
| | Lymphocytic choriomeningitis virus |
| | Guanarito virus |
| | Junin virus, |

-continued

| Family | Virus (preferred examples) |
|---|---|
| | Machupo virus |
| | Sabia virus |
| Coronaviridae | Human coronavirus |
| Picornaviridae | Human enterovirus types A-D (Poliovirus, Echovirus, Coxsackie virus A/B) |
| | Rhinovirus types A/B/C |
| | Hepatitis A virus |
| | Parechovirus |
| | Food and mouth disease virus |
| Hepeviridae | Hepatitis E virus |
| Caliciviridae | Norwalk virus |
| | Sapporo virus |
| Astroviridae | Human astrovirus 1 |
| Togaviridae | Ross River virus |
| | Chikungunya virus |
| | O'nyong-nyong virus |
| | Rubella virus |
| Flaviviridae | Tick-borne encephalitis virus |
| | Dengue virus |
| | Yellow Fever virus |
| | Japanese encephalitis virus |
| | Murray Valley virus |
| | St. Louis encephalitis virus |
| | West Nile virus |
| | Hepatitis C virus |
| | Hepatitis G virus |
| | Hepatitis GB virus |
| Deltavirus | Hepatitis deltavirus |
| Bornaviridae | Bornavirus |
| Prions | |

Preferably, the compounds of the present invention are employed to treat influenza. The present invention covers all virus genera belonging to the family of orthomyxoviridae, specifically influenza virus type A, B, and C, isavirus, and thogotovirus. Within the present invention, the term "influenza" includes influenza caused by any influenza virus such as influenza virus type A, B, and C including their various stains and isolates, and also covers influenza A virus strains commonly referred to as bird flu and swine flu. The subject to be treated is not particularly restricted and can be any vertebrate, such as birds and mammals (including humans).

Without wishing to be bound by theory it is assumed that the compounds of the present invention are capable of inhibiting endonuclease activity, particularly that of influenza virus. More specifically it is assumed that they directly interfere with the N-terminal part of the influenza virus PA protein, which harbors endonuclease activity and is essential for influenza virus replication. Influenza virus replication takes place inside the cell within the nucleus. Thus, compounds designed to inhibit PA endonuclease activity need to cross both the cellular and the nuclear membrane, a property which strongly depends on designed-in physico-chemical properties of the compounds. The present invention shows that the claimed compounds have in vitro endonuclease inhibitory activity and have antiviral activity in vitro in cell-based assays.

A possible measure of the in vitro endonuclease inhibitory activity of the compounds having the formula (I) is the FRET (fluorescence-resonance energy transfer)-based endonuclease activity assay disclosed herein. Preferably, the compounds exhibit a % reduction of at least about 50% at 25 µM in the FRET assay. In this context, the % reduction is the % reduction of the initial reaction velocity (v0) measured as fluorescence increase of a dual-labelled RNA substrate cleaved by the influenza virus endonuclease subunit (PA-Nter) upon compound treatment compared to untreated samples. Preferably, the compounds exhibit an $IC_{50}$ of less than about 40 µM, more preferably less than about 20 µM, in this assay. The half maximal inhibitory concentration (IC$_{50}$) is a measure of the effectiveness of a compound in inhibiting biological or biochemical function and was calculated from the initial reaction velocities (v0) in a given concentration series ranging from maximum 100 µM to at least 2 nM.

The compounds having the general formula (I) can be used in combination with one or more other medicaments. The type of the other medicaments is not particularly limited and will depend on the disorder to be treated. Preferably, the other medicament will be a further medicament which is useful in treating, ameliorating or preventing a viral disease, more preferably a further medicament which is useful in treating, ameliorating or preventing influenza that has been caused by influenza virus infection and conditions associated with this viral infection such as viral pneumonia or secondary bacterial pneumonia and medicaments to treat symptoms such as chills, fever, sore throat, muscle pains, severe headache, coughing, weakness and fatigue. Furthermore, the compounds having the general formula (I) can be used in combination with anti-inflammatories.

The following combinations of medicaments are envisaged as being particularly suitable:

(i) The combination of endonuclease and cap-binding inhibitors (particularly targeting influenza). The endonuclease inhibitors are not particularly limited and can be any endonuclease inhibitor, particularly any viral endonuclease inhibitor. Preferred endonuclease inhibitors are those as defined in the US applications with the Ser. Nos. 61/550,045 (filed on Oct. 21, 2011), 61/650,713 (filed on May 23, 2012), 61/650,725 (filed on May 23, 2012) and 61/679,968 (filed on Aug. 6, 2012). The complete disclosure of these applications is incorporated herein by reference. In particular, all descriptions with respect to the general formula of the compounds according to these US applications, the preferred embodiments of the various substituents as well as the medical utility and advantages of the compounds are incorporated herein by reference.

Further preferred endo nuclease inhibitors are the compounds having the general formula (II) as defined in U.S. application Ser. No. 14/149,218 (filed on Jan. 7, 2014), now U.S. Pat. No. 8,952,039, and the compounds having the general formula (V) as defined in U.S. application Ser. No. 14/149,381 (filed on Jan. 7, 2014), the complete disclosure of which is incorporated by reference. In particular, all descriptions with respect to the general formula of these compounds, the preferred embodiments of the various substituents as well as the medical utility and advantages of the compounds are incorporated herein by reference. These compounds can be optionally in the form of a pharmaceutically acceptable salt, solvate, polymorph, codrug, cocrystal, prodrug, tautomer, racemate, enantiomer, or diastereomer or mixture thereof.

The cap-binding inhibitors are not particularly limited either and can be any cap-binding inhibitor, particularly any viral cap-binding inhibitor. Preferred cap-binding inhibitors are those having the general formula (II) as defined in U.S. application 61/550,057 (filed on Oct. 21, 2011) and/or the compounds disclosed in WO2011/000566, the complete disclosure of which is incorporated by reference. In particular, all descriptions with respect to the general formula of the compounds according to U.S. 61/550,057 or WO2011/000566, the preferred embodiments of the various substituents as well as the medical utility and advantages of the compounds are incorporated herein by reference.

Widespread resistance to both classes of licensed influenza antivirals (M2 ion channel inhibitors (adamantanes) and neuraminidase inhibitors (e.g. oseltamivir)) occurs in both pandemic and seasonal emerging influenza strains, rendering these drugs to be of marginal utility in the treatment modality. For M2 ion channel inhibitors, the frequency of viral resistance has been increasing since 2003 and for seasonal influenza A/H3N2, adamantanes are now regarded as ineffective. Virtually all 2009 H1N1 and seasonal H3N2 strains are resistant to adamantanes (rimantadine and a mantadine), and for oseltamivir, the most widely prescribed neuraminidase inhibitor (NAI), the WHO reported on significant emergence of influenza A/H1N1 resistance starting in the influenza season 2007/2008; and for the second and third quarters of 2008 in the southern hemisphere. Even more serious numbers were published for the fourth quarter of 2008 (northern hemisphere) where 95% of all tested isolates revealed no oseltamivir-susceptibility. Considering the fact that now most national governments have been stockpiling NAIs as part of their influenza pandemic preparedness plan, it is obvious that the demand for new, effective drugs is growing significantly. To address the need for more effective therapy, preliminary studies using double or even triple combinations of antiviral drugs with different mechanisms of action have been undertaken. Adamantanes and neuraminidase inhibitors in combination were analysed in vitro and in vivo and were found to act highly synergistically. However, it is known that for both types of antivirals resistant viruses emerge rather rapidly and this issue is not tackled by combining these established antiviral drugs.

Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. These two targets are located within distinct subunits of the polymerase complex and thus represent unique drug targets. Due to the fact that both functions are required for the so-called "cap-snatching" mechanism which is essential for viral transcription, concurrent inhibition of both functions is expected to act highly synergistically. This highly efficient drug combination would result in lower substance concentrations and hence improved dose-response-relationships and better side effect profiles.

Both active sites are highly conserved among all influenza A strains (e.g., avian and human) and even influenza B viruses, and hence this high degree of sequence conservation underpins the perception that these targets are not likely to trigger rapid resistant virus generation. Additionally, close interaction with host proteins render these viral proteins less prone to mutations. Thus, endonuclease and cap-binding inhibitors individually and in combination are ideal drug candidates to combat both seasonal and pandemic influenza, irrespectively of the virus strain.

The combination of an endonuclease inhibitor and a cap-binding inhibitor or a dual specific polymerase inhibitor targeting both the endonuclease active site and the cap-binding domain would be effective against virus strains resistant against adamantanes and neuraminidase inhibitors and moreover combine the advantage of low susceptibility to resistance generation with activity against a broad range of virus strains.

(ii) The combination of inhibitors of different antiviral targets (particularly targeting influenza virus) focusing on the combination with (preferably influenza virus) polymerase inhibitors as dual or multiple combination therapy. Influenza virus polymerase inhibitors are novel drugs targeting the transcription and replication activity of the polymerase. Selective inhibitors against the viral polymerase severely attenuate virus infection by stopping the viral reproductive cycle. The combination of a polymerase inhibitor specifically addressing a viral intracellular target with an inhibitor of a different antiviral target is expected to act highly synergistically. This is based on the fact that these different types of antiviral drugs exhibit completely different mechanisms of action requiring different pharmacokinetics properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Typically, at least one compound selected from the first group of polymerase inhibitors (e.g., cap-binding and endonuclease inhibitors) is combined with at least one compound selected from the second group of polymerase inhibitors.

The first group of polymerase inhibitors which can be used in this type of combination therapy includes, but is not limited to, the compounds having the formula (I).

The second group of polymerase inhibitors which can be used in this type of combination therapy includes, but is not limited to, the compounds having the general formula (I) as defined in the U.S. application with the Ser. No. 61/550,045 filed on Oct. 21, 2011, the compounds having the general formula (II) as defined in U.S. application 61/550,057 filed on Oct. 21, 2011, the compounds disclosed in WO 2011/000566, WO 2010/110231, WO 2010/110409, WO 2006/030807 or U.S. Pat. No. 5,475,109 as well as flutimide and analogues, favipiravir and analogues, epigallocatechin gallate and analogues, as well as nucleoside analogs such as ribavirine.

(iii) The combination of polymerase inhibitors with neuraminidase inhibitors

Influenza virus polymerase inhibitors are novel drugs targeting the transcription and replication activity of the polymerase. The combination of a polymerase inhibitor specifically addressing a viral intracellular target with an inhibitor of a different extracellular antiviral target, especially the (e.g., viral) neuraminidase is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Typically, at least one compound selected from the above mentioned first group of polymerase inhibitors is combined with at least one neuraminidase inhibitor.

The neuraminidase inhibitor (particularly influenza neuramidase inhibitor) is not specifically limited. Examples include zanamivir, oseltamivir, peramivir, KDN DANA, FANA, and cyclopentane derivatives.

(iv) The combination of polymerase inhibitors with M2 channel inhibitors

Influenza virus polymerase inhibitors are novel drugs targeting the transcription and replication activity of the polymerase. The combination of a polymerase inhibitor specifically addressing a viral intracellular target with an inhibitor of a different extracellular and cytoplasmic antiviral target, especially the viral M2 ion channel, is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles.

Moreover, advantages described above for polymerase inhibitors would prevail for combinations of inhibitors of different antiviral targets with polymerase inhibitors.

Typically, at least one compound selected from the above mentioned first group of polymerase inhibitors is combined with at least one M2 channel inhibitor.

The M2 channel inhibitor (particularly influenza M2 channel inhibitor) is not specifically limited. Examples include amantadine and rimantadine.

(v) The combination of polymerase inhibitors with alpha glucosidase inhibitors

Influenza virus polymerase inhibitors are novel drugs targeting the transcription and replication activity of the polymerase. The combination of a polymerase inhibitor specifically addressing a viral intracellular target, with an inhibitor of a different host-cell target, especially alpha glucosidase, is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of cellular targets interacting with viral replication with polymerase inhibitors.

Typically, at least one compound selected from the above-mentioned first group of polymerase inhibitors is combined with at least one alpha glucosidase inhibitor.

The alpha glucosidase inhibitor is not specifically limited. Examples include the compounds described in Chang et al., Antiviral Research 2011, 89, 26-34.

(vi) The combination of polymerase inhibitors with ligands of other influenza targets Influenza virus polymerase inhibitors are novel drugs targeting the transcription and replication activity of the polymerase. The combination of a polymerase inhibitor specifically addressing a viral intracellular target with an inhibitor of different extracellular, cytoplasmic or nucleic antiviral targets is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Typically at least one compound selected from the above mentioned first group of polymerase inhibitors is combined with at least one ligand of another influenza target. The ligand of another influenza target is not specifically limited. Examples include compounds acting on the sialidase fusion protein (e.g., Fludase (DAS181), siRNAs and phosphorothioate oligonucleotides), signal transduction inhibitors (e.g., ErbB tyrosine kinase, Abl kinase family, MAP kinases, PKCa-mediated activation of ERK signalling) as well as interferon (inducers).

(vii) The combination of (preferably influenza) polymerase inhibitors with a compound used as an adjuvant to minimize the symptoms of the disease (antibiotics, anti-inflammatory agents like COX inhibitors (e.g., COX-1/COX-2 inhibitors, selective COX-2 inhibitors), lipoxygenase inhibitors, EP ligands (particularly EP4 ligands), bradykinin ligands, and/or cannabinoid ligands (e.g., CB2 agonists)). Influenza virus polymerase inhibitors are novel drugs targeting the transcription and replication activity of the polymerase. The combination of a polymerase inhibitor specifically addressing a viral intracellular target with a compound used as an adjuvance to minimize the symptoms of the disease address the causative and symptomatic pathological consequences of viral infection. This combination is expected to act synergistically because these different types of drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following examples are merely illustrative of the present invention and should not be construed to limit the scope of the invention as indicated by the appended claims in any way.

EXAMPLES

FRET Endonuclease Activity Assay

The influenza A virus (IAV) PA-Nter fragment (amino acids 1-209) harboring the influenza endonuclease activity was generated and purified as described in Dias et al., Nature 2009; April 16; 458(7240), 914-918. The protein was dissolved in buffer containing 20 mM Tris pH 8.0, 100 mM NaCl and 10 mM β-mercaptoethanol and aliquots were stored at −20° C.

A 20 bases dual-labelled RNA oligo with 5'-FAM fluorophore and 3'-BHQ1 quencher was used as a substrate to be cleaved by the endonuclease activity of the PA-Nter. Cleavage of the RNA substrate frees the fluorophore from the quencher resulting in an increase of the fluorescent signal.

All assay components were diluted in assay buffer containing 20 mM Tris-HCl pH 8.0, 100 mM NaCl, 1 mM $MnCl_2$, 10 mM $MgCl_2$ and 10 mM β-mercaptoethanol. The final concentration of PA-Nter was 0.5 μM and 1.6 μM RNA substrate. The test compounds were dissolved in dimethyl sulfoxide and generally tested at two concentrations or a concentration series resulting in a final plate well dimethyl sulfoxide concentration of 0.5%. In those cases where the compounds were not soluble at that concentration, they were tested at the highest soluble concentration.

5 μl of each compound dilution was provided in the wells of white 384-well microtiter plates (PerkinElmer) in eight replicates. After addition of PA-Nter dilution, the plates were sealed and incubated for 30 min at room temperature prior to the addition of 1.6 μM RNA substrate diluted in as say buffer. Subsequently, the increasing fluorescence signal of cleaved RNA was measured in a microplate reader (Synergy H T, Biotek) at 485 nm excitation and 535 nm emission wavelength. The kinetic read interval was 35 sec at a sensitivity of 35. Fluorescence signal data over a period of 20 min were used to calculate the initial velocity (v0) of substrate cleavage. Final readout was the % reduction of v0 of compound-treated samples compared to untreated. The half maximal inhibitory concentration ($IC_{50}$) is a measure of the effectiveness of a compound in inhibiting biological or biochemical function and was calculated from the initial reaction velocities (v0) in a given concentration series ranging from maximum 100 μM to at least 2 nM.

| Formula no. | FRET |
|---|---|
| 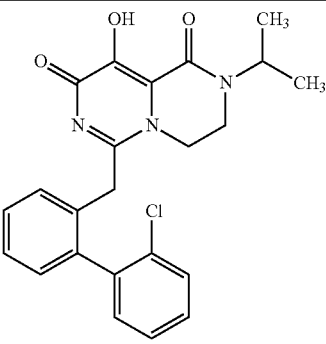 (12-04) | $IC_{50} = 0.657$ μM |

-continued
| Formula no. | FRET |
|---|---|
| 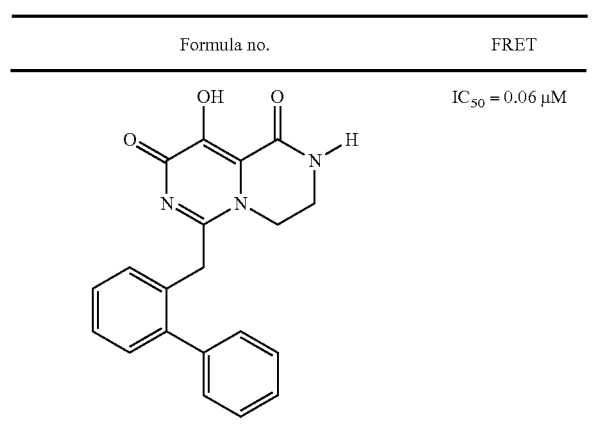 (12-03) | IC$_{50}$ = 0.06 μM |
| 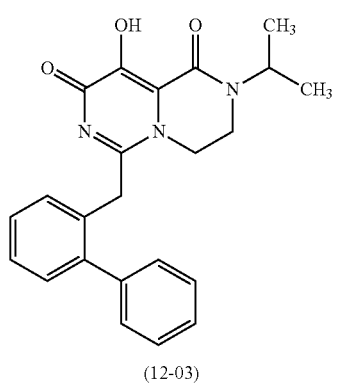 [SMILES: CC(C)N1CCn2c(Cc3ccccc3-c3ccccc3)nc(=O)c(O)c2C1=O] (12-02) | IC$_{50}$ = 0.196 μM |
| 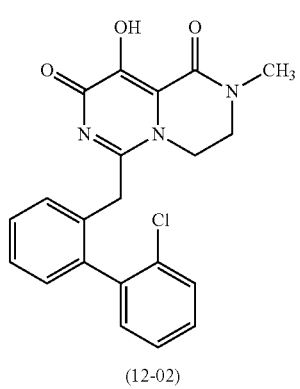 [SMILES: CN1CCn2c(Cc3ccccc3-c3ccccc3Cl)nc(=O)c(O)c2C1=O] (66) | IC$_{50}$ = 0.175 μM |
| 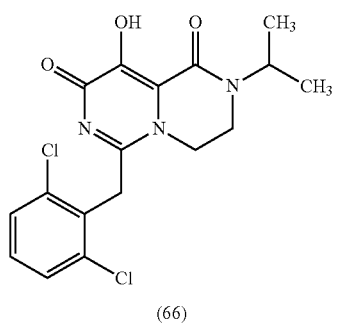 [SMILES: CC(C)N1CCn2c(Cc3c(Cl)cccc3Cl)nc(=O)c(O)c2C1=O] | IC$_{50}$ = 0.392 μM |
-continued
| Formula no. | FRET |
|---|---|
| 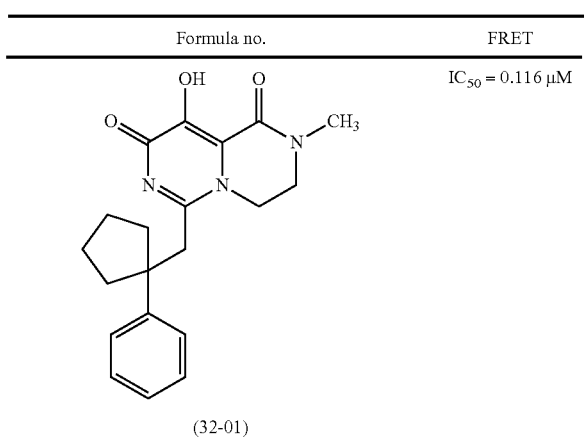 (32-01) | IC$_{50}$ = 0.116 μM |
| 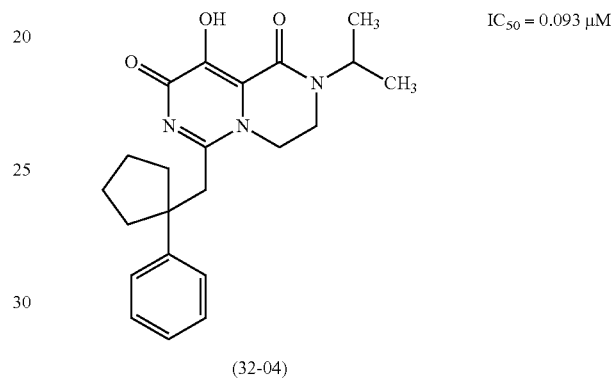 (32-04) | IC$_{50}$ = 0.093 μM |
| 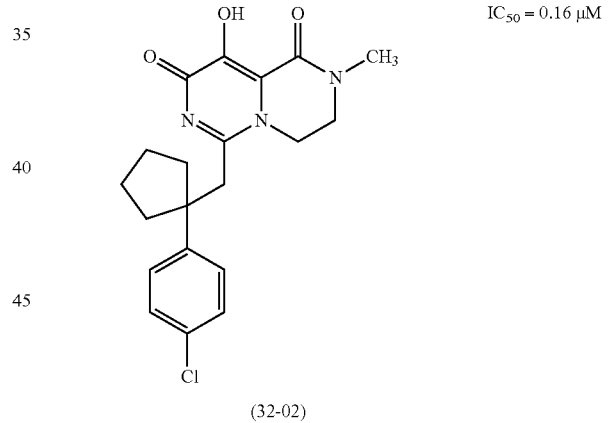 (32-02) | IC$_{50}$ = 0.16 μM |
| 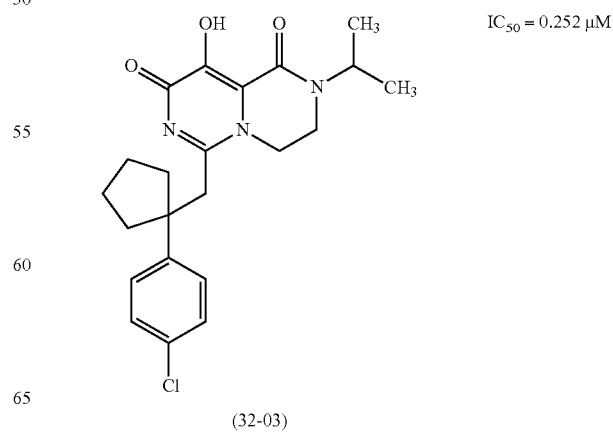 (32-03) | IC$_{50}$ = 0.252 μM |

-continued

| Formula no. | FRET |
|---|---|
| (45) | IC$_{50}$ = 0.296 μM |
| (50) | IC$_{50}$ = 1.18 μM |
| (81) | IC$_{50}$ = 1.81 μM |
| (66) | IC$_{50}$ = 0.39 μM |

-continued

| Formula no. | FRET |
|---|---|
| (74) | IC$_{50}$ = 0.35 μM |
|  | IC$_{50}$ = 0.37 μM |
| (72) | IC$_{50}$ = 2.51 μM |
| (73) | IC$_{50}$ = 1.37 μM |

-continued

| Formula no. | FRET |
|---|---|
| (89) | IC$_{50}$ = 0.43 μM |
| (100) | IC$_{50}$ = 1.70 μM |
| (38) | IC$_{50}$ = 1.39 μM |
|  | IC$_{50}$ = 1.13 μM |

-continued

| Formula no. | FRET |
|---|---|
| (60) | IC$_{50}$ = 0.25 μM |
|  | IC$_{50}$ = 0.12 μM |
|  | IC$_{50}$ = 0.61 μM |
|  | IC$_{50}$ = 0.32 μM |

-continued
| Formula no. | FRET |
|---|---|
| 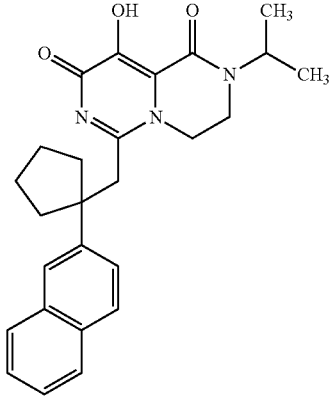 [SMILES: CC(C)N1CCn2c(CC3(c4ccc5ccccc5c4)CCCC3)nc(=O)c(O)c2C1=O] | IC$_{50}$ = 0.11 µM |
| 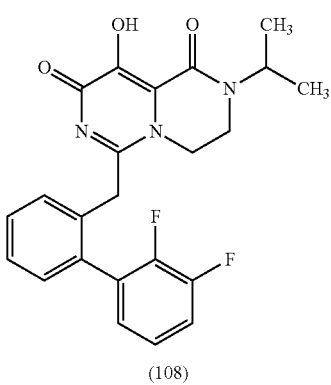 [SMILES: CC(C)N1CCn2c(Cc3ccccc3-c3cccc(F)c3F)nc(=O)c(O)c2C1=O]<br>(108) | IC$_{50}$ = 0.2 µM |
| 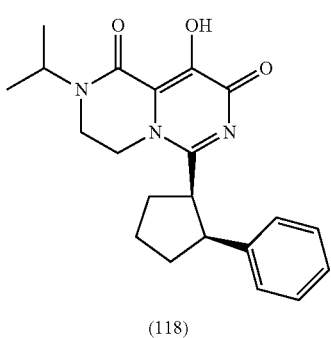 [SMILES: CC(C)N1CCn2c([C@@H]3CCC[C@@H]3c3ccccc3)nc(=O)c(O)c2C1=O]<br>(118) | IC$_{50}$ = 0.5 µM |
| 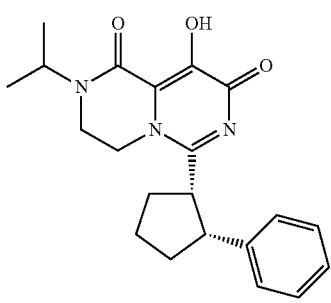<br>(119) | IC$_{50}$ = 0.23 µM |
-continued
| Formula no. | FRET |
|---|---|
| 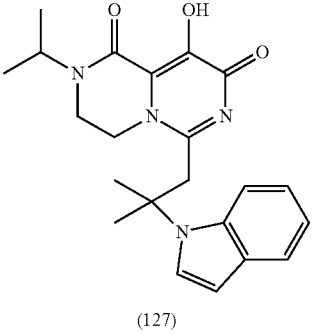 [SMILES: CC(C)N1CCn2c(CC(C)(C)n3ccc4ccccc43)nc(=O)c(O)c2C1=O]<br>(127) | IC$_{50}$ = 0.24 µM |
Scheme 1
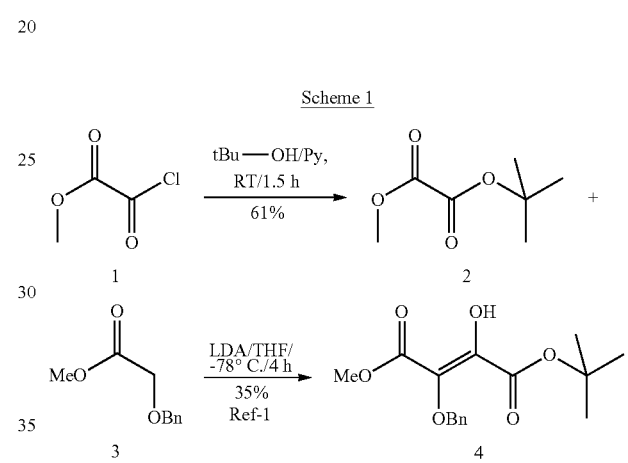
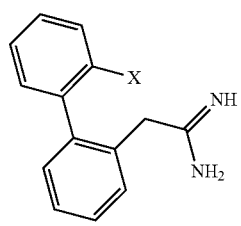
AcOH or HCl
5-01 (X = H, AcOH)
5-02 (X = Cl, HCl)
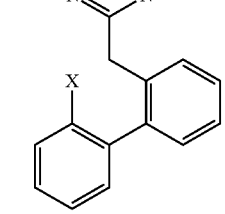
6-01 (X = H)
6-02 (X = Cl)

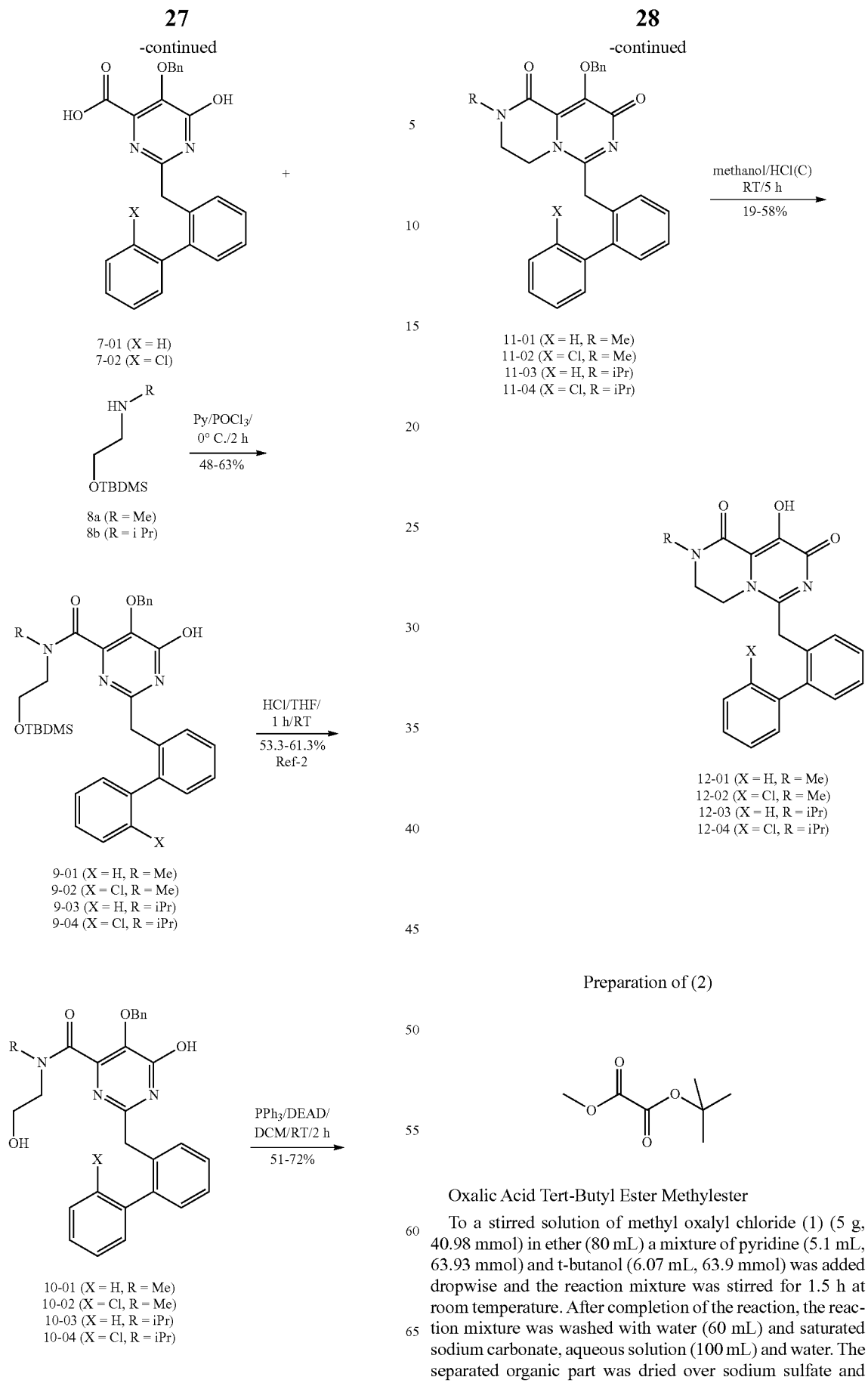

Preparation of (2)

Oxalic Acid Tert-Butyl Ester Methylester

To a stirred solution of methyl oxalyl chloride (1) (5 g, 40.98 mmol) in ether (80 mL) a mixture of pyridine (5.1 mL, 63.93 mmol) and t-butanol (6.07 mL, 63.9 mmol) was added dropwise and the reaction mixture was stirred for 1.5 h at room temperature. After completion of the reaction, the reaction mixture was washed with water (60 mL) and saturated sodium carbonate, aqueous solution (100 mL) and water. The separated organic part was dried over sodium sulfate and concentrated under reduced pressure to get oxalic acid tert-butyl ester methyl ester (2) (4 g, 60.94%) as a colourless oil.

Preparation of (3)

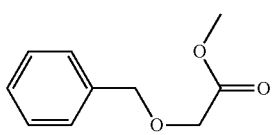

Benzyloxy-Acetic Acid Methyl Ester

To a stirred solution of benzyloxy-acetic acid (5 g, 30.12 mmol) in methanol (100 mL) was added $SOCl_2$ (2.66 mL, 35.8 mmol) at 0° C. The mixture was stirred for 30 min at 0° C., finally at room temperature for 2.5 h. After completion of the reaction, the solvent was evaporated and the reaction mixture was diluted with ethyl acetate and washed with saturated aqueous sodium bicarbonate solution. The separated organic part was dried over sodium sulfate and concentrated under reduced pressure to get benzyloxy-acetic acid methyl ester (3) as a crude colorless oil (4.98 g).

Preparation of (4)

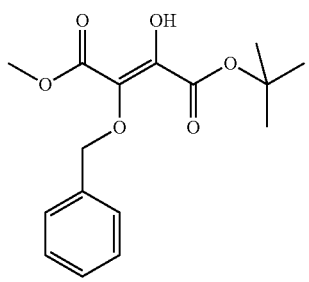 [SMILES: COC(=O)/C(OCc1ccccc1)=C(\O)C(=O)OC(C)(C)C]

(E)-2-Benzyloxy-3-hydroxy-but-2-enedioic acid 4-tert-butyl ester 1-methyl ester

Lithium diisopropylamide was generated by addition of n-butyl lithium (17 mL, 1.9M in hexane, 33.33 mmol), di-isopropyl amine (4.66 mL, 33.33 mmol) in tetrahydrofuran (15 mL) at 0° C. and stirred for 10 min. In a separate flask, a mixture of benzyloxy-acetic acid methyl ester (3) (4 g, 22.22 mmol) and oxalic acid tert-butyl ester methyl ester (2) (5.33 g, 33.33 mmol) in tetrahydrofuran (50 mL) was cooled to −78° C. and then lithium diisopropylamide was added at −78° C. The mixture was stirred at −78° C. for 1 h. After 1 h, the reaction mixture was allowed to warm to room temperature and stirred at room temperature for another 1 h. After completion of the reaction, the reaction was quenched with 1N HCl, and extracted with ethyl acetate. The separated organic part was dried over sodium sulfate and concentrated under reduced pressure, passed over a normal silica column using 25% ethyl acetate in hexane to get (E)-2-benzyloxy-3-hydroxy-but-2-enedioic acid 4-tert-butyl ester 1-methyl ester (4) (2.4 g, 35%) as ketoenol tautomers and ketone hydrate as a thick light yellow coloured oil. These were immediately used for next step.

Synthesis of 5-01

Scheme 2

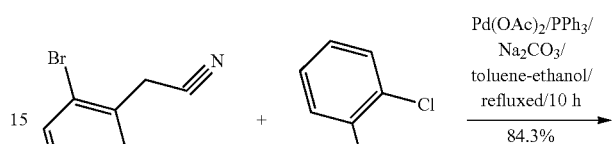

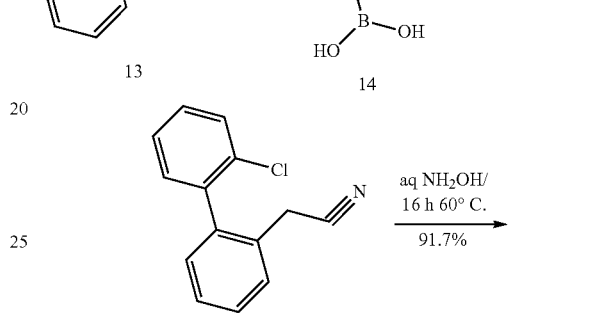

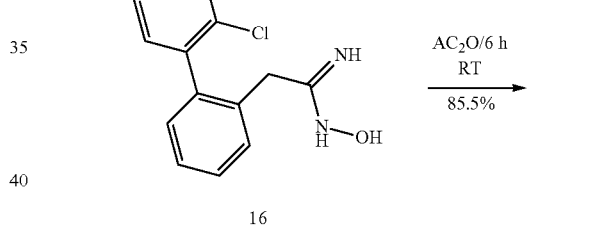

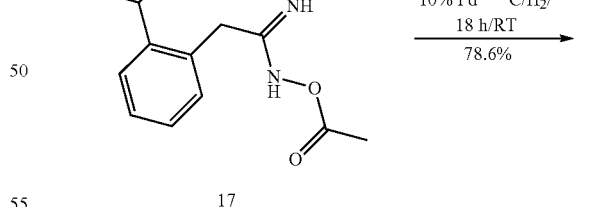

Experimental

Preparation of (15)

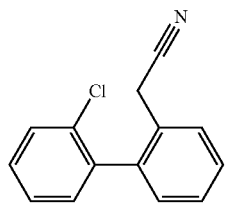 [SMILES: N#CCc1ccccc1-c1ccccc1Cl]

(2'-Chloro-biphenyl-2-yl)-acetonitrile

To a stirred solution of (2-bromophenyl)-acetonitrile (13) (5 g, 25.51 mmol) in a mixture of toluene and ethanol (1:1, 150 mL) was added 2-chloro phenyl boronic acid (14) (6 g, 38.2 mmol) and $Na_2CO_3$ (8.1 g, 76.53 mmol) at room temperature. Purging was conducting for 30 min with nitrogen. Then triphenyl phosphine (2.6 g, 10.2 mmol) was added followed by $Pd(OAc)_2$ (0.287 g, 1.27 mmol) and further degassing was conducted for another 10 min. The reaction mixture was heated to reflux for 10 h. After completion of the reaction, the mixture was concentrated under reduced pressure to get a crude product which was purified using a silica column using 2% ethyl acetate in hexane to get (2'-chloro-biphenyl-2-yl)-acetonitrile (15) (4.9 g, 84.36%) as a yellow liquid.

Preparation of (16)

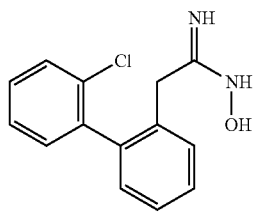 [SMILES: N=C(Cc1ccccc1-c1ccccc1Cl)NO]

2-(2'-Chloro-biphenyl-2-yl)-N-hydroxy-acetamidine

To a stirred solution of (2'-chloro-biphenyl-2-yl)-acetonitrile (15) (2 g, 8.78 mmol) in ethanol (20 mL) was added aqueous hydroxylamine (50%) (1.16 g, 17.8) The mixture was heated to 60° C. for 16 h. After completion of the reaction, the reaction mixture was evaporated, extracted with ethyl acetate and concentrated to get 2-(2'-chloro-biphenyl-2-yl)-N-hydroxy-acetamidine (16) (2.1 g, 91.7%) as an off-white solid which was directly used in the next step.

Preparation of (17)

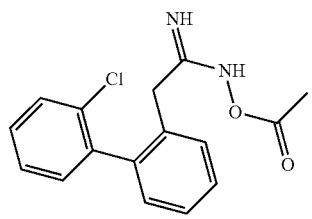 [SMILES: CC(=O)ONC(=N)Cc1ccccc1-c1ccccc1Cl]

2-(2'-Chloro-biphenyl-2-yl)-N-acetyl-acetamidine

To 10 mL acetic anhydride was added 2-(2'-chloro-biphenyl-2-yl)-N-hydroxy-acetamidine (16) (2 g, 7.692 mmol). The mixture was stirred for 6 h at room temperature. After completion of the reaction, water was added, the mixture was extracted with ethyl acetate, evaporated, dried and purified using a CombiFlash column using 25% ethyl acetate in hexane to get 2-(2'-chloro-biphenyl-2-yl)-N-acetyl-acetamidine (17) (2 g, 85.88%) as an off-white solid.

LC-MS: 302.8 (M+H).

Preparation of (5-01)

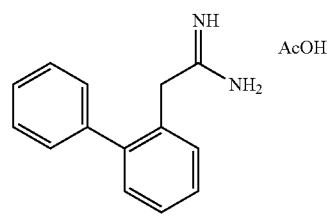 [SMILES: "AcOH" ; N=C(N)Cc1ccccc1-c1ccccc1]

2-Biphenyl-2-yl-acetamidine acetate salt

To the solution of 2-(2'-chloro-biphenyl-2-yl)-N-acetyl-acetamidine (17) (2 g, 6.623 mmol) in methanol (10 mL) was added 200 mg 10% Pd—C. The mixture was hydrogenated by balloon pressure at room temperature for 18 h. After completion of the reaction, the mixture was filtered and evaporated to afford 2-biphenyl-2-yl-acetamidine acetic acid salt (5-01) (1.4 g, 78.4%) as a white solid.

LC-MS: 211 (M+H).

Synthesis of 5-02

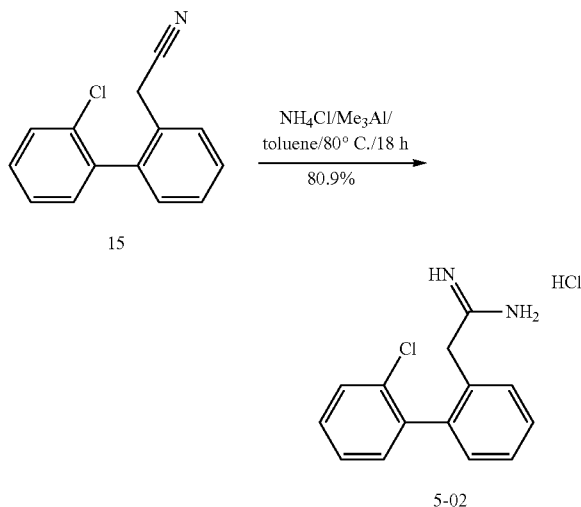

Experimental

Preparation of (5-02)

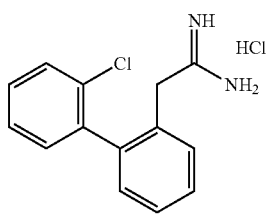 [SMILES: N=C(N)Cc1ccccc1-c1ccccc1Cl ; Cl]

2-(2'-Chloro-biphenyl-2-yl)-acetamidine
hydrochloride salt

To a stirred suspension of NH₄Cl (1.4 g, 26.43 mmol) in dry toluene (40 mL) was added tri-methyl aluminium (2M in toluene, 13.2 mL, 26.43 mmol) at 5° C. The reaction mixture was then warmed to room temperature and stirred for 2 h. A solution of (2'-chloro-biphenyl-2-yl)-acetonitrile (15) (2 g, 8.8 mmol) in toluene (10 mL) was added to the reaction mixture, which was then stirred for 14 h at 80° C. After completion of the reaction, it was quenched with a suspension of silica gel in chloroform and the reaction mixture was stirred for half an hour at room temperature and then filtered through a sintered funnel. The silica gel was washed with methanol and the combined filtrates were concentrated under reduced pressure to get 2-(2'-chloro-biphenyl-2-yl)-acetamidine hydrochloride salt as a crude product (5-02) (2 g, 80.97%) as a white solid.

LC-MS: 245 (M+H).

Preparation of (6-01)

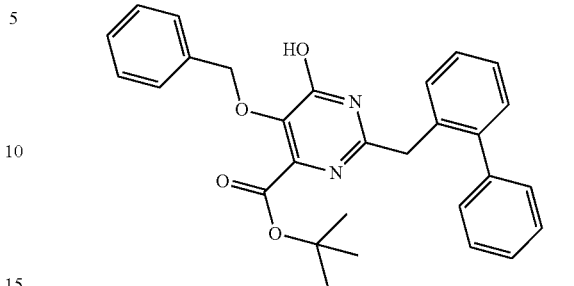

5-Benzyloxy-2-biphenyl-2-ylmethyl-6-hydroxypyrimidine-4-carboxylic acid tert-butyl ester To a stirred solution of 2-biphenyl-2-yl-acetamidine acetate salt (5-01) (2.5 g, 9.2 mmol) and (E)-2-benzyloxy-3-hydroxy-but-2-enedioic acid 4-tert-butyl ester 1-methyl ester (4) (4.2 g, 13.88 mmol) in methanol (60 mL) was added sodium methoxide (1.5 g, 27.77 mmol) at 0° C., then the reaction mixture was allowed to warm to room temperature and was stirred for 16 h. After completion of the reaction, it was quenched with 1N HCl, evaporated and water was added. The mixture was extracted with ethyl acetate and the separated organic part was dried over sodium sulfate and concentrated under reduced pressure to get a crude product, which was purified using a normal silica column using 30% ethyl acetate in hexane to get 5-benzyloxy-2-biphenyl-2-ylmethyl-6-hydroxypyrimidine-4-carboxylic acid tert-butyl ester (6-01) (2.5 g, 57.63%) as a white solid.

LC-MS: 469.2 (M+H).

Preparation of (6-02)

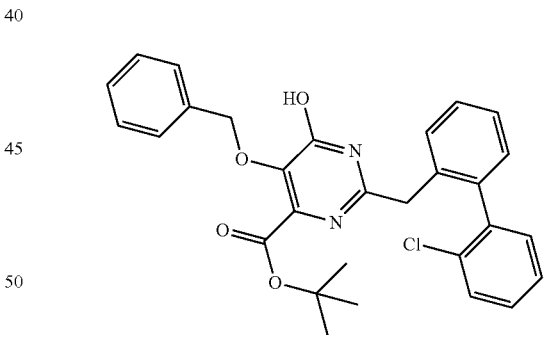

5-Benzyloxy-2-(2'-chloro-biphenyl-2-ylmethyl)-6-hydroxypyrimidine-4-carboxylic acid tert-butyl ester 5-Benzyloxy-2-(2'-chloro-biphenyl-2-ylmethyl)-6-hydroxypyrimidine-4-carboxylic acid tert-butyl ester (6-02) (5 g, 55.8%) was synthesized as a brown solid from 2-(2'-chloro-biphenyl-2-yl)-acetamidine hydrochloride salt (5-02) (5 g, 17.82 mmol) and (E)-2-benzyloxy-3-hydroxy-but-2-enedioic acid 4-tert-butyl ester 1-methyl ester (4) (9.4 g, 30.73 mmol) following the procedure as described for 5-benzyloxy-2-biphenyl-2-ylmethyl-6-hydroxypyrimidine-4-carboxylic acid tert-butyl ester (6-01).

LC-MS: 503.4 (M+H).

Preparation of (7-01)

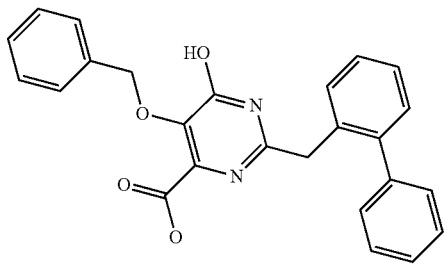 [SMILES: O=C(O)c1nc(Cc2ccccc2-c2ccccc2)nc(O)c1OCc1ccccc1]

5-Benzyloxy-2-biphenyl-2-ylmethyl-6-hydroxypyrimidine-4-carboxylic acid

To a stirred solution of 5-benzyloxy-2-biphenyl-2-ylmethyl-6-hydroxypyrimidine-4-carboxylic acid tert-butyl ester (6-01) (5 g, 10.68 mmol) in a mixture of tetrahydrofuran and water (2:1, 90 mL) was added lithium hydroxide, monohydrate (2.2 g, 53.4 mml). The mixture was refluxed for 18 h. After completion of the reaction, the volume was reduced by evaporation as much as possible, water was added and the mixture was washed with ethyl acetate to remove non-acidic impurities. The separated aqueous part was acidified with 1N HCl to bring the pH to about 5 to 6. The acidified aqueous part was extracted with dichloromethane to get 5-benzyloxy-2-biphenyl-2-ylmethyl-6-hydroxypyrimidine-4-carboxylic acid (7-01) (3 g, 68%) as a white solid.

LC-MS: 413.2 (M+H).

Preparation of (7-02)

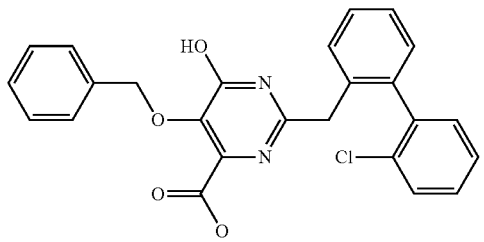 [SMILES: O=C(O)c1nc(Cc2ccccc2-c2ccccc2Cl)nc(O)c1OCc1ccccc1]

5-Benzyloxy-2-(2'-chloro-biphenyl-2-ylmethyl)-6-hydroxypyrimidine-4-carboxylic acid 5-Benzyloxy-2-(2'-chloro-biphenyl-2-ylmethyl)-6-hydroxypyrimidine-4-carboxylic acid (7-02) (3 g, 67.53%) was synthesized as a white solid from 5-benzyloxy-2-(2'-chloro-biphenyl-2-ylmethyl)-6-hydroxypyrimidine-4-carboxylic acid tert-butyl ester (6-02) (5 g, 9.94 mmol) following the procedure as described for 5-benzyloxy-2-biphenyl-2-ylmethyl-6-hydroxypyrimidine-4-carboxylic acid (7-01).

LC-MS: 447 (M+H).

Synthesis of 8

Scheme 4

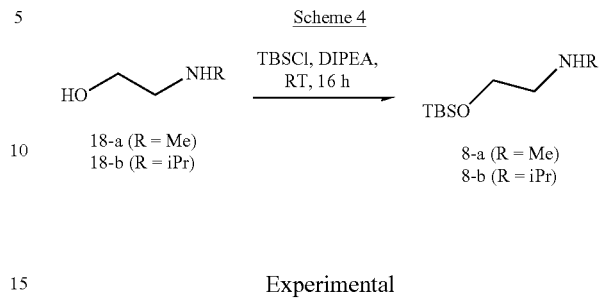

18-a (R = Me)
18-b (R = iPr)

8-a (R = Me)
8-b (R = iPr)

Experimental

Preparation of (8-a)

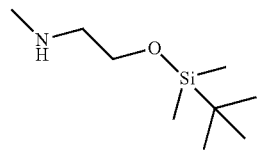

[2-(tert-Butyl-dimethylsilanyloxy)-ethyl]-methyl-amine

To a stirred solution of 2-methylamino-ethanol (18-a) (10 g, 133.13 mmol) in dichloromethane (200 mL) were added diisopropylethylamine (30.8 ml, 186.39 mmol) and tert-butyl-chloro-dimethyl-silane (20.06 g, 133.13 mmol) at room temperature. The mixture was stirred for 16 h. After completion of the reaction, water was added and the mixture was extracted with dichloromethane. The separated organic part was washed with water and was dried over sodium sulfate and concentrated under reduced pressure to get [2-(tert-butyl-dimethylsilanyloxy)-ethyl]-methyl-amine (8-a) (18 g, 71.39%) as a yellow liquid.

Preparation of (8-b)

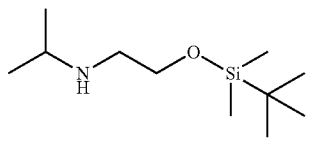

[2-(tert-Butyl-dimethylsilanyloxy)-ethyl]-isopropyl-amine

[2-(tert-Butyl-dimethylsilanyloxy)-ethyl]-isopropyl-amine (8-b) (20 gm, 37.4%) was synthesized as a yellow liquid from 2-isopropylamino-ethanol (18-b) (25 g, 242.31 mmol) and tert-butyl-chloro-dimethyl-silane (25.5 g, 242.31 mmol) following the procedure as described for [2-(tert-butyl-dimethylsilanyloxy)-ethyl]-methyl-amine (8-a).

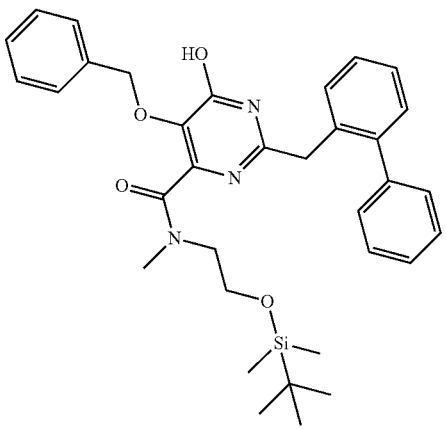 [SMILES: CN(CCO[Si](C)(C)C(C)(C)C)C(=O)c1nc(Cc2ccccc2-c2ccccc2)nc(O)c1OCc1ccccc1]

Preparation of (9-01)

5-Benzyloxy-2-biphenyl-2-ylmethyl-6-hydroxypyrimidine-4-carboxylic acid [2-(tert-butyl-dimethylsilanyloxy)-ethyl]-methyl-amide To a stirred solution of 5-benzyloxy-2-biphenyl-2-ylmethyl-6-hydroxypyrimidine-4-carboxylic acid (7-01) (3 g, 7.28 mmol) and [2-(tert-butyl-dimethylsilanyloxy)-ethyl]-methyl-amine (8-a) (1.51 g, 8.01 mmol) in pyridine (40 mL) was added POCl₃ (2 ml, 21.84 mol) at −10° C. The mixture was stirred at 0° C. for 2 h. After completion of the reaction, ice cooled-water (30 mL) was added to the reaction mixture at 0° C. The mixture was extracted with ethyl acetate (4×200 mL). The separated organic part was washed with saturated aqueous solution of NaHCO₃, dried and concentrated to get a crude product which was purified by normal silica column using 40% ethyl acetate in hexane to get 5-benzyloxy-2-biphenyl-2-ylmethyl-6-hydroxypyrimidine-4-carboxylic acid [2-(tert-butyl-dimethylsilanyloxy)-ethyl]methyl-amide (9-01) (2.1 g, 49.4%) as a yellow sticky mass.

LC-MS: 584.2 (M+H).

Preparation of (9-02)

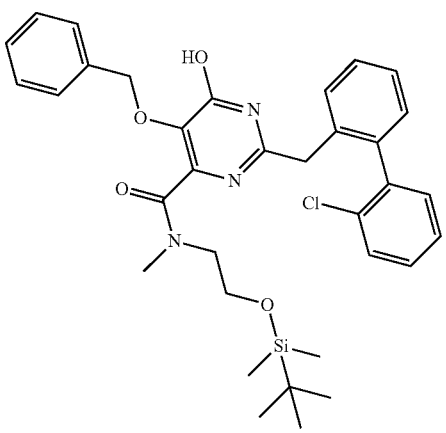 [SMILES: CN(CCO[Si](C)(C)C(C)(C)C)C(=O)c1nc(Cc2ccccc2-c2ccccc2Cl)nc(O)c1OCc1ccccc1]

5-Benzyloxy-2-(2'-chloro-biphenyl-2-ylmethyl)-6-hydroxypyrimidine-4-carboxylic acid [2-(tert-butyl-dimethylsilanyloxy)-ethyl]-methyl-amide 5-Benzyloxy-2-(2'-chloro-biphenyl-2-ylmethyl)-6-hydroxypyrimidine-4-carboxylic acid [2-(tert-butyl-dimethylsilanyloxy)-ethyl]-methyl-amide (9-02) (2 g, 48.09%) was synthesized as a yellow liquid from 5-benzyloxy-2-(2'-chloro-biphenyl-2-ylmethyl)-6-hydroxypyrimidine-4-carboxylic acid (7-02) (3 g, 6.72 mmol) and [2-(tert-butyl-dimethylsilanyloxy)-ethyl]-methyl-amine (8-a) (1.39 g, 7.399 mmol) following the procedure as described for 5-benzyloxy-2-biphenyl-2-ylmethyl-6-hydroxypyrimidine-4-carboxylic acid [2-(tert-butyl-dimethylsilanyloxy)-ethyl]-methyl-amide (9-01).

LC-MS: 618.2 (M+H).

Preparation of (9-03)

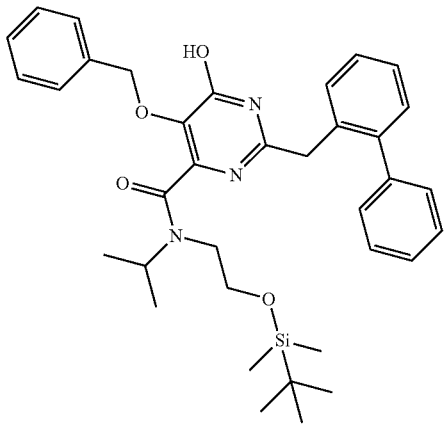 [SMILES: CC(C)N(CCO[Si](C)(C)C(C)(C)C)C(=O)c1nc(Cc2ccccc2-c2ccccc2)nc(O)c1OCc1ccccc1]

5-Benzyloxy-2-biphenyl-2-ylmethyl-6-hydroxypyrimidine-4-carboxylic acid [2-(tert-butyl-dimethylsilanyloxy)-ethyl]-isopropylamide 5-Benzyloxy-2-biphenyl-2-ylmethyl-6-hydroxypyrimidine-4-carboxylic acid [2-(tert-butyl-dimethylsilanyloxy)-ethyl]-isopropylamide (9-03) (1.7 g, 38.16%) was synthesized as a dark liquid from 5-benzyloxy-2-biphenyl-2-ylmethyl-6-hydroxypyrimidine-4-carboxylic acid (7-01) (3 g, 7.28 mmol) and [2-(tert-butyl-dimethylsilanyloxy)-ethyl]-isopropyl amine (8-b) (1.73 g, 8.01 mmol) following the procedure as described for 5-benzyloxy-2-biphenyl-2-ylmethyl-6-hydroxypyrimidine-4-carboxylic acid [2-(tert-butyl-dimethylsilanyloxy)-ethyl]-methyl-amide (9-01).

LC-MS: 611.9 (M+H).

Preparation of (9-04)

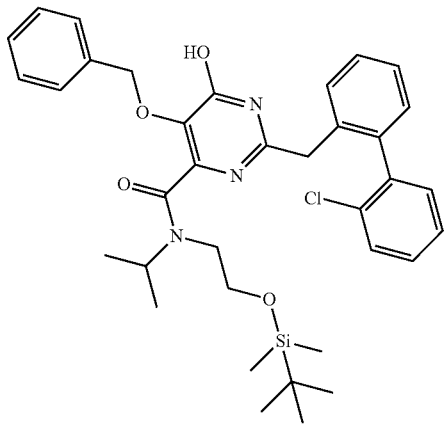 [SMILES: CC(C)N(CCO[Si](C)(C)C(C)(C)C)C(=O)c1nc(Cc2ccccc2-c2ccccc2Cl)nc(O)c1OCc1ccccc1]

5-Benzyloxy-2-(2'-chloro-biphenyl-2-ylmethyl)-6-hydroxypyrimidine-4-carboxylic acid [2-(tert-butyl-dimethylsilanyloxy)-ethyl]-isopropylamide 5-Benzyloxy-2-(2'-chloro-biphenyl-2-ylmethyl)-6-hydroxypyrimidine-4-carboxylic acid [2-(tert-butyl-dimethylsilanyloxy)-ethyl]-isopropylamide (9-04) (2.74 g, 63.03%) was synthesized as a dark liquid from 5-benzyloxy-2-(2'-chloro-biphenyl-2-ylmethyl)-6-hydroxypyrimidine-4-carboxylic acid (7-02) (3 g, 6.72 mmol) and [2-(tert-butyl-dimethylsilanyloxy)-ethyl]-isopropyl amine (8-b) (1.6 g, 7.399 mmol) following the procedure as described for 5-benzyloxy-2-biphenyl-2-ylmethyl-6-hydroxypyrimidine-4-carboxylic acid [2-(tert-butyl-dimethylsilanyloxy)-ethyl]-methyl-amide (9-01).

LC-MS: 646.3 (M+H).

Preparation of (10-01)

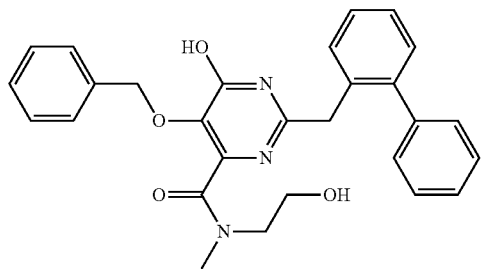 [SMILES: CN(CCO)C(=O)c1nc(Cc2ccccc2-c2ccccc2)nc(O)c1OCc1ccccc1]

5-Benzyloxy-2-biphenyl-2-ylmethyl-6-hydroxypyrimidine-4-carboxylic acid (2-hydroxyethyl)-methyl-amide To a stirred solution of 5-benzyloxy-2-biphenyl-2-ylmethyl-6-hydroxypyrimidine-4-carboxylic acid [2-(tert-butyl-dimethylsilanyloxy)-ethyl]-methyl-amide (9-01) (2.1 g, 3.602 mmol) in tetrahydrofuran (30 mL) was added 1N HCl (5.4 ml, 5.4 mmol) at room temperature. The mixture was stirred for 60 min at room temperature. After completion of the reaction, the mixture was neutralized with 1N sodium hydroxide aqueous solution, extracted with ethyl acetate, dried over sodium sulfate and concentrated under reduced pressure to get a crude product which was purified using a normal silica column using 60% ethyl acetate in hexane to get 5-benzyloxy-2-biphenyl-2-ylmethyl-6-hydroxypyrimidine-4-carboxylic acid (2-hydroxyethyl)-methyl-amide (10-01) (900 mg, 53.33%) as a floppy light yellow solid.

LC-MS: 470 (M+H).

Preparation of (10-02)

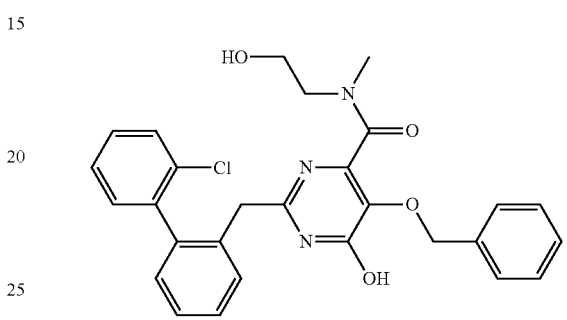

5-Benzyloxy-2-(2'-chloro-biphenyl-2-ylmethyl)-6-hydroxypyrimidine-4-carboxylic acid (2-hydroxyethyl)-methyl-amide 5-Benzyloxy-2-(2'-chloro-biphenyl-2-ylmethyl)-6-hydroxypyrimidine-4-carboxylic acid (2-hydroxyethyl)-methyl-amide (10-02) (1 g, 61.34%) was synthesized as a yellow liquid from 5-benzyloxy-2-(2'-chloro-biphenyl-2-ylmethyl)-6-hydroxypyrimidine-4-carboxylic acid [2-(tert-butyl-dimethylsilanyloxy)-ethyl]-methyl-amide (9-02) (2 g, 3.23 mmol) following the procedure as described for 5-benzyloxy-2-biphenyl-2-ylmethyl-6-hydroxypyrimidine-4-carboxylic acid (2-hydroxyethyl)-methyl-amide (10-01).

LC-MS: 504.1 (M+H).

Preparation of (10-03)

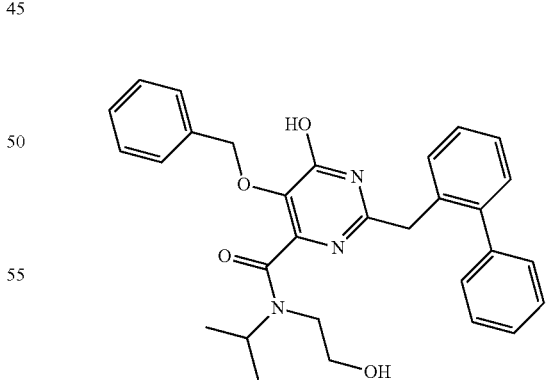

5-Benzyloxy-2-biphenyl-2-ylmethyl-6-hydroxypyrimidine-4-carboxylic acid (2-hydroxyethyl)-isopropylamide 5-Benzyloxy-2-biphenyl-2-ylmethyl-6-hydroxypyrimidine-4-carboxylic acid (2-hydroxyethyl)-isopropylamide (10-03) (650 mg, 47%) was synthesized as a yellow liquid from 5-benzyloxy-2-biphenyl-2-ylmethyl-6-hydroxypyrimidine-4-carboxylic acid [2-(tert-butyl-dimethylsilanyloxy)-ethyl]-isopropylamide (9-03) (1.7 g, 38.16 mmol) following the procedure as described for 5-benzyloxy-2-biphenyl-2-ylmethyl-6-hydroxypyrimidine-4-carboxylic acid (2-hydroxyethyl)-methyl-amide (10-01).

LC-MS: 498.2 (M+H).

Preparation of (10-04)

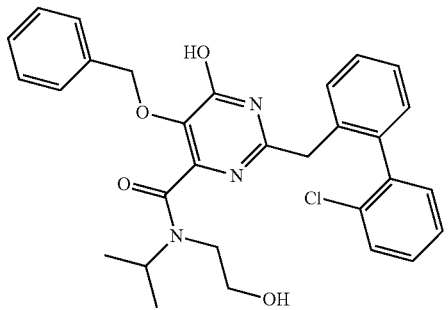 [SMILES: CC(C)N(CCO)C(=O)c1nc(Cc2ccccc2-c2ccccc2Cl)nc(O)c1OCc1ccccc1]

5-Benzyloxy-2-(2'-chloro-biphenyl-2-ylmethyl)-6-hydroxypyrimidine-4-carboxylic acid (2-hydroxy-ethyl)-isopropylamide 5-Benzyloxy-2-(2'-chloro-biphenyl-2-ylmethyl)-6-hydroxypyrimidine-4-carboxylic acid (2-hydroxyethyl)-isopropylamide (10-04) (1.2 g, 53.97%) was synthesized as a yellow liquid from 5-benzyloxy-2-(2'-chloro-biphenyl-2-ylmethyl)-6-hydroxypyrimidine-4-carboxylic acid [2-(tert-butyl-dimethylsilanyloxy)-ethyl]-isopropylamide (9-04) (2.7 g, 4.18 mmol) following the procedure as described for 5-benzyloxy-2-biphenyl-2-ylmethyl-6-hydroxypyrimidine-4-carboxylic acid (2-hydroxyethyl)-methyl-amide (10-01).

LC-MS: 532.2 (M+H).

Preparation of (11-01)

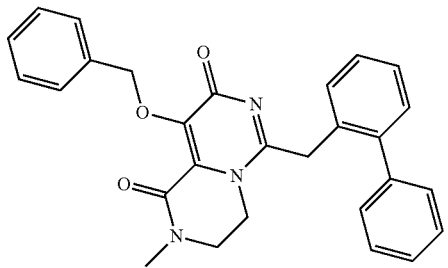 [SMILES: CN1CCn2c(Cc3ccccc3-c3ccccc3)nc(=O)c(OCc3ccccc3)c2C1=O]

9-Benzyloxy-6-biphenyl-2-ylmethyl-2-methyl-3,4-dihydro-2H-pyrazino[1,2-c]pyrimidine-1,8-dione To a stirred solution of 5-benzyloxy-2-biphenyl-2-ylmethyl-6-hydroxypyrimidine-4-carboxylic acid (2-hydroxyethyl)-methyl-amide (10-01) (400 mg, 0.853 mmol) in dichloromethane (10 mL) was added triphenyl phosphine (336.46 mg, 1.27 mmol) at room temperature. The mixture was stirred for 10 min. Then diisopropyl azodicarboxylate (diisopropylazodicarboxylate) (258.4 mg, 1.27 mmol) was added at room temperature and the resultant mixture was stirred for another 2 h. After completion of the reaction, the mixture was concentrated under reduced pressure to get a crude product, which was purified using normal silica column using 2% methanol in dichloromethane to of ford 9-benzyloxy-6-biphenyl-2-ylmethyl-2-methyl-3,4-dihydro-2H-pyrazino[1,2-c]pyrimidine-1,8-dione (11-01) (200 mg, 51.94%) as a white solid.

LC-MS: 452.2 (M+H).

Preparation of (11-02)

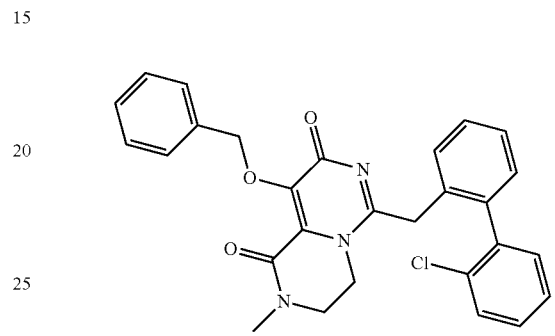

9-Benzyloxy-6-(2'-chloro-biphenyl-2-ylmethyl)-2-methyl-3,4-dihydro-2H-pyrazino[1,2-c]pyrimidine-1,8-dione 9-Benzyloxy-6-(2'-chloro-biphenyl-2-ylmethyl)-2-methyl-3,4-dihydro-2H-pyrazino[1,2-c]pyrimidine-1,8-dione (11-02) (201 mg, 52.5%) was synthesized as a white solid from 5-benzyloxy-2-(2'-chloro-biphenyl-2-ylmethyl)-6-hydroxypyrimidine-4-carboxylic acid (2-hydroxyethyl)-methyl-amide (10-02) (400 mg, 0.795 mmol) following the procedure as described for 9-benzyloxy-6-biphenyl-2-ylmethyl-2-methyl-3,4-dihydro-2H-pyrazino[1,2-c]pyrimidine-1,8-dione (11-01).

LC-MS: 486.2 (M+H).

Preparation of (11-03)

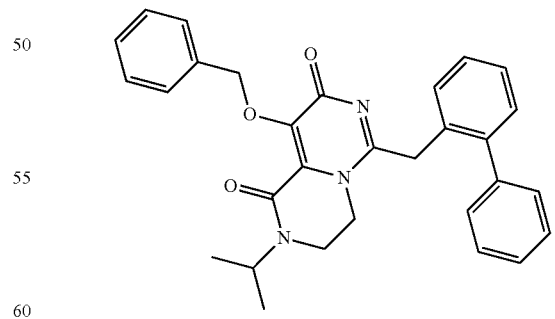

9-Benzyloxy-6-biphenyl-2-ylmethyl-2-isopropyl-3,4-dihydro-2H-pyrazino[1,2-c]pyrimidine-1,8-dione 9-Benzyloxy-6-biphenyl-2-ylmethyl-2-isopropyl-3,4-dihydro-2H-pyrazino[1,2-c]pyrimidine-1,8-dione    (11-03)

(110 mg, 17.54%) was synthesized as a white solid from 5-benzyloxy-2-biphenyl-2-ylmethyl-6-hydroxypyrimidine-4-carboxylic acid (2-hydroxyethyl)-isopropylamide (10-03) (650 mg, 1.3 mmol) following the procedure as described for 9-benzyloxy-6-biphenyl-2-ylmethyl-2-methyl-3,4-dihydro-2H-pyrazino[1,2-c]pyrimidine-1,8-dione (11-01).

LC-MS: 480.2 (M+H).

Preparation of (11-04)

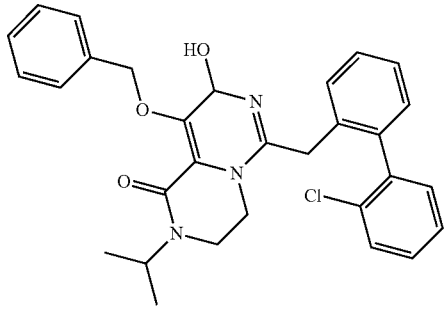 [SMILES: CC(C)N1CCN2C(Cc3ccccc3-c3ccccc3Cl)=NC(O)C(OCc3ccccc3)=C2C1=O]

9-Benzyloxy-6-(2'-chloro-biphenyl-2-ylmethyl)-8-hydroxy-2-isopropyl-3,4-dihydro-2H,8H-pyrazino[1,2-c]pyrimidin-1-one 9-Benzyloxy-6-(2'-chloro-biphenyl-2-ylmethyl)-8-hydroxy-2-isopropyl-3,4-dihydro-2H,8H-pyrazino[1,2-c]pyrimidin-1-one (11-04) (350 mg, 72.4%) was synthesized as a white solid from 5-benzyloxy-2-(2'-chloro-biphenyl-2-ylmethyl)-6-hydroxypyrimidine-4-carboxylic acid (2-hydroxyethyl)-isopropylamide (10-04) (500 mg, 0.94 mmol) following the procedure as described for 9-benzyloxy-6-biphenyl-2-ylmethyl-2-methyl-3,4-dihydro-2H-pyrazino[1,2-c]pyrimidine-1,8-dione (11-01).

LC-MS: 514 (M+H).

Preparation of (12-01)

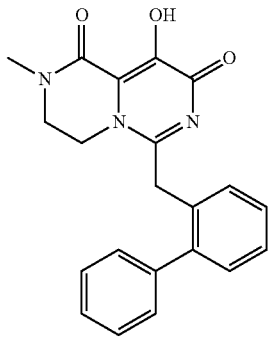 [SMILES: CN1CCn2c(Cc3ccccc3-c3ccccc3)nc(=O)c(O)c2C1=O]

6-Biphenyl-2-ylmethyl-9-hydroxy-2-methyl-3,4-dihydro-2H-pyrazino[1,2-c]pyrimidine-1,8-dione To a stirred solution of 9-benzyloxy-6-biphenyl-2-ylmethyl-2-methyl-3,4-dihydro-2H-pyrazino[1,2-c]pyrimidine-1,8-dione (11-01) (350 mg, 0.776 mmol) in methanol (6 mL) was added concentrated HCl (3 mL) and the reaction mixture was stirred for 5 h at room temperature. After completion of the reaction, the volume of the reaction mixture was reduced by evaporation and the resultant mixture was basified with saturated aqueous NaHCO₃ solution. The mixture was extracted with 10% methanol in dichloromethane, the separated organic part was dried over sodium sulfate and concentrated to get a crude product, which was purified by prep-HPLC (ammonium acetate-methanol) to afford 6-biphenyl-2-ylmethyl-9-hydroxy-2-methyl-3,4-dihydro-2H-pyrazino[1,2-c]pyrimidine-1,8-dione (12-01) (68 mg, 24.25%) as an off-white solid.

LC-MS: 362.2 (M+H).

Preparation of (12-02)

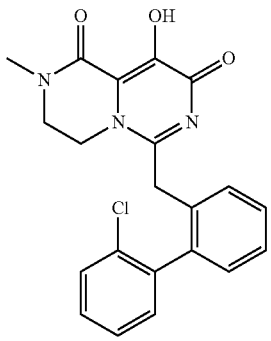 [SMILES: CN1CCn2c(Cc3ccccc3-c3ccccc3Cl)nc(=O)c(O)c2C1=O]

6-(2'-Chloro-biphenyl-2-ylmethyl)-9-hydroxy-2-methyl-3,4-dihydro-2H-pyrazino[1,2-c]pyrimidine-1,8-dione 6-(2'-Chloro-biphenyl-2-ylmethyl)-9-hydroxy-2-methyl-3,4-dihydro-2H-pyrazino[1,2-c]pyrimidine-1,8-dione (12-02) (215 mg, 58.54%) was synthesized as an off-white solid from 9-benzyloxy-6-(2'-chloro-biphenyl-2-ylmethyl)-2-methyl-3,4-dihydro-2H-pyrazino[1,2-c]pyrimidine-1,8-dione (11-02) (400 mg, 0.887 mmol) following the procedure as described for 6-biphenyl-2-ylmethyl-9-hydroxy-2-methyl-3,4-dihydro-2H-pyrazino[1,2-c]pyrimidine-1,8-dione (12-01).

LC-MS: 396 (M+H).

Preparation of (12-03)

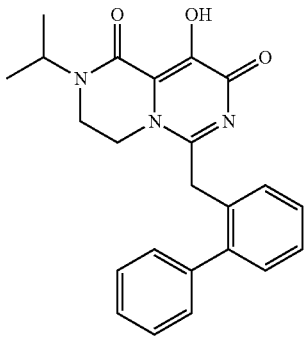

6-Biphenyl-2-ylmethyl-9-hydroxy-2-isopropyl-3,4-dihydro-2H-pyrazino[1,2-c]pyrimidine-1,8-dione 6-Biphenyl-2-ylmethyl-9-hydroxy-2-isopropyl-3,4-dihydro-2H-pyrazino[1,2-c]pyrimidine-1,8-dione (12-03) (17 mg, 19%) was synthesized as an off-white solid from 9-benzyloxy-6-biphenyl-2-ylmethyl-2-isopropyl-3,4-dihydro-2H-pyrazino[1,2-c]pyrimidine-1,8-dione (11-03) (110 mg, 0.229 mmol) following the procedure as described for 6-biphenyl-2-ylmethyl-9-hydroxy-2-methyl-3,4-dihydro-2H-pyrazino[1,2-c]pyrimidine-1,8-dione (12-01).

LC-MS: 390.2 (M+H).

Preparation of (12-04)

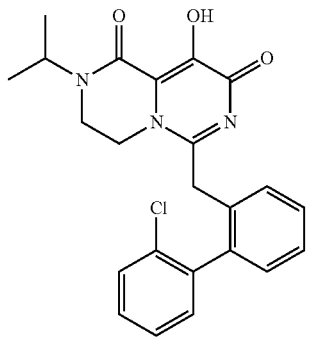

6-(2'-Chloro-biphenyl-2-ylmethyl)-9-hydroxy-2-isopropyl-3,4-dihydro-2H-pyrazino[1,2-c]pyrimidine-1,8-dione 6-(2'-Chloro-biphenyl-2-ylmethyl)-9-hydroxy-2-isopropyl-3,4-dihydro-2H-pyrazino[1,2-c]pyrimidine-1,8-dione (12-04) (107 mg, 37.07%) was synthesized as an off-white solid from 9-benzyloxy-6-(2'-chloro-biphenyl-2-ylmethyl)-8-hydroxy-2-isopropyl-3,4-dihydro-2H,8H-pyrazino[1,2-c]pyrimidin-1-one (11-04) (350 mg, 0.682 mmol) following the procedure as described for 6-biphenyl-2-ylmethyl-9-hydroxy-2-methyl-3,4-dihydro-2H-pyrazino[1,2-c]pyrimidine-1,8-dione (12-01).

LC-MS: 423.9 (M+H).

Synthesis of 32-01, 32-02 and 32-03

Scheme 5

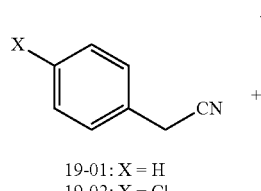

19-01: X = H
19-02: X = Cl

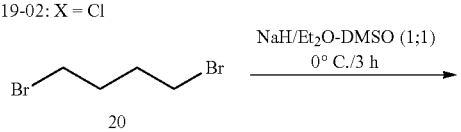

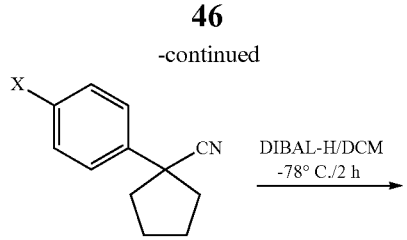

21-01: X = H
21-02: X = Cl

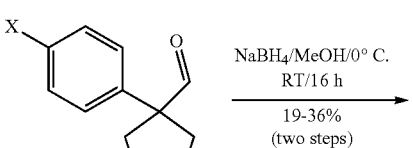

22-01: X = H
22-02: X = Cl

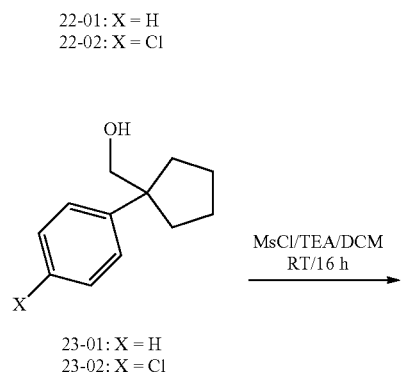

23-01: X = H
23-02: X = Cl

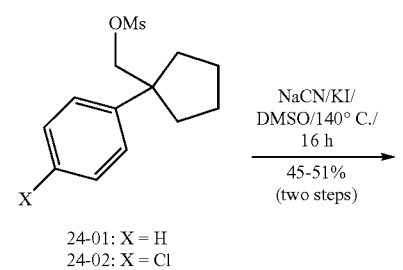

24-01: X = H
24-02: X = Cl

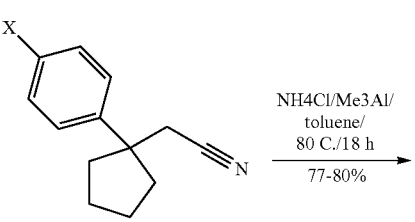

25-01: X = H
25-02: X = Cl

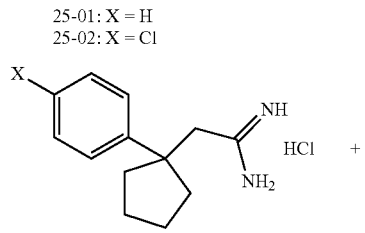

26-01: X = H
26-02: X = Cl

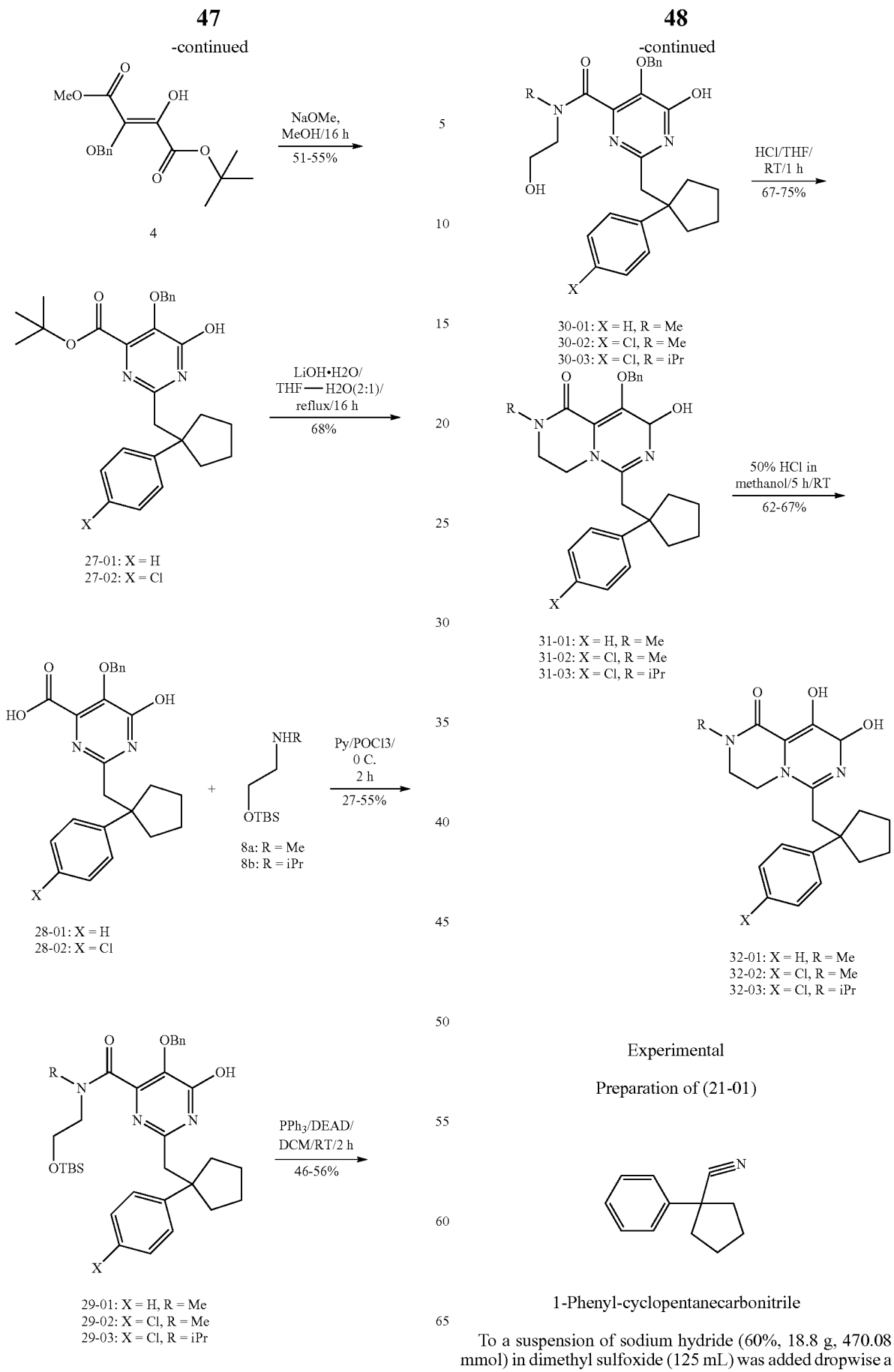
Experimental
Preparation of (21-01)
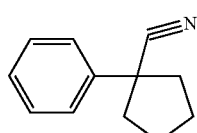
1-Phenyl-cyclopentanecarbonitrile
To a suspension of sodium hydride (60%, 18.8 g, 470.08 mmol) in dimethyl sulfoxide (125 mL) was added dropwise a mixture of phenyl acetonitrile (19-01) (25 g, 213.6 mmol) and 1,4-dibromo-butane (20) (25.5 mL, 213.67 mmol) dissolved in dimethyl sulfoxide:ether (300 mL, 1:1). The mixture was stirred at room temperature for 3 h. After completion of the reaction, it was quenched with 1N HCl. The mixture was extracted with ethyl acetate, the separated organic part was dried and concentrated to get a crude product which was purified using normal silica column using 3% ethyl acetate in hexane to of ford 1-phenyl-cyclopentanecarbonitrile (21-01) (34 g, 92.92%) as a yellow liquid.

Preparation of (21-02)

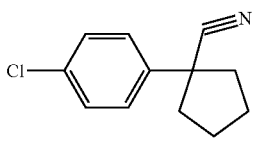

1-(4-chlorophenyl)-cyclopentanecarbonitrile 1-(4-chlorophenyl)-cyclopentanecarbonitrile (21-02) (32.01 g, 94%) was synthesized as a yellow liquid from (4-chlorophenyl)-acetonitrile (19-02) (25 g, 165.56 mmol) and 1,4-dibromo-butane (20) (19.7 mL, 165.56 mmol) following the procedure as described for 1-phenyl-cyclopentanecarbonitrile (21-01).

Preparation of (22-01)

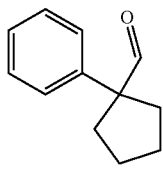 [SMILES: O=CC1(c2ccccc2)CCCC1]

1-Phenyl-cyclopentanecarbaldehyde

To a stirred solution of 1-phenyl-cyclopentanecarbonitrile (21-01) (23 gm, 134.50 mmol) in dichloromethane (270 mL), was added diisobutylaluminium hydride (25% in toluene, 190.9 mL, 336.25 mmol) at −78° C. The mixture was stirred for 2 h. After completion of the reaction, it was quenched with potassium sodium tartrate. The mixture was stirred for 16 h at room temperature, extracted with dichloromethane, washed with water and brine and the separated organic part was dried and evaporated to get 1-phenyl-cyclopentanecarbaldehyde (22-01) (23 g) as a white solid as a crude product. This was directly used for next step.

Preparation of (22-02)

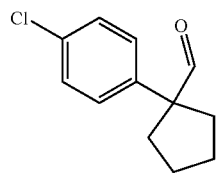 [SMILES: O=CC1(c2ccc(Cl)cc2)CCCC1]

1-(4-chlorophenyl)-cyclopentanecarbaldehyde 1-(4-chlorophenyl)-cyclopentanecarbaldehyde (22-02) (66 g, 98.23%) was synthesized from (4-chlorophenyl)-acetonitrile (21-02) (66 g, 321.95 mmol) as a white solid as a crude product following the procedure as described for 1-phenyl-cyclopentanecarbaldehyde (22-01).

GCMS: 208 (M).

Preparation of (23-01)

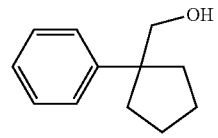 [SMILES: OCC1(c2ccccc2)CCCC1]

(1-Phenyl-cyclopentyl)-methanol

To a stirred solution of 1-phenyl-cyclopentanecarbaldehyde 22-01 (23 g, 132.18 mmol) in methanol (300 mL) was added NaBH$_4$ (10.04 g, 264.36 mmol) at 0° C. The mixture was stirred at room temperature for 16 h. After completion of the reaction, it was quenched with aqueous ammonium chloride solution. The mixture was concentrated as much as possible, then diluted with water, extracted with ethyl acetate and the separated organic part was dried over sodium sulfate and concentrated under reduced pressure to get a crude product which was purified using a normal silica column using 5% ethyl acetate in hexane to of ford (1-phenyl-cyclopentyl)-methanol (23-01) (4.5 g, 19.35%) as a yellow liquid.

Preparation of (23-02)

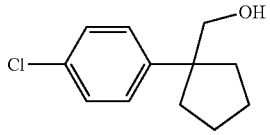 [SMILES: OCC1(c2ccc(Cl)cc2)CCCC1]

[1-(4-chlorophenyl)-cyclopentyl]-methanol

[1-(4-chlorophenyl)-cyclopentyl]-methanol (23-02) (25 g, 37.52%) was synthesized from 1-(4-chlorophenyl)-cyclopentanecarbaldehyde (22-02) (66 g, 317.3 mmol) as a colourless liquid following the procedure as described for (1-phenyl-cyclopentyl)-methanol (23-01).

Preparation of (24-01)

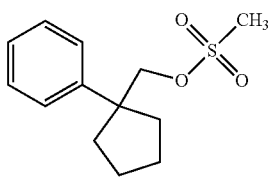 [SMILES: CS(=O)(=O)OCC1(c2ccccc2)CCCC1]

Methanesulfonic acid 1-phenyl-cyclopentylmethyl ester

To a stirred solution of 1-phenyl-cyclopentyl)-methanol (23-01) (9.1 gm, 51.70 mmol) in dichloromethane (100 mL) was added triethyl amine (14.4 mL, 104.96 mmol) followed by methanesulfonyl chloride (5.09 ml, 62.045 mmol) at cooling condition, it was stirred at room temperature for 16 h. After completion of the reaction, the mixture was diluted with dichloromethane, washed with water, sodium bicarbonate solution and brine. The separated organic part was dried over sodium sulfate and evaporated under reduced pressure to get methanesulfonic acid 1-phenyl-cyclopentylmethyl ester (24-01) (13 g) as a crude product.

Preparation of (24-02)

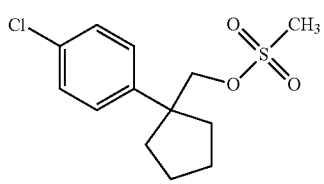 [SMILES: CS(=O)(=O)OCC1(c2ccc(Cl)cc2)CCCC1]

Methanesulfonic acid 1-(4-chlorophenyl)-cyclopentylmethyl ester

Methanesulfonic acid 1-(4-chlorophenyl)-cyclopentylmethyl ester (24-02) (32 g, 93.08%) was synthesized from [1-(4-chlorophenyl)-cyclopentyl]-methanol (23-02) (25 g, 119.04 mmol) as a crude product as a yellow liquid following the procedure as described for methanesulfonic acid 1-phenyl-cyclopentylmethyl ester (24-01).
GC-MS: 185 (M).

Preparation of (25-01)

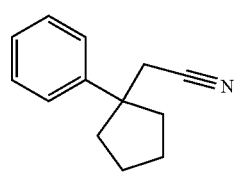 [SMILES: N#CCC1(c2ccccc2)CCCC1]

(1-Phenyl-cyclopentyl)-acetonitrile

To a stirred solution of methanesulfonic acid 1-phenyl-cyclopentylmethyl ester (24-01) (6 g, 23.59 mmol) in dimethyl sulfoxide (18 mL) were added potassium iodide (392 mg, 2.59 mmol) and sodium cyanide (1.734 g, 35.384 mmol). The mixture was stirred for 140° C. for 16 h. After completion of the reaction, water was added and the mixture was filtered through celite. The filtrate was extracted with ethyl acetate, dried and evaporated to get a crude product which was purified using a normal silica column using 15% ethyl acetate in hexane to afford (1-phenyl-cyclopentyl)-acetonitrile (25-01) (2.25 g, 51.4%) as a yellow liquid.
GCMS: 185 (M).

Preparation of (25-02)

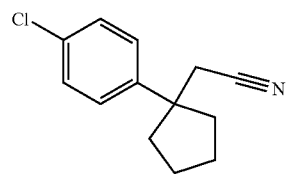 [SMILES: N#CCC1(c2ccc(Cl)cc2)CCCC1]

[1-(4-chlorophenyl)-cyclopentyl]-acetonitrile

[1-(4-chlorophenyl)-cyclopentyl]-acetonitrile (25-02) (12 g, 49.16%) was synthesized from methanesulfonic acid 1-(4-chlorophenyl)-cyclopentylmethyl ester (24-02) (32 g, 111.11 mmol) as a colourless liquid following the procedure as described for 1-phenyl-cyclopentyl)-acetonitrile (25-01).
GCMS: 219 (M).

Preparation of (26-01)

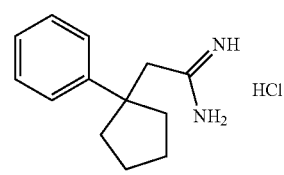 [SMILES: N=C(N)CC1(c2ccccc2)CCCC1 ; Cl]

2-(1-Phenyl-cyclopentyl)-acetamidine HCl salt 2-(1-Phenyl-cyclopentyl)-acetamidine HCl salt (26-01) (4.2 g, 77.7%) was synthesized from (1-phenyl-cyclopentyl)-acetonitrile (25-01) (4.2 g, 22.703 mmol) as a white gummy solid as a crude product following the procedure as described for 2-(2'-chloro-biphenyl-2-yl)-acetamidine hydrochloride salt (5-02).
LC-MS: 203 (M+H).

Preparation of (26-02)

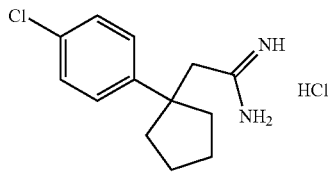 [SMILES: N=C(N)CC1(c2ccc(Cl)cc2)CCCC1 ; Cl]

2-[1-(4-chlorophenyl)-cyclopentyl]-acetamidine HCl salt

2-[1-(4-chlorophenyl)-cyclopentyl]-acetamidine HCl salt (26-02) (6 g, 80.21%) was synthesized from [1-(4-chlorophenyl)-cyclopentyl]-acetonitrile (25-02) (6 g, 27.39 mmol) as a white gummy solid as a crude product following the procedure as described for 2-(2'-chloro-biphenyl-2-yl)-acetamidine hydrochloride salt (5-02).

LC-MS: 236.8 (M+H).

Preparation of (27-01)

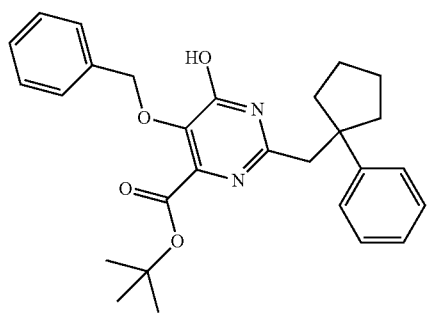 [SMILES: CC(C)(C)OC(=O)c1nc(CC2(c3ccccc3)CCCC2)nc(O)c1OCc1ccccc1]

5-Benzyloxy-6-hydroxy-2-(1-phenyl-cyclopentylmethyl)-pyrimidine-4-carboxylic acid tert-butyl ester 5-Benzyloxy-6-hydroxy-2-(1-phenyl-cyclopentylmethyl)-pyrimidine-4-carboxylic acid tert-butyl ester (27-01) (4.5 g, 51.8%) was synthesized from 2-(1-phenyl-cyclopentyl)-acetamidine HCl salt (26-01) (4.5 g, 18.86 mmol) and (E)-2-benzyloxy-3-hydroxy-but-2-enedioic acid 4-tert-butyl ester 1-methyl ester (4) (10.2 g, 33.41 mmol) as a yellow solid following the procedure as described for 5-benzyloxy-2-biphenyl-2-ylmethyl-6-hydroxypyrimidine-4-carboxylic acid tert-butyl ester (6-01).

LC-MS: 461 (M+H).

Preparation of (27-02)

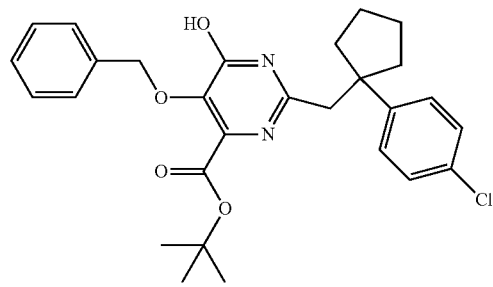 [SMILES: CC(C)(C)OC(=O)c1nc(CC2(c3ccc(Cl)cc3)CCCC2)nc(O)c1OCc1ccccc1]

5-Benzyloxy-2-[1-(4-chlorophenyl)-cyclopentylmethyl]-6-hydroxypyrimidine-4-carboxylic acid tert-butyl ester 5-Benzyloxy-2-[1-(4-chlorophenyl)-cyclopentylmethyl]-6-hydroxypyrimidine-4-carboxylic acid tert-butyl ester (27-02) (12 g, 55%) was synthesized from [1-(4-chlorophenyl)-cyclopentyl]-acetonitrile (26-02) (12 g, 44.03 mmol) and (E)-2-benzyloxy-3-hydroxy-but-2-enedioic acid 4-tert-butyl ester 1-methyl ester (4) (23.49 g, 76.27 mmol) as a yellow solid following the procedure as described for 5-benzyloxy-2-biphenyl-2-ylmethyl-6-hydroxypyrimidine-4-carboxylic acid tert-butyl ester (6-01).

LC-MS: 495.2 (M+H).

Preparation of (28-01)

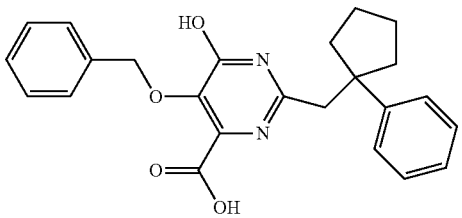 [SMILES: O=C(O)c1nc(CC2(c3ccccc3)CCCC2)nc(O)c1OCc1ccccc1]

5-Benzyloxy-6-hydroxy-2-(1-phenyl-cyclopentylmethyl)-pyrimidine-4-carboxylic acid 5-Benzyloxy-6-hydroxy-2-(1-phenyl-cyclopentylmethyl)-pyrimidine-4-carboxylic acid (28-01) (2.7 g, 68.33%) was synthesized from 5-benzyloxy-6-hydroxy-2-(1-phenyl-cyclopentylmethyl)-pyrimidine-4-carboxylic acid tert-butyl ester (27-01) (4.5 g, 9.77 mmol) as a yellow solid following the procedure as described for 5-benzyloxy-2-biphenyl-2-ylmethyl-6-hydroxypyrimidine-4-carboxylic acid (7-01).

LC-MS: 405.2 (M+H).

Preparation of (28-02)

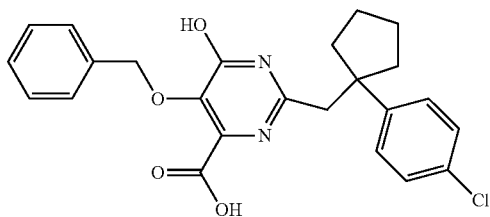 [SMILES: O=C(O)c1nc(CC2(c3ccc(Cl)cc3)CCCC2)nc(O)c1OCc1ccccc1]

5-Benzyloxy-2-[1-(4-chlorophenyl)-cyclopentylmethyl]-6-hydroxypyrimidine-4-carboxylic acid 5-Benzyloxy-2-[1-(4-chlorophenyl)-cyclopentylmethyl]-6-hydroxypyrimidine-4-carboxylic acid (28-02) (7.3 g, 68.6%) was synthesized from 5-benzyloxy-2-[1-(4-chlorophenyl)-cyclopentylmethyl]-6-hydroxypyrimidine-4-carboxylic acid tert-butyl ester (27-02) (12 g, 34.24 mmol) as a white solid following the procedure as described for 5-benzyloxy-2-biphenyl-2-ylmethyl-6-hydroxypyrimidine-4-carboxylic acid (7-01).

LC-MS: 439.2 (M+H).

Preparation of (29-01)

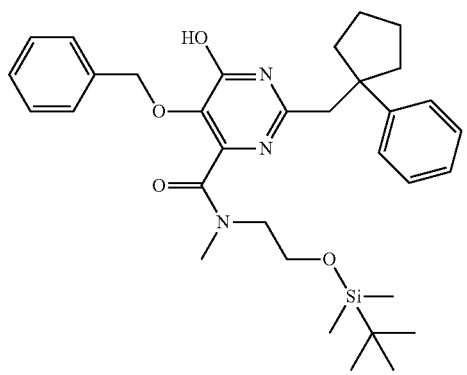 [SMILES: CN(CCO[Si](C)(C)C(C)(C)C)C(=O)c1nc(CC2(c3ccccc3)CCCC2)nc(O)c1OCc1ccccc1]

5-Benzyloxy-6-hydroxy-2-(1-phenyl-cyclopentylmethyl)-pyrimidine-4-carboxylic acid [2-(tert-butyl-dimethylsilanyloxy)-ethyl]-methyl-amide 5-Benzyloxy-6-hydroxy-2-(1-phenyl-cyclopentylmethyl)-pyrimidine-4-carboxylic acid [2-(tert-butyl-dimethylsilanyloxy)-ethyl]-methyl-amide (29-01) (1.05 g, 27.29%) was synthesized from 5-benzyloxy-6-hydroxy-2-(1-phenyl-cyclopentylmethyl)-pyrimidine-4-carboxylic acid (28-01) (2.7 g, 6.683 mmol) and [2-(tert-butyl-dimethylsilanyloxy)-ethyl]-methyl-amine (8-a) (1.38 g, 7.35 mmol) as a yellow gummy liquid following the procedure as described for 5-benzyloxy-2-biphenyl-2-ylmethyl-6-hydroxypyrimidine-4-carboxylic acid [2-(tert-butyl-dimethylsilanyloxy)-ethyl]-methyl-amide (9-01).

LC-MS: 576.2 (M+H).

Preparation of (29-02)

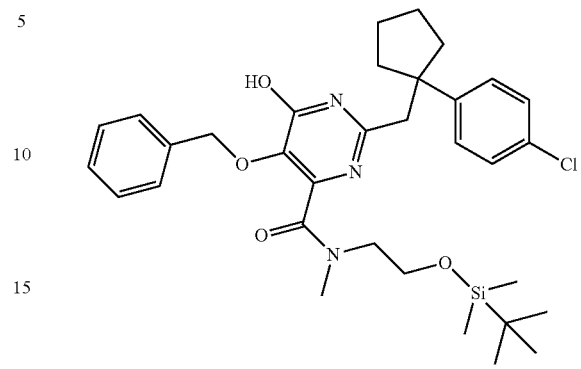

5-Benzyloxy-2-[1-(4-chlorophenyl)-cyclopentylmethyl]-6-hydroxypyrimidine-4-carboxylic acid [2-(tert-butyl-dimethylsilanyloxy)-ethyl]methyl-amide 5-Benzyloxy-2-[1-(4-chlorophenyl)-cyclopentylmethyl]-6-hydroxypyrimidine-4-carboxylic acid [2-(tert-butyl-dimethylsilanyloxy)-ethyl]methyl-amide (29-02) (2 g, 47.85%) was synthesized from 5-benzyloxy-2-[1-(4-chlorophenyl)-cyclopentylmethyl]-6-hydroxypyrimidine-4-carboxylic acid (28-02) (3 g, 6.84 mmol) and [2-(tert-butyl-dimethylsilanyloxy)-ethyl]-methyl-amine (8-a) as a gummy solid (1.4 g, 7.53 mmol) following the procedure as described for 5-benzyloxy-2-biphenyl-2-ylmethyl-6-hydroxypyrimidine-4-carboxylic acid [2-(tert-butyl-dimethylsilanyloxy)-ethyl]-methyl-amide (9-01).

LC-MS: 610.4 (M+H).

Preparation of (29-03)

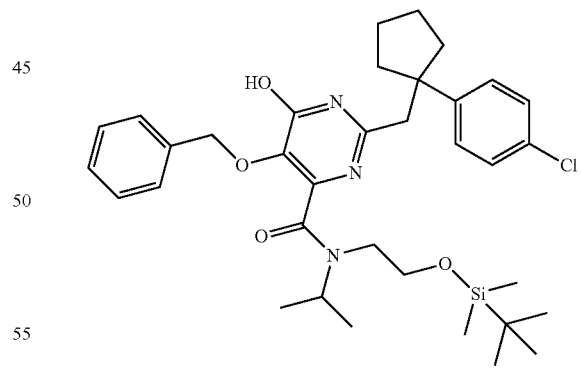

5-Benzyloxy-2-[1-(4-chlorophenyl)-cyclopentylmethyl]-6-hydroxypyrimidine-4-carboxylic acid [2-(tert-butyl-dimethylsilanyloxy)-ethyl]isopropylamide 5-Benzyloxy-2-[1-(4-chlorophenyl)-cyclopentylmethyl]-6-hydroxypyrimidine-4-carboxylic acid [2-(tert-butyl-dimethylsilanyloxy)-ethyl]-isopropylamide (29-03) (3.5 g, 55.85%) was synthesized from 5-benzyloxy-2-[1-(4-chlorophenyl)-cyclopentylmethyl]-6-hydroxypyrimidine-4-carboxylic acid (28-02) (4.3 g, 9.817 mmol) and [2-(tert-butyl-dimethylsilanyloxy)-ethyl]-isopropyl-amine (8-b) (2.34 g, 10.79 mmol) as a colourless gummy solid following the procedure as described for 5-benzyloxy-2-biphenyl-2-ylmethyl-6-hydroxypyrimidine-4-carboxylic acid [2-(tert-butyl-dimethylsilanyloxy)-ethyl]-methyl-amide (9-01).

LC-MS: 638.2 (M+H).

Preparation of (30-01)

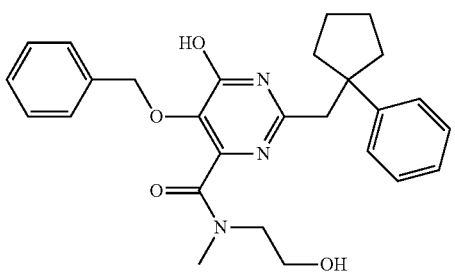 [SMILES: CN(CCO)C(=O)c1nc(CC2(c3ccccc3)CCCC2)nc(O)c1OCc1ccccc1]

5-Benzyloxy-6-hydroxy-2-(1-phenyl-cyclopentylmethyl)-pyrimidine-4-carboxylic acid (2-hydroxyethyl)-methyl-amide 5-Benzyloxy-6-hydroxy-2-(1-phenyl-cyclopentylmethyl)-pyrimidine-4-carboxylic acid (2-hydroxyethyl)-methyl-amide (30-01) (600 mg, 74.75%) was synthesized from 5-benzyloxy-6-hydroxy-2-(1-phenyl-cyclopentylmethyl)-pyrimidine-4-carboxylic acid [2-(tert-butyl-dimethylsilanyloxy)-ethyl]-methyl-amide (29-01) (1.0 g, 1.739 mmol) as a yellow solid following the procedure as described for 5-benzyloxy-2-biphenyl-2-ylmethyl-6-hydroxypyrimidine-4-carboxylic acid (2-hydroxyethyl)-methyl-amide (10-01).

LC-MS: 462.2 (M+H).

Preparation of (30-02)

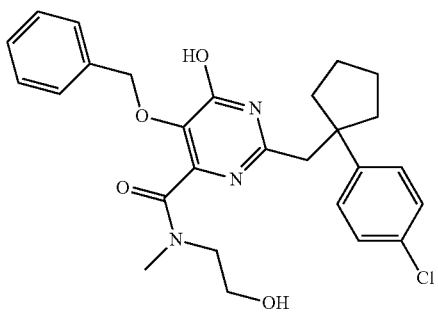 [SMILES: CN(CCO)C(=O)c1nc(CC2(c3ccc(Cl)cc3)CCCC2)nc(O)c1OCc1ccccc1]

5-Benzyloxy-2-[1-(4-chlorophenyl)-cyclopentylmethyl]-6-hydroxypyrimidine-4-carboxylic acid (2-hydroxyethyl)-methyl-amide 5-Benzyloxy-2-[1-(4-chlorophenyl)-cyclopentylmethyl]-6-hydroxypyrimidine-4-carboxylic acid (2-hydroxyethyl)-methyl-amide (30-02) (1.1 g, 67.53%) was synthesized from 5-benzyloxy-2-[1-(4-chlorophenyl)-cyclopentylmethyl]-6-hydroxypyrimidine-4-carboxylic acid [2-(tert-butyl-dimethylsilanyloxy)-ethyl]-methyl-amide (29-02) (2 g, 3.28 mmol) as an off-white solid following the procedure as described for 5-benzyloxy-2-biphenyl-2-ylmethyl-6-hydroxypyrimidine-4-carboxylic acid (2-hydroxyethyl)-methyl-amide (10-01).

LC-MS: 496.2 (M+H).

Preparation of (30-03)

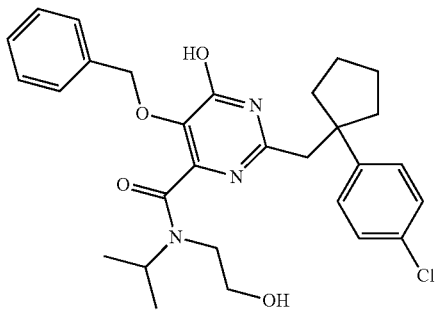 [SMILES: CC(C)N(CCO)C(=O)c1nc(CC2(c3ccc(Cl)cc3)CCCC2)nc(O)c1OCc1ccccc1]

5-Benzyloxy-2-[1-(4-chlorophenyl)-cyclopentylmethyl]-6-hydroxypyrimidine-4-carboxylic acid (2-hydroxyethyl)isopropylamide 5-Benzyloxy-2-[1-(4-chlorophenyl)-cyclopentylmethyl]-6-hydroxypyrimidine-4-carboxylic acid (2-hydroxyethyl)-isopropylamide (30-03) (2 g, 69.57%) was synthesized from 5-benzyloxy-2-[1-(4-chlorophenyl)-cyclopentylmethyl]-6-hydroxypyrimidine-4-carboxylic acid [2-(tert-butyl-dimethylsilanyloxy)-ethyl]-isopropylamide (29-03) (3.5 g, 5.4 mmol) as an off-white solid following the procedure as described for 5-benzyloxy-2-biphenyl-2-ylmethyl-6-hydroxypyrimidine-4-carboxylic acid (2-hydroxyethyl)-methyl-amide (10-01).

LC-MS: 524.4 (M+H).

Preparation of (31-01)

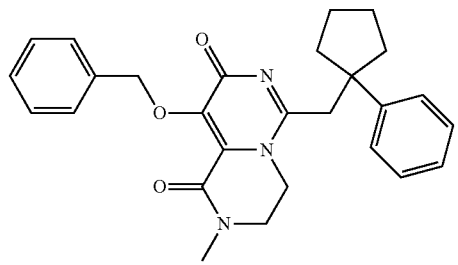 [SMILES: CN1CCn2c(CC3(c4ccccc4)CCCC3)nc(=O)c(OCc3ccccc3)c2C1=O]

9-Benzyloxy-2-methyl-6-(1-phenyl-cyclopentylmethyl)-3,4-dihydro-2H-pyrazino[1,2-c]pyrimidine-1,8-dione 9-Benzyloxy-2-methyl-6-(1-phenyl-cyclopentylmethyl)-3,4-dihydro-2H-pyrazino[1,2-c]pyrimidine-1,8-dione (31-01) (300 mg, 56.69%) was synthesized from 5-benzyloxy-6-hydroxy-2-(1-phenyl-cyclopentylmethyl)-pyrimidine-4-carboxylic acid (2-hydroxyethyl)-methyl-amide (30-01) (550 mg, 1.193 mmol) as a white solid following the procedure as described for 9-benzyloxy-6-biphenyl-2-ylm-ethyl-2-methyl-3,4-dihydro-2H-pyrazino[1,2-c]pyrimidine-1,8-dione (11-01).
LC-MS: 444.2 (M+H).

Preparation of (31-02)

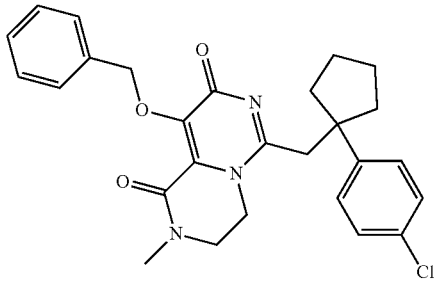 [SMILES: CN1CCn2c(CC3(c4ccc(Cl)cc4)CCCC3)nc(=O)c(OCc3ccccc3)c2C1=O]

9-Benzyloxy-6-[1-(4-chlorophenyl)-cyclopentylm-ethyl]-2-methyl-3,4-dihydro-2H-pyrazino[1,2-c]pyrimidine-1,8-dione 9-Benzyloxy-6-[1-(4-chlorophenyl)-cyclopentylmethyl]-2-methyl-3,4-dihydro-2H-pyrazino[1,2-c]pyrimidine-1,8-dione (31-02) (500 mg, 51.88%) was synthesized from 5-benzyloxy-2-[1-(4-chlorophenyl)-cyclopentylmethyl]-6-hydroxypyrimidine-4-carboxylic acid (2-hydroxyethyl)-methyl-amide (30-02) (1 g, 2.016 mmol) as an off-white solid following the procedure as described for 9-benzyloxy-6-biphenyl-2-ylmethyl-2-methyl-3,4-dihydro-2H-pyrazino[1,2-c]pyrimidine-1,8-dione (11-01).
LC-MS: 478.2 (M+H).

Preparation of (31-03)

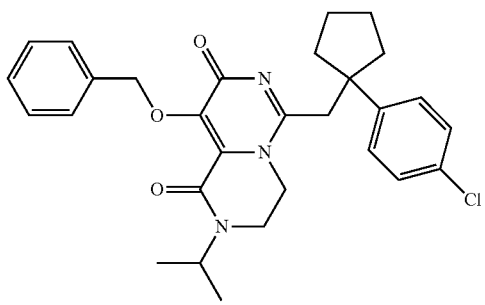 [SMILES: CC(C)N1CCn2c(CC3(c4ccc(Cl)cc4)CCCC3)nc(=O)c(OCc3ccccc3)c2C1=O]

9-Benzyloxy-6-[1-(4-chlorophenyl)-cyclopentylm-ethyl]-2-isopropyl-3,4-dihydro-2H-pyrazino[1,2-c]pyrimidine-1,8-dione 9-Benzyloxy-6-[1-(4-chlorophenyl)-cyclopentylmethyl]-2-isopropyl-3,4-dihydro-2H-pyrazino[1,2-c]pyrimidine-1,8-dione 31-03 (900 mg, 46.51%) was synthesized from 5-benzyloxy-2-[1-(4-chlorophenyl)-cyclopentylmethyl]-6-hydroxypyrimidine-4-carboxylic acid (2-hydroxyethyl)-isopropylamide (30-03) (2 g, 3.824 mmol) as a white solid following the procedure as described for 9-benzyloxy-6-biphenyl-2-ylmethyl-2-methyl-3,4-dihydro-2H-pyrazino[1,2-c]pyrimidine-1,8-dione (11-01)
LC-MS: 506.2 (M+H). .

Preparation of (32-01)

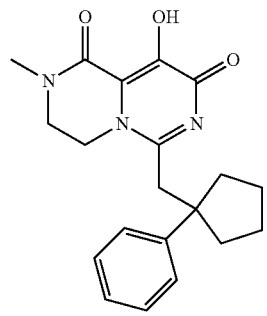 [SMILES: CN1CCn2c(CC3(c4ccccc4)CCCC3)nc(=O)c(O)c2C1=O]

9-Hydroxy-2-methyl-6-(1-phenyl-cyclopentylm-ethyl)-3,4-dihydro-2H-pyrazino[1,2-c]pyrimidine-1,8-dione 9-Hydroxy-2-methyl-6-(1-phenyl-cyclopentylmethyl)-3,4-dihydro-2H-pyrazino[1,2-c]pyrimidine-1,8-dione (32-01) (164 mg, 69%) was synthesized from 9-benzyloxy-2-methyl-6-(1-phenyl-cyclopentylmethyl)-3,4-dihydro-2H-pyrazino[1,2-c]pyrimidine-1,8-dione (31-01) (300 mg, 0.67 mmol) as an off-white solid following the procedure as described for 6-biphenyl-2-ylmethyl-9-hydroxy-2-methyl-3,4-dihydro-2H-pyrazino[1,2-c]pyrimidine-1,8-dione (12-01).
LC-MS: 354 (M+H).

Preparation of (32-02)

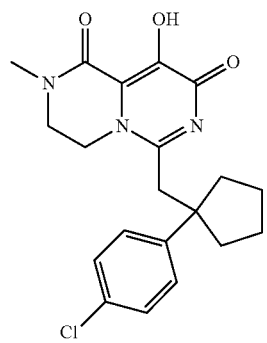 [SMILES: CN1CCn2c(CC3(c4ccc(Cl)cc4)CCCC3)nc(=O)c(O)c2C1=O]

6-[1-(4-chlorophenyl)-cyclopentylmethyl]-9-hy-droxy-2-methyl-3,4-dihydro-2H-pyrazino[1,2-c]pyrimidine-1,8-dione 6-[1-(4-chlorophenyl)-cyclopentylmethyl]-9-hydroxy-2-methyl-3,4-dihydro-2H-pyrazino[1,2-c]pyrimidine-1,8-dione (32-02) (296 mg, 66.3%) was synthesized from 9-benzyloxy-6-[1-(4-chlorophenyl)cyclopentylmethyl]-2-methyl-3,4-dihydro-2H-pyrazino[1,2-c]pyrimidine-1,8-dione (31-02) (500 mg, 1.151 mmol) as an off-white solid following the procedure as described for 6-biphenyl-2-ylmethyl-9-hydroxy-2-methyl-3,4-dihydro-2H-pyrazino[1,2-c]pyrimidine-1,8-dione (12-01).
LC-MS: 388.2 (M+H).

Preparation of (32-03)

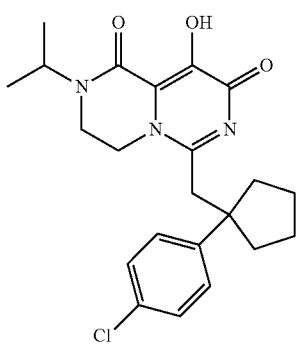

6-[1-(4-chlorophenyl)-cyclopentylmethyl]-9-hydroxy-2-isopropyl-3,4-dihydro-2H-pyrazino[1,2-c]pyrimidine-1,8-dione 6-[1-(4-chlorophenyl)-cyclopentylmethyl]-9-hydroxy-2-isopropyl-3,4-dihydro-2H-pyrazino[1,2-c]pyrimidine-1,8-dione (32-03) (465 mg, 62.8%) was synthesized from 9-benzyloxy-6-[1-(4-chlorophenyl)-cyclopentylmethyl]-2-isopropyl-3,4-dihydro-2H-pyrazino[1,2-c]pyrimidine-1,8-dione (31-03) (900 mg, 1.779 mmol) as an off-white solid following the procedure as described for 6-biphenyl-2-ylmethyl-9-hydroxy-2-methyl-3,4-dihydro-2H-pyrazino[1,2-c]pyrimidine-1,8-dione (12-01).

LC-MS: 416 (M+H).

Synthesis of 32-04

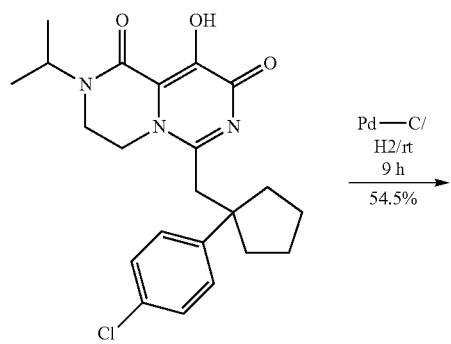

Scheme 6

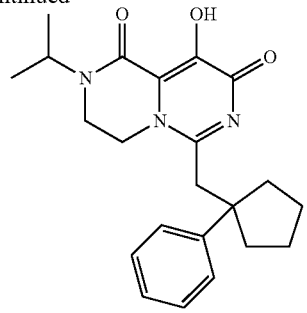

32-04

Experimental

Preparation of (32-04)

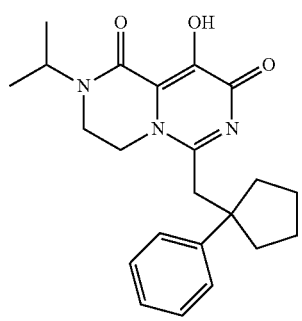 [SMILES: CC(C)N1CCn2c(CC3(c4ccccc4)CCCC3)nc(=O)c(O)c2C1=O]

9-Hydroxy-2-isopropyl-6-(1-phenyl-cyclopentylmethyl)-3,4-dihydro-2H-pyrazino[1,2-c]pyrimidine-1,8-dione To a stirred solution of 6-[1-(4-chlorophenyl)-cyclopentylmethyl]-9-hydroxy-2-isopropyl-3,4-dihydro-2H-pyrazino[1,2-c]pyrimidine-1,8-dione (32-03) (350 mg, 0.842 mmol) was added 35 mg 10% Pd—C. Hydrogenation was conducted by balloon pressure at room temperature for 9 h. After completion of the reaction, the mixture was filtered over a celite bed, which was washed with methanol, followed by 10% methanol in dichloromethane. The filtrate was concentrated to a pasty mass, which was washed with ether, followed by pentane to get 9-hydroxy-2-isopropyl-6-(1-phenyl-cyclopentylmethyl)-3,4-dihydro-2H-pyrazino[1,2-c]pyrimidine-1,8-dione (32-04) (175 mg, 54.5%) as a yellow solid.

LC-MS: 382 (M+H).

Preparation of (38)

6-((1-(4-Chlorophenyl)cyclopentyl)methyl)-9-hydroxy-2-(1-phenylethyl)-3,4-dihydro-1H-pyrazino[1,2-c]pyrimidine-1,8(2H)-dione (38)

The synthetic procedure used in this preparation is outlined in Scheme 7

Scheme 7

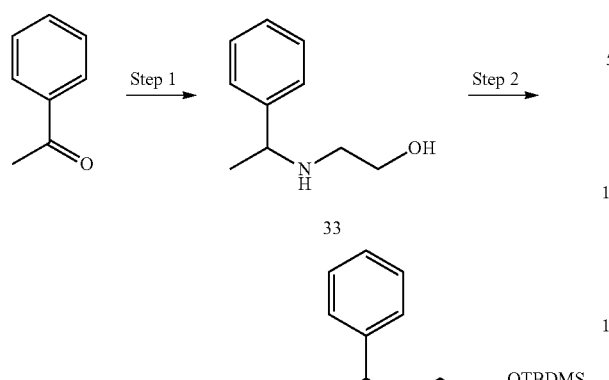

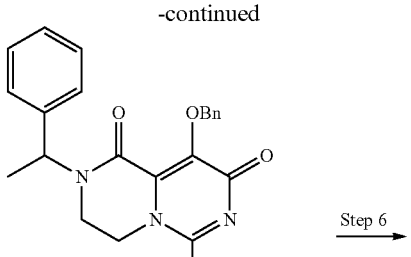

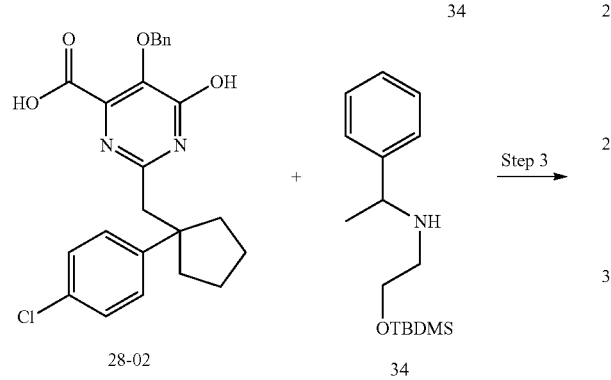

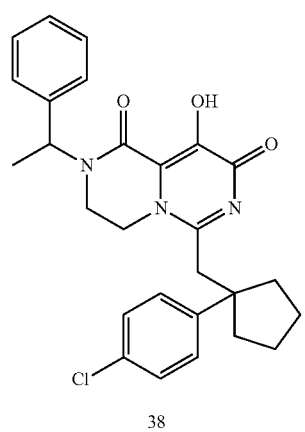

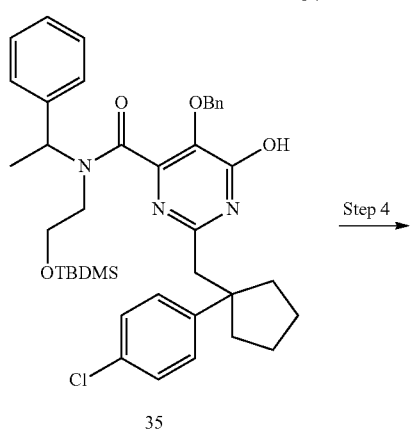

Preparation of (33)

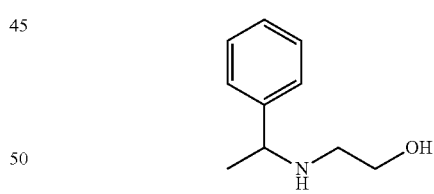

Step 1: 2-(1-phenylethylamino)ethanol

A mixture of acetophenone (2.00 g, 16.6 mmol, Eq: 1.00), 2-aminoethanol (3.05 g, 49.9 mmol, Eq: 3.00) and titanium (IV) isopropoxide (6.15 g, 6.41 ml, 21.6 mmol, Eq: 1.3) in absolute methanol (25 ml) was stirred under nitrogen at room temperature for 48 hrs. Sodium borohydride (630 mg, 16.6 mmol, Eq: 1.00) was then added at 0° C. and the resulting mixture was stirred for an additional 2 hr. The reaction was then quenched by adding water (1 ml). Stirring was continued at room temperature for 20 min., then the reaction mixture was acidified with 1N HCl. After filtration over a pad of Celite, washing with ethyl acetate, any drying over magnesium sulfate, the mixture was concentrated to obtain 2-(1-phenylethylamino)ethanol (oil, 2.71 g, 16.4 mmol, 98.5% yield).

Preparation of (34)

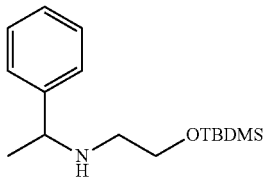 [SMILES: CC(NCCO[Si](C)(C)C(C)(C)C)c1ccccc1]

Step 2: 2-(tert-Butyldimethylsilyloxy)-N-(1-phenylethyl)ethanamine

To a stirred solution of 2-(1-phenylethylamino)ethanol (33) (2.71 g, 16.4 mmol, Eq: 1.00) in dichloromethane (60 ml) were added diisopropylethylamine (2.97 g, 4.01 ml, 23.0 mmol, Eq: 1.4) followed by tert-butyldimethylsilyl chloride (2.72 g, 18.0 mmol, Eq: 1.1) at room temperature under nitrogen atmosphere. The resulting solution was stirred for 16 hrs and then it was poured into water (200 ml). The organic layer was separated, washed with brine, and dried with MgSO$_4$, concentrated, and chromatographed (silica gel, gradient 0 to 10% ethyl acetate-hexane) to obtain 2-(tert-butyldimethylsilyloxy)-N-(1-phenylethyl)ethanamine (34) (oil, 3.75 g, 13.4 mmol, 81.8% yield).

Preparation of (35)

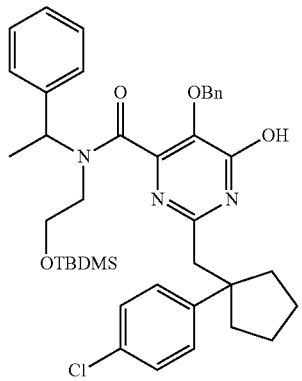 [SMILES: CC(c1ccccc1)N(CCO[Si](C)(C)C(C)(C)C)C(=O)c1nc(CC2(c3ccc(Cl)cc3)CCCC2)nc(O)c1OCc1ccccc1]

Step 3: 5-(Benzyloxy)-N-(2-(tert-butyldimethylsilyloxy)ethyl)-2-(1-(4-chlorophenyl)cyclopentyl)-methyl)-6-hydroxy-N-(1-phenylethyl)pyrimidine-4-carboxamide To a solution of 5-(benzyloxy)-2-((1-(4-chlorophenyl)cyclopentyl)methyl)-6-hydroxypyrimidine-4-carboxylic acid (28-02) (170 mg, 387 µmol, Eq: 1.00) and 2-(tert-butyldimethylsilyloxy)-N-(1-phenylethyl)ethanamine (34) (108 mg, 387 µmol, Eq: 1.00) in pyridine (2.00 ml) was added POCl$_3$ (178 mg, 108 µl, 1.16 mmol, Eq: 3.00) at −10° C. (ethylene glycol-dry-ice bath), then the reaction mixture was stirred at 0° C. for 2 hr. The reaction mixture was quenched with ice cooled-water (0.5 ml), concentrated, and chromatographed (silica gel, gradient 5 to 30% ethyl acetate-hexane) to obtain 5-(benzyloxy)-N-(2-(tert-butyldimethylsilyloxy)ethyl)-2-((1-(4-chlorophenyl)cyclopentyl)methyl)-6-hydroxy-N-(1-phenylethyl)pyrimidine-4-carboxamide (35) (220 mg, 314 µmol, 81.1% yield).

LC/MS: (M+H)$^+$=701.

Preparation of (36)

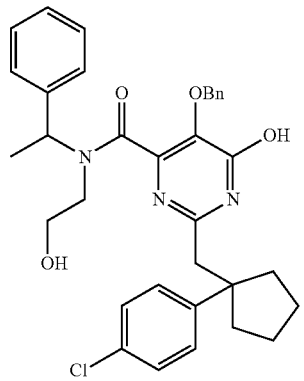 [SMILES: CC(c1ccccc1)N(CCO)C(=O)c1nc(CC2(c3ccc(Cl)cc3)CCCC2)nc(O)c1OCc1ccccc1]

Step 4: 5-(Benzyloxy)-2-((1-(4-chlorophenyl)cyclopentyl)methyl)-6-hydroxy-N-(2-hydroxyethyl)-N-(1-phenylethyl)pyrimidine-4-carboxamide To a stirred solution of 5-(benzyloxy)-N-(2-(tert-butyldimethylsilyloxy)ethyl)-2-((1-(4-chlorophenyl)cyclopentyl)methyl)-6-hydroxy-N-(1-phenylethyl)pyrimidine-4-carboxamide (35) (220 mg, 314 µmol, Eq: 1.00) in tetrahydrofuran (5 ml) was added HCl (1N) (471 µl, 471 µmol, Eq: 1.5) at room temperature. The reaction mixture was stirred for 6 hrs, neutralized with 1N NaOH aq. solution, extracted with ethyl acetate, dried (MgSO$_4$), concentrated and chromatographed (silica gel, gradient, 0 to 5% methanol-dichloromethane) to obtain 5-(benzyloxy)-2-((1-(4-chlorophenyl)cyclopentyl)methyl)-6-hydroxy-N-(2-hydroxyethyl)-N-(1-phenylethyl)pyrimidine-4-carboxamide (36) (white foam, 161.2 mg, 275 µmol, 87.6% yield).

LC/MS: (M+H)$^+$=587

Preparation of (37)

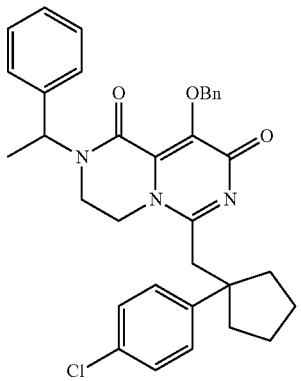 [SMILES: CC(c1ccccc1)N1CCn2c(CC3(c4ccc(Cl)cc4)CCCC3)nc(=O)c(O)c2C1=O]

Step 5: 9-(Benzyloxy)-6-((1-(4-chlorophenyl)cyclopentyl)methyl)-2-(1-phenylethyl)-3,4-dihydro-1H-pyrazino[1,2-c]pyrimidine-1,8(2H)-dione To a stirred solution of 5-(benzyloxy)-2-((1-(4-chlorophenyl)cyclopentyl)methyl)-6-hydroxy-N-(2-hydroxyethyl)-N-(1-phenylethyl)pyrimidine-4-carboxamide (36) (158 mg, 270 µmol, Eq: 1.00) in dichloromethane (15 ml) at room temperature was added triphenylphosphine (106 mg, 404 µmol, Eq: 1.5). The reaction mixture was stirred for 10 min. Then diisopropyl azodicarboxylate (81.8 mg, 78.6 µl, 404 µmol, Eq: 1.5) was added. The reaction mixture was stirred for 18 hrs, concentrated, and chromatographed (silica gel, gradient 0 to 5% methanol-dichloromethane) to obtain 9-(benzyloxy)-6-((1-(4-chlorophenyl)cyclopentyl)methyl)-2-(1-phenylethyl)-3,4-dihydro-1H-pyrazino[1,2-c]pyrimidine-1,8(2H)-dione (37) (colorless of 1,120 mg, 211 µmol, 78.4% yield).

LC/MS: $(M+H)^+=569$.

Preparation of (38)

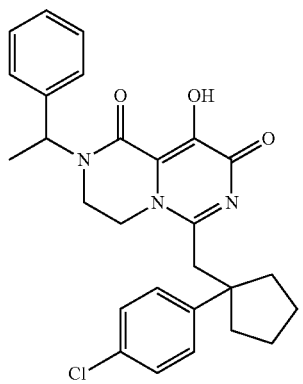

Step 6: 6-((1-(4-Chlorophenyl)cyclopentyl)methyl)-9-hydroxy-2-(1-phenylethyl)-3,4-dihydro-1H-pyrazino[1,2-c]pyrimidine-1,8(2H)-dione To a stirred solution of 9-(benzyloxy)-6-((1-(4-chlorophenyl)cyclopentyl)methyl)-2-(1-phenylethyl)-3,4-dihydro-1H-pyrazino[1,2-c]pyrimidine-1,8(2H)-dione (37) (76 mg, 134 µmol, Eq: 1.00) in methanol (5 ml) was added HCl (conc) (195 mg, 163 µl, 5.35 mmol, Eq: 40) and the reaction mixture was heated at 70° C. for 48 hrs. The reaction mixture was neutralized with saturated aqueous NaHCO₃ solution, extracted with dichloromethane, dried (MgSO₄), concentrated, and chromatographed (silica gel, gradient 0 to 5% methanol-dichloromethane) to obtain an off-white solid. The solid was triturated with diethyl ether, filtered, and dried to obtain 6-((1-(4-chlorophenyl)cyclopentyl)methyl)-9-hydroxy-2-(1-phenylethyl)-3,4-dihydro-1H-pyrazino[1,2-c]pyrimidine-1,8(2H)-dione (38) (off-white powder, 51 mg, 107 µmol, 79.8% yield).

LC/MS: $(M+H)^+=478$ $^1$H NMR (300 MHz, dimethyl sulfoxide-$d_6$) δ ppm 1.47 (d, J=6.22 Hz, 4H) 1.59 (br. s., 3H) 1.78 (br. s., 4H) 1.98 (s, 1H) 2.26 (br. s., 3H) 2.67 (br. s., 1H) 2.85 (br. s., 2H) 2.99 (d, J=11.87 Hz, 1H) 3.19 (br. s., 1H) 3.59 (br. s., 1H) 5.70 (d, J=6.40 Hz, 1H) 7.08-7.54 (m, 9H) 12.19 (br. s., 1H).

Preparation of (45)

6-((1-(4-Chlorophenyl)cyclopentyl)methyl)-9-hydroxy-2-(1,1,1-trifluoropropan-2-yl)-3,4-dihydro-1H-pyrazino[1,2-c]pyrimidine-1,8(2H)-dione (45)

The synthetic procedure used in this preparation is outlined in Scheme 8

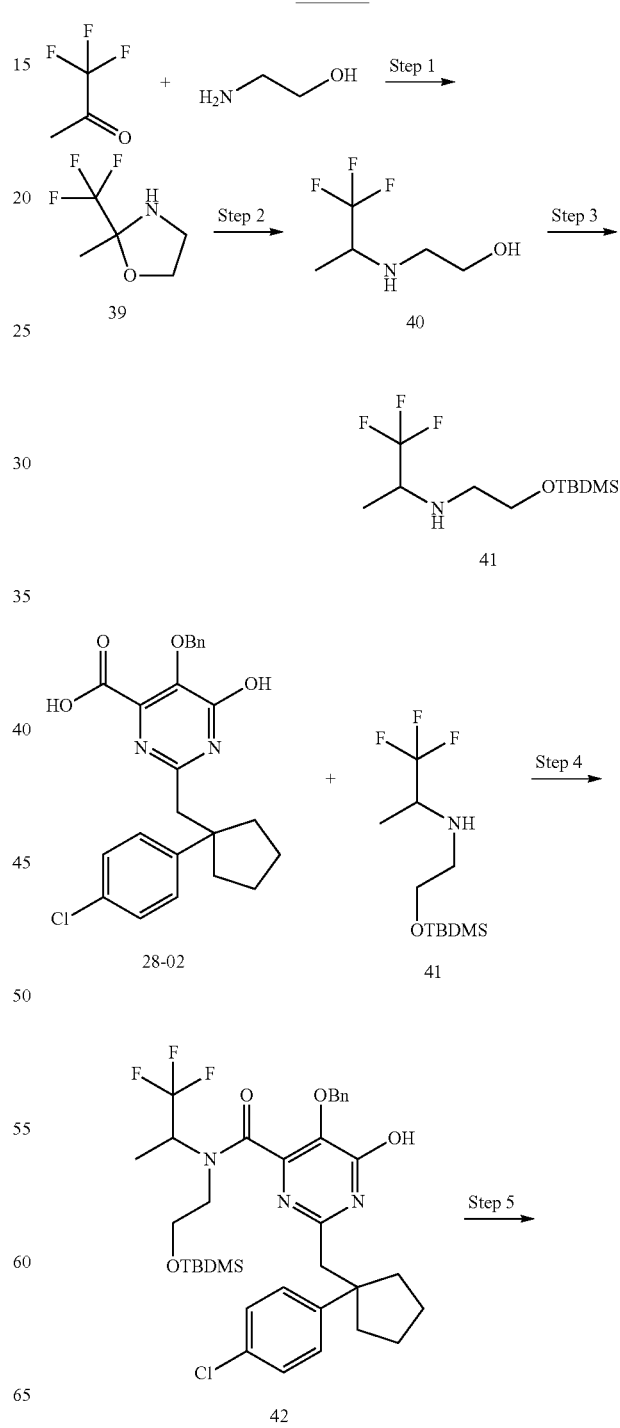

-continued

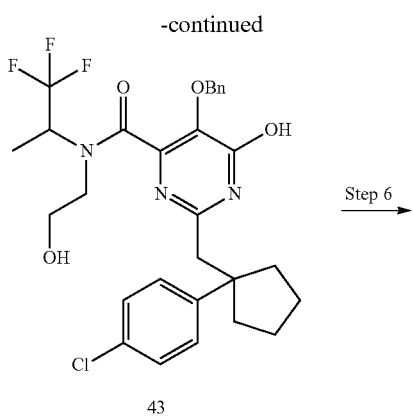

Preparation of (39)

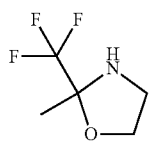

Step 1: 2-Methyl-2-(trifluoromethyl)oxazolidine

A solution of 2-aminoethanol (10.15 g, 10.0 ml, 166 mmol, Eq: 1.00) in dichloromethane (250 ml) was cooled to −30° C. and stirred while 1,1,1-trifluoropropan-2-one (20.1 g, 16.1 ml, 179 mmol, Eq: 1.08), followed by molecular sieves (4 Å, powder <5 micron, activated; 20.0 g, 166 mmol, Eq: 1.00) were added. The mixture was stirred at −30° C. for 3 h and then allowed to warm to room temperature and left stirring for overnight. The mixture was filtered, washed with dichloromethane, and concentrated to obtain 2-methyl-2-(trifluoromethyl)oxazolidine (39) (oil, 15.60 g, 101 mmol, 60.5% yield).

Preparation of (40)

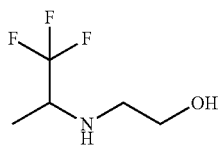

Step 2: 2-(1,1,1-Trifluoropropan-2-ylamino)ethanol

To a solution of 2-methyl-2-(trifluoromethyl)oxazolidine (39) (5.58 g, 36.0 mmol, Eq: 1.00) in tetrahydrofuran (30 ml) at 0° C. was added lithium aluminum hydride (2M solution in tetrahydrofuran) (18.0 ml, 36.0 mmol, Eq: 1.00) and the reaction mixture was stirred at room temperature for 1 hr, quenched slowly with 1 ml of cold water, stirred for 20 min. Then 1 ml of 1N NaOH aq. solution was added and the reaction mixture was stirred for 10 m in. 3 ml of water were added and the reaction mixture was stirred for 1 hr. Granular salt was formed. The white solid was filtered off, washed with diethyl ether (100 ml). The mixture was concentrated to obtain a crude product 2-(1,1,1-trifluoropropan-2-ylamino)ethanol (40) (oil, 5.50 g, 35.0 mmol, 97.3% yield) which was used as such in the next step.

Preparation of (41)

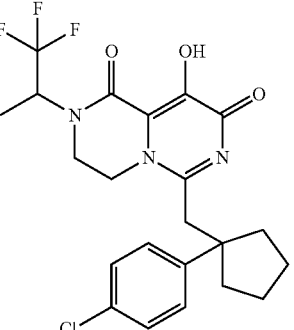

Step 3: N-(2-(tert-Butyldimethylsilyloxy)ethyl)-1,1,1-trifluoropropan-2-amine

To a stirred solution of 2-(1,1,1-trifluoropropan-2-ylamino)ethanol (40) (5.50 g, 35.0 mmol, Eq: 1.00) in dichloromethane (100 ml) were added diisopropylethylamine (6.33 g, 8.56 ml, 49.0 mmol, Eq: 1.4) followed by tert-butyldimethylsilyl chloride (5.8 g, 38.5 mmol, Eq: 1.1) at room temperature under a nitrogen atmosphere. The resulting solution was stirred for 16 hrs and then it was poured into water (100 ml) and the organic layer was separated, washed with brine, dried (MgSO₄), concentrated, and chromatographed (silica gel, gradient 0 to 10% ethyl acetate-hexane) to obtain N-(2-

(tert-butyldimethylsilyloxy)ethyl)-1,1,1-trifluoropropan-2-amine (41) (oil, 3.52 g, 13.0 mmol, 37.1% yield).

Preparation of (42)

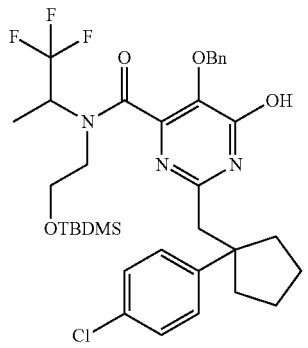 [SMILES: CC(N(CCO[Si](C)(C)C(C)(C)C)C(=O)c1nc(CC2(c3ccc(Cl)cc3)CCCC2)nc(O)c1OCc1ccccc1)C(F)(F)F]

Step 4: 5-(Benzyloxy)-N-(2-(tert-butyldimethylsilyloxy)ethyl)-2-((1-(4-chlorophenyl)cyclopentyl)-methyl)-6-hydroxy-N-(1,1,1-trifluoropropan-2-yl)pyrimidine-4-carboxamide To a solution of 5-(benzyloxy)-2-((1-(4-chlorophenyl)cyclopentyl)methyl)-6-hydroxypyrimidine-4-carboxylic acid (28-02) (150 mg, 342 μmol, Eq: 1.00) and N-(2-(tert-butyldimethylsilyloxy)ethyl)-1,1,1-trifluoropropan-2-amine (41) (102 mg, 376 μmol, Eq: 1.1) in pyridine (1.5 ml) was added POCl$_3$ (157 mg, 95.6 μl, 1.03 mmol, Eq: 3.00) at −10° C. (ethylene glycol-dry-ice bath), then the reaction mixture was stirred at 0° C. for 2 hr. Ice cooled-water was slowly added to the reaction mixture at 0° C., which was extracted with ethyl acetate. The organic layer was washed with aqueous saturated NaHCO$_3$ solution, dried (MgSO$_4$), concentrated, and chromatographed (silica gel, gradient 5 to 50% ethyl acetate-hexane) to obtain 5-(benzyloxy)-N-(2-(tert-butyldimethylsilyloxy)ethyl)-2-((1-(4-chlorophenyl)cyclopentyl)methyl)-6-hydroxy-N-(1,1,1-trifluoropropan-2-yl)pyrimidine-4-carboxamide (42) (oil, 138 mg, 199 μmol, 58.3% yield).

LC/MS: (M+H)$^+$=693.

Preparation of (43)

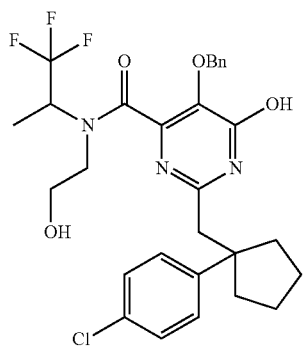 [SMILES: CC(N(CCO)C(=O)c1nc(CC2(c3ccc(Cl)cc3)CCCC2)nc(O)c1OCc1ccccc1)C(F)(F)F]

Step 5: 5-(Benzyloxy)-2-((1-(4-chlorophenyl)cyclopentyl)methyl)-6-hydroxy-N-(2-hydroxyethyl)-N-(1,1,1-trifluoropropan-2-yl)pyrimidine-4-carboxamide To a stirred solution of 5-(benzyloxy)-N-(2-(tert-butyldimethylsilyloxy)ethyl)-2-((1-(4-chlorophenyl)cyclopentyl)methyl)-6-hydroxy-N-(1,1,1-trifluoropropan-2-yl)pyrimidine-4-carboxamide (42) (138 mg, 199 μmol, Eq: 1.00) in tetrahydrofuran (5 ml) was added HCl (1N) (299 μl, 299 μmol, Eq: 1.5) at room temperature and the reaction mixture was stirred for 4 hrs, neutralized with aqueous 1N NaoH solution, extracted with ethyl acetate, dried (MgSO$_4$), concentrated, and chromatographed (silica gel, gradient, 0 to 5% methanol-dichloromethane) to obtain 5-(benzyloxy)-2-((1-(4-chlorophenyl)cyclopentyl)methyl)-6-hydroxy-N-(2-hydroxyethyl)-N-(1,1,1-trifluoropropan-2-yl)pyrimidine-4-carboxamide (43) (white foam, 102 mg, 176 μmol, 88.5% yield).

LC/MS: (M+H)$^+$=579

Preparation of (44)

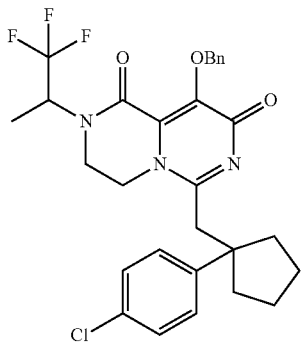

Step 6: 9-(Benzyloxy)-6-((1-(4-chlorophenyl)cyclopentyl)methyl)-2-(1,1,1-trifluoropropan-2-yl)-3,4-dihydro-1H-pyrazino[1,2-c]pyrimidine-1,8(2H)-dione To a stirred solution of 5-(benzyloxy)-2-((1-(4-chlorophenyl)cyclopentyl)methyl)-6-hydroxy-N-(2-hydroxyethyl)-N-(1,1,1-trifluoropropan-2-yl)pyrimidine-4-carboxamide (43) (102 mg, 176 μmol, Eq: 1.00) in dichloromethane (5 ml) was added triphenylphosphine (69.4 mg, 265 μmol, Eq: 1.5) at room temperature and the reaction mixture was stirred for 10 min. Then diisopropyl azodicarboxylate (53.5 mg, 51.5 μl, 265 μmol, Eq: 1.5) was added and the reaction mixture was stirred for 18 hrs at room temperature, concentrated, and chromatographed (silica gel, gradient, 0 to 5% methanol-dichloromethane) to obtain 9-(benzyloxy)-6-((1-(4-chlorophenyl)cyclopentyl)methyl)-2-(1,1,1-trifluoropropan-2-yl)-3,4-dihydro-1H-pyrazino[1,2-c]pyrimidine-1,8(2H)-dione (44) (white foam, 90.8 mg, 162 μmol, 91.9% yield)

LC/MS: (M+H)$^+$=561.

Preparation of (45)

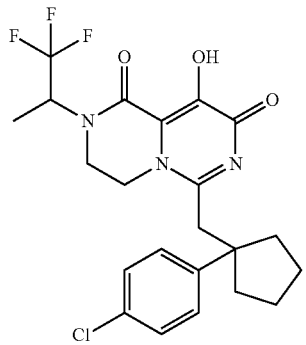 [SMILES: CC(N1CCn2c(CC3(c4ccc(Cl)cc4)CCCC3)nc(=O)c(O)c2C1=O)C(F)(F)F]

Step 7: 6-((1-(4-Chlorophenyl)cyclopentyl)methyl)-9-hydroxy-2-(1,1,1-trifluoropropan-2-yl)-3,4-dihydro-1H-pyrazino[1,2-c]pyrimidine-1,8(2H)-dione To a stirred solution of 9-(benzyloxy)-6-((1-(4-chlorophenyl)cyclopentyl)methyl)-2-(1,1,1-trifluoropropan-2-yl)-3,4-dihydro-1H-pyrazino[1,2-c]pyrimidine-1,8(2H)-dione (44) (90.8 mg, 162 μmol, Eq: 1.00) in methanol (5 ml) was added HCl (conc) (240 mg, 0.2 ml, 6.58 mmol, Eq: 40.6) and the reaction mixture was heated at 70° C. for 18 hrs. The reaction mixture was neutralized with saturated aqueous NaHCO$_3$ solution, extracted with dichloromethane, dried (MgSO$_4$), concentrated, triturated with diethyl ether, filtered, and dried to obtain 6-((1-(4-chlorophenyl)cyclopentyl)methyl)-9-hydroxy-2-(1,1,1-trifluoropropan-2-yl)-3,4-dihydro-1H-pyrazino[1,2-c]pyrimidine-1,8(2H)-dione (45) (pink powder, 40.1 mg, 85.3 μmol, 52.6% yield).

LC/MS: (M+H)$^+$=470.

$^1$H NMR (400 MHz, dimethyl sulfoxide-d$_6$) ppm 1.36 (d, J=7.03 Hz, 3H) 1.62 (br. s., 2H) 1.74-1.97 (m, 4H) 2.19-2.39 (m, 2H) 2.83-3.03 (m, 3H) 3.19-3.29 (m, 1H) 3.65-3.77 (m, 1H) 5.24 (dt, J=15.25, 7.56 Hz, 1H) 7.13-7.42 (m, 4H) 11.53 (br. s., 1H).

Preparation of (50)

6-((1-(4-Chlorophenyl)cyclopentyl)methyl)-9-hydroxy-2-phenyl-3,4-dihydro-1H-pyrazino[1,2-c]pyrimidine-1,8(2H)-dione (50)

The synthetic procedure used in this preparation is outlined in Scheme 9

Scheme 9

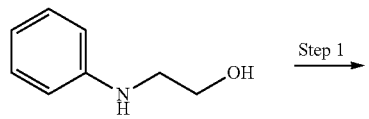

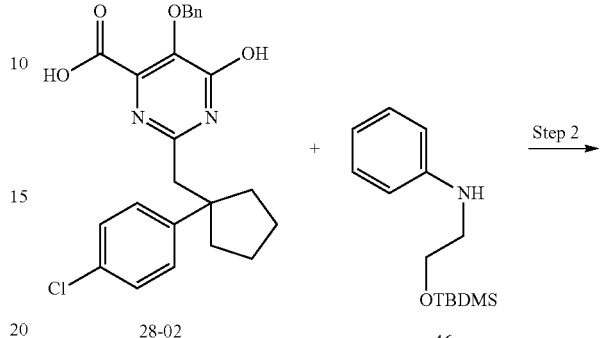

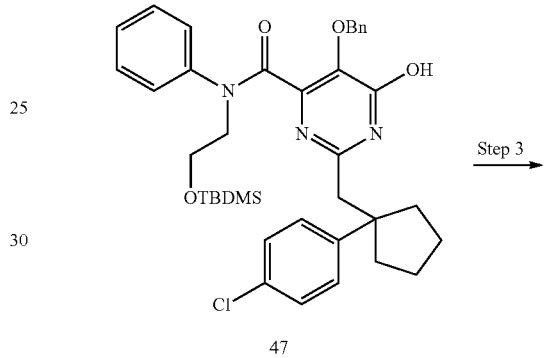

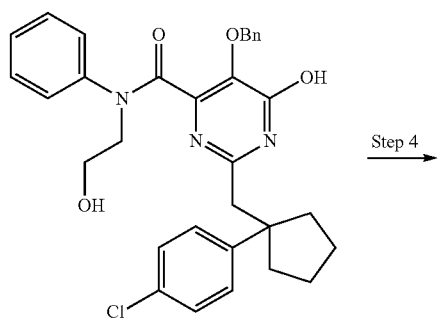

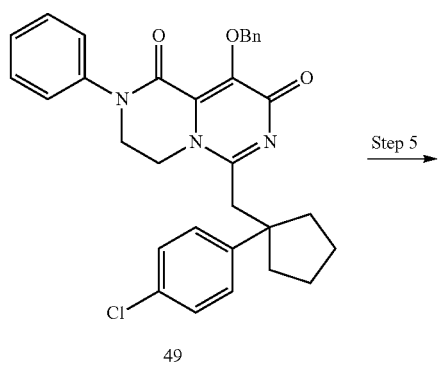

-continued

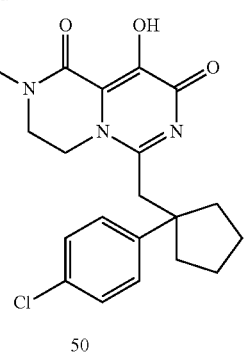

(50)

Preparation of (46)

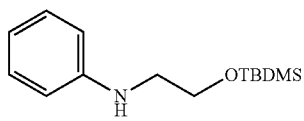 [SMILES: CC(C)(C)[Si](C)(C)OCCNc1ccccc1]

Step 1
N-(2-(tert-Butyldimethylsilyloxy)ethyl)aniline

To a stirred solution of 2-(phenylamino)ethanol (10 g, 72.9 mmol, Eq: 1.00) in dichloromethane (200 ml) were added diisopropylethylamine (13.2 g, 17.8 ml, 102 mmol, Eq: 1.4) followed by tert-butyldimethylsilyl chloride (11.0 g, 72.9 mmol, Eq: 1.00) at room temperature under a nitrogen atmosphere. The resulting solution was stirred for 16 hrs and then it was poured into water (200 ml) and the organic layer was separated, washed with brine, dried (MgSO$_4$), concentrated, and chromatographed (silica gel, gradient 0 to 10% ethyl acetate-hexane) to obtain N-(2-(tert-butyldimethylsilyloxy)ethyl)aniline (46) (8.45 g, 33.6 mmol, 46.1% yield).

Preparation of (47)

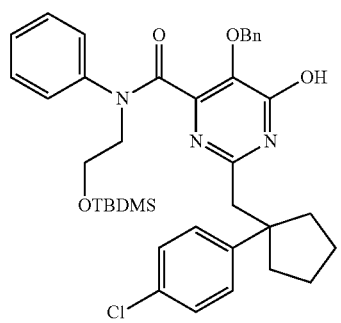 [SMILES: CC(C)(C)[Si](C)(C)OCCN(C(=O)c1nc(CC2(c3ccc(Cl)cc3)CCCC2)nc(O)c1OCc1ccccc1)c1ccccc1]

Step 2: 5-(Benzyloxy)-N-(2-(tert-butyldimethylsilyloxy)ethyl)-2-((1-(4-chlorophenyl)cyclopentyl)-methyl)-6-hydroxy-N-phenylpyrimidine-4-carboxamide To a solution of 5-(benzyloxy)-2-((1-(4-chlorophenyl)cyclopentyl)methyl)-6-hydroxypyrimidine-4-carboxylic acid (28-02) (200 mg, 456 µmol, Eq: 1.00) and N-(2-(tert-butyldimethylsilyloxy)ethyl)aniline (46) (126 mg, 501 µmol, Eq: 1.1) in pyridine (2.00 ml) was added POCl$_3$ (210 mg, 127 µl, 1.37 mmol, Eq: 3.00) at −10° C. (ethylene glycol-dry-ice bath), then the reaction mixture was stirred at 0° C. for 2 hr. Ice cooled water was slowly added to the reaction mixture at 0° C., the reaction mixture was extracted with ethyl acetate, the organic layer was washed with aqueous saturated NaHCO$_3$ solution, dried (MgSO$_4$), concentrated, and chromatographed (silica gel, gradient 5 to 30% ethyl acetate-hexane) to obtain 5-(benzyloxy)-N-(2-(tert-butyldimethylsilyloxy)ethyl)-2-((1-(4-chlorophenyl)cyclopentyl)methyl)-6-hydroxy-N-phenylpyrimidine-4-carboxamide (47) (colorless oil, 287 mg, 427 µmol, 93.7% yield).

LC/MS: (M+H)$^+$=673.

Preparation of (48)

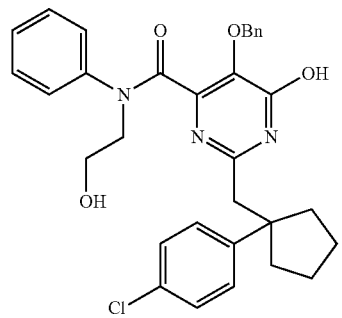 [SMILES: O=C(c1nc(CC2(c3ccc(Cl)cc3)CCCC2)nc(O)c1OCc1ccccc1)N(CCO)c1ccccc1]

Step 3: 5-(Benzyloxy)-2-(1-(4-chlorophenyl)cyclopentyl)methyl)-6-hydroxy-N-(2-hydroxyethyl)-N-phenylpyrimidine-4-carboxamide To a stirred solution of 5-(benzyloxy)-N-(2-(tert-butyldimethylsilyloxy)ethyl)-2-((1-(4-chlorophenyl)cyclopentyl)methyl)-6-hydroxy-N-phenylpyrimidine-4-carboxamide (47) (287 mg, 427 µmol, Eq: 1.00) in tetrahydrofuran (10 ml) was added HCl (1N) (640 µl, 640 µmol, Eq: 1.5) at room temperature and the reaction mixture was stirred for 6 hrs, neutralized with 1N NaOH aqueous solution, extracted with ethyl acetate, dried (MgSO$_4$), concentrated, and chromatographed (silica gel, gradient, 0 to 5% methanol-dichloromethane) to obtain 5-(benzyloxy)-2-((1-(4-chlorophenyl)cyclopentyl)methyl)-6-hydroxy-N-(2-hydroxyethyl)-N-phenylpyrimidine-4-carboxamide (48) (white foam, 179 mg, 321 µmol, 75.1% yield).

LC/MS: (M+H)$^+$=559.

Preparation of (49)

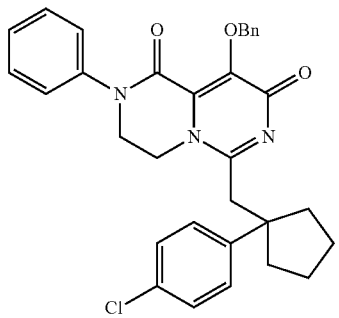

Step 4: 9-(Benzyloxy)-6-(1-(4-chlorophenyl)cyclopentyl)methyl)-2-phenyl-3,4-dihydro-1H-pyrazino[1,2-c]pyrimidine-1,8(2H)-dione To a stirred solution of 5-(benzyloxy)-2-((1-(4-chlorophenyl)cyclopentyl)methyl)-6-hydroxy-N-(2-hydroxyethyl)-N-phenylpyrimidine-4-carboxamide (48) (100.1 mg, 179 μmol, Eq: 1.00) in dichloromethane (5 ml) at room temperature was added triphenylphosphine (70.6 mg, 269 μmol, Eq: 1.5) and stirred for 10 min. Then diisopropyl azodicarboxylate (54.4 mg, 52.3 μl, 269 μmol, Eq: 1.5) was added and the reaction mixture was stirred for 18 hrs, concentrated, and chromatographed (silica gel, gradient 0 to 5% methanol-dichloromethane) to obtain 9-(benzyloxy)-6-((1-(4-chlorophenyl)cyclopentyl)methyl)-2-phenyl-3,4-dihydro-1H-pyrazino[1,2-c]pyrimidine-1,8(2H)-dione (49) (white foam, 88.5 mg, 164 μmol, 91.4% yield).

LC/MS: (M+H)$^+$=541

Preparation of (50)

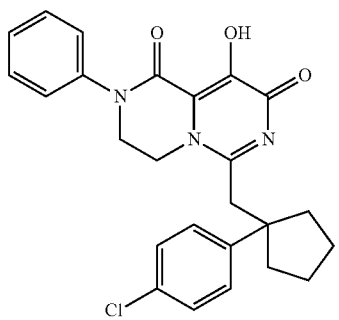 [SMILES: O=C1c2c(O)c(=O)nc(CC3(c4ccc(Cl)cc4)CCCC3)n2CCN1c1ccccc1]

Step 5: 6-((1-(4-Chlorophenyl)cyclopentyl)methyl)-9-hydroxy-2-phenyl-3,4-dihydro-1H-pyrazino[1,2-c]pyrimidine-1,8(2H)-dione To a stirred solution of 9-(benzyloxy)-6-((1-(4-chlorophenyl)cyclopentyl)methyl)-2-phenyl-3,4-dihydro-1H-pyrazino[1,2-c]pyrimidine-1,8(2H)-dione (49) (88.5 mg, 164 μmol, Eq: 1.00) in methanol (5 ml) was added HCl (conc) (240 mg, 0.2 ml, 6.58 mmol, Eq: 40.2). The reaction mixture was heated at 70° C. for 18 hrs, neutralized with saturated aqueous NaHCO$_3$ solution, extracted with dichloromethane, dried (MgSO$_4$), concentrated, triturated with diethyl ether, filtered, and dried to obtain 6-((1-(4-chlorophenyl)cyclopentyl)methyl)-9-hydroxy-2-phenyl-3,4-dihydro-1H-pyrazino[1,2-c]pyrimidine-1,8(2H)-dione (50) (pink powder, 48.2 mg, 107 μmol, 65.4% yield).

LC/MS: (M+H)$^+$=450

$^1$H NMR (400 MHz, dimethyl sulfoxide-d$_6$) ppm 1.63 (br. s., 2H) 1.75-1.99 (m, 4H) 2.21-2.39 (m, 2H) 2.98 (s, 2H) 3.56 (br. s., 2H) 3.78 (br. s., 2H) 7.20-7.57 (m, 9H) 12.95-13.74 (m, 1H).

Preparation of (60)

9-Hydroxy-2-isopropyl-6-(2-methyl-2-phenyl-propyl)-3,4-dihydro-2H-pyrazino[1,2-c]pyrimidine-1,8-dione The synthetic procedure used in this preparation is outlined in Scheme 10:

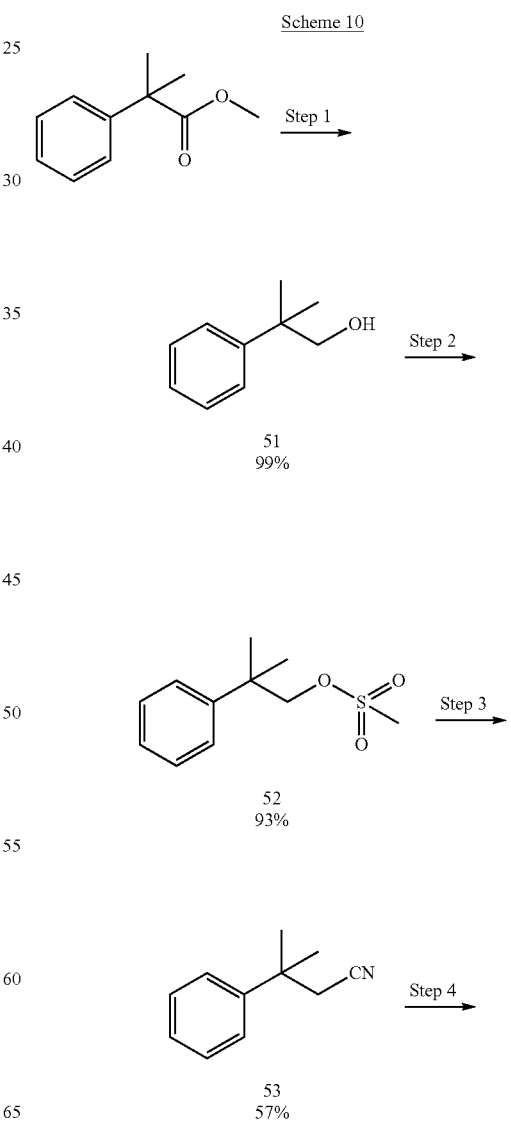

Scheme 10

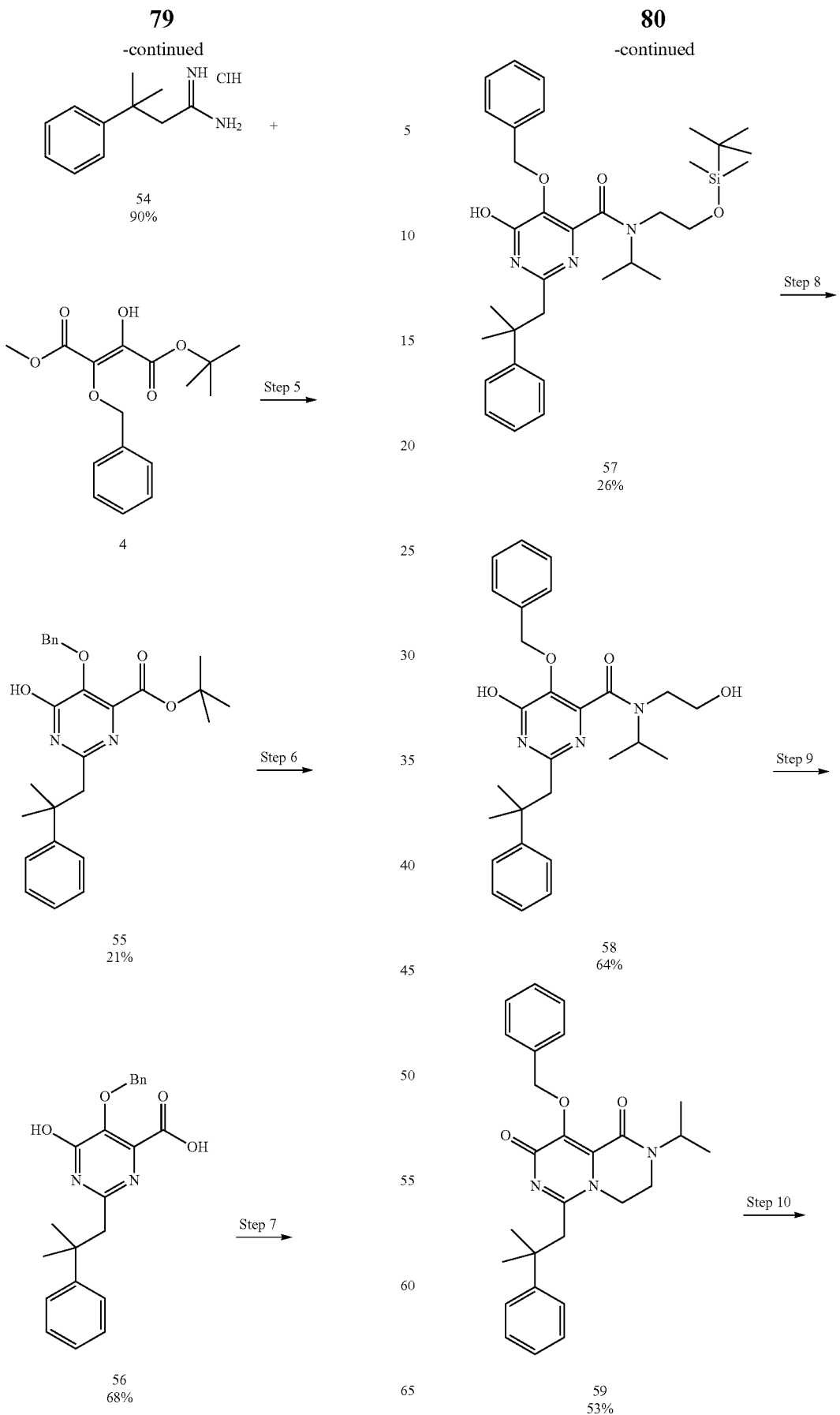

-continued

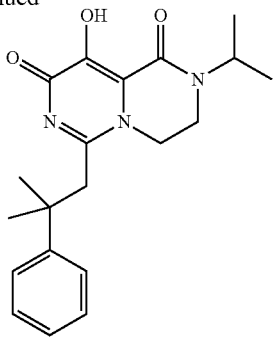

60
51%

Preparation of (51)

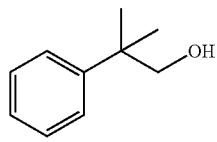

Step 1: 2-Methyl-2-phenyl-propan-1-ol

Methyl 2-methyl-2-phenylpropanoate (10.8 g, 60.6 mmol, Eq: 1.00) in tetrahydrofuran (193 ml) was cooled to 0° C., lithium aluminium hydride was added (30.3 ml, 60.6 mmol, Eq: 1.00) via a syringe over 5 minutes. The mixture was stirred at 0° C. for 3 hours, and 2.3 ml water was added over 2 minutes. The mixture was stirred for 10 minutes, 2.3 ml 1N NaOH was added, the mixture was stirred for 5 minutes (a gel forms), 7 ml water was added, the mixture was stirred for 15 minutes, filtered through a pad of celite. The celite was washed with ether and the solvent was removed under vacuum to give methyl-2-phenyl-propan-1-ol (51) (9.0 g, 99%) as a clear oil.

$^1$H NMR (400 MHz, dimethyl sulfoxide-$d_6$) δ ppm 1.23 (s, 6H) 3.43 (d, J=5.27 Hz, 2H) 4.66 (t, J=5.27 Hz, 1H) 7.06-7.51 (m, 5H).

Preparation of (52)

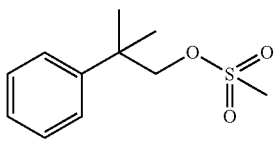

Step 2: 2-Methyl-2-phenylpropyl methanesulfonate

2-Methyl-2-phenylpropan-1-ol (51) (8.5 g, 56.6 mmol, Eq: 1.00) was stirred in dichloromethane (90.4 ml) at 0° C., triethylamine (6.87 g, 9.46 ml, 67.9 mmol, Eq: 1.2) and then methanesulfonyl chloride (7.13 g, 4.82 ml, 62.2 mmol, Eq: 1.1) were added over 3 minutes. The reaction mixture was stirred at 0° C. for 30 minutes, removed from the ice bath and allowed to warm to room temperature and stirred for 15 hours. The reaction mixture was diluted with dichloromethane, washed with water, saturated sodium bicarbonate, and brine, and dried with magnesium sulfate. The solvent was removed on a rotary evaporator to give 2-methyl-2-phenylpropyl methanesulfonate (52) as a clear oil, (12.0 g, 93%).

Preparation of (53)

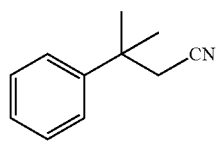

Step 3: 3-Methyl-3-phenylbutanenitrile

2-Methyl-2-phenylpropyl methanesulfonate (52) (12 g, 52.6 mmol) was stirred in dimethyl sulfoxide (106 ml), sodium cyanide (10.3 g, 210 mmol, Eq: 4) was added and the reaction mixture was heated to 110° C. for 20 hours. The reaction mixture was cooled, diluted with water, extracted three times with ether, washed with ether, water, and brine, and dried over magnesium sulfate. The solvent was removed on a rotary evaporator. Chromatography was conducted (2% to 15% over 20 min on a 40 g silica gel column) to give 3-methyl-3-phenylbutanenitrile (53) as a clear oil (4.8 g, 57%).

$^1$H NMR (400 MHz, dimethyl sulfoxide-$d_6$) δ ppm 1.41 (s, 6H) 2.92 (s, 2H) 7.11-7.53 (m, 5H).

Preparation of (54)

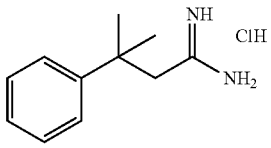

Step 4: 3-Methyl-3-phenylbutanimidamide

Ammonium chloride (2.52 g, 47.1 mmol, Eq: 3) as a suspension in toluene (56.8 ml) was cooled to 0° C., trimethylaluminum (23.6 ml, 47.1 mmol, Eq: 3) was added via a syringe. The reaction mixture was stirred for 5 minutes, allowed to warm to room temperature and stirred at room temperature for 2.0 hours. Then 3-methyl-3-phenylbutanenitrile (53) (2.5 g, 15.7 mmol, Eq: 1.00) dissolved in toluene was added in two 5 ml aliquots. The reaction mixture was heated to 80° C. for 24 hours, and then cooled. About 10 g silica gel in dichloromethane were added. The reaction mixture was stirred for 45 minutes, filtered through a sintered glass funnel and washed to a solid pad with a minimum amount of methanol: The solvent was removed on a rotary evaporator to give 325 mg white solid, which was not the product. The solid from the filter was placed in 1:1 dichloromethane/toluene=50 ml. Then 50 grams silica gel were added and the reaction mixture was stirred at room temperature overnight. The mixture was filtered through a sintered glass funnel to give a milky solution, the filter was washed four times with methanol (total of about 80 ml). The solvents were removed from filtrate on a rotary evaporator and the residue was dried under high vacuum to give 3-methyl-3-phenylbutanimidamide hydrochloride (54) as a white solid (3.0 g, 90%).

LC/MS calcd. for $C_{11}H_{16}N_2$ (m/e) 176.26, obsd. 177.1 [M+H, ES$^+$].

Preparation of (55)

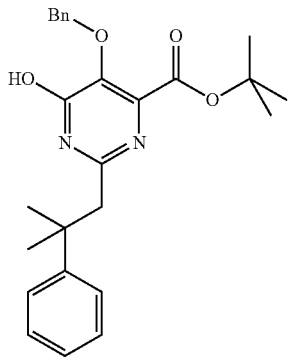 [SMILES: CC(C)(C)OC(=O)c1nc(CC(C)(C)c2ccccc2)nc(O)c1OCc1ccccc1]

Step 5: tert-Butyl 5-(benzyloxy)-6-hydroxy-2-(2-methyl-2-phenylpropyl)pyrimidine-4-carboxylate 4-tert-Butyl 1-methyl 2-(benzyloxy)-3-hydroxyfumarate (4) (652 mg, 2.12 mmol, Eq: 1.5,) and 3-methyl-3-phenylbutanimidamide hydrochloride (54) (300 mg, 1.41 mmol, Eq: 1.00) were stirred in methanol (7.2 ml). The reaction mixture was cooled to 0° C. and sodium methoxide (229 mg, 4.23 mmol, Eq: 3) (powdered, Aldrich) was added. The reaction mixture was stirred at room temperature. The reaction mixture is a suspension. It was stirred overnight. 5 ml 1N aqueous HCl was added and the mixture was diluted with water, filtered through a sintered glass funnel. The solid was washed with water. The solid was placed under high vacuum to dry to give tert-butyl 5-(benzyloxy)-6-hydroxy-2-(2-methyl-2-phenylpropyl)pyrimidine-4-carboxylate as a yellow solid (260 mg, 21%) as a 1:1 mixture of tert-butyl 5-(benzyloxy)-6-hydroxy-2-(2-methyl-2-phenylpropyl)pyrimidine-4-carboxylate (55) and 3-methyl-3-phenylbutanimidamide. The product was used without further purification.

Preparation of (56)

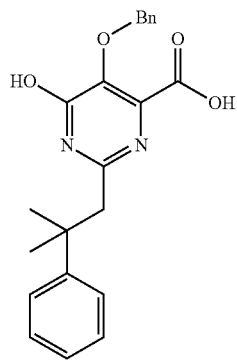 [SMILES: CC(C)(Cc1nc(O)c(OCc2ccccc2)c(C(=O)O)n1)c1ccccc1]

Step 6: 5-(Benzyloxy)-6-hydroxy-2-(2-methyl-2-phenylpropyl)pyrimidine-4-carboxylic acid tert-Butyl 5-(benzyloxy)-6-hydroxy-2-(2-methyl-2-phenylpropyl)pyrimidine-4-carboxylate (55) (260 mg, 598 µmol, Eq: 1.00) was stirred in tetrahydrofuran/water. Lithium hydroxide monohydrate (126 mg, 2.99 mmol, Eq: 5) was added. The reaction mixture was heated at 85° C. for 7 hours, cooled, and stirred at room temperature for 16 hours. 1N HCl was added until precipitate forms (about 10 ml). The mixture was diluted with water, extracted three times with ethyl acetate, washed with brine and dried over magnesium sulfate. The solvent was removed on a rotary evaporator to give 5-(benzyloxy)-6-hydroxy-2-(2-methyl-2-phenylpropyl)pyrimidine-4-carboxylic acid (56) as a white solid (155 mg, 68%).

LC/MS calcd. for $C_{22}H_{22}N_2O_4$ (m/e) 378.43, obsd. 379.3 [M+H, ES$^+$].

Preparation of (57)

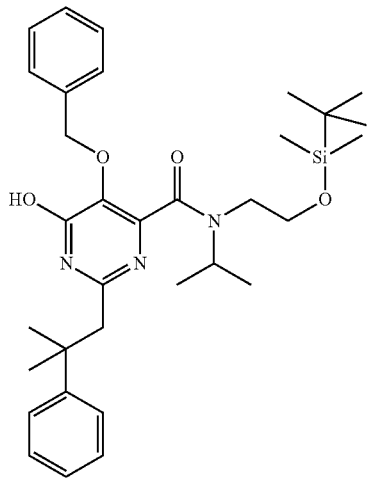 [SMILES: CC(C)N(CCO[Si](C)(C)C(C)(C)C)C(=O)c1nc(CC(C)(C)c2ccccc2)nc(O)c1OCc1ccccc1]

Step 7: 5-(Benzyloxy)-N-(2-(tert-butyldimethylsilyloxy)ethyl)-6-hydroxy-N-isopropyl-2-(2-methyl-2-phenylpropyl)pyrimidine-4-carboxamide N-(2-(tert-Butyldimethylsilyloxy)ethyl)propan-2-amine (8b) (98.0 mg, 451 µmol, Eq: 1.1, prepared as previously described) was added to 5-(benzyloxy)-6-hydroxy-2-(2-methyl-2-phenylpropyl)pyrimidine-4-carboxylic acid (56) (155 mg, 410 µmol, Eq: 1.00), then pyridine (2.5 ml) was added, and the reaction mixture was cooled to −10° C. with stirring. POCl$_3$ (188 mg, 115 µl, 1.23 mmol, Eq: 3) was added dropwise, then the reaction mixture was stirred at −10° C. for 1 hour, allowed to warm to 0° C. and stirred for one hour. 10 drops of water were added at 0° C., the reaction mixture was stirred for 5 min and the solvent was removed on a rotary evaporator to almost dryness. The mixture was placed on 12 g silica gel column and eluted with 5% to 50% ethyl acetate/hexane over 20 min. to give 5-(benzyloxy)-N-(2-(tert-butyldimethylsilyloxy)ethyl)-6-hydroxy-N-isopropyl-2-(2-methyl-2-phenylpropyl)pyrimidine-4-carboxamide (57) (62 mg, 26%).

LC/MS calcd. for =C$_{33}$H$_{47}$N$_3$O$_4$Si (m/e) 577.85 obsd. 578.5 [M+H, ES$^+$].

Preparation of (58)

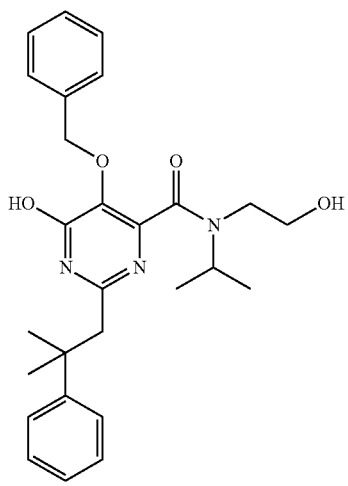 [SMILES: CC(C)N(CCO)C(=O)c1nc(CC(C)(C)c2ccccc2)nc(O)c1OCc1ccccc1]

Step 8: 5-(Benzyloxy)-6-hydroxy-N-(2-hydroxy-ethyl)-N-isopropyl-2-(2-methyl-2-phenylpropyl)-pyrimidine-4-carboxamide 5-(Benzyloxy)-N-(2-(tert-butyldimethylsilyloxy)ethyl)-6-hydroxy-N-isopropyl-2-(2-methyl-2-phenylpropyl)pyrimidine-4-carboxamide (57) (62 mg, 107 μmol, Eq: 1.00) was stirred in tetrahydrofuran (2 ml), HCl (aqueous) (161 μl, 161 μmol, Eq: 1.5) was added. The reaction mixture was stirred at room temperature for 3.0 hours, 160 μl 1N NaOH was added and the reaction mixture was diluted with water, extracted twice with ethyl acetate. The combined organic layers were washed with brine and dried over magnesium sulfate. Trituration in hexanes/ether was conducted to give 5-(benzyloxy)-6-hydroxy-N-(2-hydroxyethyl)-N-isopropyl-2-(2-methyl-2-phenylpropyl)pyrimidine-4-carboxamide (58) (32 mg, 64%).

LC/MS calcd. for C$_{27}$H$_{33}$N$_3$O$_4$ (m/e)=463.58, obsd. 464.4 [M+H, ES$^+$], 486.4 [M+Na, ES$^+$].

Preparation of (59)

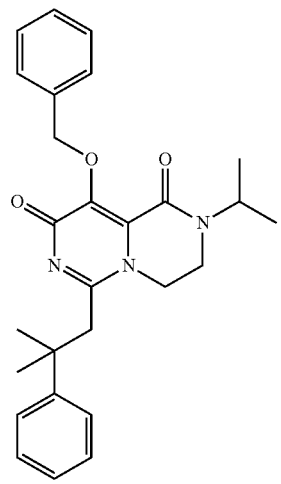 [SMILES: CC(C)N1CCn2c(CC(C)(C)c3ccccc3)nc(=O)c(OCc3ccccc3)c2C1=O]

Step 9: 9-(Benzyloxy)-2-isopropyl-6-(2-methyl-2-phenylpropyl)-3,4-dihydro-1H-pyrazino[1,2-c]pyrimidine-1,8(2H)-dione To a stirred solution of 5-(benzyloxy)-6-hydroxy-N-(2-hydroxyethyl)-N-isopropyl-2-(2-methyl-2-phenylpropyl)pyrimidine-4-carboxamide (58) (35 mg, 75.5 μmol, Eq: 1.00) in dichloromethane (5.00 ml) was added triphenylphosphine (29.7 mg, 113 μmol, Eq: 1.5) at room temperature and the reaction mixture was stirred for 10 min. Then diisopropyl azodicarboxylate (22.9 mg, 22.0 μl, 113 μmol, Eq: 1.5) was added and the reaction mixture was stirred for 18 hrs at room temperature. The reaction mixture was concentrated on a rotary evaporator and chromatographed (silica gel, gradient, 2 to 5% methanol-dichloromethane) to obtain 9-(benzyloxy)-2-isopropyl-6-(2-methyl-2-phenylpropyl)-3,4-dihydro-1H-pyrazino[1,2-c]pyrimidine-1,8(2H)-dione (59) (18 mg, 53.5% yield).

LC/MS calcd. for Ia=C$_{27}$H$_{31}$N$_3$O$_3$ (m/e) 445.57, obsd. 446.4 [M+H, ES$^+$].

Preparation of (60)

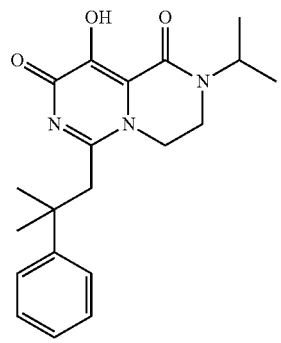 [SMILES: CC(C)N1CCn2c(CC(C)(C)c3ccccc3)nc(=O)c(O)c2C1=O]

Step 10: 9-Hydroxy-2-isopropyl-6-(2-methyl-2-phenyl-propyl)-3,4-dihydro-2H-pyrazino[1,2-c]pyrimidine-1,8-dione To a stirred solution of 9-(benzyloxy)-2-isopropyl-6-(2-methyl-2-phenylpropyl)-3,4-dihydro-1H-pyrazino[1,2-c]pyrimidine-1,8(2H)-dione (59) (15 mg, 33.7 µmol, Eq: 1.00) in methanol (5.00 ml) was added HCl (conc) (49.1 mg, 40.9 µl, 1.35 mmol, Eq: 40); the mixture was heated at 70° C. for 48 hrs. The reaction mixture was cooled and stirred overnight at room temperature. The solvent was removed on a rotary evaporator, and saturated aqueous NaHCO$_3$ solution was added, this was extracted with dichloromethane, and the organic layers were combined and dried over magnesium sulfate. This was filtered, the solvents were removed on a rotary evaporator and the residue was triturated three times with diethyl ether. The resulting white solid was dried to obtain the title compound (60) (6.1 mg, 51%).

LC/MS calcd. for Ia=C$_{20}$H$_{25}$N$_3$O$_3$ (m/e) 355.44, obsd. 356.3 [M+H, ES$^+$].

Example 66

6-(2,6-Dichlorobenzyl)-9-hydroxy-2-isopropyl-3,4-dihydro-2H-pyrazino[1,2-c]pyrimidine-1,8-dione (66)

The synthetic procedure used in this preparation is outlined in Scheme 11.

Scheme 11

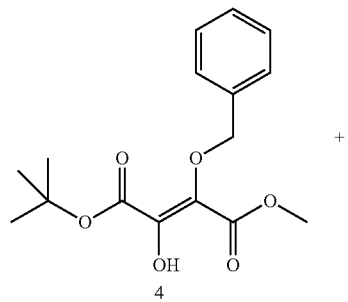
4

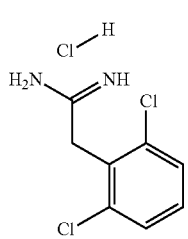

Step 1

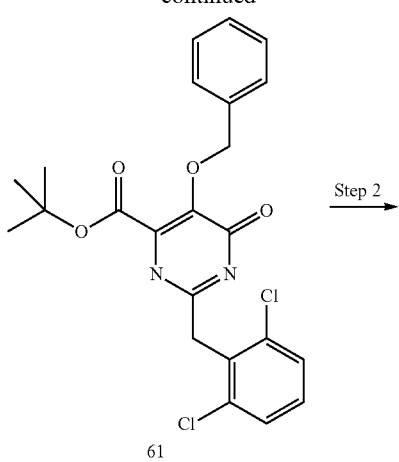
61

Step 2

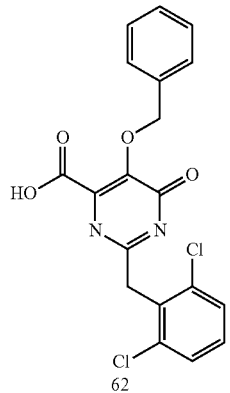
62

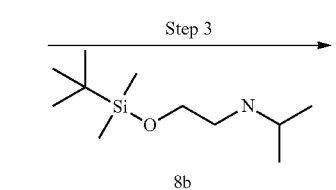
8b

Step 3

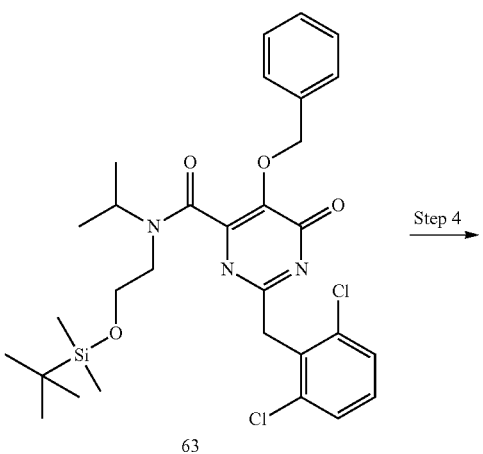
63

Step 4

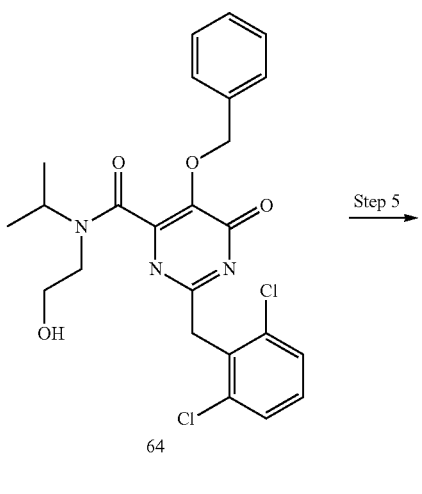

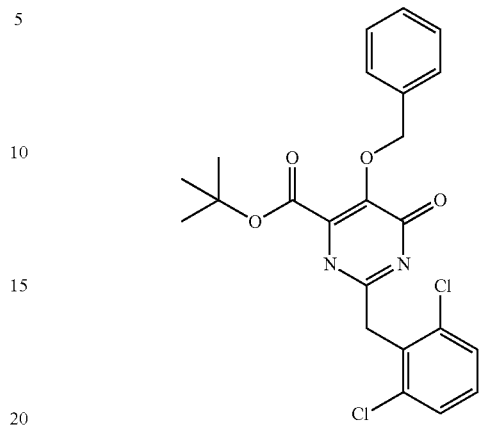

Preparation of (61)

Step 1: 5-Benzyloxy-2-(2,6-dichlorobenzyl)-6-oxo-3,6-dihydro-pyrimidine-4-carboxylic acid tert-butyl ester 2-(2,6-Dichlorophenyl)acetimidamide hydrochloride (0.2 g, 835 μmol, Eq: 1.00) and 4-tert-butyl 1-methyl 2-(benzyloxy)-3-hydroxyfumarate (4) (386 mg, 1.25 mmol, Eq: 1.5) were dissolved in methanol (6.00 ml) and cooled to 0° C. At that temperature, sodium methoxide (142 mg, 2.5 mmol, Eq: 3) was added. After another 15 minutes at this temperature, the resulting suspension was allowed to warm to room temperature overnight.

The mixture was diluted with 2 ml of methanol and cooled to 0° C. 1M HCl was added and a precipitate formed. After stirring for approx. 30 minutes the solid was collected by filtration, washed with little methanol/water 9/1 and dried to afford 5-(benzyloxy)-2-(2,6-dichlorobenzyl)-6-oxo-3,6-dihydro-pyrimidine-4-carboxylic acid tert-butyl ester (61) (0.245 g, 531 μmol, 63.6% yield) as a white solid.

$^1$H NMR (dimethyl sulfoxide-$d_6$) δ: 13.25 (br. s., 1H), 7.51 (d, J=8.0 Hz, 2H), 7.30-7.47 (m, 6H), 5.14 (s, 2H), 4.25 (s, 2H), 1.35 (s, 9H).

Preparation of (62)

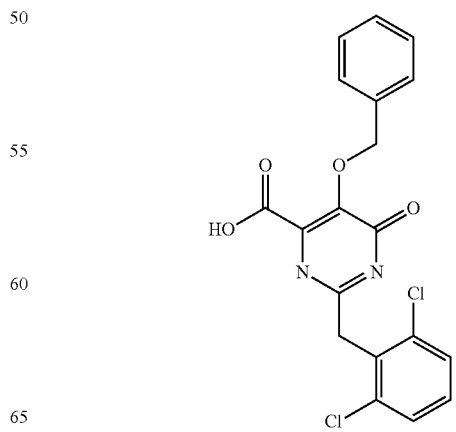

Step 2: 5-Benzyloxy-2-(2,6-dichlorobenzyl)-6-oxo-3,6-dihydro-pyrimidine-4-carboxylic acid 5-(Benzyloxy)-2-(2,6-dichlorobenzyl)-6-oxo-3,6-dihydro-pyrimidine-4-carboxylic acid tert-butyl ester (61) (0.24 g, 520 μmol, Eq: 1.00) and LiOH (62.3 mg, 2.6 mmol, Eq: 5) were stirred in tetrahydrofuran (2 ml)/water (1.00 ml) at reflux overnight. The solvent was mostly removed. The residue was taken up in water and was extracted once with ethyl acetate. The aqueous layer was acidified with HCl conc. The precipitate was collected by filtration, washed with water and dried to afford 5-benzyloxy-2-(2,6-dichlorobenzyl)-6-oxo-3,6-dihydro-pyrimidine-4-carboxylic acid (62) (0.202 g, 498 μmol, 95.8% yield) as a white solid.

$^1$H NMR (dimethyl sulfoxide-d$_6$) δ: 13.49 (br. s., 1H), 13.24 (br. s., 1H), 7.50 (d, J=8.0 Hz, 2H), 7.32-7.46 (m, 6H), 5.13 (s, 2H), 4.25 (s, 2H).

Preparation of (63)

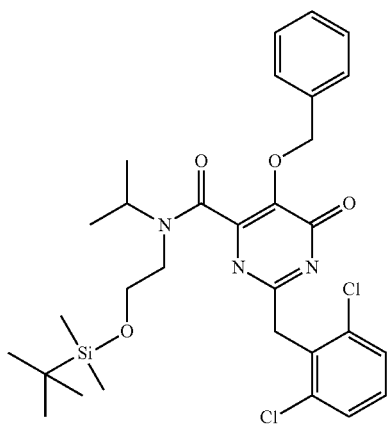

63

Step 3: 5-Benzyloxy-2-(2,6-dichlorobenzyl)-6-oxo-3,6-dihydro-pyrimidine-4-carboxylic acid [2-(tert-butyl-dimethylsilanyloxy)-ethyl]-isopropylamide 5-(Benzyloxy)-2-(2,6-dichlorobenzyl)-6-oxo-3,6-dihydro-pyrimidine-4-carboxylic acid (62) (0.2 g, 494 μmol, Eq: 1.00) and N-(2-(tert-butyldimethylsilyloxy)ethyl)propan-2-amine (118 mg, 543 μmol, Eq: 1.1) were dissolved in pyridine (3 ml) and cooled in an ice/NaCl bath. POCl$_3$ (227 mg, 138 μl, 1.48 mmol, Eq: 3) was added dropwise. After the addition was complete, stirring of the reaction mixture was continued at 0° C. for approx. 40 minutes. The reaction mixture was quenched with ice and extracted twice with ethyl acetate. The organic layers were washed with NaHCO$_3$, were combined, dried over Na$_2$SO$_4$, filtered and concentrated. The remaining oil was purified by SiO$_2$ flash chromatography (24 g SiO$_2$, hexanes/ethyl acetate 0-50% ethyl acetate). Product containing fractions were combined and concentrated. The remaining oil was treated with hexanes and concentrated again to afford 5-benzyloxy-2-(2,6-dichlorobenzyl)-6-oxo-3,6-dihydro-pyrimidine-4-carboxylic acid [2-(tert-butyl-dimethylsilanyloxy)-ethyl]-isopropylamide (63) (0.17 g, 281 μmol, 57.0% yield) as a white solid.

LC/MS (M+H)=604.

Preparation of (64)

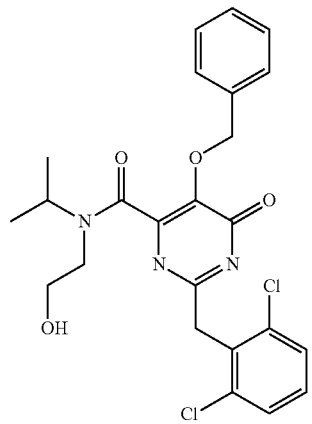 [SMILES: CC(C)N(CCO)C(=O)c1[nH]c(Cc2c(Cl)cccc2Cl)nc(=O)c1OCc1ccccc1]

Step 4: 5-Benzyloxy-2-(2,6-dichlorobenzyl)-6-oxo-3,6-dihydro-pyrimidine-4-carboxylic acid (2-hydroxyethyl)-isopropylamide 5-Benzyloxy-2-(2,6-dichlorobenzyl)-6-oxo-3,6-dihydro-pyrimidine-4-carboxylic acid [2-(tert-butyl-dimethylsilanyloxy)-ethyl]-isopropylamide (63) (0.17 g, 281 μmol, Eq: 1.00) was dissolved in tetrahydrofuran (1 ml). HCl (211 μl, 422 μmol, Eq: 1.5) was added and the resulting mixture was stirred at room temperature for 30 minutes. The solvent was mostly removed. The residue was partitioned between ethyl acetate and 1M NaOH. The aqueous layer was washed with ethyl acetate, the organic layers were washed with brine, combined, dried over Na$_2$SO$_4$, filtered and concentrated. The remaining oil was triturated and concentrated several times with ether/hexanes to afford 5-benzyloxy-2-(2,6-dichlorobenzyl)-6-oxo-3,6-dihydro-pyrimidine-4-carboxylic acid (2-hydroxyethyl)-isopropylamide (64) (0.113 g, 230 μmol, 82.0% yield) as a white solid.

LC/MS (M+H)=490.

Preparation of (65)

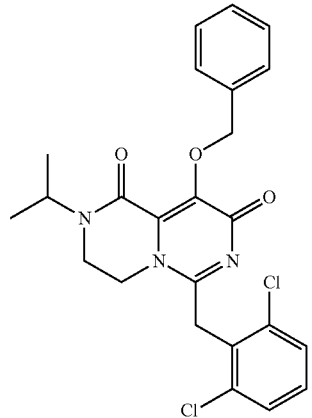 [SMILES: CC(C)N1CCn2c(Cc3c(Cl)cccc3Cl)nc(=O)c(OCc3ccccc3)c2C1=O]

Step 5: 9-Benzyloxy-6-(2,6-dichlorobenzyl)-2-isopropyl-3,4-dihydro-2H-pyrazino[1,2-c]pyrimidine-1,8-dione 5-Benzyloxy-2-(2,6-dichlorobenzyl)-6-oxo-3,6-dihydropyrimidine-4-carboxylic acid (2-hydroxyethyl)-isopropylamide (64) (0.11 g, 224 µmol, Eq: 1.00) was dissolved in dichloromethane (1.5 ml) and Ph₃P (88.3 mg, 336 µmol, Eq: 1.5) was added. The clear colorless solution was stirred at room temperature for approx. 10 min and then diisopropyl azodicarboxylate (diisopropylazodicarboxylate) (71.6 mg, 68.9 µl, 336 µmol, Eq: 1.5) was added. Stirring was continued at room temperature for 1 h. The solvent was removed and the remaining oil was purified by SiO₂ flash chromatography (12 g SiO₂, dichloromethane/methanol 0-3% methanol). SiO₂ flash chromatography was repeated (12 g SiO₂, hexanes/ethyl acetate 7-50% ethyl acetate, then dichloromethane/methanol 0-3% methanol) to afford 9-benzyloxy-6-(2,6-dichlorobenzyl)-2-isopropyl-3,4-dihydro-2H-pyrazino[1,2-c]pyrimidine-1,8-dione (65) (0.045 g, 95.3 µmol, 42.5% yield) as a white solid.

LC/MS (M+H)=472.

Preparation of (66)

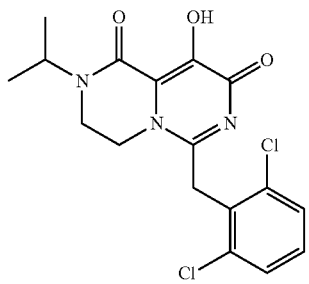 [SMILES: CC(C)N1CCn2c(Cc3c(Cl)cccc3Cl)nc(=O)c(O)c2C1=O]

Step 6: 6-(2,6-Dichlorobenzyl)-9-hydroxy-2-isopropyl-3,4-dihydro-2H-pyrazino[1,2-c]pyrimidine-1,8-dione 9-Benzyloxy-6-(2,6-dichlorobenzyl)-2-isopropyl-3,4-dihydro-2H-pyrazino[1,2-c]pyrimidine-1,8-dione (65) (0.04 g, 84.7 µmol, Eq: 1.00) was suspended in methanol (0.5 ml) and HCl conc (600 mg, 0.5 ml, 16.5 mmol, Eq: 194) was added. The resulting mixture was stirred at room temperature overnight. The organic solvent was mostly removed. Aqueous NaHCO₃ was added slowly. The water was removed under reduced pressure. The residue was taken up in ethanol and stirred at room temperature overnight. The suspension was filtered and the filtrate was concentrated to dryness. The remaining solid was purified by reverse phase flash chromatography (13 g C18, water/acetonitrile 0-100% acetonitrile). Product containing fractions were combined and lyophilized to of ford 6-(2,6-dichlorobenzyl)-9-hydroxy-2-isopropyl-3,4-dihydro-2H-pyrazino[1,2-c]pyrimidine-1,8-dione (66) (0.01 g, 30.6% yield) as a white solid.

$^1$H NMR (methanol-$d_4$) δ: 7.28-7.34 (m, 1H), 7.15-7.21 (m, 1H), 4.34-4.41 (m, 4H), 3.64-3.70 (m, 2H), 1.18 (d, J=6.8 Hz, 6H). LC/MS calcd. for C17H18Cl2N3O3 [(M+H)+] 382, obsd. 382.

Example 72

6-(3',4'-Dichloro-biphenyl-2-ylmethyl)-9-hydroxy-2-isopropyl-3,4-dihydro-2H-pyrazino[1,2-c]pyrimidine-1,8-dione The synthetic procedure used in this preparation is outlined in Scheme 12.

Scheme 12

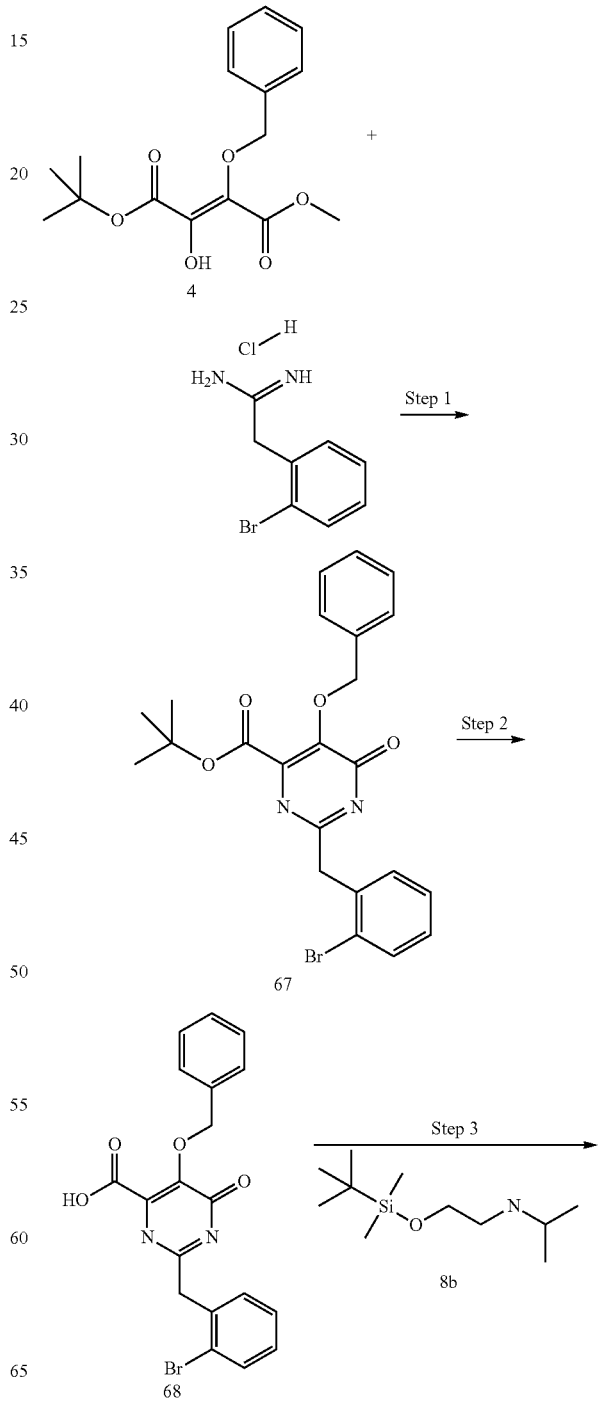

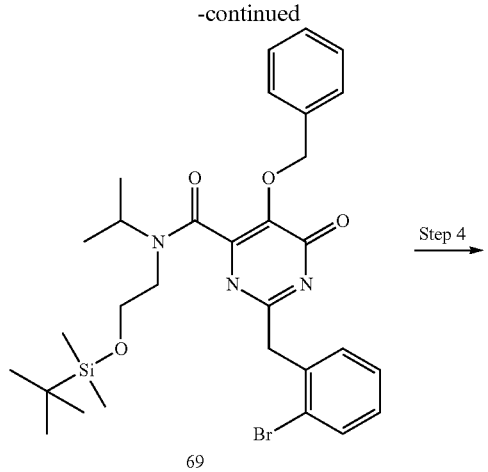

69

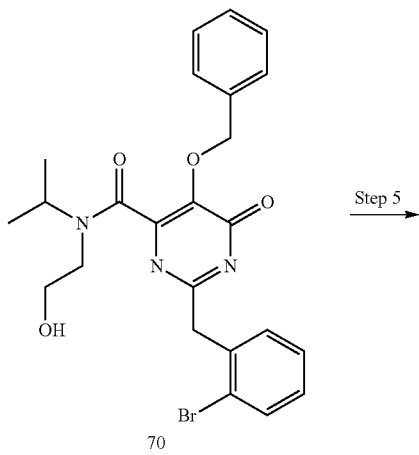

70

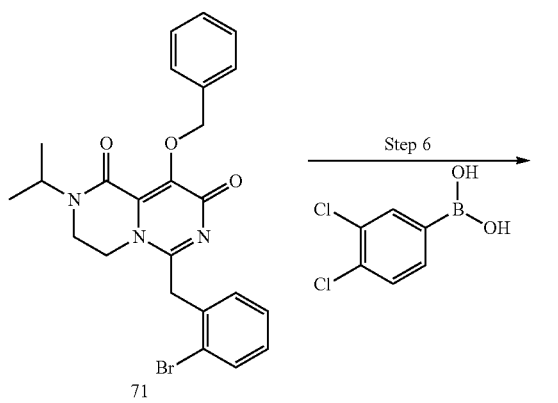

71

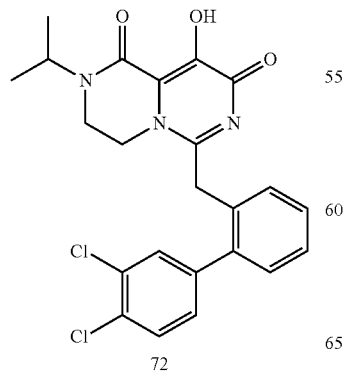

72

Preparation of (67)

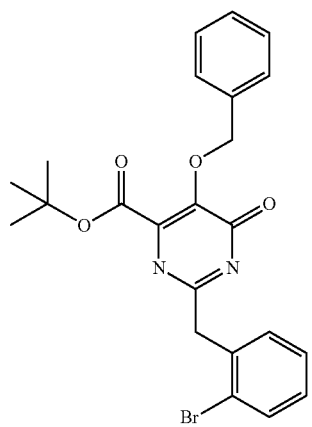 [SMILES: CC(C)(C)OC(=O)c1[nH]c(Cc2ccccc2Br)nc(=O)c1OCc1ccccc1]

Step 1: 5-Benzyloxy-2-(2-bromobenzyl)-6-oxo-3,6-dihydro-pyrimidine-4-carboxylic acid tert-butyl ester 2-(2-Bromophenyl)acetimidamide hydrochloride (2 g, 8.01 mmol, Eq: 1.00) and 4-tert-butyl 1-methyl 2-(benzyloxy)-3-hydroxyfumarate (4) (3.44 g, 11.2 mmol, Eq: 1.39) were dissolved in methanol (40.0 ml) and cooled down to 0° C. At that temperature sodium methoxide (1.37 g, 24.0 mmol, Eq: 3) was added. After another 15 minutes at this temperature, the resulting suspension was allowed to warm to room temperature overnight. A little methanol (~5 ml) was added and the yellow suspension was cooled to 0° C. 1M HCl (~50 ml) was added and a precipitate formed. The suspension was stirred for ~20 minutes. The solid was collected by filtration, washed with water and a little methanol/water 9/1 and dried to afford 5-(benzyloxy)-2-(2-bromobenzyl)-6-oxo-3,6-dihydro-pyrimidine-4-carboxylic acid tert-butyl ester (2.69 g, 5.71 mmol, 71.2% yield) (67) as an off-white solid.

$^1$H NMR (dimethyl sulfoxide-d$_6$) δ: 13.18 (br. s., 1H), 7.62-7.67 (m, 1H), 7.33-7.46 (m, 6H), 7.21-7.30 (m, 2H), 5.16 (s, 2H), 4.04 (s, 2H), 1.39 (s, 9H).

Preparation of (68)

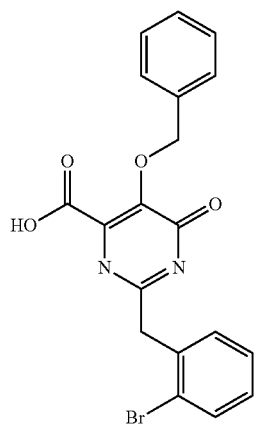

Step 2: 5-Benzyloxy-2-(2-bromobenzyl)-6-oxo-3,6-dihydro-pyrimidine-4-carboxylic acid 5-(Benzyloxy)-2-(2-bromobenzyl)-6-oxo-3,6-dihydro-pyrimidine-4-carboxylic acid tert-butyl ester (67) (2.69 g, 5.71 mmol, Eq: 1.00) and LiOH (683 mg, 28.5 mmol, Eq: 5) were stirred in tetrahydrofuran (18 ml)/water (9.00 ml) under reflux for 6 h, at room temperature overnight and again to reflux for 3 h. Then the solvent was mostly removed. The remaining oil was diluted with water and extracted with ethyl acetate. The aqueous layer was cooled in an ice bath and was acidified with HCl conc. Precipitate formed, was collected by filtration, washed with water and dried to afford 5-(benzyloxy)-2-(2-bromobenzyl)-6-oxo-3,6-dihydro-pyrimidine-4-carboxylic acid (68) (2.14 g, 5.15 mmol, 90.3% yield) as a white solid.

$^1$H NMR (dimethyl sulfoxide-$d_6$) δ: 13.48 (br. s., 1H), 13.16 (br. s., 1H), 7.60-7.67 (m, 1H), 7.29-7.47 (m, 7H), 7.21-7.28 (m, 1H), 5.14 (s, 2H), 4.05 (s, 2H).

Preparation of (69)

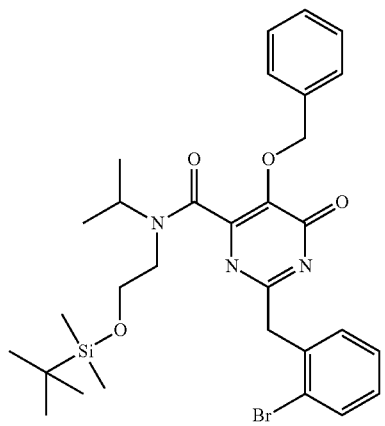 [SMILES: CC(C)N(CCO[Si](C)(C)C(C)(C)C)C(=O)c1[nH]c(Cc2ccccc2Br)nc(=O)c1OCc1ccccc1]

Step 3: 5-Benzyloxy-2-(2-bromobenzyl)-6-oxo-3,6-dihydro-pyrimidine-4-carboxylic acid [2-(tert-butyl-dimethylsilanyloxy)-ethyl]-isopropylamide 5-(Benzyloxy)-2-(2-bromobenzyl)-6-oxo-3,6-dihydro-pyrimidine-4-carboxylic acid (68) (1 g, 2.41 mmol, Eq: 1.00) was dissolved in pyridine (20 ml) and N-(2-(tert-butyldimethylsilyloxy)ethyl)propan-2-amine (8b) (576 mg, 2.65 mmol, Eq: 1.1) was added. Precipitate formed and gave a thick slurry. Additional 5 ml of pyridine were added to ease stirring. The suspension was cooled in an ice/NaCl bath. POCl$_3$ (1.11 g, 673 μl, 7.22 mmol, Eq: 3) was added dropwise, keeping the inside temperature below 0° C. After the addition was complete the mixture was stirred for 45 minutes at 0° C. The reaction was quenched with ice and the organic solvent was mostly removed. The remaining aqueous layer was extracted three times with ethyl acetate. The organic layers were washed with brine, combined, dried over Na$_2$SO$_4$, filtered and concentrated. The remaining oil was taken up in a little dichloromethane, was filtered through Celite and then purified by SiO$_2$ flash chromatography (80 g SiO$_2$, hexanes/ethyl acetate 0-50% ethyl acetate) to afford 5-benzyloxy-2-(2-bromobenzyl)-6-oxo-3,6-dihydro-pyrimidine-4-carboxylic acid [2-(tert-butyl-dimethylsilanyloxy)-ethyl]-isopropylamide (69) (0.758 g, 1.23 mmol, 51.2% yield) as a light brown oil.

LC/MS (M+H)=614/616.

Preparation of (70)

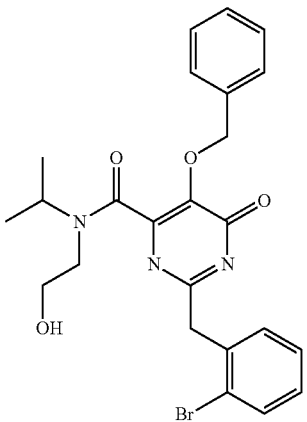 [SMILES: CC(C)N(CCO)C(=O)c1[nH]c(Cc2ccccc2Br)nc(=O)c1OCc1ccccc1]

Step 4: 5-Benzyloxy-2-(2-bromobenzyl)-6-oxo-3,6-dihydro-pyrimidine-4-carboxylic acid (2-hydroxyethyl)-isopropylamide 5-Benzyloxy-2-(2-bromobenzyl)-6-oxo-3,6-dihydro-pyrimidine-4-carboxylic acid [2-(tert-butyl-dimethylsilanyloxy)-ethyl]-isopropylamide (69) (0.75 g, 1.22 mmol, Eq: 1.00) was dissolved in tetrahydrofuran (10 ml). HCl (915 μl, 1.83 mmol, Eq: 1.5) was added and the resulting mixture was stirred at room temperature. After 30 minutes the solvent was mostly removed. The residue was partitioned between ethyl acetate and 1M NaOH. The aqueous layer was washed with ethyl acetate, the organic layers were washed with brine, combined, dried over Na$_2$SO$_4$, filtered and concentrated. The remaining brown oil was triturated in ethyl acetate/ether. The solid was collected by filtration, washed with a little ethyl acetate and dried to afford 5-benzyloxy-2-(2-bromobenzyl)-6-oxo-3,6-dihydro-pyrimidine-4-carboxylic acid (2-hydroxyethyl)-isopropylamide (70) (0.21 g, 420 μmol, 34.4% yield) as an off-white solid. The mother liquor also showed clean product (0.43 g, 68% yield) of brown solid.

LC/MS (M+H)=500/502.

Preparation of (71)

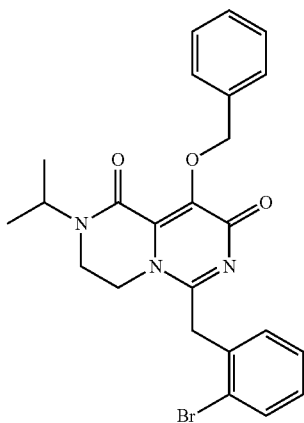 [SMILES: CC(C)N1CCn2c(Cc3ccccc3Br)nc(=O)c(OCc3ccccc3)c2C1=O]

Step 5: 9-Benzyloxy-6-(2-bromobenzyl)-2-isopropyl-3,4-dihydro-2H-pyrazino[1,2-c]pyrimidine-1,8-dione 5-Benzyloxy-2-(2-bromobenzyl)-6-oxo-3,6-dihydro-pyrimidine-4-carboxylic acid (2-hydroxyethyl)-isopropylamide (70) (0.21 g, 420 μmol, Eq: 1.00) and Ph₃P (143 mg, 546 μmol, Eq: 1.3) were stirred in dichloromethane (5 ml) at room temperature for ~15 min. Then diisopropyl azodicarboxylate (116 mg, 112 μl, 546 μmol, Eq: 1.3) was added and the resulting mixture was stirred at room temperature overnight. The solvent was removed. The remaining material was purified by SiO₂ flash chromatography (hexanes/ethyl acetate 5-50%, then dichloromethane/methanol 0-4% methanol). 300 mg of 9-benzyloxy-6-(2-bromobenzyl)-2-isopropyl-3,4-dihydro-2H-pyrazino[1,2-c]pyrimidine-1,8-dione (71) (~40% pure, ~60% yield) as light yellow solid were isolated and used as obtained.

LC/MS (M+H)=482/484.

Preparation of (72)

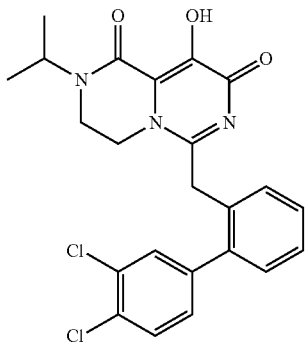 [SMILES: CC(C)N1CCn2c(Cc3ccccc3-c3ccc(Cl)c(Cl)c3)nc(=O)c(O)c2C1=O]

Step 6: 6-(3',4'-Dichloro-biphenyl-2-ylmethyl)-9-hydroxy-2-isopropyl-3,4-dihydro-2H-pyrazino[1,2-c]pyrimidine-1,8-dione 9-Benzyloxy-6-(2-bromobenzyl)-2-isopropyl-3,4-dihydro-2H-pyrazino[1,2-c]pyrimidine-1,8-dione (71) (0.1 g, 207 μmol, Eq: 1.00, ~40% pure), 3,4-dichlorophenylboronic acid (47.5 mg, 249 μmol, Eq: 1.2), Na₂CO₃ (65.9 mg, 622 μmol, Eq: 3) and tetrakis(triphenylphosphine)palladium (0) (24.0 mg, 20.7 μmol, Eq: 0.1) were stirred in methanol (0.9 ml)/dichloromethane (300 μl) in the microwave at 115° C. for 30 minutes. The reaction mixture stood at room temperature overnight. The supernatant was pipetted off, concentrated and purified by SiO₂ flash chromatography (4 g SiO₂, dichloromethane/methanol 0-5% methanol) to afford 6-(3',4'-dichloro-biphenyl-2-ylmethyl)-9-hydroxy-2-isopropyl-3,4-dihydro-2H-pyrazino[1,2-c]pyrimidine-1,8-dione (72) (0.016 g, 31.4 μmol, 15.2% yield, 90% pure) as a light yellow solid.

LC/MS (M+H)=458.

¹H NMR (methanol-d₄) δ: 7.60 (d, J=8.3 Hz, 1H), 7.52 (d, J=2.0 Hz, 1H), 7.39-7.43 (m, 2H), 7.28-7.32 (m, 2H), 7.22-7.26 (m, 1H), 4.79-4.85 (m, 1H), 4.13 (s, 2H), 3.87-3.93 (m, 2H), 3.49-3.54 (m, 2H), 1.22 (d, J=7.0 Hz, 6H).

Example 73

6-(4'-Chloro-biphenyl-2-ylmethyl)-9-hydroxy-2-isopropyl-3,4-dihydro-2H-pyrazino[1,2-d]pyrimidine-1,8-dione

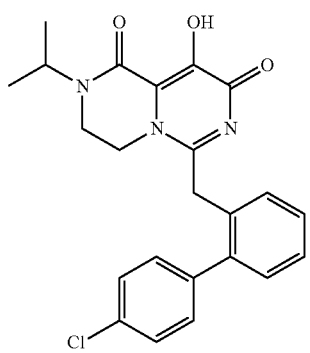

The title compound was prepared as example 2 using 4-chlorophenylboronic acid in step 6 to afford 6-(4'-chloro-biphenyl-2-ylmethyl)-9-hydroxy-2-isopropyl-3,4-dihydro-2H-pyrazino[1,2-c]pyrimidine-1,8-dione (73) (0.005 g, 10.6 μmol, 6.4% yield) as a light yellow solid.

LC/MS (M+H)=424.

Example 74

6-(2',3'-Dichloro-biphenyl-2-ylmethyl)-9-hydroxy-2-isopropyl-3,4-dihydro-2H-pyrazino[1,2-c]pyrimidine-1,8-dione

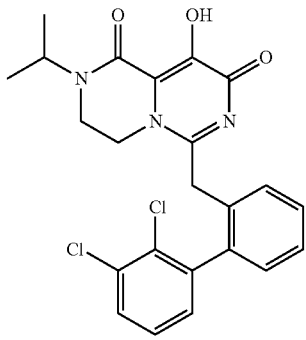 [SMILES: CC(C)N1CCn2c(Cc3ccccc3-c3cccc(Cl)c3Cl)nc(=O)c(O)c2C1=O]

The title compound was prepared as example 2 using 2,3-dichlorophenylboronic acid in step 6 to afford 6-(2',3'-dichloro-biphenyl-2-ylmethyl)-9-hydroxy-2-isopropyl-3,4-dihydro-2H-pyrazino[1,2-c]pyrimidine-1,8-dione (74) (0.017 g, 33.4 μmol, 16.1% yield) as a light yellow solid.

LC/MS (M+H)=458.

$^1$H NMR (methanol-$d_4$) δ: 7.58 (dd, J=7.9, 1.4 Hz, 1H), 7.40-7.47 (m, 2H), 7.36 (t, J=7.8 Hz, 1H), 7.23-7.31 (m, 3H), 4.78-4.86 (m, 1H), 3.90-4.12 (m, 3H), 3.81-3.89 (m, 1H), 3.51 (t, J=5.6 Hz, 2H), 1.21 (dd, J=6.8, 1.5 Hz, 6H).

Example 81

9-Hydroxy-2-isopropyl-6-naphthalen-1-ylmethyl-3,4-dihydro-2H-pyrazino[1,2-c]pyrimidine-1,8-dione The synthetic procedure used in this preparation is outlined in Scheme 13.

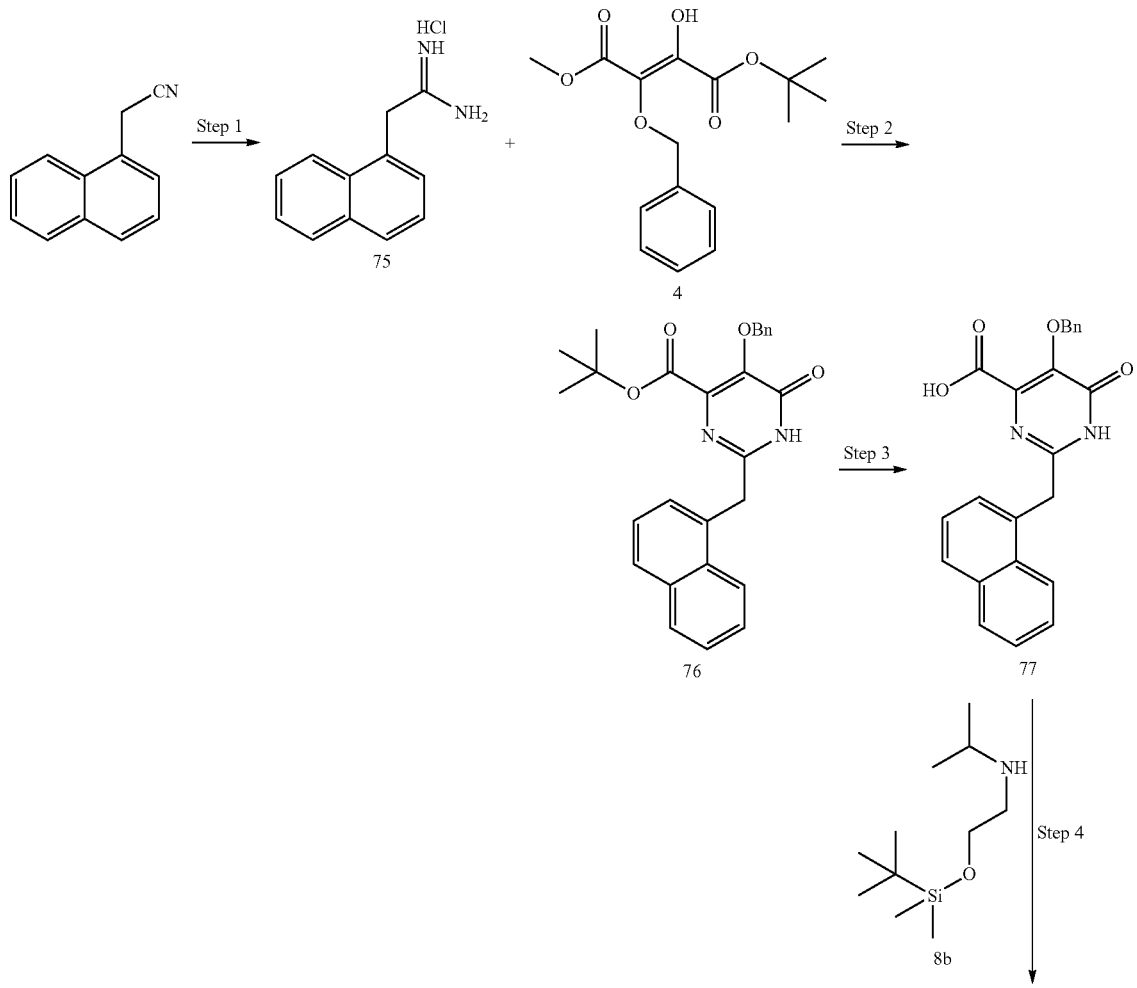

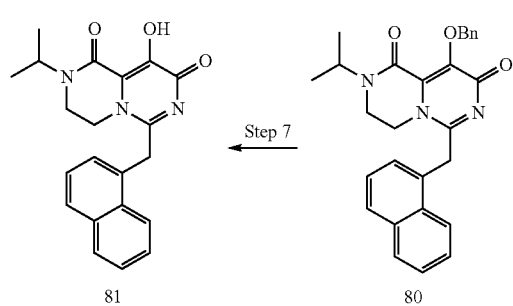
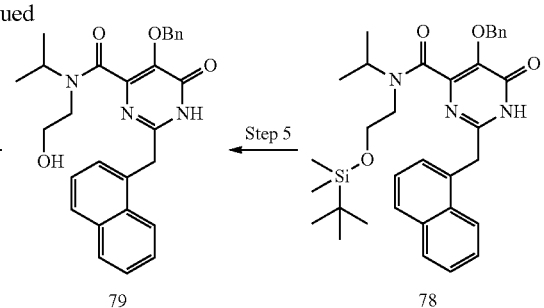

Preparation of (75)

Preparation of (76)

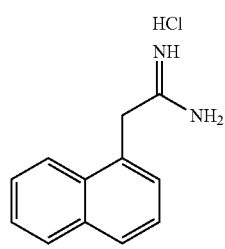 [SMILES: Cl ; N=C(N)Cc1cccc2ccccc12]

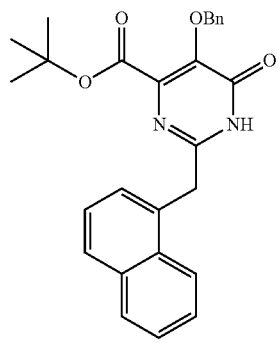 [SMILES: CC(C)(C)OC(=O)c1nc(Cc2cccc3ccccc23)[nH]c(=O)c1OCc1ccccc1]

Step 1: 2-Naphthalen-1-yl-acetamidine hydrochloride

To a stirred suspension of NH₄Cl (1.6 g, 30 mmol) in anhydrous toluene (50 mL) was added trimethyl aluminium (2M in toluene, 15 mL, 30 mmol) at 0° C. The mixture was then warmed to room temperature and stirred for 2 h. A solution of 2-(naphthalen-1-yl)acetonitrile (1.67 g, 10 mmol) in toluene (10 mL) was added to the above reaction mixture and the reaction mixture was stirred at 80° C. for 18 h. After completion of the reaction, the reaction mixture was quenched with a suspension of silica gel in chloroform. The mixture was stirred at room temperature for 0.5 h before being filtered through a sintered funnel. The silica gel was washed with methanol. The combined filtrate was concentrated under reduced pressure to give the crude product as an off-white solid (2 g, 91%), which was used directly without further purification.

MS (M+H)=185.3.

Step 2: 5-Benzyloxy-2-naphthalen-1-ylmethyl-6-oxo-1,6-dihydro-pyrimidine-4-carboxylic acid tert-butyl ester To a stirred solution of 2-naphthalen-1-yl-acetamidine hydrochloride (75) (0.9 g, 4.1 mmol) and (E)-2-benzyloxy-3-hydroxy-but-2-enedioic acid 4-tert-butyl ester 1-methyl ester (4) (1.3 g, 4.1 mmol) in anhydrous methanol (60 mL) at 0° C. was added a methanolic solution (Aldrich, 25%) of sodium methoxide (1.8 g, 8.2 mmol). The reaction mixture was slowly warmed to room temperature and stirred for 18 h. The reaction was quenched with aqueous HCl solution (1N). The pH of the mixture was adjusted to 6-7, then the mixture was evaporated. The residue was partitioned between ethyl acetate and water. The organic layer was separated, and the aqueous layer was extracted with ethyl acetate. The combined organic extract was washed with brine, dried over MgSO₄ and concentrated. The residue was purified by chromatography (30-50% ethyl acetate in hexanes) to give the product (76) as a white solid (1 g, 55%).

MS (M+H)=443.2.

Preparation of (77)

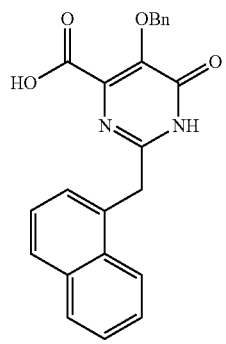 [SMILES: O=C(O)c1nc(Cc2cccc3ccccc23)[nH]c(=O)c1OCc1ccccc1]

Step 3: 5-Benzyloxy-2-naphthalen-1-ylmethyl-6-oxo-1,6-dihydro-pyrimidine-4-carboxylic acid To a solution of 5-benzyloxy-2-naphthalen-1-ylmethyl-6-oxo-1,6-dihydro-pyrimidine-4-carboxylic acid tert-butyl ester (76) (0.8 g, 1.8 mmol) in tetrahydrofuran (30 mL) and water (15 mL) was added LiOH (0.2 g, 9 mmol). The reaction mixture was heated at 80° C. for 18 h. TLC analysis indicated the completion of reaction, and the mixture was concentrated to a small volume, then washed with ethyl acetate. The aqueous portion was acidified with aqueous HCl solution (1N) to pH 3-4, then extracted with ethyl acetate and dichloromethane. The combined organic extract was washed with brine, dried over MgSO$_4$, and concentrated to give the crude product (77) as a white solid (0.69 g, 99%), which was used directly without further purification.

MS (M+H)=387.2.

Preparation of (78)

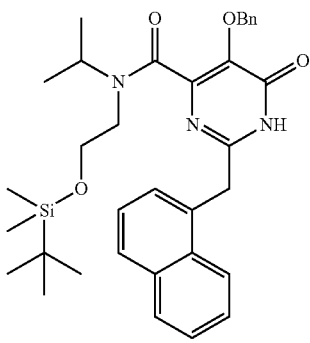 [SMILES: CC(C)N(CCO[Si](C)(C)C(C)(C)C)C(=O)c1nc(Cc2cccc3ccccc23)[nH]c(=O)c1OCc1ccccc1]

Step 4: 5-Benzyloxy-2-naphthalen-1-ylmethyl-6-oxo-1,6-dihydro-pyrimidine-4-carboxylic acid [2-(tert-butyl-dimethylsilanyloxy)-ethyl]-isopropylamide To a stirred solution of 5-benzyloxy-2-naphthalen-1-ylmethyl-6-oxo-1,6-dihydro-pyrimidine-4-carboxylic acid (77) (0.6 g, 1.6 mmol) and [2-(tert-butyl-dimethylsilanyloxy)-ethyl]-isopropyl-amine (8b) (0.5 g, 2.3 mmol) in pyridine (40 mL) was slowly added POCl$_3$ (0.43 mL, 4.7 mmol) at −10° C. The reaction mixture was stirred at 0° C. for 2 h. The mixture was loaded into a pad of silica gel and directly purified by chromatography (40-60% ethyl acetate in hexanes) to give the product (78) as an off-white solid (0.45 g, 50%).

MS (M+H)=586.3.

Preparation of (79)

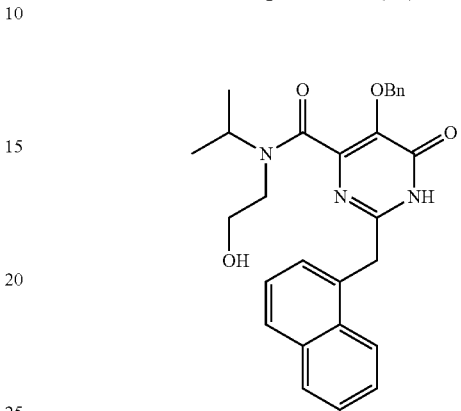

Step 5: 5-Benzyloxy-2-naphthalen-1-ylmethyl-6-oxo-1,6-dihydro-pyrimidine-4-carboxylic acid (2-hydroxyethyl)-isopropylamide To a stirred solution of 5-benzyloxy-2-naphthalen-1-ylmethyl-6-oxo-1,6-dihydro-pyrimidine-4-carboxylic acid [2-(tert-butyl-dimethylsilanyloxy)-ethyl]-isopropylamide (78) (0.45 g, 0.77 mmol) in tetrahydrofuran (30 mL) was added aqueous HCl (1N, 1 mL, 1 mmol). The reaction mixture was stirred at room temperature for 1 h. The mixture was neutralized with aqueous saturated NaHCO$_3$ solution to pH 7, then extracted with ethyl acetate. The organic layer was separated, and the aqueous layer was extracted with ethyl acetate. The combined organic extract was dried over MgSO$_4$ and concentrated. The residue was purified by chromatography (50-80% ethyl acetate in hexanes) to give the product (79) as a white solid (0.36 g, 99%).

MS (M+H)=472.2.

Preparation of (80)

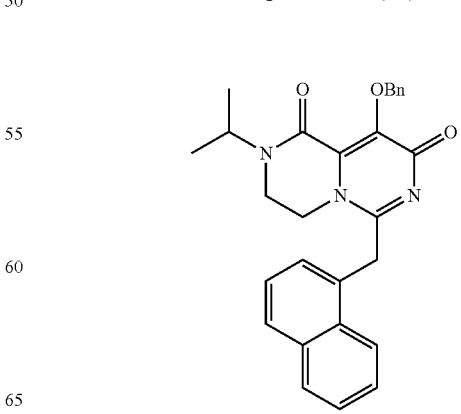

Step 6: 9-Benzyloxy-2-isopropyl-6-naphthalen-1-ylmethyl-2,3,4,7-tetrahydro-pyrazino[1,2-c]pyrimidine-1,8-dione To a stirred solution of 5-benzyloxy-2-naphthalen-1-ylmethyl-6-oxo-1,6-dihydro-pyrimidine-4-carboxylic acid (2-hydroxyethyl)-isopropylamide (79) (0.36 g, 0.76 mmol) in dichloromethane (20 mL) was added triphenylphosphine (0.2 g, 0.76 mmol). The mixture was stirred at room temperature for 10 min. Then diisopropyl azodicarboxylate (DIAD) (0.15 mL, 0.76 mmol) was added. The reaction mixture was stirred at room temperature for 2 h. The mixture was concentrated, and the residue was purified by chromatography (0-10% methanol in ethyl acetate) to give the product (80) as a white solid (0.23 g, 66%).
MS (M+H)=454.2.

Preparation of (81)

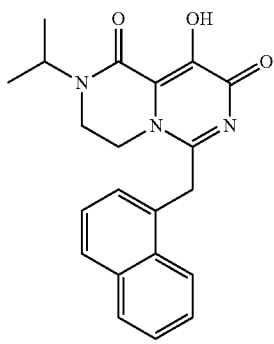 [SMILES: CC(C)N1CCn2c(Cc3cccc4ccccc34)nc(=O)c(O)c2C1=O]

Step 7: 9-Hydroxy-2-isopropyl-6-naphthalen-1-ylmethyl-3,4-dihydro-2H-pyrazino[1,2-c]pyrimidine-1,8-dione To a solution of 9-benzyloxy-2-isopropyl-6-naphthalen-1-ylmethyl-2,3,4,7-tetrahydro-pyrazino[1,2-c]pyrimidine-1,8-dione (80) (0.23 g, 0.51 mmol) in methanol (10 mL) was added concentrated HCl (aq 37%, 3 mL). The reaction mixture was stirred at room temperature for 24 h, then concentrated. To the residue was added aqueous saturated NaHCO₃ solution, extraction with 10% methanol in dichloromethane was conducted twice. The combined organic extract was concentrated. The residue was purified by chromatography (10-20% methanol in dichloromethane) to give the title compound (81) as a white solid (0.1 g, 54%).
MS (M+H)=364.2.
$^1$H NMR (dimethyl sulfoxide-d$_6$) δ: 8.06-8.30 (m, 1H), 7.94-8.04 (m, 1H), 7.90 (d, J=8.3 Hz, 1H), 7.54-7.65 (m, 2H), 7.49 (t, J=7.7 Hz, 1H), 7.15 (d, J=6.5 Hz, 1H), 4.80-4.96 (m, 1H), 4.54-4.72 (m, 2H), 4.00-4.27 (m, 2H), 3.63 (br. s., 1H), 3.52 (br. s., 1H), 1.06-1.29 (m, 6H)

Example 89

6-(1-Biphenyl-2-yl-ethyl)-9-hydroxy-2-isopropyl-3,4-dihydro-2H-pyrazino[1,2-c]pyrimidine-1,8-dione The synthetic procedure used in this preparation is outlined in Scheme 14.

Scheme 14

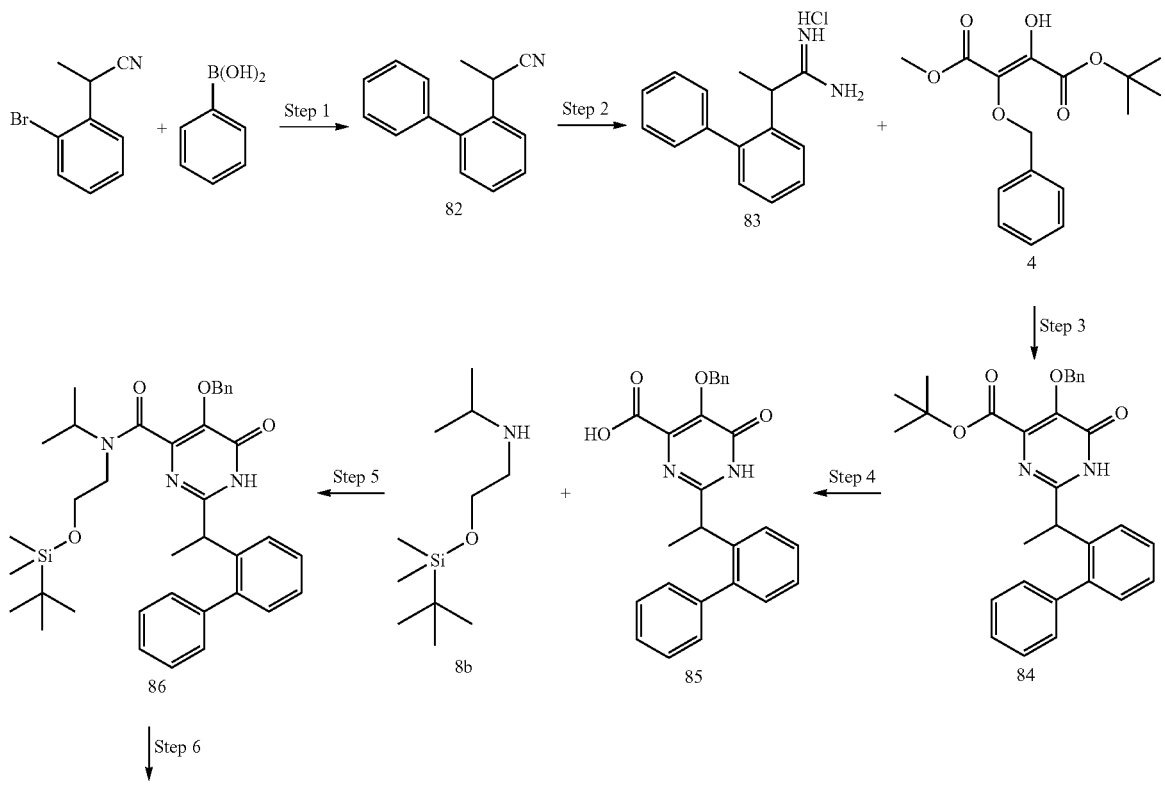

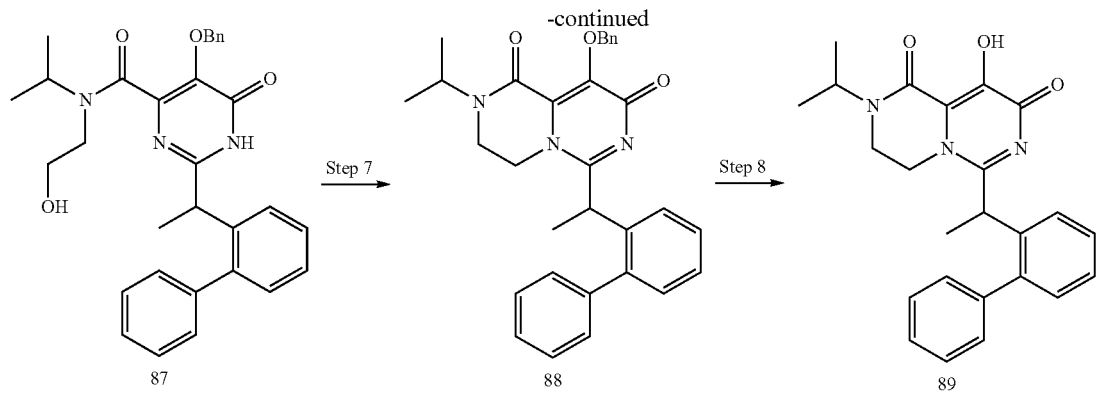

87 88 89

Preparation of (82)

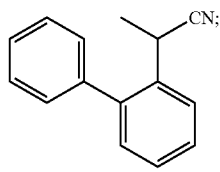 [SMILES: CC(C#N)c1ccccc1-c1ccccc1]

Step 1 2-Biphenyl-2-yl-propionitrile

To a suspension of 2-(2-bromophenyl)-propionitrile (2.1 g, 10 mmol) and phenylboronic acid (1.8 g, 15 mmol) in anhydrous methanol (10 mL) and toluene (20 mL) was added $Cs_2CO_3$ (9.8 g, 30 mmol). The mixture was degassed with nitrogen, followed by the addition of tetrakis(triphenylphosphine)palladium (0.58 g, 0.5 mmol). The reaction mixture was heated at 80° C. and stirred for 24 h. The mixture was cooled to room temperature and filtered through a short pad of silica gel. The silica gel was washed with ethyl acetate. The filtrate was concentrated. The residue was purified by chromatography (10-30% ethyl acetate in hexanes) to give the product (82) as a colorless oil (1.8 g, 87%).

Preparation of (83)

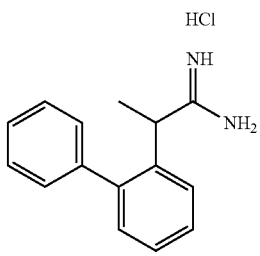 [SMILES: Cl ; CC(C(=N)N)c1ccccc1-c1ccccc1]

Step 2: 2-Biphenyl-2-yl-propionamidine hydrochloride

To a stirred suspension of $NH_4Cl$ (1.4 g, 26 mmol) in anhydrous toluene (40 mL) was added trimethylaluminum (2M in toluene, 13 mL, 26 mmol) at 0° C. The mixture was then warmed to room temperature and stirred for 2 h. A solution of 2-biphenyl-2-yl-propionitrile (82) (1.8 g, 8.7 mmol) in toluene (10 mL) was added to the above reaction mixture and the reaction mixture was stirred at 80° C. for 18 h. After completion of the reaction, the mixture was quenched with a suspension of silica gel in chloroform. The mixture was stirred at room temperature for 0.5 h, then filtered through a sintered funnel. The silica gel was washed with methanol. The combined filtrate was concentrated under reduced pressure to give the crude product (83) as an off-white solid (2.3 g, 100%), which was used directly without further purification.

Preparation of (84)

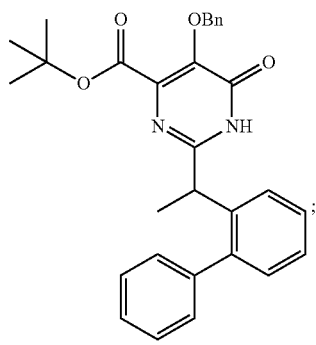 [SMILES: CC(c1nc(C(=O)OC(C)(C)C)c(OCc2ccccc2)c(=O)[nH]1)c1ccccc1-c1ccccc1]

Step 3: 5-Benzyloxy-2-(1-biphenyl-2-yl-ethyl)-6-oxo-1,6-dihydro-pyrimidine-4-carboxylic acid tert-butyl ester To a stirred solution of 2-biphenyl-2-yl-propionamidine hydrochloride (83) (2.3 g, 8.7 mmol) and (E)-2-benzyloxy-3-hydroxy-but-2-enedioic acid 4-tert-butyl ester 1-methyl ester (4) (2.7 g, 8.7 mmol) in anhydrous methanol (40 mL) at 0° C. was added a methanolic solution (Aldrich, 25%) of sodium methoxide (5.6 g, 26 mmol). The reaction mixture was slowly warmed to room temperature and stirred for 18 h. The reaction was quenched with aqueous HCl solution (1N). The pH of the mixture was adjusted to 6-7, then the mixture was evaporated. The residue was partitioned between ethyl acetate and water. The organic layer was separated, and the aqueous layer was extracted with ethyl acetate. The combined organic extract was washed with brine, dried over $MgSO_4$ and concentrated. The residue was purified by chromatography (30-50% ethyl acetate in hexanes) to give the product (84) as a white solid (2.4 g, 57%).

MS (M+H)=483.6.

Preparation of (85)

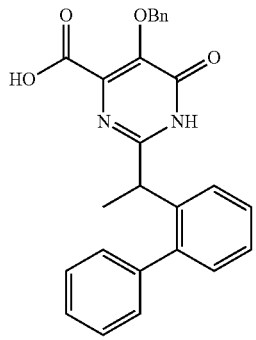 [SMILES: CC(c1nc(C(=O)O)c(OCc2ccccc2)c(=O)[nH]1)c1ccccc1-c1ccccc1]

Step 4: 5-Benzyloxy-2-(1-biphenyl-2-yl-ethyl)-6-oxo-1,6-dihydro-pyrimidine-4-carboxylic acid To a solution of 5-benzyloxy-2-(1-biphenyl-2-yl-ethyl)-6-oxo-1,6-dihydro-pyrimidine-4-carboxylic acid tert-butyl ester (84) (2.4 g, 4.9 mmol) in tetrahydrofuran (60 mL) and water (30 mL) was added LiOH (0.6 g, 30 mmol). The reaction mixture was heated at 80° C. for 24 h. TLC analysis indicated the completion of reaction. The mixture was concentrated to a small volume, then extracted with ethyl acetate. The aqueous portion was acidified with aqueous HCl solution (1N) to pH 3, then extracted with ethyl acetate and dichloromethane. The combined organic extract was washed with brine, dried over MgSO$_4$, and concentrated to give the crude product (85) as a white foam (1.5 g, 71%), which was used directly without further purification.

Preparation of (86)

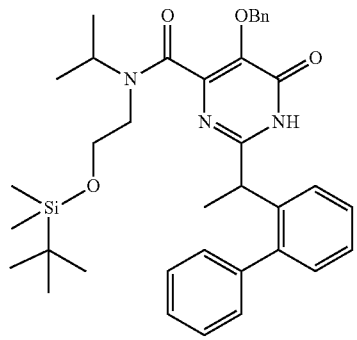 [SMILES: CC(c1nc(C(=O)N(CCO[Si](C)(C)C(C)(C)C)C(C)C)c(OCc2ccccc2)c(=O)[nH]1)c1ccccc1-c1ccccc1]

Step 5: 5-Benzyloxy-2-(1-biphenyl-2-yl-ethyl)-6-oxo-1,6-dihydro-pyrimidine-4-carboxylic acid [2-(tert-butyl-dimethylsilanyloxy)-ethyl]-isopropylamide To a stirred solution of 5-benzyloxy-2-(1-biphenyl-2-yl-ethyl)-6-oxo-1,6-dihydro-pyrimidine-4-carboxylic acid (85) (1.5 g, 3.5 mmol) and [2-(tert-butyl-dimethylsilanyloxy)-ethyl]-isopropyl-amine (8b) (1.2 g, 5.3 mmol) in pyridine (40 mL) was slowly added POCl$_3$ (0.49 g, 5.3 mmol) at −10° C. The reaction mixture was stirred at 0° C. for 2 h. The mixture was loaded into a pad of silica gel and directly purified by chromatography (40-60% ethyl acetate in hexanes) to give the product (86) as a white foam (1.5 g, 68%).

MS (M+H)=626.3.

Preparation of (87)

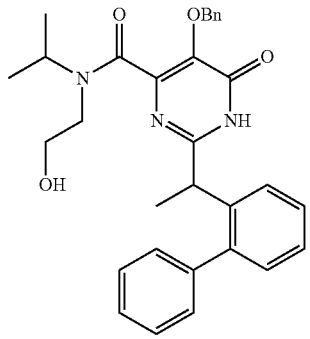 [SMILES: CC(c1nc(C(=O)N(CCO)C(C)C)c(OCc2ccccc2)c(=O)[nH]1)c1ccccc1-c1ccccc1]

Step 6: 5-Benzyloxy-2-(1-biphenyl-2-yl-ethyl)-6-oxo-1,6-dihydro-pyrimidine-4-carboxylic acid (2-hydroxyethyl)-isopropylamide To a stirred solution of 5-benzyloxy-2-(1-biphenyl-2-yl-ethyl)-6-oxo-1,6-dihydro-pyrimidine-4-carboxylic acid [2-(tert-butyl-dimethylsilanyloxy)-ethyl]-isopropylamide (86) (1.5 g, 2.4 mmol) in tetrahydrofuran (20 mL) was added aqueous HCl (1N, 2.4 mL, 2.4 mmol). The reaction mixture was stirred at room temperature for 1 h. The mixture was neutralized with aqueous saturated NaHCO$_3$ solution to pH 7, then extracted with ethyl acetate. The organic layer was separated, and the aqueous layer was extracted with ethyl acetate. The combined organic extract was dried over MgSO$_4$ and concentrated. The residue was purified by chromatography (50-80% ethyl acetate in hexanes) to give the product (87) as a white solid (0.9 g, 73%).

MS (M+H)=512.2.

Preparation of (88)

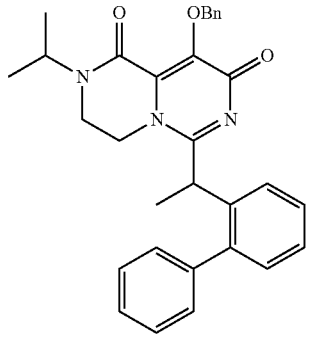 [SMILES: CC(c1ccccc1-c1ccccc1)c1nc(=O)c(OCc2ccccc2)c2n1CCN(C(C)C)C2=O]

Step 7: 9-Benzyloxy-6-(1-biphenyl-2-yl-ethyl)-2-isopropyl-3,4-dihydro-2H-pyrazino[1,2-c]pyrimidine-1,8-dione To a stirred solution of 5-benzyloxy-2-(1-biphenyl-2-yl-ethyl)-6-oxo-1,6-dihydro-pyrimidine-4-carboxylic acid (2-hydroxyethyl)-isopropylamide (87) (0.9 g, 1.8 mmol) in dichloromethane (30 mL) was added triphenylphosphine (0.47 g, 1.8 mmol). The mixture was stirred at room temperature for 10 min. Then diisopropyl azodicarboxylate (DIAD) (0.35 mL, 1.8 mmol) was added. The reaction mixture was stirred at room temperature for 0.5 h. The mixture was concentrated, and the residue was purified by chromatography (50-100% ethyl acetate in hexanes) to give the product (88) as a white foam (0.22 g, 25%).

MS (M+H)=494.2

Preparation of (89)

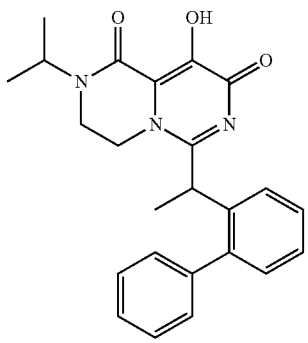

Step 8: 6-(1-Biphenyl-2-yl-ethyl)-9-hydroxy-2-isopropyl-3,4-dihydro-2H-pyrazino[1,2-c]pyrimidine-1,8-dione To a solution of 9-benzyloxy-6-(1-biphenyl-2-yl-ethyl)-2-isopropyl-3,4-dihydro-2H-pyrazino[1,2-c]pyrimidine-1,8-dione (88) (0.22 g, 0.45 mmol) in methanol (10 mL) was added concentrated HCl (aq 37%, 6 mL). The reaction mixture was stirred at 40° C. for 48 h, then concentrated to dryness. To the residue was added aqueous saturated NaHCO$_3$ solution, extraction with 10% methanol in dichloromethane was conducted twice. The combined organic extract was concentrated. The residue was purified by chromatography (10-20% methanol in dichloromethane) to give the title compound (89) as a white solid (45 mg, 25%).

MS (M+H)=404.2.

$^1$H NMR (dimethyl sulfoxide-d$_6$) δ: 7.10-7.69 (m, 9H), 4.52-4.68 (m, 1H), 4.06-4.26 (m, 3H), 2.94-3.22 (m, 4H), 1.36-1.56 (m, 2H), 0.98-1.25 (m, 6H)

Example 100

9-Hydroxy-2-isopropyl-6-(4-phenyl-thiophen-3-ylmethyl)-3,4-dihydro-2H-pyrazino[1,2-c]pyrimidine-1,8-dione The synthetic procedure used in this preparation is outlined in Scheme 15

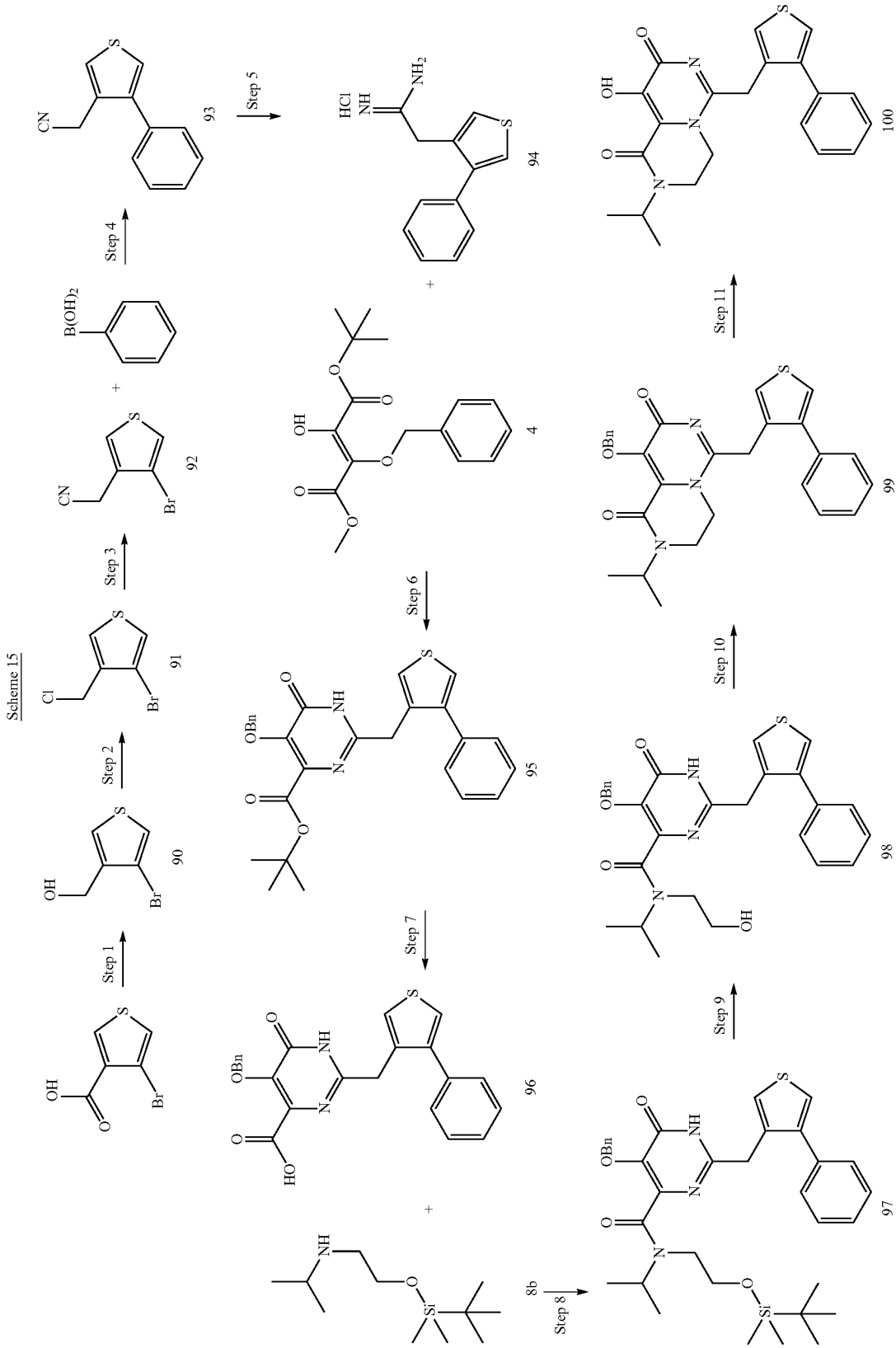

Preparation of 90

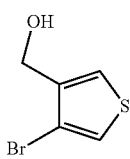

Step 1: (4-Bromo-thiophen-3-yl)-methanol

To a solution of 4-bromothiophene-3-carboxylic acid (3.6 g, 17 mmol) in anhydrous tetrahydrofuran at 0° C. was added a tetrahydrofuran solution (Aldrich, 1M) of BH$_3$.tetrahydrofuran (243 mL, 0.24 mol). The reaction mixture was stirred at 0° C. for 0.5 h, then at room temperature for 2 h. The mixture was concentrated, and the residue was partitioned between ethyl acetate and aqueous dilute HCl solution. The organic layer was separated, and the aqueous layer was extracted with ethyl acetate. The combined organic extract was washed with saturated NaHCO$_3$ solution and brine, and then dried over MgSO$_4$, and concentrated. The residue was purified by chromatography (10-50% ethyl acetate in hexanes) to give the product (90) as a colorless oil (2.6 g, 78%).

Preparation of (91)

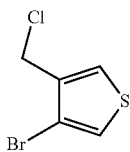

Step 2: 3-Bromo-4-chloromethyl-thiophene

To a solution of (4-bromothiophen-3-yl)methanol (90) (2.6 g, 14 mmol) and triethylamine (5.6 mL, 40 mmol) in dichloromethane (20 mL) at 0° C. was added methanesulfonic chloride (1.6 mL, 20 mmol). The reaction mixture was stirred at 0° C. for 0.5 h, then warmed to room temperature for 2 h, and then quenched by aqueous HCl solution. The mixture was partitioned between water and ethyl acetate. The organic layer was separated, and the aqueous layer was extracted with ethyl acetate and chloroform. The combined organic extract was dried over MgSO$_4$, and concentrated. The residue was purified by chromatography (10-20% ethyl acetate in hexanes) to give the product (91) as a colorless oil (1 g, 35%).

Preparation of (92)

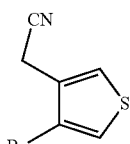

Step 3: (4-Bromo-thiophen-3-yl)-acetonitrile

To a solution of 3-bromo-4-chloromethyl-thiophene (91) (1 g, 4.7 mmol) in anhydrous dimethyl sulfoxide at room temperature was added sodium cyanide. The reaction mixture was heated at 80° C. for 3 h, then cooled to room temperature. The mixture was partitioned between ethyl ether and water. The organic layer was separated, and the aqueous layer was extracted with ethyl acetate. The combined organic extract was washed with water and brine and then dried over MgSO$_4$, and concentrated. The residue was purified by chromatography (20-40% ethyl acetate in hexanes) to give the product (92) as a light yellow oil (0.7 g, 73%).

Preparation of (93)

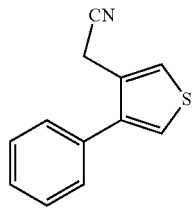 [SMILES: N#CCc1cscc1-c1ccccc1]

Step 4: (4-Phenyl-thiophen-3-yl)-acetonitrile

To a suspension of (4-bromo-thiophen-3-yl)-acetonitrile (92) (0.7 g, 3.5 mmol) and phenylboronic acid (0.6 g, 5.2 mmol) in anhydrous methanol (10 mL) and toluene (20 mL) was added Cs$_2$CO$_3$ (3.4 g, 10 mmol). The mixture was degassed with nitrogen, followed by the addition of tetrakis(triphenylphosphine)palladium (0.4 g, 0.3 mmol). The reaction mixture was heated at 80° C. and stirred for 18 h. The mixture was cooled to room temperature and filtered through a short pad of silica gel. The silica gel was washed with ethyl acetate. The filtrate was concentrated. The residue was purified by chromatography (10-30% ethyl acetate in hexanes) to give the product (93) as a brown oil (0.7 g, 100%).

Preparation of (94)

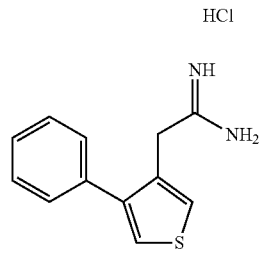 [SMILES: Cl ; N=C(N)Cc1cscc1-c1ccccc1]

Step 5: 2-(4-Phenyl-thiophen-3-yl)-acetamidine hydrochloride

To a stirred suspension of NH$_4$Cl (0.55 g, 10 mmol) in anhydrous toluene (20 mL) was added trimethylaluminum (2M in toluene, 5.2 mL, 10 mmol) at 0° C. The mixture was then warmed to room temperature and stirred for 2 h. A solution of (4-phenyl-thiophen-3-yl)-acetonitrile (93) (0.7 g, 3.5 mmol) in toluene (10 mL) was added to the above reaction mixture and was stirred at 80° C. for 18 h. After completion of the reaction, the mixture was quenched with a suspension of silica gel in chloroform. The mixture was stirred at room temperature for 0.5 h, then filtered through a sintered funnel. The silica gel was washed with methanol. The combined filtrate was concentrated under reduced pressure to give the crude product (94) as an off-white solid (0.9 g, 100%), which was used directly without further purification.

MS (M+H)=217.1.

Preparation of (95)

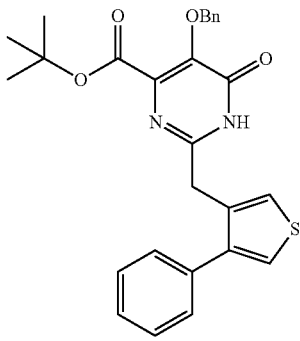 [SMILES: CC(C)(C)OC(=O)c1nc(Cc2cscc2-c2ccccc2)[nH]c(=O)c1OCc1ccccc1]

Step 6: 5-Benzyloxy-6-oxo-2-(4-phenyl-thiophen-3-ylmethyl)-1,6-dihydro-pyrimidine-4-carboxylic acid tert-butyl ester To a stirred solution of 2-(4-phenyl-thiophen-3-yl)-acetamidine hydrochloride (94) (0.9 g, 3.5 mmol) and (E)-2-benzyloxy-3-hydroxy-but-2-enedioic acid 4-tert-butyl ester 1-methyl ester (4) (1.6 g, 5.2 mmol) in anhydrous methanol (40 mL) was added a methanolic solution (Aldrich, 25%) of sodium methoxide (2.3 g, 11 mmol) at 0° C. The reaction mixture was slowly warmed to room temperature and stirred for 18 h. The reaction was quenched with aqueous HCl solution (1N). The pH of the mixture was adjusted to 6-7, then the mixture was evaporated. The residue was partitioned between ethyl acetate and water. The organic layer was separated, and the aqueous layer was extracted with ethyl acetate. The combined organic extract was washed with brine, dried over MgSO4 and concentrated. The residue was purified by chromatography (30-50% ethyl acetate in hexanes) to give the product (95) as a white solid (0.9 g, 53%).

MS (M+H)=475.1.

Preparation of (96)

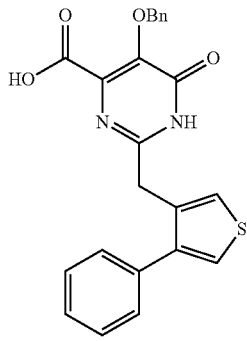

Step 7: 5-Benzyloxy-6-oxo-2-(4-phenyl-thiophen-3-ylmethyl)-1,6-dihydro-pyrimidine-4-carboxylic acid To a solution of 5-benzyloxy-6-oxo-2-(4-phenyl-thiophen-3-ylmethyl)-1,6-dihydro-pyrimidine-4-carboxylic acid tert-butyl ester (95) (0.9 g, 1.9 mmol) in tetrahydrofuran (40 mL) and water (20 mL) was added LiOH (0.2 g, 9.5 mmol). The reaction mixture was heated at 80° C. for 24 h. TLC analysis indicated the completion of reaction, and the mixture was concentrated to a small volume, then extracted with ethyl acetate. The aqueous potion was acidified with aqueous HCl solution (1N) to pH 6-7, then extracted with ethyl acetate and dichloromethane. The combined organic extract was washed with brine, dried over MgSO4, and concentrated to give the crude product (96) as a white foam (0.3 g, 38%), which was used directly without further purification.

MS (M+H)=419.1.

Preparation of (97)

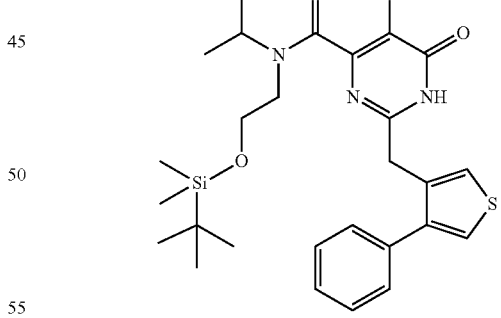

Step 9: 5-Benzyloxy-6-oxo-2-(4-phenyl-thiophen-3-ylmethyl)-1,6-dihydro-pyrimidine-4-carboxylic acid [2-(tert-butyl-dimethylsilanyloxy)-ethyl]-isopropylamide To a stirred solution of 5-benzyloxy-6-oxo-2-(4-phenyl-thiophen-3-ylmethyl)-1,6-dihydro-pyrimidine-4-carboxylic acid (96) (0.3 g, 0.7 mmol) and [2-(tert-butyl-dimethylsilanyloxy)-ethyl]-isopropyl-amine (8b) (0.2 g, 1.1 mmol) in pyridine (30 mL) was slowly added POCl₃ (0.2 g, 2.2 mmol) at −10° C. The reaction mixture was stirred at 0° C. for 2 h. The mixture was loaded into a pad of silica gel and directly purified by chromatography (40-60% ethyl acetate in hexanes) to give the product (97) as a white solid (0.22 g, 50%).

MS (M+H)=618.4.

Preparation of (98)

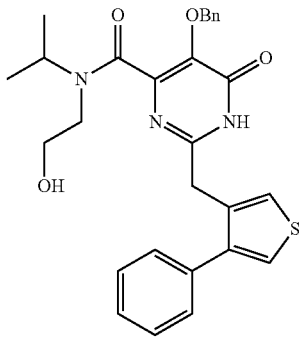 [SMILES: CC(C)N(CCO)C(=O)c1nc(Cc2cscc2-c2ccccc2)[nH]c(=O)c1OCc1ccccc1]

Step 10: 5-Benzyloxy-6-oxo-2-(4-phenyl-thiophen-3-ylmethyl)-1,6-dihydro-pyrimidine-4-carboxylic acid (2-hydroxyethyl)-isopropylamide To a stirred solution of 5-benzyloxy-6-oxo-2-(4-phenyl-thiophen-3-ylmethyl)-1,6-dihydro-pyrimidine-4-carboxylic acid [2-(tert-butyl-dimethylsilanyloxy)-ethyl]-isopropylamide (97) (0.22 g, 0.35 mmol) in tetrahydrofuran (10 mL) was added aqueous HCl (1N, 1 mL, 1 mmol). The reaction mixture was stirred at room temperature for 1 h. The mixture was neutralized with aqueous saturated NaHCO₃ solution to pH 7, then extracted with ethyl acetate. The organic layer was separated, and the aqueous layer was extracted with ethyl acetate. The combined organic extract was dried over MgSO₄ and concentrated. The residue was purified by chromatography (50-80% ethyl acetate in hexanes) to give the product (98) as a white solid (0.12 g, 67%).

MS (M+H)=504.2.

Preparation of (99)

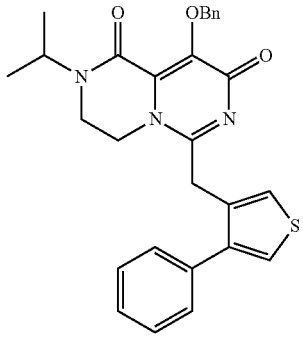 [SMILES: CC(C)N1CCn2c(Cc3cscc3-c3ccccc3)nc(=O)c(OCc3ccccc3)c2C1=O]

Step 11: 9-Benzyloxy-2-isopropyl-6-(4-phenyl-thiophen-3-ylmethyl)-3,4-dihydro-2H-pyrazino[1,2-c]pyrimidine-1,8-dione To a stirred solution of 5-benzyloxy-6-oxo-2-(4-phenyl-thiophen-3-ylmethyl)-1,6-dihydro-pyrimidine-4-carboxylic acid (2-hydroxyethyl)-isopropylamide (98) (0.12 g, 0.24 mmol) in dichloromethane (20 mL) was added triphenylphosphine (0.06 g, 0.24 mmol). The mixture was stirred at room temperature for 10 min. Then diisopropyl azodicarboxylate (DIAD) (0.046 mL, 0.24 mmol) was added. The reaction mixture was stirred at room temperature for 2 h. The mixture was concentrated, and the residue was purified by chromatography (0-10% methanol in ethyl acetate) to give the product (99) as a white foam (0.08 g, 69%).

MS (M+H)=486.3.

Preparation of (100)

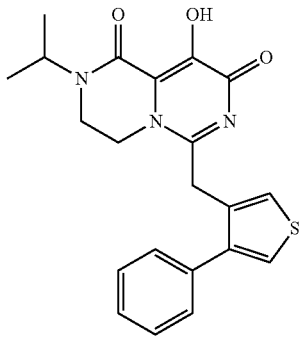 [SMILES: CC(C)N1CCn2c(Cc3cscc3-c3ccccc3)nc(=O)c(O)c2C1=O]

Step 12: 9-Hydroxy-2-isopropyl-6-(4-phenyl-thiophen-3-ylmethyl)-3,4-dihydro-2H-pyrazino[1,2-c]pyrimidine-1,8-dione To a solution of 9-benzyloxy-2-isopropyl-6-(4-phenyl-thiophen-3-ylmethyl)-3,4-dihydro-2H-pyrazino[1,2-c]pyrimidine-1,8-dione (99) (0.08 g, 0.17 mmol) in methanol (5 mL) was added concentrated HCl (aq 37%, 5 mL). The reaction mixture was stirred at 40° C. for 48 h, then concentrated to dryness. To the residue was added aqueous saturated NaHCO₃ solution. The mixture was extracted with 10% methanol in dichloromethane twice. The combined organic extract was concentrated. The residue was purified by chromatography (10-20% methanol in dichloromethane) to give the title compound (100) as a white solid (35 mg, 54%).

MS (M+H)=396.2.

¹H NMR (dimethyl sulfoxide-d₆) δ: 12.34 (s, 1H), 7.25-7.69 (m, 7H), 5.04 (s, 2H), 4.52-4.68 (m, 1H), 3.92-4.08 (m, 2H), 3.64-3.73 (m, 2H), 0.98-1.11 (m, 6H)

Example 108

6-(2',3'-Difluoro-biphenyl-2-ylmethyl)-9-hydroxy-2-isopropyl-3,4-dihydro-2H-pyrazino[1,2-c]pyrimidine-1,8-dione The synthetic procedure used in this preparation is outlined in Scheme 16.

123 124
Scheme 16
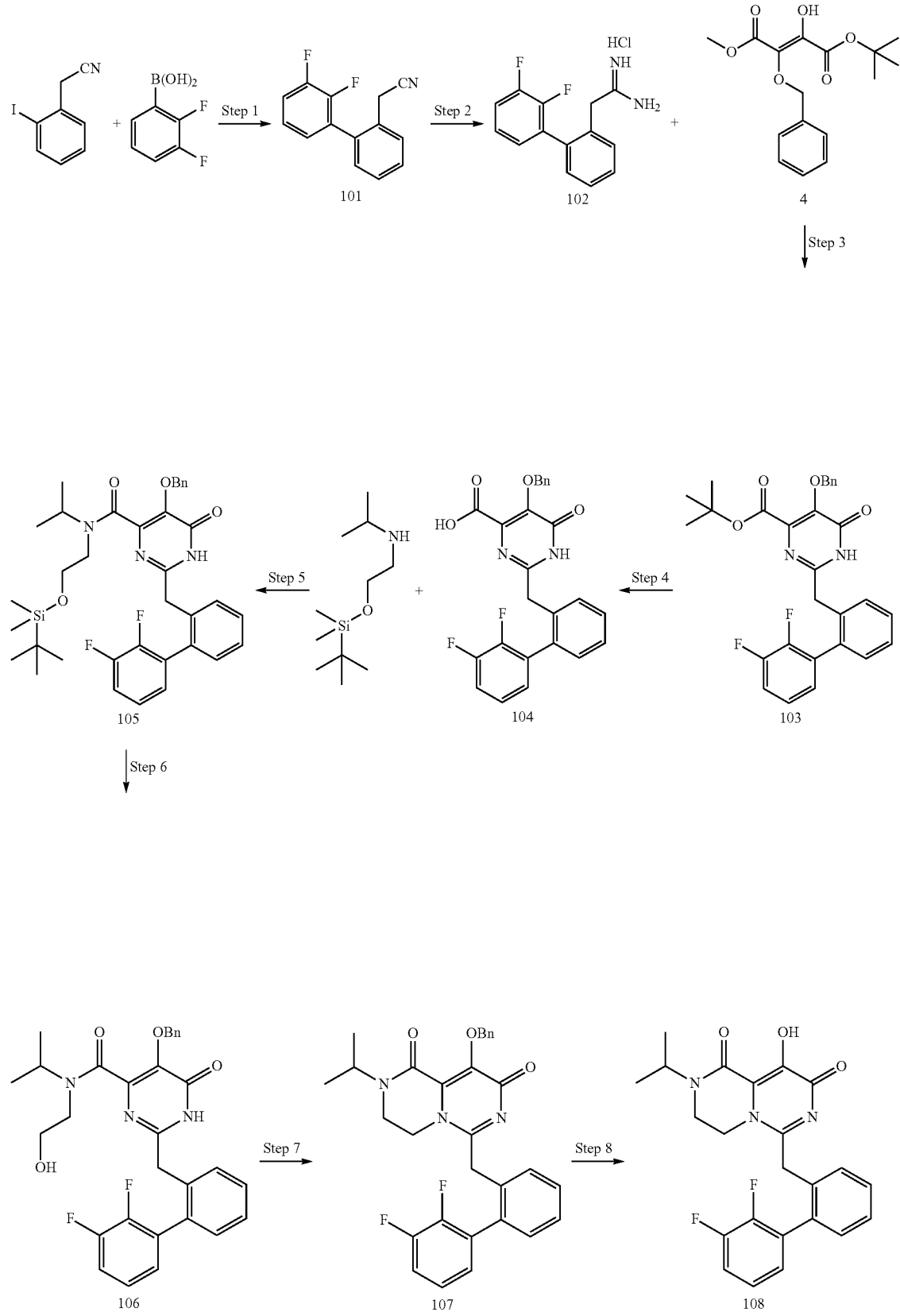

Preparation of (101)

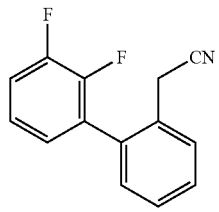 [SMILES: N#CCc1ccccc1-c1cccc(F)c1F]

Step 1: (2',3'-Difluoro-biphenyl-2-yl)-acetonitrile

To a suspension of (2-iodo-phenyl)-acetonitrile (Aldrich, 2.4 g, 10 mmol) and 2,3-difluorophenylboronic acid (Aldrich, 2.4 g, 15 mmol) in anhydrous methanol (10 mL) and toluene (20 mL) was added $Cs_2CO_3$ (9.8 g, 30 mmol). The mixture was degassed with nitrogen, followed by the addition of tetrakis(triphenylphosphine)palladium (1.2 g, 1 mmol).

The reaction mixture was heated at 80° C. and stirred for 18 h. The mixture was cooled to room temperature and filtered through a short pad of silica gel. The silica gel was washed with ethyl acetate. The filtrate was concentrated. The residue was purified by chromatography (10-30% ethyl acetate in hexanes) to give the product (101) as a colorless oil (1.4 g, 62%)

Preparation of (102)

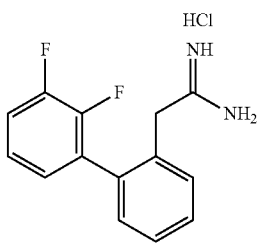 [SMILES: Cl ; N=C(N)Cc1ccccc1-c1cccc(F)c1F]

Step 2: 2-(2',3'-Difluoro-biphenyl-2-yl)-acetamidine hydrochloride

To a stirred suspension of $NH_4Cl$ (0.62 g, 11.5 mmol) in anhydrous toluene (50 mL) was added trimethylaluminum (2M in toluene, 13 mL, 26 mmol) at 0° C. The mixture was then warmed to room temperature and stirred for 2 h. A solution of (2',3'-difluoro-biphenyl-2-yl)-acetonitrile (101) (0.88 g, 3.9 mmol) in toluene (10 mL) was added to the above reaction mixture and stirred at 80° C. for 18 h. After completion of the reaction, the mixture was quenched with a suspension of silica gel in chloroform. The mixture was stirred at room temperature for 0.5 h, then filtered through a sintered funnel. The silica gel was washed with methanol. The combined filtrate was concentrated under reduced pressure to give the crude product (102) as an off-white solid (0.94 g, 100%), which was used directly without further purification.

MS (M+H)=247.2.

Preparation of (103)

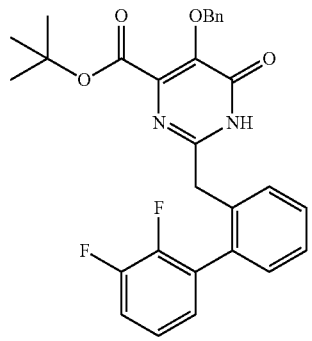 [SMILES: CC(C)(C)OC(=O)c1nc(Cc2ccccc2-c2cccc(F)c2F)[nH]c(=O)c1OCc1ccccc1]

Step 3: 5-Benzyloxy-2-(2',3'-difluoro-biphenyl-2-ylmethyl)-6-oxo-1,6-dihydro-pyrimidine-4-carboxylic acid tert-butyl ester To a stirred solution of 2-(2',3'-difluoro-biphenyl-2-yl)-acetamidine hydrochloride (102) (0.94 g, 3.3 mmol) and (E)-2-benzyloxy-3-hydroxy-but-2-enedioic acid 4-tert-butyl ester 1-methyl ester (4) (1.0 g, 3.3 mmol) in anhydrous methanol (40 mL) at 0° C. was added a methanolic solution (Aldrich, 25%) of sodium methoxide (2.2 g, 10 mmol). The reaction mixture was slowly warmed to room temperature and stirred for 18 h. The reaction was quenched with aqueous HCl solution (1N). The pH of the mixture was adjusted to 6-7, then the mixture was evaporated. The residue was partitioned between ethyl acetate and water. The organic layer was separated, and the aqueous layer was extracted with ethyl acetate. The combined organic extract was washed with brine, dried over $MgSO_4$ and concentrated. The residue was purified by chromatography (30-50% ethyl acetate in hexanes) to give the product (103) as a white solid (1.2 g, 72%).

MS (M+H)=505.2.

Preparation of (104)

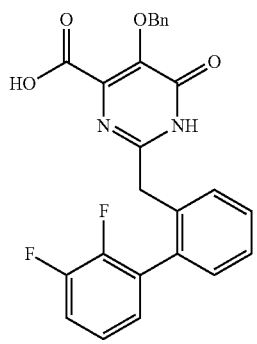 [SMILES: O=C(O)c1nc(Cc2ccccc2-c2cccc(F)c2F)[nH]c(=O)c1OCc1ccccc1]

Step 4: 5-Benzyloxy-2-(2',3'-difluoro-biphenyl-2-ylmethyl)-6-oxo-1,6-dihydro-pyrimidine-4-carboxylic acid To a solution of 5-benzyloxy-2-(2',3'-difluoro-biphenyl-2-ylmethyl)-6-oxo-1,6-dihydro-pyrimidine-4-carboxylic acid tert-butyl ester (103) (1.2 g, 2.4 mmol) in tetrahydrofuran (40 mL) and water (20 mL) was added LiOH (0.29 g, 12 mmol). The reaction mixture was heated at 80° C. for 24 h. TLC analysis indicated the completion of reaction, and the mixture was concentrated to a small volume, then extracted with ethyl acetate. The aqueous portion was acidified with aqueous HCl solution (1N) to pH 3, then extracted with ethyl acetate and dichloromethane. The combined organic extract was washed with brine, dried over MgSO$_4$, and concentrated to give the crude product (104) as a white solid (0.85 g, 71%), which was used directly without further purification.

Preparation of (105)

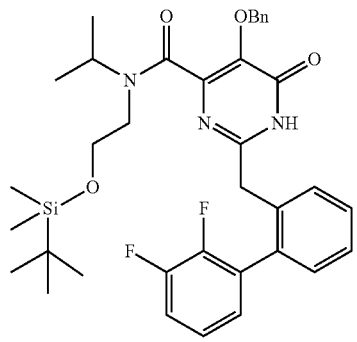 [SMILES: CC(C)N(CCO[Si](C)(C)C(C)(C)C)C(=O)c1nc(Cc2ccccc2-c2cccc(F)c2F)[nH]c(=O)c1OCc1ccccc1]

Step 5: 5-Benzyloxy-2-(2',3'-difluoro-biphenyl-2-ylmethyl)-6-oxo-1,6-dihydro-pyrimidine-4-carboxylic acid [2-(tert-butyl-dimethylsilanyloxy)-ethyl]-isopropylamide To a stirred solution of 5-benzyloxy-2-(2',3'-difluoro-biphenyl-2-ylmethyl)-6-oxo-1,6-dihydro-pyrimidine-4-carboxylic acid (104) (0.85 g, 1.9 mmol) and [2-(tert-butyl-dimethylsilanyloxy)-ethyl]-isopropyl-amine (8b) (0.62 g, 2.8 mmol) in pyridine (25 mL) was slowly added POCl$_3$ (0.27 g, 2.8 mmol) at −10° C. The reaction mixture was stirred at 0° C. for 2 h. The mixture was loaded into a pad of silica gel and directly purified by chromatography (40-60% ethyl acetate in hexanes) to give the product (105) as a white foam (0.7 g, 57%).
MS (M+H)=648.3.

Preparation of (106)

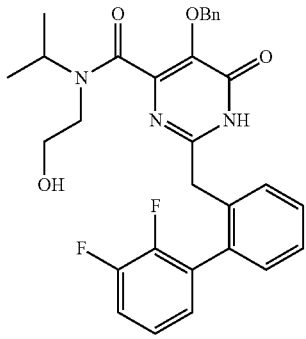 [SMILES: CC(C)N(CCO)C(=O)c1nc(Cc2ccccc2-c2cccc(F)c2F)[nH]c(=O)c1OCc1ccccc1]

Step 6: 5-Benzyloxy-2-(2',3'-difluoro-biphenyl-2-ylmethyl)-6-oxo-1,6-dihydro-pyrimidine-4-carboxylic acid (2-hydroxyethyl)-isopropylamide To a stirred solution of 5-benzyloxy-2-(2',3'-difluoro-biphenyl-2-ylmethyl)-6-oxo-1,6-dihydro-pyrimidine-4-carboxylic acid [2-(tert-butyl-dimethylsilanyloxy)-ethyl]-isopropylamide (105) (0.7 g, 1.1 mmol) in tetrahydrofuran (20 mL) was added aqueous HCl (1N, 2 mL, 6.6 mmol). The reaction mixture was stirred at room temperature for 1 h. The mixture was neutralized with aqueous saturated NaHCO$_3$ solution to pH 7, then extracted with ethyl acetate. The organic layer was separated, and the aqueous layer was extracted with ethyl acetate. The combined organic extract was dried over MgSO$_4$ and concentrated. The residue was purified by chromatography (50-80% ethyl acetate in hexanes) to give the product (106) as a white solid (0.57 g, 99%).
MS (M+H)=534.2.

Preparation of (107)

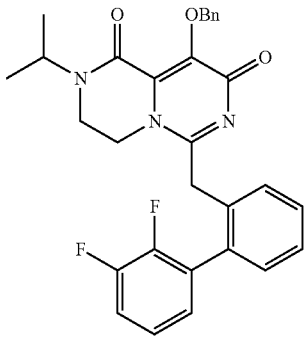 [SMILES: CC(C)N1CCn2c(Cc3ccccc3-c3cccc(F)c3F)nc(=O)c(OCc3ccccc3)c2C1=O]

Step 7: 9-Benzyloxy-6-(2',3'-difluoro-biphenyl-2-ylmethyl)-2-isopropyl-3,4-dihydro-2H-pyrazino[1,2-c]pyrimidine-1,8-dione To a stirred solution of 5-benzyloxy-2-(2',3'-difluoro-biphenyl-2-ylmethyl)-6-oxo-1,6-dihydro-pyrimidine-4-carboxylic acid (2-hydroxyethyl)-isopropylamide (106) (0.57 g, 1.8 mmol) in dichloromethane (20 mL) was added triphenylphosphine (0.28 g, 1.1 mmol). The mixture was stirred at room temperature for 10 min. Then diisopropyl azodicarboxylate (DIAD) (0.21 mL, 1.1 mmol) was added. The reaction mixture was stirred at room temperature for 0.5 h. The mixture was concentrated, and the residue was purified by chromatography (50-100% ethyl acetate in hexanes) to give the product (107) as a white foam (0.34 g, 62%).
MS (M+H)=516.2.

Preparation of (108)

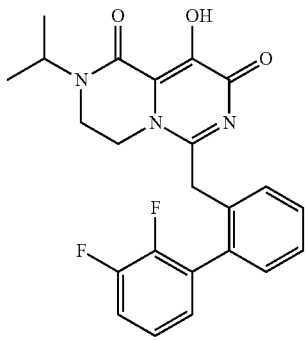

Step 8: 6-(2',3'-Difluoro-biphenyl-2-ylmethyl)-9-hydroxy-2-isopropyl-3,4-dihydro-2H-pyrazino[1,2-c]pyrimidine-1,8-dione To a solution of 9-benzyloxy-6-(2',3'-difluoro-biphenyl-2-ylmethyl)-2-isopropyl-3,4-dihydro-2H-pyrazino[1,2-c]pyrimidine-1,8-dione (107) (0.3 g, 0.58 mmol) in methanol (10 mL) was added concentrated HCl (aq 37%, 5 mL). The reaction mixture was stirred at 50° C. for 24 h, then concentrated to dryness. To the residue was added aqueous saturated NaHCO$_3$ solution, the mixture was extracted with 10% methanol in dichloromethane twice. The combined organic extract was concentrated. The residue was purified by chromatography (10-20% methanol in dichloromethane) to give the title compound (108) as a white solid (150 mg, 62%).

MS (M+H)=426.2.

$^1$H NMR (dimethyl sulfoxide-d$_6$) δ: 12.16-12.41 (m, 1H), 7.10-7.55 (m, 7H), 4.67 (quin, J=6.8 Hz, 1H), 3.94 (br. s., 2H), 3.77-3.90 (m, 2H), 3.48 (t, J=5.3 Hz, 2H), 1.13 (d, J=6.8 Hz, 6H)

Examples 118 and 119

Chiral 9-hydroxy-2-isopropyl-6-((1R,2S)-2-phenyl-cyclopentyl)-3,4-dihydro-2H-pyrazino[1,2-c]pyrimidine-1,8-dione & chiral 9-hydroxy-2-isopropyl-6-((1S,2R)-2-phenyl-cyclopentyl)-3,4-dihydro-2H-pyrazino[1,2-c]pyrimidine-1,8-dione The synthetic procedure used in this preparation is outlined in Scheme 17.

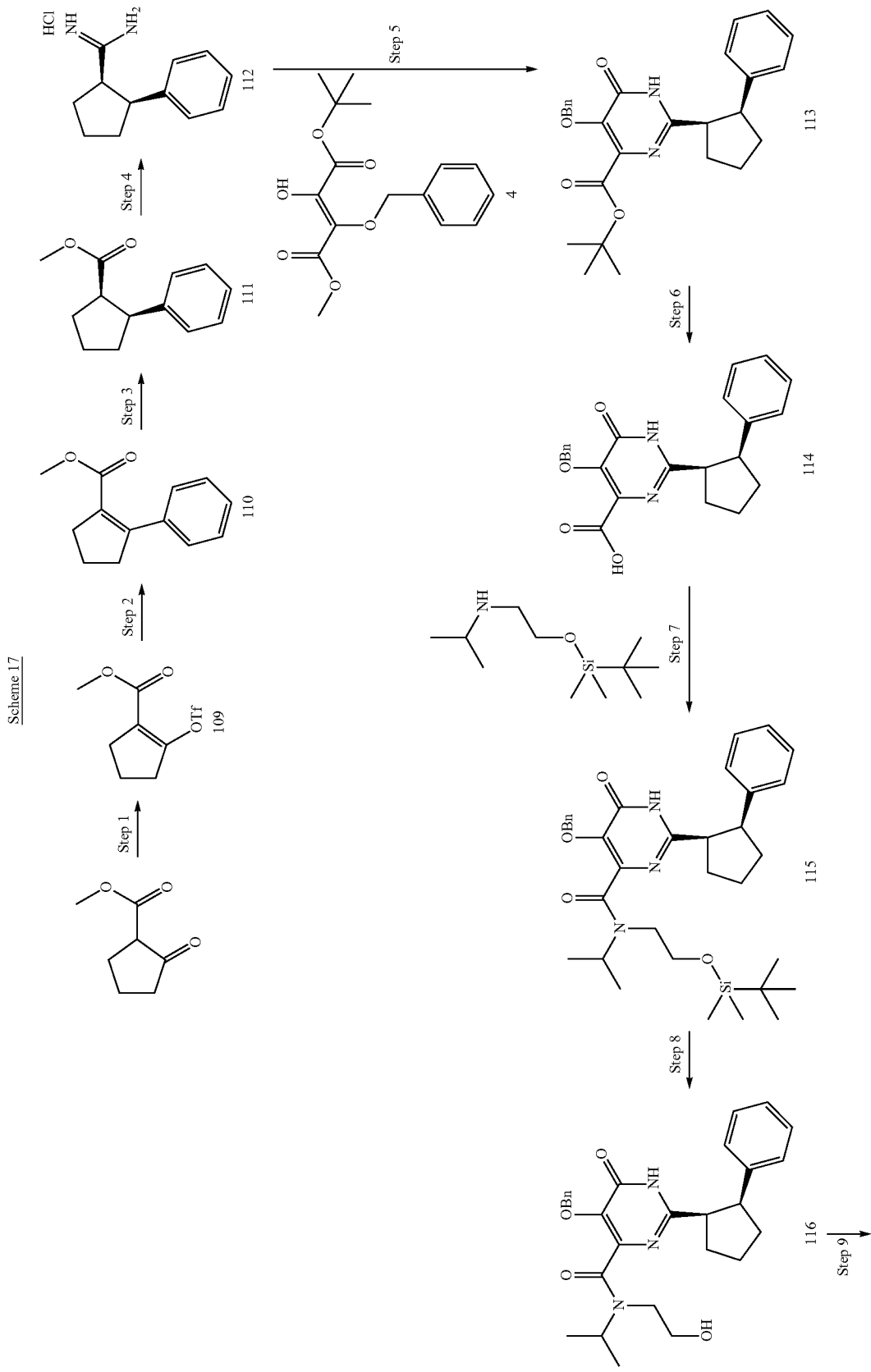

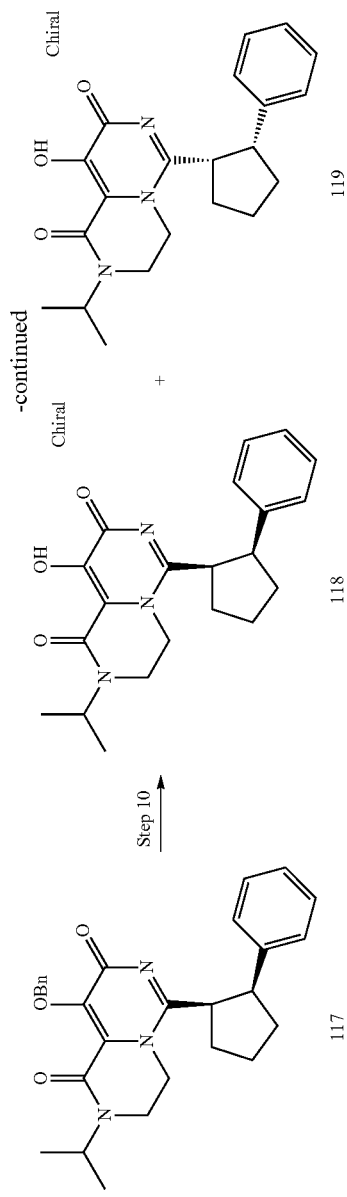

135

Preparation of (109)

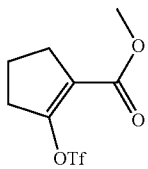 [SMILES: COC(=O)C1=C(OS(=O)(=O)C(F)(F)F)CCC1]

Step 1: 2-Trifluoromethanesulfonyloxy-cyclopent-1-enecarboxylic acid methyl ester Follow the procedure described by Joel R. Calvin et al Org. Lett. 2012, Vol 14, No. 4, 1038-1041:

To a solution of methyl 2-oxocyclopentanecarboxylate (Aldrich, 7.5 g, 53 mmol) in anhydrous dichloromethane (100 mL) at −25° C. was added diisopropylethylamine (Aldrich, 14 mL, 79 mmol), followed by slow addition of trifluoromethanesulfonic anhydride (9.8 mL, 58 mmol). The reaction mixture was stirred at −25° C. for 1 h, then warmed to room temperature and stirred for 1 h. The mixture was poured into aqueous NaHCO₃ solution. The organic layer was separated, and the aqueous layer was extracted with ethyl acetate. The combined organic extract was washed with water and brine, and dried over MgSO₄, and concentrated. The residue was purified by chromatography (10-30% ethyl acetate in hexanes) to give the product (109) as a colorless oil (14 g, 97%).

Preparation of (110)

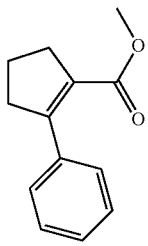

Step 2: 2-Phenyl-cyclopent-1-enecarboxylic acid methyl ester

To a suspension of 2-trifluoromethanesulfonyloxy-cyclopent-1-enecarboxylic acid methyl ester (109) (14 g, 51 mmol) and phenylboronic acid (9.3 g, 77 mmol) in anhydrous methanol (40 mL) and toluene (80 mL) was added Cs₂CO₃ (33 g, 102 mmol). The mixture was degassed with nitrogen, followed by the addition of tetrakis(triphenylphosphine)palladium (2.1 g, 1.8 mmol). The reaction mixture was heated at 80° C. and stirred for 18 h. The mixture was cooled to room temperature and filtered through a short pad of silica gel. The silica gel was washed with ethyl acetate. The filtrate was concentrated. The residue was purified by chromatography (10-30% ethyl acetate in hexanes) to give the product (110) as a colorless oil (8.8 g, 85%).

MS (M+H)=203.2.

136

Preparation of (111)

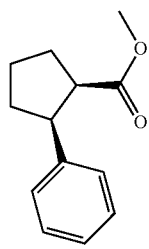

Step 3: Racemic (1R,2S)-2-phenyl-cyclopentanecarboxylic acid methyl ester

To a solution of 2-phenyl-cyclopent-1-enecarboxylic acid methyl ester (110) (8.8 g, 43.5 mmol) in methanol (100 mL) under nitrogen was added Pd—C (Aldrich, 10%, 4.4 g). The mixture was vigorously shaken under a hydrogen atmosphere (55 psi) in a Parr for 4 h. The mixture was filtered through a short pad of celite. The filtrate was concentrated to give the crude product (111) as a colorless oil (8.4 g, 95%).

Preparation of (112)

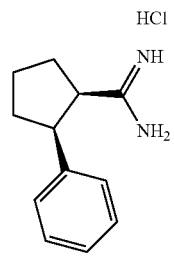 [SMILES: Cl ; N=C(N)[C@@H]1CCC[C@@H]1c1ccccc1]

Step 4: Racemic (1R,2S)-2-phenyl-cyclopentanecarboxamidine hydrochloride

To a stirred suspension of NH₄Cl (6.6 g, 122 mmol) in anhydrous toluene (100 mL) was added trimethylaluminum (2M in toluene, 61 mL, 122 mmol) at 0° C. The mixture was then warmed to room temperature and stirred for 2 h. A solution of racemic (1R,2S)-2-phenyl-cyclopentanecarboxylic acid methyl ester (111) (5 g, 24.5 mmol) in toluene (10 mL) was added to the above reaction mixture and the mixture was stirred at 80° C. for 18 h. After completion of the reaction, the mixture was quenched with a suspension of silica gel in chloroform. The mixture was stirred at room temperature for 0.5 h, then filtered through a sintered funnel. The silica gel was washed with methanol. The combined filtrate was concentrated under reduced pressure to give the crude product (112) as an off-white solid (5.4 g, 98%), which was used directly without further purification.

MS (M+H)=189.3.

Preparation of (113)

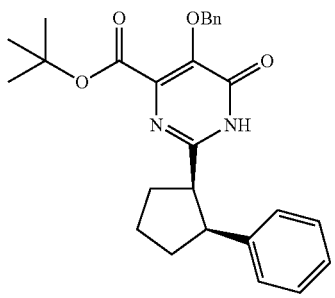 [SMILES: CC(C)(C)OC(=O)c1nc([C@@H]2CCC[C@@H]2c2ccccc2)[nH]c(=O)c1OCc1ccccc1]

Step 5: Racemic 5-benzyloxy-6-oxo-2-((1R,2S)-2-phenyl-cyclopentyl)-1,6-dihydro-pyrimidine-4-carboxylic acid tert-butyl ester To a stirred solution of racemic (1R,2S)-2-phenyl-cyclopentanecarboxamidine hydrochloride (112) (3.2 g, 14 mmol) and (E)-2-benzyloxy-3-hydroxy-but-2-enedioic acid 4-tert-butyl ester 1-methyl ester (4) (4.4 g, 14 mmol) in anhydrous methanol (100 mL) at 0° C. was added a methanolic solution (Aldrich, 25%) of sodium methoxide (9.2 g, 43 mmol). The reaction mixture was slowly warmed to room temperature and stirred for 18 h. The reaction was quenched with aqueous HCl solution (1N). The pH of the mixture was adjusted to 6-7, then the mixture was evaporated. The residue was partitioned between ethyl acetate and water. The organic layer was separated, and the aqueous layer was extracted with ethyl acetate. The combined organic extract was washed with brine, dried over $MgSO_4$ and concentrated. The residue was purified by chromatography (30-50% ethyl acetate in hexanes) to give the product (113) as a white solid (2.5 g, 39%).

MS (M+H)=447.2.

Preparation of (114)

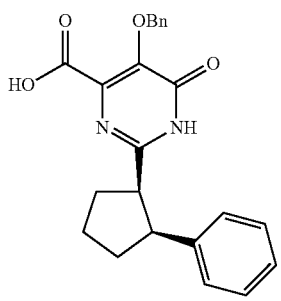 [SMILES: O=C(O)c1nc([C@@H]2CCC[C@@H]2c2ccccc2)[nH]c(=O)c1OCc1ccccc1]

Step 6: Racemic 5-benzyloxy-6-oxo-2-((1R,2S)-2-phenyl-cyclopentyl)-1,6-dihydro-pyrimidine-4-carboxylic acid To a solution of racemic 5-benzyloxy-6-oxo-2-((1R,2S)-2-phenyl-cyclopentyl)-1,6-dihydro-pyrimidine-4-carboxylic acid tert-butyl ester (113) (2.5 g, 5.6 mmol) in tetrahydrofuran (45 mL) and water (15 mL) and methanol (15 mL) was added LiOH (1.8 g, 75 mmol). The reaction mixture was heated at 80° C. for 4 h. TLC analysis indicated the completion of the reaction, and the mixture was concentrated to a small volume, and then extracted with ethyl acetate. The aqueous portion was acidified with aqueous HCl solution (1N) to pH 2-3, and then extracted with ethyl acetate and dichloromethane. The combined organic extract was washed with brine, dried over $MgSO_4$, and concentrated to give the crude product (114) as a white solid (1.75 g, 80%), which was used directly without further purification.

MS (M+H)=391.2.

Preparation of (115)

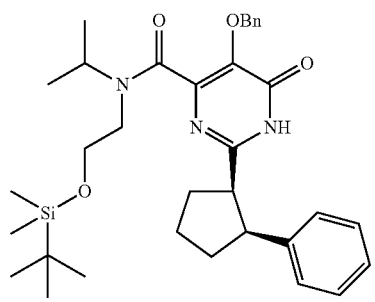 [SMILES: CC(C)N(CCO[Si](C)(C)C(C)(C)C)C(=O)c1nc([C@@H]2CCC[C@@H]2c2ccccc2)[nH]c(=O)c1OCc1ccccc1]

Step 7: Racemic 5-benzyloxy-6-oxo-2-((1R,2S)-2-phenyl-cyclopentyl)-1,6-dihydro-pyrimidine-4-carboxylic acid [2-(tert-butyl-dimethylsilanyloxy)-ethyl]-isopropylamide To a stirred solution of racemic 5-benzyloxy-6-oxo-2-((1R,2S)-2-phenyl-cyclopentyl)-1,6-dihydro-pyrimidine-4-carboxylic acid (114) (1.75 g, 4.5 mmol) and [2-(tert-butyl-dimethylsilanyloxy)-ethyl]-isopropyl-amine (8b) (1.95 g, 9.0 mmol) in pyridine (40 mL) was slowly added $POCl_3$ (0.84 mL, 9.0 mmol) at −10° C. The reaction mixture was stirred at 0° C. for 2 h. The mixture was loaded into a pad of silica gel and directly purified by chromatography (40-60% ethyl acetate in hexanes) to give the product (115) as a white solid (1.84 g, 70%).

MS (M+H)=590.3.

Preparation of (116)

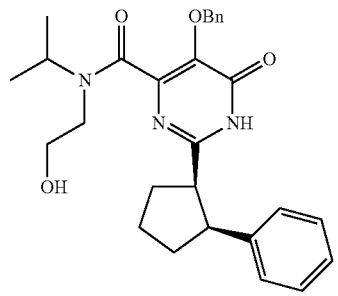 [SMILES: CC(C)N(CCO)C(=O)c1nc([C@@H]2CCC[C@@H]2c2ccccc2)[nH]c(=O)c1OCc1ccccc1]

Step 8: Racemic 5-benzyloxy-6-oxo-2-((1R,2S)-2-phenyl-cyclopentyl)-1,6-dihydro-pyrimidine-4-carboxylic acid (2-hydroxyethyl)-isopropylamide To a stirred solution of racemic 5-benzyloxy-6-oxo-2-((1R,2S)-2-phenyl-cyclopentyl)-1,6-dihydro-pyrimidine-4- carboxylic acid [2-(tert-butyl-dimethylsilanyloxy)-ethyl]-isopropylamide (115) (1.84 g, 3.1 mmol) in tetrahydrofuran (10 mL) was added aqueous HCl (1N, 3.1 mL, 3.1 mmol). The reaction mixture was stirred at room temperature for 1 h. The mixture was neutralized with aqueous saturated $NaHCO_3$ solution to pH 7, and then extracted with ethyl acetate. The organic layer was separated, and the aqueous layer was extracted with ethyl acetate. The combined organic extract was dried over $MgSO_4$ and concentrated. The residue was purified by chromatography (50-80% ethyl acetate in hexanes) to give the product (116) as a white foam (1.2 g, 81%).

MS (M+H)=476.2.

Preparation of (117)

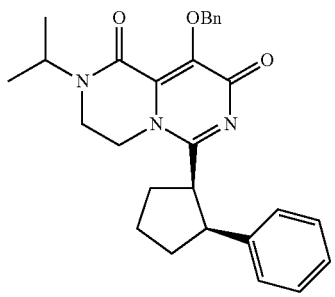 [SMILES: CC(C)N1CCn2c([C@@H]3CCC[C@@H]3c3ccccc3)nc(=O)c(OCc3ccccc3)c2C1=O]

Step 9: Racemic 9-benzyloxy-2-isopropyl-6-((1R,2S)-2-phenyl-cyclopentyl)-3,4-dihydro-2H-pyrazino[1,2-c]pyrimidine-1,8-dione To a stirred solution of racemic 5-benzyloxy-6-oxo-2-((1R,2S)-2-phenyl-cyclopentyl)-1,6-dihydro-pyrimidine-4-carboxylic acid (2-hydroxyethyl)-isopropylamide (116) (1.2 g, 2.5 mmol) in dichloromethane (50 mL) was added triphenylphosphine (0.66 g, 2.5 mmol) at 0° C. The mixture was stirred at 0° C. for 10 min. Then diisopropyl azodicarboxylate (DIAD) (0.49 mL, 2.5 mmol) was added. The reaction mixture was stirred at room temperature for 2 h. The mixture was concentrated, and the residue was purified by chromatography (50-100% ethyl acetate in hexanes) to give the product (117) as a white solid (0.3 g, 26%).

MS (M+H)=458.2.

Preparation of (118) and (119)

Step 10: Chiral 9-hydroxy-2-isopropyl-6-((1R,2S)-2-phenyl-cyclopentyl)-3,4-dihydro-2H-pyrazino[1,2-c]pyrimidine-1,8-dione & chiral 9-hydroxy-2-isopropyl-6-((1S,2R)-2-phenyl-cyclopentyl)-3,4-dihydro-2H-pyrazino[1,2-c]pyrimidine-1,8-dione To a solution of racemic 9-benzyloxy-2-isopropyl-6-((1R,2S)-2-phenyl-cyclopentyl)-3,4-dihydro-2H-pyrazino[1,2-c]pyrimidine-1,8-dione (117) (0.3 g, 0.66 mmol) in methanol (10 mL) was added concentrated HCl (aq 37%, 5 mL). The reaction mixture was stirred at room temperature for 48 h, then concentrated to dryness. To the residue was added aqueous saturated $NaHCO_3$ solution, the mixture was extracted with 10% methanol in dichloromethane twice. The combined organic extract was concentrated. The residue was purified first by reverse phase chromatography (C18 column, 50% MeCN in water), and then separated by chiral SFC into two enantiomers.

Chiral 9-hydroxy-2-isopropyl-6-((1R,2S)-2-phenyl-cyclopentyl)-3,4-dihydro-2H-pyrazino[1,2-c]pyrimidine-1,8-dione (118)

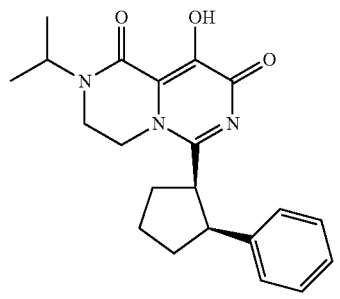 [SMILES: CC(C)N1CCn2c([C@@H]3CCC[C@@H]3c3ccccc3)nc(=O)c(O)c2C1=O]

as a white solid (37 mg, 15%).

MS (M+H)=368.2

$^1H$ NMR (dimethyl sulfoxide-$d_6$) δ: 12.40 (br. s., 1H), 7.27 (d, J=4.3 Hz, 4H), 6.95-7.24 (m, 1H), 4.65 (s, 1H), 3.89-4.16 (m, 2H), 3.41-3.66 (m, 3H), 3.19-3.36 (m, 1H), 2.06-2.30 (m, 2H), 1.72-1.95 (m, 4H), 0.86-1.27 (m, 6H)

Chiral 9-hydroxy-2-isopropyl-6-((1S,2R)-2-phenyl-cyclopentyl)-3,4-dihydro-2H-pyrazino[1,2-c]pyrimidine-1,8-dione (119)

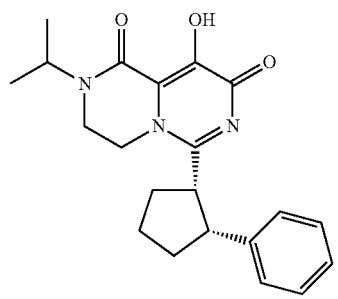 [SMILES: CC(C)N1CCn2c([C@H]3CCC[C@H]3c3ccccc3)nc(=O)c(O)c2C1=O]

as a white solid (41 mg, 17%).

MS (M+H)=368.2.

$^1H$ NMR (dimethyl sulfoxide-$d_6$) δ: 12.39 (s, 1H), 7.27 (d, J=4.3 Hz, 4H), 7.08-7.22 (m, 1H), 4.51-4.79 (m, 1H), 3.89-4.15 (m, 2H), 3.41-3.66 (m, 3H), 3.19-3.36 (m, 1H), 1.95-2.33 (m, 2H), 1.63-1.90 (m, 4H), 0.91-1.36 (m, 6H)

Example 127

9-Hydroxy-6-(2-indol-1-yl-2-methyl-propyl)-2-isopropyl-3,4-dihydro-2H-pyrazino[1,2-c]pyrimidine-1,8-dione The synthetic procedure used in this preparation is outlined in Scheme 17.

Scheme 17

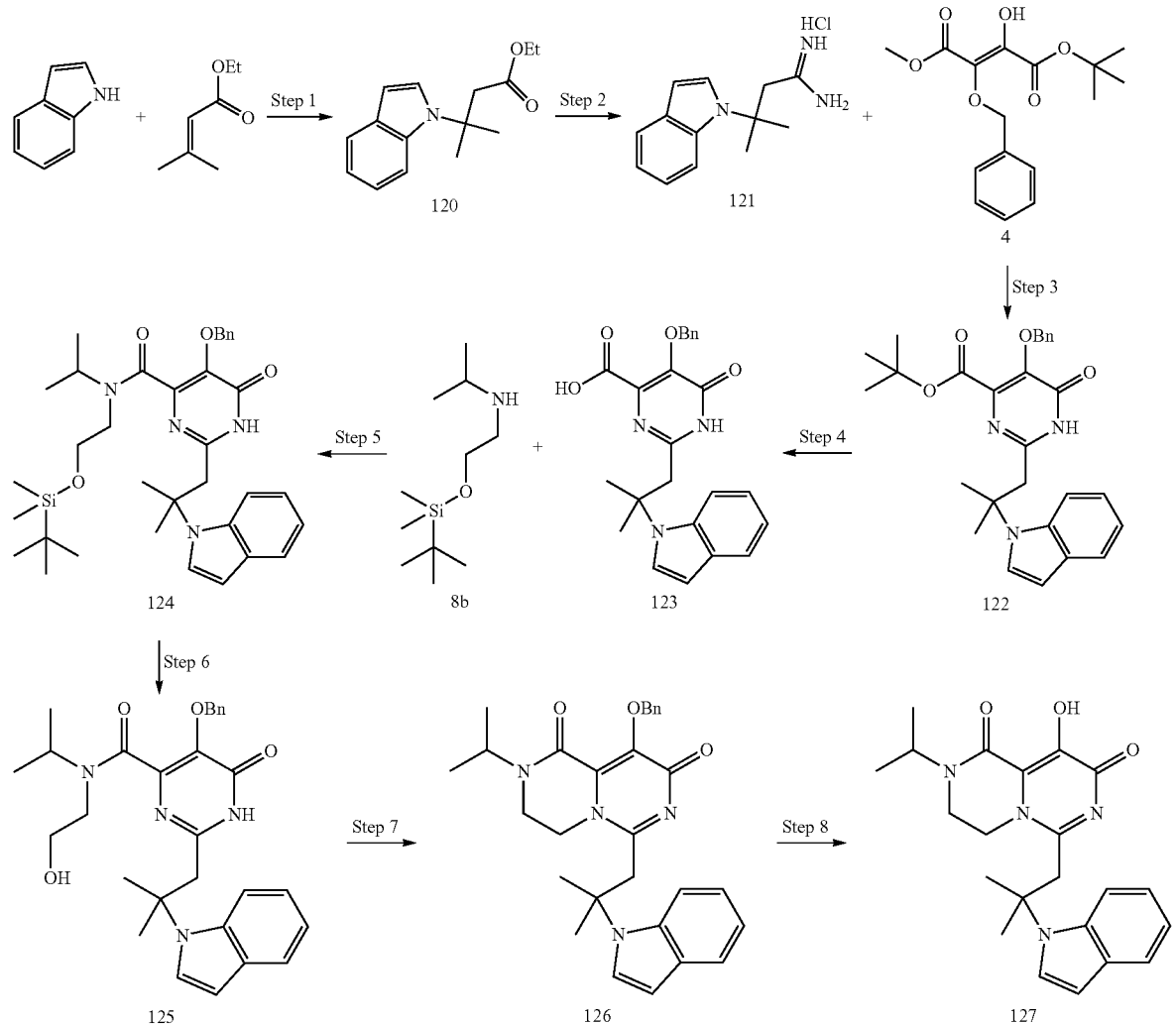

Preparation of (120)

Step 1: 3-Indol-1-yl-3-methyl-butyric acid ethyl ester

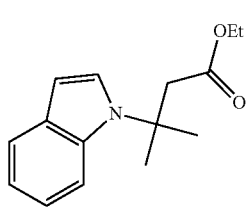 [SMILES: CCOC(=O)CC(C)(C)n1ccc2ccccc21]

To a solution of ethyl 3,3-dimethylacrylate (Aldrich, 1 g, 7.8 mmol) and indole (0.3 g, 2.6 mmol) in anhydrous dichloromethane (20 mL) was added potassium tert-butoxide (0.9 g, 7.7 mmol). The reaction mixture was heated at 50° C. for 24 h, then cooled to room temperature. The mixture was partitioned between ethyl acetate and water. The organic layer was separated, and the aqueous layer was extracted with ethyl acetate. The combined organic extract was washed with water, dried over MgSO₄, and concentrated. The residue was purified by chromatography (10-20% ethyl acetate in hexanes) to give the product (120) as a white solid. (0.4 g, 64%). MS (M+H)=246.2.

Preparation of (121)

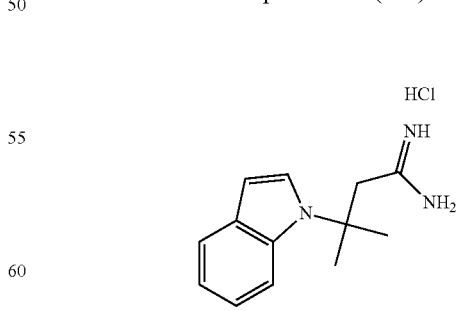

Step 2: 3-Indol-1-yl-3-methyl-butyramidine

To a stirred suspension of NH₄Cl (0.44 g, 8.2 mmol) in anhydrous toluene (40 mL) was added trimethylaluminum (2M in toluene, 4.1 mL, 8.2 mmol) at 0° C. The mixture was then warmed to room temperature and stirred for 2 h. A solution of 3-indol-1-yl-3-methyl-butyric acid ethyl ester (120) (0.4 g, 1.6 mmol) in toluene (10 mL) was added to the above reaction mixture and stirred at 80° C. for 18 h. After completion of the reaction, the mixture was quenched with a suspension of silica gel in chloroform. The mixture was stirred at room temperature for 0.5 h, then filtered through a sintered funnel. The silica gel was washed with methanol. The combined filtrate was concentrated under reduced pressure. The crude product was purified by chromatography (10-100% methanol in dichloromethane) to give the product (121) as a brown solid (0.4 g, 100%).

MS (M+H)=216.3

Preparation of (122)

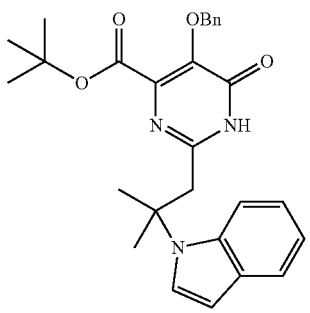 [SMILES: CC(C)(C)OC(=O)c1nc(CC(C)(C)n2ccc3ccccc32)[nH]c(=O)c1OCc1ccccc1]

Step 3: 5-Benzyloxy-2-(2-indol-1-yl-2-methyl-propyl)-6-oxo-1,6-dihydro-pyrimidine-4-carboxylic acid tert-butyl ester To a stirred solution of 3-indol-1-yl-3-methyl-butyramidine hydrochloride (121) (0.4 g, 1.6 mmol) and (E)-2-benzyloxy-3-hydroxy-but-2-enedioic acid 4-tert-butyl ester 1-methyl ester (4) (0.5 g, 1.6 mmol) in anhydrous methanol (40 mL) at 0° C. was added a methanolic solution (Aldrich, 25%) of sodium methoxide (1 g, 4.8 mmol). The reaction mixture was slowly warmed to room temperature and stirred for 18 h. The reaction was quenched with aqueous HCl solution (1N). The pH of the mixture was adjusted to 6-7, then the mixture was evaporated. The residue was partitioned between ethyl acetate and water. The organic layer was separated, and the aqueous layer was extracted with ethyl acetate. The combined organic extract was washed with brine, dried over MgSO$_4$ and concentrated. The residue was purified by chromatography (30-50% ethyl acetate in hexanes) to give the product (122) as a white solid (0.18 g, 24%).

Preparation of (123)

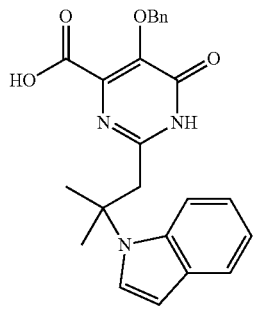 [SMILES: CC(C)(Cc1nc(C(=O)O)c(OCc2ccccc2)c(=O)[nH]1)n1ccc2ccccc21]

Step 4: 5-Benzyloxy-2-(2-indol-1-yl-2-methyl-propyl)-6-oxo-1,6-dihydro-pyrimidine-4-carboxylic acid To a solution of 5-benzyloxy-2-(2-indol-1-yl-2-methyl-propyl)-6-oxo-1,6-dihydro-pyrimidine-4-carboxylic acid tert-butyl ester (122) (0.18 g, 0.38 mmol) in tetrahydrofuran (30 mL) and water (10 mL) and methanol (10 mL) was added LiOH (46 mg, 1.9 mmol). The reaction mixture was heated at 80° C. for 4 h. TLC analysis indicated the completion of reaction. The mixture was concentrated to a small volume, and then extracted with ethyl acetate. The aqueous potion was acidified with aqueous HCl solution (1N) to pH 3, then extracted with ethyl acetate and dichloromethane. The combined organic extract was washed with brine, dried over MgSO$_4$, and concentrated to give the crude product (123) as an off-white solid (0.14 g, 88%), which was used directly without further purification.

MS (M+H)=418.

Preparation of (124)

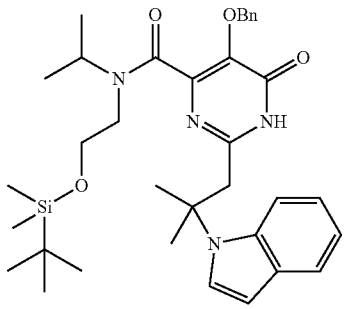 [SMILES: CC(C)N(CCO[Si](C)(C)C(C)(C)C)C(=O)c1nc(CC(C)(C)n2ccc3ccccc32)[nH]c(=O)c1OCc1ccccc1]

Step 5: 5-Benzyloxy-2-(2-indol-1-yl-2-methyl-propyl)-6-oxo-1,6-dihydro-pyrimidine-4-carboxylic acid [2-(tert-butyl-dimethylsilanyloxy)-ethyl]-isopropylamide To a stirred solution of 5-benzyloxy-2-(2-indol-1-yl-2-methyl-propyl)-6-oxo-1,6-dihydro-pyrimidine-4-carboxylic acid (123) (0.14 g, 0.34 mmol) and [2-(tert-butyl-dimethylsilanyloxy)-ethyl]-isopropyl-amine (8b) (0.15 g, 0.67 mmol) in pyridine (20 mL) at −10° C. was slowly added POCl₃ (0.06 g, 0.67 mmol). The reaction mixture was stirred at 0° C. for 2 h. The mixture was loaded into a pad of silica gel and directly purified by chromatography (40-60% ethyl acetate in hexanes) to give the product (124) as a white solid (0.16 g, 77%).

MS (M+H)=617.3.

Preparation of (125)

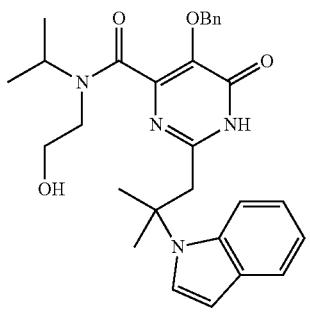 [SMILES: CC(C)N(CCO)C(=O)c1nc(CC(C)(C)n2ccc3ccccc32)[nH]c(=O)c1OCc1ccccc1]

Step 6: 5-Benzyloxy-2-(2-indol-1-yl-2-methyl-propyl)-6-oxo-1,6-dihydro-pyrimidine-4-carboxylic acid (2-hydroxyethyl)-isopropylamide To a stirred solution of 5-benzyloxy-2-(2-indol-1-yl-2-methyl-propyl)-6-oxo-1,6-dihydro-pyrimidine-4-carboxylic acid [2-(tert-butyl-dimethylsilanyloxy)-ethyl]-isopropylamide (124) (0.16 g, 0.26 mmol) in tetrahydrofuran (10 mL) was added aqueous HCl (1N, 1 mL, 1 mmol). The reaction mixture was stirred at room temperature for 1 h. The mixture was neutralized with aqueous saturated NaHCO₃ solution to pH 7, then extracted with ethyl acetate. The organic layer was separated, and the aqueous layer was extracted with ethyl acetate. The combined organic extract was dried over MgSO₄ and concentrated. The residue was purified by chromatography (0-10% methanol in ethyl acetate) to give the product (125) as a white solid (98 mg, 75%).

MS (M+H)=503.2.

Preparation of (126)

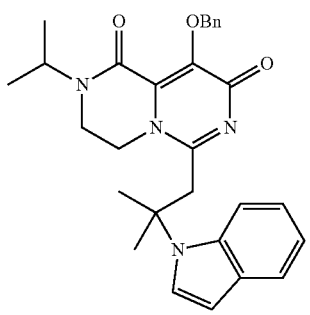 [SMILES: CC(C)N1CCn2c(CC(C)(C)n3ccc4ccccc43)nc(=O)c(OCc3ccccc3)c2C1=O]

Step 7: 9-Benzyloxy-6-(2-indol-1-yl-2-methyl-propyl)-2-isopropyl-3,4-dihydro-2H-pyrazino[1,2-c]pyrimidine-1,8-dione To a stirred solution of 5-benzyloxy-2-(2-indol-1-yl-2-methyl-propyl)-6-oxo-1,6-dihydro-pyrimidine-4-carboxylic acid (2-hydroxyethyl)-isopropylamide (125) (98 mg, 0.2 mmol) in dichloromethane (20 mL) was added triphenylphosphine (51 g, 0.2 mmol). The mixture was stirred at room temperature for 10 min. Then diisopropyl azodicarboxylate (DIAD) (0.038 mL, 0.2 mmol) was added. The reaction mixture was stirred at room temperature for 2 h. The mixture was concentrated, and the residue was purified by chromatography (0-10% methanol in ethyl acetate) to give the product (126) as a white solid (43 mg, 46%).

MS (M+H)=485.2.

Preparation of (127)

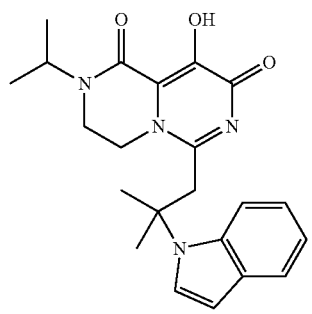 [SMILES: CC(C)N1CCn2c(CC(C)(C)n3ccc4ccccc43)nc(=O)c(O)c2C1=O]

Step 8: 9-Hydroxy-6-(2-indol-1-yl-2-methyl-propyl)-2-isopropyl-3,4-dihydro-2H-pyrazino[1,2-c]pyrimidine-1,8-dione To a solution of 9-benzyloxy-6-(2-indol-1-yl-2-methyl-propyl)-2-isopropyl-3,4-dihydro-2H-pyrazino[1,2-c]pyrimidine-1,8-dione (126) (43 mg, 0.09 mmol) in methanol (10 mL) was added concentrated HCl (aq 37%, 5 mL). The reaction mixture was stirred at room temperature for 24 h, then concentrated to dryness. The residue was purified by reverse phase chromatography (20-50% MeCN-TFA in water-TFA) to give the title compound (127) as trifluoroacetic acid salt: off-white solid (22 mg, 63%).

MS (M+H)=395.2.

<sup>1</sup>H NMR (dimethyl sulfoxide-d<sub>6</sub>) δ: 12.43 (s, 1H), 6.74-7.86 (m, 5H), 6.45 (d, J=3.3 Hz, 1H), 4.62-4.74 (m, 1H), 3.35 (s, 2H), 2.81-2.89 (m, 2H), 2.48-2.52 (m, 2H), 1.11-1.28 (m, 6H), 0.95-1.06 (m, 6H)
Example 135
6-(2,3-Dichlorobenzyl)-9-hydroxy-2-isopropyl-3,4-dihydro-2H-pyrazino[1,2-c]pyrimidine-1,8-dione
The synthetic procedure used in this preparation is outlined in Scheme 18.
Synthetic Route for 135
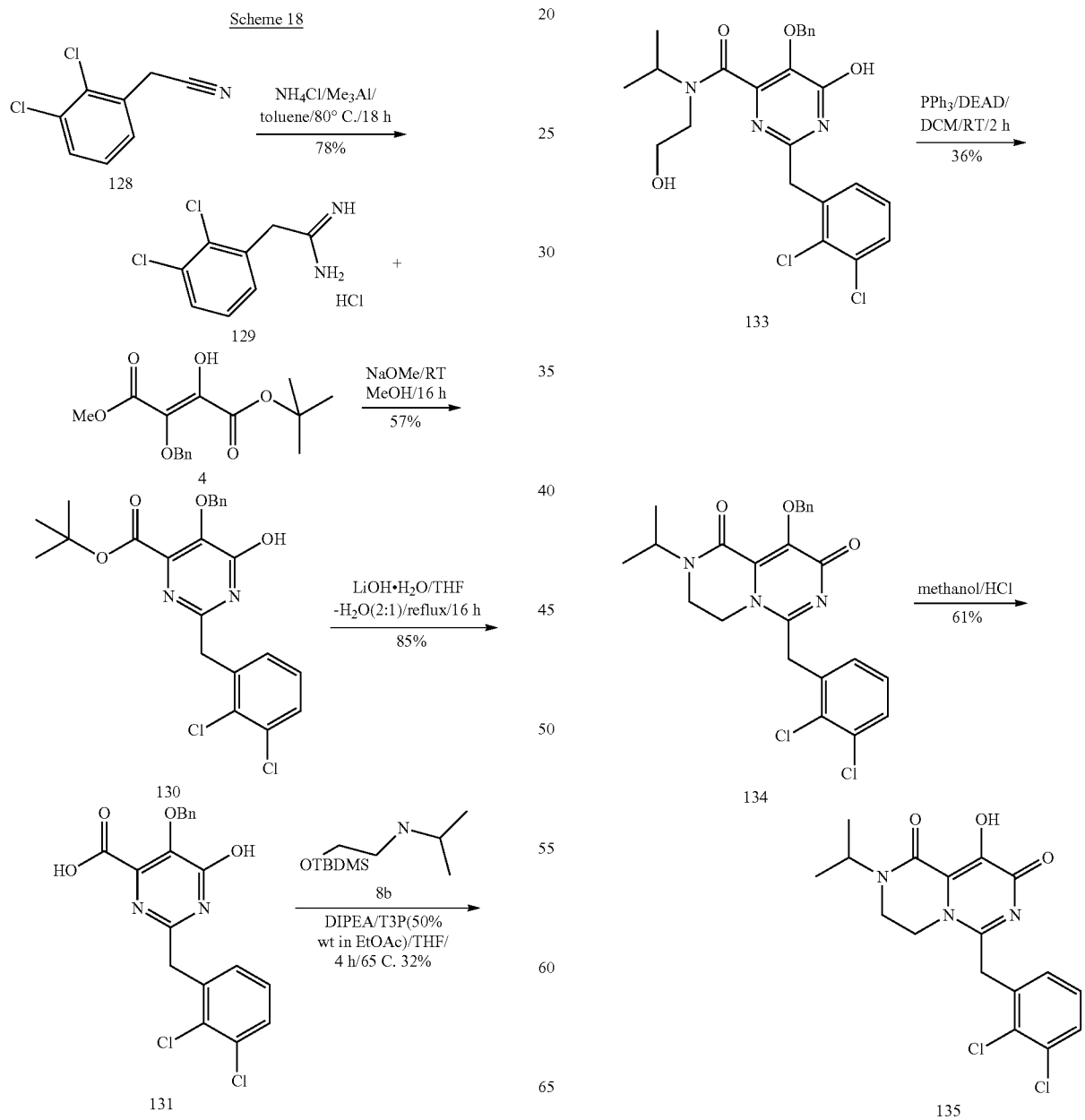

149

Preparation of (129)

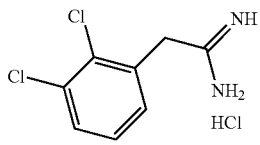 [SMILES: N=C(N)Cc1cccc(Cl)c1Cl ; Cl]

Step 1: 2-(2,3-Dichlorophenyl)-acetamidine hydrochloride

To a stirred suspension of NH₄Cl (4.29 g, 80.21 mmol) in dry toluene (120 mL) was added trimethyl aluminium (2M in toluene, 41 mL, 80.21 mmol) at 5° C. The mixture was then warmed to room temperature and stirred for 2 h. A solution of (2,3-dichlorophenyl)-acetonitrile (128) (5 g, 26.73 mmol) in toluene (25 mL) was added to the mixture and stirred for 14 h at 80° C. After completion of the reaction, it was quenched with a suspension of silica gel in chloroform and the reaction mixture was stirred for half an hour at room temperature and filtered through a sintered funnel. The silica gel was washed with methanol and the combined filtrate was concentrated under reduced pressure to get 2-(2,3-dichlorophenyl)-acetamidine hydrochloride salt (129) (5 g, 78%) as an off-white solid.

LC-MS: 203 (M+H).

Preparation of (130)

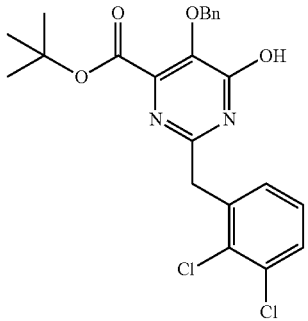 [SMILES: CC(C)(C)OC(=O)c1nc(Cc2cccc(Cl)c2Cl)nc(O)c1OCc1ccccc1]

Step 2: 5-Benzyloxy-2-(2,3-dichlorobenzyl)-6-hydroxypyrimidine-4-carboxylic acid tert-butyl ester To a stirred solution of 2-(2,3-dichlorophenyl)-acetamidine hydrochloride salt (129) (10 g, 41.84 mmol) and (E)-2-benzyloxy-3-hydroxy-but-2-enedioic acid 4-tert-butyl ester 1-methyl ester (4) (19.33 g, 62.76 mmol) in methanol (300 mL) was added sodium methoxide (6.7 g, 125.52 mmol) at 0° C. Then the reaction mixture was allowed to warm to room temperature, and was stirred for 16 h. After completion of the reaction, it was quenched with 1N HCl, the methanol was evaporated and water was added. The mixture was extracted with ethyl acetate and the separated organic part was dried over sodium sulfate and concentrated under reduced pressure to get a crude product, which was purified by a normal silica column using 30% ethyl acetate in hexane to get 5-benzyloxy-2-(2,3-dichlorobenzyl)-6-hydroxypyrimidine-4-carboxylic acid tert-butyl ester (130) (10 g, 57.8%) as a brown solid.

LC-MS: 461 (M+H).

150

Preparation of (131)

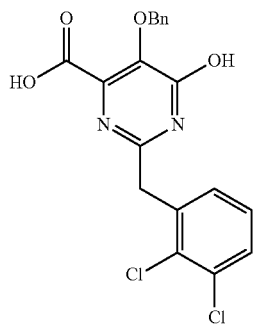 [SMILES: O=C(O)c1nc(Cc2cccc(Cl)c2Cl)nc(O)c1OCc1ccccc1]

Step 3: 5-Benzyloxy-2-(2,3-dichlorobenzyl)-6-hydroxypyrimidine-4-carboxylic acid To a stirred solution of 5-benzyloxy-2-(2,3-dichlorobenzyl)-6-hydroxypyrimidine-4-carboxylic acid tert-butyl ester (130) (10 g, 21.69 mmol) in a mixture of tetrahydrofuran-water (2:1, 90 mL) was added lithium hydroxide, monohydrate (4.55 g, 108.42 mmol). The mixture was refluxed for 18 h. After completion of the reaction, the volume was reduced by evaporation as much as possible, water was added, and the residue was washed with ethyl acetate to remove non-acidic impurities. The separated aqueous part was acidified with 2(N)HCl to bring the pH to approx. 5 to 6. The acidified aqueous part was extracted with dichloromethane, the separated organic part was dried over sodium sulfate and concentrated under reduced pressure to get 5-benzyloxy-2-(2,3-dichlorobenzyl)-6-hydroxypyrimidine-4-carboxylic acid (131) (7.5 g, 85.32%) as a white solid.

LC-MS: 405.4 (M+H).

Preparation of (132)

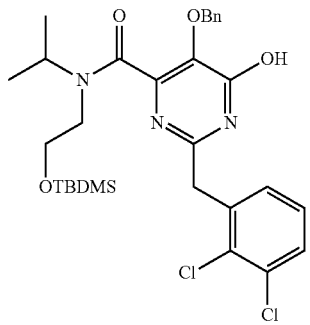 [SMILES: CC(C)N(CCO[Si](C)(C)C(C)(C)C)C(=O)c1nc(Cc2cccc(Cl)c2Cl)nc(O)c1OCc1ccccc1]

Step 4: 5-Benzyloxy-2-(2,3-dichlorobenzyl)-6-hydroxypyrimidine-4-carboxylic acid [2-(tert-butyl-dimethylsilanyloxy)-ethyl]-isopropylamide To a stirred solution of 5-benzyloxy-2-(2,3-dichlorobenzyl)-6-hydroxypyrimidine-4-carboxylic acid (131) (5.5 g, 13.58 mmol) in tetrahydrofuran (70 mL) were added N,N-diisopropylethylamine (9.36 mL, 54.32 mmol) and T₃P (17.3 mL, 27.16 mmol) followed by [2-(tert-butyl-dimethylsilany-loxy)-ethyl]-isopropyl-amine (8b) (5.89 g, 27.16 mmol) at room temperature. The mixture was heated at 65° C. for 4 h. After completion of the reaction, water was added and the mixture was extracted with ethyl acetate. The separated organic part was dried and concentrated to get a crude product which was purified by a normal silica column using 10 to 20% ethyl acetate in hexane to obtain 5-benzyloxy-2-(2,3-dichlorobenzyl)-6-hydroxypyrimidine-4-carboxylic acid [2-(tert-butyl-dimethylsilanyloxy)-ethyl]isopropylamide (132) (2.7 g, 32.8%) as a light yellow solid.

LC-MS: 604.2 (M+H).

Preparation of (133)

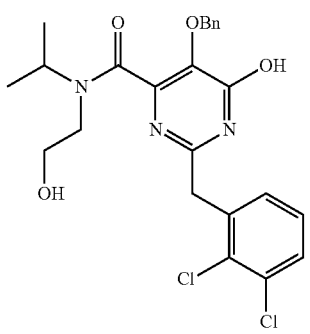 [SMILES: CC(C)N(CCO)C(=O)c1nc(Cc2cccc(Cl)c2Cl)nc(O)c1OCc1ccccc1]

Step 5: 5-Benzyloxy-2-(2,3-dichlorobenzyl)-6-hydroxypyrimidine-4-carboxylic acid (2-hydroxyethyl)-isopropylamide To a stirred solution of 5-benzyloxy-2-biphenyl-2-ylmethyl-6-hydroxypyrimidine-4-carboxylic acid [2-(tert-butyl-dimethylsilanyloxy)-ethyl]-methyl-amide (132) (3 g, 4.967 mmol) in tetrahydrofuran (45 mL) was added 1N HCl (7.5 ml, 7.5 mmol) at room temperature and the mixture was stirred for 60 min at room temperature. After completion of the reaction, the mixture was neutralized with 1N sodium hydroxide aqueous solution, extracted with ethyl acetate, dried over sodium sulfate and concentrated under reduced pressure to get a crude product which was purified by a normal silica column using 60% ethyl acetate in hexane to get 5-benzyloxy-2-biphenyl-2-ylmethyl-6-hydroxypyrimidine-4-carboxylic acid (2-hydroxyethyl)-methyl-amide (133) (1.7 g, 69.8%) as a white solid.

LC-MS: 490.2 (M+H).

Preparation of (134)

Step 6: 9-Benzyloxy-6-(2,3-dichlorobenzyl)-2-isopropyl-3,4-dihydro-2H-pyrazino[1,2-c]pyrimidine-1,8-dione To a stirred solution of 5-benzyloxy-2-(2,3-dichlorobenzyl)-6-hydroxypyrimidine-4-carboxylic acid (2-hydroxyethyl)-isopropylamide (133) (200 mg, 0.408 mmol) in dichloromethane (5 mL) was added triphenyl phosphine (161 mg, 0.612 mmol) at room temperature and the mixture was stirred for 10 min. Then DEAD (106 mg, 0.612 mmol) was added at room temperature and the mixture was stirred for another 2 h. After completion of the reaction, the mixture was concentrated under reduced pressure to get a crude product, which was purified by a normal silica column using 2% methanol in dichloromethane to afford 9-benzyloxy-6-(2,3-dichlorobenzyl)-2-isopropyl-3,4-dihydro-2H-pyrazino[1,2-c]pyrimidine-1,8-dione (134) (70 mg, 36.3%) as a white solid.

LC-MS: 472 (M+H).

Preparation of (135)

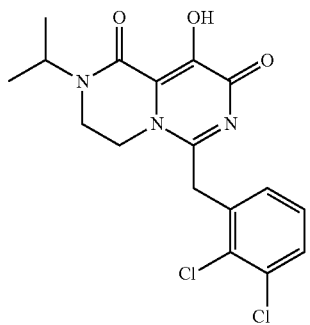 [SMILES: CC(C)N1CCn2c(Cc3cccc(Cl)c3Cl)nc(=O)c(O)c2C1=O]

Step 7: 6-(2,3-Dichlorobenzyl)-9-hydroxy-2-isopropyl-3,4-dihydro-2H-pyrazino[1,2-c]pyrimidine-1,8-dione To a stirred solution of 9-benzyloxy-6-(2,3-dichlorobenzyl)-2-isopropyl-3,4-dihydro-2H-pyrazino[1,2-c]pyrimidine-1,8-dione (134) (70 mg, 0.095 mmol) in methanol (3 mL) was added concentrated HCl (3 mL) and the reaction mixture was stirred for 5 h at room temperature. After completion of the reaction, the mixture was evaporation and the residue was basified with saturated aqueous NaHCO₃ solution. The mixture was extracted with 10% methanol in dichloromethane, the organic part was separated. The drying over sodium sulfate was conducted and concentration to get a crude product, which was washed with ether followed by pentene to get 6-(2,3-dichlorobenzyl)-9-hydroxy-2-isopropyl-3,4-dihydro-2H-pyrazino[1,2-c]pyrimidine-1,8-dione (135) (35 mg, 61.7%) as a brown colored solid.

LC-MS: 381.8 (M+H).

Example 144

9-Hydroxy-2-isopropyl-6-(4-methoxy-biphenyl-2-ylmethyl)-3,4-dihydro-2H-pyrazino[1,2-c]pyrimidine-1,8-dione The synthetic procedure used in this preparation is outlined in Scheme 19.

Synthetic Route for 144

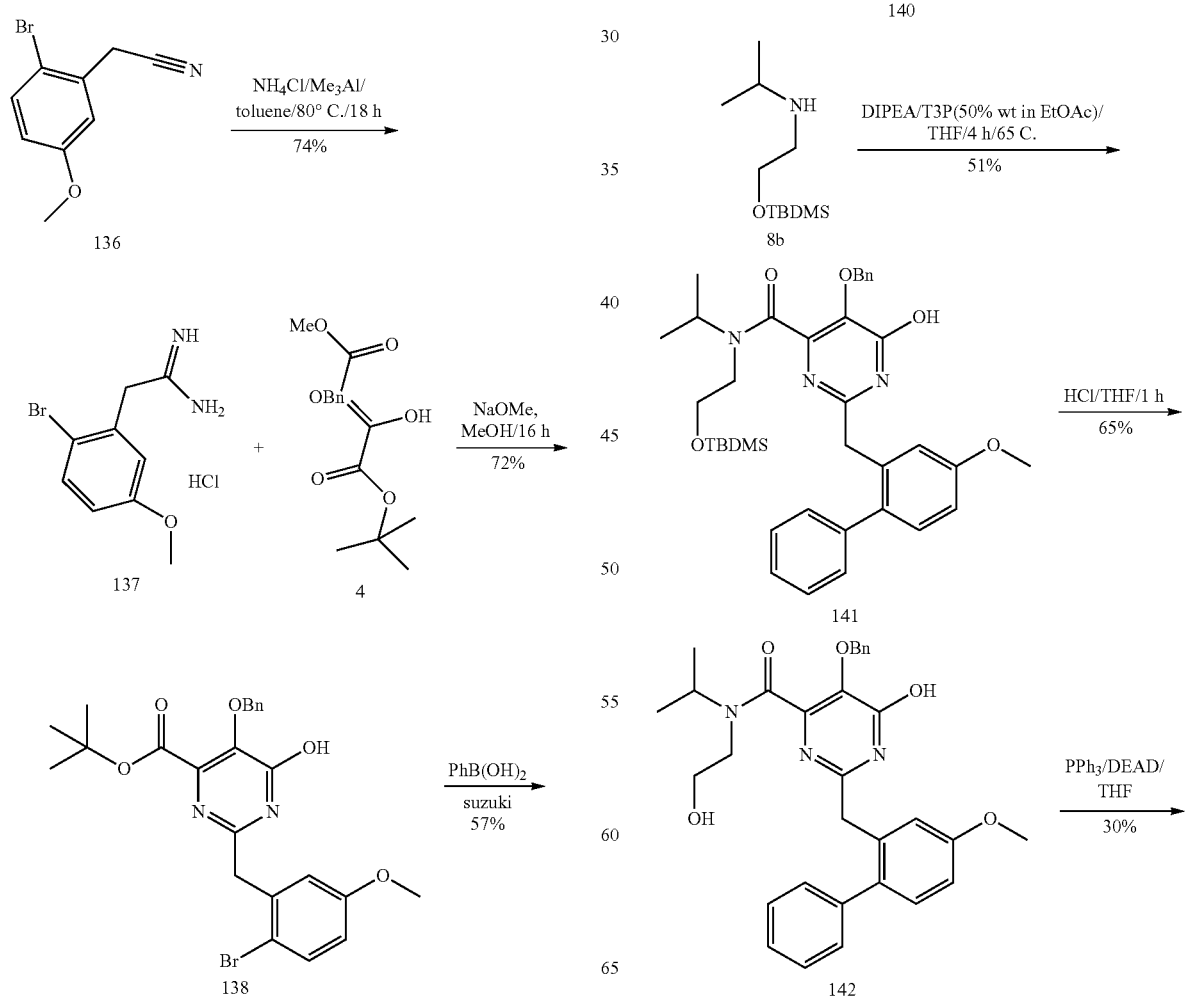

-continued

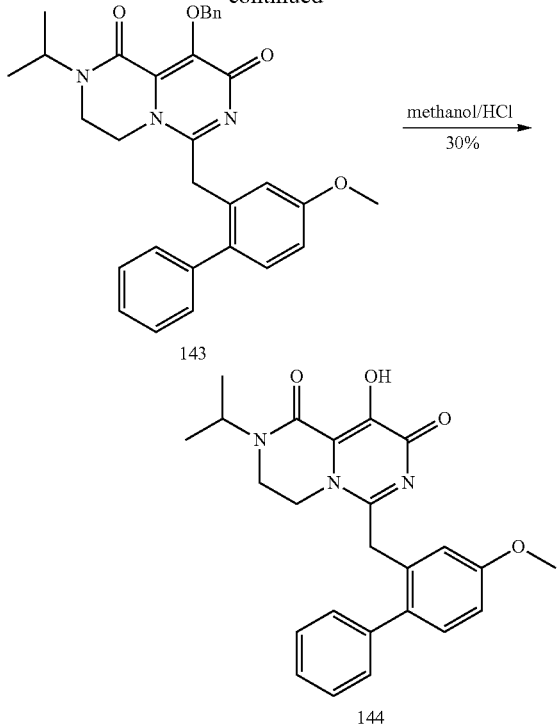

143 methanol/HCl
30%

144

Preparation of (137)

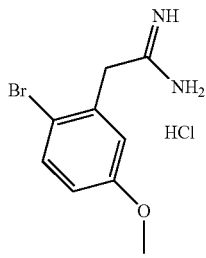

Step 1: 2-(2-Bromo-5-methoxy-phenyl)-acetamidine hydrochloride salt

To a stirred suspension of NH₄Cl (3.58 g, 66.37 mmol) in dry toluene (100 mL) was added trimethyl aluminium (2M in toluene, 33.18 mL, 66.37 mmol) at 5° C., then the mixture was warmed to room temperature and stirred for 2 h. A solution of (2-bromo-5-methoxy-phenyl)-acetonitrile (136) (5 g, 22.12 mmol) in toluene (25 mL) was added to the above reaction mixture and the mixture was then stirred for 14 h at 80° C. After completion of the reaction, it was quenched with a suspension of silica gel in chloroform and the reaction mixture was stirred for half an hour at room temperature and filtered through a sintered funnel, the silica gel was washed with methanol and the combined filtrate was concentrated under reduced pressure to get 2-(2-bromo-5-methoxyphenyl)-acetamidine hydrochloride salt as a crude product (137) (4 g, 74.37%) a as white solid.

LC-MS: 244 (M+H).

Preparation of (138)

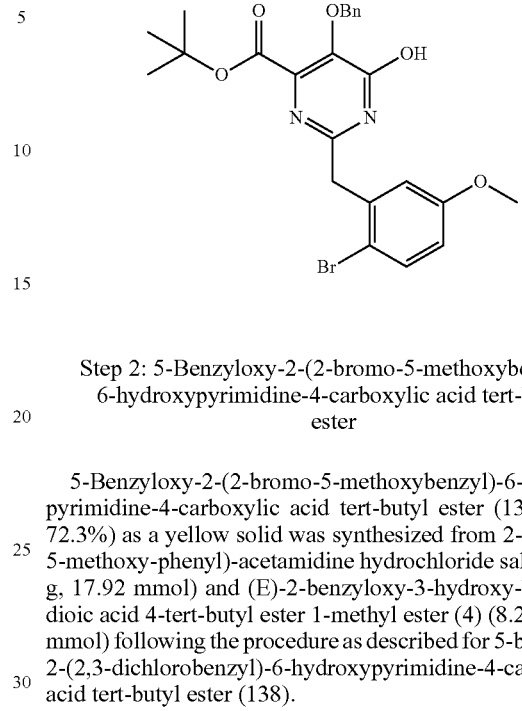

Step 2: 5-Benzyloxy-2-(2-bromo-5-methoxybenzyl)-6-hydroxypyrimidine-4-carboxylic acid tert-butyl ester 5-Benzyloxy-2-(2-bromo-5-methoxybenzyl)-6-hydroxypyrimidine-4-carboxylic acid tert-butyl ester (138) (6.5 g, 72.3%) as a yellow solid was synthesized from 2-(2-bromo-5-methoxy-phenyl)-acetamidine hydrochloride salt. (137) (5 g, 17.92 mmol) and (E)-2-benzyloxy-3-hydroxy-but-2-enedioic acid 4-tert-butyl ester 1-methyl ester (4) (8.28 g, 26.88 mmol) following the procedure as described for 5-benzyloxy-2-(2,3-dichlorobenzyl)-6-hydroxypyrimidine-4-carboxylic acid tert-butyl ester (138).

LC-MS: 503.4 (M+H).

Preparation of (139)

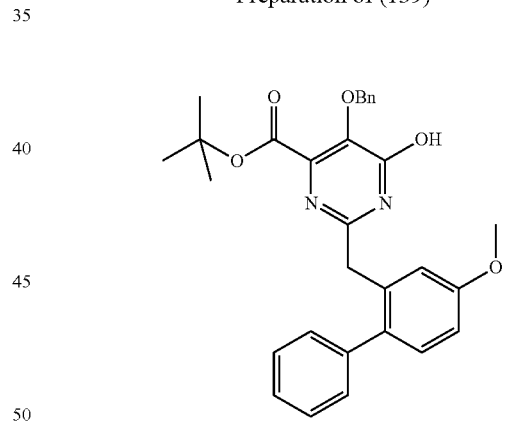

Step 3: 5-Benzyloxy-6-hydroxy-2-(4-methoxybiphenyl-2-ylmethyl)-pyrimidine-4-carboxylic acid tert-butyl ester To a stirred solution of 5-benzyloxy-2-(2-bromo-5-methoxybenzyl)-6-hydroxypyrimidine-4-carboxylic acid tert-butyl ester (138) (3 g, 5.988 mmol) in n-butanol:water (3:1, 12 mL) were added phenyl boronic acid (1.096 g, 8.982 mmol), X-Phos (427 mg, 0.898 mmol), K₃PO₄ (4.44 g, 20.958 mmol) and Pd(dba)₂ (275 mg, 0.479 mmol). The reaction mixture was refluxed for 10 h. After completion of the reaction, the mixture was evaporated to get a crude product which was purified by a normal silica column using 2% methanol in dichloromethane to afford 5-benzyloxy-6-hydroxy-2-(4- methoxybiphenyl-2-ylmethyl)-pyrimidine-4-carboxylic acid tert-butyl ester (139) (1.7 g, 56.94%) as an off-white solid.
LC-MS: 499.2 (M+H).

Preparation of (140)

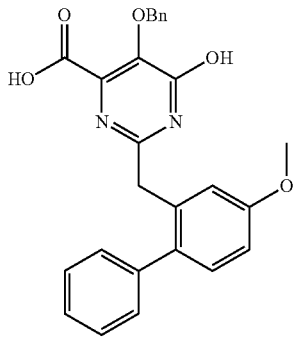 [SMILES: COc1ccc(-c2ccccc2)c(Cc2nc(O)c(OCc3ccccc3)c(C(=O)O)n2)c1]

Step 4: 5-Benzyloxy-6-hydroxy-2-(4-methoxy-biphenyl-2-ylmethyl)-pyrimidine-4-carboxylic acid 5-Benzyloxy-6-hydroxy-2-(4-methoxy-biphenyl-2-ylmethyl)-pyrimidine-4-carboxylic acid (140) (700 mg, 65.6%) as a white solid was synthesized from 5-benzyloxy-6-hydroxy-2-(4-methoxybiphenyl-2-ylmethyl)-pyrimidine-4-carboxylic acid tert-butyl ester (139) (1.2 g, 2.41 mmol) following the procedure as described for 5-benzyloxy-2-(2,3-dichlorobenzyl)-6-hydroxypyrimidine-carboxylic acid (140).
LC-MS: 441.4 (M+H).

Preparation of (141)

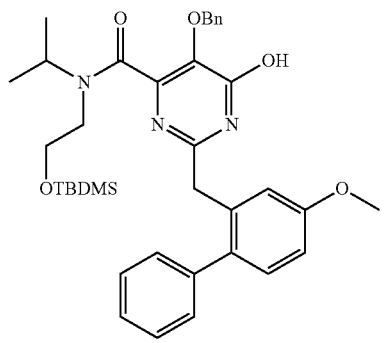 [SMILES: COc1ccc(-c2ccccc2)c(Cc2nc(O)c(OCc3ccccc3)c(C(=O)N(CCO[Si](C)(C)C(C)(C)C)C(C)C)n2)c1]

Step 5: 5-Benzyloxy-6-hydroxy-2-(4-methoxybiphenyl-2-ylmethyl)-pyrimidine-4-carboxylic acid [2-(tert-butyl-dimethylsilanyloxy)-ethyl]isopropylamide 5-Benzyloxy-6-hydroxy-2-(4-methoxybiphenyl-2-ylmethyl)-pyrimidine-4-carboxylic acid [2-(tert-butyl-dimethylsilanyloxy)-ethyl]-isopropylamide (141) (520 mg, 51.15%) as a yellow sticky liquid was synthesized from 5-benzyloxy-6-hydroxy-2-(4-methoxybiphenyl-2-ylmethyl)-pyrimidine-4-carboxylic acid (140) (700 mg, 1.584 mmol) and [2-(tert-butyl-dimethylsilanyloxy)-ethyl]-isopropyl-amine (8b) (687 mg, 3.167 mmol) following the procedure as described for 5-benzyloxy-2-(2,3-dichlorobenzyl)-6-hydroxypyrimidine-4-carboxylic acid [2-(tert-butyl-dimethylsilanyloxy)-ethyl]-isopropylamide (141).
LC-MS: 642.2 (M+H).

Preparation of (142)

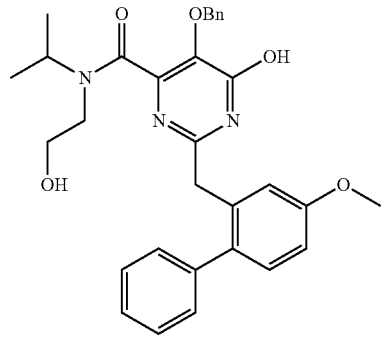 [SMILES: COc1ccc(-c2ccccc2)c(Cc2nc(O)c(OCc3ccccc3)c(C(=O)N(CCO)C(C)C)n2)c1]

Step 6: 5-Benzyloxy-6-hydroxy-2-(4-methoxybiphenyl-2-yl-methyl)-pyrimidine-4-carboxylic acid (2-hydroxyethyl)-isopropylamide 5-Benzyloxy-6-hydroxy-2-(4-methoxy-biphenyl-2-yl-methyl)-pyrimidine-4-carboxylic acid (2-hydroxyethyl)-isopropylamide (142) (280 mg, 65.42%) was synthesized from 5-benzyloxy-6-hydroxy-2-(4-methoxy-biphenyl-2-ylmethyl)-pyrimidine-4-carboxylic acid [2-(tert-butyl-dimethylsilanyloxy)-ethyl]-isopropylamide (141) (520 mg, 0.861 mmol) following the procedure as described for 5-benzyloxy-2-biphenyl-2-yl-methyl-6-hydroxypyrimidine-4-carboxylic acid (2-hydroxyethyl)-methyl-amide (142).
LC-MS: 526.6 (M+H).

Preparation of (143)

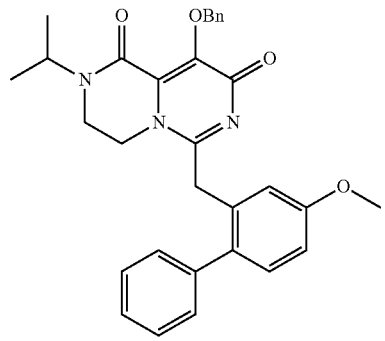 [SMILES: COc1ccc(-c2ccccc2)c(Cc2nc(=O)c(OCc3ccccc3)c3n2CCN(C(C)C)C3=O)c1]

Step 7: 9-Benzyloxy-2-isopropyl-6-(4-methoxy-biphenyl-2-ylmethyl)-3,4-dihydro-2H-pyrazino[1,2-c]pyrimidine-1,8-dione 9-Benzyloxy-2-isopropyl-6-(4-methoxy-biphenyl-2-ylmethyl)-3,4-dihydro-2H-pyrazino[1,2-c]pyrimidine-1,8-dione (143) (33 mg, 29.68%) as a white solid was synthesized from 5-benzyloxy-6-hydroxy-2-(4-methoxybiphenyl-2-ylmethyl)-pyrimidine-4-carboxylic acid (2-hydroxyethyl)-isopropylamide (142) (115 mg, 0.218 mmol) following the procedure as described for 9-benzyloxy-6-(2,3-dichlorobenzyl)-2-isopropyl-3,4-dihydro-2H-pyrazino[1,2-c]pyrimidine-1,8-dione (143).
LC-MS: 510 (M+H).

159
Preparation of (144)

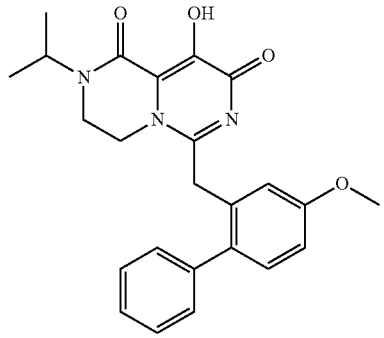 [SMILES: COc1ccc(-c2ccccc2)c(Cc2nc(=O)c(O)c3n2CCN(C(C)C)C3=O)c1]

Step 8: 9-Hydroxy-2-isopropyl-6-(4-methoxy-biphenyl-2-ylmethyl)-3,4-dihydro-2H-pyrazino[1,2-c]pyrimidine-1,8-dione 9-Hydroxy-2-isopropyl-6-(4-methoxy-biphenyl-2-ylmethyl)-3,4-dihydro-2H-pyrazino[1,2-c]pyrimidine-1,8-dione (144) (18 mg, 29.69%) as a white solid was synthesized from 9-benzyloxy-2-isopropyl-6-(4-methoxy-biphenyl-2-ylmethyl)-3,4-dihydro-2H-pyrazino[1,2-c]pyrimidine-1,8-dione (143) (82 mg, 0.161 mmol) following the procedure as described for 6-(2,3-dichlorobenzyl)-9-hydroxy-2-isopropyl-3,4-dihydro-2H-pyrazino[1,2-c]pyrimidine-1,8-dione (144).

LC-MS: 420.2 (M+H).

Example 145

9-Hydroxy-6-(4-hydroxy-biphenyl-2-ylmethyl)-2-isopropyl-3,4-dihydro-2H-pyrazino[1,2-d]pyrimidine-1,8-dione The synthetic procedure used in this preparation is outlined in Scheme 20.

Synthetic Route for (145)

Scheme 20

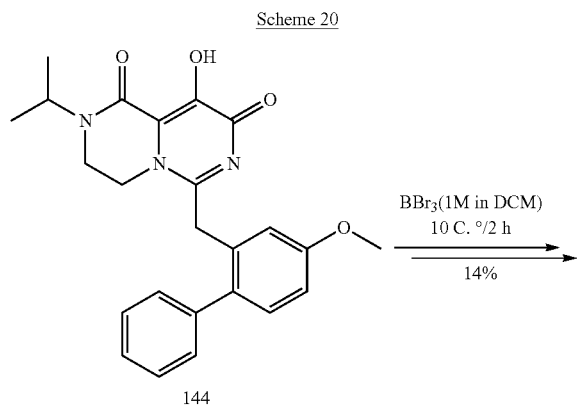

144

160

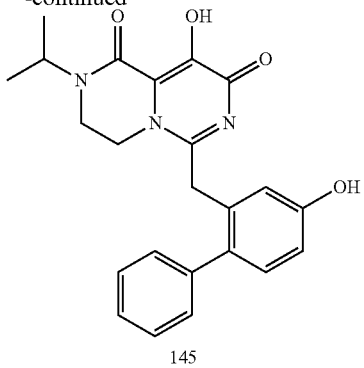

145

Preparation of (145)

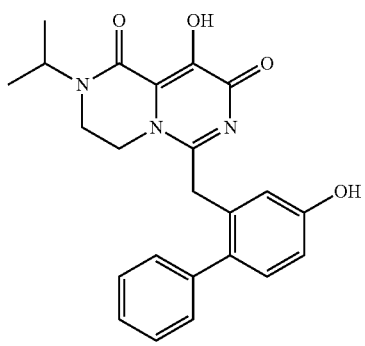 [SMILES: CC(C)N1CCn2c(Cc3cc(O)ccc3-c3ccccc3)nc(=O)c(O)c2C1=O]

9-Hydroxy-6-(4-hydroxy-biphenyl-2-ylmethyl)-2-isopropyl-3,4-dihydro-2H-pyrazino[1,2-c]pyrimidine-1,8-dione To a stirred solution of 9-hydroxy-2-isopropyl-6-(4-methoxy-biphenyl-2-ylmethyl)-3,4-dihydro-2H-pyrazino[1,2-c]pyrimidine-1,8-dione (145) (230 mg, 0.548 mmol) in dichloromethane (10 mL) was added $BBr_a$ (1M in dichloromethane, 1.64 mL, 1.64 mmol) at ice temperature under nitrogen and the mixture was allowed to stirred for 2 h at room temperature. On completion of the reaction, the mixture was evaporated under reduced pressure and the residue was diluted with dichloromethane (100 mL) and water. The separated organic layer was washed with saturated $NaHCO_3$ solution (50 mL), water (50 mL), brine (50 mL), and dried over sodium sulfate and concentrated under reduced pressure. The obtained crude product was purified by preparative HPLC to obtain 9-hydroxy-6-(4-hydroxy-biphenyl-2-ylmethyl)-2-isopropyl-3,4-dihydro-2H-pyrazino[1,2-c]pyrimidine-1,8-dione (145) (32 mg, 14.39%) as an off-white solid.

LC-MS: 406.4 (M+H).

Example 154
9-Hydroxy-2-isopropyl-6-(2-pyridin-4-yl-benzyl)-3,4-dihydro-2H-pyrazino[1,2-c]pyrimidine-1,8-dione
The synthetic procedure used in this preparation is outlined in Scheme 21.
Synthetic Route for (154)
Scheme 21
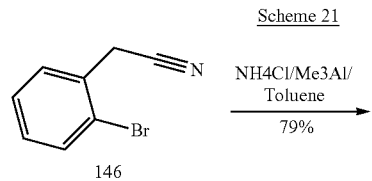
146
NH4Cl/Me3Al/
Toluene
79%
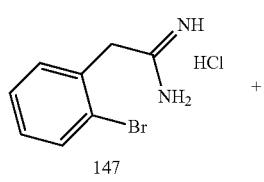
147
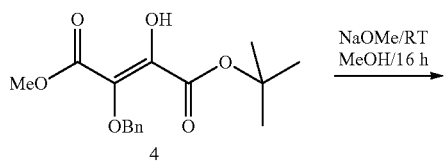
4
NaOMe/RT
MeOH/16 h
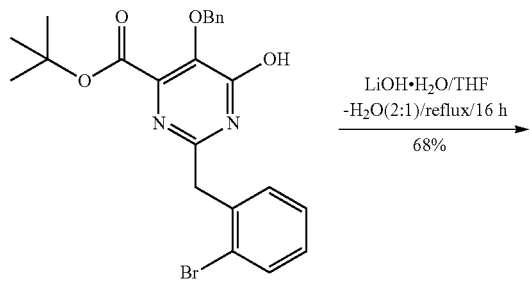
148
LiOH·H2O/THF
-H2O(2:1)/reflux/16 h
68%
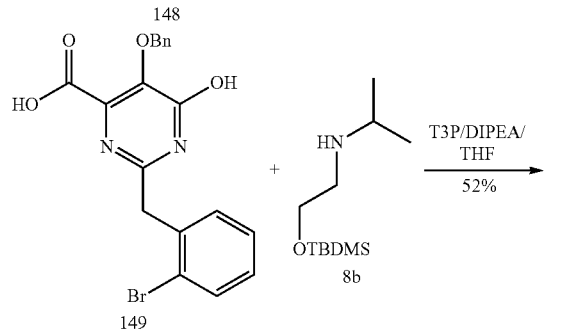
149
T3P/DIPEA/
THF
52%
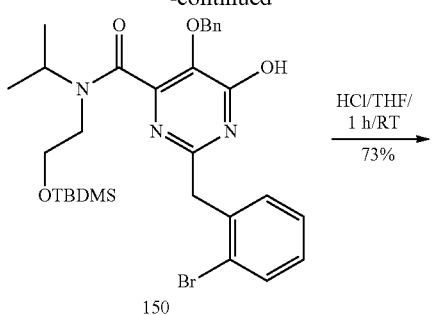
150
HCl/THF/
1 h/RT
73%
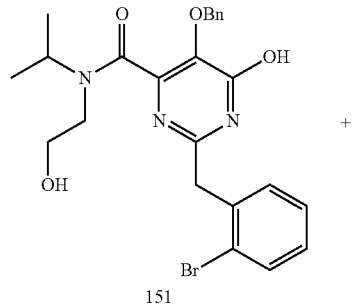
151
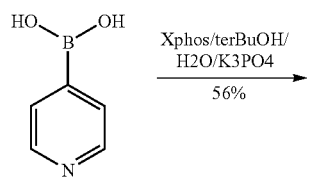
Xphos/terBuOH/
H2O/K3PO4
56%
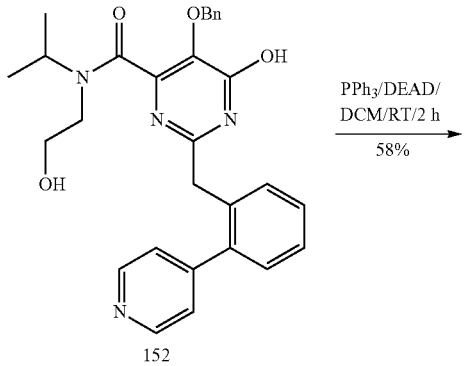
152
PPh3/DEAD/
DCM/RT/2 h
58%
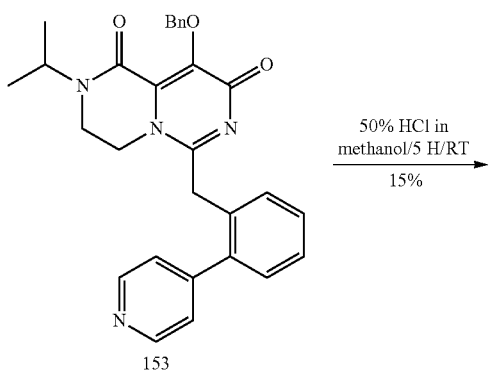
153
50% HCl in
methanol/5 H/RT
15%

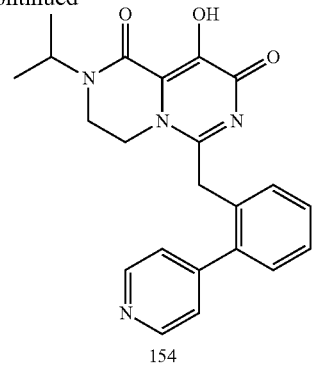

154

Preparation of (147)

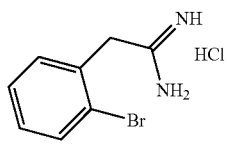 [SMILES: N=C(N)Cc1ccccc1Br ; Cl]

Step 1: 2-(2-Bromophenyl)-acetamidine hydrochloride salt 2-(2-Bromophenyl)-acetamidine hydrochloride salt (147) (20 g, 78.58%) as a white solid was synthesized from (2-bromophenyl)-acetonitrile (146) (5 g, 25.50 mmol) following the procedure as described for 2-(2-bromo-5-methoxy-phenyl)-acetamidine hydrochloride salt as a crude product (147).

LC-MS: 215 (M+H).

Preparation of (148)

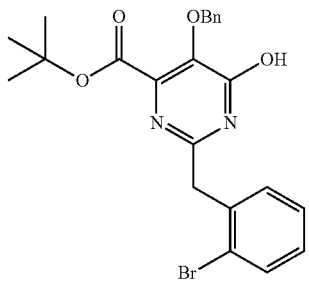 [SMILES: CC(C)(C)OC(=O)c1nc(Cc2ccccc2Br)nc(O)c1OCc1ccccc1]

Step 2: 5-Benzyloxy-2-(2-bromobenzyl)-6-hydroxy-pyrimidine-4-carboxylic acid tert-butyl ester 5-Benzyloxy-2-(2-bromobenzyl)-6-hydroxypyrimidine-4-carboxylic acid tert-butyl ester (148) (28 g, crude) as a brown solid was synthesized from 2-(2-bromophenyl)-acetamidine hydrochloride salt (147) (17.76 g, 71.32 mmol) and (E)-2-benzyloxy-3-hydroxy-but-2-enedioic acid 4-tert-butyl ester 1-methyl ester (4) (32.95 g, 106.98 mmol) following the procedure as described for 5-benzyloxy-2-(2,3-dichlorobenzyl)-6-hydroxypyrimidine-4-carboxylic acid tert-butyl ester (130). The product was used without purification for further synthesis.

Preparation of (149)

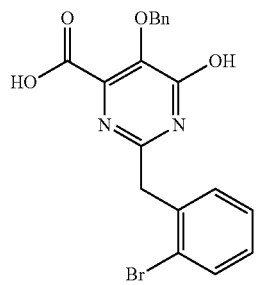 [SMILES: O=C(O)c1nc(Cc2ccccc2Br)nc(O)c1OCc1ccccc1]

Step 3: 5-Benzyloxy-2-(2-bromobenzyl)-6-hydroxypyrimidine-4-carboxylic acid

5-Benzyloxy-2-(2-bromobenzyl)-6-hydroxypyrimidine-4-carboxylic acid (149) (16.5 g, 68%) as a brown solid was synthesized from 5-benzyloxy-2-(2-bromobenzyl)-6-hydroxypyrimidine-4-carboxylic acid tert-butyl ester (148) (30 g, 63.69 mmol) following the procedure as described for 5-benzyloxy-2-(2,3-dichlorobenzyl)-6-hydroxypyrimidine-4-carboxylic acid (131).

LC-MS: 415.2 (M+H).

Preparation of (150)

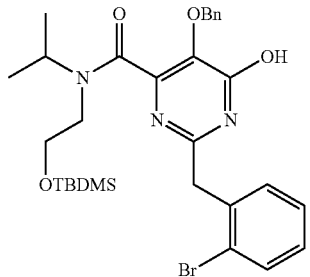 [SMILES: CC(C)N(CCO[Si](C)(C)C(C)(C)C)C(=O)c1nc(Cc2ccccc2Br)nc(O)c1OCc1ccccc1]

Step 4: 5-Benzyloxy-2-(2-bromobenzyl)-6-hydroxypyrimidine-4-carboxylic acid 2-(tert-butyl-dimethylsilanyloxy)-ethyl]-isopropylamide 5-Benzyloxy-2-(2-bromobenzyl)-6-hydroxypyrimidine-4-carboxylic acid 2-(tert-butyl-dimethylsilanyloxy)-ethyl]-isopropylamide (150) (382 mg, 51.6%) as an off-white solid was synthesized from 5-benzyloxy-2-(2-bromobenzyl)-6-hydroxypyrimidine-4-carboxylic acid (149) (500 mg, 1.20 mmol) and [2-(tert-butyl-dimethylsilanyloxy)-ethyl]-isopropyl-amine (8b) (523.6 mg, 2.40 mmol) following the procedure as described for 5-benzyloxy-2-(2,3-dichlorobenzyl)-6-hydroxypyrimidine-4-carboxylic acid [2-(tert-butyl-dimethylsilanyloxy)-ethyl]-isopropylamide (132).

LC-MS: 616.2 (M+H).

Preparation of (151)

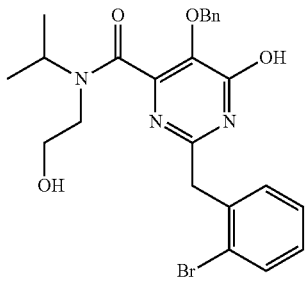 [SMILES: CC(C)N(CCO)C(=O)c1nc(Cc2ccccc2Br)nc(O)c1OCc1ccccc1]

Step 5: 5-Benzyloxy-2-(2-bromobenzyl)-6-hydroxy-pyrimidine-4-carboxylic acid (2-hydroxyethyl)-isopropylamide 5-Benzyloxy-2-(2-bromobenzyl)-6-hydroxypyrimidine-4-carboxylic acid (2-hydroxyethyl)-isopropylamide (151) (1.3 g, 72.5%) as an off-white solid was synthesized from 5-benzyloxy-2-(2-bromobenzyl)-6-hydroxypyrimidine-4-carboxylic acid 2-(tert-butyl-dimethylsilanyloxy)-ethyl]-isopropylamide (150) (2.2 g, 3.57 mmol) following the procedure as described for 5-Benzyloxy-2-(2,3-dichlorobenzyl)-6-hydroxypyrimidine-4-carboxylic acid (2-hydroxyethyl)-isopropylamide (133).

LC-MS: 500.2 (M+H).

Preparation of (152)

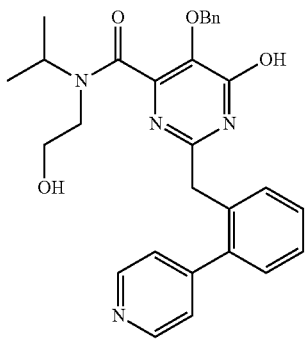 [SMILES: CC(C)N(CCO)C(=O)c1nc(Cc2ccccc2-c2ccncc2)nc(O)c1OCc1ccccc1]

Step 6: 5-Benzyloxy-6-hydroxy-2-(2-pyridin-4-yl-benzyl)-pyrimidine-4-carboxylic acid (2-hydroxyethyl)-isopropylamide 5-Benzyloxy-6-hydroxy-2-(2-pyridin-4-yl-benzyl)-pyrimidine-4-carboxylic acid (2-hydroxyethyl)-isopropylamide (152) (251 mg, 56.02%) as an off-white solid was synthesized from 5-benzyloxy-2-(2-bromobenzyl)-6-hydroxypyrimidine-4-carboxylic acid (2-hydroxyethyl)-isopropylamide (151) (450 mg, 0.89 mmol) and pyridine-4-boronic acid (165.78 mg, 1.34 mmol) following the procedure as described for 5-benzyloxy-6-hydroxy-2-(4-methoxybiphenyl-2-ylmethyl)-pyrimidine-4-carboxylic acid tert-butyl ester (139).

LC-MS: 499 (M+H).

Preparation of (153)

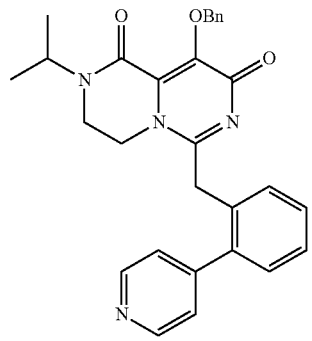 [SMILES: CC(C)N1CCn2c(Cc3ccccc3-c3ccncc3)nc(=O)c(OCc3ccccc3)c2C1=O]

Step 7: 9-Benzyloxy-2-isopropyl-6-(2-pyridin-4-yl-benzyl)-3,4-dihydro-2H-pyrazino[1,2-c]pyrimidine-1,8-dione 9-Benzyloxy-2-isopropyl-6-(2-pyridin-4-yl-benzyl)-3,4-dihydro-2H-pyrazino[1,2-c]pyrimidine-1,8-dione (153) (83 mg, 57.73%) as an off-white solid was synthesized from 5-benzyloxy-6-hydroxy-2-(2-pyridin-4-yl-benzyl)-pyrimidine-4-carboxylic acid (2-hydroxyethyl)-isopropylamide (152) (150 mg, 0.90 mmol) following the procedure as described for 9-benzyloxy-6-(2,3-dichlorobenzyl)-2-isopropyl-3,4-dihydro-2H-pyrazino[1,2-c]pyrimidine-1,8-dione (134).

LC-MS: 481.2 (M+H).

Preparation of (154)

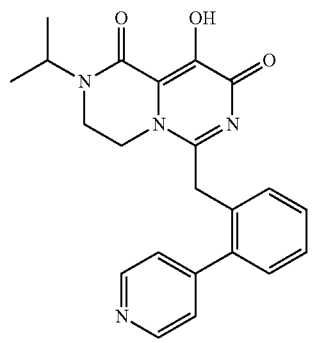 [SMILES: CC(C)N1CCn2c(Cc3ccccc3-c3ccncc3)nc(=O)c(O)c2C1=O]

Step 8: 9-Hydroxy-2-isopropyl-6-(2-pyridin-4-yl-benzyl)-3,4-dihydro-2H-pyrazino[1,2-c]pyrimidine-1,8-dione 9-Hydroxy-2-isopropyl-6-(2-pyridin-4-yl-benzyl)-3,4-dihydro-2H-pyrazino[1,2-c]pyrimidine-1,8-dione (154) (30 mg, 14.77%) as a light yellow solid was synthesized from 9-benzyloxy-2-isopropyl-6-(2-pyridin-4-yl-benzyl)-3,4-dihydro-2H-pyrazino[1,2-c]pyrimidine-1,8-dione (153) (250 mg, 0.52 mmol) following the procedure as described for 6-(2,3-dichlorobenzyl)-9-hydroxy-2-isopropyl-3,4-dihydro-2H-pyrazino[1,2-c]pyrimidine-1,8-dione (135).

LC-MS: 391.2 (M+H).

Example 157

6-(2-Cyclohexyl-benzyl)-9-hydroxy-2-isopropyl-3,4-dihydro-2H-pyrazino[1,2-c]pyrimidine-1,8-dione The synthetic procedure used in this preparation is outlined in Scheme 22.

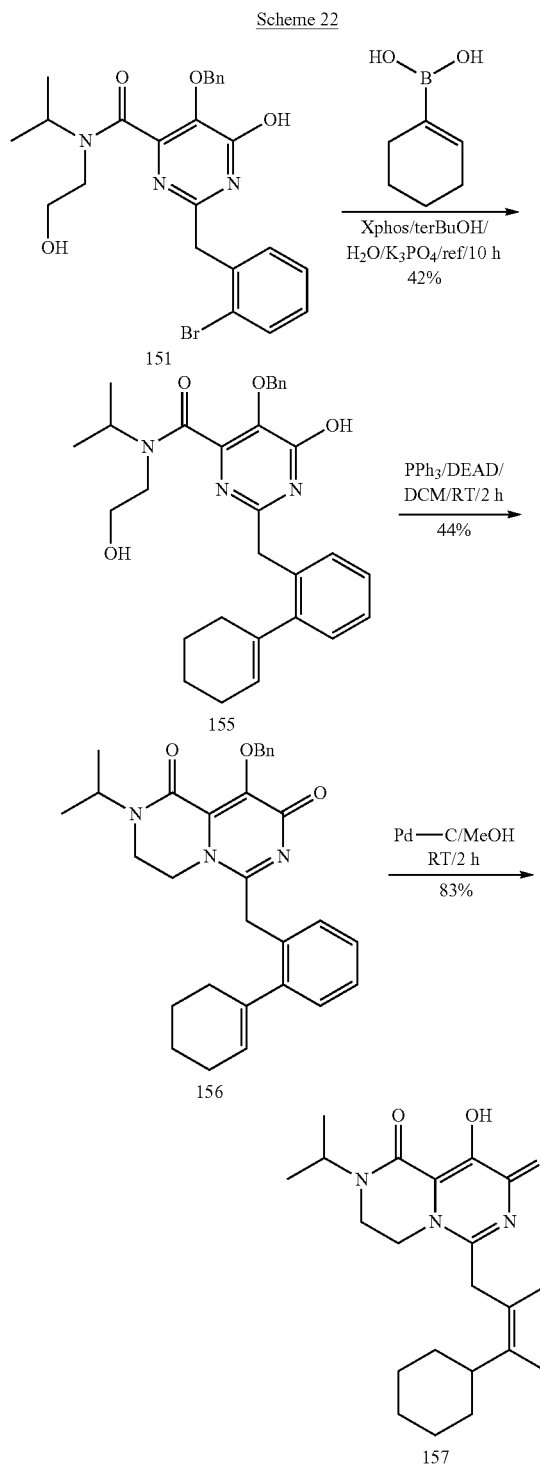

Preparation of (155)

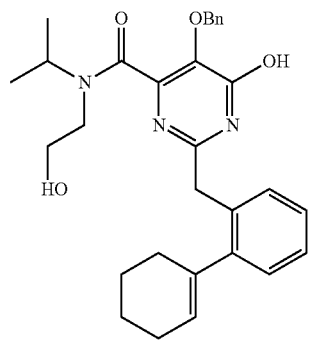 [SMILES: CC(C)N(CCO)C(=O)c1nc(Cc2ccccc2C2=CCCCC2)nc(O)c1OCc1ccccc1]

5-Benzyloxy-2-(2-cyclohex-1-enyl-benzyl)-6-hydroxypyrimidine-4-carboxylic acid (2-hydroxyethyl)-isopropylamide 5-Benzyloxy-2-(2-cyclohex-1-enyl-benzyl)-6-hydroxypyrimidine-4-carboxylic acid (2-hydroxyethyl)-isopropylamide (155) (210 mg, 41.9%) as a colorless sticky liquid was synthesized from 5-benzyloxy-2-(2-bromobenzyl)-6-hydroxypyrimidine-4-carboxylic acid (2-hydroxyethyl)-isopropylamide (151) (500 mg, 0.999 mmol) and cyclohexene boronic acid (188.84 mg, 1.49 mmol) following the procedure as described for 5-benzyloxy-6-hydroxy-2-(4-methoxybiphenyl-2-ylmethyl)-pyrimidine-4-carboxylic acid tert-butyl ester (139).

LC-MS: 502.2 (M+H).

Preparation of (156)

9-Benzyloxy-6-(2-cyclohex-1-enyl-benzyl)-2-isopropyl-3,4-dihydro-2H-pyrazino[1,2-c]pyrimidine-1,8-dione 9-Benzyloxy-6-(2-cyclohex-1-enyl-benzyl)-2-isopropyl-3,4-dihydro-2H-pyrazino[1,2-c]pyrimidine-1,8-dione (156) (42.5 mg, 44.15%) as an off-white solid was synthesized from 5-benzyloxy-2-(2-cyclohex-1-enyl-benzyl)-6-hydroxypyrimidine-4-carboxylic acid (2-hydroxyethyl)-isopropylamide (155) (100 mg, 0.199 mmol) following the procedure as described for 9-benzyloxy-6-(2,3-dichlorobenzyl)-2-isopropyl-3,4-dihydro-2H-pyrazino[1,2-c]pyrimidine-1,8-dione (134).

LC-MS: 484.2 (M+H).

169

Preparation of (157)

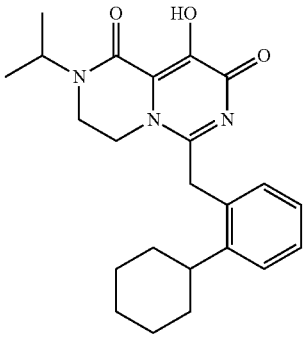 [SMILES: CC(C)N1CCn2c(Cc3ccccc3C3CCCCC3)nc(=O)c(O)c2C1=O]

6-(2-Cyclohexyl-benzyl)-9-hydroxy-2-isopropyl-3,4-dihydro-2H-pyrazino[1,2-c]pyrimidine-1,8-dione To a stirred solution of 9-benzyloxy-6-(2-cyclohex-1-enyl-benzyl)-2-isopropyl-3,4-dihydro-2H-pyrazino[1,2-c]pyrimidine-1,8-dione (156) (170 mg, 0.352 mmol) in methanol (20 mL) was added Pd/C(10%) (170 mg) and hydrogenated under balloon pressure for 2 h at room temperature. After completion of the reaction, the mixture was filtered through a celite pad, washed with methanol (30 mL), evaporated under reduced pressure to get a crude product which was purified by preparative HPLC to get 6-(2-cyclohexyl-benzyl)-9hydroxy-2-isopropyl-3,4-dihydro-2H-pyrazino[1,2-c]pyrimidine-1,8-dione (157) (115 mg, 82.72%) as an off-white solid.

LC-MS: 396 (M+H).

Example 168

9-Hydroxy-2-isopropyl-6-(3-phenyl-pyridin-2-ylmethyl)-3,4-dihydro-2H-pyrazino[1,2-c]pyrimidine-1,8-dione The synthetic procedure used in this preparation is outlined in Scheme 23.

Scheme 23

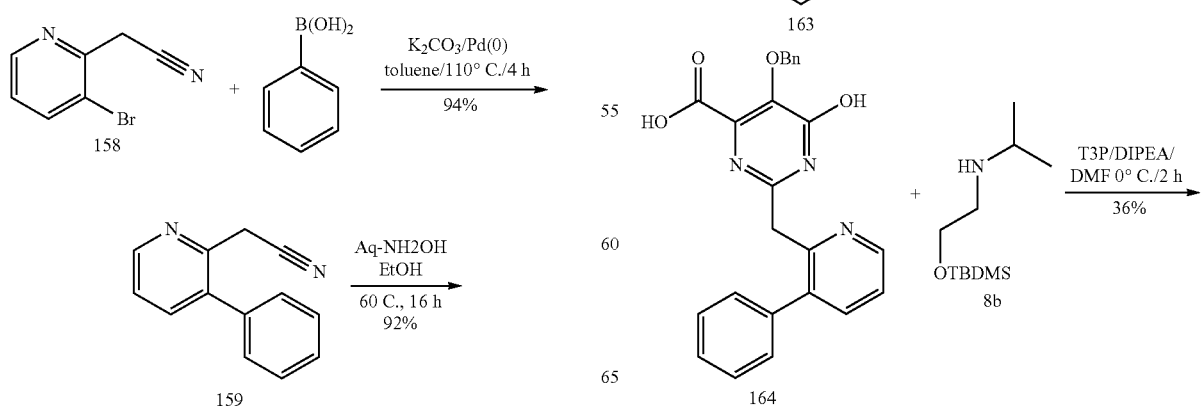

170

-continued

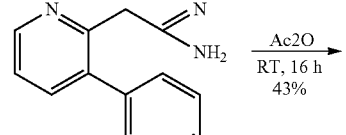

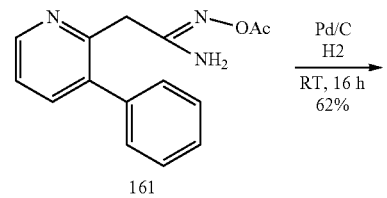

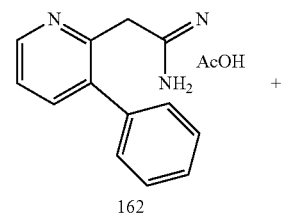

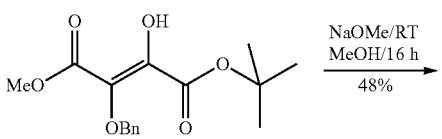

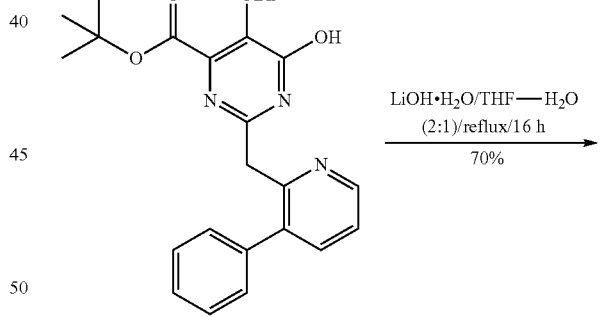

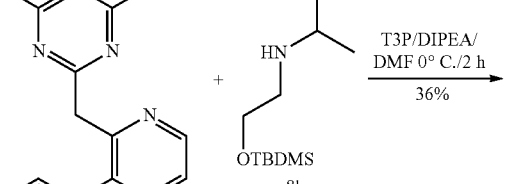

-continued

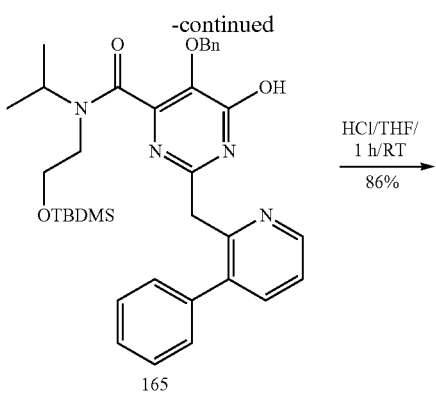

165

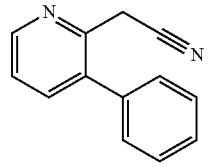 [SMILES: N#CCc1ncccc1-c1ccccc1]

HCl/THF/
1 h/RT
———————→
86%

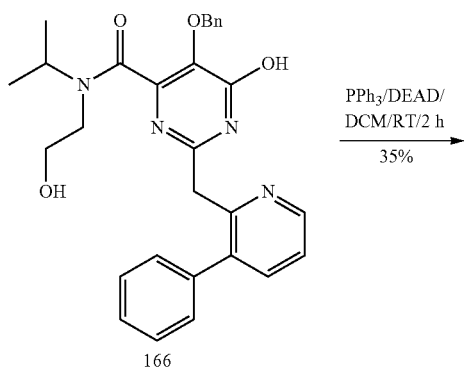

166

PPh₃/DEAD/
DCM/RT/2 h
———————→
35%

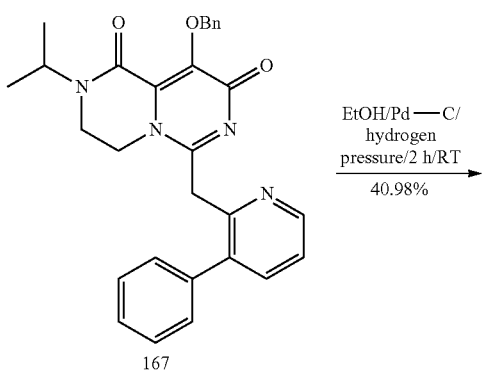

167

EtOH/Pd—C/
hydrogen
pressure/2 h/RT
———————→
40.98%

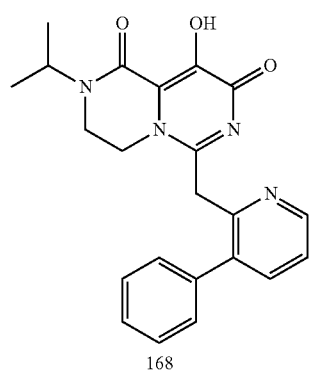

168

Preparation of (159)

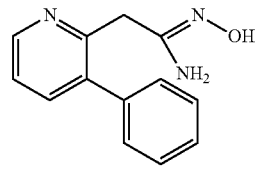 [SMILES: N/C(Cc1ncccc1-c1ccccc1)=N\O]

Step 1: (3-Phenyl-pyridin-2-yl)-acetonitrile

To a stirred solution of (3-bromo-pyridin-2-yl)-acetonitrile (158) (1 g, 5.07 mmol) and phenyl boronic acid (928 mg g, 7.16 mmol) in a solvent mixture of toluene (25 mL) and ethanol (25 mL) was added K₂CO₃ (2.1 g, 15.23 mmol). The mixture was degassed by argon, X-Phos (484 mg, 1.01 mmol) and Pd(triphenyl phosphine)₄ (586 mg g, 0.51 mmol) were added and the mixture was again degassed. The reaction mixture was refluxed (110° C.) for 4 h. Silica thin layer chromatography was performed (30% ethyl acetate in hexane, R$_f$=0.45). The catalyst was filtered off through a celite bed, washing with ethyl acetate (3×50 mL) was conducted, the mixture was concentrated, the crude product was purified by a CombiFlash column (eluted at 15% ethyl acetate in hexane) to get (3-phenyl-pyridin-2-yl)-acetonitrile (159) (930 mg, 94.34%) as a light yellow solid.

LC-MS: 195.2 (M+H).

Preparation of (160)

Step 2:
N-Hydroxy-2-(3-phenyl-pyridin-2-yl)-acetamidine

To a stirred solution of (3-phenyl-pyridin-2-yl)-acetonitrile (159) (4.9 g, 25.26 mmol) in ethanol (250 mL) was added 50% aqueous NH₂OH (3.4 mL, 50.51 mmol) and the mixture was heated at 60° C. for 16 h. Silica thin layer chromatography was performed (40% ethyl acetate in hexane, R$_f$=0.2). Ethanol was evaporated, water (50 mL) was added, the mixture was extracted with etylacetate (3×50 mL), dried and concentrated to get N-hydroxy-2-(3-phenyl-pyridin-2-yl)-acetamidine (160) (5.3 g, 92.33%, crude) as a yellow solid.

LC-MS: 228.0 (M+H).

Preparation of (161)

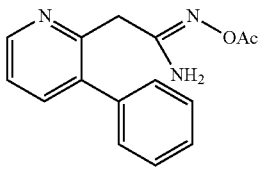 [SMILES: CC(=O)O/N=C(\N)Cc1ncccc1-c1ccccc1]

Step 3: 2-(3-phenylpyridin-2-yl)ethanimidamido acetate

Ac₂O (30 mL) was added to N-hydroxy-2-(3-phenyl-pyridin-2-yl)-acetamidine (160) (5.3 g, 23.35 mmol) at room temperature. A purple colored solution was formed, after a few hours a dark brown solution was formed which was stirred for 6 h at room temperature. Silica thin layer chromatography was performed (100% ethyl acetate, $R_f$=0.6). Cold water was added, the mixture was extracted with ethyl acetate (3×50 mL), the organic part was dried and concentrated, the crude product was purified by a CombiFlash column (eluted at 50% ethyl acetate in hexane) to get 2-(3-phenylpyridin-2-yl)ethanimidamido acetate (161) (2.7 g, 42.94% pure and 2 g mixture) as a yellow solid.

LC-MS: 269.8 (M+H).

Preparation of (162)

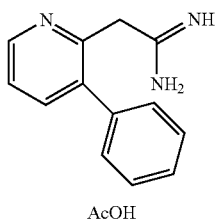 [SMILES: "AcOH" ; N=C(N)Cc1ncccc1-c1ccccc1]

AcOH

Step 4: 2-(3-Phenyl-pyridin-2-yl)-acetamidine with acetic acid

To a stirred degassed solution of (161) (2.7 g, 10.04 mmol) in ethanol (135 mL) was added 10% Pd—C (270 mg), the mixture was stirred 16 h under H₂ (hydrogen bubbler) at room temperature. Silica thin layer chromatography was performed (ethyl acetate, $R_f$=0.1). The reaction mixture was filtered through celite, washed with 10% methanol in dichloromethane (5×100 mL), dried and concentrated. The yellow solid was washed with 10% ethyl acetate in hexane (3×30 mL) to get pure 2-(3-phenyl-pyridin-2-yl)-acetamidine with acetic acid (162) (1.7 g, 62.5%) as an off-white solid.

LC-MS: 212.0 (M+H).

Preparation of (163)

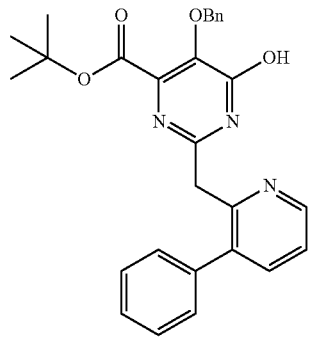 [SMILES: CC(C)(C)OC(=O)c1nc(Cc2ncccc2-c2ccccc2)nc(O)c1OCc1ccccc1]

Step 5: 5-Benzyloxy-6-hydroxy-2-(3-phenyl-pyridin-2-ylmethyl)-pyrimidine-4-carboxylic acid tert-butyl ester To a stirred solution of 2-(3-phenyl-pyridin-2-yl)-acetamidine (162) (300 mg, 1.10 mmol) and (E)-2-benzyloxy-3-hydroxy-but-2-enedioic acid 4-tert-butyl ester (4) (511 mg, 1.66 mmol) in methanol (5 mL) was added sodium methoxide (1.3 mL, 3.32 mmol) at 0° C., then the reaction mixture was allowed to warm to room temperature, stirred for 16 h. Silica thin layer chromatography was performed (50% ethyl acetate in hexane, $R_f$=0.3). After completion of the reaction, it was quenched with water, methanol was evaporated and water (30 mL) was added. The mixture was extracted with ethyl acetate (3×30 mL) and the separated organic part was dried and concentrated to get a crude product, which was purified by a CombiFlash column (eluted at 90% ethyl acetate in hexane) to get 5-benzyloxy-6-hydroxy-2-(3-phenyl-pyridin-2-ylmethyl)-pyrimidine-4-carboxylic acid tert-butyl ester (163) (250 mg, 48.1%) as a yellow sticky product.

LC-MS: 470.2 (M+H).

Preparation of (164)

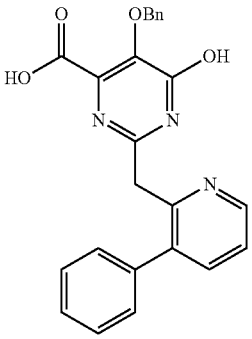 [SMILES: O=C(O)c1nc(Cc2ncccc2-c2ccccc2)nc(O)c1OCc1ccccc1]

Step 6: 5-Benzyloxy-6-hydroxy-2-(3-phenyl-pyridin-2-ylmethyl)-pyrimidine-4-carboxylic acid 5-Benzyloxy-6-hydroxy-2-(3-phenyl-pyridin-2-ylmethyl)-pyrimidine-4-carboxylic (164) (370 mg, 69.96%) as an off-white solid was synthesized from 5-benzyloxy-6-hydroxy-2-(3-phenyl-pyridin-2-ylmethyl)-pyrimidine-4-carboxylic acid tert-butyl ester (163) (600 mg, 1.28 mmol) following the procedure as described for 5-benzyloxy-2-(2,3-dichlorobenzyl)-6-hydroxypyrimidine-4-carboxylic acid (131). S silica thin layer chromatography was performed (5% methanol in dichloromethane, $R_f$=0.1).

LC-MS: 414.4 (M+H).

Preparation of (165)

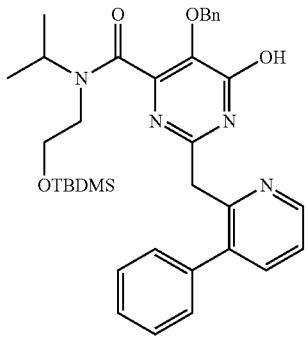 [SMILES: CC(C)N(CCO[Si](C)(C)C(C)(C)C)C(=O)c1nc(Cc2ncccc2-c2ccccc2)nc(O)c1OCc1ccccc1]

Step 7: 5-Benzyloxy-6-hydroxy-2-(3-phenyl-pyridin-2-ylmethyl)-pyrimidine-4-carboxylic acid [2-(tert-butyl-dimethylsilanyloxy)-ethyl]-isopropylamide To a stirred solution of 5-benzyloxy-6-hydroxy-2-(3-phenyl-pyridin-2-ylmethyl)-pyrimidine-4-carboxylic acid (164) (370 mg, 0.89 mmol) and [2-(tert-butyl-dimethylsilanyloxy)-ethyl]-isopropyl-amine (8b) (292 mg, 1.34 mmol) in dimethylformamide (5 mL) was added N,N-diisopropylethylamine (0.5 mL, 2.69 mmol), the mixture was cooled to 0° C., $T_3P$ (50 wt % in ethyl acetate) (1.8 g, 2.69 mmol) was added, and the mixture was stirred for 16 h at room temperature. Silica thin layer chromatography was performed (5% methanol in dichloromethane, $R_f$=0.3). Water (100 mL) was added, the mixture was extracted with ethyl acetate, dried and concentrated, and purified by a CombiFlash column (eluted at 2-5% methanol in dichloromethane) to get 5-benzyloxy-6-hydroxy-2-(3-phenyl-pyridin-2-ylmethyl)-pyrimidine-4-carboxylic acid [2-(tert-butyl-dimethylsilanyloxy)-ethyl]-isopropylamide (165) (200 mg, 36.46%) as a yellow sticky product.

LC-MS: 613.2 (M+H).

Preparation of (166)

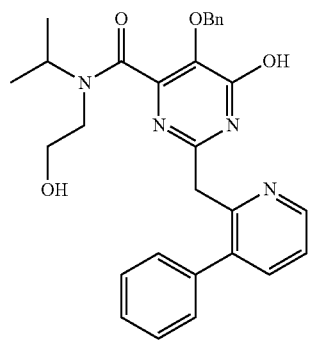 [SMILES: CC(C)N(CCO)C(=O)c1nc(Cc2ncccc2-c2ccccc2)nc(O)c1OCc1ccccc1]

Step 8: 5-Benzyloxy-6-hydroxy-2-(3-phenyl-pyridin-2-ylmethyl)-pyrimidine-4-carboxylic acid (2-hydroxyethyl)-isopropylamide 5-Benzyloxy-6-hydroxy-2-(3-phenyl-pyridin-2-ylmethyl)-pyrimidine-4-carboxylic acid (2-hydroxyethyl)-isopropylamide (166) (140 mg, 85.93%) as a light yellow sticky solid was synthesized from 5-benzyloxy-6-hydroxy-2-(3-phenyl-pyridin-2-ylmethyl)-pyrimidine-4-carboxylic acid [2-(tert-butyl-dimethylsilanyloxy)-ethyl]isopropylamide (165) (200 mg, 0.33 mmol) following the procedure as described for 5-benzyloxy-2-(2,3-dichlorobenzyl)-6-hydroxypyrimidine-4-carboxylic acid [2-(tert-butyl-dimethylsilanyloxy)-ethyl]isopropylamide (132). Silica thin layer chromatography was performed (5% methanol in dichloromethane, $R_f$=0.4).

LC-MS: 499.0 (M+H).

Preparation of (167)

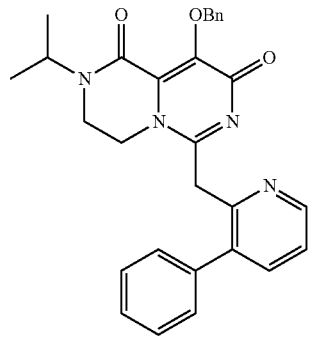

Step 9: 9-Benzyloxy-2-isopropyl-6-(3-phenyl-pyridin-2-ylmethyl)-3,4-dihydro-2H-pyrazino[1,2-c]pyrimidine-1,8-dione To a stirred solution of 5-benzyloxy-6-hydroxy-2-(3-phenyl-pyridin-2-ylmethyl)-pyrimidine-4-carboxylic acid (2-hydroxyethyl)-isopropylamide (166) in tetrahydrofuran (20 mL) were added triphenyl phosphine (66 mg, 0.25 mL) and DTAD (58 mg, 0.25 mmol) at room temperature. A yellow clear solution was formed, which was sonicated for 20 min. It was stirred at room temperature for 24 h. Silica thin layer chromatography was performed (5% methanol in dichloromethane, $R_f$=0.2). The mixture was concentrated under reduced pressure to get a crude product, which was purified by a preparative thin layer chromatography plate (mobile phase 5% methanol in dichloromethane) to get pure 9-benzyloxy-2-isopropyl-6-(3-phenyl-pyridin-2-ylmethyl)-3,4-dihydro-2H-pyrazino[1,2-c]pyrimidine-1,8-dione (167) (17 mg, 35.23%) as a yellow sticky solid.

LC-MS: 481.3 (M+H).

Preparation of (168)

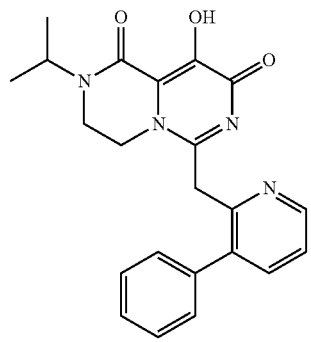

Step 10: 9-Hydroxy-2-isopropyl-6-(3-phenyl-pyridin-2-ylmethyl)-3,4-dihydro-2H-pyrazino[1,2-c]pyrimidine-1,8-dione 9-Hydroxy-2-isopropyl-6-(3-phenyl-pyridin-2-ylmethyl)-3,4-dihydro-2H-pyrazino[1,2-c]pyrimidine-1,8-dione (168) (12 mg, 40.98%) as a light yellow solid was synthesized from 9-benzyloxy-2-isopropyl-6-(3-phenyl-pyridin-2-ylmethyl)-3,4-dihydro-2H-pyrazino[1,2-c]pyrimidine-1,8-dione (167) (36 mg, 0.07 mmol) following the procedure as described for 9-hydroxy-2-isopropyl-6-[1-(4-trifluoromethyl-phenyl)-cyclopentylmethyl]-3,4-dihydro-2H-pyrazino[1,2-c]pyrimidine-1,8-dione (168).

LC-MS: 391.0 (M+H).

Example 169 (Intermediate)

9-Benzyloxy-6-(2-bromobenzyl)-2-isopropyl-3,4-dihydro-2H-pyrazino[1,2-c]pyrimidine-1,8-dione The synthetic procedure used in this preparation is outlined in Scheme 24.

Scheme 24

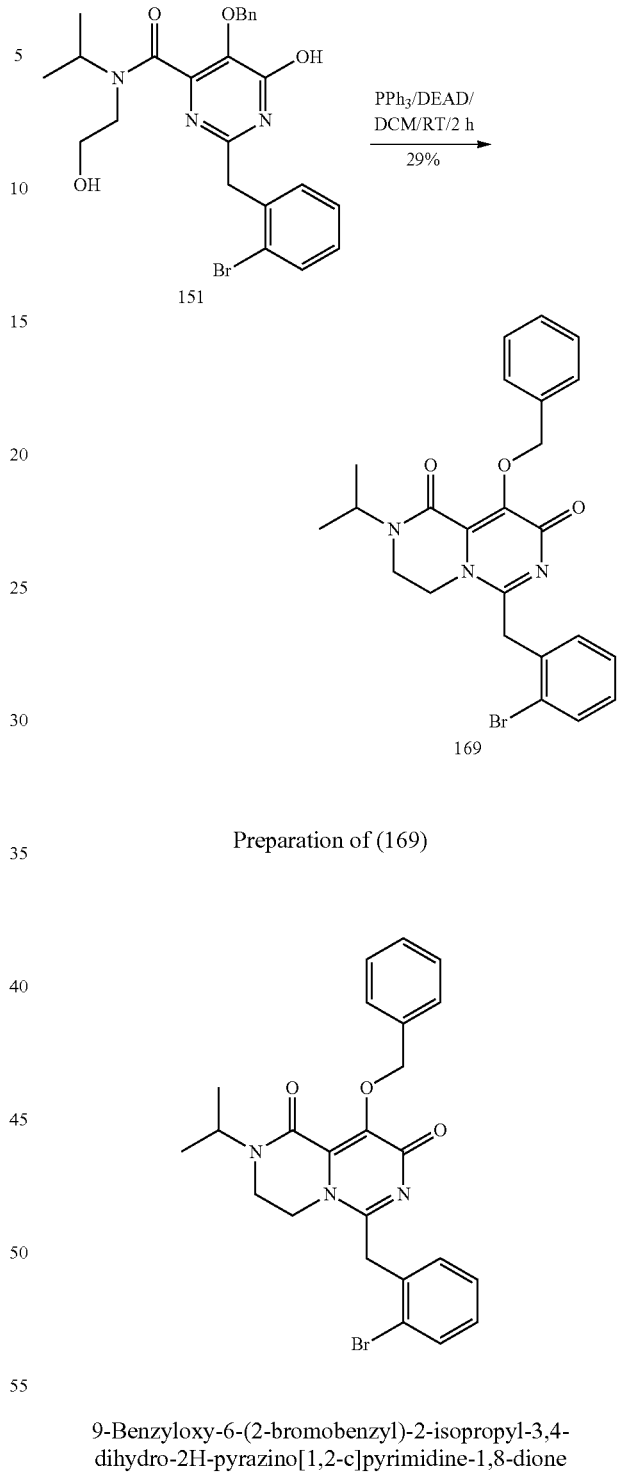

Preparation of (169)

9-Benzyloxy-6-(2-bromobenzyl)-2-isopropyl-3,4-dihydro-2H-pyrazino[1,2-c]pyrimidine-1,8-dione To a stirred solution of 5-benzyloxy-2-(2-bromobenzyl)-6-hydroxypyrimidine-4-carboxylic acid (2-hydroxyethyl)-isopropylamide (151) (400 mg, 0.8 mmol) in dichloromethane (10 mL) was added triphenyl phosphine (310.55 mg, 1.18 mmol) at room temperature. The mixture was stirred for 10 min. Then DEAD (0.186 mL, 1.18 mmol) was added at room temperature and the mixture was stirred for another 2 h. After completion of the reaction, the mixture was concentrated under reduced pressure to get a crude product, which was purified using a normal silica column using 2% methanol in dichloromethane to afford 9-benzyloxy-6-(2-bromobenzyl)-2-isopropyl-3,4-dihydro-2H-pyrazino[1,2-c]pyrimidine-1,8-dione (169) (112 mg, 29%) as a white solid.

LC-MS: 482.0 (M+H).

Example 171

6-[[2-(3,4-Difluorophenyl)phenyl]methyl]-9-hydroxy-2-isopropyl-3,4-dihydropyrazino[1,2-c]pyrimidine-1,8-dione The synthetic procedure used in this preparation is outlined in Scheme 25.

Scheme 25

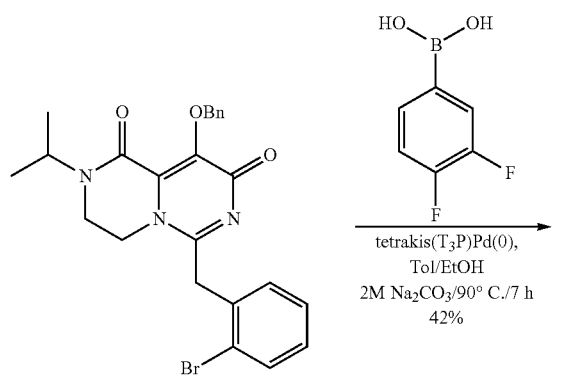

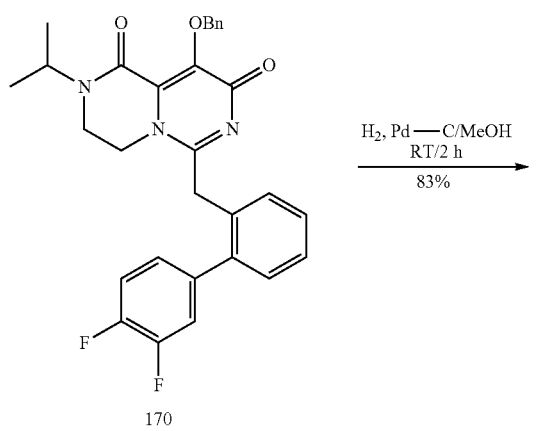

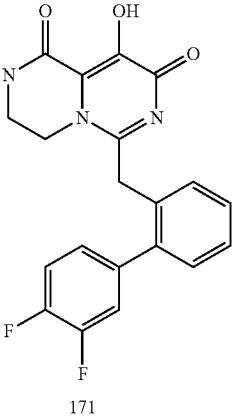

Preparation of (170)

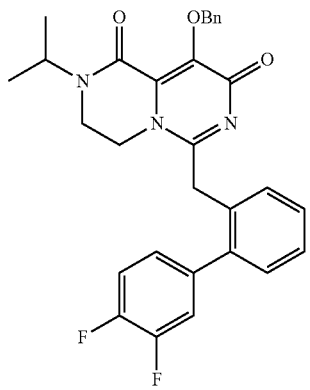 [SMILES: CC(C)N1CCn2c(Cc3ccccc3-c3ccc(F)c(F)c3)nc(=O)c(OCc3ccccc3)c2C1=O]

Step 1: 9-Benzyloxy-6-[[2-(3,4-difluorophenyl)phenyl]methyl]-2-isopropyl-3,4-dihydropyrazino-[1,2-c]pyrimidine-1,8-dione 9-Benzyloxy-6-[(2-bromophenyl)methyl]-2-isopropyl-3,4-dihydropyrazino[1,2-c]pyrimidine-1,8-dione (169) (150 mg, 0.311 mmol) and 3,4-difluorphenylboronic acid (56.5 mg, 0.358 mmol) were suspended in a mixture of toluene/ethanol (10 ml/1 ml), treated at room temperature under argon with tetrakis(triphenylphosphine)palladium(0) (14.4 mg, 12.4 µmol) and 2M sodium carbonate solution (342 µl, 684 µmol) and the reaction mixture was then heated at 90° C. for 7 h. The reaction was quenched with water and the mixture was extracted twice with ethyl acetate. The organic layers were combined, washed with brine, dried over sodium sulfate, filtered and concentrated. The residue was purified by chromatography over 25 g silica gel with methanol/dichloromethane (gradient: 0 to 10% methanol). All fractions containing product were combined and concentrated to afford 9-benzyloxy-6-[[2-(3,4-difluorophenyl)phenyl]methyl]-2-isopropyl-3,4-dihydropyrazino[1,2-c]pyrimidine-1,8-dione (160 mg) as a white solid.

LC/HR-MS: (M+H)$^+$=516.20993.

Preparation of (171)

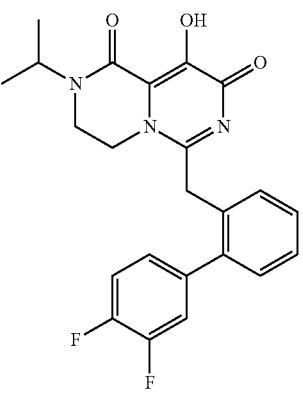 [SMILES: CC(C)N1CCn2c(Cc3ccccc3-c3ccc(F)c(F)c3)nc(=O)c(O)c2C1=O]

Step 2: 6-[[2-(3,4-Difluorophenyl)phenyl]methyl]-9-hydroxy-2-isopropyl-3,4-dihydropyrazino-[1,2-c]pyrimidine-1,8-dione 9-Benzyloxy-6-[[2-(3,4-difluorophenyl)phenyl]methyl]-2-isopropyl-3,4-dihydropyrazino[1,2-c]pyrimidine-1,8-dione (170) (160 mg) in methanol (20 ml) was hydrogenated over 10% Pd/C (20.6 mg) at room temperature and at atmospheric pressure for 2 h. The catalyst was filtered off, the filtrate was concentrated in vacuo to give the desired product as a light yellow foam (112 mg).

LC/HR-MS: (M+H)$^+$=426.16318.

Example 172

9-Hydroxy-2-isopropyl-6-[[2-(4-methoxyphenyl)phenyl]methyl]-3,4-dihydropyrazino[1,2-c]pyrimidine-1,8-dione The synthetic procedure used in this preparation is outlined in Scheme 26.

Scheme 26

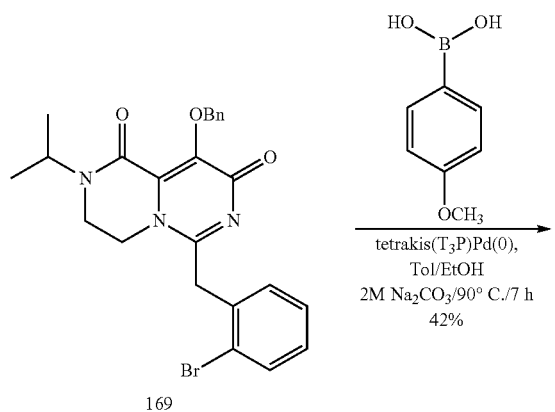

Preparation of (172)

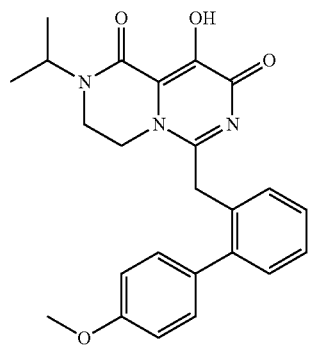 [SMILES: COc1ccc(-c2ccccc2Cc2nc(=O)c(O)c3n2CCN(C(C)C)C3=O)cc1]

9-Hydroxy-2-isopropyl-6-[[2-(4-methoxyphenyl)phenyl]methyl]-3,4-dihydropyrazino[1,2-c]pyrimidine-1,8-dione The title compound (172) was prepared in analogy to example 170 from 9-benzyloxy-6-[(2-bromophenyl)methyl]-2-isopropyl-3,4-dihydropyrazino[1,2-c]pyrimidine-1,8-dione (169) (120 mg) and 4-methoxyphenylboronic acid (45.4 mg). The product could be obtained directly from the coupling reaction (step 1). White solid (20 mg).

LC/MS: (M+H)$^+$=420.

Example 173

6-[[2-(3-Fluorophenyl)phenyl]methyl]-9-hydroxy-2-isopropyl-3,4-dihydropyrazino[1,2-c]pyrimidine-1,8-dione The synthetic procedure used in this preparation is outlined in Scheme 27.

Scheme 27

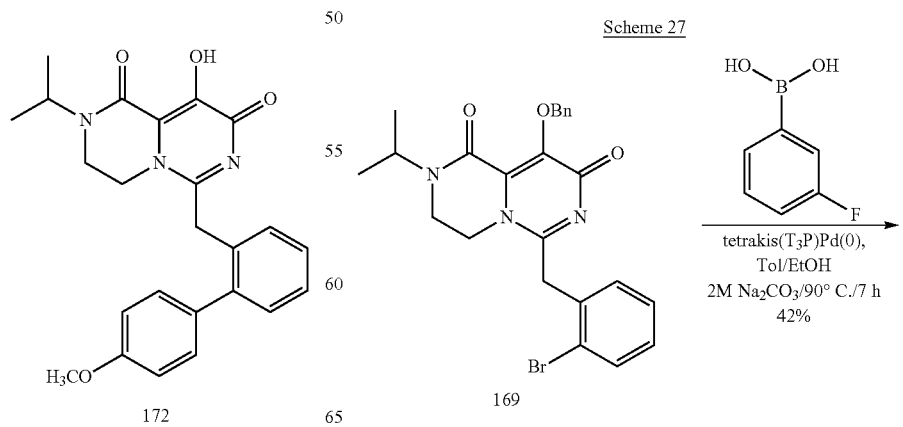

Scheme 28

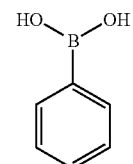

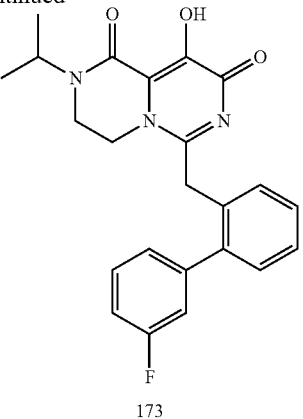

173

Preparation of (173)

6-[[2-(3-Fluorophenyl)phenyl]methyl]-9-hydroxy-2-isopropyl-3,4-dihydropyrazino[1,2-c]pyrimidine-1,8-dione The title compound (173) was prepared in analogy to example 170 from 9-benzyloxy-6-[(2-bromophenyl)methyl]-2-isopropyl-3,4-dihydropyrazino[1,2-c]pyrimidine-1,8-dione (169) (150 mg) and 3-fluorophenylboronic acid (50 mg). The product could be obtained directly from the coupling reaction (step 1). White solid (20 mg).

LC/HR-MS: (M+H)⁺=408.17294.

Example 175

9-Hydroxy-2-isopropyl-6-[[2-(4-isopropylphenyl)phenyl]methyl]-3,4-dihydropyrazino[1,2-c]pyrimidine-1,8-dione The synthetic procedure used in this preparation is outlined in Scheme 28.

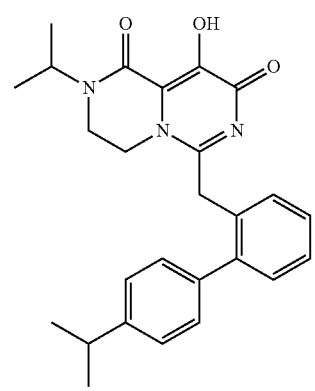

Preparation of (174)

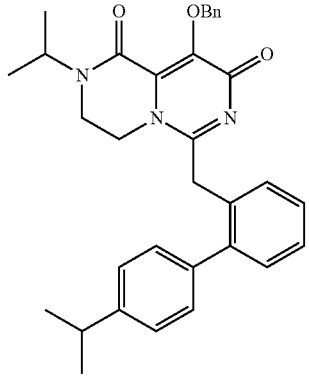 [SMILES: CC(C)c1ccc(-c2ccccc2Cc2nc(=O)c(OCc3ccccc3)c3n2CCN(C(C)C)C3=O)cc1]

Step 1: 9-Benzyloxy-2-isopropyl-6-[[2-(4-isopropylphenyl)phenyl]methyl]-3,4-dihydropyrazino-[1,2-c]pyrimidine-1,8-dione The title compound (174) was obtained in analogy to example (170) from 9-benzyloxy-6-[(2-bromophenyl)methyl]-2-isopropyl-3,4-dihydropyrazino[1,2-c]pyrimidine-1,8-dione (169) (150 mg) and 4-isopropylphenylboronic acid (58.7 mg) as a white foam (150 mg).

LC/HR-MS: (M+H)$^+$=522.27619.

Preparation of (175)

Step 2: 9-Hydroxy-2-isopropyl-6-[[2-(4-isopropylphenyl)phenyl]methyl]-3,4-dihydropyrazino-[1,2-c]pyrimidine-1,8-dione The desired title compound was obtained in analogy to (171) from 9-benzyloxy-2-isopropyl-6-[[2-(4-isopropylphenyl)phenyl]methyl]-3,4-dihydropyrazino[1,2-c]pyrimidine-1,8-dione (174) (80 mg) as an off-white solid (57.2 mg).

LC/HR-MS: (M+H)$^+$=432.22910.

Example 177

6-[[2-(4-Fluorophenyl)phenyl]methyl]-9-hydroxy-2-isopropyl-3,4-dihydropyrazino[1,2-c]pyrimidine-1,8-dione The synthetic procedure used in this preparation is outlined in Scheme 29.

Scheme 29

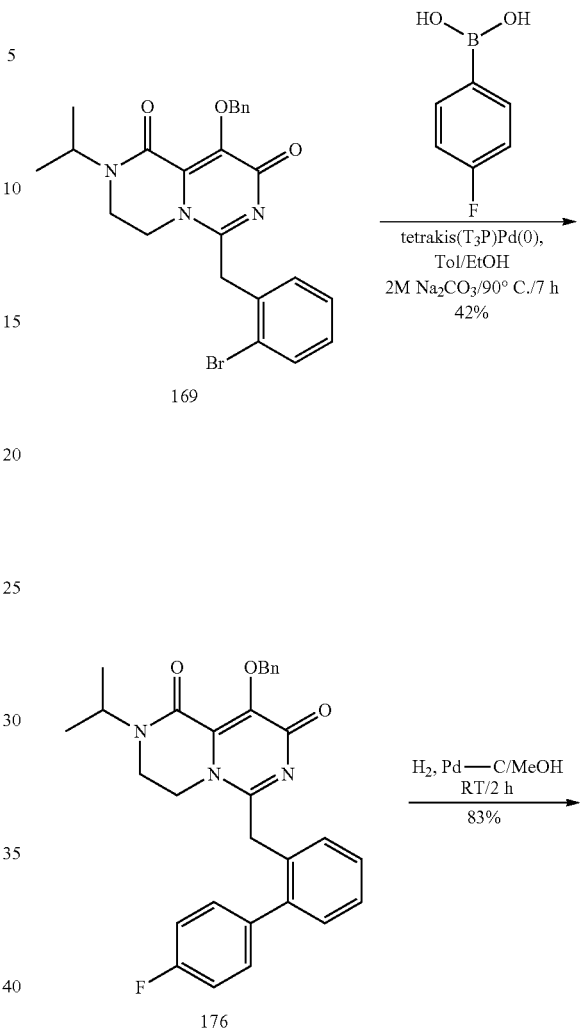

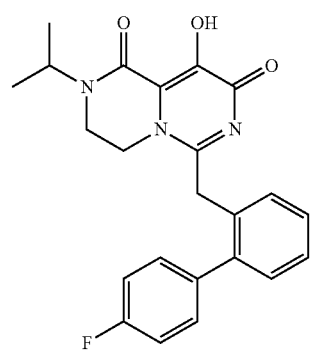

Preparation of (176)

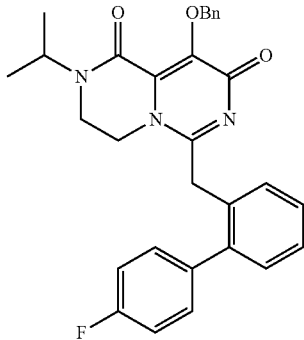 [SMILES: CC(C)N1CCn2c(Cc3ccccc3-c3ccc(F)cc3)nc(=O)c(OCc3ccccc3)c2C1=O]

Step 1: 9-Benzyloxy-6-[[2-(4-fluorophenyl)phenyl]methyl]-2-isopropyl-3,4-dihydropyrazino[1,2-c]pyrimidine-1,8-dione The title compound (176) was obtained in analogy to example (170) from 9-benzyloxy-6-[(2-bromophenyl)methyl]-2-isopropyl-3,4-dihydropyrazino[1,2-c]pyrimidine-1,8-dione (169) (150 mg) and 4-fluorophenylboronic acid (50 mg) as an off-white solid (120 mg).
LC/HR-MS: (M+H)$^+$=498.2196.

Preparation of (177)

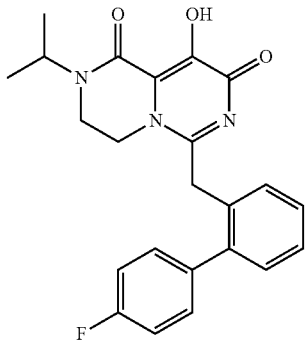 [SMILES: CC(C)N1CCn2c(Cc3ccccc3-c3ccc(F)cc3)nc(=O)c(O)c2C1=O]

Step 2: 6-[[2-(4-fluorophenyl)phenyl]methyl]-9-hydroxy-2-isopropyl-3,4-dihydropyrazino[1,2-c]pyrimidine-1,8-dione The title compound (177) was obtained in analogy to example (171) from 9-benzyloxy-6-[[2-(4-fluorophenyl)phenyl]methyl]-2-isopropyl-3,4-dihydropyrazino[1,2-c]pyrimidine-1,8-dione (120 mg) (176) as an amorphous off-white solid, 34.2 mg.
LC/HR-MS: (M+H)$^+$=408.17303.

Example 179

4-[2-[(9-hydroxy-2-isopropyl-1,8-dioxo-3,4-dihydropyrazino[1,2-c]pyrimidin-6-yl)methyl]phenyl]-benzonitrile The synthetic procedure used in this preparation is outlined in Scheme 30.

Scheme 30

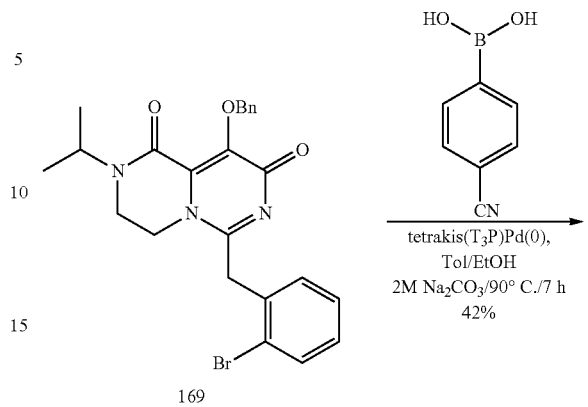

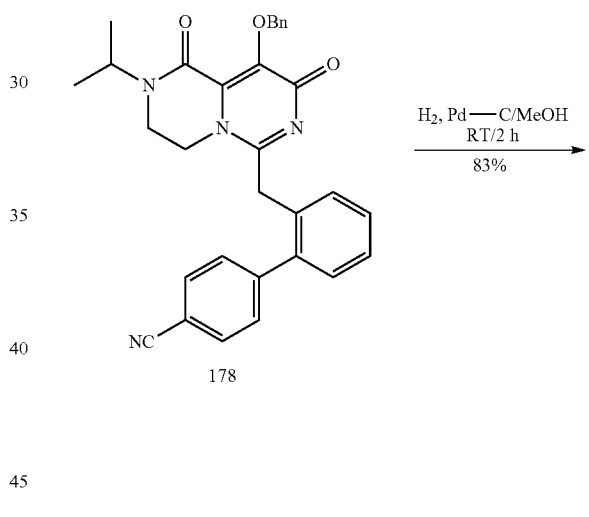

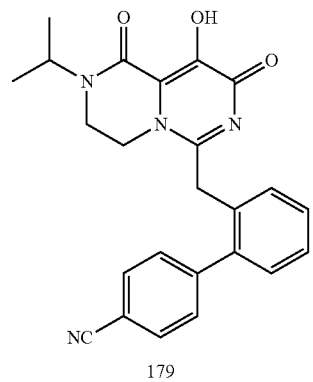

189

Preparation of (178)

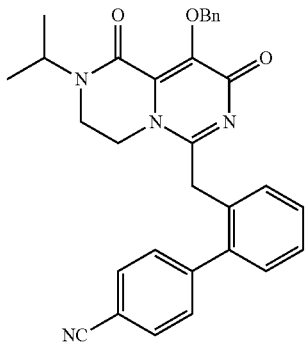 [SMILES: CC(C)N1CCn2c(Cc3ccccc3-c3ccc(C#N)cc3)nc(=O)c(OCc3ccccc3)c2C1=O]

Step 1: 4-[2-[(9-benzyloxy-2-isopropyl-1,8-dioxo-3,4-dihydropyrazino[1,2-c]pyrimidin-6-yl)methyl]phenyl]benzonitrile The title compound (178) was obtained in analogy to example (170) from 9-benzyloxy-6-[(2-bromophenyl)methyl]-2-isopropyl-3,4-dihydropyrazino[1,2-c]pyrimidine-1,8-dione (169) (150 mg) and 4-cyanophenylboronic acid (52.5 mg) as an off-white solid (45 mg).
LC/HR-MS: (M+H)⁺=505.2244.

Preparation of (179)

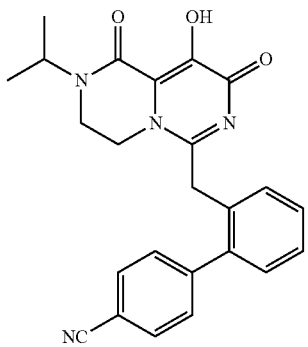 [SMILES: CC(C)N1CCn2c(Cc3ccccc3-c3ccc(C#N)cc3)nc(=O)c(O)c2C1=O]

Step 2: 4-[2-[(9-hydroxy-2-isopropyl-1,8-dioxo-3,4-dihydropyrazino[1,2-c]pyrimidin-6-yl)methyl]phenyl]benzonitrile The title compound (179) was obtained in analogy to example (171) from 4-[2-[(9-benzyloxy-2-isopropyl-1,8-dioxo-3,4-dihydropyrazino[1,2-c]pyrimidin-6-yl)methyl]phenyl] (40 mg) (178) as an amorphous white solid, 11.4 mg.
LC/HR-MS: (M+H)⁺=415.17719.

Example 181

6-[[2-[3-fluoro-4-(trifluoromethyl)phenyl]phenyl]methyl]-9-hydroxy-2-isopropyl-3,4-dihydropyrazino[1,2-c]pyrimidine-1,8-dione The synthetic procedure used in this preparation is outlined in Scheme 31.

190

Scheme 31

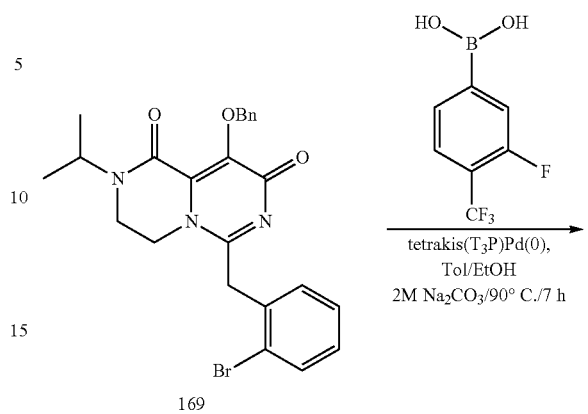

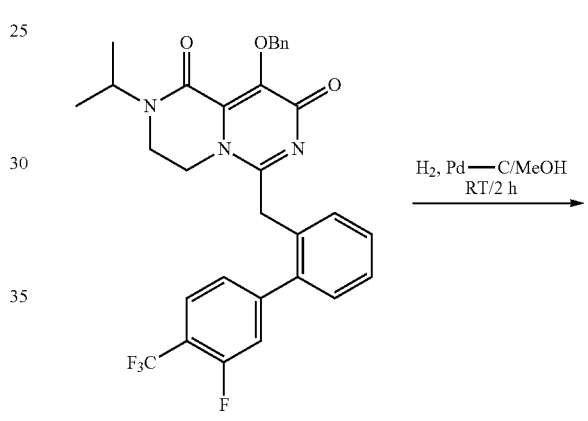

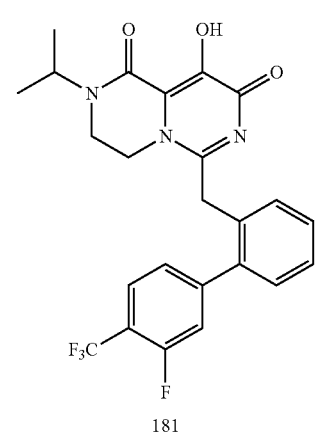

191

Preparation of (180)

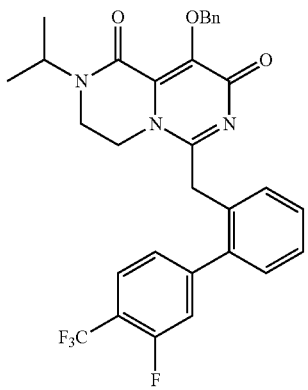 [SMILES: CC(C)N1CCn2c(Cc3ccccc3-c3ccc(C(F)(F)F)c(F)c3)nc(=O)c(OCc3ccccc3)c2C1=O]

Step 1: 9-Benzyloxy-6-[[2-[3-fluoro-4-(trifluoromethyl)phenyl]phenyl]methyl]-2-isopropyl-3,4-dihydropyrazino[1,2-c]pyrimidine-1,8-dione The title compound (180) was obtained in analogy to example (170) from 9-benzyloxy-6-[(2-bromophenyl)methyl]-2-isopropyl-3,4-dihydropyrazino[1,2-c]pyrimidine-1,8-dione (169) (150 mg) and 3-fluoro-4-trifluoromethyl-phenylboronic acid (74.3 mg) as an amorphous light yellow solid (142 mg).

LC/HR-MS: (M+H)$^+$=566.2049.

Preparation of (181)

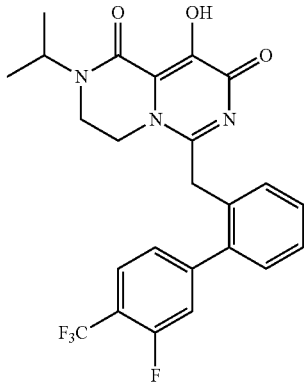 [SMILES: CC(C)N1CCn2c(Cc3ccccc3-c3ccc(C(F)(F)F)c(F)c3)nc(=O)c(O)c2C1=O]

Step 2: 6-[[2-[3-fluoro-4-(trifluoromethyl)phenyl]phenyl]methyl]-9-hydroxy-2-isopropyl-3,4-dihydropyrazino[1,2-c]pyrimidine-1,8-dione The title compound (181) was obtained in analogy to example (171) from 9-benzyloxy-6-[[2-[3-fluoro-4-(trifluoromethyl)phenyl]phenyl]methyl]-2-isopropyl-3,4-dihydropyrazino[1,2-c]pyrimidine-1,8-dione (180) as an amorphous white solid, 18 mg.

LC/HR-MS: (M+H)$^+$=476.15986.

192

Example 183

9-Hydroxy-2-isopropyl-6-[[2-[4-(trifluoromethyl)phenyl]phenyl]methyl]-3,4-dihydropyrazino[1,2-c]pyrimidine-1,8-dione The synthetic procedure used in this preparation is outlined in Scheme 32.

Scheme 32

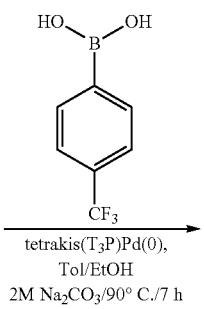

tetrakis(T$_3$P)Pd(0),
Tol/EtOH
2M Na$_2$CO$_3$/90° C./7 h

169

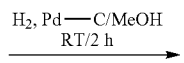

H$_2$, Pd—C/MeOH
RT/2 h

182

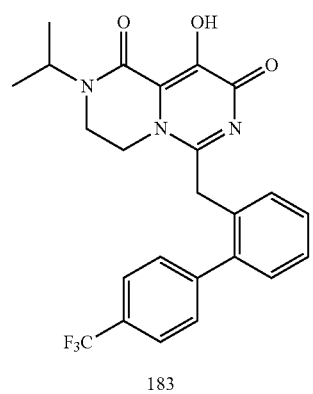

183

Preparation of (182)

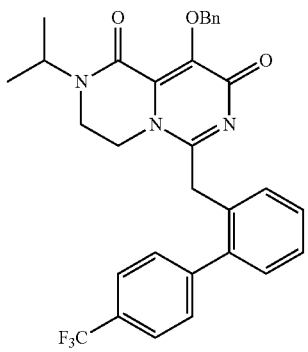 [SMILES: CC(C)N1CCn2c(Cc3ccccc3-c3ccc(C(F)(F)F)cc3)nc(=O)c(OCc3ccccc3)c2C1=O]

Step 1: 9-Benzyloxy-2-isopropyl-6-[[2-[4-(trifluoromethyl)phenyl]phenyl]methyl]-3,4-dihydropyrazino[1,2-c]pyrimidine-1,8-dione The title compound (182) was obtained in analogy to example (170) from 9-benzyloxy-6-[(2-bromophenyl)methyl]-2-isopropyl-3,4-dihydropyrazino[1,2-c]pyrimidine-1,8-dione (169) (150 mg) and 4-trifluoromethyl-phenylboronic acid (68 mg) as an off-white solid (151 mg) which was directly used in the subsequent reaction step.

Preparation of (183)

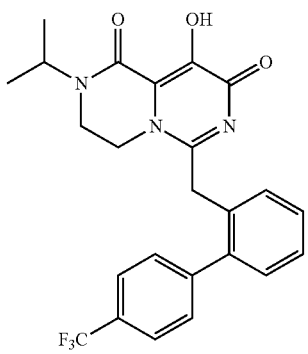 [SMILES: CC(C)N1CCn2c(Cc3ccccc3-c3ccc(C(F)(F)F)cc3)nc(=O)c(O)c2C1=O]

Step 2: 9-Hydroxy-2-isopropyl-6-[[2-[4-(trifluoromethyl)phenyl]phenyl]methyl]-3,4-dihydropyrazino[1,2-c]pyrimidine-1,8-dione The title compound (183) was obtained in analogy to example (171) from 9-benzyloxy-2-isopropyl-6-[[2-[4-(trifluoromethyl)phenyl]phenyl]methyl]-3,4-dihydropyrazino[1,2-c]pyrimidine-1,8-dione (140 mg) (182) as an off-white solid, 22.8 mg.
LC/HR-MS: (M+H)$^+$=458.16956.

Example 185

9-Hydroxy-2-isopropyl-6-[[2-[4-(trifluoromethoxy)phenyl]phenyl]methyl]-3,4-dihydropyrazino[1,2-c]pyrimidine-1,8-dione The synthetic procedure used in this preparation is outlined in Scheme 33.

Scheme 33

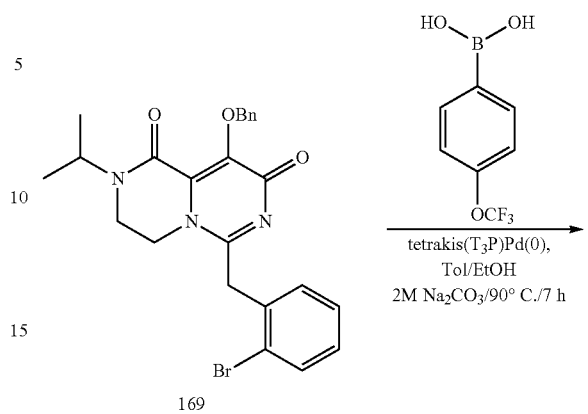

169

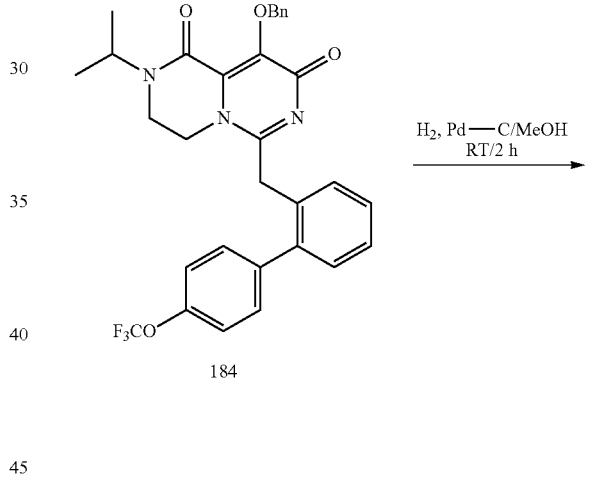

184

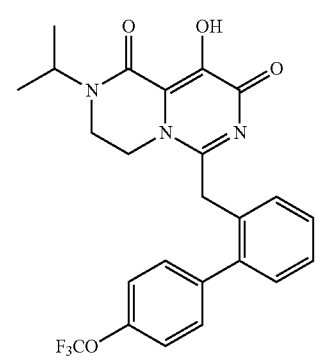

185

Preparation of (184)

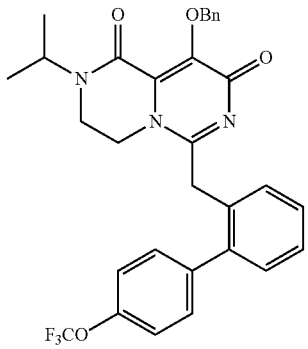 [SMILES: CC(C)N1CCn2c(Cc3ccccc3-c3ccc(OC(F)(F)F)cc3)nc(=O)c(OCc3ccccc3)c2C1=O]

Step 1: 9-Benzyloxy-2-isopropyl-6-[[2-[4-(trifluoromethoxy)phenyl]phenyl]methyl]-3,4-dihydropyrazino[1,2-c]pyrimidine-1,8-dione The title compound (184) was obtained in analogy to example (170) from 9-benzyloxy-6-[(2-bromophenyl)methyl]-2-isopropyl-3,4-dihydropyrazino[1,2-c]pyrimidine-1,8-dione (169) (150 mg) and 4-trifluoromethoxy-phenylboronic acid (73.6 mg) as a white solid (150 mg). The crude product was directly used in the next reaction step.

Preparation of (185)

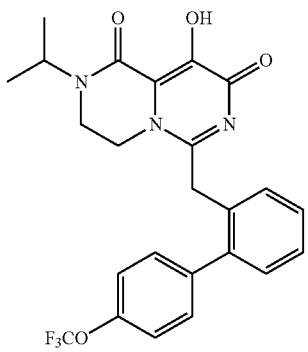 [SMILES: CC(C)N1CCn2c(Cc3ccccc3-c3ccc(OC(F)(F)F)cc3)nc(=O)c(O)c2C1=O]

Step 2: 9-Hydroxy-2-isopropyl-6-[[2-[4-(trifluoromethoxy)phenyl]phenyl]methyl]-3,4-dihydropyrazino[1,2-c]pyrimidine-1,8-dione The title compound (185) was obtained in analogy to example (171) from 9-benzyloxy-2-isopropyl-6-[[2-[4-(trifluoromethoxy)phenyl]phenyl]methyl]-3,4-dihydropyrazino[1,2-c]pyrimidine-1,8-dione (150 mg) (184) as an off-white solid, 9 mg.
LC/HR-MS: $(M+H)^+=474.16440$.

Example 187

6-[[2-(1,3-Benzodioxol-5-yl)phenyl]methyl]-9-hydroxy-2-isopropyl-3,4-dihydropyrazino[1,2-c]pyrimidine-1,8-dione The synthetic procedure used in this preparation is outlined in Scheme 34.

Scheme 34

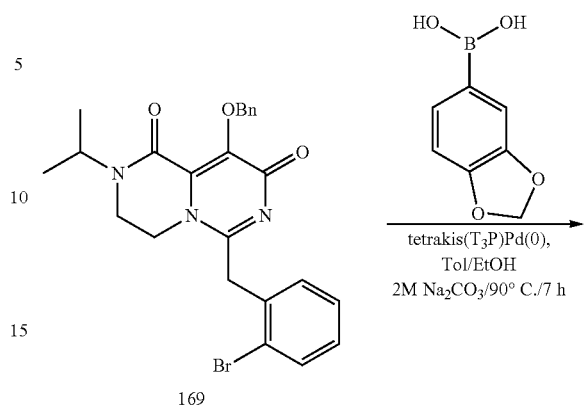

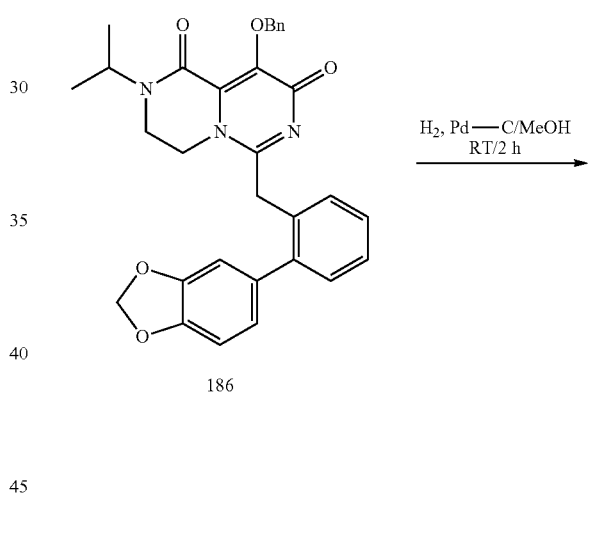

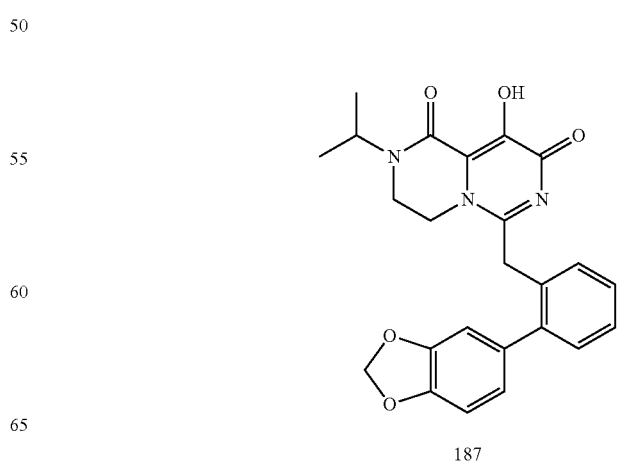

Preparation of (186)

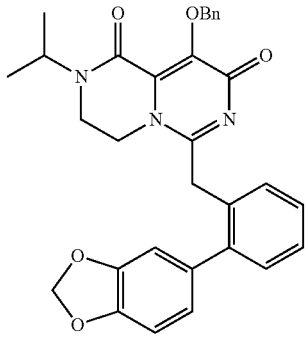 [SMILES: CC(C)N1CCn2c(Cc3ccccc3-c3ccc4c(c3)OCO4)nc(=O)c(OCc3ccccc3)c2C1=O]

Scheme 35

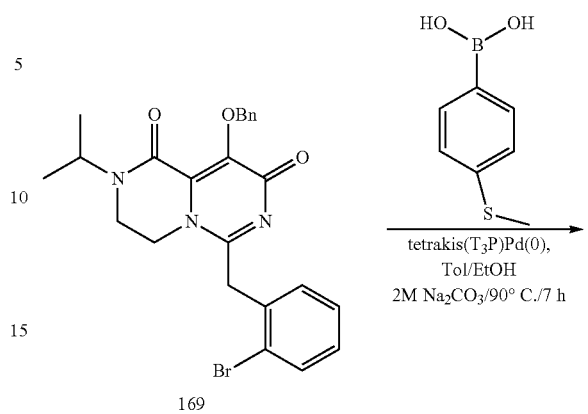

Step 1: 6-[[2-(1,3-benzodioxol-5-yl)phenyl]methyl]-9-benzyloxy-2-isopropyl-3,4-dihydropyrazino[1,2-c]pyrimidine-1,8-dione The title compound (186) was obtained in analogy to example (170) from 9-benzyloxy-6-[(2-bromophenyl)methyl]-2-isopropyl-3,4-dihydropyrazino[1,2-c]pyrimidine-1,8-dione (169) (150 mg) and 1,3-benzodioxol-5-ylboronic acid (59.3 mg). The crude material (130 mg) was directly used in the next reaction step.

Preparation of (187)

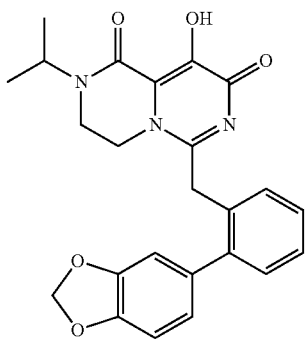 [SMILES: CC(C)N1CCn2c(Cc3ccccc3-c3ccc4c(c3)OCO4)nc(=O)c(O)c2C1=O]

Step 2: 6-[[2-(1,3-benzodioxol-5-yl)phenyl]methyl]-9-hydroxy-2-isopropyl-3,4-dihydropyrazino[1,2-c]pyrimidine-1,8-dione The title compound (187) was obtained in analogy to example (171) from 9-benzyloxy-2-isopropyl-6-[[2-[4-(trifluoromethoxy)phenyl]phenyl]methyl]-3,4-dihydropyrazino[1,2-c]pyrimidine-1,8-dione (130 mg) (186) as an off-white solid, 7 mg.
LC/HR-MS: (M+H)$^+$=434.17153.

Example 189

9-Hydroxy-2-isopropyl-6-[[2-(4-methylsulfanylphenyl)phenyl]methyl]-3,4-dihydropyrazino[1,2-c]pyrimidine-1,8-dione The synthetic procedure used in this preparation is outlined in Scheme 35.

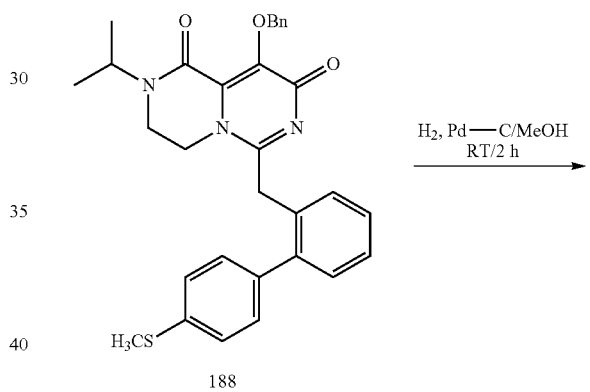

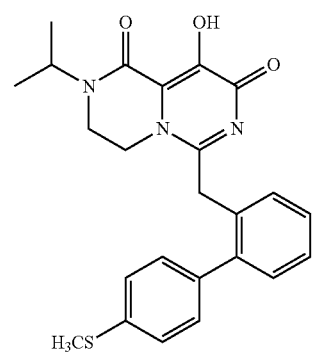

199
Preparation of (188)

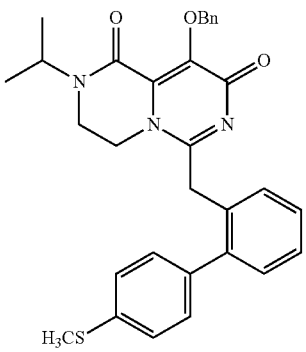

Step 1: 9-Benzyloxy-2-isopropyl-6-[[2-(4-methylsulfanyl)phenyl]phenyl]methyl]-3,4-dihydropyrazino[1,2-c]pyrimidine-1,8-dione The title compound (188) was obtained in analogy to example (170) from 9-benzyloxy-6-[(2-bromophenyl)methyl]-2-isopropyl-3,4-dihydropyrazino[1,2-c]pyrimidine-1,8-dione (169) (150 mg) and 4-(methylthio)phenylboronic acid (115 mg) as a light yellow solid (152 mg). The material was directly used in the subsequent reaction step.

Preparation of (189)

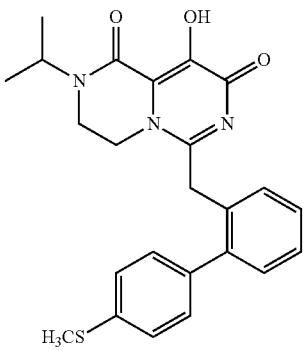

Step 2: 9-Hydroxy-2-isopropyl-6-[[2-(4-methylsulfanyl)phenyl]phenyl]methyl]-3,4-dihydropyrazino[1,2-c]pyrimidine-1,8-dione The title compound (189) was obtained in analogy to example (171) from 9-benzyloxy-2-isopropyl-6-[[2-[4-(trifluoromethoxy)phenyl]phenyl]methyl]-3,4-dihydropyrazino[1,2-c]pyrimidine-1,8-dione (100 mg) (188) as an off-white solid, 68.4 mg.
LC/HR-MS: $(M+H)^+$=436.1708.

Example 196

9-Hydroxy-2-isopropyl-6-(2-pyridyl)-3,4-dihydropyrazino[1,2-c]pyrimidine-1,8-dione The synthetic procedure used in this preparation is outlined in Scheme 36.

200

Scheme 36

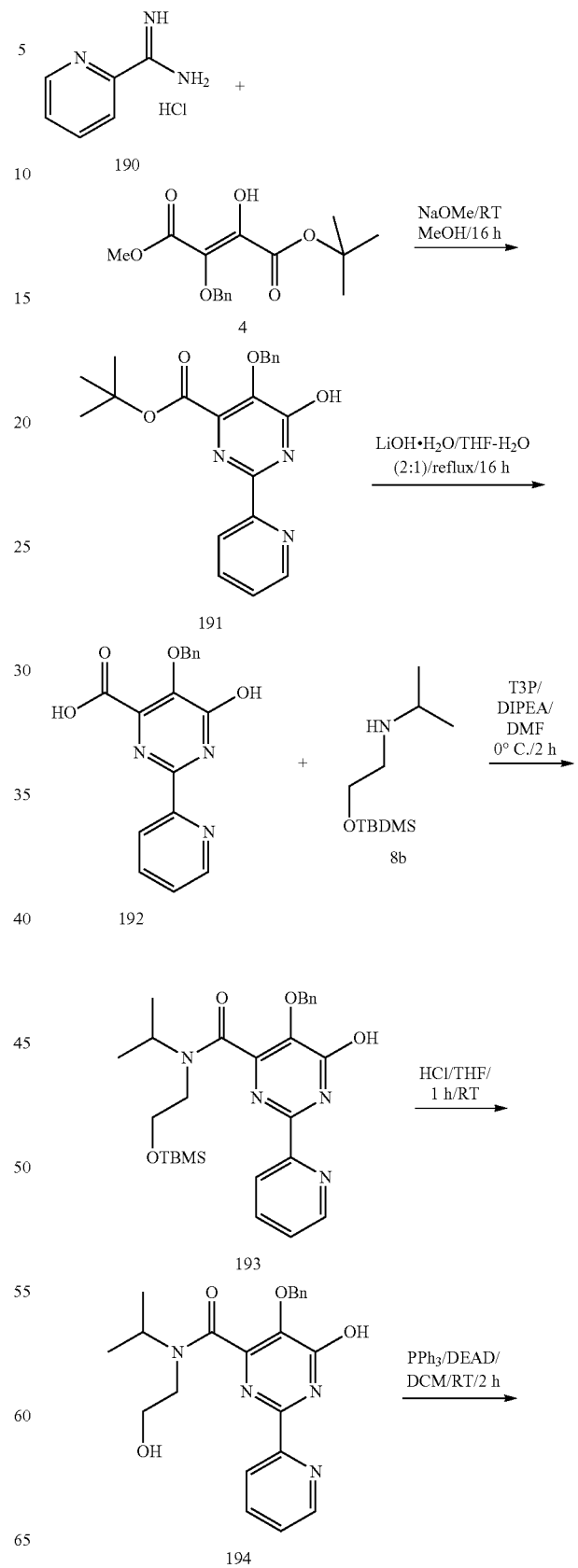

-continued

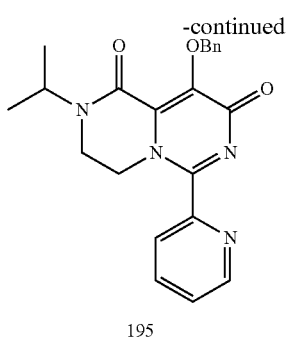

195

EtOH/Pd—C/
hydrogen
pressure/2 h/
RT

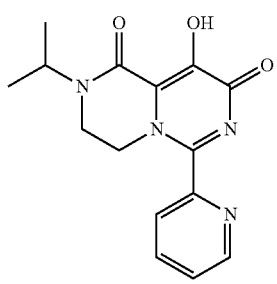

196

Preparation of (191)

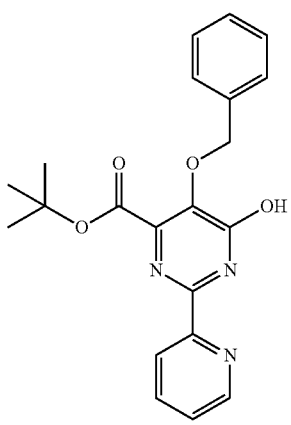 [SMILES: CC(C)(C)OC(=O)c1nc(-c2ccccn2)nc(O)c1OCc1ccccc1]

Step 1: tert-Butyl 5-benzyloxy-6-hydroxy-2-(2-pyridyl)pyrimidine-4-carboxylate

The title compound (191) was obtained in analogy to example (163) from pyridine-2-carboximidamide HCl (190) and 4-tert-butyl 1-methyl 2-(benzyloxy)-3-hydroxyfumarate (4) as an off-white solid.

LC/HR-MS: (M+H)$^+$=338.114.

Preparation of (192)

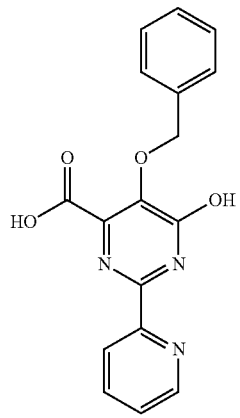 [SMILES: O=C(O)c1nc(-c2ccccn2)nc(O)c1OCc1ccccc1]

Step 2: 5-Benzyloxy-6-hydroxy-2-(2-pyridyl)pyrimidine-4-carboxylic acid

The title compound (192) was obtained in analogy to (164) from tert-butyl 5-benzyloxy-6-hydroxy-2-(2-pyridyl)pyrimidine-4-carboxylate (191) as a white solid.

LC/HR-MS: (M+H)$^+$=338.114.

Preparation of (193)

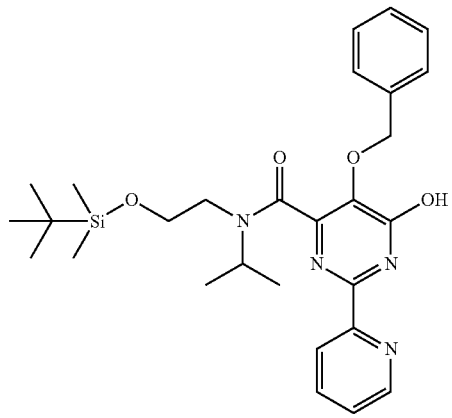 [SMILES: CC(C)N(CCO[Si](C)(C)C(C)(C)C)C(=O)c1nc(-c2ccccn2)nc(O)c1OCc1ccccc1]

Step 3: 5-Benzyloxy-N-[2-[tert-butyl(dimethyl)silyl]oxyethyl]-6-hydroxy-N-isopropyl-2-(2-pyridyl)pyrimidine-4-carboxamide The title compound (193) was obtained in analogy to (165) from 5-benzyloxy-6-hydroxy-2-(2-pyridyl)pyrimidine-4-carboxylic acid (192) and N-[2-[tert-butyl(dimethyl)silyl]oxyethyl]propan-2-amine (8b) as a white solid.

LC/HR-MS: (M+H)$^+$=523.27392.

Preparation of (194)

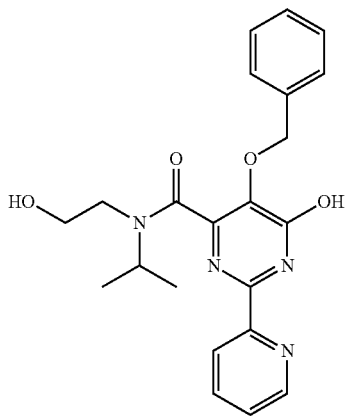 [SMILES: CC(C)N(CCO)C(=O)c1nc(-c2ccccn2)nc(O)c1OCc1ccccc1]

Step 4: 5-Benzyloxy-6-hydroxy-N-(2-hydroxyethyl)-N-isopropyl-2-(2-pyridyl)pyrimidine-4-carboxamide The title compound was obtained in analogy to (166) from 5-benzyloxy-N-[2-[tert-butyl(dimethyl)silyl]oxyethyl]-6-hydroxy-N-isopropyl-2-(2-pyridyl)pyrimidine-4-carboxamide (193) on treatment with 1M HCl in tetrahydrofuran as a light yellow gum.

LC/HR-MS: (M+H)$^+$=409.1880.

Preparation of (195)

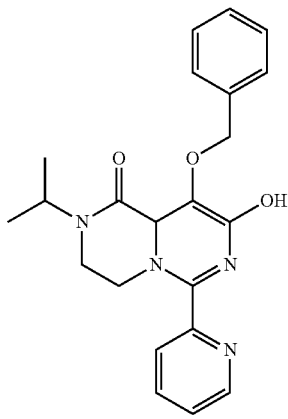 [SMILES: CC(C)N1CCN2C(c3ccccn3)=NC(O)=C(OCc3ccccc3)C2C1=O]

Step 5: 9-Benzyloxy-8-hydroxy-2-isopropyl-6-(2-pyridyl)-4,9a-dihydro-3H-pyrazino[1,2-c]pyrimidin-1-one The title compound was prepared in analogy to (167) from 5-benzyloxy-6-hydroxy-N-(2-hydroxyethyl)-N-isopropyl-2-(2-pyridyl)pyrimidine-4-carboxamide (194) as a light yellow gum.

LC/HR-MS: (M+H)$^+$=391.1769.

Preparation of (196)

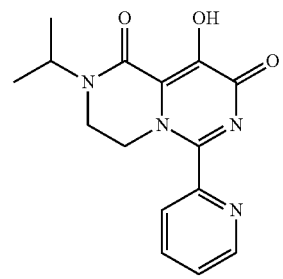 [SMILES: CC(C)N1CCn2c(-c3ccccn3)nc(=O)c(O)c2C1=O]

Step 6: 9-Hydroxy-2-isopropyl-6-(2-pyridyl)-3,4-dihydropyrazino[1,2-c]pyrimidine-1,8-dione The title compound was prepared in analogy to (168) from 9-benzyloxy-8-hydroxy-2-isopropyl-6-(2-pyridyl)-4,9a-dihydro-3H-pyrazino[1,2-c]pyrimidin-1-one (195) as an off-white solid.

LC/HR-MS: (M+H)$^+$=301.13013.

Example 209

6-[1-(2,5-Dichloro-phenyl)-cyclopentylmethyl]-9-hydroxy-2-isopropyl-3,4-dihydro-2H-pyrazino[1,2-c]pyrimidine-1,8-dione The synthetic procedure used in this preparation is outlined in Scheme 37.

Scheme 37

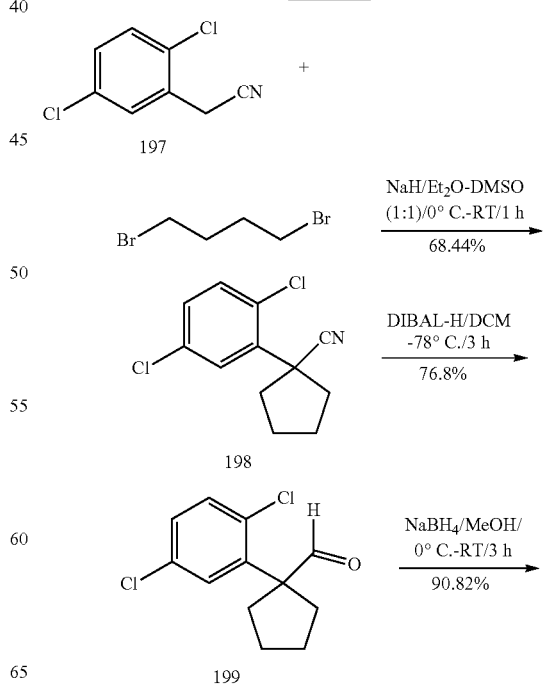

-continued

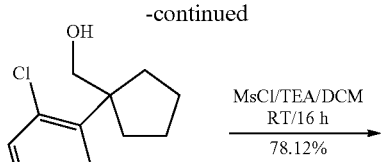
200

MsCl/TEA/DCM
RT/16 h
───────────────→
78.12%

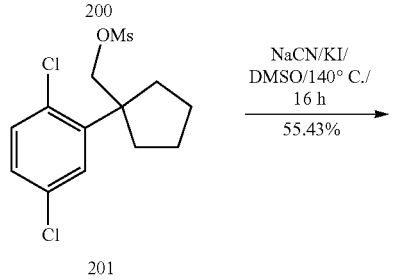
201

NaCN/KI/
DMSO/140° C./
16 h
───────────────→
55.43%

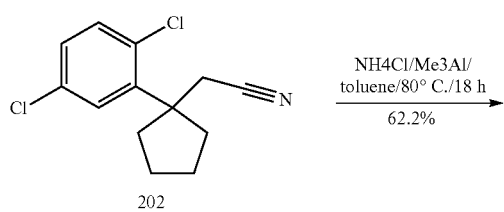
202

NH4Cl/Me3Al/
toluene/80° C./18 h
───────────────→
62.2%

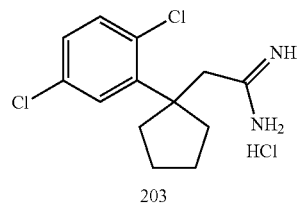
203

+

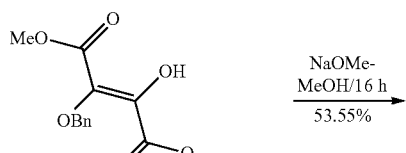
4

NaOMe-
MeOH/16 h
───────────────→
53.55%

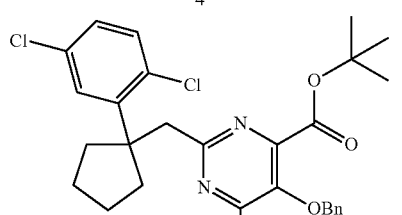
204

LiOH·H2O/
THF-H2O
(2:1)/reflux/
16 h
───────────────→
72.5%

-continued

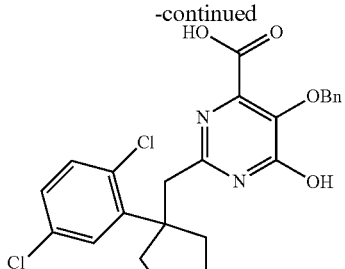
205

+

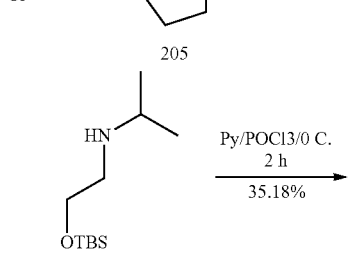
8b

Py/POCl3/0 C.
2 h
───────────────→
35.18%

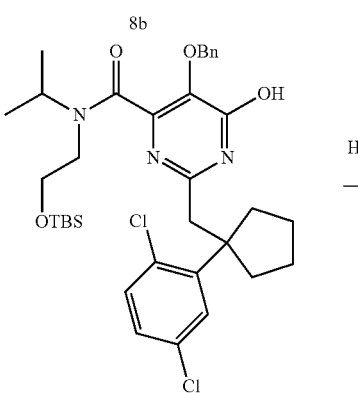
206

HCl/THF/
RT/1 h
───────────────→
96.26%

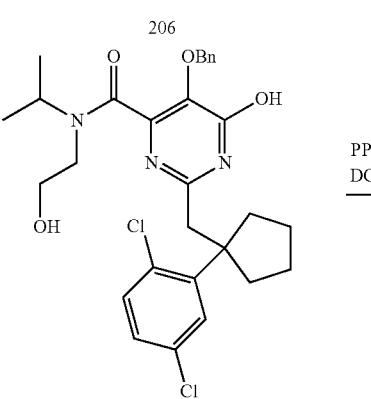
207

PPh3/DEAD/
DCM/RT/2 h
───────────────→
33.07%

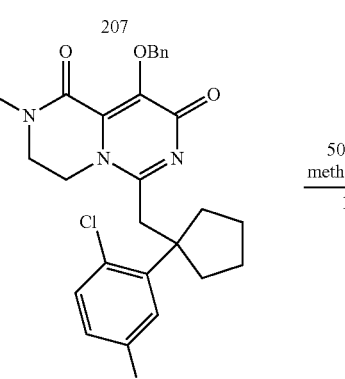
208

50% HCl in
methanol/5 h/RT
───────────────→
11.34%

-continued

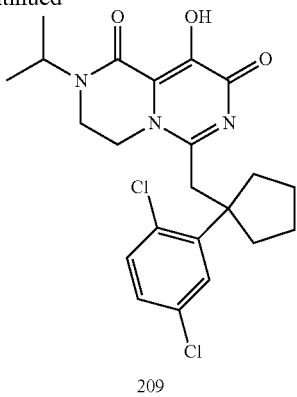

209

Preparation of (198)

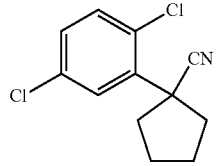 [SMILES: N#CC1(c2cc(Cl)ccc2Cl)CCCC1]

Step 1:
1-(2,5-Dichloro-phenyl)-cyclopentanecarbonitrile

To a suspension of NaH (60% w/w suspension in paraffin oil) (14.19 g, 354.76 mmol) in dimethyl sulfoxide (300 mL), was added (2,5-dichloro-phenyl)-acetonitrile (197) (30 g, 161.256 mmol) and 1,4-dibromobutane (19.34 mL, 161.26 mmol) by dissolving in dimethyl sulfoxide-ether (1:1, 600 mL) dropwise at 0° C. The reaction mixture was stirred at room temperature for 1 h. Silica thin layer chromatography was conducted (10% ethyl acetate in hexane, Rf=0.8). After completion of the reaction, water (500 mL) and 10% HCl solution (200 mL) were added and the mixture was extracted with ethyl acetate. The organic part was dried, and evaporated to get a crude residue, which was purified with silica gel (normal, 100-200 mesh) column chromatography using a gradient eluent of 2 to 10% ethyl acetate in hexane to get pure (198) (26.5 g, 68.44%) as a white solid.

GCMS: 239 (M).

Preparation of (199)

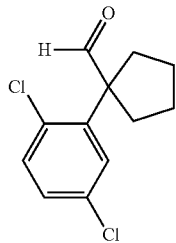 [SMILES: O=CC1(c2cc(Cl)ccc2Cl)CCCC1]

Step 2:
1-(2,5-Dichloro-phenyl)-cyclopentanecarbaldehyde

To a stirred solution of 1-(2,5-dichloro-phenyl)-cyclopentanecarbonitrile (198) (32 g, 133.891 mmol) in dichloromethane (350 mL), was added Diisobutylaluminiumhydrid (25% in toluene, 191.0 mL, mmol) for 1 h at −70° C. and the reaction mixture was stirred 2 h at the same temperature (silica TLC, 10% ethyl acetate in hexane, Rf=0.7) The reaction mixture was quenched with saturated potassium sodium tartarate solution very slowly and stirred at room temperature for 16 h. It was extracted with dichloromethane, washed with brine and dried, concentrated to get the crude residue which was purified over nor mal silica gel (100-200 mesh) column chromatography using gradient eluent 2-20% ethyl acetate in hexane to get 1-(2,5-dichloro-phenyl)-cyclopentanecarbaldehyde (199) (25 g, 76.8%), as colorless liquid.

GCMS: 242 (M)

Preparation of (200)

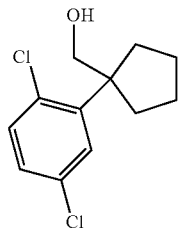 [SMILES: OCC1(c2cc(Cl)ccc2Cl)CCCC1]

Step 3:
[1-(2,5-Dichloro-phenyl)-cyclopentyl]-methanol

A solution of 1-(2,5-dichlorophenyl)-cyclopentanecarbaldehyde (199) (25 g, 103.305 mmol) in methanol (300 mL), was cooled in ice bath, NaBH$_4$ (7.816 g, 206.612 mmol) was added portion-wise and the mixture was stirred for 3 h at room temperature. Silica thin layer chromatography was performed (10% ethyl acetate in hexane, Rf=0.5). After completion of the reaction, it was quenched with saturated NH$_4$Cl solution (100 mL), methanol was removed from the reaction mixture under reduced pressure, the residue was diluted with water and the mixture was extracted with dichloromethane, the combined organic layer was washed with brine, dried, and concentrated. The concentrate was purified using normal silica gel (100-200 mesh) column chromatography using a gradient eluent of 2 to 10% ethyl acetate in hexane to get [1-(2,5-dichlorophenyl)-cyclopentyl]-methanol (200) (23 g, 90.82%) as a colorless liquid.

GCMS: 244 (M).

Preparation of (201)

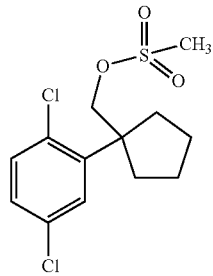 [SMILES: CS(=O)(=O)OCC1(c2cc(Cl)ccc2Cl)CCCC1]

Step 4: Methanesulfonic acid 1-(2,5-dichlorophenyl)-cyclopentylmethyl ester

To a stirred solution of [1-(2,5-dichlorophenyl)-cyclopentyl]-methanol (200) (23 g, 95.04 mmol) in dry dichloromethane (250 mL) was added dry triethylamine (26.42 mL, 190.083 mmol) slowly, then mesyl chloride (8.785 mL, 114.05 mmol) was added and the mixture was stirred for 16 h at room temperature. Silica thin layer chromatography was performed (10% ethyl acetate in hexane, Rf=0.5) After completion of the reaction, the mixture was diluted with water, and extracted with dichloromethane. The combined organic layer was washed with brine, and dried over $Na_2SO_4$ and concentrated under reduced pressure. The resulting crude product was purified using normal silica gel (100-200 mesh) column chromatography using a gradient eluent of 2 to 10% ethyl acetate in hexane to get pure methanesulfonic acid 1-(2,5-dichlorophenyl)-cyclopentylmethyl ester (201) (24 g, 78.12%) as a white solid.

GCMS: 322 (M).

Preparation of (202)

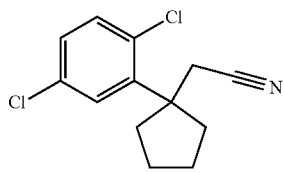 [SMILES: N#CCC1(c2cc(Cl)ccc2Cl)CCCC1]

Step 5: [1-(2,5-Dichlorophenyl)-cyclopentyl]-acetonitrile

To a stirred solution of methanesulfonic acid 1-(2,5-dichlorophenyl)-cyclopentylmethyl ester (201) (24 g, 74.53 mmol) in dimethyl sulfoxide (200 mL) KI (1.237 g, 7.453 mmol) and NaCN (5.478 g, 111.801 mmol) were added. The mixture was heated to 140° C. and stirred for 5 h. Silica TLC was performed (10% ethyl acetate in hexane, Rf=0.6). The reaction mixture was cooled to room temperature, diluted with water, extracted with ethyl acetate, washed with brine, dried, concentrated. The obtained crude product was purified using normal silica gel (100-200 mesh) column chromatography using a gradient eluent of 2 to 10% ethyl acetate in hexane to get pure [1-(2,5-dichlorophenyl)-cyclopentyl]-acetonitrile (202) (10.5 g, 55.43%) as a white solid.

GCMS: 253 (M).

Preparation of (203)

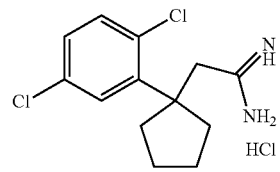 [SMILES: N=C(N)CC1(c2cc(Cl)ccc2Cl)CCCC1 ; Cl]

Step 6: 2-[1-(2,5-Dichlorophenyl)-cyclopentyl]-acetamidine hydrochloride

To a suspension of $NH_4Cl$ (1.939 g, 35.573 mmol) in toluene (30 mL) was added dropwise a solution of $AlMe_3$ (2M in toluene; 9.48 mL, 18.972 mmol) at 0° C. and the mixture was stirred for 2 h at room temperature prior to the addition of a solution of [1-(2,5-dichlorophenyl)-cyclopentyl]-acetonitrile (202) in toluene (20 mL). It was then heated to 80° C. for 16 h. Silica thin layer chromatography was performed (40% ethyl acetate in hexane, Rf=0.1). The cooled reaction mixture was poured into a slurry of normal silica gel (100-200 mesh; 8 g) in $CHCl_3$ (60 mL), followed by vigorous stirring for 30 min. The mixture was filtered off and the cake was rinsed with methanol. The combined filtrate was evaporated and the crude residue was taken in 10% methanol in dichloromethane (100 mL). The mixture was stirred for 30 min. The suspended solid was removed by filtration and the filtrate was evaporated. The crude product was triturated in diethylether and the solid was collected by filtration, dried under vacuum to afford 2-[1-(2,5-dichlorophenyl)-cyclopentyl]-acetamidine hydrochloride (203) (2.0 g, 62.2%) as a white solid.

LC-MS: 271 (M+H).

Preparation of (204)

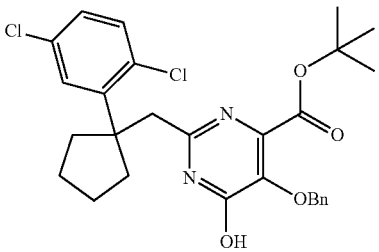 [SMILES: CC(C)(C)OC(=O)c1nc(CC2(c3cc(Cl)ccc3Cl)CCCC2)nc(O)c1OCc1ccccc1]

Step 7: 5-Benzyloxy-2-[1-(2,5-dichlorophenyl)-cyclopentylmethyl]-6-hydroxypyrimidine-4-carboxylic acid tert-butyl ester To a stirred solution of 2-[1-(2,5-dichlorophenyl)-cyclopentyl]-acetamidine hydrochloride (2=3) (2.0, 7.407 mmol) and (E)-2-benzyloxy-3-hydroxy-but-2-enedioic acid 4-tert-butyl ester (4) (3.422 g, 11.111 mmol) in methanol (50 mL) NaOMe (25% in methanol; 4.8 mL) was added dropwise at 0°

C. and stirred at room temperature for 16 h. Silica thin layer chromatography was performed (40% ethyl acetate in hexane, Rf=0.6). The reaction mixture was quenched with HCl (1N; 5 mL), methanol was removed, the product was diluted with water and the mixture was extracted with ethyl acetate. The combined organic part was dried, the product was concentrated and the crude product was purified using a normal silica gel column using a gradient eluent of 10 to 40% ethyl acetate in hexane to get pure 5-benzyloxy-2-[1-(2,5-dichlorophenyl)-cyclopentylmethyl]-6-hydroxypyrimidine-4-carboxylic acid tert-butyl ester (204) (2.1 g, 53.55%) as a yellow solid.

LC-MS: 529.2 (M+H).

Preparation of (205)

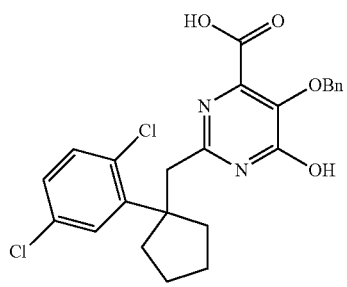 [SMILES: O=C(O)c1nc(CC2(c3cc(Cl)ccc3Cl)CCCC2)nc(O)c1OCc1ccccc1]

Step 8: 5-Benzyloxy-2-[1-(2,5-dichlorophenyl)-cyclopentylmethyl]-6-hydroxypyrimidine-4-carboxylic acid To a stirred solution of 5-benzyloxy-2-[1-(2,5-dichlorophenyl)-cyclopentylmethyl]-6-hydroxypyrimidine-4-carboxylic acid tert-butyl ester (204) (2.0 g, 3.788 mmol) in tetrahydrofuran-H$_2$O (2:1) (30 mL) Li(OH).H$_2$O (1.591 g, 37.88 mmol) was added, then the reaction mixture was stirred under reflux for 16 h. Silica thin layer chromatography was performed (40% ethyl acetate in hexane, Rf=0.1). After completion of the reaction, volatiles were removed, the reaction mixture was diluted with water, the pH was adjusted to pH ~7 with 1N HCl, then the reaction mixture was extracted with ethyl acetate. The organic part was dried with Na$_2$SO$_4$, then concentrated to get pure 5-benzyloxy-2-[1-(2,5-dichlorophenyl)-cyclopentylmethyl]-6-hydroxypyrimidine-4-carboxylic acid (205) (1.3 g, 72.5%) as a white solid.

LC-MS: 473.2 (M+H)

Preparation of (206)

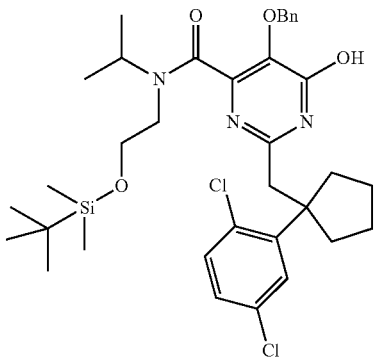 [SMILES: CC(C)N(CCO[Si](C)(C)C(C)(C)C)C(=O)c1nc(CC2(c3cc(Cl)ccc3Cl)CCCC2)nc(O)c1OCc1ccccc1]

Step 9: 5-Benzyloxy-2-[1-(2,5-dichlorophenyl)-cyclopentylmethyl]-6-hydroxypyrimidine-4-carboxylic acid [2-(tert-butyl-dimethylsilanyloxy)-ethyl]isopropylamide To a stirred white suspension of 5-benzyloxy-2-[1-(2,5-dichlorophenyl)-cyclopentylmethyl]-6-hydroxypyrimidine-4-carboxylic acid (205) (500 mg, 1.05 mmol) in pyridine (5.5 mL) was added [2-(tert-butyl-dimethylsilanyloxy)-ethyl]-isopropyl-amine (8b) (344 mg, 1.58 mmol), cooled to −10° C., POCl$_3$ (0.3 mL, 3.17 mmol) was added at the same temperature. The mixture was stirred at 0° C. for 2 h. Silica thin layer chromatography was performed (50% ethyl acetate in hexane, R$_f$=0.8). After completion of the reaction, ice cooled-water (30 mL) was added to the reaction mixture at 0° C., a saturated solution of NaHCO$_3$ (pH~8) was added, the mixture was extracted with ethyl acetate (4×50 mL), the organic part was dried and concentrated, the crude product was purified by a CombiFlash column (eluted at 30%-50% ethyl acetate in hexane) to get 5-benzyloxy-2-[1-(2,5-dichlorophenyl)-cyclopentylmethyl]-6-hydroxypyrimidine-4-carboxylic acid [2-(tert-butyl-dimethylsilanyloxy)-ethyl]-isopropylamide (206) (250 mg, 35.18%) as a yellow sticky mass.

LC-MS: 672.4 (M+H).

Preparation of (207)

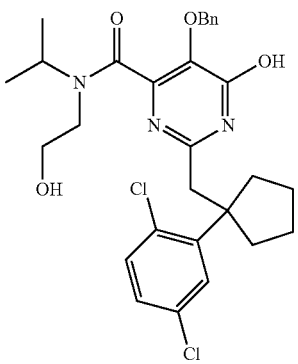 [SMILES: CC(C)N(CCO)C(=O)c1nc(CC2(c3cc(Cl)ccc3Cl)CCCC2)nc(O)c1OCc1ccccc1]

Step 10: 5-Benzyloxy-2-[1-(2,5-dichlorophenyl)-cyclopentylmethyl]-6-hydroxypyrimidine-4-carboxylic acid (2-hydroxyethyl)-isopropylamide To a stirred solution of 5-benzyloxy-2-[1-(2,5-dichlorophenyl)-cyclopentylmethyl]-6-hydroxypyrimidine-4-carboxylic acid [2-(tert-butyl-dimethylsilanyloxy)-ethyl]-isopropylamide (206) (250 mg, 0.37 mmol) in tetrahydrofuran (3.3 mL) was added 1N HCl (1.9 mL, 1.86 mmol) at room temperature and the mixture was stirred for 2 h at room temperature. Silica thin layer chromatography was performed (50% ethyl acetate in hexane, $R_f$=0.2). After completion of the reaction, the mixture was basified (pH ~8) with a saturated solution of NaHCO$_3$, extracted with ethyl acetate, dried over sodium sulfate and concentrated to get a crude product which was purified by a CombiFlash column (eluted at 30% ethyl acetate in hexane) to get 5-benzyloxy-2-[1-(2,5-dichlorophenyl)-cyclopentylmethyl]-6-hydroxypyrimidine-4-carboxylic acid (2-hydroxyethyl)-isopropylamide (207) (200 mg, 96.26%) as a white foam-like solid.

LC-MS: 558.0 (M+H).

Preparation of (208)

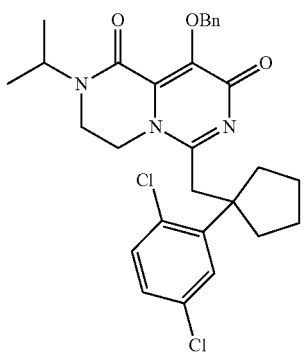 [SMILES: CC(C)N1CCn2c(CC3(c4cc(Cl)ccc4Cl)CCCC3)nc(=O)c(OCc3ccccc3)c2C1=O]

Step 11: 9-Benzyloxy-6-[1-(2,5-dichlorophenyl)-cyclopentylmethyl]-2-isopropyl-3,4-dihydro-2H-pyrazino[1,2-c]pyrimidine-1,8-dione To a stirred solution of 5-benzyloxy-2-[1-(2,5-dichlorophenyl)-cyclopentylmethyl]-6-hydroxypyrimidine-4-carboxylic acid (2-hydroxyethyl)-isopropylamide (207) (125 mg, 0.22 mmol) in tetrahydrofuran (5 mL) were added triphenyl phosphine (117 mg, 0.45 mmol) and diisopropyl azodicarboxylate (0.09 mL, 0.45 mmol) at room temperature, a yellow clear solution was formed, after 5 min it turned into a light yellow hazy solution. The solution was stirred for 2 h at room temperature. Silica thin layer chromatography was performed (100% ethyl acetate, $R_f$=0.3). The mixture was concentrated under reduced pressure to get a crude product, which was purified by a CombiFlash column (eluted at 2-5% methanol in dichloromethane) to get 9-benzyloxy-6-[1-(2,5-dichlorophenyl)-cyclopentylmethyl]-2-isopropyl-3,4-dihydro-2H-pyrazino[1,2-c]pyrimidine-1,8-dione (208) (40 mg, 33.07%) as a white sticky solid.

LC-MS: 540.2 (M+H).

Preparation of (209)

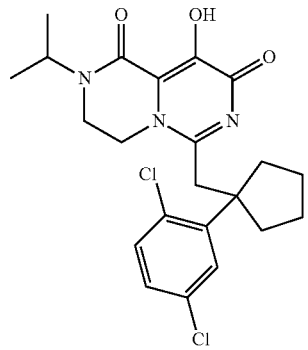 [SMILES: CC(C)N1CCn2c(CC3(c4cc(Cl)ccc4Cl)CCCC3)nc(=O)c(O)c2C1=O]

Step 12: 6-[1-(2,5-Dichlorophenyl)-cyclopentylmethyl]-9-hydroxy-2-isopropyl-3,4-dihydro-2H-pyrazino[1,2-c]pyrimidine-1,8-dione To a stirred solution of 9-benzyloxy-6-[1-(2,5-dichlorophenyl)-cyclopentylmethyl]-2-isopropyl-3,4-dihydro-2H-pyrazino[1,2-c]pyrimidine-1,8-dione (208) (500 mg, 0.93 mmol) in methanol (5.5 mL) was added concentrated HCl (4 mL) and the mixture was stirred for 20 h. Silica thin layer chromatography was performed (100% ethyl acetate, $R_f$=0.3). Methanol was removed, water was added, the mixture was basified (pH~8) with solid NaHCO$_3$, extracted with ethyl acetate (3×20 mL), and the organic part was dried and concentrated. The crude product was purified by preparative HPLC purification to get 6-[1-(2,5-dichlorophenyl)-cyclopentylmethyl]-9-hydroxy-2-isopropyl-3,4-dihydro-2H-pyrazino[1,2-c]pyrimidine-1,8-dione (209) (32 mg, 11.34%) as a light brown solid.

LC-MS: 450.0 (M+H).

Example 222

9-Hydroxy-2-isopropyl-6-(1-naphthalen-2-yl-cyclopentylmethyl)-3,4-dihydro-2H-pyrazino[1,2-c]pyrimidine-1,8-dione The synthetic procedure used in this preparation is outlined in Scheme 38.

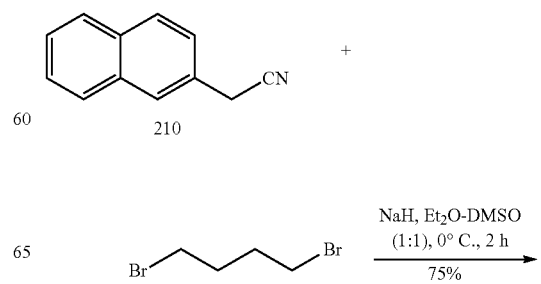

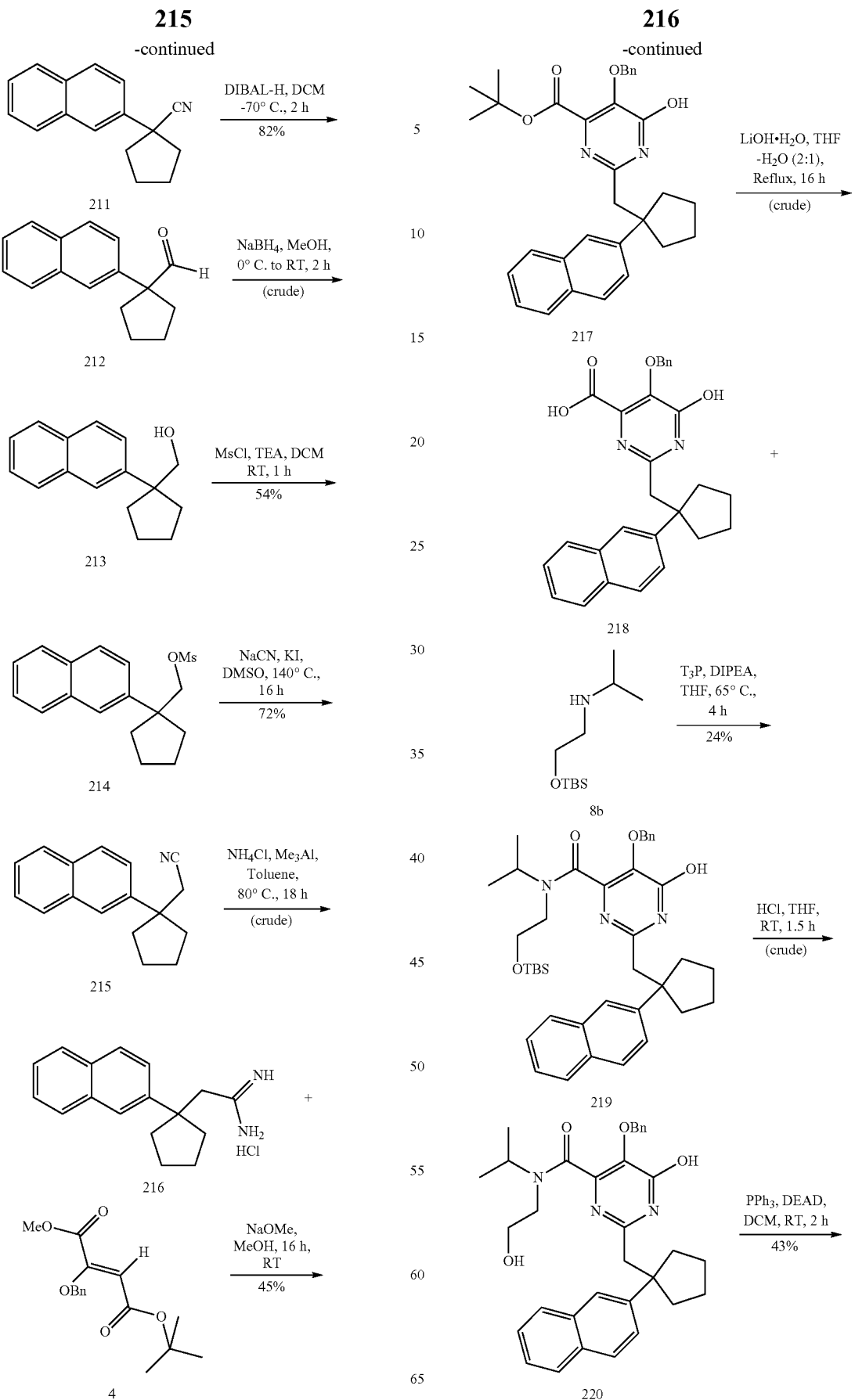

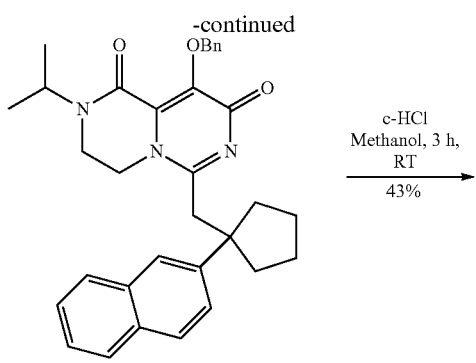

221

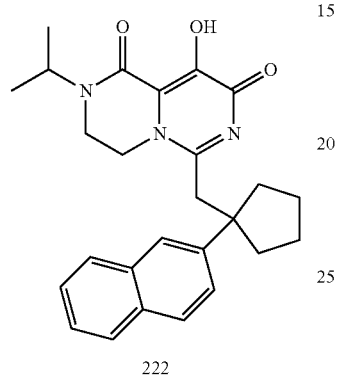

222

Preparation of (211)

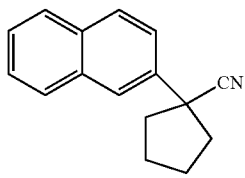 [SMILES: N#CC1(c2ccc3ccccc3c2)CCCC1]

Step: 1 1-Naphthalen-2-yl-cyclopentanecarbonitrile

1-Naphthalen-2-yl-cyclopentanecarbonitrile (211) (25.0 g, 75.46%) was synthesized as a white solid from naphthalen-2-yl-acetonitrile (210) (25.0 g, 149.7 mmol) and 1,4-dibromobutane (17.8 mL, 149.7 mmol) following the procedure described for 1-(2,5-dichlorophenyl)-cyclopentanecarbonitrile (198).

Preparation of (212)

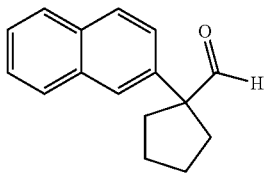 [SMILES: O=CC1(c2ccc3ccccc3c2)CCCC1]

Step 2: 1-Naphthalen-2-yl-cyclopentanecarbaldehyde

1-Naphthalen-2-yl-cyclopentanecarbaldehyde (212) (21.0 g, 82.77%) was synthesized as a colourless liquid from 1-naphthalen-2-yl-cyclopentanecarbonitrile (211) (25.0 g, 113.12 mmol) following the procedure described for 1-(2,5-dichlorophenyl)-cyclopentanecarbaldehyde (199).

Preparation of (213)

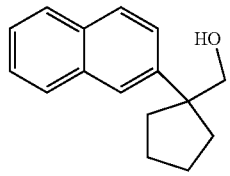 [SMILES: OCC1(c2ccc3ccccc3c2)CCCC1]

Step 3: (1-Naphthalen-2-yl-cyclopentyl)-methanol (1-Naphthalen-2-yl-cyclopentyl)-methanol (213) (22.0 g, crude) was synthesized as a colourless liquid from 1-naphthalen-2-yl-cyclopentanecarbaldehyde (212) (22.0 g, 98.21 mmol) following the procedure described for 1-(2,5-dichlorophenyl)-cyclopentane-methanol (200).

Preparation of (214)

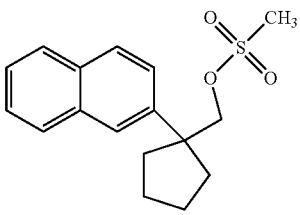 [SMILES: CS(=O)(=O)OCC1(c2ccc3ccccc3c2)CCCC1]

Step 4: Methanesulfonic acid 1-naphthalen-2-yl-cyclopentylmethyl ester

Methanesulfonic acid 1-naphthalen-2-yl-cyclopentylmethyl ester (214) (16.0 g, 54.0%) was synthesized as a white solid from (1-naphthalen-2-yl-cyclopentyl)-methanol (213) (22.0 g, 97.34 mmol) following the procedure described for methanesulfonic acid 1-(2,5-dichlorophenyl)-cyclopentylmethyl ester (201).

Preparation of (215)

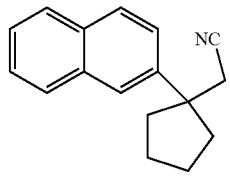

Step 5: (1-Naphthalen-2-yl-cyclopentyl)-acetonitrile (1-Naphthalen-2-yl-cyclopentyl)-acetonitrile (215) (9.0 g, 72.67%) was synthesized as a brown solid from methanesulfonic acid 1-naphthalen-2-yl-cyclopentylmethyl ester 214) (16.0 g, 52.63 mmol) following the procedure described for [1-(2,5-dichlorophenyl)-cyclopentyl]-acetonitrile (202).

Preparation of (216)

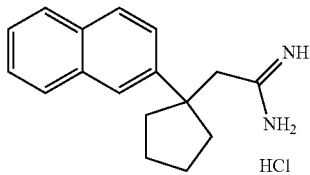 [SMILES: N=C(N)CC1(c2ccc3ccccc3c2)CCCC1 ; Cl]

Step 6: 2-(1-Naphthalen-2-yl-cyclopentyl)-acetamidine hydrochloride 2-(1-Naphthalen-2-yl-cyclopentyl)-acetamidine hydrochloride (216) (5.0 g, crude) was synthesized as a white solid from (1-naphthalen-2-yl-cyclopentyl)-acetonitrile (215) (5.0 g, 21.27 mmol) following the procedure described for the HCl-salt of 2-[1-(2,5-dichlorophenyl)-cyclopentyl]-acetamidine hydrochloride (203).

LC-MS: 252.8 (M+H).

Preparation of (217)

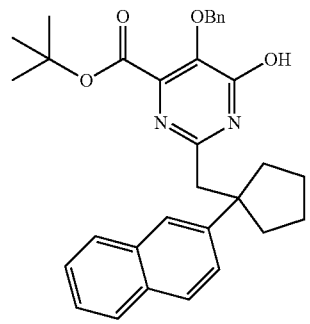 [SMILES: CC(C)(C)OC(=O)c1nc(CC2(c3ccc4ccccc4c3)CCCC2)nc(O)c1OCc1ccccc1]

5-Benzyloxy-6-hydroxy-2-(1-naphthalen-2-yl-cyclopentylmethyl)-pyrimidine-4-carboxylic acid tert-butyl ester 5-Benzyloxy-6-hydroxy-2-(1-naphthalen-2-yl-cyclopentylmethyl)-pyrimidine-4-carboxylic acid tert-butyl ester (217) (4.0 g, 45.2%) was synthesized as a white solid from 2-(1-naphthalen-2-yl-cyclopentyl)-acetamidine hydrochloride (216) (5.0 g, 17.33 mmol) following the procedure described for 5-benzyloxy-2-[1-(2,5-dichlorophenyl)-cyclopentylmethyl]-6-hydroxypyrimidine-4-carboxylic acid tert-butyl ester (204).

Preparation of (218)

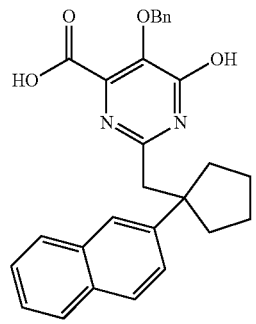 [SMILES: O=C(O)c1nc(CC2(c3ccc4ccccc4c3)CCCC2)nc(O)c1OCc1ccccc1]

5-Benzyloxy-6-hydroxy-2-(1-naphthalen-2-yl-cyclopentylmethyl)-pyrimidine-4-carboxylic acid 5-Benzyloxy-6-hydroxy-2-(1-naphthalen-2-yl-cyclopentylmethyl)-pyrimidine-4-carboxylic acid (218) (300.0 mg, crude) was synthesized as a white solid from 5-benzyloxy-6-hydroxy-2-(1-naphthalen-2-yl-cyclopentylmethyl)-pyrimidine-4-carboxylic acid tert-butyl ester (217) (300.0 mg, 0.588 mmol) following the procedure described for 5-benzyloxy-2-[1-(2,5-dichlorophenyl)-cyclopentylmethyl]-6-hydroxy-pyrimidine-4-carboxylic acid (205).

LC-MS: 455.2 (M+H).

Preparation of (219)

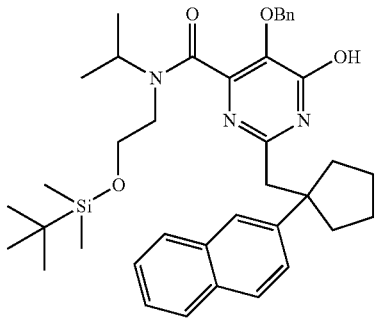 [SMILES: CC(C)N(CCO[Si](C)(C)C(C)(C)C)C(=O)c1nc(CC2(c3ccc4ccccc4c3)CCCC2)nc(O)c1OCc1ccccc1]

5-Benzyloxy-6-hydroxy-2-(1-naphthalen-2-yl-cyclopentylmethyl)-pyrimidine-4-carboxylic acid [2-(tert-butyl-dimethylsilanyloxy)-ethyl]isopropylamide 5-Benzyloxy-6-hydroxy-2-(1-naphthalen-2-yl-cyclopentylmethyl)-pyrimidine-4-carboxylic acid [2-(tert-butyl-dimethylsilanyloxy)-ethyl]-isopropylamide (219) (300.0 mg, 24.5%) was synthesized as a colorless liquid from 5-benzyloxy-6-hydroxy-2-(1-naphthalen-2-yl-cyclopentylmethyl)-pyrimidine-4-carboxylic acid (218) (850.0 mg, 1.87 mmol) and [2-(tert-butyl-dimethylsilanyloxy)-ethyl]-isopropylamine (8b) (610.5 mg, 2.80 mmol) following the procedure described for 5-benzyloxy-2-[1-(2,5-dichlorophenyl)-cyclopentylmethyl]-6-hydroxypyrimidine-4-carboxylic acid [2-(tert-butyl-dimethylsilanyloxy)-ethyl]-isopropylamide (206).

LC-MS: 654.4 (M+H).

Preparation of (220)

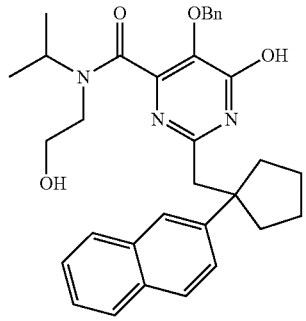 [SMILES: CC(C)N(CCO)C(=O)c1nc(CC2(c3ccc4ccccc4c3)CCCC2)nc(O)c1OCc1ccccc1]

5-Benzyloxy-6-hydroxy-2-(1-naphthalen-2-yl-cyclopentylmethyl)-pyrimidine-4-carboxylic acid (2-hydroxyethyl)isopropylamide 5-Benzyloxy-6-hydroxy-2-(1-naphthalen-2-yl-cyclopentylmethyl)-pyrimidine-4-carboxylic acid (2-hydroxyethyl)-isopropylamide (220) (80.0 mg, crude) was synthesized as a colorless liquid from 5-benzyloxy-6-hydroxy-2-(1-naphthalen-2-yl-cyclopentylmethyl)-pyrimidine-4-carboxylic acid [2-(tert-butyl-dimethylsilanyloxy)-ethyl]-isopropylamide (219) (300.0 mg, 0.459 mmol) following the procedure described 5-benzyloxy-2-[1-(2,5-dichlorophenyl)-cyclopentylmethyl]-6-hydroxypyrimidine-4-carboxylic acid (2-hydroxyethyl)-isopropylamide (207).

LC-MS: 540.2 (M+H).

Preparation of (221)

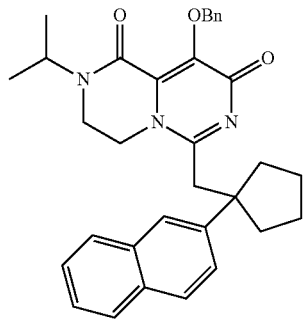 [SMILES: CC(C)N1CCn2c(CC3(c4ccc5ccccc5c4)CCCC3)nc(=O)c(OCc3ccccc3)c2C1=O]

9-Benzyloxy-2-isopropyl-6-(1-naphthalen-2-yl-cyclopentylmethyl)-3,4-dihydro-2H-pyrazino[1,2-c]pyrimidine-1,8-dione 9-Benzyloxy-2-isopropyl-6-(1-naphthalen-2-yl-cyclopentylmethyl)-3,4-dihydro-2H-pyrazino[1,2-c]pyrimidine-1,8-dione (221) (90.0 mg, 41.33%) was synthesized as a white solid from 5-benzyloxy-6-hydroxy-2-(1-naphthalen-2-yl-cyclopentylmethyl)-pyrimidine-4-carboxylic acid (2-hydroxyethyl)-isopropylamide (220) (225.0 mg, 0.417 mmol) following the procedure described for 9-benzyloxy-6-[1-(2,5-dichlorophenyl)-cyclopentylmethyl]-2-isopropyl-3,4-dihydro-2H-pyrazino[1,2-c]pyrimidine-1,8-dione (208).

LC-MS: 522.0 (M+H).

Preparation of (222)

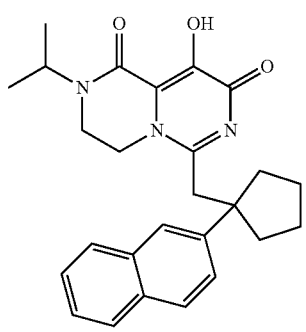 [SMILES: CC(C)N1CCn2c(CC3(c4ccc5ccccc5c4)CCCC3)nc(=O)c(O)c2C1=O]

9-Hydroxy-2-isopropyl-6-(1-naphthalen-2-yl-cyclopentylmethyl)-3,4-dihydro-2H-pyrazino[1,2-c]pyrimidine-1,8-dione 9-Hydroxy-2-isopropyl-6-(1-naphthalen-2-yl-cyclopentylmethyl)-3,4-dihydro-2H-pyrazino[1,2-c]pyrimidine-1,8-dione (222) (50.0 mg, 43.12%) was synthesized as a light pink solid from 9-benzyloxy-2-isopropyl-6-(1-naphthalen-2-yl-cyclopentylmethyl)-3,4-dihydro-2H-pyrazino[1,2-c]pyrimidine-1,8-dione (221) (140.0 mg, 0.269 mmol) following the procedure described for 6-[1-(2,5-dichlorophenyl)-cyclopentylmethyl]-9-hydroxy-2-isopropyl-3,4-dihydro-2H-pyrazino[1,2-c]pyrimidine-1,8-dione (209).

LC-MS: 432.0 (M+H).

Example 235

4-[1-(9-Hydroxy-2-isopropyl-1,8-dioxo-1,3,4,8-tetrahydro-2H-pyrazino[1,2-c]pyrimidin-6-ylmethyl)-cyclopentyl]-benzonitrile The synthetic procedure used in this preparation is outlined in Scheme 39.

Scheme 39

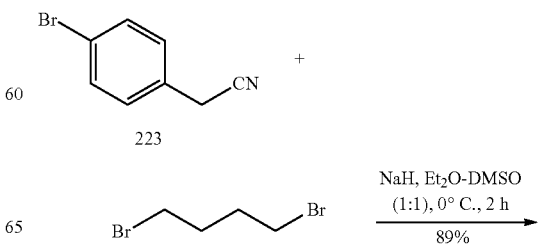

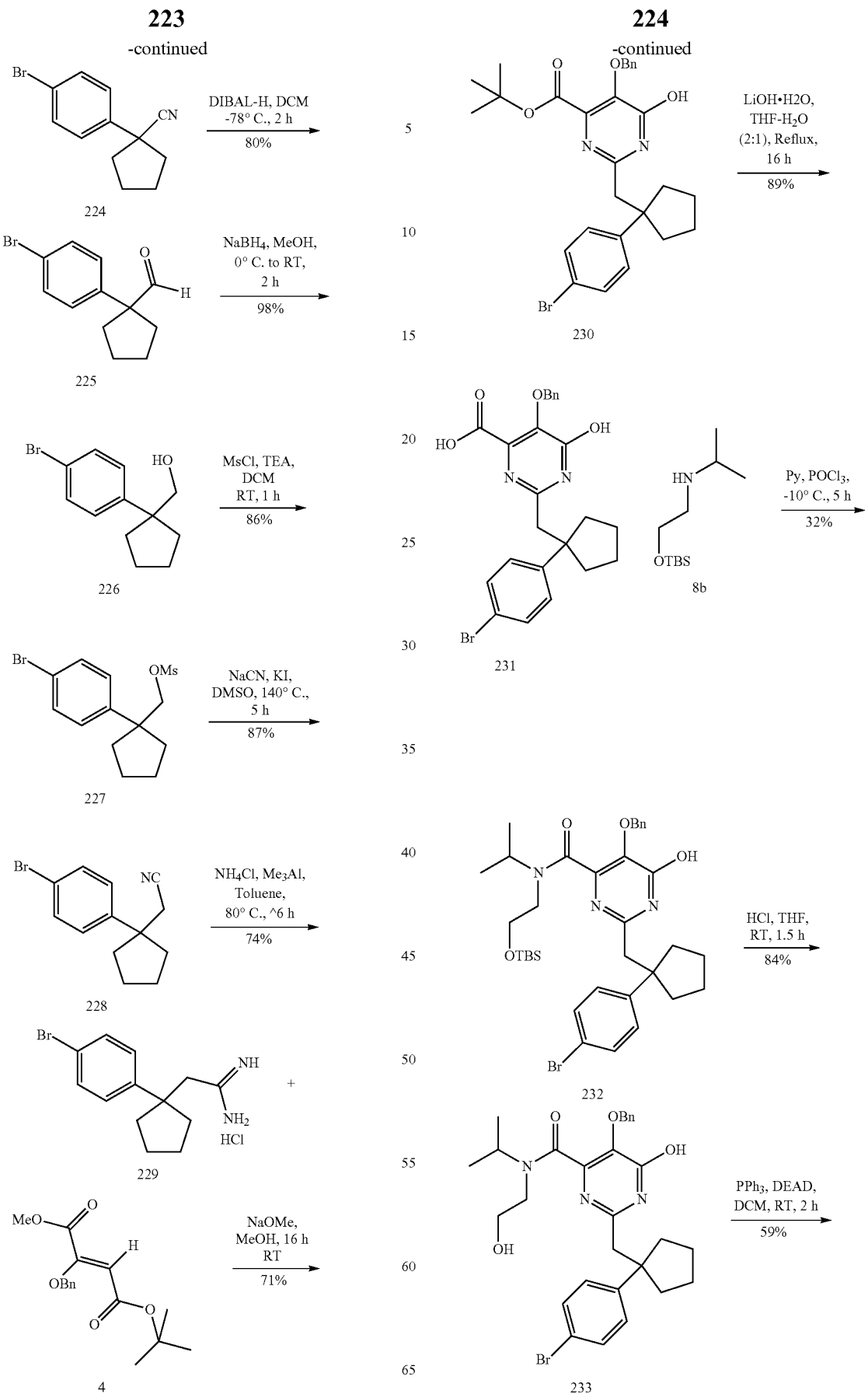

225

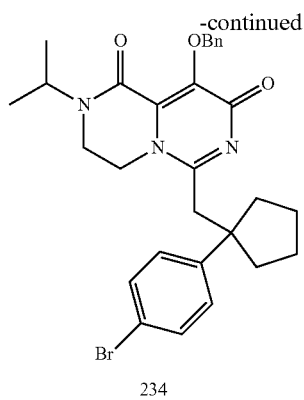

234

Zn/Zn(CN)$_2$/dpp/
Pd$_2$(dba)$_3$
120° C./16 h
———————→
43%

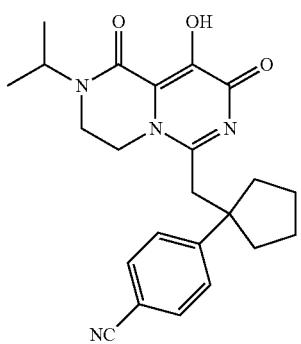

235

Preparation of (224)

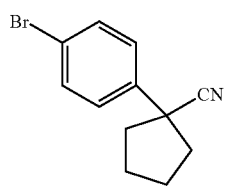 [SMILES: N#CC1(c2ccc(Br)cc2)CCCC1]

1-(4-Bromophenyl)-cyclopentanecarbonitrile

To a suspension of NaH (2.55 g, 63.75 mmol, 60%) in dimethyl sulfoxide (50 mL) were added dropwise a mixture of 4-bromophenyl-acetonitrile (223) (5 g, 25.51 mmol) and 1,4-dibromobutane (3.04 mL, 25.51 mmol) dissolved in dimethyl sulfoxide:ether (1:1) (50 mL) at 0° C. and the reaction mixture was stirred at this temperature for 2 h. After completion of the reaction, water (20 mL) and 10% HCl solution (50 mL) were added to the mixture and the mixture was extracted with ethyl acetate (2×200 ml). The organic layer was dried over Na$_2$SO$_4$, concentrated and purified by 100-200 silica column chromatography using hexane as the eluent to give 1-(4-bromophenyl)-cyclopentanecarbonitrile (224) (5.7 g, 89%) as a white crystalline solid.

GC-MS: 250 (M+)

226

Preparation of (225)

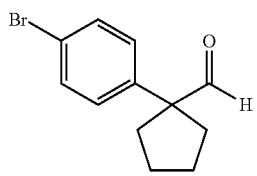 [SMILES: O=CC1(c2ccc(Br)cc2)CCCC1]

1-(4-Bromophenyl)-cyclopentanecarbaldehyde

To a stirred solution of 1-(4-bromophenyl)-cyclopentanecarbonitrile (224) (5.7 g, 22.78 mmol) in dichloromethane (50 mL), was added slowly diisobutylaluminium hydride (33 mL, 56.96 mmol, 25% in toluene) at −70° C. The reaction mixture was stirred at this temperature for 2 h. After completion of the reaction, it was quenched by slow addition of aqueous potassium sodium tartarate tetrahydrate solution (20 mL). The reaction mixture was stirred at room temperature for 16 h. The mixture was extracted with dichloromethane thrice, the organic part was dried over Na$_2$SO$_4$ and concentrated. The crude product was purified by 100-200 silica column chromatography using hexane as the eluent to give 1-(4-bromophenyl)-cyclopentanecarbaldehyde (225) (4.7 g, 81%) as a white solid.

GC-MS: 253 (M+).

Preparation of (226)

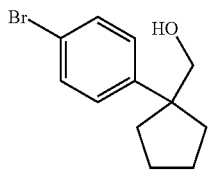

[1-(4-Bromophenyl)-cyclopentyl]-methanol

To a stirred solution of 1-(4-bromophenyl)-cyclopentanecarbaldehyde (225) (51.0 g, 201.47 mmol) in methanol (400 mL), was added NaBH$_4$ (15.31 g, 402.94 mmol) portion-wise at 0° C.

The reaction mixture was then stirred at room temperature for 2 h. After completion, the solvent was concentrated, diluted with water and the crude product was extracted with ethyl acetate (2×300 mL). The organic part was dried over Na$_2$SO$_4$ and evaporated to give [1-(4-bromophenyl)-cyclopentyl]-methanol (226) (50.8 g, 98%) as white solid which was sufficiently pure to be used in the next step.

Preparation of (227)

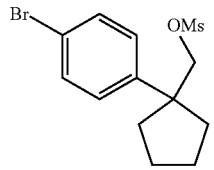 [SMILES: CS(=O)(=O)OCC1(c2ccc(Br)cc2)CCCC1]

Methanesulfonic acid 1-(4-bromophenyl)-cyclopentylmethyl ester

To a stirred of [1-(4-bromophenyl)-cyclopentyl]-methanol (226) (47.0 g, 184.19 mmol) in dichloromethane (300 mL) was added $Et_3N$ (51.3 mL, 368.39 mmol) followed by dropwise addition of mesyl chloride (17.1 mL, 221.03 mmol) at 0° C., and the reaction mixture stirred at room temperature for 1 h. The reaction was quenched by the addition of water, extracted with dichloromethane, washed with water, dried over $Na_2SO_4$ and concentrated. The crude product was purified by 100-200 silica column chromatography using 5% ethyl acetate in hexane as the eluent to give methanesulfonic acid 1-(4-bromophenyl)-cyclopentylmethyl ester (227) (52.8 g, 86%) as a white solid.

GC-MS: 334 (M+).

Preparation of (228)

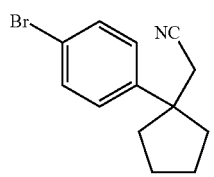

[1-(4-Bromophenyl)-cyclopentyl]-acetonitrile

To a stirred solution of methanesulfonic acid 1-(4-bromophenyl)-cyclopentylmethyl ester (227) (20 g, 60.01 mmol) in dimethyl sulfoxide (100 mL) were added KI (0.99 g, 6.00 mmol) and NaCN (4.41 g, 90.02 mmol). The reaction mixture was then stirred at 140° C. for 5 h. After completion of the reaction, the reaction mixture was diluted with water, extracted with ethyl acetate (2×250 mL) and the organic layer was washed with water and brine. It was then dried over $Na_2SO_4$, and concentrated. The crude product was purified by 100-200 silica column chromatography using 5% ethyl acetate in hexane as the eluent to give [1-(4-bromophenyl)-cyclopentyl]-acetonitrile (228) (13.9 g, 87%) as a colorless thick liquid.

GC-MS: 264 (M+).

Preparation of (229)

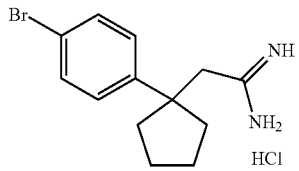 [SMILES: N=C(N)CC1(c2ccc(Br)cc2)CCCC1 ; Cl]

HCl-salt of 2-[1-(4-Bromophenyl)-cyclopentyl]-acetamidine

To a suspension of $NH_4Cl$ (1.21 g, 43.65 mmol) in toluene (30 mL) was added dropwise a solution of trimethyl aluminium (1.64 g, 43.65 mmol, 2M in toluene) at 0° C. and stirred for 2 h at room temperature prior to the addition of a solution of [1-(4-bromophenyl)-cyclopentyl]-acetonitrile (228) (2.0 g, 7.57 mmol) in toluene (10 mL). The resulting solution was heated to 80° C. for 16 h. The cooled reaction mixture was poured into a slurry of silica gel (10 g) in $CHCl_3$ (20 mL), followed by vigorous stirring for 30 min. The silica gel was filtered off and the cake was rinsed in turn with methanol. The solvent was evaporated and the crude product was taken up in 10% methanol in dichloromethane (200 mL) and stirred for 30 min. The solid suspension was removed by filtration and the filtrate was evaporated. The crude product was triturated in diethyl ether and the solid was collected by filtration and dried under vacuum to afford HCl-salt of 2-[1-(4-bromophenyl)-cyclopentyl]-acetamidine (229) (1.78 g, 74%) as a white solid.

LC-MS: 281.0 (M+H).

Preparation of (230)

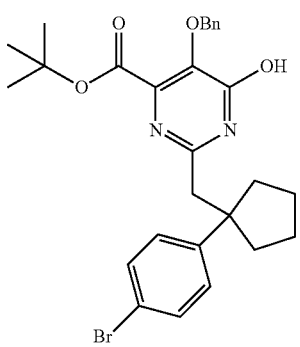 [SMILES: CC(C)(C)OC(=O)c1nc(CC2(c3ccc(Br)cc3)CCCC2)nc(O)c1OCc1ccccc1]

5-Benzyloxy-2-[1-(4-bromophenyl)-cyclopentylmethyl]-6-hydroxypyrimidine-4-carboxylic acid tert-butyl ester To a mixture of the HCl-salt of 2-[1-(4-bromophenyl)-cyclopentyl]-acetamidine (229) (6.5 g, 20.47 mmol) and (E)-2-benzyloxy-3-hydroxy-but-2-enedioic acid 4-tert-butyl ester 1-methyl ester (4) (9.47 g, 30.71 mmol) in methanol (100 mL) was added sodium methoxide (3.32 g, 23.73 mmol, 25% in methanol) at 0° C. Then the reaction mixture was allowed to warm to room temperature and was stirred for 16 h. After completion of the reaction, solvent was reduced and the crude product was dissolved in dichloromethane (150 mL). The organic part was washed with 1N HCl, separated and dried over Na₂SO₄. After evaporation, the crude product was purified by 100-200 silica gel column chromatography using 20% ethyl acetate in hexane as the eluent to give 5-benzyloxy-2-[1-(4-bromophenyl)-cyclopentylmethyl]-6-hydroxypyrimidine-4-carboxylic acid tert-butyl ester (230) (7.9 g, 71%) as a yellow solid.

LC-MS: 541.4 (M+H).

Preparation of (231)

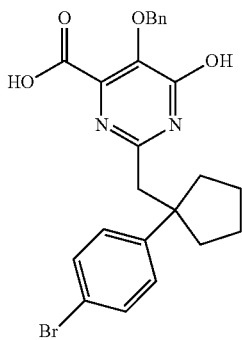 [SMILES: O=C(O)c1nc(CC2(c3ccc(Br)cc3)CCCC2)nc(O)c1OCc1ccccc1]

5-Benzyloxy-2-[1-(4-bromophenyl)-cyclopentylmethyl]-6-hydroxypyrimidine-4-carboxylic acid To a stirred solution of 5-benzyloxy-2-[1-(4-bromophenyl)-cyclopentylmethyl]-6-hydroxypyrimidine-4-carboxylic acid tert-butyl ester (230) (7.9 g, 14.64 mmol) in tetrahydrofuran (200 mL) was added an aqueous solution (100 mL) of LiOH.H₂O (6.15 g, 146.44 mmol). The resulting mixture was refluxed for 16 h. After completion of the reaction the organic solvent was removed on a rotary evaporator and water (30 mL) was added. The aqueous solution was acidified (pH 5) with concentrated HCl at 0° C. to give a white solid which was filtered off. The solid residue was triturated in diethyl ether and filtered. After drying, 5-benzyloxy-2-[1-(4-bromophenyl)-cyclopentylmethyl]-6-hydroxypyrimidine-4-carboxylic acid (231) was obtained (6.3 g, 89%) as a white solid.

LC-MS: 485.2 (M+H).

Preparation of (232)

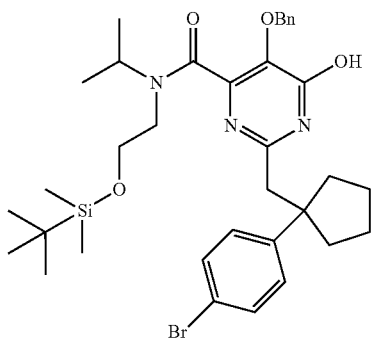 [SMILES: CC(C)N(CCO[Si](C)(C)C(C)(C)C)C(=O)c1nc(CC2(c3ccc(Br)cc3)CCCC2)nc(O)c1OCc1ccccc1]

5-Benzyloxy-2-[1-(4-bromophenyl)-cyclopentylmethyl]-6-hydroxypyrimidine-4-carboxylic acid [2-(tert-butyl-dimethylsilanyloxy)-ethyl]isopropylamide To a stirred solution of 5-benzyloxy-2-[1-(4-bromophenyl)-cyclopentylmethyl]-6-hydroxypyrimidine-4-carboxylic acid (231) (2.0 g, 4.14 mmol) and [2-(tert-butyl-dimethylsilanyloxy)-ethyl]-isopropyl-amine (8b) (2.7 g, 12.41 mmol) in pyridine (25 ml), was added POCl₃ (1.16 ml, 12.41 ml) at −10° C. The reaction mixture was stirred at this temperature for 5 h. After completion of the reaction, the reaction mixture was quenched with water and the mixture was extracted with ethyl acetate. The organic part was washed with water, separated and dried over Na₂SO₄. After evaporation, the crude product was purified by 100-200 silica gel column chromatography using 30% ethyl acetate in hexane as the eluent to give 5-benzyloxy-2-[1-(4-bromophenyl)-cyclopentylmethyl]-6-hydroxypyrimidine-4-carboxylic acid [2-(tert-butyl-dimethylsilanyloxy)-ethyl]-isopropylamide (232) (0.9 g, 32%) as a brown solid.

LC-MS: 684.6 (M+H).

Preparation of (233)

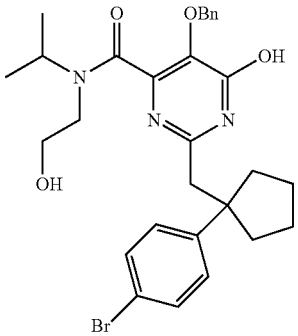 [SMILES: CC(C)N(CCO)C(=O)c1nc(CC2(c3ccc(Br)cc3)CCCC2)nc(O)c1OCc1ccccc1]

5-Benzyloxy-2-[1-(4-bromophenyl)-cyclopentylmethyl]-6-hydroxypyrimidine-4-carboxylic acid (2-hydroxyethyl)-isopropylamide To a stirred solution of 5-benzyloxy-2-[1-(4-bromophenyl)-cyclopentylmethyl]-6-hydroxypyrimidine-4-carboxylic acid [2-(tert-butyl-dimethylsilanyloxy)-ethyl]isopropylamide (232) (1.0 g, 1.46 mmol) in tetrahydrofuran (10 mL) was added HCl (37% aqueous, 1.70 mmol) and the reaction mixture was stirred at room temperature for 1.5 h. After completion of the reaction, the mixture was diluted with ethyl acetate (30 mL), washed with water, separated and the organic phase dried over Na₂SO₄. After evaporation of the solvent, the crude product was purified by 100-200 silica gel column chromatography using 60% ethyl acetate in hexane followed by 5% methanol in dichloromethane as the eluent to obtain 5-benzyloxy-2-[1-(4-bromophenyl)-cyclopentylmethyl]-6-hydroxypyrimidine-4-carboxylic acid (2-hydroxyethyl)-isopropylamide (233) (0.7 g, 84%) as a white solid.

LC-MS: 568.2 (M+H).

231

Preparation of (234)

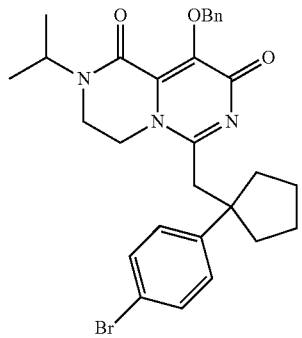 [SMILES: CC(C)N1CCn2c(CC3(c4ccc(Br)cc4)CCCC3)nc(=O)c(OCc3ccccc3)c2C1=O]

9-Benzyloxy-6-[1-(4-bromophenyl)-cyclopentylmethyl]-2-isopropyl-3,4-dihydro-2H-pyrazino[1,2-c]pyrimidine-1,8-dione To a mixture of 5-benzyloxy-2-[1-(4-bromophenyl)-cyclopentylmethyl]-6-hydroxypyrimidine-4-carboxylic acid (2-hydroxyethyl)-isopropylamide (233) (0.7 g, 1.23 mmol) and triphenyl phosphine (0.807 g, 3.08 mmol) in dry dichloromethane (10 mL) was added diethyl azidocarboxylate (0.58 mL, 3.69 mmol) at room temperature. The reaction mixture was stirred at room temperature for 2 h. After completion, the solvent was evaporated and the crude product was purified by 100-200 silica gel column chromatography using 2% methanol in dichloromethane as the eluent to give 9-benzyloxy-6-[1-(4-bromophenyl)-cyclopentylmethyl]-2-isopropyl-3,4-dihydro-2H-pyrazino[1,2-c]pyrimidine-1,8-dione (234) (0.40 g, 59%) as a white solid.

LC-MS: 550.2 (M+H).

Preparation of (235)

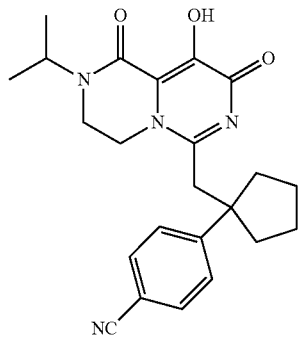 [SMILES: CC(C)N1CCn2c(CC3(c4ccc(C#N)cc4)CCCC3)nc(=O)c(O)c2C1=O]

4-[1-(9-Hydroxy-2-isopropyl-1,8-dioxo-1,3,4,8-tetrahydro-2H-pyrazino[1,2-c]pyrimidin-6-ylmethyl)-cyclopentyl]-benzonitrile A stirred solution of 9-benzyloxy-6-[1-(4-bromophenyl)-cyclopentylmethyl]-2-isopropyl-3,4-dihydro-2H-pyrazino[1,2-c]pyrimidine-1,8-dione (234) (100 mg, 0.182 mmol) in N-Methyl-2-pyrrolidon (1 mL) in a sealed tube was purged with argon for 10 min. To this solution, Zn (1.188 mg, 0.018 mmol), 1,1'-bis(diphenylphosphino)ferrocen (3.021 mg, 0.0050 mmol), Zn(CN)$_2$ (17.067 mg, 0.145 mmol) and Pd$_2$(dba)$_3$ (3.327 mg, 0.0040 mmol) were added and the reaction mixture was heated at 120° C. for 16 h. After completion of the reaction, the reaction mixture was diluted with water and extracted with ethyl acetate, washed with water, followed by brine, separated, dried over sodium sulfate and evaporated to get a crude product which was purified by normal silica column using 10% methanol in dichloromethane containing 10% ammonia to get 4-[1-(9-hydroxy-2-isopropyl-1,8-dioxo-1,3,4,8-tetrahydro-2H-pyrazino[1,2-c]pyrimidin-6-ylmethyl)-cyclopentyl]-benzonitrile (235) (41 mg, 55.53%) as an off-white solid.

LC-MS: 407 (M+H).

Example 248

9-Hydroxy-2-isopropyl-6-[1-(4-trifluoromethyl-phenyl)-cyclopentylmethyl]-3,4-dihydro-2H-pyrazino[1,2-c]pyrimidine-1,8-dione The synthetic procedure used in this preparation is outlined in Scheme 40.

Synthetic Route for 248

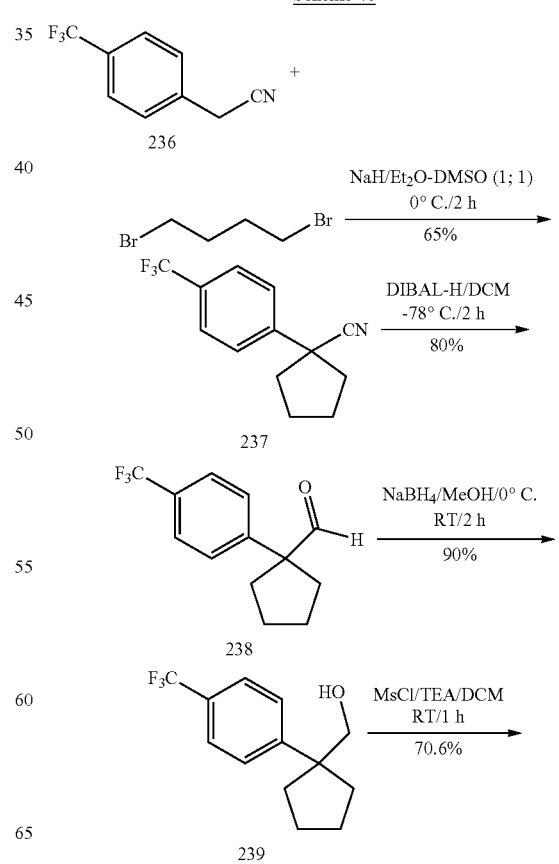

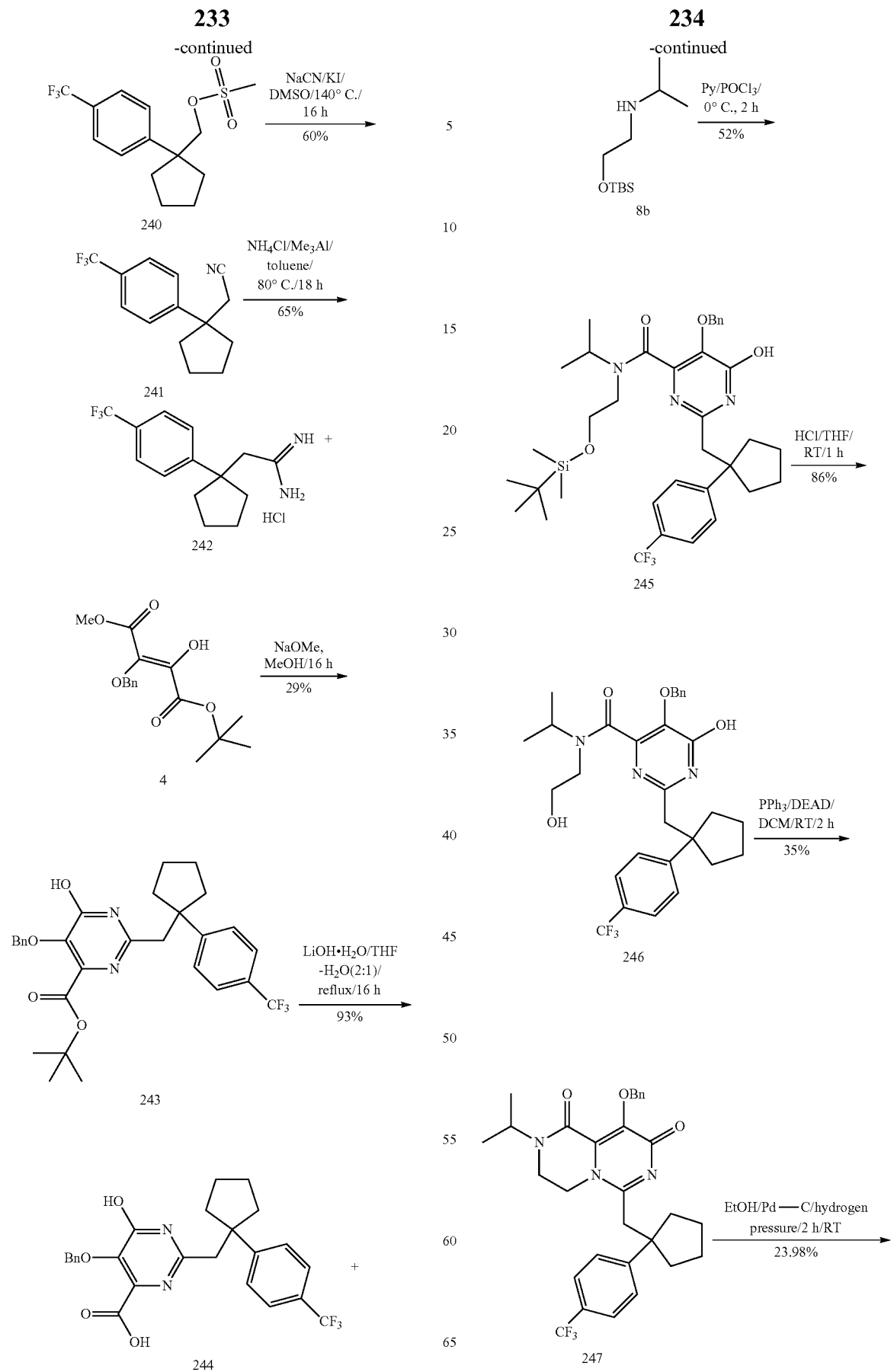

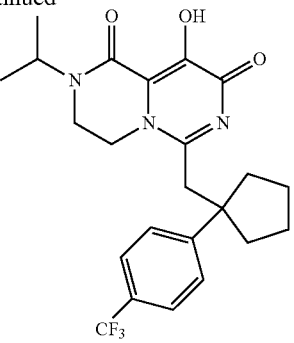

248

Preparation of (237)

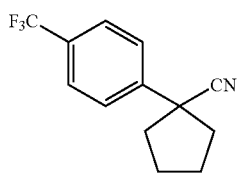 [SMILES: N#CC1(c2ccc(C(F)(F)F)cc2)CCCC1]

1-(4-Trifluoromethyl-phenyl)-cyclopentanecarbonitrile

To a suspension of NaH (8.18 g, 135.13 mmol, 60%) in dimethyl sulfoxide (100 mL) were added dropwise a mixture of (4-trifluoromethyl-phenyl)-acetonitrile (236) (25 g, 135.13 mmol) and 1,4-dibromobutane (16 mL, 135.13 mmol) dissolved in dimethyl sulfoxide:ether (1:1) (300 mL) at 0° C. and the reaction mixture was stirred at this temperature for 2 h. After completion of the reaction, water (100 mL) and 10% HCl solution (50 mL) were added to the mixture and extracted with ethyl acetate (2×400 ml). The organic layer was dried over $Na_2SO_4$, concentrated and purified by 100-200 silica column chromatography using hexane as the eluent to give 1-(4-trifluoromethyl-phenyl)-cyclopentanecarbonitrile (237) (21 g, 65%) as a colorless liquid.
GC-MS: 239 (M/H).

Preparation of (238)

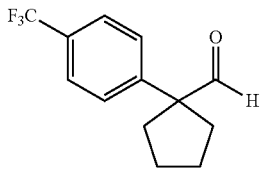 [SMILES: O=CC1(c2ccc(C(F)(F)F)cc2)CCCC1]

1-(4-Trifluoromethyl-phenyl)-cyclopentanecarbaldehyde

To a stirred solution of 1-(4-trifluoromethyl-phenyl)-cyclopentanecarbonitrile (237) (21 g, 87.86 mmol) in dichloromethane (300 mL), was slowly added diisobutylaluminiumhydrid (130 mL, 219.66 mmol, 25% in toluene) at −70° C. The reaction mixture was stirred at this temperature for 2 h. After completion of the reaction, it was quenched by slow addition of aqueous potassium sodium tartarate tetrahydrate solution (130 mL). The reaction mixture was stirred at room temperature for 16 h. The mixture was extracted with dichloromethane; the organic part was dried over $Na_2SO_4$ and concentrated. The crude product was purified by 100-200 silica column chromatography using hexane as the eluent to give 1-(4-trifluoromethyl-phenyl)-cyclopentanecarbaldehyde (238) (17 g, 80%) as a colorless liquid.

Preparation of (239)

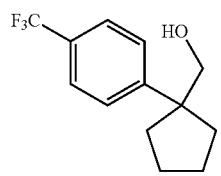 [SMILES: OCC1(c2ccc(C(F)(F)F)cc2)CCCC1]

[1-(4-Trifluoromethyl-phenyl)-cyclopentyl]-methanol

To a stirred solution of 1-(4-trifluoromethyl-phenyl)-cyclopentanecarbaldehyde (238) (17.0 g, 70.24 mmol) in methanol (200 mL), was added $NaBH_4$ (5.33 g, 140.5 mmol) portion-wise at 0° C. The reaction mixture was then stirred at room temperature for 2 h. After completion of the reaction, the solvent was concentrated and the crude product was diluted with water and extracted with ethyl acetate (2×300 mL). The organic part was dried over $Na_2SO_4$ and evaporated to give [1-(4-trifluoromethyl-phenyl)-cyclopentyl]-methanol (239) (15 g, 90%) as a white solid which was used for the next step without further purification.

Preparation of (240)

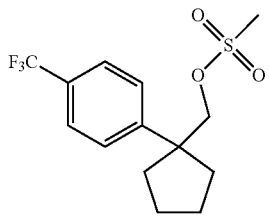

Methanesulfonic acid 1-(4-trifluoromethyl-phenyl)-cyclopentylmethyl ester

To a stirred of 1-(4-trifluoromethyl-phenyl)-cyclopentyl]-methanol (239) (15 g, 61.47 mmol) in dichloromethane (200 mL) was added $Et_3N$ (17.1 mL, 123 mmol) followed by mesyl chloride (5.7 mL, 73.77 mmol) dropwise at 0° C. The reaction mixture was stirred at room temperature for 1 h. After completion, the reaction was quenched by the addition of water. The reaction mixture was diluted with dichloromethane. The organic part was washed with water, separated, dried over $Na_2SO_4$ and finally concentrated. The crude product was purified by 100-200 silica column chromatography using 10% ethyl acetate in hexane as the eluent to give methanesulfonic acid 1-(4-trifluoromethyl-phenyl)-cyclopentylmethyl ester (240) (14 g, 70.6%) as a white solid.

Preparation of (241)

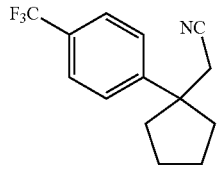 [SMILES: N#CCC1(c2ccc(C(F)(F)F)cc2)CCCC1]

[1-(4-Trifluoromethyl-phenyl)cyclopentyl]-acetonitrile

To a stirred solution of methanesulfonic acid 1-(4-trifluoromethyl-phenyl)-cyclopentylmethyl ester (240) (7 g, 21.73 mmol) in dimethyl sulfoxide (200 mL) were added KI (0.361 g, 2.17 mmol) and NaCN (1.6 g, 32.6 mmol). The reaction mixture was then stirred at 140° C. for 6 h. After completion of the reaction, the reaction mixture was diluted with water, extracted with ethyl acetate (2×300 mL) and the organic layer was washed with water and brine. It was then dried over $Na_2SO_4$ and concentrated. The crude product was purified by 100-200 silica column chromatography using 5% ethyl acetate in hexane as the eluent to give [1-(4-trifluoromethyl-phenyl)-cyclopentyl]-acetonitrile (241) (3.3 g, 60%) as a colorless thick liquid.

Preparation of (242)

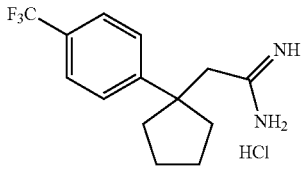 [SMILES: N=C(N)CC1(c2ccc(C(F)(F)F)cc2)CCCC1 ; Cl]

2-(1-p-Tolyl-cyclopentyl)-acetamidine (hydrochloride salt)

To a stirred suspension of $NH_4Cl$ (1.3 g, 23.69 mmol) in dry toluene (30 mL) was added trimethylaluminium (2M solution in toluene) dropwise at 0° C., stirred at 0° C. for 15 min, then stirred at room temperature for 2 h. The solution of [1-(4-trifluoromethyl-phenyl)-cyclopentyl]-acetonitrile (241) (2 g, 7.89 mmol) in toluene (10 mL) was added dropwise at the room temperature and the reaction mixture was heated at 80° C. for 16 h, the reaction mixture was cooled to 0° C., and the reaction mixture was poured into the slurry of silica gel (4 g) in $CHCl_3$ (4 mL), stirred vigorously for 30 min at 0° C., the solid was filtered off through celite and washed with methanol (5×100 mL). The filtrate was concentrated and the crude product was taken up in 10% methanol in dichloromethane (200 mL) and stirred for 30 min. The solid was discarded by filtration and the filtrate was concentrated. The crude product was suspended in ether and a solid was collected by filtration and dried to get 2-(1-p-tolyl-cyclopentyl)-acetamidine (hydrochloride salt) (242) (1.4 g, 65.59%) as a light yellow solid.

LC-MS: 271.0 (M+H).

Preparation of (243)

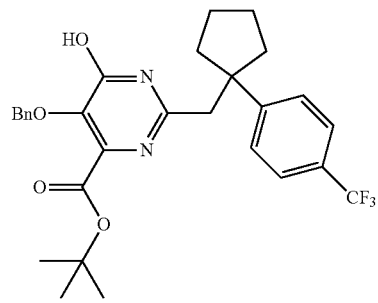 [SMILES: CC(C)(C)OC(=O)c1nc(CC2(c3ccc(C(F)(F)F)cc3)CCCC2)nc(O)c1OCc1ccccc1]

5-Benzyloxy-6-hydroxy-2-[1-(4-trifluoromethyl-phenyl)-cyclopentylmethyl]-pyrimidine-4-carboxylic acid tert-butyl ester To a stirred solution of 2-(1-p-tolyl-cyclopentyl)-acetamidine (HCl salt) (242) (600 mg, 1.96 mmol) and (E)-2-benzyloxy-3-hydroxy-but-2-enedioic acid 4-tert-butyl ester (4) (907 mg, 2.94 mmol) in methanol (10.6 mL) was added sodium methoxide (25 wt % in methanol) (1.3 mL, 5.88 mmol) at 0° C. then the reaction mixture was allowed to warm to room temperature and stirred for 16 h. Silica thin layer chromatography was performed (30% ethyl acetate in hexane, $R_f$=0.4). After completion of the reaction, it was quenched with water, methanol was evaporated and water (30 mL) was added. The mixture was extracted with ethyl acetate (3×30 mL) and separated. The organic part was dried and concentrated to get a crude product, which was purified by CombiFlash column (eluted at 90% ethyl acetate in hexane) to get 5-benzyloxy-6-hydroxy-2-[1-(4-trifluoromethyl-phenyl)-cyclopentylmethyl]-pyrimidine-4-carboxylic acid tert-butyl ester (243) (300 mg, 28.95%) as an off-white solid.

LC-MS: 539.2 (M+H).

Preparation of (244)

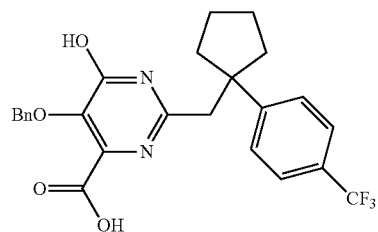 [SMILES: O=C(O)c1nc(CC2(c3ccc(C(F)(F)F)cc3)CCCC2)nc(O)c1OCc1ccccc1]

5-Benzyloxy-6-hydroxy-2-[1-(4-trifluoromethyl-phenyl)-cyclopentylmethyl]-pyrimidine-4-carboxylic acid To a stirred solution 5-benzyloxy-6-hydroxy-2-[1-(4-trifluoromethyl-phenyl)-cyclopentylmethyl]-pyrimidine-4-carboxylic acid tert-butyl ester (243) (250 mg, 0.53 mmol) in the mixture of tetrahydrofuran-water (2:1, 10 mL) was added lithium-hydroxide monohydrate (477 mg, 11.36 mmol) and the reaction mixture was refluxed for 20 h. Very small amounts of the starting ester remained. Silica thin layer chromatography was performed (50% ethyl acetate in hexane, $R_f$=0.1). Volatiles were evaporated, water added (10 mL) and the aqueous part was extracted with ethyl acetate (2×30 mL). The ethyl acetate part was thereafter discarded and the aqueous part was acidified with 1N HCl to a pH of about 5-6. The acidified aqueous part was extracted with ethyl acetate (3×30 mL), dried and concentrated to get 5-benzyloxy-6-hydroxy-2-[1-(4-trifluoromethyl-phenyl)-cyclopentylmethyl]-pyrimidine-4-carboxylic acid (244) (250 mg, 93.13%) as an off-white solid.

LC-MS: 473.2 (M+H).

Preparation of (245)

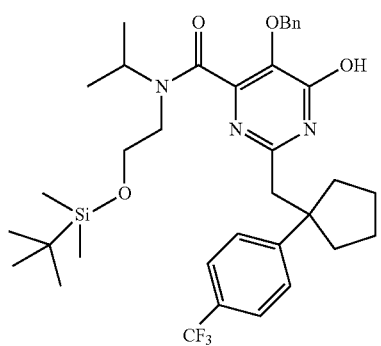 [SMILES: CC(C)N(CCO[Si](C)(C)C(C)(C)C)C(=O)c1nc(CC2(c3ccc(C(F)(F)F)cc3)CCCC2)nc(O)c1OCc1ccccc1]

5-Benzyloxy-6-hydroxy-2-[1-(4-trifluoromethyl-phenyl)-cyclopentylmethyl]-pyrimidine-4-carboxylic acid [2-(tert-butyl-dimethylsilanyloxy)-ethyl]isopropylamide 5-Benzyloxy-6-hydroxy-2-[1-(4-trifluoromethyl-phenyl)-cyclopentylmethyl]-pyrimidine-4-carboxylic acid [2-(tert-butyl-dimethylsilanyloxy)-ethyl]-isopropylamide (245) (187 mg, 52.55%) as a yellow sticky solid was synthesized from 5-benzyloxy-6-hydroxy-2-[1-(4-trifluoromethyl-phenyl)-cyclopentylmethyl]-pyrimidine-4-carboxylic acid (244) (250 mg, 0.53 mmol) and 2-(tert-butyl-dimethylsilanyloxy)-ethyl]-isopropylamine (8b) following the procedure as described for 5-benzyloxy-2-[1-(2,5-dichlorophenyl)-cyclopentylmethyl]-6-hydroxypyrimidine-4-carboxylic acid [2-(tert-butyl-dimethylsilanyloxy)-ethyl]isopropylamide (206).

LC-MS: 672.2 (M+H).

Preparation of (246)

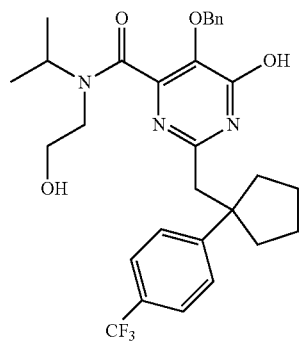 [SMILES: CC(C)N(CCO)C(=O)c1nc(CC2(c3ccc(C(F)(F)F)cc3)CCCC2)nc(O)c1OCc1ccccc1]

5-Benzyloxy-6-hydroxy-2-[1-(4-trifluoromethyl-phenyl)-cyclopentylmethyl]-pyrimidine-4-carboxylic acid (2-hydroxyethyl)-isopropylamide 5-Benzyloxy-6-hydroxy-2-[1-(4-trifluoromethyl-phenyl)-cyclopentylmethyl]-pyrimidine-4-carboxylic acid (2-hydroxyethyl)-isopropylamide (246) (110 mg, 70.79%) as a white sticky solid was synthesized from 5-benzyloxy-6-hydroxy-2-[1-(4-trifluoromethyl-phenyl)-cyclopentylmethyl]-pyrimidine-4-carboxylic acid [2-(tert-butyl-dimethylsilanyloxy)-ethyl]-isopropylamide (245) (187 mg, 0.28 mmol) and 1N HCl (0.05 mL, 1.39 mmol) following the procedure as described for 5-benzyloxy-2-[1-(2,5-dichlorophenyl)-cyclopentylmethyl]-6-hydroxypyrimidine-4-carboxylic acid (2-hydroxyethyl)-isopropylamide (207).

LC-MS: 558.2 (M+H).

Preparation of (247)

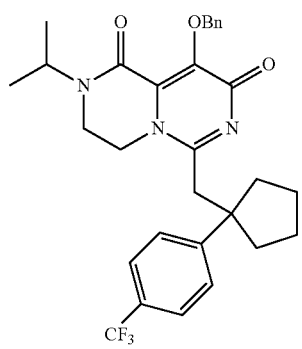 [SMILES: CC(C)N1CCn2c(CC3(c4ccc(C(F)(F)F)cc4)CCCC3)nc(=O)c(OCc3ccccc3)c2C1=O]

9-Benzyloxy-2-isopropyl-6-[1-(4-trifluoromethyl-phenyl)-cyclopentylmethyl]-3,4-dihydro-2H-pyrazino[1,2-c]pyrimidine-1,8-dione 9-Benzyloxy-2-isopropyl-6-[1-(4-trifluoromethyl-phenyl)-cyclopentylmethyl]-3,4-dihydro-2H-pyrazino[1,2-c]pyrimidine-1,8-dione (247) (40 mg, 45.93%) as a white sticky solid was synthesized from 5-benzyloxy-6-hydroxy-2-[1-(4-trifluoromethyl-phenyl)-cyclopentylmethyl]-pyrimidine-4-carboxylic acid (2-hydroxyethyl)-isopropylamide (246) (90 mg, 0.16 mmol) following the procedure as described for 9-benzyloxy-6-[1-(2,5-dichlorophenyl)-cyclopentylmethyl]-2-isopropyl-3,4-dihydro-2H-pyrazino[1,2-c]pyrimidine-1,8-dione (208). Silica thin layer chromatography was performed (ethyl acetate, $R_f$=0.3).

LC-MS: 540.2 (M+H).

Preparation of (248)

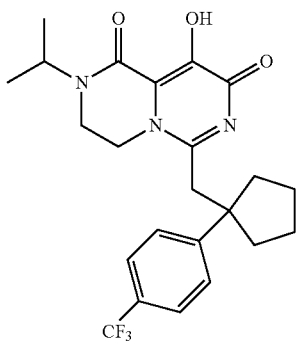 [SMILES: CC(C)N1CCn2c(CC3(c4ccc(C(F)(F)F)cc4)CCCC3)nc(=O)c(O)c2C1=O]

9-Hydroxy-2-isopropyl-6-[1-(4-trifluoromethyl-phenyl)-cyclopentylmethyl]-3,4-dihydro-2H-pyrazino[1,2-c]pyrimidine-1,8-dione To a stirred degassed solution of 9-benzyloxy-2-isopropyl-6-[1-(4-trifluoromethyl-phenyl)-cyclopentylmethyl]-3,4-dihydro-2H-pyrazino[1,2-c]pyrimidine-1,8-dione (247) in EtOH (10 mL) was added 10% Pd—C (5 mg) and the reaction mixture was stirred for 2 h under $H_2$ at balloon pressure. Silica thin layer chromatography was performed (5% methanol in dichloromethane, $R_f$=0.4). Pd—C was filtered off through a small bed of celite and washed with ethanol (5×20 mL). The ethanol was evaporated and the crude product was purified by preparative TLC plate (mobile phase 5% methanol in dichloromethane) to get 9-hydroxy-2-isopropyl-6-[1-(4-trifluoromethyl-phenyl)-cyclopentylmethyl]-3,4-dihydro-2H-pyrazino[1,2-c]pyrimidine-1,8-dione (248) (8 mg, 23.98%) as an off-white solid.

LC-MS: 450.0 (M+H).

Example 260

9-Hydroxy-2-isopropyl-6-(1-phenyl-cyclohexylmethyl)-3,4-dihydro-2H-pyrazino[1,2-c]pyrimidine-1,8-dione The synthetic procedure used in this preparation is outlined in Scheme 41.

Synthetic Route for 260

Scheme 41

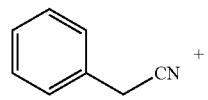

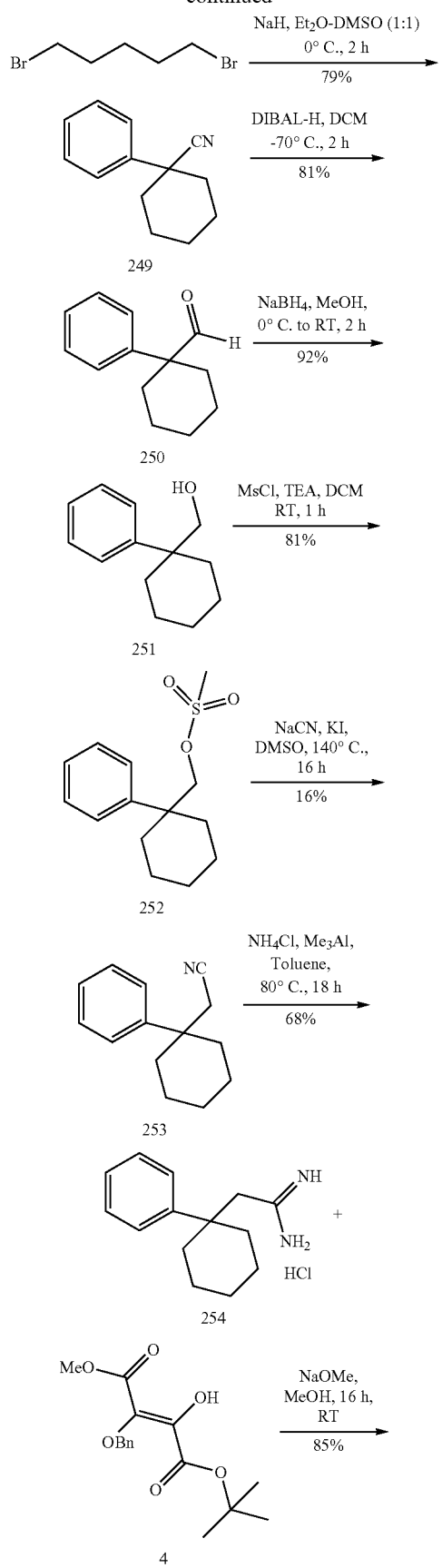

-continued

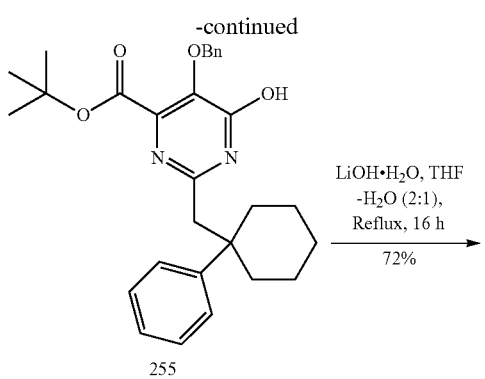
255

LiOH·H₂O, THF
-H₂O (2:1),
Reflux, 16 h
——————→
72%

-continued

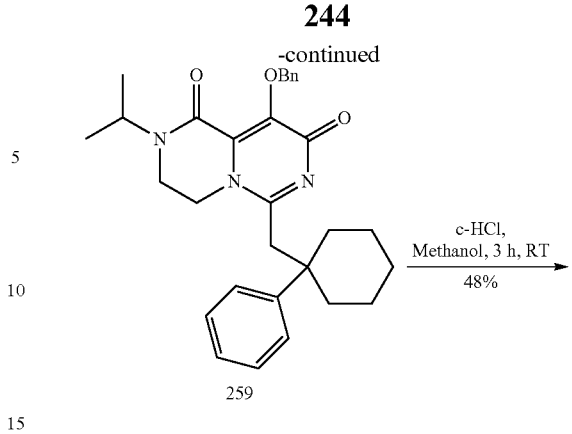
259 c-HCl,
Methanol, 3 h, RT
——————→
48%

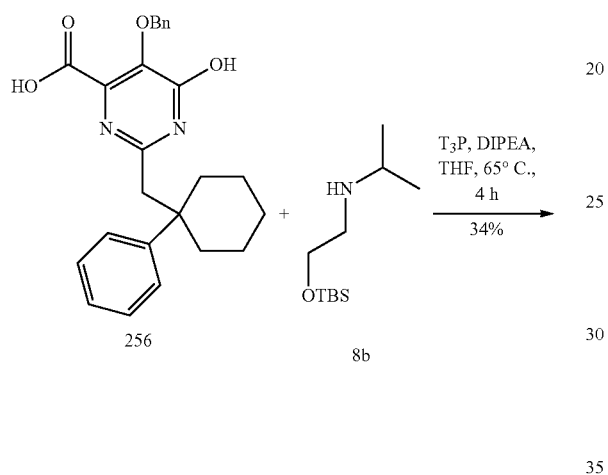
256

+ 8b

T₃P, DIPEA,
THF, 65° C.,
4 h
——————→
34%

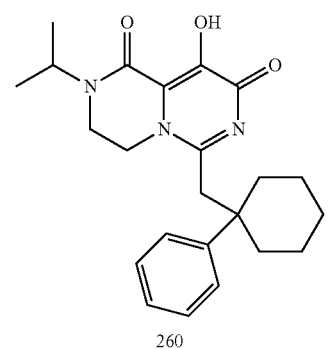
260

Preparation of (249)

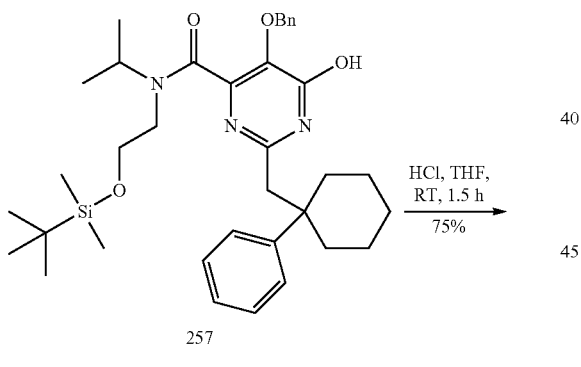
257

HCl, THF,
RT, 1.5 h
——————→
75%

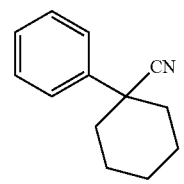 [SMILES: N#CC1(c2ccccc2)CCCCC1]

1-Phenyl-cyclohexanecarbonitrile

To a suspension of NaH (42.7 g, 1067.0 mmol, 60%) in dimethyl sulfoxide (600.0 mL) were added drop-wise a mixture of phenylacetonitrile (50.0 g, 426.8 mmol) and 1,5-dibromopentane (58.1 mL, 426.8 mmol) dissolved in dimethyl sulfoxide:ether (1:1) (200.0 mL) at 0° C. and the reaction mixture was stirred at this temperature for 2 h. After completion of the reaction, water and a 10% HCl solution were added to the mixture and the mixture was extracted with ethyl acetate. The combined organic layer was then washed with water and brine and dried over sodium sulfate and concentrated under reduced pressure to obtain a crude product. This crude product was then purified by normal silica gel column chromatography (using hexane) to get 1-phenyl-cyclohexanecarbonitrile (249) (52.0 g, 65.76%) as a colorless oil.

GC-MS: 185.0 (m/z).

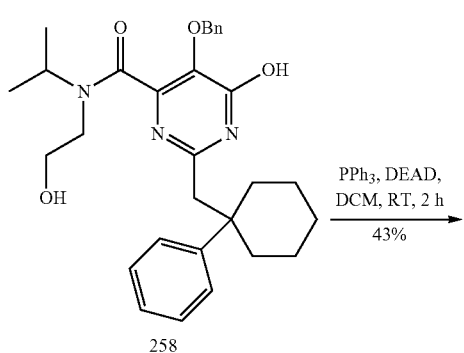
258

PPh₃, DEAD,
DCM, RT, 2 h
——————→
43%

Preparation of (250)

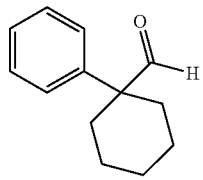 [SMILES: O=CC1(c2ccccc2)CCCCC1]

1-Phenyl-cyclohexanecarbaldehyde

To a stirred solution of 1-phenyl-cyclohexanecarbonitrile (249) (20.0 g, 107.9 mmol) in dichloromethane (200.0 mL) was slowly added diisobutylaluminium hydride (153.5 mL, 269.87 mmol, 25% in toluene) at −70° C. and stirred for 2 h. After completion of the reaction, the reaction mixture was quenched by slow addition of an aqueous potassium sodium tartarate tetrahydrate solution and the reaction mixture was stirred at room temperature for 16 h. Then, it was extracted with dichloromethane, the organic layer was washed with water and brine and dried over sodium sulfate and concentrated under reduced pressure to get the crude. It was purified by nor mal silica gel column chromatography (using hexane) to get 1-phenyl-cyclohexanecarbaldehyde (250) (16.48 g, 81.09%) as colorless oil.

GC-MS: 188.0 (m/z).

Preparation of (251)

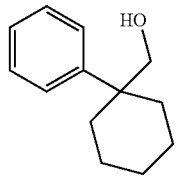

(1-Phenyl-cyclohexyl)-methanol

To a stirred solution of 1-phenyl-cyclohexanecarbaldehyde (250) (16.4 g, 87.1 mmol) in methanol (200.0 mL) was added NaBH$_4$ (6.62 g, 174.2 mmol) portion-wise at 0° C. The reaction mixture was then stirred at room temperature for 2 h. After completion of the reaction, the solvent was concentrated and the crude product was extracted with ethyl acetate. The organic layer was then washed with water and brine and dried over sodium sulfate and concentrated under reduced pressure to get (1-phenyl-cyclohexyl)-methanol (251) (15.2 g, 91.7%) as a white solid which was sufficiently pure to be used for the next step.

GC-MS: 190.0 (m/z).

Preparation of (252)

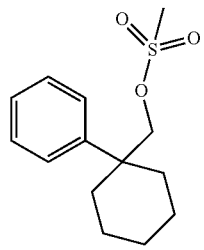 [SMILES: CS(=O)(=O)OCC1(c2ccccc2)CCCCC1]

Methanesulfonic acid 1-phenyl-cyclohexylmethyl ester

To a stirred solution of (1-phenyl-cyclohexyl)-methanol (251) (43.0 g, 225.97 mmol) in dichloromethane (250.0 mL) was added Et$_3$N (63.0 mL, 451.9 mmol), followed by dropwise addition of mesyl chloride (21.0 mL, 271.16 mmol) at 0° C. and the reaction mixture was stirred at room temperature for 1 h. After completion of the reaction, the reaction mixture was quenched by the addition of water and extracted with dichloromethane. The organic layer was then washed with water and brine and dried over sodium sulfate and concentrated under reduced pressure to get a crude product. It was purified by normal silica gel column chromatography (using 5% ethyl acetate in hexane) to get methanesulfonic acid 1-phenyl-cyclohexylmethyl ester (252) (49.3 g, 81.0%) as a white solid.

GC-MS: 268.0 (m/z).

Preparation of (253)

(1-Phenyl-cyclohexyl)-acetonitrile

To a stirred solution of methanesulfonic acid 1-phenyl-cyclohexylmethyl ester (252) (20.0 g, 74.52 mmol) in dimethyl sulfoxide (100.0 mL) were added KI (1.24 g, 7.45 mmol) and NaCN (5.48 g, 111.78 mmol) and the reaction mixture was stirred at 140° C. for 16 h. After completion of the reaction, the reaction mixture was diluted with water, extracted with ethyl acetate and the organic layer was washed with water and brine. The organic layer was then dried over Na$_2$SO$_4$ and concentrated. The crude product was purified by normal silica gel column chromatography (using 5% ethyl acetate in hexane) to get (1-phenyl-cyclohexyl)-acetonitrile (253) (2.4 g, 16.1%) as a colorless liquid.

Preparation of (254)

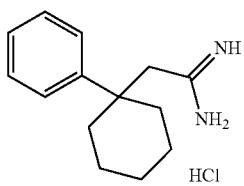 [SMILES: N=C(N)CC1(c2ccccc2)CCCCC1 ; Cl]

HCl-salt of 2-(1-phenyl-cyclohexyl)-acetamidine

To a suspension of NH$_4$Cl (2.34 g, 43.65 mmol) in toluene (20.0 mL) was added drop-wise a solution of trimethyl aluminium (3.15 g, 43.65 mmol, 2M in toluene) at 0° C. The reaction mixture was warmed to room temperature and stirred for 2 h prior to the addition of a solution of (1-phenyl-cyclohexyl)-acetonitrile (253) (2.9 g, 14.55 mmol) in toluene (10.0 mL). The resulting solution was heated to 80° C. for 16 h. The cooled reaction mixture was poured into a slurry of silica-gel (10.0 g) in CHCl$_3$ (20.0 mL) followed by vigorous stirring for 30 min. The silica gel was filtered off and the cake was rinsed in turn with methanol. The solvent was evaporated and the crude product was taken up in 10% methanol in dichloromethane (200.0 mL) and stirred for 30 min. The solid suspension was removed by filtration and the filtrate was evaporated. The crude product was triturated in diethyl ether and the solid was collected by filtration and dried under vacuum to afford HCl-salt of 2-(1-phenyl-cyclohexyl)-acetamidine (254) (2.5 g, 68.0%) as a white solid.

LC-MS: 217.2 (M+H).

Preparation of (255)

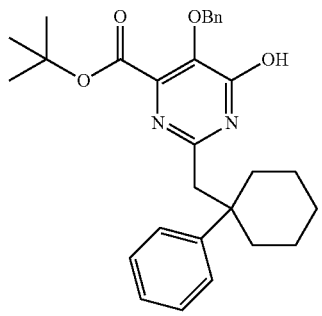 [SMILES: CC(C)(C)OC(=O)c1nc(CC2(c3ccccc3)CCCCC2)nc(O)c1OCc1ccccc1]

5-Benzyloxy-6-hydroxy-2-(1-phenyl-cyclohexylmethyl)-pyrimidine-4-carboxylic acid tert-butyl ester To a mixture of HCl-salt of 2-(1-phenyl-cyclohexyl)-acetamidine (254) (2.0 g, 7.91 mmol) and (E)-2-benzyloxy-3-hydroxy-but-2-enedioic acid 4-tert-butyl ester 1-methyl ester (9) (3.66 g, 11.86 mmol) in methanol (50.0 mL) was added sodium methoxide (1.28 g, 23.73 mmol, 25% in methanol) at 0° C. Then the reaction mixture was allowed to warm up to room temperature and was stirred for 16 h. After completion of the reaction, the solvent was reduced and the crude product was dissolved in dichloromethane and the resultant mixture extracted with dichloromethane. The organic layer was washed with 1N HCl and with water and brine. It was then dried over Na$_2$SO$_4$ and concentrated. The crude product was purified by normal silica gel column chromatography (using 10% ethyl acetate in hexane) to get 5-benzyloxy-6-hydroxy-2-(1-phenyl-cyclohexylmethyl)-pyrimidine-4-carboxylic acid tert-butyl ester (255) (3.2 g, 85.0%) as a yellowish thick liquid which turned into a solid after storing at room temperature.

LC-MS: 475.2 (M+H).

Preparation of (256)

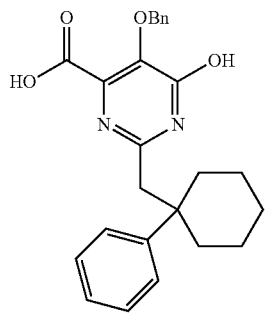 [SMILES: O=C(O)c1nc(CC2(c3ccccc3)CCCCC2)nc(O)c1OCc1ccccc1]

5-Benzyloxy-6-hydroxy-2-(1-phenyl-cyclohexylmethyl)-pyrimidine-4-carboxylic acid To a stirred solution of 5-benzyloxy-6-hydroxy-2-(1-phenyl-cyclohexylmethyl)-pyrimidine-4-carboxylic acid tert-butyl ester (255) (2.5 g, 5.27 mmol) in tetrahydrofuran (60.0 mL) was added a aqueous solution (30.0 mL) of LiOH.H$_2$O (2.21 g, 52.67 mmol) and the reaction mixture was refluxed for 16 h. After completion of the reaction, the organic solvent was removed on a rotary evaporator and water (10.0 mL) was added. The aqueous solution was acidified with concentrated HCl to pH=5.0 at 0° C. to give a white solid which was filtered off. The solid residue was triturated in diethyl ether and filtered. After drying, 5-benzyloxy-6-hydroxy-2-(1-phenyl-cyclohexylmethyl)-pyrimidine-4-carboxylic acid (256) was obtained (1.6 g, 72.58%) as a white solid.

LC-MS: 417.4 (M−H).

Preparation of (257)

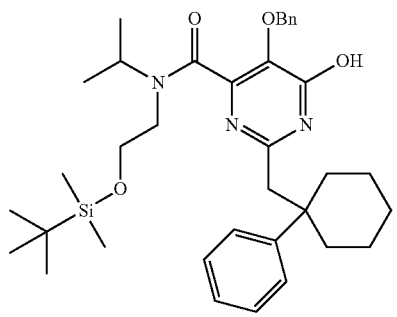 [SMILES: CC(C)N(CCO[Si](C)(C)C(C)(C)C)C(=O)c1nc(CC2(c3ccccc3)CCCCC2)nc(O)c1OCc1ccccc1]

5-Benzyloxy-6-hydroxy-2-(1-phenyl-cyclohexylmethyl)-pyrimidine-4-carboxylic acid [2-(tert-butyl-dimethylsilanyloxy)-ethyl]-isopropylamide To a stirred solution of 5-benzyloxy-6-hydroxy-2-(1-phenyl-cyclohexylmethyl)-pyrimidine-4-carboxylic acid (256) (0.5 g, 1.19 mmol) and [2-(tert-butyl-dimethylsilanyloxy)-ethyl]-isopropyl-amine (8b) (0.78 g, 3.58 mmol) in dry tetrahydrofuran (20.0 mL) were added propylphosphonic anhydride (0.76 g, 2.39 mmol, 50% in ethyl acetate) and diisopropyl ethylamine (0.8 mL, 4.78 mmol) at room temperature and the reaction mixture was heated at 65° C. for 4 h. After completion of the reaction, the mixture was portioned between ethyl acetate and water. The organic layer was separated, dried over $Na_2SO_4$ and concentrated under reduced pressure to get a crude product which was purified by normal silica gel column chromatography (using 30% ethyl acetate in hexane) to get 5-benzyloxy-6-hydroxy-2-(1-phenyl-cyclohexylmethyl)-pyrimidine-4-carboxylic acid [2-(tert-butyl-dimethylsilanyloxy)-ethyl]-isopropylamide (257) (0.25 g, 34.0%) as a colorless liquid.

LC-MS: 618.2 (M+H).

Preparation of (258)

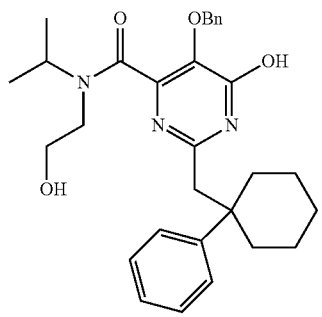 [SMILES: CC(C)N(CCO)C(=O)c1nc(CC2(c3ccccc3)CCCCC2)nc(O)c1OCc1ccccc1]

5-Benzyloxy-6-hydroxy-2-(1-phenyl-cyclohexylmethyl)-pyrimidine-4-carboxylic acid (2-hydroxyethyl)-isopropylamide To a stirred solution of 5-benzyloxy-6-hydroxy-2-(1-phenyl-cyclohexylmethyl)-pyrimidine-4-carboxylic acid [2-(tert-butyl-dimethylsilanyloxy)-ethyl]-isopropylamide (257) (0.7 g, 1.13 mmol) in tetrahydrofuran (10.0 mL) was added HCl (0.062 g, 1.70 mmol) and the reaction mixture was stirred at room temperature for 1.5 h. After completion of the reaction, the mixture was extracted with ethyl acetate. The combined organic layer was washed with water, separated and dried over $Na_2SO_4$. After evaporation of the solvent, the crude product was purified by normal silica gel column chromatography (using 60% ethyl acetate in hexane followed by 5% methanol in ethyl acetate) to get 5-benzyloxy-6-hydroxy-2-(1-phenyl-cyclohexylmethyl)-pyrimidine-4-carboxylic acid (2-hydroxyethyl)-isopropylamide (258) (0.43 g, 75.0%) as a white solid.

LC-MS: 504.2 (M+H).

Preparation of (259)

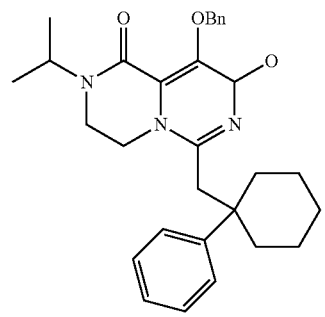 [SMILES: CC(C)N1CCN2C(CC3(c4ccccc4)CCCCC3)=NC(O)C(OCc3ccccc3)=C2C1=O]

9-Benzyloxy-2-isopropyl-6-(1-phenyl-cyclohexylmethyl)-3,4-dihydro-2H-pyrazino[1,2-c]pyrimidine-1,8-dione To a mixture of 5-benzyloxy-6-hydroxy-2-(1-phenyl-cyclohexylmethyl)-pyrimidine-4-carboxylic acid (2-hydroxyethyl)-isopropylamide (258) (0.43 g, 0.85 mmol) and triphenyl phosphine (0.45 g, 1.71 mmol) in dry dichloromethane (10.0 mL) was added diethyl azidocarboxylate (0.34 mL, 2.13 mmol) at room temperature and the reaction stirred for 2 h. After completion of the reaction, the solvent was evaporated and the crude product was purified by normal silica gel column chromatography (using 2% methanol in dichloromethane) to get 9-benzyloxy-2-isopropyl-6-(1-phenyl-cyclohexylmethyl)-3,4-dihydro-2H-pyrazino[1,2-c]pyrimidine-1,8-dione (259) (0.18 g, 43.0%) as a white solid.

LC-MS: 486.2 (M+H).

Preparation of (260)

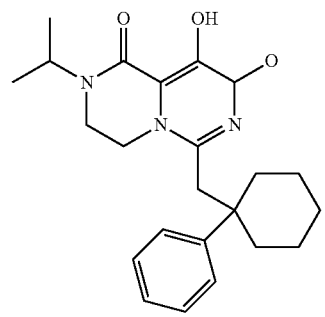 [SMILES: CC(C)N1CCN2C(CC3(c4ccccc4)CCCCC3)=NC(O)C(O)=C2C1=O]

9-Hydroxy-2-isopropyl-6-(1-phenyl-cyclohexylmethyl)-3,4-dihydro-2H-pyrazino[1,2-c]pyrimidine-1,8-dione To the stirred solution of 9-benzyloxy-2-isopropyl-6-(1-phenyl-cyclohexylmethyl)-3,4-dihydro-2H-pyrazino[1,2-c]pyrimidine-1,8-dione (259) (0.18 g, 0.37 mmol) in methanol (5.0 mL) was added concentrated HCl (5.0 mL) and the reaction mixture was stirred at room temperature for 3 h. After completion of the reaction, the solvent was reduced and the crude product was extracted with 10% methanol in dichloromethane. The organic part was washed with saturated NaHCO$_3$ solution, separated and dried over Na$_2$SO$_4$. After evaporation, the crude product was purified by normal silica gel column chromatography (using 3% methanol in dichloromethane) to get 9-hydroxy-2-isopropyl-6-(1-phenyl-cyclohexylmethyl)-3,4-dihydro-2H-pyrazino[1,2-c]pyrimidine-1,8-dione (260) (70.0 mg, 48.0%) as a white solid.

LC-MS: 396.2 (M+H).

Example 275

6-(4,4-Difluoro-1-phenyl-cyclohexylmethyl)-9-hydroxy-2-isopropyl-3,4-dihydro-2H-pyrazino[1,2-c]pyrimidine-1,8-dione The synthetic procedure used in this preparation is outlined in Scheme 42.

Synthetic Route for 275

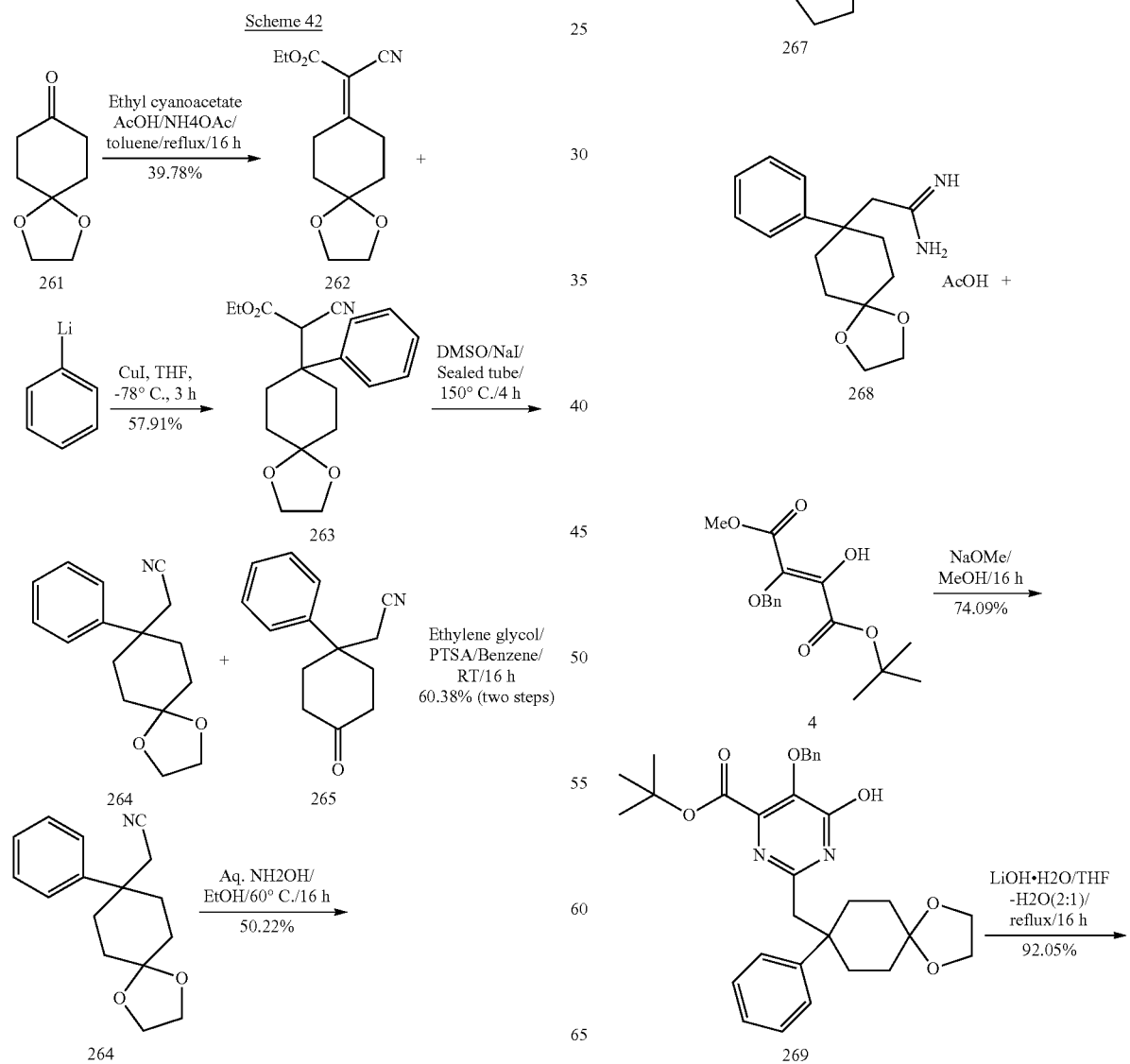

-continued

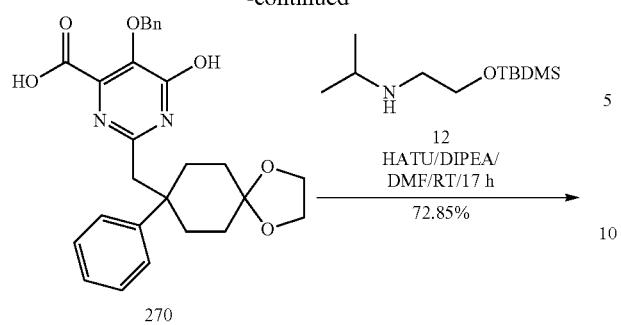

270

HATU/DIPEA/
DMF/RT/17 h
72.85%

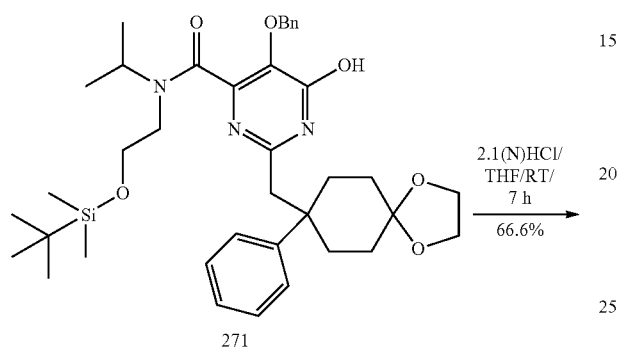

271

2.1(N)HCl/
THF/RT/
7 h
66.6%

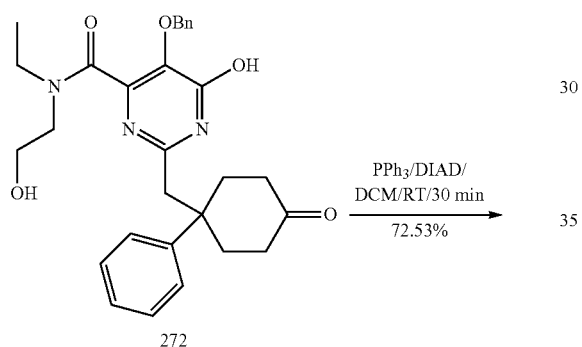

272

PPh₃/DIAD/
DCM/RT/30 min
72.53%

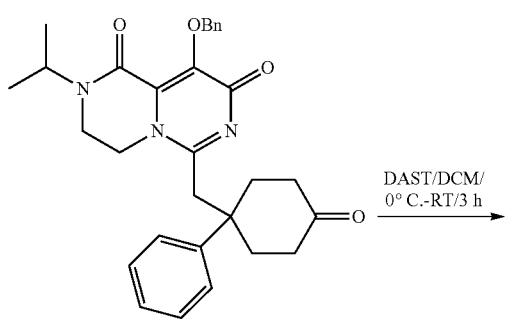

273

DAST/DCM/
0° C.-RT/3 h

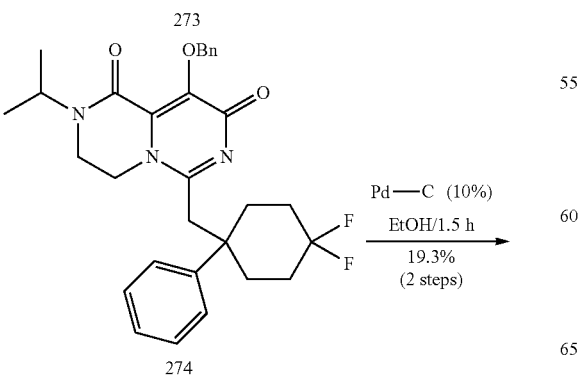

274

Pd—C (10%)
EtOH/1.5 h
19.3%
(2 steps)

-continued

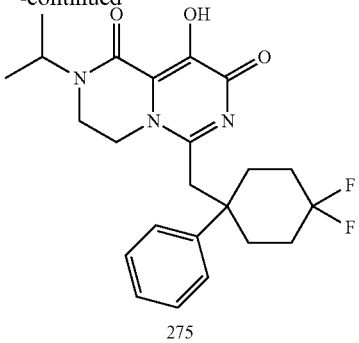

275

Synthesis of (262)

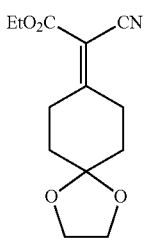 [SMILES: CCOC(=O)C(C#N)=C1CCC2(CC1)OCCO2]

Cyano-(1,4-dioxa-spiro[4.5]dec-8-ylidene)-acetic acid ethyl ester

To a stirred solution of 1,4-dioxa-spiro[4.5]decan-8-one (261) (5.0 g, 32.01 mmol) and cyano-acetic acid ethyl ester (3.99 g, 35.31 mmol) in toluene (50 mL) were added acetic acid (0.3 mL, 5.09 mmol) and ammonium acetate (123 mg, 1.60 mmol). A Dean Stark trap and reflux condenser were attached to the reaction flask and the mixture was heated to reflux and stirred for 16 h. Thereafter, the reaction mixture was cooled to 0° C. and quenched with saturated aqueous NaHCO₃ (100 ml). The aqueous layer was extracted with ethyl acetate (2×200 ml) and the combined organic layer was dried with sodium sulfate, filtered and concentrated under reduced pressure. The crude yellow oil was re-crystallized with 20% ethyl acetate in hexane to afford pure cyano-(1,4-dioxa-spiro[4.5]dec-8-ylidene)-acetic acid ethyl ester (262) (3.2 g, 39.78%) as a light yellow solid.

LC-MS; 330.2 (M+H)

Synthesis of (263)

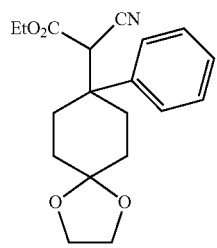 [SMILES: CCOC(=O)C(C#N)C1(c2ccccc2)CCC2(CC1)OCCO2]

Cyano-(8-phenyl-1,4-dioxa-spiro[4.5]dec-8-yl)acetic acid ethyl ester

To a stirred suspension of CuI (5.67 g, 29.88 mmol) in tetrahydrofuran (70 mL) was added phenyl lithium (1.8M dibutyl ether) (33.2 mL, 59.76 mmol) at −78° C. and the resulting mixture was allowed to stir at −30° C. for 2 h. To the resulting reaction mixture at −78° c. was added the pre-cooled solution of cyano-(1,4-dioxa-spiro[4.5]dec-8-ylidene)-acetic acid ethyl ester (262) in tetrahydrofuran (30 mL) and the resulting mixture was allowed to stir at −30° C. for 1 h. The reaction was monitored by silica TLC (P-anisaldehyde active). The reaction mixture was quenched with saturated NH$_4$Cl-solution and the reaction mixture was diluted with ethyl acetate and the organic layer was separated. The organic part was dried over Na$_2$SO$_4$ and concentrated under reduced pressure, The resulting crude product was purified over silica gel (normal, 100-200 mesh) column chromatography using a gradient eluent 2% to 10% ethyl acetate in hexane to get cyano-(8-phenyl-1,4-dioxa-spiro[4.5]dec-8-yl)-acetic acid ethyl ester (263) (3.8 g, 57.91%), as colorless gummy liquid.

LC-MS: 330.2 (M+H).

Synthesis of (264+265)

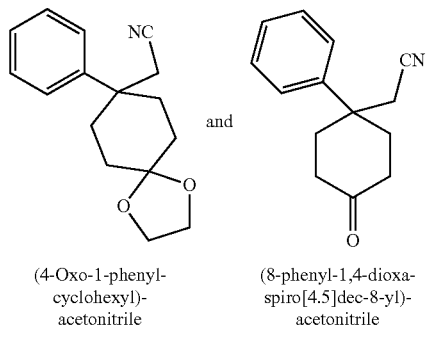 [SMILES: N#CCC1(c2ccccc2)CCC2(CC1)OCCO2 ; N#CCC1(c2ccccc2)CCC(=O)CC1]

(4-Oxo-1-phenyl-cyclohexyl)-acetonitrile (8-phenyl-1,4-dioxa-spiro[4.5]dec-8-yl)-acetonitrile To a solution of cyano-(8-phenyl-1,4-dioxa-spiro[4.5]dec-8-yl)-acetic acid ethyl ester (263) (500 mg, 1.52 mmol) in dimethyl sulfoxide (5 mL) was added NaI (910 mg, 6.07 mmol) and put in a sealed tube. The reaction mixture was then heated at 150° C. for 3 h until TLC [silica TLC; ethyl acetate:hexane=1:4; Rf=0.3 (panisaldehyde active)] indicated that the formation of the desired product along with the ketal de-protected product was completed. To the reaction mixture was added ethyl acetate (50 ml) and the mixture was subsequently washed with brine (3×25 ml). The organic layer was dried and concentrated in vacuo to get a crude mixture which showed the formation of (4-oxo-1-phenyl-cyclohexyl)-acetonitrile (265) and (8-phenyl-1,4-dioxa-spiro[4.5]dec-8-yl)-acetonitrile (264) (400 mg, crude mixture) as a brown sticky liquid which was used directly in the next step without further purification.

Synthesis of (264)

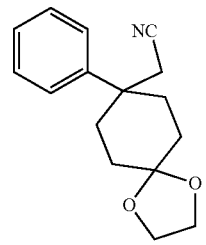 [SMILES: N#CCC1(c2ccccc2)CCC2(CC1)OCCO2]

(8-Phenyl-1,4-dioxa-spiro[4.5]dec-8-yl)-acetonitrile

To a stirred solution of (4-oxo-1-phenyl-cyclohexyl)-acetonitrile (265) and (8-phenyl-1,4-dioxa-spiro[4.5]dec-8-yl)-acetonitrile (264) (350 mg, crude mixture) in benzene (50 mL) were added a catalytic amount of PTSA (31.2 mg, 0.164 mmol) and ethanediol (0.28 mL, 4.92 mmol) and the mixture was stirred at room temperature for 16 h [silica TLC; ethyl acetate-hexane=1:4; Rf=0.4 (panisaldehyde active)]. The reaction was diluted with ethyl acetate (50 mL) and washed with brine (2×50 mL). The organic part was dried and concentrated in vacuo to get a crude mass which was purified by silica gel (normal, 100-200 mesh) column chromatography using an eluent gradient of 5% to 10% ethyl acetate in hexane to obtain pure (8-phenyl-1,4-dioxa-spiro[4.5]dec-8-yl)-acetonitrile (264) (0.25 g, 60.38%, two step yield) as a yellow liquid.

LC-MS; 258.2 (M+H)

Synthesis of (266)

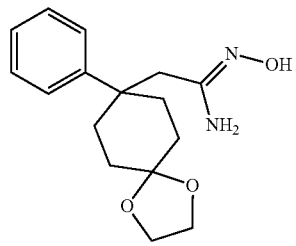 [SMILES: N/C(CC1(c2ccccc2)CCC2(CC1)OCCO2)=N\O]

N-Hydroxy-2-(8-phenyl-1,4-dioxa-spiro[4.5]dec-8-yl)acetamidine

To a stirred solution of 8-phenyl-1,4-dioxa-spiro[4.5]decane-8-carbonitrile (264) (1.5 g, 5.83 mmol) in ethanol (30 mL) was added NH$_2$OH (50% aqueous solution, 1.1 mL, 17.49 mmol) and the reaction mixture was heated at 60° C. for 16 h. Silica thin layer chromatography was performed (ethyl acetate:Hexane=1:1, Rf=0.15). The reaction mixture was concentrated in vacuo to yield a crude mixture which was triturated with diethyl ether to obtain pure N-hydroxy-2-(8-phenyl-1,4-dioxa-spiro[4.5]dec-8-yl)-acetamidine (266)

(850 mg, 50.22%) as an off-white solid which was used in the next step without further purification.

LC-MS: 291.2 (M+H).

Synthesis of (267)

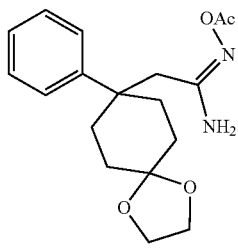 [SMILES: CC(=O)O/N=C(/N)CC1(c2ccccc2)CCC2(CC1)OCCO2]

(Z)-(1-amino-2-{8-phenyl-1,4-dioxaspiro[4.5]decan-8-yl}ethylidene)amino acetate

A mixture of N-hydroxy-2-(8-phenyl-1,4-dioxa-spiro[4.5]dec-8-yl)-acetamidine (266) (600 mg, 2.01 mmol) and acetic anhydride (2 mL) was stirred at room temperature for 16 h (TLC, ethyl acetate:hexane=7:3/UV/SiO$_2$, Rf=0.4). The reaction mixture was diluted with ethyl acetate (50 mL), washed with water (2×25 mL), brine (25 mL), dried and concentrated in vacuo to get crude mass which was purified by CombiFlash using a gradient eluent mixture of ethyl acetate and hexane to get pure (Z)-(1-amino-2-{8-phenyl-1,4-dioxaspiro[4.5]decan-8-yl}ethylidene)amino acetate (267) (585 mg, 85.17%) as a white sticky solid.

LC-MS; 333.3 (M+H)

Synthesis of (268)

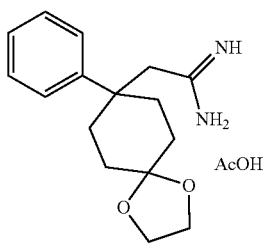 [SMILES: "AcOH" ; N=C(N)CC1(c2ccccc2)CCC2(CC1)OCCO2]

2-(8-Phenyl-1,4-dioxa-spiro[4.5]dec-8-yl)acetamidine, acetic acid salt

To a stirred solution of (Z)-(1-amino-2-{8-phenyl-1,4-dioxaspiro[4.5]decan-8-yl}ethylidene)amino acetate (267) (1.4 g, 4.21 mmol) in methanol was added Pd—C (10%) under nitrogen atmosphere and the mixture was kept under a hydrogen atmosphere of balloon pressure at room temperature for 2 h (reaction was monitored by LC-MS). The reaction mixture was filtered and the filtrate was concentrated in vacuo to get a sticky mass which was triturated with diethyl ether to get pure 2-(8-phenyl-1,4-dioxa-spiro[4.5]dec-8-yl)acetamidine acetic acid salt (268) (1.25 g, 88.79%) as a white solid.

LC-MS: 275.3 (M+H)

Synthesis of (269)

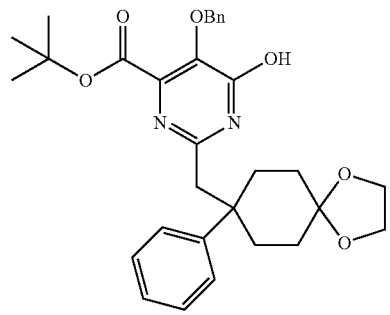 [SMILES: CC(C)(C)OC(=O)c1nc(CC2(c3ccccc3)CCC3(CC2)OCCO3)nc(O)c1OCc1ccccc1]

5-Benzyloxy-6-hydroxy-2-(8-phenyl-1,4-dioxa-spiro[4.5]dec-8-ylmethyl)-pyrimidine-4-carboxylicacid tert-butyl ester A mixture of 2-(8-phenyl-1,4-dioxa-spiro[4.5]dec-8-yl)-acetamidine acetic acid salt (268) (500 mg, 1.5 mmol) and 2-benzyloxy-3-hydroxy-but-2-enedioic acid 4-tert-butyl ester 1-methyl ester (4) (553 mg, 1.8 mmol) in methanol (15 mL) were cooled to 0° C., followed by the addition of NaOMe (25% in methanol) (1 mL, 4.5 mmol) and the reaction mixture was stirred at room temperature for 16 h while silica thin layer chromatography was performed (ethyl acetate:hexane=7:3, Rf=0.6). The reaction mixture was diluted with ethyl acetate (40 ml) and washed with brine (2×20 mL). the reaction mixture was subsequently dried and concentrated in vacuo to get a crude mixture which was purified by normal silica gel (100-200 mesh) column chromatography using an eluent gradient (30-50% ethyl acetate in hexane) to obtain pure 5-benzyloxy-6-hydroxy-2-(8-phenyl-1,4-dioxa-spiro[4.5]dec-8-ylmethyl)-pyrimidine-4-carboxylic acid tert-butyl ester (269) (590 mg, 74.09%) as a brown sticky mass.

LC-MS: 533.4 (M+H)

Synthesis of (270)

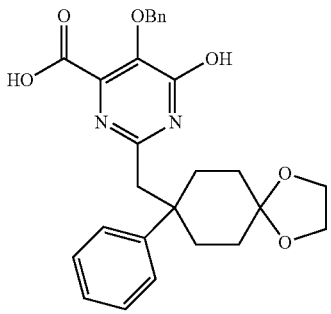 [SMILES: O=C(O)c1nc(CC2(c3ccccc3)CCC3(CC2)OCCO3)nc(O)c1OCc1ccccc1]

5-Benzyloxy-6-hydroxy-2-(8-phenyl-1,4-dioxa-spiro[4.5]dec-8-ylmethyl)-pyrimidine-4-carboxylic acid A mixture of 5-benzyloxy-6-hydroxy-2-(8-phenyl-1,4-dioxa-spiro[4.5]dec-8-ylmethyl)-pyrimidine-4-carboxylic acid tert-butyl ester (269) (850 mg, 1.60 mmol), LiOH.H$_2$O (670 mg, 15.96 mmol) in tetrahydrofuran-water (5:1, 48 mL) was refluxed for 20 h while silica thin layer chromatography was performed (methanol:dichloromethane=1:9, Rf=0.1). Tetrahydrofuran was removed from the reaction mixture in vacuo and the residue was diluted with water (25 mL), cooled in ice water, neutralized to about pH 7 with 1N aqueous HCl and extracted with ethyl acetate (2×50 mL). The combined organic parts were washed with brine (25 mL), dried and concentrated in vacuo to get pure 5-benzyloxy-6-hydroxy-2-(8-phenyl-1,4-dioxa-spiro[4.5]dec-8-ylmethyl)-pyrimidine-4-carboxylic acid (270) (700 mg, 92.05%) as a yellow solid.

LC-MS; 477.4 (M+H)

Synthesis of (271)

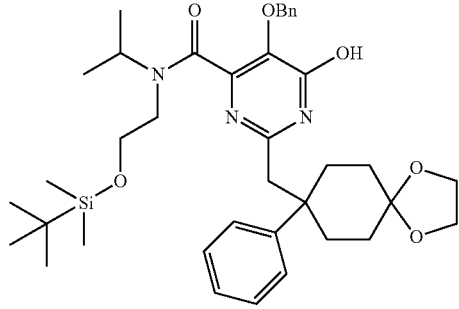 [SMILES: CC(C)N(CCO[Si](C)(C)C(C)(C)C)C(=O)c1nc(CC2(c3ccccc3)CCC3(CC2)OCCO3)nc(O)c1OCc1ccccc1]

5-Benzyloxy-6-hydroxy-2-(8-phenyl-1,4-dioxa-spiro[4.5]dec-8-ylmethyl)-pyrimidine-4-carboxylic acid [2-(tert-butyl-dimethylsilanyloxy)-ethyl]isopropylamide To a stirred solution of 5-benzyloxy-6-hydroxy-2-(8-phenyl-1,4-dioxa-spiro[4.5]dec-8-ylmethyl)-pyrimidine-4-carboxylic acid (270) (600 mg, 1.26 mmol) in dimethylformamide (12 mL) were added [2-(tert-butyl-dimethylsilanyloxy)-ethyl]-isopropyl-amine (8b) (411 mg, 1.89 mmol), N,N-diisopropylethylamine (0.63 mL, 3.78 mmol) and HATU (1-[Bis(dimethylamino)methylene]-1H-1,2,3-triazolo[4,5-b]pyridinium 3-oxide hexafluorophosphate) (574 mg, 1.51 mmol) and stirred at room temperature for 17 h (TLC, ethyl acetate:hexane=1:1/UV/SiO₂, Rf=0.6). The reaction mixture was diluted with ethyl acetate (100 mL), washed with brine (3×50 mL), dried and concentrated in vacuum to get a crude mass which was purified by normal silica gel (100-200 mesh) column chromatography using gradient polarity eluent (1-2% methanol in dichloromethane) to get pure 5-benzyloxy-6-hydroxy-2-(8-phenyl-1,4-dioxa-spiro[4.5]dec-8-ylmethyl)-pyrimidine-4-carboxylic acid [2-(tert-butyl-dimethylsilanyloxy)-ethyl]-isopropylamide (271) (620 mg, 72.85%) as a brown sticky solid.

LC-MS; 676.3 (M+H)

Synthesis of (272)

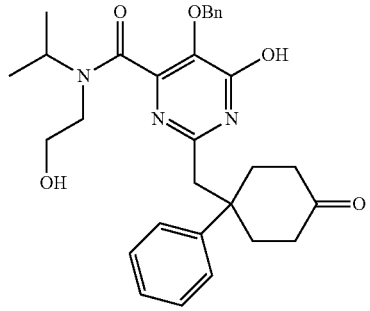 [SMILES: CC(C)N(CCO)C(=O)c1nc(CC2(c3ccccc3)CCC(=O)CC2)nc(O)c1OCc1ccccc1]

5-Benzyloxy-6-hydroxy-2-(4-oxo-1-phenyl-cyclohexylmethyl)-pyrimidine-4-carboxylic acid (2-hydroxyethyl)-isopropylamide To a solution of 5-benzyloxy-6-hydroxy-2-(8-phenyl-1,4-dioxa-spiro[4.5]dec-8-ylmethyl)-pyrimidine-4-carboxylic acid [2-(tert-butyl-dimethylsilanyloxy)-ethyl]-isopropylamide (271) (500 mg, 0.74 mmol) in tetrahydrofuran (30.0 mL) was added 2.1N aqueous HCl (6.0 mL) and stirred at room temperature for 7 h while silica thin layer chromatography was performed (only ethyl acetate; Rf=0.25). The reaction mixture was concentrated in vacuum and diluted with ethyl acetate (50 mL), washed with aqueous NaHCO₃ solution (20 mL) and brine (30 mL) and dried and concentrated in vacuum to get a crude mass which was purified by Combi-Flash using a gradient eluent mixture of methanol and dichloromethane to get pure 5-benzyloxy-6-hydroxy-2-(4-oxo-1-phenyl-cyclohexylmethyl)-pyrimidine-4-carboxylic acid (2-hydroxyethyl)-isopropylamide (272) (255 mg, 66.6%) as a white sticky solid.

LC-MS; 518.3 (M+H)

Synthesis of (273)

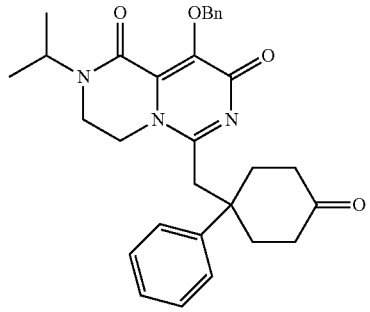 [SMILES: CC(C)N1CCn2c(CC3(c4ccccc4)CCC(=O)CC3)nc(=O)c(OCc3ccccc3)c2C1=O]

9-Benzyloxy-2-isopropyl-6-(4-oxo-1-phenyl-cyclohexylmethyl)-3,4-dihydro-2H-pyrazino[1,2-c]pyrimidine-1,8-dione To a solution of 5-benzyloxy-6-hydroxy-2-(4-oxo-1-phenyl-cyclohexylmethyl)-pyrimidine-4-carboxylic acid (2-hydroxyethyl)-isopropylamide (272) (200 mg, 0.39 mmol) in dichloromethane (25.0 mL) was added triphenyl phosphine (152 mg, 0.58 mmol) and diisopropyl azodicarboxylate (0.12 mL, 0.58 mmol) at room temperature and stirred for 30 min (silica TLC, 5% methanol in ethyl acetate, Rf=0.5). The reaction mixture was concentrated under reduced pressure and purified by normal silica gel (100-200 mesh) column chromatography using gradient polarity mobile phase (50% ethyl acetate in hexane to 5% methanol in dichloromethane) to get pure 9-benzyloxy-2-isopropyl-6-(4-oxo-1-phenyl-cyclohexylmethyl)-3,4-dihydro-2H-pyrazino[1,2-c]pyrimidine-1,8-dione (273) (140 mg, 72.53%) as a white solid.

LC-MS; 500.2 (M+H)

Synthesis of (274)

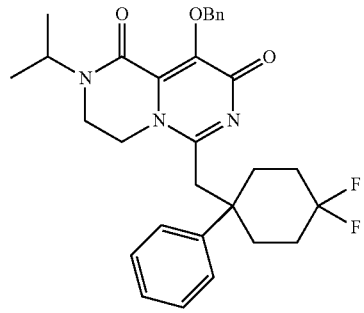 [SMILES: CC(C)N1CCn2c(CC3(c4ccccc4)CCC(F)(F)CC3)nc(=O)c(OCc3ccccc3)c2C1=O]

Synthesis of (275)

9-Benzyloxy-6-(4,4-difluoro-1-phenyl-cyclohexylmethyl)-2-isopropyl-3,4-dihydro-2H-pyrazino[1,2-c]pyrimidine-1,8-dione A solution of 9-benzyloxy-2-isopropyl-6-(4-oxo-1-phenyl-cyclohexylmethyl)-3,4-dihydro-2H-pyrazino[1,2-c]pyrimidine-1,8-dione (273) (120 mg, 0.24 mmol) in dichloromethane (8 mL) was added to a solution of dimethylaminosulfur trifluoride (0.18 mL, 1.80 mmol) in dichloromethane (12 mL) at 0° C. and stirred for 3 h at room temperature wile silica thin layer chromatography was performed (5% methanol in ethyl acetate, Rf=0.2). The reaction mixture was cooled to 0° C. and quenched with saturated aqueous NaHCO₃ solution (1 mL) and water (30 mL). The mixture was extracted with dichloromethane (40 mL×2), dried and concentrated in vacuum to get a crude mass which was purified by preparative TLC (silica) using as a solvent 3% methanol in dichloromethane to get 9-benzyloxy-6-(4,4-difluoro-1-phenyl-cyclohexylmethyl)-2-isopropyl-3,4-dihydro-2H-pyrazino[1,2-c]pyrimidine-1,8-dione (274) (80 mg, mixture) as a brown sticky solid.

LC-MS-analysis indicated the presence of a mixture. The next step was performed with this mixture.

LC-MS; 522.0 (M+H)

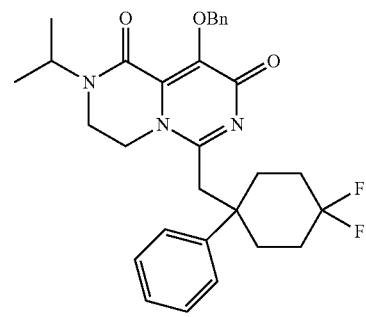 [SMILES: CC(C)N1CCn2c(CC3(c4ccccc4)CCC(F)(F)CC3)nc(=O)c(OCc3ccccc3)c2C1=O]

6-(4,4-Difluoro-1-phenyl-cyclohexylmethyl)-9-hydroxy-2-isopropyl-3,4-dihydro-2H-pyrazino[1,2-c]pyrimidine-1,8-dione A solution of 9-benzyloxy-6-(4,4-difluoro-1-phenyl-cyclohexylmethyl)-2-isopropyl-3,4-dihydro-2H-pyrazino[1,2-c]pyrimidine-1,8-dione (274) in ethanol was degassed with argon followed by the addition of Pd—C (10%) under an argon atmosphere and the reaction was stirred at room temperature under a hydrogen atmosphere for 1.5 h. The reaction mass was filtered through a celite bed and the filtrate was concentrated under reduced pressure to get a crude mixture which was purified by preparative HPLC to get pure 6-(4,4-difluoro-1-phenyl-cyclohexylmethyl)-9-hydroxy-2-isopropyl-3,4-dihydro-2H-pyrazino[1,2-c]pyrimidine-1,8-dione (275) [20 mg, 19.3% (2 steps)] as a brown sticky solid.

LC-MS; 330.2 (M+H)

General Procedure for Examples 287 to 315

The synthetic procedures are outlined in Scheme 43.

General Synthetic Route for 287, 291, 295, 299, 303, 307, 311 and 315

Scheme 43

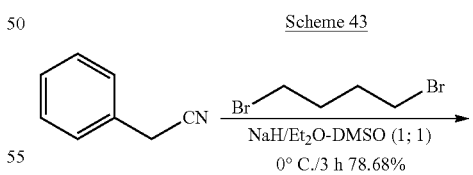

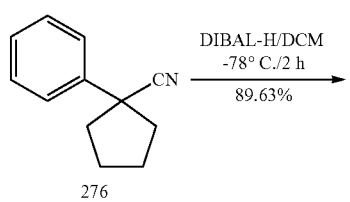

276

-continued
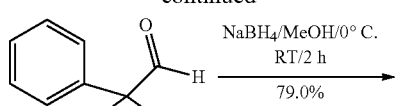
277
278
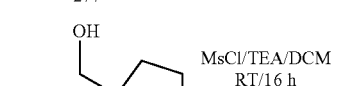
279
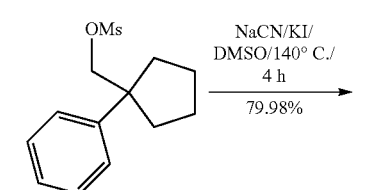
280
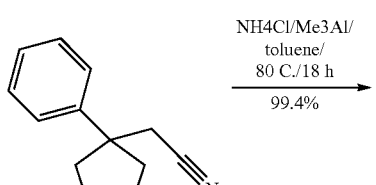
281
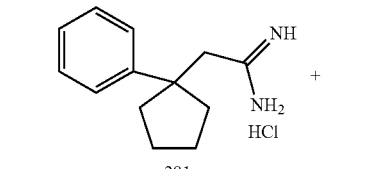
4
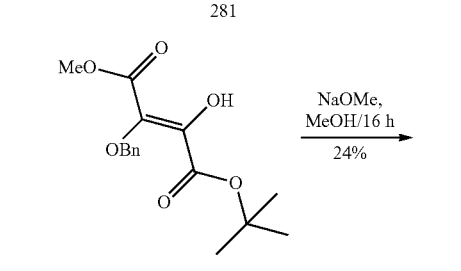
282
-continued
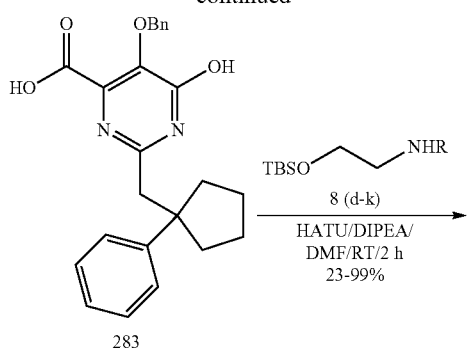
283
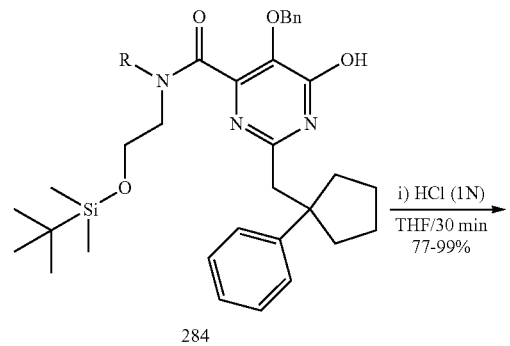
284
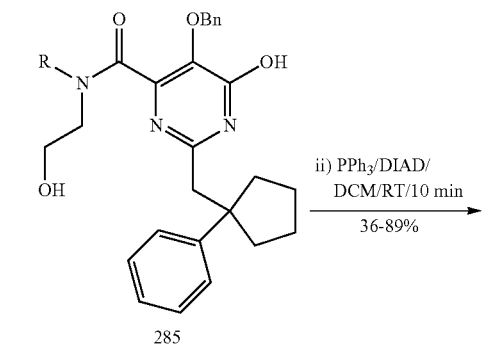
285
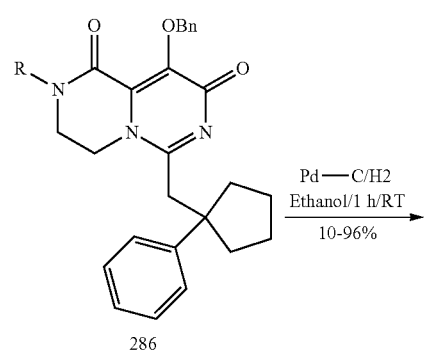
286

-continued

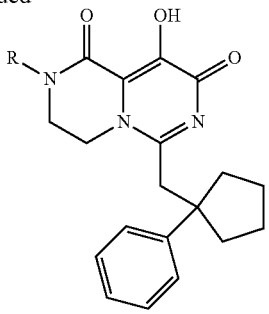

287 R = cyclopropyl
291 = cyclopentyl
295 = cyclobutyl
299 = oxetan-3-yl
303 = 2,2-dimethylpropyl
307 = cyclopropylmethyl
311 = 2H-pyran-4-yl
315 = 4-fluorobenzyl Synthesis of (276)

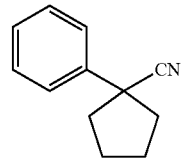 [SMILES: N#CC1(c2ccccc2)CCCC1]

1-Phenyl-cyclopentanecarbonitrile

To a suspension of sodium hydride (60%) (7.5 g, 187.79 mmol) in dimethyl sulfoxide (100 mL) was added dropwise a mixture of phenyl acetonitrile (10 g, 85.36 mmol) and 1,4-dibromobutane (18.43 g, 187.79 mmol) dissolved in dimethyl sulfoxide: ether (120 mL, 1:1) at 0° C. Stirring was continued for 30 min at same temperature and at room temperature for 3 h. After completion of the reaction, the reaction mixture was quenched with 1N HCl (10 mL) and water (100 mL) was added. This mixture was extracted with ethyl acetate (3×100 mL), and the organic part separated and washed with water (3×100 mL) and brine (100 mL). The organic part was dried over sodium sulfate and concentrated to get a crude product which was purified on a CombiFlash column (eluted at 3% ethyl acetate in hexane) to afford 1-phenyl-cyclopentanecarbonitrile (276) (11.5 g, 78.68%) as a colorless liquid.

Synthesis of (277)

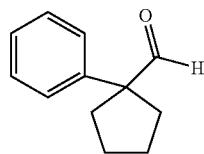 [SMILES: O=CC1(c2ccccc2)CCCC1]

1-Phenyl-cyclopentanecarbaldehyde

To a stirred solution of 1-phenyl-cyclopentanecarbonitrile (276) (12.5 g, 73.00 mmol) in dichloromethane (125 mL), was added diisobutylaluminiumhydrid (25% in toluene) (104 mL, 182.50 mmol) at −78° C. and stirring was continued for 2 h at the same temperature. After completion of the reaction, the reaction mixture was quenched with a saturated solution of potassium sodium tartrate (75 mL) and stirring was continued for 16 h at room temperature. The dichloromethane layer was separated and the aqueous layer was re-extracted with dichloromethane (1×100 mL). The combined solvents were dried and concentrated and the crude product was purified by Combi-Flash column (eluted at 5% ethyl acetate in hexane) to get 1-phenyl-cyclopentanecarbaldehyde (277) (11.4 g, 89.63%) as a colorless liquid.
GC-MS: 174 (m/z).

Synthesis of (278)

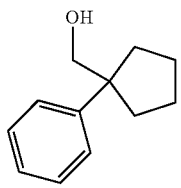 [SMILES: OCC1(c2ccccc2)CCCC1]

(1-Phenyl-cyclopentyl)-methanol]

To a stirred solution of 1-phenyl-cyclopentanecarbaldehyde (277) (11.5 g, 71.82 mmol) in methanol (150 mL) was added NaBH$_4$ at 0° C. portion-wise and the reaction was stirred at room temperature for 2 h. After completion of the reaction, the reaction mixture was quenched with a saturated aqueous solution of ammonium chloride (20 mL). Subsequently, the methanol was removed, the residue diluted with water (100 mL) and extracted with ethyl acetate (3×100 mL) and the separated organic part was dried and concentrated. The crude product was purified by Combi-Flash column (eluted at 5-10% ethyl acetate in hexane) to get (1-phenyl-cyclopentyl)-methanol] (278) (10 g, 79.0%) as a white solid.
GC-MS: 176 (m/z).

Synthesis of (279)

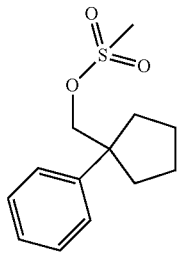 [SMILES: CS(=O)(=O)OCC1(c2ccccc2)CCCC1]

Methanesulfonic acid 1-phenyl-cyclopentylmethyl ester

To a stirred solution of (1-phenyl-cyclopentyl)-methanol] (278) (10 g, 56.73 mmol) in dichloromethane (110 mL) was added triethyl amine (16 mL, 113.47 mmol) followed by mesyl chloride (5.3 mL, 68.08 mmol) at 0° C. Stirring was continued at room temperature for 16 h. After completion of the reaction, the reaction mixture was diluted with dichloromethane (50 mL) and washed with water (100 mL) and saturated aqueous sodium bicarbonate solution (50 mL) and brine (50 mL). The separated organic fraction was dried and concentrated. The crude product was purified by Combi-Flash column (eluted at 10-20% ethyl acetate in hexane) to get methanesulfonic acid 1-phenyl-cyclopentylmethyl ester (279) (12 g, 83.16%) as a yellow semi-solid.

Synthesis of (280)

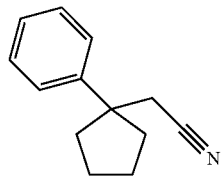 [SMILES: N#CCC1(c2ccccc2)CCCC1]

(1-Phenyl-cyclopentyl)-acetonitrile

To a stirred solution of methanesulfonic acid 1-phenyl-cyclopentylmethyl ester (279) (12 g, 47.24 mmol) in dimethyl sulfoxide (36 mL) were added KI (784 mg, 4.72 mmol) and NaCN (3.5 g, 70.87 mmol) and stirring was continued at 140° C. for 4 h and at room temperature for 16 h. After completion of the reaction, water (100 mL) was added. The mixture was extracted with ethyl acetate (3×100 mL) and the combined organic parts were washed with saturated ferrous sulfate solution (100 mL), water (3×10 0 mL) and brine (100 mL). After drying and concentrating the mixture, a crude product was obtained and purified by Combi-Flash column (eluted at 10-20% ethyl acetate in hexane) to get (1-phenyl-cyclopentyl)-acetonitrile (280) (7 g, 79.98%) as a light yellow liquid.
GC-MS: 185 (m/z).

Synthesis of (281)

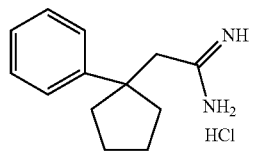 [SMILES: N=C(N)CC1(c2ccccc2)CCCC1 ; Cl]

2-(1-Phenyl-cyclopentyl)-acetamidine hydrochloride

To a stirred suspension of NH₄Cl (2 g, 37.29 mmol) in dry toluene (50 mL) was added tri-methyl aluminium (2M in toluene) (18.6 mL, 37.29 mmol) at 5° C. The reaction mixture was then warmed to room temperature and stirred for 2 h. A solution of (1-phenyl-cyclopentyl)-acetonitrile (280) (2.3 g, 12.4 mmol) in toluene (10 mL) was added to the reaction mixture and stirring continued at 80° C. for 14 h. After completion of the reaction, the reaction mixture was quenched with a suspension of silica gel (8 g) in chloroform (8 mL) at 0° C. The reaction mixture was further stirred for 30 min at room temperature and filtered through a short bed of celite, washed with methanol and the combined filtrates were concentrated. The residue was stirred with 10% methanol in dichloromethane (200 mL). The white solid was discarded by filtration and filtrate was concentrated to get 2-(1-phenyl-cyclopentyl)-acetamidine hydrochloride salt (281) 2.5 g, 99.4% (crude yield) as a yellow gummy oil.
LC-MS: 203.2 (M+H)

Synthesis of (282)

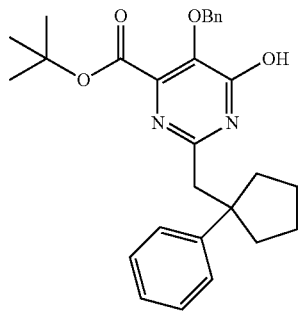 [SMILES: CC(C)(C)OC(=O)c1nc(CC2(c3ccccc3)CCCC2)nc(O)c1OCc1ccccc1]

5-Benzyloxy-6-hydroxy-2-(1-phenyl-cyclopentylmethyl)-pyrimidine-4-carboxylic acid tert-butyl ester To a stirred solution of 2-(1-phenyl-cyclopentyl)-acetamidine hydrochloride salt (281) (500 mg, 2.09 mmol) and (E)-3-benzyloxy-2-hydroxy-4-oxo-pent-2-enoic acid tert-butyl ester (4) (970 mg, 3.15 mmol) in methanol (10 mL) was added a sodium methoxide solution (25% in methanol) (1.4 mL, 6.29 mmol) at 0° C. and then the reaction mixture was allowed to warm slowly up to room temperature while stirring was continued for 16 h. After completion of the reaction, the reaction mixture was quenched with 1N HCl (5 mL) and the methanol was evaporated and water (20 mL) was added. The mixture was extracted with ethyl acetate (3×20 mL) and the phases separated. The organic part was dried and concentrated to get a crude product, which was purified by Combi-Flash column (eluted at 10-20% ethyl acetate in hexane) to obtain 5-benzyloxy-6-hydroxy-2-(1-phenyl-cyclopentylmethyl)-pyrimidine-4-carboxylic acid tert-butyl ester (282) (230 mg, 23.82%) as a white solid.
LC-MS: 461.1 (M+H).

Synthesis of (283)

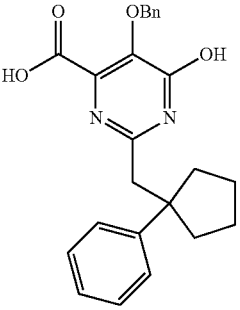 [SMILES: O=C(O)c1nc(CC2(c3ccccc3)CCCC2)nc(O)c1OCc1ccccc1]

5-Benzyloxy-6-hydroxy-2-(1-phenyl-cyclopentylmethyl)-pyrimidine-4-carboxylic acid To a stirred solution of 5-benzyloxy-6-hydroxy-2-(1-phenyl-cyclopentylmethyl)-pyrimidine-4-carboxylic acid tert-butyl ester (282) (1.6 g. 3.48 mmol) in a mixture of tetrahydrofuran:water (2:1) (90 mL), was added lithium-hydroxide monohydrate (2.9 g, 69.57 mmol) and the reaction mixture was refluxed for 18 h. After completion of the reaction, all volatiles were evaporated, added water (30 mL) and washed with ethyl acetate (2×20 mL) to remove non acidic impurities. The separated aqueous part was acidified with 1N HCl to reach a pH of about 5 to 6. The acidified aqueous part was extracted with ethyl acetate (4×50 mL), dried and concentrated to get 5-benzyloxy-6-hydroxy-2-(1-phenyl-cyclopentylmethyl)-pyrimidine-4-carboxylic acid (283) (780 mg, 55.44%) as a white solid.

LC-MS: 405.2 (M+H).

Synthesis of 8 (c-k)

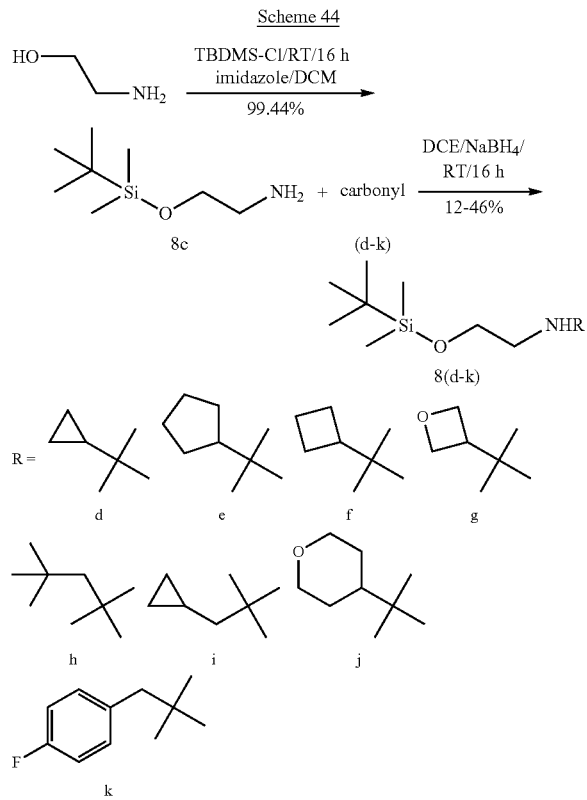

Synthesis of (8c)

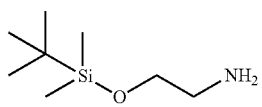

2-(tert-Butyl-dimethylsilanyloxy)-ethylamine

To a stirred solution of 2-amino-ethanol (55 g, 900.46 mmol) in dichloromethane (1000 mL) were added N,N-diisopropylethylamine (220 mL, 1260.64 mmol) and tert-butyl-chloro-dimethyl-silane (135.7 g, 900.46 mmol) at 0° C. followed by stirring for 16 h at room temperature. After completion of the reaction, water (500 mL) was added and the resulting mixture extracted with dichloromethane. The separated organic part was washed with water (2×100 mL) and brine (100 mL) and dried and concentrated to get 2-(tert-butyl-dimethylsilanyloxy)-ethylamine (8c) (157 g, 99.44%) as a light yellow oil.

Example 287

2-Cyclopropyl-9-hydroxy-6-(1-phenyl-cyclopentylmethyl)-3,4-dihydro-2H-pyrazino[1,2-c]pyrimidine-1,8-dione The synthetic procedure used in this preparation is outlined in Schemes 43 and 45.

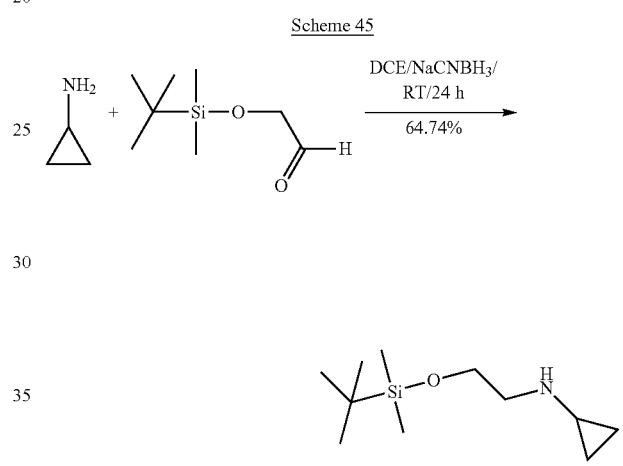

Synthesis of (8d)

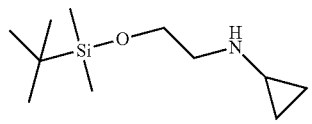

[2-(tert-Butyl-dimethylsilanyloxy)-ethyl]-cyclopropyl-amine

To a stirred solution of cyclopropylamine (500 mg, 8.76 mmol) in dichloroethane (10 mL) were added tert-butyl-dimethylsilanyloxy)-acetaldehyde (553 mg, 3.16 mmol) and acetic acid (0.02 mL, 0.29 mmol) at 0° C. After stirring for 30 min at the same temperature, NaCNBH$_3$ (360 mg, 5.74 mmol) was added portion-wise at 0° C. and stirring was continued for 24 h at room temperature. The reaction mixture was quenched with water, extracted with dichloromethane (3×30 mL) and the organic part was concentrated, dried and the crude product obtained thereby was purified by Combi-Flash column (eluted at 10-20% ethyl acetate in hexane) to get [2-(tertbutyl-dimethylsilanyloxy)-ethyl]-cyclopropyl-amine (8d) (400 mg, 21.2%) as a light yellow liquid.

Synthesis of (284)

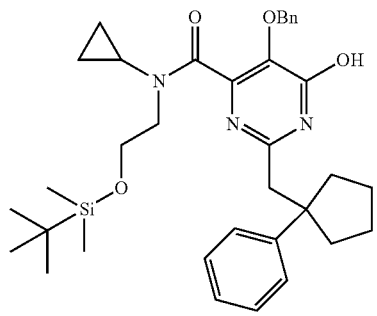 [SMILES: CC(C)(C)[Si](C)(C)OCCN(C(=O)c1nc(CC2(c3ccccc3)CCCC2)nc(O)c1OCc1ccccc1)C1CC1]

5-Benzyloxy-6-hydroxy-2-(1-phenyl-cyclopentylmethyl)-pyrimidine-4-carboxylic acid [2-(tert-butyl-dimethylsilanyloxy)-ethyl]-cyclopropyl-amide To a stirred solution mixture of 5-benzyloxy-6-hydroxy-2-(1-phenyl-cyclopentylmethyl)-pyrimidine-4-carboxylic acid (283) (300 mg, 0.74 mmol) and [2-(tert-butyl-dimethylsilanyloxy)-ethyl]-cyclopropyl-amine (8d) (329 mg, 1.48 mmol) in dimethylformamide (5 mL) were added N,N-diisopropylethylamine (0.4 mL, 2.22 mmol) and HATU (423 mg, 1.11 mmol). After stirring at room temperature for 1 h, water (50 mL) was added and the mixture was extracted with ethyl acetate (3×20 mL). The combined organic part was washed with water (3×50 mL) and brine (2×30 mL) and dried and concentrated. The crude product was purified by Combi-Flash column (eluted at 20-30% ethyl acetate in hexane) to get 5-benzyloxy-6-hydroxy-2-(1-phenyl-cyclopentylmethyl)-pyrimidine-4-carboxylic acid [2-(tert-butyl-dimethylsilanyloxy)-ethyl]-cyclopropyl-amide (284) (430 mg, 96.32%) as a yellow solid.

LC-MS: 602.2 (M+H).

Synthesis of (285)

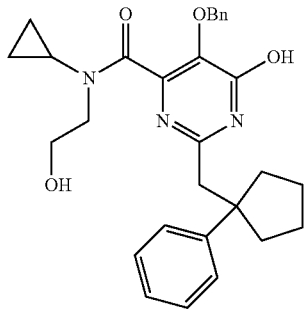

5-Benzyloxy-6-hydroxy-2-(1-phenyl-cyclopentylmethyl)-pyrimidine-4-carboxylic acid cyclopropyl-(2-hydroxyethyl)-amide To a stirred solution of 5-benzyloxy-6-hydroxy-2-(1-phenyl-cyclopentylmethyl)-pyrimidine-4-carboxylic acid [2-(tert-butyl-dimethylsilanyloxy)-ethyl]-cyclopropyl-amide (284) (430 mg, 0.69 mmol) in tetrahydrofuran (20 mL) was added 1N HCl (3.5 mL. 3.48 mmol) at room temperature and the reaction mixture was stirred for 30 min. After completion of the reaction, solid NaHCO$_3$ was added, basified up to pH 8. Water (10 mL) was added and the mixture was extracted with ethyl acetate (3×30 mL). The organic part was dried and concentrated to get 5-benzyloxy-6-hydroxy-2-(1-phenyl-cyclopentylmethyl)-pyrimidine-4-carboxylic acid cyclopropyl-(2-hydroxyethyl)-amide (285) (300 mg, 88.4%) as a light yellow sticky mass.

LC-MS: 488.0 (M+H).

Synthesis of (286)

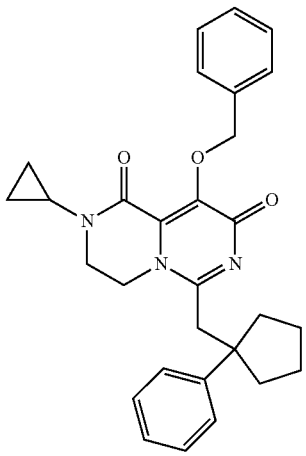 [SMILES: O=C1c2c(OCc3ccccc3)c(=O)nc(CC3(c4ccccc4)CCCC3)n2CCN1C1CC1]

9-Benzyloxy-2-cyclopropyl-6-(1-phenyl-cyclopentylmethyl)-3,4-dihydro-2H-pyrazino[1,2-c]pyrimidine-1,8-dione To a stirred solution of 5-benzyloxy-6-hydroxy-2-(1-phenyl-cyclopentylmethyl)-pyrimidine-4-carboxylic acid cyclopropyl-(2-hydroxyethyl)-amide (285) (300 mg, 0.62 mmol) in dichloromethane (30 mL) were added triphenyl phosphine (242 mg, 0.92 mmol) and diisopropyl azodicarboxylate (0.2 mL, 1.23 mmol) at room temperature. Stirring was continued for 10 min at room temperature. The reaction mixture was concentrated under reduced pressure to get a crude product, which was purified by Combi-Flash column (triphenyl phosphine oxide was eluted in ethyl acetate and the product was eluted at 2% methanol in dichloromethane). It was again purified by preparative TLC plate to remove traces of triphenyl phosphine oxide (mobile phase: ethyl acetate) and 9-benzyloxy-2-cyclopropyl-6-(1-phenyl-cyclopentylmethyl)-3,4-dihydro-2H-pyrazino[1,2-c]pyrimidine-1,8-dione (286) (180 mg, 62.3%) was obtained as a white sticky solid.

LC-MS: 470.0 (M+H).

Synthesis of (287)

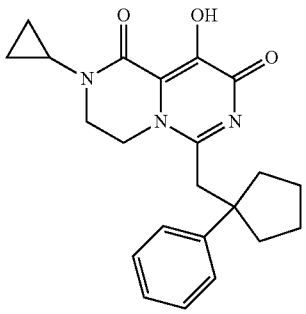 [SMILES: O=C1c2c(O)c(=O)nc(CC3(c4ccccc4)CCCC3)n2CCN1C1CC1]

2-Cyclopropyl-9-hydroxy-6-(1-phenyl-cyclopentyl-methyl)-3,4-dihydro-2H-pyrazino[1,2-c]pyrimidine-1,8-dione A solution of 9-benzyloxy-2-cyclopropyl-6-(1-phenyl-cyclopentylmethyl)-3,4-dihydro-2H-pyrazino[1,2-c]pyrimidine-1,8-dione (286) (180 mg, 0.38 mmol) in ethanol (20 mL) was degassed, Pd—C (10%) (15 mg) added and hydrogenated for 1 h. The catalyst was filtered off, washed with ethanol (3×20 mL) and dichloromethane (2×15 mL). The combined solvent was concentrated and the solid was washed with n-pentane to get pure 2-cyclopropyl-9-hydroxy-6-(1-phenyl-cyclopentylmethyl)-3,4-dihydro-2H-pyrazino[1,2-c]pyrimidine-1,8-dione (287) (140 mg, 96.25%) as a white solid.

LC-MS: 380.0 (M+H).

Example 291

2-Cyclopentyl-9-hydroxy-6-(1-phenyl-cyclopentyl-methyl)-3,4-dihydro-2H-pyrazino[1,2-c]pyrimidine-1,8-dione The synthetic procedure used in this preparation is outlined in Schemes 43.

Synthesis of (8e)

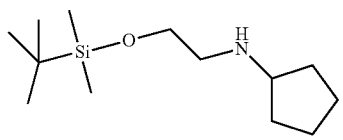 [SMILES: CC(C)(C)[Si](C)(C)OCCNC1CCCC1]

[2-(tert-Butyl-dimethylsilanyloxy)-ethyl]-cyclopentyl-amine

To a stirred solution of cyclopropylamine (1 g, 13.15 mmol) in dichlorethane (20 mL) were added 2-(tert-butyl-dimethylsilanyloxy)acetaldehyde (2.3 mg, 2.30 mmol) and acetic acid (0.08 mL, 0.29 mmol) at 0° C. Stirring was continued for 24 h at room temperature and NaBH₄ (995 mg, 26.29 mmol) was added portion-wise at 0° C. The reaction mixture was further stirred for 2 h at room temperature, quenched with water and extracted with dichloromethane (3×30 mL). The organic part was dried and concentrated to yield a crude product which was purified by Combi-Flash column (eluted at 10-20% ethyl acetate in hexane) to get [2-(tert-butyl-dimethylsilanyloxy)-ethyl]-cyclopentylamine (8e) (1.2 g, 37.48%) as a yellow oil.

Synthesis of (288)

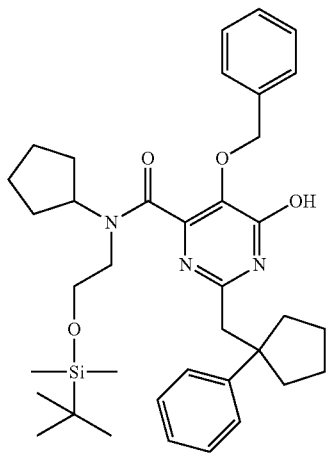 [SMILES: CC(C)(C)[Si](C)(C)OCCN(C(=O)c1nc(CC2(c3ccccc3)CCCC2)nc(O)c1OCc1ccccc1)C1CCCC1]

5-Benzyloxy-6-hydroxy-2-(1-phenyl-cyclopentylmethyl)-pyrimidine-4-carboxylic acid [2-(tert-butyl-dimethylsilanyloxy)-ethyl]-cyclopentyl-amide To a stirred solution mixture of 5-benzyloxy-6-hydroxy-2-(1-phenyl-cyclopentylmethyl)-pyrimidine-4-carboxylic acid (283) (100 mg, 0.25 mmol) and [2-(tert-butyl-dimethylsilanyloxy)-ethyl]-cyclopentyl-amine (8e) (72 mg, 0.29 mmol) in dimethylformamide (2.5 mL) were added N,N-diisopropylethylamine (0.1 mL, 0.74 mmol) and HATU (141 mg, 0.37 mmol). Stirring was continued at room temperature for 20 h, whereafter water (25 mL) was added and the mixture extracted with ethyl acetate (3×20 mL). The combined organic part was washed with water (3×50 mL) and brine (2×30 mL) and dried and concentrated. The crude product was purified by Combi-Flash column (eluted at 20-30% ethyl acetate in hexane) to get 5-benzyloxy-6-hydroxy-2-(1-phenyl-cyclopentylmethyl)-pyrimidine-4-carboxylic acid [2-(tert-butyl-dimethylsilanyloxy)-ethyl]-cyclopentyl-amide (288) (97 mg, 62.28%) as a light yellow sticky solid.

LC-MS: 630.4 (M+H).

Synthesis of (289)

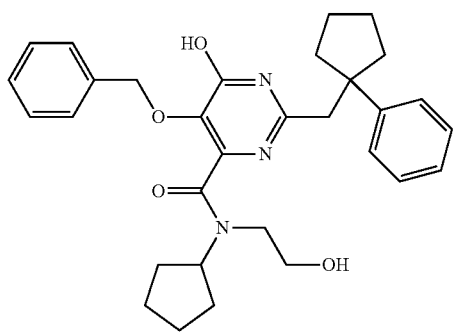 [SMILES: O=C(c1nc(CC2(c3ccccc3)CCCC2)nc(O)c1OCc1ccccc1)N(CCO)C1CCCC1]

5-Benzyloxy-6-hydroxy-2-(1-phenyl-cyclopentylmethyl)-pyrimidine-4-carboxylic acid cyclopentyl-(2-hydroxyethyl)-amide This compound was prepared following the same method as described for 5-benzyloxy-6-hydroxy-2-(1-phenyl-cyclopentylmethyl)-pyrimidine-4-carboxylic acid cyclopropyl-(2-hydroxyethyl)-amide (285) from 5-benzyloxy-6-hydroxy-2-(1-phenyl-cyclopentylmethyl)-pyrimidine-4-carboxylic acid [2-(tert-butyl-dimethylsilanyloxy)-ethyl]-cyclopentyl-amide (288) (250 mg, 0.39 mmol). The product was obtained as an off-white sticky solid (180 mg, 87.83%).

LC-MS: 516.4 (M+H).

Synthesis of (290)

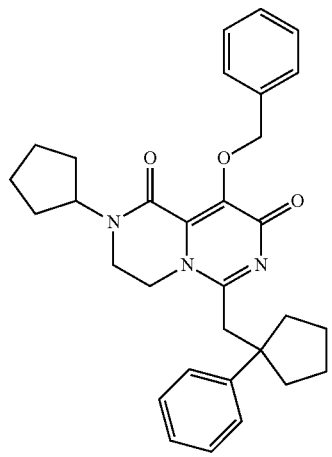 [SMILES: O=C1c2c(OCc3ccccc3)c(=O)nc(CC3(c4ccccc4)CCCC3)n2CCN1C1CCCC1]

9-Benzyloxy-2-cyclopentyl-6-(1-phenyl-cyclopentylmethyl)-3,4-dihydro-2H-pyrazino[1,2-c]pyrimidine-1,8-dione This compound was prepared following the same method as described for 9-benzyloxy-2-cyclopropyl-6-(1-phenyl-cyclopentylmethyl)-3,4-dihydro-2H-pyrazino[1,2-c]pyrimidine-1,8-dione (286) from 5-benzyloxy-6-hydroxy-2-(1-phenyl-cyclopentylmethyl)-pyrimidine-4-carboxylic acid cyclopentyl-(2-hydroxyethyl)-amide (289) (175 mg, 0.34 mmol). The product was obtained as an off-white sticky solid (80 mg, 47.31%).

LC-MS: 498.4 (M+H).

Synthesis of (291)

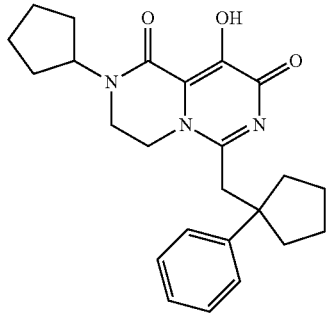 [SMILES: O=C1c2c(O)c(=O)nc(CC3(c4ccccc4)CCCC3)n2CCN1C1CCCC1]

2-Cyclopentyl-9-hydroxy-6-(1-phenyl-cyclopentylmethyl)-3,4-dihydro-2H-pyrazino[1,2-c]pyrimidine-1,8-dione This compound was prepared following the same method as described for 2-cyclopropyl-9-hydroxy-6-(1-phenyl-cyclopentylmethyl)-3,4-dihydro-2H-pyrazino[1,2-c]pyrimidine-1,8-dione (287) from 9-benzyloxy-2-cyclopentyl-6-(1-phenyl-cyclopentylmethyl)-3,4-dihydro-2H-pyrazino[1,2-c]pyrimidine-1,8-dione (290) (80 mg, 0.16 mmol). The product was obtained as a white solid (16 mg, 24.42%).

LC-MS: 408.2 (M+H).

Example 295

2-Cyclobutyl-9-hydroxy-6-(1-phenyl-cyclopentylmethyl)-3,4-dihydro-2H-pyrazino[1,2-c]pyrimidine-1,8-dione The synthetic procedure used in this preparation is outlined in Schemes 43.

Synthesis of (8f)

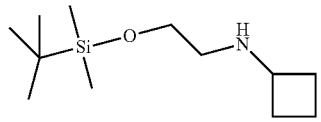

[2-(tert-Butyl-dimethylsilanyloxy)-ethyl]-cyclobutylamine

This compound was prepared following the same method as described for [2-(tert-butyl-dimethylsilanyloxy)-ethyl]-cyclopentyl-amine (8e) from cyclobutylamine (1 g, 14.27 mmol) and 2-(tert-butyl-dimethylsilanyloxy)acetaldehyd (2.6 mg, 14.26 mmol). The product was obtained as a yellow gummy mass (400 mg, 12.22%).

Synthesis of (292)

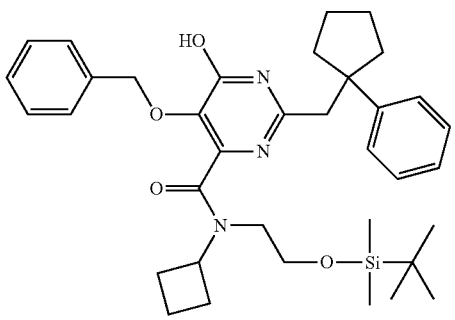 [SMILES: CC(C)(C)[Si](C)(C)OCCN(C(=O)c1nc(CC2(c3ccccc3)CCCC2)nc(O)c1OCc1ccccc1)C1CCC1]

5-Benzyloxy-6-hydroxy-2-(1-phenyl-cyclopentylmethyl)-pyrimidine-4-carboxylic acid [2-(tert-butyl-dimethylsilanyloxy)-ethyl]-cyclobutyl-amide To a stirred solution mixture of 5-benzyloxy-6-hydroxy-2-(1-phenyl-cyclopentylmethyl)-pyrimidine-4-carboxylic acid (283) (300 mg, 0.74 mmol) and [2-(tert-butyl-dimethylsilanyloxy)-ethyl]-cyclobutyl-amine (8e) (204 mg, 0.89 mmol) in dimethylformamide (5 mL) were added N,N-diisopropylethylamine (0.4 mL, 2.22 mmol) and HATU (423 mg, 1.11 mmol). After stirring at room temperature for 1 h, water (50 mL) was added and the mixture was extracted with ethyl acetate (3×20 mL). The combined organic part was washed with water (3×50 mL) and brine (2×30 mL) and dried and concentrated. The crude product was purified by Combi-Flash column (eluted at 20-30% ethyl acetate in hexane) to get 5-benzyloxy-6-hydroxy-2-(1-phenyl-cyclopentylmethyl)-pyrimidine-4-carboxylic acid [2-(tert-butyl-dimethylsilanyloxy)-ethyl]-cyclobutyl-amide (292) (420 mg, 91.94%) as a yellow sticky solid.

LC-MS: 616.4 (M+H).

Synthesis of (293)

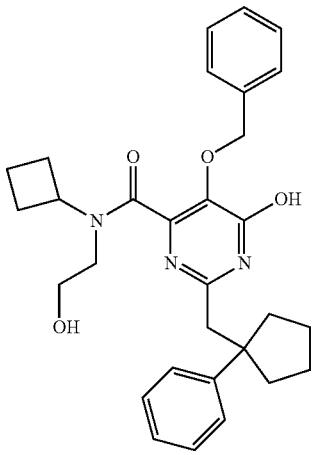 [SMILES: O=C(c1nc(CC2(c3ccccc3)CCCC2)nc(O)c1OCc1ccccc1)N(CCO)C1CCC1]

5-Benzyloxy-6-hydroxy-2-(1-phenyl-cyclopentylmethyl)-pyrimidine-4-carboxylic acid cyclobutyl-(2-hydroxyethyl)-amide This compound was prepared following the same method as described for 5-Benzyloxy-6-hydroxy-2-(1-phenyl-cyclopentylmethyl)-pyrimidine-4-carboxylic acid cyclopropyl-(2-hydroxyethyl)-amide (285) from 5-Benzyloxy-6-hydroxy-2-(1-phenyl-cyclopentylmethyl)-pyrimidine-4-carboxylic acid cyclobutyl-(2-hydroxyethyl)-amide (292) (420 mg, 0.68 mmol). The product was obtained as a white sticky solid (340 mg, 99.39%).

LC-MS: 502.2 (M+H).

Synthesis of (294)

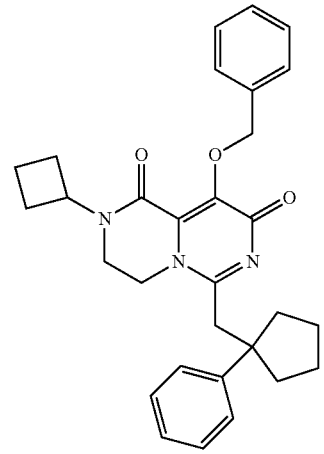 [SMILES: O=C1c2c(OCc3ccccc3)c(=O)nc(CC3(c4ccccc4)CCCC3)n2CCN1C1CCC1]

9-Benzyloxy-2-cyclobutyl-6-(1-phenyl-cyclopentylmethyl)-3,4-dihydro-2H-pyrazino[1,2-c]pyrimidine-1,8-dione This compound was prepared following the same method as described for 9-benzyloxy-2-cyclopropyl-6-(1-phenyl-cyclopentylmethyl)-3,4-dihydro-2H-pyrazino[1,2-c]pyrimidine-1,8-dione (286) from 5-benzyloxy-6-hydroxy-2-(1-phenyl-cyclopentylmethyl)-pyrimidine-4-carboxylic acid cyclobutyl-(2-hydroxyethyl)-amide (293) (100 mg, 0.19 mmol). The product was obtained as a white solid (35 mg, 36.3%).

LC-MS: 484.2 (M+H).

Synthesis of (295)

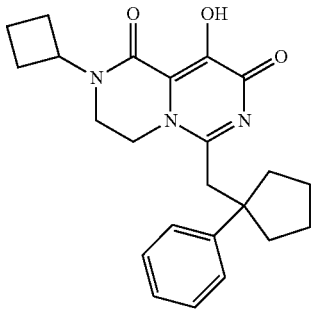 [SMILES: O=C1c2c(O)c(=O)nc(CC3(c4ccccc4)CCCC3)n2CCN1C1CCC1]

2-Cyclobutyl-9-hydroxy-6-(1-phenyl-cyclopentylmethyl)-3,4-dihydro-2H-pyrazino[1,2-c]pyrimidine-1,8-dione This compound was prepared following the same method as described for 2-cyclopropyl-9-hydroxy-6-(1-phenyl-cyclopentylmethyl)-3,4-dihydro-2H-pyrazino[1,2-c]pyrimidine-1,8-dione (287) from 9-benzyloxy-2-cyclobutyl-6-(1-phenyl-cyclopentylmethyl)-3,4-dihydro-2H-pyrazino[1,2-c]pyrimidine-1,8-dione (294) (140 mg, 0.29 mmol). The product was obtained as a white solid (48 mg, 42.14%).

LC-MS: 394.2 (M+H).

Example 299

9-Hydroxy-2-oxetan-3-yl-6-(1-phenyl-cyclopentylmethyl)-3,4-dihydro-2H-pyrazino[1,2-c]pyrimidine-1,8-dione The synthetic procedure used in this preparation is outlined in Schemes 43.

Synthesis of (8 g)

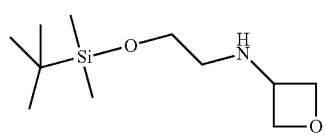

[2-(tert-Butyl-dimethylsilanyloxy)-ethyl]-oxetan-3-yl-amine

To a stirred solution of oxetan-3-one (1 g, 13.87 mmol) in methanol (40 mL) was added 2-(tert-butyl-dimethylsilanyloxy)-ethylamine (2.7 mg, 15.27 mmol). The mixture was stirred for 30 min at room temperature after cooling, Na(CN)BH$_3$ was added portion-wise, followed by stirring at room temperature for 2 h. The reaction mixture was quenched with water, extracted with dichloromethane (3×30 mL). The organic part was concentrated, dried and purified by Combi-Flash column (eluted at 20-50% ethyl acetate in hexane) to get [2-(tert-butyl-dimethylsilanyloxy)-ethyl]-oxetan-3-yl-amine (8 g) (1.5 g, 46.71%) as a light yellow oil.

Synthesis of (296)

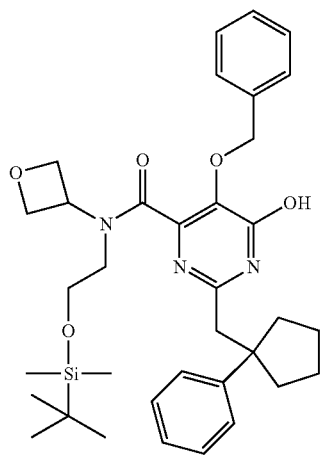 [SMILES: CC(C)(C)[Si](C)(C)OCCN(C(=O)c1nc(CC2(c3ccccc3)CCCC2)nc(O)c1OCc1ccccc1)C1COC1]

5-Benzyloxy-6-hydroxy-2-(1-phenyl-cyclopentylmethyl)-pyrimidine-4-carboxylic acid [2-(tert-butyl-dimethylsilanyloxy)-ethyl]-oxetan-3-yl-amide To a stirred solution mixture of 5-benzyloxy-6-hydroxy-2-(1-phenyl-cyclopentylmethyl)-pyrimidine-4-carboxylic acid (283) (158 mg, 0.39 mmol) and [2-(tert-butyl-dimethylsilanyloxy)-ethyl]-oxetan-3-yl-amine (8 g) (104 mg, 0.47 mmol) in dimethylformamide (3 mL) were added N,N-diisopropylethylamine (0.2 mL, 1.17 mmol) and HATU (222 mg, 0.59 mmol). The reaction mixture was stirred at room temperature for 1 h, followed by the addition of water (50 mL). the mixture was extracted with ethyl acetate (3×20 mL) and the combined organic part was washed with water (3×50 mL) and brine (2×30 mL) and dried and concentrated. The crude product was purified by Combi-Flash column (eluted at 20-30% ethyl acetate in hexane) to get 5-benzyloxy-6-hydroxy-2-(1-phenyl-cyclopentylmethyl)-pyrimidine-4-carboxylic acid [2-(tert-butyl-dimethylsilanyloxy)-ethyl]-oxetan-3-yl-amide (296) (240 mg, 99.43%) as a yellow gummy mass.

LC-MS: 618.2 (M+H).

Synthesis of (297)

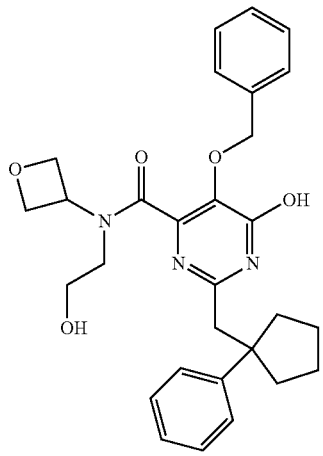 [SMILES: O=C(c1nc(CC2(c3ccccc3)CCCC2)nc(O)c1OCc1ccccc1)N(CCO)C1COC1]

5-Benzyloxy-6-hydroxy-2-(1-phenyl-cyclopentylmethyl)-pyrimidine-4-carboxylic acid (2-hydroxy-ethyl)-oxetan-3-yl-amide To a stirred solution of 5-benzyloxy-6-hydroxy-2-(1-phenyl-cyclopentylmethyl)-pyrimidine-4-carboxylic acid [2-(tert-butyl-dimethylsilanyloxy)-ethyl]-oxetan-3-yl-amide (296) (240 mg, 0.39 mmol) in tetrahydrofuran (20 mL) was added a 1M solution of tetrabutylammoniumfluorid in tetrahydrofuran (1.2 mL, 1.16 mmol) at room temperature and stirring was continued for 60 min at room temperature. After completion of the reaction, the reaction mixture was concentrated and the residue purified by Combi-Flash column (eluted at 5% methanol in dichloromethane) to get 5-Benzyloxy-6-hydroxy-2-(1-phenyl-cyclopentylmethyl)-pyrimidine-4-carboxylic acid (2-hydroxyethyl)-oxetan-3-yl-amide (297) as an off-white sticky solid (150 mg, 76.68%).

LC-MS: 504.2 (M+H).

Synthesis of (298)

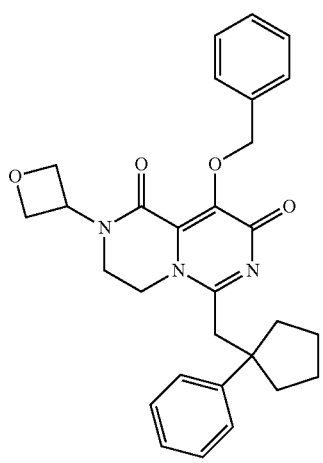 [SMILES: O=C1c2c(OCc3ccccc3)c(=O)nc(CC3(c4ccccc4)CCCC3)n2CCN1C1COC1]

9-Benzyloxy-2-oxetan-3-yl-6-(1-phenyl-cyclopentylmethyl)-3,4-dihydro-2H-pyrazino[1,2-c]pyrimidine-1,8-dione This compound was prepared following the same method as described for 9-benzyloxy-2-cyclopropyl-6-(1-phenyl-cyclopentylmethyl)-3,4-dihydro-2H-pyrazino[1,2-c]pyrimidine-1,8-dione (286) from 5-benzyloxy-6-hydroxy-2-(1-phenyl-cyclopentylmethyl)-pyrimidine-4-carboxylic acid (2-hydroxyethyl)-oxetan-3-yl-amide (297) (150 mg, 0.28 mmol). The product was obtained as off-white solid (110 mg, 80.65%).

LC-MS: 486.2 (M+H).

Synthesis of (299)

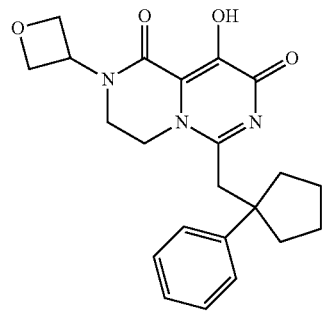 [SMILES: O=C1c2c(O)c(=O)nc(CC3(c4ccccc4)CCCC3)n2CCN1C1COC1]

9-Hydroxy-2-oxetan-3-yl-6-(1-phenyl-cyclopentylmethyl)-3,4-dihydro-2H-pyrazino[1,2-c]pyrimidine-1,8-dione This compound was prepared following the same method as described for 2-cyclopropyl-9-hydroxy-6-(1-phenyl-cyclopentylmethyl)-3,4-dihydro-2H-pyrazino[1,2-c]pyrimidine-1,8-dione (287) from 9-benzyloxy-2-oxetan-3-yl-6-(1-phenyl-cyclopentylmethyl)-3,4-dihydro-2H-pyrazino[1,2-c]pyrimidine-1,8-dione (298) (100 mg, 0.21 mmol). The product was obtained as a white solid (8 mg, 9.82%).

LC-MS: 396.2 (M+H).

Example 303

2-(2,2-Dimethyl-propyl)-9-hydroxy-6-(1-phenyl-cyclopentylmethyl)-3,4-dihydro-2H-pyrazino[1,2-c]pyrimidine-1,8-dione The synthetic procedure used in this preparation is outlined in Schemes 43.

Synthesis of (8h)

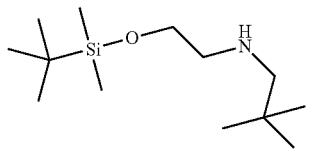 [SMILES: CC(C)(C)CNCCO[Si](C)(C)C(C)(C)C]

[2-(tert-Butyl-dimethylsilanyloxy)-ethyl]-(2,2-dimethyl-propyl)-amine

This compound was prepared following the same method as described for [2-(tert-butyl-dimethylsilanyloxy)-ethyl]-cyclopentyl-amine (8e) from 2,2-dimethyl-propionaldehyde (1 g, 11.61 mmol) and 2-(tert-butyl-dimethylsilanyloxy)-ethylamine (8c) (2.0 g, 11.6 mmol) as colorless oil (1.1 g, 38.6%).

Synthesis of (300)

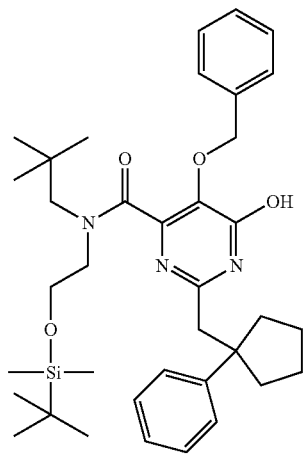 [SMILES: CC(C)(C)CN(CCO[Si](C)(C)C(C)(C)C)C(=O)c1nc(CC2(c3ccccc3)CCCC2)nc(O)c1OCc1ccccc1]

5-Benzyloxy-6-hydroxy-2-(1-phenyl-cyclopentylmethyl)-pyrimidine-4-carboxylic acid [2-(tert-butyl-dimethylsilanyloxy)-ethyl]-(2,2-dimethyl-propyl)-amide To a stirred solution mixture of 5-benzyloxy-6-hydroxy-2-(1-phenyl-cyclopentylmethyl)-pyrimidine-4-carboxylic acid (283) (230 mg, 0.57 mmol) and [2-(tert-butyl-dimethylsilanyloxy)-ethyl]-(2,2-dimethyl-propyl)-amine (8h) (167 mg, 0.68 mmol) in dimethylformamide (2.2 mL) were added N,N-diisopropylethylamine (0.3 mL, 1.70 mmol) and HATU (324 mg, 0.85 mmol). The reaction was stirred at room temperature for 20 h. Water (75 mL) was added and the mixture was extracted with ethyl acetate (3×20 mL). The combined organic part was washed with water (3×50 mL) and brine (2×30 mL) and dried and concentrated. The crude product was purified by Combi-Flash column (eluted at 20-30% ethyl acetate in hexane) to get 5-benzyloxy-6-hydroxy-2-(1-phenyl-cyclopentylmethyl)-pyrimidine-4-carboxylic acid [2-(tert-butyl-dimethylsilanyloxy)-ethyl]-(2,2-dimethyl-propyl)-amide (300) (310 mg, 86.27%) as an off-white sticky solid.

LC-MS: 632.6 (M+H).

Synthesis of (301)

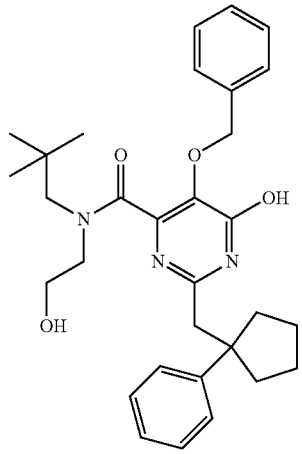 [SMILES: CC(C)(C)CN(CCO)C(=O)c1nc(CC2(c3ccccc3)CCCC2)nc(O)c1OCc1ccccc1]

5-Benzyloxy-6-hydroxy-2-(1-phenyl-cyclopentylmethyl)-pyrimidine-4-carboxylic acid (2,2-dimethyl-propyl)-(2-hydroxyethyl)-amide This compound was prepared following the same method as described for 5-benzyloxy-6-hydroxy-2-(1-phenyl-cyclopentylmethyl)-pyrimidine-4-carboxylic acid cyclopropyl-(2-hydroxyethyl)-amide (285) from 5-benzyloxy-6-hydroxy-2-(1-phenyl-cyclopentylmethyl)-pyrimidine-4-carboxylic acid [2-(tert-butyl-dimethylsilanyloxy)-ethyl]-(2,2-dimethyl-propyl)-amide (300) (350 mg, 0.55 mmol). The product was obtained as a light yellow sticky solid (270 mg, 94.03%).
LC-MS: 518.2 (M+H).

Synthesis of (302)

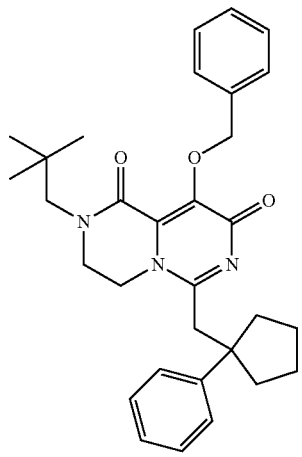 [SMILES: CC(C)(C)CN1CCn2c(CC3(c4ccccc4)CCCC3)nc(=O)c(OCc3ccccc3)c2C1=O]

9-Benzyloxy-2-(2,2-dimethyl-propyl)-6-(1-phenyl-cyclopentylmethyl)-3,4-dihydro-2H-pyrazino[1,2-c]pyrimidine-1,8-dione This compound was prepared following the same method as described for 9-benzyloxy-2-cyclopropyl-6-(1-phenyl-cyclopentylmethyl)-3,4-dihydro-2H-pyrazino[1,2-c]pyrimidine-1,8-dione (286) from 5-benzyloxy-6-hydroxy-2-(1-phenyl-cyclopentylmethyl)-pyrimidine-4-carboxylic acid (2,2-dimethyl-propyl)-(2-hydroxyethyl)-amide (301) (140 mg, 0.27 mmol). Off-white sticky solid (120 mg, 88.8%).

LC-MS: 500.4 (M+H).

Synthesis of (303)

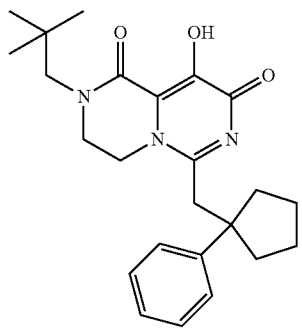 [SMILES: CC(C)(C)CN1CCn2c(CC3(c4ccccc4)CCCC3)nc(=O)c(O)c2C1=O]

2-(2,2-Dimethyl-propyl)-9-hydroxy-6-(1-phenyl-cyclopentylmethyl)-3,4-dihydro-2H-pyrazino[1,2-c]pyrimidine-1,8-dione This compound was prepared following the same method as described for 2-cyclopropyl-9-hydroxy-6-(1-phenyl-cyclopentylmethyl)-3,4-dihydro-2H-pyrazino[1,2-c]pyrimidine-1,8-dione (287) from 9-benzyloxy-2-(2,2-dimethyl-propyl)-6-(1-phenyl-cyclopentyl methyl)-3,4-dihydro-2 H-pyrazino[1,2-c]pyrimidine-1,8-dione (302) (120 mg, 0.24 mmol). The product was obtained as a white solid (30 mg, 30.5%).

LC-MS: 410.2 (M+H).

Example 307

2-Cyclopropylmethyl-9-hydroxy-6-(1-phenyl-cyclopentylmethyl)-3,4-dihydro-2H-pyrazino[1,2-c]pyrimidine-1,8-dione The synthetic procedure used in this preparation is outlined in Schemes 43.

Synthesis of (8i)

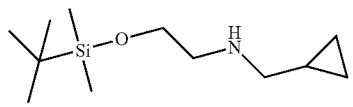

[2-(tert-Butyl-dimethylsilanyloxy)-ethyl]-cyclopropylmethyl-amine

This compound was prepared following the same method as described for [2-(tert-butyl-dimethylsilanyloxy)-ethyl]-cyclopentyl-amine (8e) from cyclopropanecarbaldehyde (300 mg, 4.23 mmol) and 2-(tert-butyl-dimethylsilanyloxy)-ethylamine (8c) (975 mg, 5.56 mmol). The product was obtained as a colourless liquid (280 mg, 28.51%).

Synthesis of (304)

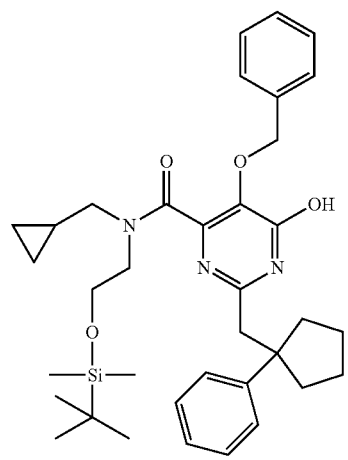 [SMILES: CC(C)(C)[Si](C)(C)OCCN(CC1CC1)C(=O)c1nc(CC2(c3ccccc3)CCCC2)nc(O)c1OCc1ccccc1]

5-Benzyloxy-6-hydroxy-2-(1-phenyl-cyclopentylmethyl)-pyrimidine-4-carboxylic acid [2-(tert-butyl-dimethylsilanyloxy)-ethyl]-cyclopropylmethyl-amide To a stirred solution mixture of 5-benzyloxy-6-hydroxy-2-(1-phenyl-cyclopentylmethyl)-pyrimidine-4-carboxylic acid (283) (250 mg, 0.62 mmol) and [2-(tert-butyl-dimethylsilanyloxy)-ethyl]-cyclopropylmethyl-amine (8i) (170 mg, 0.74 mmol) in dimethylformamide (3 mL) were added N,N-diisopropylethylamine (0.3 mL, 1.85 mmol) and HATU (352 mg, 0.93 mmol). The reaction mixture was stirred at room temperature for 20 h. Water (75 mL) was added and the mixture was extracted with ethyl acetate (3×20 mL). The combined organic part was washed with water (3×50 mL) and brine (2×30 mL) and dried and concentrated. The crude product was purified by Combi-Flash column (eluted at 20-30% ethyl acetate in hexane) to get 5-benzyloxy-6-hydroxy-2-(1-phenyl-cyclopentylmethyl)-pyrimidine-4-carboxylic acid 5-benzyloxy-6-hydroxy-2-(1-phenyl-cyclopentylmethyl)-pyrimidine-4-carboxylic acid [2-(tert-butyl-dimethylsilanyloxy)-ethyl]-cyclopropylmethyl-amide (304) (380 mg, 99.82%) as a light yellow sticky solid.

LC-MS: 616.2 (M+H).

Synthesis of (305)

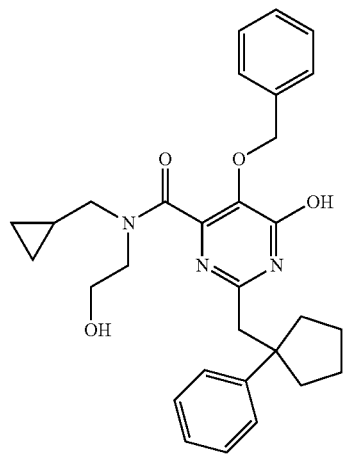 [SMILES: O=C(c1nc(CC2(c3ccccc3)CCCC2)nc(O)c1OCc1ccccc1)N(CCO)CC1CC1]

5-Benzyloxy-6-hydroxy-2-(1-phenyl-cyclopentylmethyl)-pyrimidine-4-carboxylic acid cyclopropylmethyl-(2-hydroxyethyl)-amide This compound was prepared following the same method as described for 5-benzyloxy-6-hydroxy-2-(1-phenyl-cyclopentylmethyl)-pyrimidine-4-carboxylic acid cyclopropyl-(2-hydroxyethyl)-amide (285) from 5-Benzyloxy-6-hydroxy-2-(1-phenyl-cyclopentylmethyl)-pyrimidine-4-carboxylic acid [2-(tert-butyl-dimethylsilanyloxy)-ethyl]-cyclopropylmethyl-amide (304) (380 mg, 0.62 mmol). The product was obtained as a light yellow sticky solid (300 mg, 96.93%).
LC-MS: 502.2 (M+H).

Synthesis of (306)

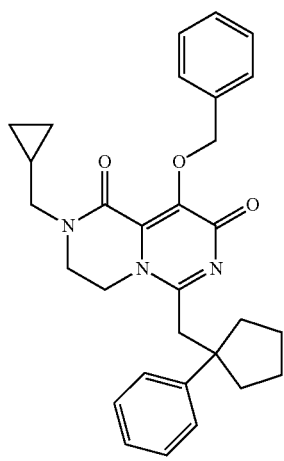 [SMILES: O=C1c2c(OCc3ccccc3)c(=O)nc(CC3(c4ccccc4)CCCC3)n2CCN1CC1CC1]

9-Benzyloxy-2-cyclopropylmethyl-6-(1-phenyl-cyclopentylmethyl)-3,4-dihydro-2H-pyrazino[1,2-c]pyrimidine-1,8-dione This compound was prepared following the same method as described for 9-benzyloxy-2-cyclopropyl-6-(1-phenyl-cyclopentylmethyl)-3,4-dihydro-2H-pyrazino[1,2-c]pyrimidine-1,8-dione (286) from 5-benzyloxy-6-hydroxy-2-(1-phenyl-cyclopentylmethyl)-pyrimidine-4-carboxylic acid cyclopropylmethyl-(2-hydroxyethyl)-amide (305) (150 mg, 0.29 mmol). The product was obtained as a colourless sticky solid (65 mg, 44.95%).
LC-MS: 484.4 (M+H).

Synthesis of (307)

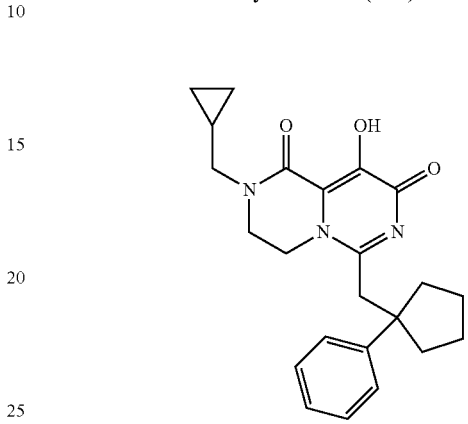

2-Cyclopropylmethyl-9-hydroxy-6-(1-phenyl-cyclopentylmethyl)-3,4-dihydro-2H-pyrazino[1,2-c]pyrimidine-1,8-dione This compound was prepared following the same method as described for 2-cyclopropyl-9-hydroxy-6-(1-phenyl-cyclopentylmethyl)-3,4-dihydro-2H-pyrazino[1,2-c]pyrimidine-1,8-dione (287) from 9-benzyloxy-2-cyclopropylmethyl-6-(1-phenyl-cyclopentylmethyl)-3,4-dihydro-2H-pyrazino[1,2-c]pyrimidine-1,8-dione (306) (130 mg, 0.32 mmol). The product was obtained as a white solid (20 mg, 16%).
LC-MS: 394.2 (M+H).

Example 311

9-Hydroxy-6-(1-phenyl-cyclopentylmethyl)-2-(tetrahydro-pyran-4-yl)-3,4-dihydro-2H-pyrazino[1,2-c]pyrimidine-1,8-dione The synthetic procedure used in this preparation is outlined in Schemes 43.

Synthesis of (8j)

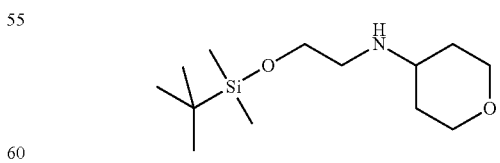

[2-(tert-Butyl-dimethylsilanyloxy)-ethyl]-(tetrahydro-pyran-4-yl)-amine

To a stirred cooled solution of tetrahydro-pyran-4-one (2 g, 19.98 mmol) in methanol (30 mL) were added 2-(tert-butyldimethylsilanyloxy)-ethylamine (8c) (2.5 mg, 13.98 mmol). Stirring was continued for 1 h at room temperature. The reaction mixture was cooled and Na(CN)BH$_3$ (2.5 g, 39.96 mmol) was added portion-wise, followed by stirring at room temperature for 20 h. The reaction mixture was quenched with water and the methanol was removed. The mixture was subsequently extracted with dichloromethane (3×30 mL) and the organic part was concentrated, dried and purified by Combi-Flash column (eluted at 20-50% ethyl acetate in hexane) to get [2-(tert-butyl-dimethylsilanyloxy)-ethyl]-(tetrahydro-pyran-4-yl)-amine (8j) (2.5 g, 48.23 mmol) as a light yellow oil.

Synthesis of (308)

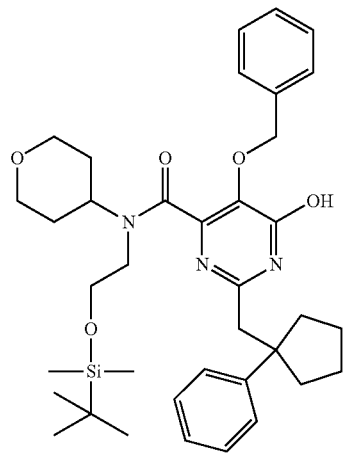 [SMILES: CC(C)(C)[Si](C)(C)OCCN(C(=O)c1nc(CC2(c3ccccc3)CCCC2)nc(O)c1OCc1ccccc1)C1CCOCC1]

5-Benzyloxy-6-hydroxy-2-(1-phenyl-cyclopentylmethyl)-pyrimidine-4-carboxylic acid [2-(tert-butyl-dimethylsilanyloxy)-ethyl]-(tetrahydro-pyran-4-yl)-amide To a stirred solution mixture of 5-benzyloxy-6-hydroxy-2-(1-phenyl-cyclopentylmethyl)-pyrimidine-4-carboxylic acid (283) (400 mg, 0.99 mmol) and [2-(tert-butyl-dimethylsilanyloxy)-ethyl]-(tetrahydro-pyran-4-yl)-amine (8j) (513 mg, 1.98 mmol) in dimethylformamide (6 mL) were added N,N-diisopropylethylamine (0.5 mL, 2.97 mmol) and HATU (564 mg, 1.48 mmol). Stirring was continued at room temperature for 1 h. Water (75 mL) was added and the mixture was extracted with ethyl acetate (3×20 mL). The combined organic part was washed with water (3×50 mL) and brine (2×30 mL) and dried and concentrated. The crude product was purified by Combi-Flash column (eluted at 20-30% ethyl acetate in hexane) to get 5-benzyloxy-6-hydroxy-2-(1-phenyl-cyclopentylmethyl)-pyrimidine-4-carboxylic acid [2-(tert-butyl-dimethylsilanyloxy)-ethyl]-(tetrahydro-pyran-4-yl)-amide (308) (540 mg, 84.53%) as a colorless sticky solid.
LC-MS: 646.2 (M+H).

Synthesis of (309)

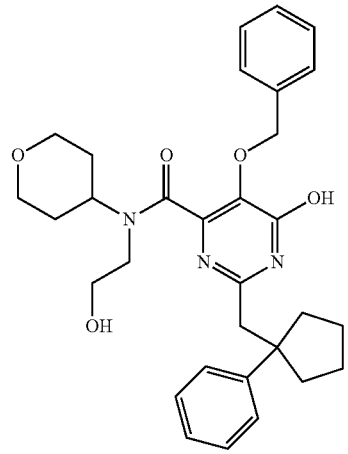 [SMILES: O=C(c1nc(CC2(c3ccccc3)CCCC2)nc(O)c1OCc1ccccc1)N(CCO)C1CCOCC1]

5-Benzyloxy-6-hydroxy-2-(1-phenyl-cyclopentylmethyl)-pyrimidine-4-carboxylic acid (2-hydroxyethyl)-(tetrahydro-pyran-4-yl)-amide This compound was prepared following the same method as described for 5-benzyloxy-6-hydroxy-2-(1-phenyl-cyclopentylmethyl)-pyrimidine-4-carboxylic acid cyclopropyl-(2-hydroxyethyl)-amide (285) from 5-benzyloxy-6-hydroxy-2-(1-phenyl-cyclopentylmethyl)-pyrimidine-4-carboxylic acid [2-(tert-butyl-dimethylsilanyloxy)-ethyl]-(tetrahydro-pyran-4-yl)-amide (308) (540 mg, 0.83 mmol). The product was obtained as a white solid (400 mg, 89.99%).
LC-MS: 532.2 (M+H).

Synthesis of (310)

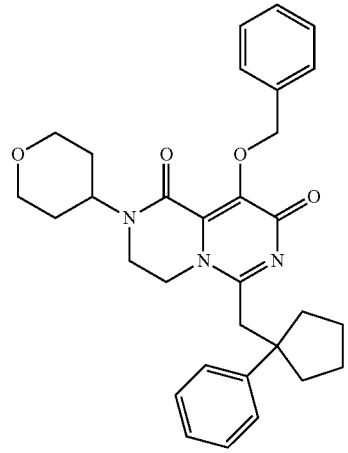 [SMILES: O=C1c2c(OCc3ccccc3)c(=O)nc(CC3(c4ccccc4)CCCC3)n2CCN1C1CCOCC1]

9-Benzyloxy-6-(1-phenyl-cyclopentylmethyl)-2-(tetrahydro-pyran-4-yl)-3,4-dihydro-2H-pyrazino[1,2-c]pyrimidine-1,8-dione This compound was prepared following the same method as described for 9-benzyloxy-2-cyclopropyl-6-(1-phenyl-cyclopentylmethyl)-3,4-dihydro-2H-pyrazino[1,2-c]pyrimidine-1,8-dione (286) from 5-benzyloxy-6-hydroxy-2-(1-phenyl-cyclopentylmethyl)-pyrimidine-4-carboxylic acid (2-hydroxyethyl)-(tetrahydro-pyran-4-yl)-amide (309) (440 mg, 0.90 mmol). The product was obtained as a white solid (260 mg, 56.1%).

LC-MS: 514.0 (M+H).

Synthesis of (311)

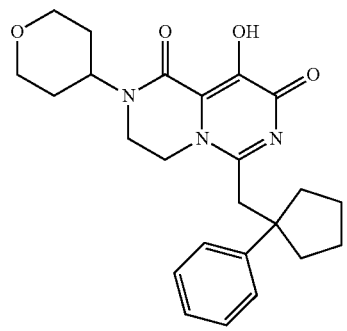 [SMILES: O=C1c2c(O)c(=O)nc(CC3(c4ccccc4)CCCC3)n2CCN1C1CCOCC1]

9-Hydroxy-6-(1-phenyl-cyclopentylmethyl)-2-(tetrahydro-pyran-4-yl)-3,4-dihydro-2H-pyrazino[1,2-c]pyrimidine-1,8-dione This compound was prepared following the same method as described for 2-cyclopropyl-9-hydroxy-6-(1-phenyl-cyclopentylmethyl)-3,4-dihydro-2H-pyrazino[1,2-c]pyrimidine-1,8-dione (287) from 9-benzyloxy-6-(1-phenyl-cyclopentylmethyl)-2-(tetrahydro-pyran-4-yl)-3,4-dihydro-2H-pyrazino[1,2-c]pyrimidine-1,8-dione (310) (240 mg, 0.47 mmol). The product was obtained as a white solid (180 mg, 90.96%).

LC-MS: 424.0 (M+H).

Example 315

2-(4-Fluoro-benzyl)-9-hydroxy-6-(1-phenyl-cyclopentylmethyl)-3,4-dihydro-2H-pyrazino[1,2-c]pyrimidine-1,8-dione The synthetic procedure used in this preparation is outlined in Schemes 43.

Synthesis of (8k)

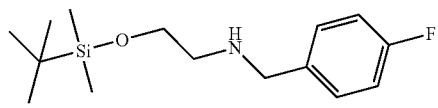 [SMILES: CC(C)(C)[Si](C)(C)OCCNCc1ccc(F)cc1]

[2-(tert-Butyl-dimethylsilanyloxy)-ethyl]-(4-fluorobenzyl)-amine

This compound was prepared following the same method as described for [2-(tert-butyl-dimethylsilanyloxy)-ethyl]-cyclopentyl-amine (8e) from 4-fluorobenzaldehyde (1 g, 8.06 mmol) and 2-(tert-butyl-dimethylsilanyloxy)-ethylamine (8c) (1.8 g, 10.48 mmol). The product was obtained as a light yellow liquid (800 mg, 35.03%).

LC-MS: 283.8

Synthesis of (312)

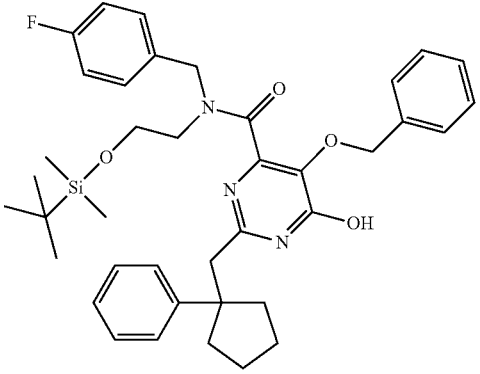 [SMILES: CC(C)(C)[Si](C)(C)OCCN(Cc1ccc(F)cc1)C(=O)c1nc(CC2(c3ccccc3)CCCC2)nc(O)c1OCc1ccccc1]

5-Benzyloxy-6-hydroxy-2-(1-phenyl-cyclopentylmethyl)-pyrimidine-4-carboxylic acid [2-(tert-butyl-dimethylsilanyloxy)-ethyl]-(4-fluoro-benzyl)-amide To a stirred solution mixture of 5-benzyloxy-6-hydroxy-2-(1-phenyl-cyclopentylmethyl)-pyrimidine-4-carboxylic acid (283) (250 mg, 0.62 mmol) and [2-(tert-butyl-dimethylsilanyloxy)-ethyl]-(4-fluoro-benzyl)-amine (8k) (210 mg, 0.74 mmol) in dimethylformamide (5 mL) was added propylphosphonic anhydride (50 wt % in ethyl acetate) (1.3 g, 1.85 mmol) at 0° C. After stirring at room temperature for 20 h, water (20 mL) was added and the mixture was extracted with ethyl acetate (3×20 mL). The combined organic part was washed with water (3×50 mL) and brine (2×30 mL) and dried and concentrated. The crude product was purified by Combi-Flash column (eluted at 20-30% ethyl acetate in hexane) to yield 5-benzyloxy-6-hydroxy-2-(1-phenyl-cyclopentylmethyl)-pyrimidine-4-carboxylic acid [2-(tert-butyl-dimethylsilanyloxy)-ethyl]-(4-fluoro-benzyl)-amide (312) (96 mg, 23.18%) as a colourless sticky solid.

LC-MS: 668.0 (M−H).

Synthesis of (313)

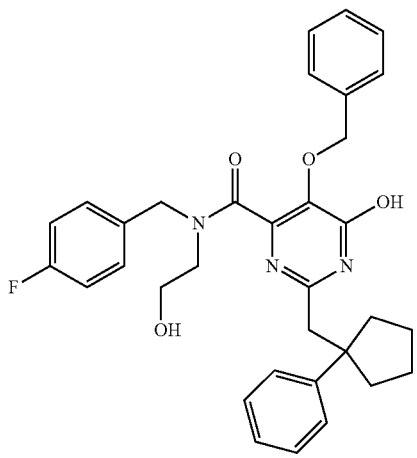 [SMILES: O=C(c1nc(CC2(c3ccccc3)CCCC2)nc(O)c1OCc1ccccc1)N(CCO)Cc1ccc(F)cc1]

5-Benzyloxy-6-hydroxy-2-(1-phenyl-cyclopentylmethyl)-pyrimidine-4-carboxylic acid (4-fluoro-benzyl)-(2-hydroxyethyl)-amide This compound was prepared following the same method as described for 5-benzyloxy-6-hydroxy-2-(1-phenyl-cyclopentylmethyl)-pyrimidine-4-carboxylic acid cyclopropyl-(2-hydroxyethyl)-amide (285) from 5-benzyloxy-6-hydroxy-2-(1-phenyl-cyclopentylmethyl)-pyrimidine-4-carboxylic acid [2-(tert-butyl-dimethylsilanyloxy)-ethyl]-(4-fluoro-benzyl)-amide (312) (146 mg, 0.22 mmol). The product was obtained as colourless sticky solid (116 mg, 95.66%).

LC-MS: 556.4 (M+H).

Synthesis of (314)

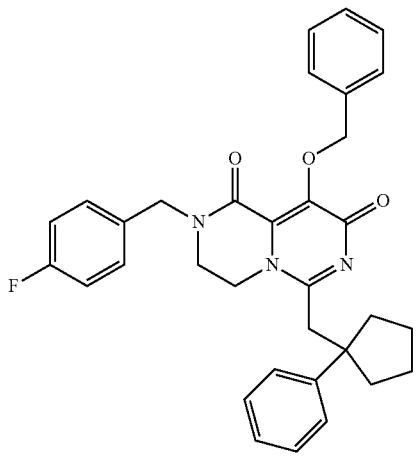 [SMILES: O=C1c2c(OCc3ccccc3)c(=O)nc(CC3(c4ccccc4)CCCC3)n2CCN1Cc1ccc(F)cc1]

9-Benzyloxy-2-(4-fluoro-benzyl)-6-(1-phenyl-cyclopentylmethyl)-3,4-dihydro-2H-pyrazino[1,2-c]pyrimidine-1,8-dione This compound was prepared following the same method as described for 9-benzyloxy-2-cyclopropyl-6-(1-phenyl-cyclopentylmethyl)-3,4-dihydro-2H-pyrazino[1,2-c]pyrimidine-1,8-dione (286) from 5-benzyloxy-6-hydroxy-2-(1-phenyl-cyclopentylmethyl)-pyrimidine-4-carboxylic acid (4-fluoro-benzyl)-(2-hydroxyethyl)-amide (313) (91 mg, 0.16 mmol). The product was obtained as a colorless sticky solid (46 mg, 52.2%).

LC-MS: 538.2 (M+H).

Synthesis of (315)

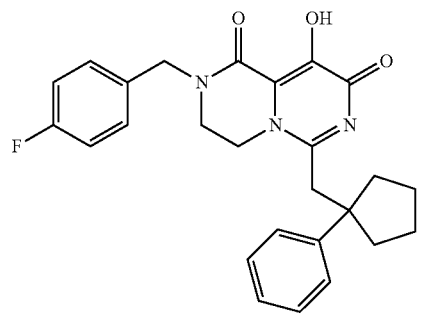 [SMILES: O=C1c2c(O)c(=O)nc(CC3(c4ccccc4)CCCC3)n2CCN1Cc1ccc(F)cc1]

2-(4-Fluoro-benzyl)-9-hydroxy-6-(1-phenyl-cyclopentylmethyl)-3,4-dihydro-2H-pyrazino[1,2-c]pyrimidine-1,8-dione This compound was prepared following the same method as described for 2-cyclopropyl-9-hydroxy-6-(1-phenyl-cyclopentylmethyl)-3,4-dihydro-2H-pyrazino[1,2-c]pyrimidine-1,8-dione (287) from 9-benzyloxy-2-(4-fluoro-benzyl)-6-(1-phenyl-cyclopentylmethyl)-3,4-dihydro-2H-pyrazino[1,2-c]pyrimidine-1,8-dione (314) (45 mg, 0.08 mmol). It was purified by preparative TLC plate (mobile phase 5% methanol in dichloromethane) to get 15h as a white solid (8 mg, 21.33%).

LC-MS: 448.2 (M+H).

General Procedure for Examples 317 to 315

The synthetic procedures are outlined in Scheme 46.

General Synthetic Route for 317, 291, 295, 299, 303, 307, 311 and 315

Scheme 46

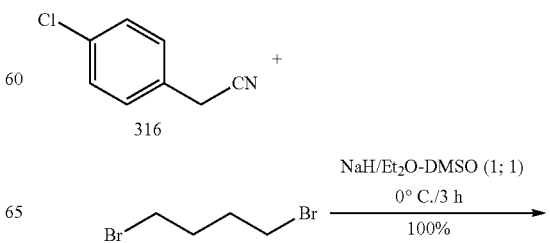

295
-continued
296
-continued
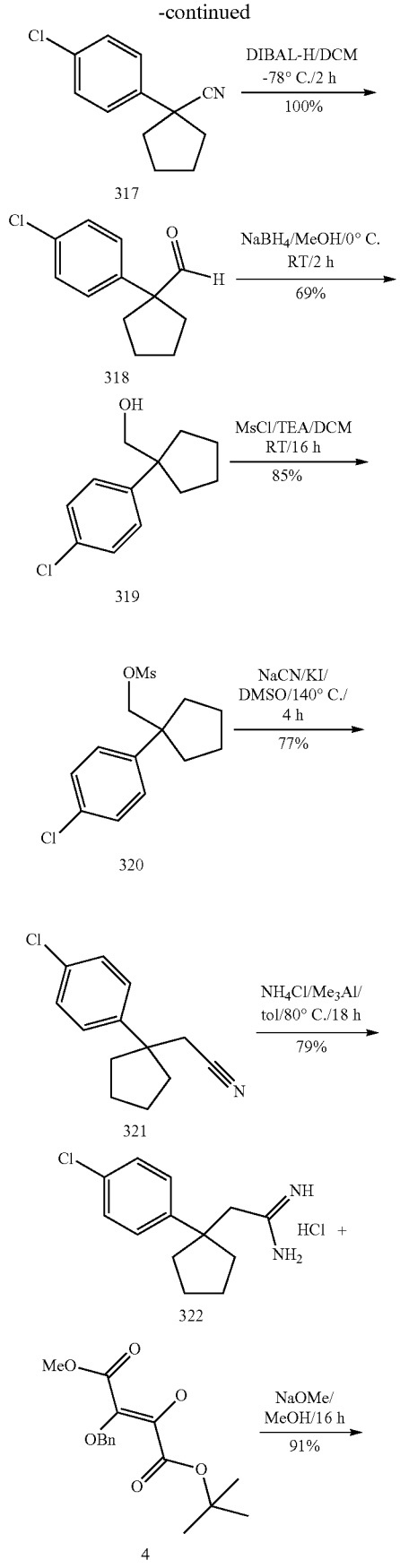
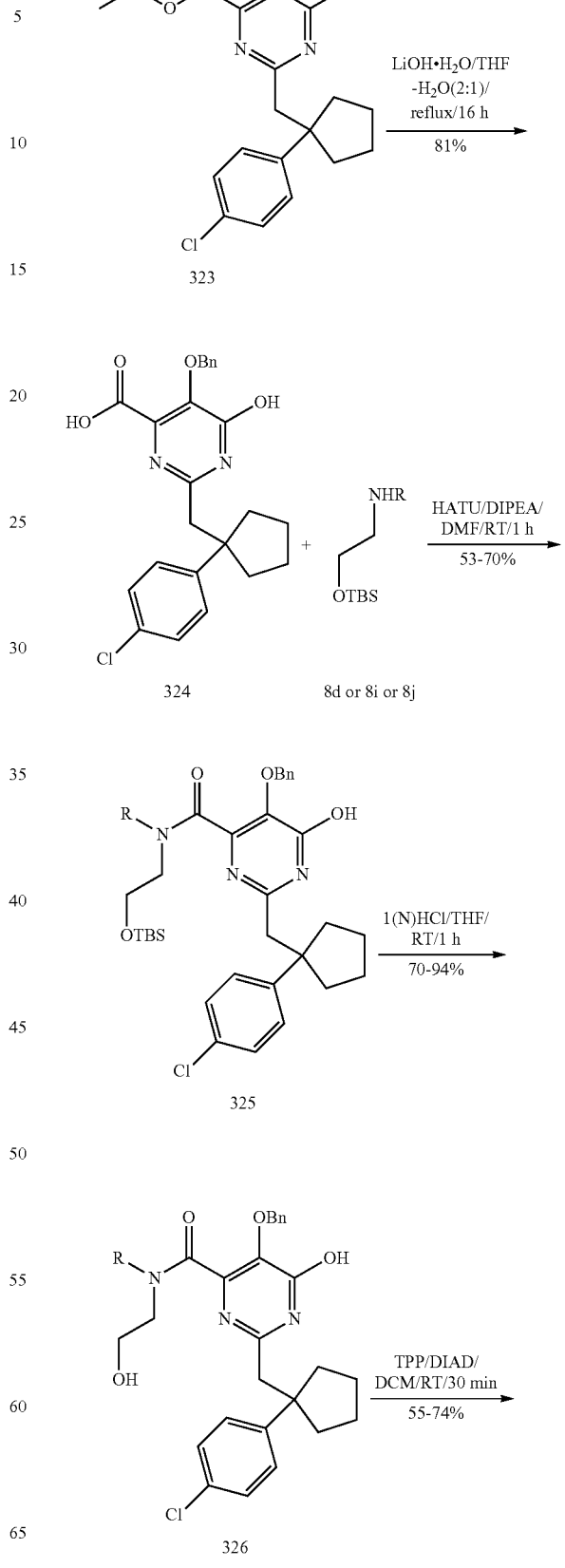

-continued

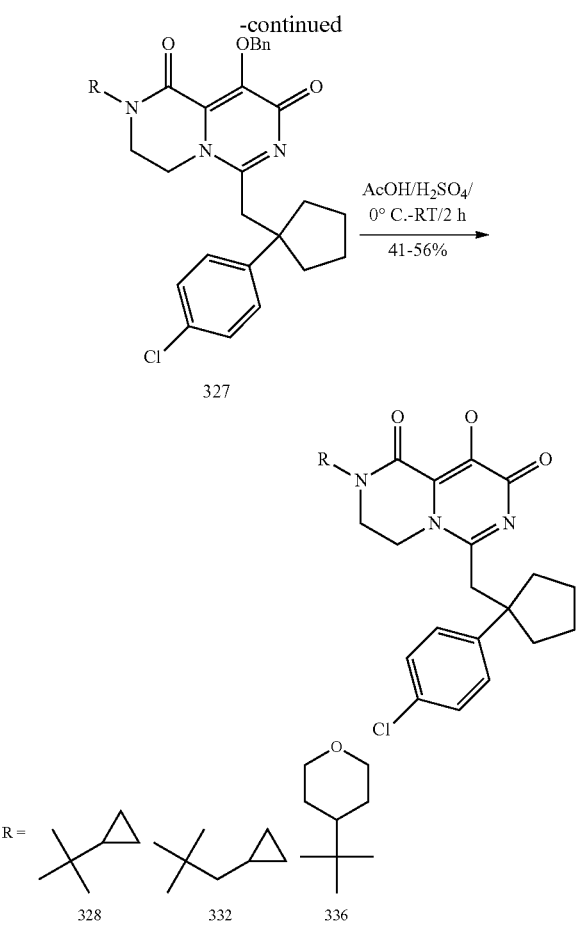

Synthesis of (317)

1-(4-chlorophenyl)-cyclopentanecarbonitrile

To a suspension of sodium hydride (60% suspension in mineral oil) (14.5 g, 362.96 mmol) in dimethyl sulfoxide (250 mL) was added dropwise a mixture of (4-chlorophenyl)acetonitrile (316) (25 g, 164.98 mmol) and 1,4-dibromobutane (35.6 g, 164.98 mmol) dissolved in dimethyl sulfoxide:ether (1:1; 300 mL) at 0° C. The reaction mixture was stirred for 30 min at same temperature and at room temperature for 3 h. After completion of the reaction, the reaction mixture was quenched with HCl (1N; 25 mL) and water (200 mL) and extracted with ethyl acetate (3×100 mL). The separated organic part was washed with water (3×100 mL) and brine (100 mL) and dried and concentrated to get a crude product which was purified by silica CombiFlash column (3-5% ethyl acetate in hexane used as eluent) to afford 1-(4-chlorophenyl)-cyclopentanecarbonitrile (317) (33.9 g, 100%) as a light yellow oil.

Synthesis of (318)

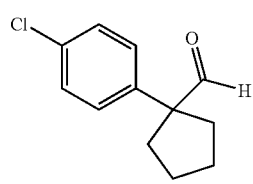

1-(4-chlorophenyl)-cyclopentanecarbaldehyde

To a stirred solution of 1-(4-chlorophenyl)-cyclopentanecarbonitrile (317) (20 g, 97.24 mmol) in dichloromethane (270 mL), was added diisobutylaluminium hydride (25% in toluene) (138 mL, 243.09 mmol) at −78° C. and the reaction mixture was stirred for 2 h at the same temperature. After completion of the reaction, the reaction mixture was quenched with a saturated solution of potassium sodium tartrate (75 mL) and stirred for 16 h at room temperature. The dichloromethane part was separated and the aqueous part was re-extracted with dichloromethane (1×100 mL). The combined organic parts were dried and concentrated. The obtained crude product was purified by silica CombiFlash column (5% ethyl acetate in hexane was used as eluent) to get 1-(4-chlorophenyl)-cyclopentanecarbaldehyde (318) (20.2 g, 100%) as a light yellow oil.

Synthesis of (319)

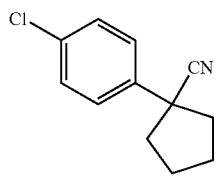 [SMILES: N#CC1(c2ccc(Cl)cc2)CCCC1]

[1-(4-chlorophenyl)-cyclopentyl]-methanol

To a stirred solution of 1-(4-chlorophenyl)-cyclopentanecarbaldehyde (318) (19 g, 91.06 mmol) in methanol (250 mL) was added NaBH$_4$ (6.9 g, 182.13 mmol) portion-wise at 0° C. and the reaction mixture was stirred at room temperature for 2 h. After completion of the reaction, the reaction mixture was quenched with a saturated aqueous solution of ammonium chloride (20 mL). The methanol was removed and the residue was diluted with water (100 mL). The mixture was extracted with ethyl acetate (3×100 mL) and the combined organic parts were dried and concentrated. The crude product was purified by silica CombiFlash column (5% ethyl acetate in hexane was used as eluent) to get [1-(4-chlorophenyl)-cyclopentyl]-methanol (319) (13.3 g, 69%) as a colourless oil.

GC-MS: 210 (M+).

Synthesis of (320)

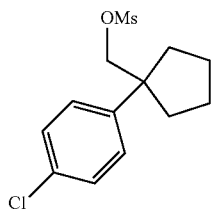 [SMILES: CS(=O)(=O)OCC1(c2ccc(Cl)cc2)CCCC1]

Methanesulfonic acid 1-(4-chlorophenyl)-cyclopentylmethyl ester

To a stirred solution of 1-(4-chlorophenyl)-cyclopentyl]-methanol (319) (12 g, 56.95 mmol) in dichloromethane (110 mL) was added triethyl amine (16 mL, 113.90 mmol) followed by mesyl chloride (5.3 mL, 68.34 mmol) at 0° C. The reaction mixture was stirred at room temperature for 4 h, diluted with dichloromethane (50 mL) and washed with water (100 mL), saturated aqueous sodium bicarbonate solution (50 mL) and brine (50 mL). The organic part was dried, concentrated and purified by CombiFlash column (eluted at 10-20% ethyl acetate in hexane) to get methanesulfonic acid 1-(4-chlorophenyl)-cyclopentylmethyl ester (320) (14 g, 85%) as a light yellow crystalline solid.

Synthesis of (321)

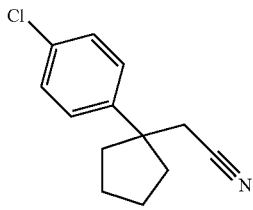 [SMILES: N#CCC1(c2ccc(Cl)cc2)CCCC1]

[1-(4-chlorophenyl)-cyclopentyl]-acetonitrile

To a stirred solution of methanesulfonic acid 1-(4-chlorophenyl)-cyclopentylmethyl ester (320) (14 g, 48.48 mmol) in dimethyl sulfoxide (50 mL) were added KI (805 mg, 4.85 mmol) and NaCN (3.6 g, 72.72 mmol) and stirred for 130° C. for 4 h. After completion of reaction, cold water (200 mL) was added. After extraction with ethyl acetate (3×100 mL), the combined organic parts were washed with saturated ferrous sulphate solution (2×100 mL), water (2×100 mL) and brine (100 mL) and dried and concentrated. The crude product was purified by CombiFlash column (10-20% ethyl acetate in hexane was used as eluent) to get [1-(4-chlorophenyl)-cyclopentyl]-acetonitrile (321) (8.2 g, 77%) as a light yellow liquid.

Synthesis of (322)

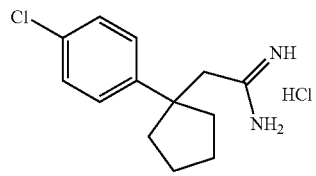 [SMILES: N=C(N)CC1(c2ccc(Cl)cc2)CCCC1 ; Cl]

2-[1-(4-chlorophenyl)-cyclopentyl]-acetamidine, hydrochloride

To a stirred suspension of NH$_4$Cl (5.9 g, 111.97 mmol) in toluene (200 mL) was added trimethylaluminium (2 M in toluene) (56 mL, 111.96 mmol) at 5° C. The reaction mixture was allowed to warm up to room temperature and stirred for 2 h. A solution of [1-(4-chlorophenyl)-cyclopentyl]-acetonitrile (321) (8.2 g, 37.32 mmol) in toluene (20 mL) was added to the reaction mixture at room temperature and the reaction mixture was heated at 80° C. for 14 h. After completion of the reaction, the reaction mixture was quenched with a suspension of silica gel (32 g) in chloroform (32 mL) at 0° C. The quenched mixture was stirred for 30 min at room temperature and filtered through a pad of celite. The residue was washed with methanol (5×50 mL) and the combined filtrate was concentrated. The residue was stirred in 10% methanol in dichloromethane (150 mL) and the resulting white solid was discarded by filtration and the filtrate was concentrated to get 2-(1-phenyl-cyclopentyl)-acetamidine, hydrochloride (322) (7 g, 79%, crude) as a yellow gummy oil.

Synthesis of (323)

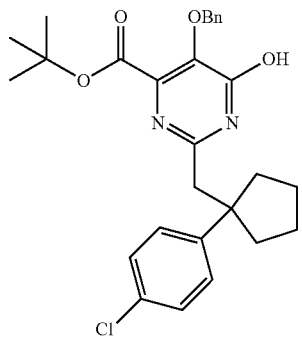 [SMILES: CC(C)(C)OC(=O)c1nc(CC2(c3ccc(Cl)cc3)CCCC2)nc(O)c1OCc1ccccc1]

5-Benzyloxy-2-[1-(4-chlorophenyl)-cyclopentylmethyl]-6-hydroxypyrimidine-4-carboxylic acid tert-butyl ester To a stirred solution of 2-[1-(4-chlorophenyl)-cyclopentyl]-acetamidine; hydrochloride (322) (3.1 g, 11.34 mmol) in methanol (25 mL) was added (E,Z)-2-benzyloxy-3-hydroxy-but-2-enedioic acid 4-tert-butyl ester 1-methyl ester (4) (4.19 g, 13.61 mmol) and cooled to 0° C. To this reaction mixture was then added sodium methoxide (25% in methanol) (7.4 mL, 34.03 mmol) and stirred at room temperature for 16 h (TLC; ethyl acetate:hexane=1:1, Rf=0.5). The reaction mixture was diluted with ethyl acetate (300 mL), washed with water (60 mL) and brine (60 mL) and dried and concentrated in vacuo to get crude mass which was purified by CombiFlash eluted with gradient polarity mobile phase (hexane to 50% ethyl acetate in hexane) to get pure 5-benzyloxy-2-[1-(4-chlorophenyl)-cyclopentylmethyl]-6-hydroxypyrimidine-4-carboxylic acid tert-butyl ester (323) (5.1 g, 91%) as a light brown solid.

LC-MS: 495.2 (M+H)

Synthesis of (324)

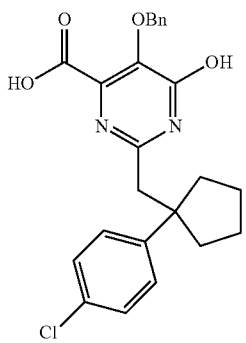 [SMILES: O=C(O)c1nc(CC2(c3ccc(Cl)cc3)CCCC2)nc(O)c1OCc1ccccc1]

5-Benzyloxy-2-[1-(4-chlorophenyl)-cyclopentylmethyl]-6-hydroxypyrimidine-4-carboxylic acid To a solution of 5-benzyloxy-2-[1-(4-chlorophenyl)-cyclopentylmethyl]-6-hydroxypyrimidine-4-carboxylic acid tert-butyl ester (323) (4.82 g, 9.74 mmol) in tetrahydrofuran (90 mL) and water (45 mL) was added LiOH.H$_2$O (4.086 g, 97.37 mmol). The reaction mixture was heated to reflux for 20 h (the reaction was monitored by LC-MS). The tetrahydrofuran was removed in vacuo and the reaction mixture was diluted with water (100 mL) and extracted with ethyl acetate (2×50 mL). The aqueous layer was acidified with 1N HCl to about pH 3. A white solid was separated by filtration and dried in vacuo to get pure 5-benzyloxy-2-[1-(4-chlorophenyl)-cyclopentylmethyl]-6-hydroxypyrimidine-4-carboxylic acid (324) (3.47 g, 81%).

LC-MS: 439.0 (M+H)

Example 328

6-[1-(4-chlorophenyl)-cyclopentylmethyl]-2-cyclopropyl-9-hydroxy-3,4-dihydro-2H-pyrazino[1,2-c]pyrimidine-1,8-dione The synthetic procedure used in this preparation is outlined in Schemes 46.

Synthesis of (325)

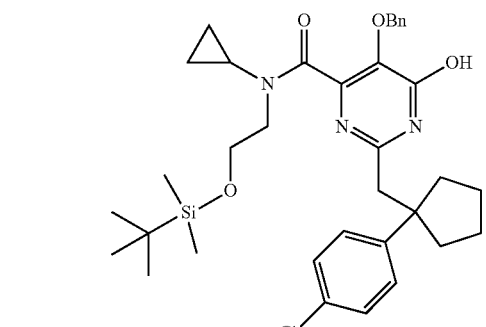

5-Benzyloxy-2-[1-(4-chlorophenyl)-cyclopentylmethyl]-6-hydroxypyrimidine-4-carboxylic acid [2-(tert-butyl-dimethylsilanyloxy)-ethyl]-cyclopropylamide 5-Benzyloxy-2-[1-(4-chlorophenyl)-cyclopentylmethyl]-6-hydroxypyrimidine-4-carboxylic acid (324) (150.0 mg, 0.34 mmol) and [2-(tert-butyl-dimethylsilanyloxy)-ethyl]-cyclopropyl-amine (8d) (110.4 mg, 0.51 mmol) were taken up in dimethylformamide (3 ml), HATU (123.3 mg, 0.41 mmol) and N,N-diisopropylethylamine (132.5 mg, 1.03 mmol) were added at room temperature and stirred for 16 h while silica thin layer chromatography was performed (40% ethyl acetate in hexane; Rf=0.4). To the reaction, water (10 ml) was added and stirred for 5 min and the aqueous mixture was extracted with ethyl acetate (2×15 ml). The combined extracts were washed with water (3×10 ml), dried and concentrated under reduced pressure. The obtained crude product was purified by normal silica gel column chromatography (100-200 mesh) using 30% ethyl acetate in hexane as mobile phase to get pure 5-benzyloxy-2-[1-(4-chlorophenyl)-cyclopentylmethyl]-6-hydroxypyrimidine-4-carboxylic acid [2-

(tert-butyl-dimethylsilanyloxy)-ethyl]-cyclopropyl-amide (325) (120 mg, 55%) as a yellow sticky solid.

Synthesis of (326)

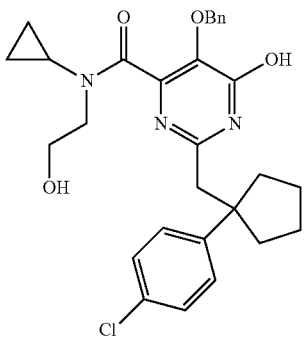 [SMILES: O=C(c1nc(CC2(c3ccc(Cl)cc3)CCCC2)nc(O)c1OCc1ccccc1)N(CCO)C1CC1]

5-Benzyloxy-2-[1-(4-chlorophenyl)-cyclopentylmethyl]-6-hydroxypyrimidine-4-carboxylic acid cyclopropyl-(2-hydroxyethyl)-amide To a stirred solution of 5-benzyloxy-2-[1-(4-chlorophenyl)-cyclopentylmethyl]-6-hydroxypyrimidine-4-carboxylic acid [2-(tert-butyl-dimethylsilanyloxy)-ethyl]-cyclopropyl-amide (325) (100 mg, 0.16 mmol) in tetrahydrofuran was added 1N HCl (5 ml) at room temperature and stirring was continued for 30 min wile silica thin layer chromatography was performed (60% ethyl acetate in hexane; Rf=0.4). After completion of the reaction, solid NaHCO$_3$ was added to the reaction mixture which was basified up to about pH 8 and extracted with ethyl acetate (3×30 mL). The combined extracts were dried and concentrated to get 5-benzyloxy-2-[1-(4-chlorophenyl)-cyclopentylmethyl]-6-hydroxypyrimidine-4-carboxylic acid cyclopropyl-(2-hydroxyethyl)-amide (326) as a brown sticky mass. This was used in the next step without purification.

LC-MS: 522.0 (M+H).

Synthesis of (327)

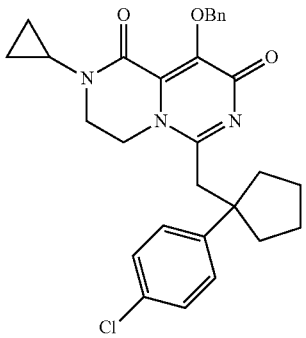 [SMILES: O=C1c2c(OCc3ccccc3)c(=O)nc(CC3(c4ccc(Cl)cc4)CCCC3)n2CCN1C1CC1]

9-Benzyloxy-6-[1-(4-chlorophenyl)-cyclopentylmethyl]-2-cyclopropyl-3,4-dihydro-2H-pyrazino[1,2-c]pyrimidine-1,8-dione 5-Benzyloxy-2-[1-(4-chlorophenyl)-cyclopentylmethyl]-6-hydroxypyrimidine-4-carboxylic acid cyclopropyl-(2-hy-droxyethyl)-amide (326) (90 mg, 0.17 mmol) and triphenylphosphine (90.5 mg, 0.35 mmol) were taken up in dichloromethane (3 ml) at room temperature followed by the slow addition of diisopropyl azodicarboxylate (52.34 mg, 0.26 mmol) and stirring for 1 h. Dichloromethane (15 ml) was added to the reaction mixture, which was subsequently washed with water (10 ml) and brine (10 ml). The organic part was dried and concentrated under reduced pressure. The obtained residue was purified by normal silica column using 30% ethyl acetate in hexane to get 9-benzyloxy-6-[1-(4-chlorophenyl)-cyclopentylmethyl]-2-cyclopropyl-3,4-dihydro-2H-pyrazino[1,2-c]pyrimidine-1,8-dione (327) (130 mg, 56%; 2 steps) as a sticky yellow solid.

LC-MS: 504.0 (M+H)

Synthesis of (328)

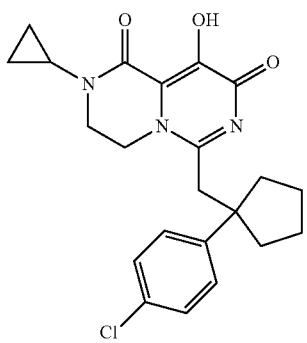 [SMILES: O=C1c2c(O)c(=O)nc(CC3(c4ccc(Cl)cc4)CCCC3)n2CCN1C1CC1]

6-[1-(4-chlorophenyl)-cyclopentylmethyl]-2-cyclopropyl-9-hydroxy-3,4-dihydro-2H-pyrazino[1,2-c]pyrimidine-1,8-dione 9-benzyloxy-6-[1-(4-chlorophenyl)-cyclopentylmethyl]-2-cyclopropyl-3,4-dihydro-2H-pyrazino[1,2-c]pyrimidine-1,8-dione (327) (30 mg, 0.06 mmol) was taken up in acetic acid (1 mL) and H$_2$SO$_4$ (0.2 mL) was added slowly to the reaction at 0° C. and stirring was continued at room temperature for 1 h. The reaction was quenched with aqueous saturated NaHCO$_3$ and extracted with ethyl acetate (2×15 ml). The combined extracts were dried and concentrated under reduced pressure. The obtained crude product was purified by preparative HPLC to get 6-[1-(4-chlorophenyl)-cyclopentylmethyl]-2-cyclopropyl-9-hydroxy-3,4-dihydro-2H-pyrazino[1,2-c]pyrimidine-1,8-dione (328) as an off-white solid (14 mg, 57%).

LC-MS: 414.0 (M+H)

Example 332

6-[1-(4-chlorophenyl)-cyclopentylmethyl]-2-cyclopropylmethyl-9-hydroxy-3,4-dihydro-2H-pyrazino[1,2-c]pyrimidine-1,8-dione The synthetic procedure used in this preparation is outlined in Scheme 46.

Synthesis of (329)

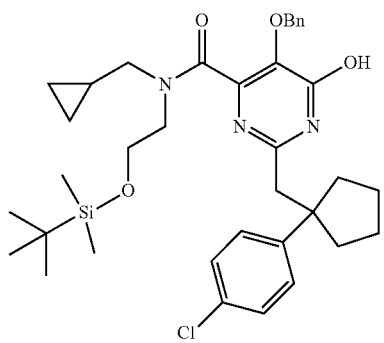 [SMILES: CC(C)(C)[Si](C)(C)OCCN(CC1CC1)C(=O)c1nc(CC2(c3ccc(Cl)cc3)CCCC2)nc(O)c1OCc1ccccc1]

5-Benzyloxy-2-[1-(4-chlorophenyl)-cyclopentylmethyl]-6-hydroxypyrimidine-4-carboxylic acid [2-(tert-butyl-dimethylsilanyloxy)-ethyl]-cyclopropylmethyl-amide To a stirred solution of 5-benzyloxy-2-[1-(4-chlorophenyl)-cyclopentylmethyl]-6-hydroxypyrimidine-4-carboxylic acid (324) (350 mg, 0.79 mmol) in dimethylformamide (7.5 mL) were added [2-(tert-butyl-dimethylsilanyloxy)-ethyl]-cyclopropylmethyl-amine (8i) (274 mg, 1.19 mmol) N,N-diisopropylethylamine (0.4 mL), 2.39 mmol) and HATU (364 mg, 0.96 mmol). The reaction mixture was stirred at room temperature for 1 h while silica thin layer chromatography was performed (ethyl acetate:hexane=1:1/UV/SiO$_2$, Rf=0.5). The reaction mixture was diluted with ethyl acetate (60 mL), washed with brine (3×30 mL) and dried and concentrated in vacuo to get a crude mass of 5-benzyloxy-2-[1-(4-chlorophenyl)-cyclopentylmethyl]-6-hydroxypyrimidine-4-carboxylic acid [2-(tert-butyl-dimethylsilanyloxy)-ethyl]-cyclopropylmethyl-amide (329) (600 mg) which was used directly in the next step without further purification.

LC-MS: 650.4 (M+H)

Synthesis of (330)

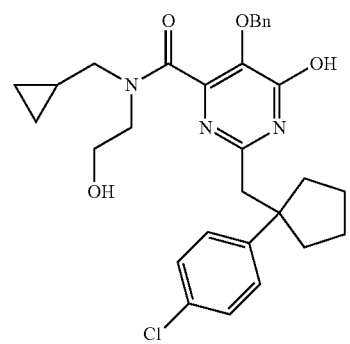 [SMILES: O=C(c1nc(CC2(c3ccc(Cl)cc3)CCCC2)nc(O)c1OCc1ccccc1)N(CCO)CC1CC1]

5-Benzyloxy-2-[1-(4-chlorophenyl)-cyclopentylmethyl]-6-hydroxypyrimidine-4-carboxylic acid cyclopropylmethyl-(2-hydroxyethyl)-amide To a stirred solution of 5-benzyloxy-2-[1-(4-chlorophenyl)-cyclopentylmethyl]-6-hydroxypyrimidine-4-carboxylic acid [2-(tert-butyl-dimethylsilanyloxy)-ethyl]-cyclopropylmethyl-amide (329) (580 mg, crude) in tetrahydrofuran (30 mL) was added 1N aq.HCl (6 mL) at room temperature and stirring was continued for 1 h (TLC; 100% ethyl acetate/UV/SiO$_2$, Rf=0.2). Tetrahydrofuran was removed in vacuo and the crude mass was dissolved in ethyl acetate (50 mL) and washed with NaHCO$_3$ solution (10 mL), water (20 mL) and brine (20 mL); The organic phase was dried and concentrated in vacuo to get a crude mass which was purified by Combi-Flash using a gradient eluent mixture of ethyl acetate and hexane to get pure 5-benzyloxy-2-[1-(4-chlorophenyl)-cyclopentylmethyl]-6-hydroxypyrimidine-4-carboxylic acid cyclopropylmethyl-(2-hydroxyethyl)-amide (330) (390 mg, 94% two steps) as an off-white sticky solid.

LC-MS: 536.0 (M+H)

Synthesis of (331)

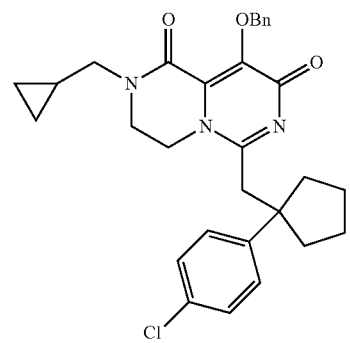 [SMILES: O=C1c2c(OCc3ccccc3)c(=O)nc(CC3(c4ccc(Cl)cc4)CCCC3)n2CCN1CC1CC1]

9-Benzyloxy-6-[1-(4-chlorophenyl)-cyclopentylmethyl]-2-cyclopropylmethyl-3,4-dihydro-2H-pyrazino[1,2-c]pyrimidine-1,8-dione To a solution of 5-benzyloxy-2-[1-(4-chlorophenyl)-cyclopentylmethyl]-6-hydroxypyrimidine-4-carboxylic acid cyclopropylmethyl-(2-hydroxyethyl)-amide (330) (390 mg, 0.73 mmol) in dichloromethane (30 mL) was added triphenyl phosphine (286 mg, 1.09 mmol) and diisopropyl azodicarboxylate (0.22 mL, 1.09 mmol) at room temperature the reaction was stirred for 30 minutes (TLC; 5% methanol in ethyl acetate/UV/SiO$_2$, Rf=0.05). The dichloromethane was removed in vacuo and the crude mass was purified by silica gel (normal, 100-200 mesh) column chromatography using gradient eluent of 1% to 5% methanol in dichloromethane to get pure 9-benzyloxy-6-[1-(4-chlorophenyl)-cyclopentylmethyl]-2-cyclopropylmethyl-3,4-dihydro-2H-pyrazino[1,2-c]pyrimidine-1,8-dione (331) (280 mg, 74%) as a white sticky solid.

LC-MS: 518.0 (M+H)

Synthesis of (332)

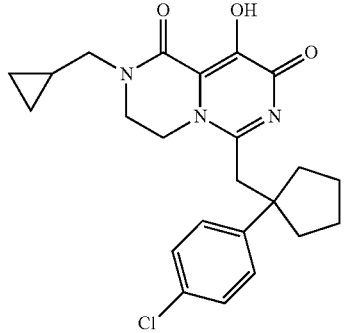 [SMILES: O=C1c2c(O)c(=O)nc(CC3(c4ccc(Cl)cc4)CCCC3)n2CCN1CC1CC1]

6-[1-(4-chlorophenyl)-cyclopentylmethyl]-2-cyclopropylmethyl-9-hydroxy-3,4-dihydro-2H-pyrazino[1,2-c]pyrimidine-1,8-dione To a solution of 9-benzyloxy-6-[1-(4-chlorophenyl)-cyclopentylmethyl]-2-cyclopropylmethyl-3,4-dihydro-2H-pyrazino[1,2-c]pyrimidine-1,8-dione (331) (200 mg, 0.38 mmol) in acetic acid (6.0 mL) was added H$_2$SO$_4$ (0.05 mL) at 0° C. and the reaction mixture was stirred at room temperature for 2 h (TLC; 5% methanol in dichloromethane/UV/SiO$_2$, Rf=0.3). The reaction mixture was quenched with NaHCO$_3$ solution, diluted with water and extracted with ethyl acetate (2×50 mL). The organic part was washed with water (40 mL) and brine (40 mL). The organic phase was thereafter dried and concentrated in vacuo to get a brownish gummy mass which was dissolved in dichloromethane (1 mL). 5 mL of hexane was added to the solution and the solid formed was allowed to settle down. The liquid phase was removed by decantation and the solid was triturated with diethyl ether and n-pentane to get pure 6-[1-(4-chlorophenyl)-cyclopentylmethyl]-2-cyclopropylmethyl-9-hydroxy-3,4-dihydro-2H-pyrazino[1,2-c]pyrimidine-1,8-dione (332) (86 mg, 52%) as a light brown solid.

LC-MS: 427.8 (M+H)

Example 336

6-[1-(4-chlorophenyl)-cyclopentylmethyl]-9-hydroxy-2-(tetrahydro-pyran-4-yl)-3,4-dihydro-2H-pyrazino[1,2-c]pyrimidine-1,8-dione The synthetic procedure used in this preparation is outlined in Schemes 46.

Synthesis of (333)

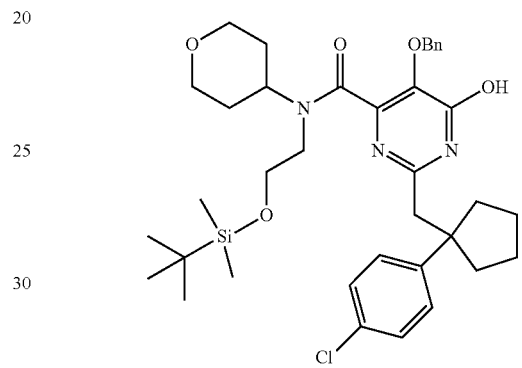

5-Benzyloxy-2-[1-(4-chlorophenyl)-cyclopentylmethyl]-6-hydroxypyrimidine-4-carboxylic acid [2-(tert-butyl-dimethylsilanyloxy)-ethyl]-(tetrahydro-pyran-4-yl)-amide 5-Benzyloxy-2-[1-(4-chlorophenyl)-cyclopentylmethyl]-6-hydroxypyrimidine-4-carboxylic acid (324) (150 mg, 0.34 mmol) and [2-(tert-butyl-dimethylsilanyloxy)-ethyl]-(tetrahydro-pyran-4-yl)-amine (8j) were taken up in dimethylformamide (3 ml). HATU (195.2 mg, 0.51 mmol) and N,N-diisopropylethylamine (110.4 mg, 0.86 mmol) were added at room temperature and the reaction mixture was stirred for 16 h (monitored by LC-MS). To the reaction, water was added (10 ml) and the mixture was stirred for 5 min. Thereafter, the aqueous mixture was extracted with ethyl acetate (2×15 ml) and the combined extracts were washed with water (3×10 ml), dried and concentrated under reduced pressure. The obtained crude product was purified by normal silica gel column chromatography (100-200 mesh) using 30% ethyl acetate in hexane as mobile phase to get pure 5-benzyloxy-2-[1-(4-chlorophenyl)-cyclopentylmethyl]-6-hydroxypyrimidine-4-carboxylic acid [2-(tert-butyl-dimethylsilanyloxy)-ethyl]-(tetrahydro-pyran-4-yl)-amide (333) (130 mg, 56%) as a yellow sticky solid.

LC-MS: 680.2 (M+H).

Synthesis of (334)

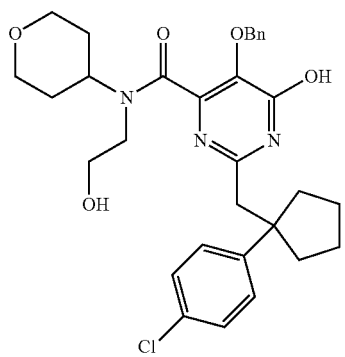 [SMILES: O=C(c1nc(CC2(c3ccc(Cl)cc3)CCCC2)nc(O)c1OCc1ccccc1)N(CCO)C1CCOCC1]

5-Benzyloxy-2-[1-(4-chlorophenyl)-cyclopentylmethyl]-6-hydroxypyrimidine-4-carboxylic acid (2-hydroxyethyl)-(tetrahydro-pyran-4-yl)-amide To a stirred solution of 5-benzyloxy-2-[1-(4-chlorophenyl)-cyclopentylmethyl]-6-hydroxypyrimidine-4-carboxylic acid [2-(tert-butyl-dimethylsilanyloxy)-ethyl]-(tetrahydro-pyran-4-yl)-amide (333) in tetrahydrofuran (3 ml) was added 1N HCl (1 ml) at room temperature and the reaction mixture was stirred for 30 min at room temperature while silica thin layer chromatography was performed (ethyl acetate:hexane=3:2, Rf=0.4). After completion of the reaction, solid NaHCO₃ was added and the mixture basified up to about pH 8. After extraction with ethyl acetate (3×30 mL), the combined extracts were dried and concentrated to get 5-benzyloxy-2-[1-(4-chlorophenyl)-cyclopentylmethyl]-6-hydroxypyrimidine-4-carboxylic acid (2-hydroxyethyl)-(tetrahydro-pyran-4-yl)-amide (334) which was used in the next step without purification.

Synthesis of (335)

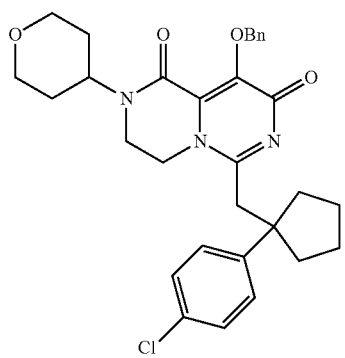 [SMILES: O=C1c2c(OCc3ccccc3)c(=O)nc(CC3(c4ccc(Cl)cc4)CCCC3)n2CCN1C1CCOCC1]

9-Benzyloxy-6-[1-(4-chlorophenyl)-cyclopentylmethyl]-2-(tetrahydro-pyran-4-yl)-3,4-dihydro-2H-pyrazino[1,2-c]pyrimidine-1,8-dione 5-Benzyloxy-2-[1-(4-chlorophenyl)-cyclopentylmethyl]-6-hydroxypyrimidine-4-carboxylic acid (2-hydroxyethyl)-(tetrahydro-pyran-4-yl)-amide (334) (90 mg, 0.16 mmol) and triphenylphosphine were taken up in dichloromethane (3 ml) at room temperature and diisopropyl azodicarboxylate was added slowly. Stirring was continued for 1 h while silica thin layer chromatography was performed (ethyl acetate:hexane=1:1, Rf=0.6). Dichloromethane (15 ml) was added to the reaction mixture, which was thereafter washed with water (10 ml) and brine (10 ml). The organic part was dried and concentrated under reduced pressure. The obtained residue was purified by normal silica gel (100-20 mesh) column chromatography using 30% ethyl acetate in hexane to get 9-benzyloxy-6-[1-(4-chlorophenyl)-cyclopentylmethyl]-2-(tetrahydro-pyran-4-yl)-3,4-dihydro-2H-pyrazino[1,2-c]pyrimidine-1,8-dione (335) (50 mg, 60%; 2 steps yield).

LC-MS: 548.0 (M+H)

Preparation of (336)

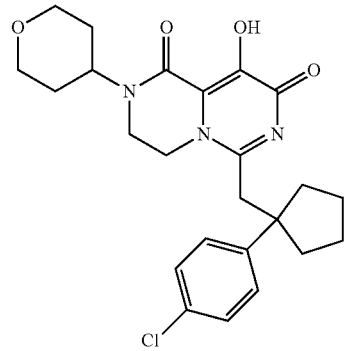 [SMILES: O=C1c2c(O)c(=O)nc(CC3(c4ccc(Cl)cc4)CCCC3)n2CCN1C1CCOCC1]

6-[1-(4-chlorophenyl)-cyclopentylmethyl]-9-hydroxy-2-(tetrahydro-pyran-4-yl)-3,4-dihydro-2H-pyrazino [1,2-c]pyrimidine-1,8-dione (16252)

To a stirred solution of 9-benzyloxy-6-[1-(4-chlorophenyl)-cyclopentylmethyl]-2-(tetrahydro-pyran-4-yl)-3,4-dihydro-2H-pyrazino[1,2-c]pyrimidine-1,8-dione (335) in acetic acid (1 mL), concentrated $H_2SO_4$ (0.001 mL, 0.02 mmol) was added and stirred for 4 h at room temperature (monitored by LC-MS). After completion of the reaction, volatiles were removed from the reaction mixture, and the mixture was quenched with ice-cold water (5 mL). Saturated aqueous NaHCO₃ (adjusted pH to 8) was added and the quenched mixture was extracted with ethyl acetate (2×15 mL). The combined extracts were dried and concentrated. The resulting residue was washed with 10% dichloromethane in ether to get 6-[1-(4-chlorophenyl)-cyclopentylmethyl]-9-hydroxy-2-(tetrahydro-pyran-4-yl)-3,4-dihydro-2H-pyrazino[1,2-c]pyrimidine-1,8-dione (336) (19 mg, 41%) as an off-white solid.

LC-MS: 457.8 (M+H).

General Procedure for Examples 337 to 373
The synthetic procedures are outlined in Scheme 47.
General Synthetic Route for 349, 353, 357, 361, 365, 369, 373
Scheme 47
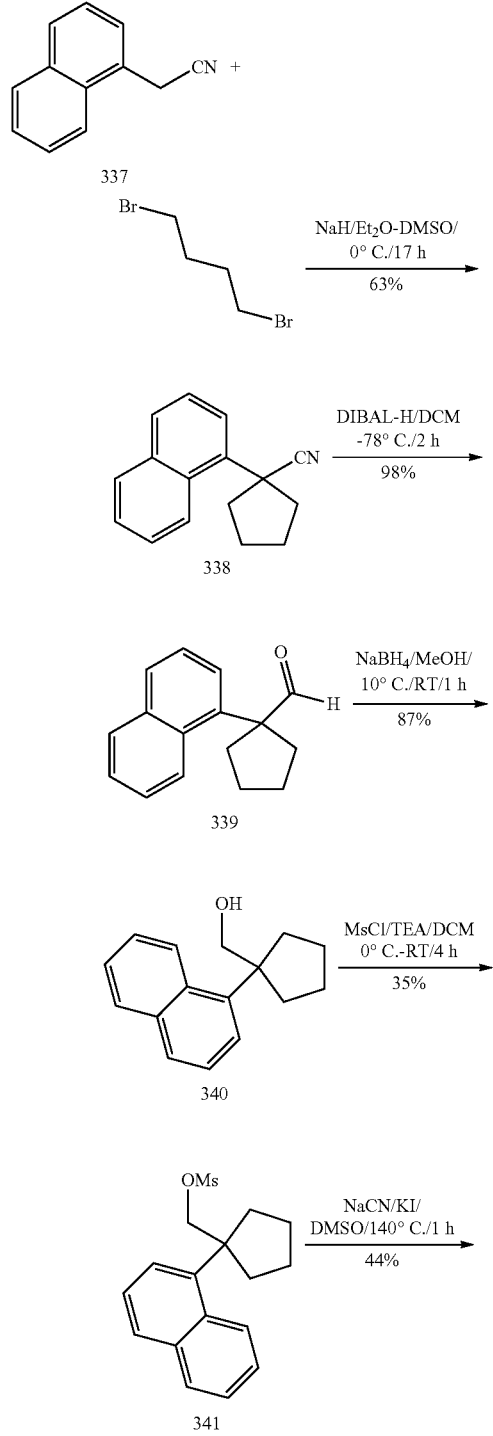
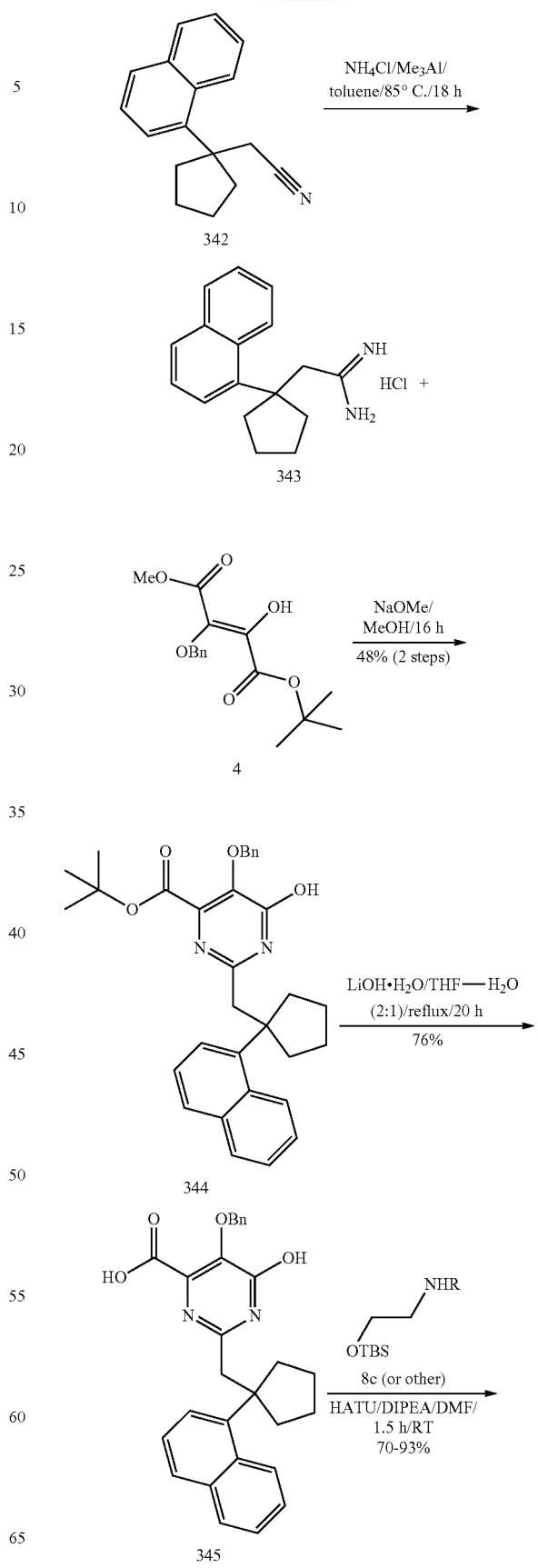

313
-continued

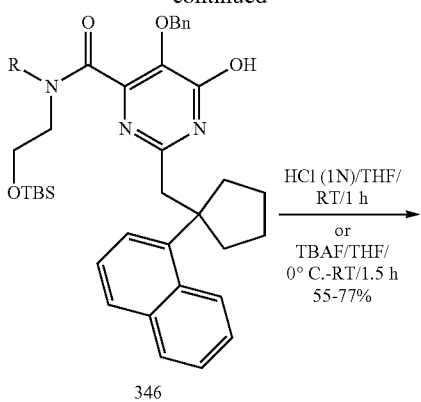

346

HCl (1N)/THF/
RT/1 h
or
TBAF/THF/
0° C.-RT/1.5 h
55-77%

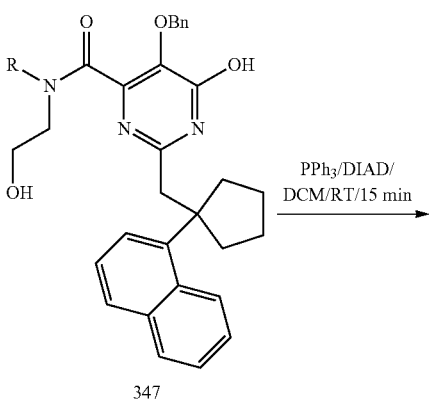

347

PPh₃/DIAD/
DCM/RT/15 min

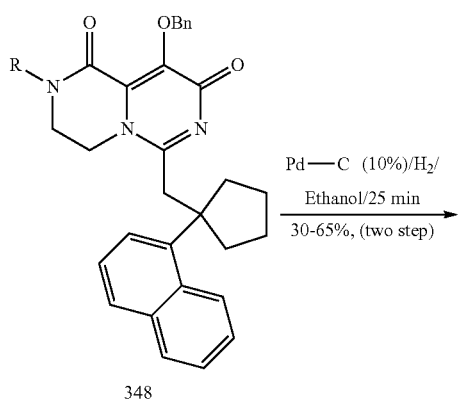

348

Pd—C (10%)/H₂/
Ethanol/25 min
30-65%, (two step)

314
-continued

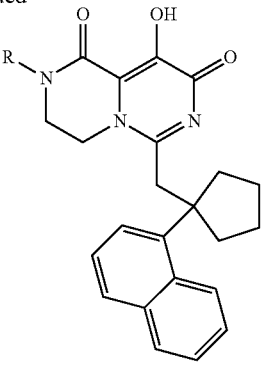

349
349 R = H
353 R = methyl
357 R = cyclopropyl
361 R = cyclopropylmethyl
365 R = oxetan-3-yl
369 R = 2H-pyran-4-yl
373 R = benzyl Synthesis of (338)

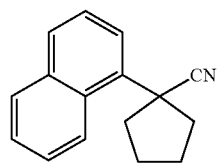 [SMILES: N#CC1(c2cccc3ccccc23)CCCC1]

1-Naphthalen-1-yl-cyclopentanecarbonitrile

To a suspension of sodium hydride (60% in mineral oil, 5.24 g, 131.6 mmol) in dimethyl sulfoxide (50 mL) was added dropwise a mixture of naphthalen-1-yl-acetonitrile (337) (10.0 g, 59.8 mmol) and 1,4-dibromobutane (12.91 g, 59.8 mmol) dissolved in dimethyl sulfoxide-ether (1:1; 120 mL) at 0° C. and stirred for 30 min at the same temperature and then stirred at room temperature for 4 h (silica TLC, 10% ethyl acetate in hexane, Rf=0.65). The reaction mixture was quenched with HCl [1N; 20 mL] at 0° C. Ethyl acetate (400 mL) was added and the mixture was washed with water (500 mL) and brine (2×200 ml) and dried and concentrated in vacuo to get a crude mass which was purified by CombiFlash using a gradient eluent; mixture of ethyl acetate and hexane to get pure 1-naphthalen-1-yl-cyclopentanecarbonitrile (338) (8.4 g, 63%) as a white solid.

Synthesis of (339)

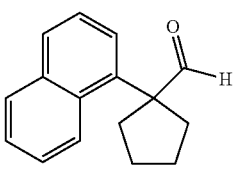 [SMILES: O=CC1(c2cccc3ccccc23)CCCC1]

1-Naphthalen-1-yl-cyclopentanecarbaldehyde

To a solution of 1-naphthalen-1-yl-cyclopentanecarbonitrile (338) (10.5 g, 47.4 mmol) in dichloromethane (150 mL) was added dropwise diisobutylaluminium hydride (25% in toluene, 67.5 mL, 118.6 mmol) at −78° C. and stirred for 2 h at the same temperature (silica TLC, 5% ethyl acetate in hexane; Rf=0.6). The reaction mixture was quenched with a saturated aqueous solution of potassium sodium tarterate (35 mL) and stirred for 17 h at room temperature. The reaction mixture was filtered and the residue was washed with dichloromethane. The organic phase was separated and the aqueous part was back extracted with dichloromethane (100 mL). The combined organic part was dried, filtered and concentrated in vacuo to get a crude mass which was purified by CombiFlash using gradient eluent mixture of ethyl acetate and hexane to obtain pure 1-naphthalen-1-yl-cyclopentanecarbaldehyde (339) (10.4 g, 98%) as a colorless sticky liquid.

Synthesis of (340)

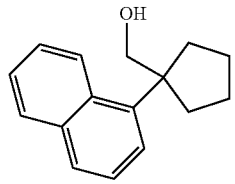 [SMILES: OCC1(c2cccc3ccccc23)CCCC1]

(1-Naphthalen-1-yl-cyclopentyl)-methanol

A solution of 1-naphthalen-1-yl-cyclopentanecarbaldehyde (339) (10 g, 44.6 mmol) in methanol (150 mL) was cooled to 0° C. and NaBH$_4$ (3.373 g, 89.2 mmol) was added in portions (8 portions). After the addition was completed the reaction mixture was allowed to stir at room temperature for 1 h (silica TLC, 10% ethyl acetate in hexane; Rf=0.3). The reaction mixture was quenched with aqueous NH$_4$Cl solution and concentrated in vacuo as much as possible; diluted with water (100 mL) and extracted with ethyl acetate (2×100 mL). The organic part was washed with brine (50 mL), dried and concentrated in vacuo to get a crude mass which was purified by CombiFlash using gradient eluent mixture of ethyl acetate and hexane to get pure (1-naphthalen-1-yl-cyclopentyl)-methanol (340) (8.75 g, 87%) as a white solid.

Synthesis of (341)

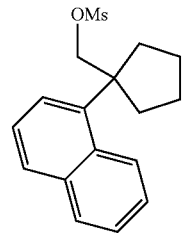 [SMILES: CS(=O)(=O)OCC1(c2cccc3ccccc23)CCCC1]

Methanesulfonic acid 1-naphthalen-1-yl-cyclopentylmethyl ester

To a solution of (1-naphthalen-1-yl-cyclopentyl)-methanol (340) (9.0 g, 39.8 mmol) in dichloromethane (180 mL) was added triethylamine (11.0 mL, 79.5 mL) and the reaction mixture was cooled to 0° C. To this reaction mixture was added mesylchloride and stirring was continued at room temperature for 18 h (silica TLC, 10% ethyl acetate in hexane; Rf=0.2). The reaction mass was diluted with dichloromethane (100 mL), washed with water (2×100 mL) and brine (100 mL) and dried and concentrated in vacuum to get a crude mass which was purified by Combi-Flash using gradient eluent mixture of ethyl acetate and hexane to get pure methanesulfonic acid 1-naphthalen-1-yl-cyclopentylmethyl ester (341) (4.25 g, 35%) as a white solid.

Synthesis of (342)

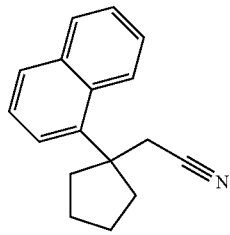 [SMILES: N#CCC1(c2cccc3ccccc23)CCCC1]

(1-Naphthalen-1-yl-cyclopentyl)-acetonitrile

To a stirred solution of methanesulfonic acid 1-naphthalen-1-yl-cyclopentylmethyl ester (341) (2.1 g, 6.90 mmol) in dimethyl sulfoxide (10.0 mL) were added KI (115 mg, 0.69 mmol) and NaCN (507 mg, 10.35 mmol) and the reaction mixture was stirred at 140° C. for 2 h (silica TLC, 10% ethyl acetate in hexane; Rf=0.5). The reaction mass was cooled to room temperature, quenched with FeSO$_4$ solution (15 mL) and diluted with water (100 mL). The resulting solid was separated through filtration and washed well with ethyl acetate. The biphasic layer was separated in a separating funnel. The organic part was washed with brine (2×50 mL), dried and concentrated in vacuo to get a crude mass which was purified by Combi-Flash using a mixture of ethyl acetate and hexane as gradient eluent to get pure (1-naphthalen-1-yl-cyclopentyl)-acetonitrile (342) (710 mg, 44%) as a yellow gummy liquid.

Synthesis of (343)

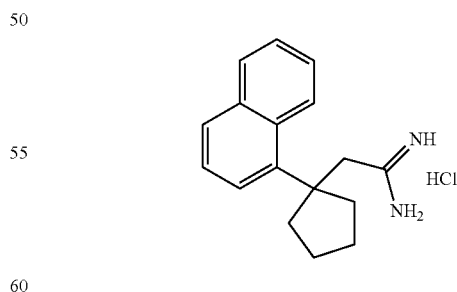

2-(1-Naphthalen-1-yl-cyclopentyl)-acetamidine; hydrochloride

To a stirred suspension of NH$_4$Cl (2.659 g, 49.72 mmol) in dry toluene (80 mL) was added tri-methyl aluminum (2M in toluene, 25.0 mL, 49.72 mmol) slowly at 5° C. then warm to room temperature and stirred for 2 h. A solution of (1-naphthalen-1-yl-cyclopentyl)-acetonitrile (342) (3.9 g, 16.57 mmol) in toluene (5 mL) was added to the above reaction mixture and stirred for 18 h at 85° C. (reaction was monitored by LC-MS). The reaction mixture was cooled to 0° C. and quenched with a suspension of silica gel in chloroform and then stirred for 0.5 h at room temperature. After being filtered through a sintered funnel, the residue was washed well with methanol and the combined filtrate was concentrated under reduced pressure to get a crude mass. 10% methanol in dichloromethane was added to the residue, from which the insoluble material was again filtered off and the filtrate was concentrated in vacuum to get semi pure 2-(1-naphthalen-1-yl-cyclopentyl)-acetamidine; hydrochloride (343) (4.5 g) as a brown sticky mass. This raw product was used in the next step without purification.

LC-MS: 252.6 (M+H)

Synthesis of (344)

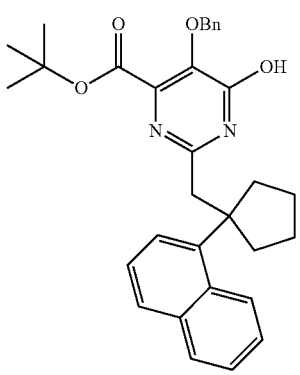 [SMILES: CC(C)(C)OC(=O)c1nc(CC2(c3cccc4ccccc34)CCCC2)nc(O)c1OCc1ccccc1]

5-Benzyloxy-6-hydroxy-2-(1-naphthalen-1-yl-cyclopentylmethyl)-pyrimidine-4-carboxylic acid tert-butyl ester To a stirred solution of 2-(1-naphthalen-1-yl-cyclopentyl)-acetamidine; hydrochloride (343) (4.5 g, crude) in methanol (30 mL) were added (E,Z)-2-benzyloxy-3-hydroxy-but-2-enedioic acid 4-tert-butyl ester 1-methyl ester (4) (5.759 g, 18.7 mmol) and the reaction mixture was cooled to 0° C. in a ice bath. To this reaction mixture was then added sodium methoxide (25% in methanol, 10.1 mL, 46.74 mmol) and the reaction mixture was stirred at room temperature for 18 h (silica TLC, 50% ethyl acetate in hexane; Rf=0.5). The reaction mixture was diluted with ethyl acetate (100 mL) and washed with water (50 mL) and brine (50 mL). The organic phase was thereafter dried and concentrated under vacuum to get a crude mass which was purified by CombiFlash eluted with a gradient mixture of ethyl acetate and hexane to get pure 5-benzyloxy-6-hydroxy-2-(1-naphthalen-1-yl-cyclopentylmethyl)-pyrimidine-4-carboxylic acid tert-butyl ester (344) (4.1 g, 48%, 2 steps) as a brown sticky mass.

LC-MS: 511.0 (M+H)

Synthesis of (345)

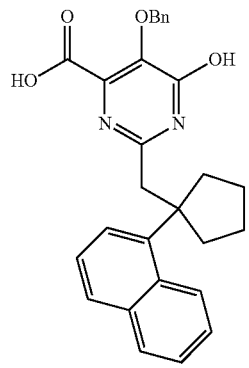 [SMILES: O=C(O)c1nc(CC2(c3cccc4ccccc34)CCCC2)nc(O)c1OCc1ccccc1]

5-Benzyloxy-6-hydroxy-2-(1-naphthalen-1-yl-cyclopentylmethyl)-pyrimidine-4-carboxylic acid To a solution of 5-benzyloxy-6-hydroxy-2-(1-naphthalen-1-yl-cyclopentylmethyl)-pyrimidine-4-carboxylic acid tert-butyl ester (344) (3.9 g, 7.64 mmol) in tetrahydrofuran (60 mL) and water (12 mL) was added LiOH.H$_2$O (3.2 g, 76.4 mmol) and the reaction mixture heated to reflux for 20 h (the reaction was monitored by LC-MS), tetrahydrofuran was removed from the reaction mixture under vacuum and the residue was diluted with water (50 mL). The aqueous layer was washed with ethyl acetate (2×50 mL) and then acidified with 1N HCl to pH 3. A white solid was separated by filtration and dried in vacuum to get pure 5-benzyloxy-6-hydroxy-2-(1-naphthalen-1-yl-cyclopentylmethyl)-pyrimidine-4-carboxylic acid (345) (2.65 g, 76%) as a white solid.

LC-MS: 455.0 (M+H)

Example 349

9-Hydroxy-6-(1-naphthalen-1-yl-cyclopentylmethyl)-3,4-dihydro-2H-pyrazino[1,2-c]pyrimidine-1,8-dione The synthetic procedure used in this preparation is outlined in Schemes 47.

Synthesis of (346)

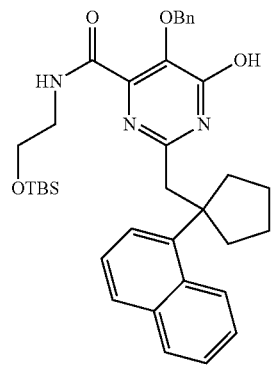 [SMILES: CC(C)(C)[Si](C)(C)OCCNC(=O)c1nc(CC2(c3cccc4ccccc34)CCCC2)nc(O)c1OCc1ccccc1]

319

5-Benzyloxy-6-hydroxy-2-(1-naphthalen-1-yl-cyclopentylmethyl)-pyrimidine-4-carboxylic acid [2-(tert-butyl-dimethylsilanyloxy)-ethyl]-amide To a stirred solution of 5-benzyloxy-6-hydroxy-2-(1-naphthalen-1-yl-cyclopentylmethyl)-pyrimidine-4-carboxylic acid (345) (250 mg, 0.55 mmol) in dimethylformamide (7.5 mL) were added N,N-diisopropylethylamine (0.27 mL, 1.65 mmol), 2-(tert-butyl-dimethylsilanyloxy)-ethylamine (8c) (145 mg, 0.83 mmol) and HATU (251 mg, 0.66 mmol) and the reaction mixture was stirred at room temperature for 1.5 h (silica TLC, 50% ethyl acetate in hexane, Rf=0.5). The reaction mass was diluted with ethyl acetate (60 ml) and washed with brine (3×30 mL). The organic phase was thereafter dried and concentrated in vacuo to get a crude mass which was purified by CombiFlash using a gradient eluent mixture of ethyl acetate and hexane to get pure 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-amide (346) (315 mg, 94%) as a white solid.

LC-MS: 612.2 (M+H)

Synthesis of (347)

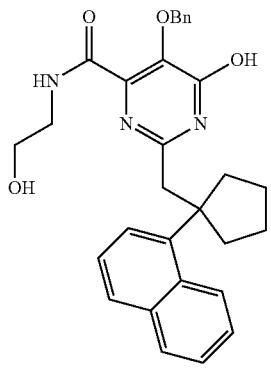 [SMILES: O=C(NCCO)c1nc(CC2(c3cccc4ccccc34)CCCC2)nc(O)c1OCc1ccccc1]

5-Benzyloxy-6-hydroxy-2-(1-naphthalen-1-yl-cyclopentylmethyl)-pyrimidine-4-carboxylic acid (2-hydroxyethyl)-amide To a stirred solution of 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-amide (346) (290 mg, 0.48 mmol) in tetrahydrofuran (15.0 mL) was added 1N HCl (3.0 mL) at room temperature and the reaction mixture was stirred for 1 h at the same temperature (silica TLC, 5% methanol in dichloromethane/SiO$_2$/UV, Rf=0.5). The tetrahydrofuran was removed in vacuum and the solid obtained was filtered through a sintered funnel, washed with water and ether and dried in vacuum to get pure 5-benzyloxy-6-hydroxy-2-(1-naphthalen-1-yl-cyclopentylmethyl)-pyrimidine-4-carboxylic acid (2-hydroxyethyl)-amide (347) (140 mg, 59%) as a white solid.

LC-MS: 498.4 (M+H)

320

Synthesis of (348)

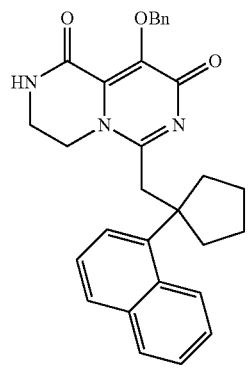 [SMILES: O=C1NCCn2c(CC3(c4cccc5ccccc45)CCCC3)nc(=O)c(OCc3ccccc3)c21]

9-Benzyloxy-6-(1-naphthalen-1-yl-cyclopentylmethyl)-3,4-dihydro-2H-pyrazino[1,2-c]pyrimidine-1,8-dione To a solution mixture of 5-benzyloxy-6-hydroxy-2-(1-naphthalen-1-yl-cyclopentylmethyl)-pyrimidine-4-carboxylic acid (2-hydroxyethyl)-amide (347) (140 mg, 0.28 mmol) and diisopropyl azodicarboxylate (0.28 mL, 1.41 mmol) in dichloromethane (70 mL) was added triphenyl phosphine (443 mg, 1.69 mmol) at room temperature and the reaction mixture was stirred for 15 min at the same temperature. The yellow color disappeared (silica TLC, ethyl acetate 100%; Rf=0.2). The dichloromethane was removed in vacuum to get 9-benzyloxy-6-(1-naphthalen-1-yl-cyclopentylmethyl)-3,4-dihydro-2H-pyrazino[1,2-c]pyrimidine-1,8-dione (348) (650 mg, crude) which was used directly in the next step without purification.

LC-MS: 480.0 (M+H)

Synthesis of (349)

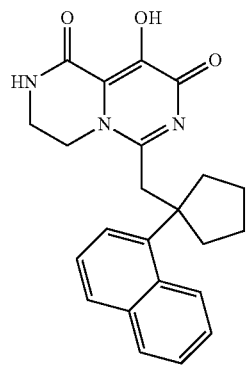 [SMILES: O=C1NCCn2c(CC3(c4cccc5ccccc45)CCCC3)nc(=O)c(O)c21]

9-Hydroxy-6-(1-naphthalen-1-yl-cyclopentylmethyl)-3,4-dihydro-2H-pyrazino[1,2-c]pyrimidine-1,8-dione A solution of 9-benzyloxy-6-(1-naphthalen-1-yl-cyclopentylmethyl)-3,4-dihydro-2H-pyrazino[1,2-c]pyrimidine- 1,8-dione (348) (650 mg, crude) in ethanol (50 mL) was degassed under nitrogen, followed by the addition of Pd—C (10%) (100 mg) and again degassed under nitrogen. The reaction mixture was then stirred under hydrogen atmosphere of balloon pressure for 25 min at room temperature (while the reaction was monitored by LC-MS). The reaction mixture was filtered through a celite bed and the filtrate was concentrated in vacuo to obtain crude sticky mass. The crude mass was dissolved in dichloromethane (5 mL), and hexane (20 mL) was added dropwise with constant stirring to get a precipitated solid. The solid was separated by decantation and washed well with diethyl ether and then with n-pentane and dried in vacuum to get pure 9-hydroxy-6-(1-naphthalen-1-yl-cyclopentylmethyl)-3,4-dihydro-2H-pyrazino[1,2-c]pyrimidine-1,8-dione (349) (48 mg, 44%, two step yield) as an off-white solid.

LC-MS: 390.3 (M+H)

Example 353

9-Hydroxy-2-methyl-6-(1-naphthalen-1-yl-cyclopentylmethyl)-3,4-dihydro-2H-pyrazino[1,2-c]pyrimidine-1,8-dione The synthetic procedure used in this preparation is outlined in Schemes 47.

Synthesis of (350)

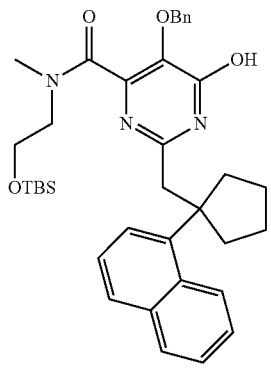 [SMILES: CN(CCO[Si](C)(C)C(C)(C)C)C(=O)c1nc(CC2(c3cccc4ccccc34)CCCC2)nc(O)c1OCc1ccccc1]

5-Benzyloxy-6-hydroxy-2-(1-naphthalen-1-yl-cyclopentylmethyl)-pyrimidine-4-carboxylic acid [2-(tert-butyl-dimethylsilanyloxy)-ethyl]methyl-amide To a stirred solution of 5-benzyloxy-6-hydroxy-2-(1-naphthalen-1-yl-cyclopentylmethyl)-pyrimidine-4-carboxylic acid (345) (300 mg, 0.66 mmol) in dimethylformamide (7.5 mL) were added N,N-diisopropylethylamine (0.33 mL, 1.98 mmol), [2-(tert-butyl-dimethylsilanyloxy)-ethyl]-methylamine (8a) (187 mg, 0.99 mmol) and HATU (301 mg, 0.79 mmol) and the reaction mixture was stirred at room temperature for 1.5 h (silica TLC, 50% ethyl acetate in hexane/SiO$_2$/UV, Rf=0.6) The reaction mass was diluted with ethyl acetate (100 ml) and washed with brine (3×50 mL). The organic phase was thereafter dried and concentrated in vacuo to get a crude mass which was purified by Combi-Flash using a mixture of ethyl acetate and hexane as eluting solvent to get pure 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-methyl-amide (350) (310 mg, 75%) as a light yellow sticky solid.

LC-MS: 625.8 (M+H)

Synthesis of (351)

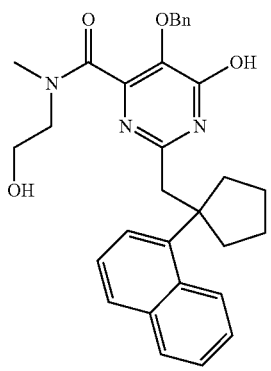 [SMILES: CN(CCO)C(=O)c1nc(CC2(c3cccc4ccccc34)CCCC2)nc(O)c1OCc1ccccc1]

5-Benzyloxy-6-hydroxy-2-(1-naphthalen-1-yl-cyclopentylmethyl)-pyrimidine-4-carboxylic acid (2-hydroxyethyl)-methyl-amide To a stirred solution of 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-methyl-amide (350) (280 mg, 0.45 mmol) in tetrahydrofuran (30.0 mL) was added 1N HCl (6.0 mL) at room temperature and the reaction mixture was stirred for 1 h at the same temperature (silica TLC, 5% methanol in dichloromethane, Rf=0.5). The tetrahydrofuran was removed under vacuum and the residue was diluted with water and extracted with ethyl acetate (2×25 mL). The organic layer was washed with NaHCO$_3$ solution (10 mL), water (20 mL) and brine (20 mL). The organic layer was dried and concentrated in vacuum to get a crude mass which was purified by CombiFlash using gradient eluent of ethyl acetate and hexane mixture to get pure 5-benzyloxy-6-hydroxy-2-(1-naphthalen-1-yl-cyclopentylmethyl)-pyrimidine-4-carboxylic acid (2-hydroxyethyl)-methyl-amide (351) (145 mg, 63%) as a white solid.

LC-MS: 512.0 (M+H)

Synthesis of (352)

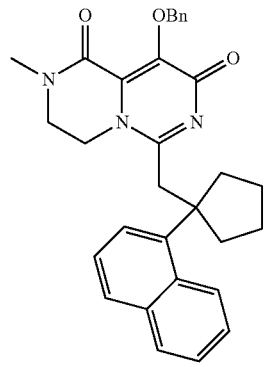 [SMILES: CN1CCn2c(CC3(c4cccc5ccccc45)CCCC3)nc(=O)c(OCc3ccccc3)c2C1=O]

9-Benzyloxy-2-methyl-6-(1-naphthalen-1-yl-cyclopentylmethyl)-3,4-dihydro-2H-pyrazino[1,2-c]pyrimidine-1,8-dione To a solution of 5-benzyloxy-6-hydroxy-2-(1-naphthalen-1-yl-cyclopentylmethyl)-pyrimidine-4-carboxylic acid (2-hydroxyethyl)-methyl-amide (351) (85 mg, 0.17 mmol) in dichloromethane (20 mL) was added triphenyl phosphine (174 mg, 0.67 mmol) and the reaction mixture was cooled to 0° C., followed by the addition of diisopropyl azodicarboxylate (0.2 mL, 0.1 mmol). The reaction mixture was stirred for 15 min at the same temperature (silica TLC, 5% methanol in ethyl acetate; Rf=0.3). The dichloromethane was removed in vacuum and the crude mass was purified by silica gel (normal, 100-200 mesh) column chromatography using a gradient eluent mixture of 50% ethyl acetate in hexane to 100% ethyl acetate to get 9-benzyloxy-2-methyl-6-(1-naphthalen-1-yl-cyclopentylmethyl)-3,4-dihydro-2H-pyrazino[1,2-c]pyrimidine-1,8-dione (352) (85 mg, semi pure) as a white sticky solid.

LC-MS: 494.0 (M+H)

Synthesis of (353): (16251)

9-Hydroxy-2-methyl-6-(1-naphthalen-1-yl-cyclopentylmethyl)-3,4-dihydro-2H-pyrazino[1,2-c]pyrimidine-1,8-dione This compound was prepared by following the same method as described for pure 9-hydroxy-6-(1-naphthalen-1-yl-cyclopentylmethyl)-3,4-dihydro-2H-pyrazino[1,2-c]pyrimidine-1,8-dione (349) from 9-benzyloxy-2-methyl-6-(1-naphthalen-1-yl-cyclopentylmethyl)-3,4-dihydro-2H-pyrazino[1,2-c]pyrimidine-1,8-dione (352) (85 mg, 0.17 mmol). The yield was 35 mg, 50% (white solid).

LC-MS: 404.2 (M+H)

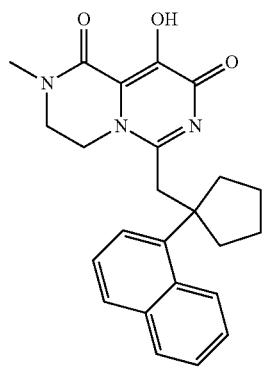 [SMILES: CN1CCn2c(CC3(c4cccc5ccccc45)CCCC3)nc(=O)c(O)c2C1=O]

Example 357

2-Cyclopropyl-9-hydroxy-6-(1-naphthalen-1-yl-cyclopentylmethyl)-3,4-dihydro-2H-pyrazino[1,2-c]pyrimidine-1,8-dione The synthetic procedure used in this preparation is outlined in Schemes 47.

Synthesis of (354)

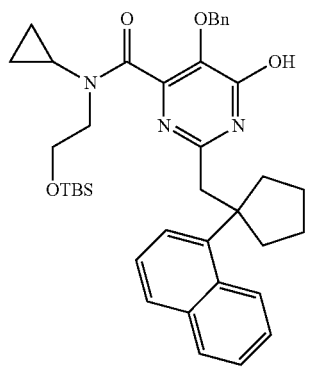 [SMILES: CC(C)(C)[Si](C)(C)OCCN(C(=O)c1nc(CC2(c3cccc4ccccc34)CCCC2)nc(O)c1OCc1ccccc1)C1CC1]

5-Benzyloxy-6-hydroxy-2-(1-naphthalen-1-yl-cyclopentylmethyl)-pyrimidine-4-carboxylic acid [2-(tert-butyl-dimethylsilanyloxy)-ethyl]-cyclopropyl-amide This compound was prepared following the same method as described for 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-methyl-amide (350) from 5-benzyloxy-6-hydroxy-2-(1-naphthalen-1-yl-cyclopentylmethyl)-pyrimidine-4-carboxylic acid (345) (250 mg, 0.55 mmol) and [2-(tert-butyl-dimethylsilanyloxy)-ethyl]-cyclopropyl-amine (8d) (177 mg, 0.83 mmol). The yield was 279 mg, 78% (white sticky mass).

LC-MS: 652.2 (M+H)

Synthesis of (355)

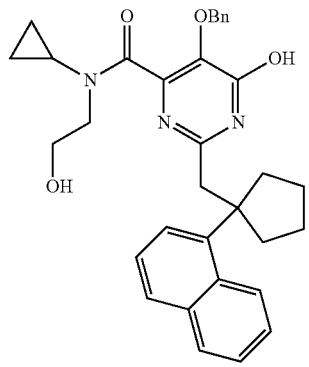 [SMILES: O=C(c1nc(CC2(c3cccc4ccccc34)CCCC2)nc(O)c1OCc1ccccc1)N(CCO)C1CC1]

325

5-Benzyloxy-6-hydroxy-2-(1-naphthalen-1-yl-cyclopentylmethyl)-pyrimidine-4-carboxylic acid cyclopropyl-(2-hydroxyethyl)-amide This compound was prepared following the same method as described for 5-benzyloxy-6-hydroxy-2-(1-naphthalen-1-yl-cyclopentylmethyl)-pyrimidine-4-carboxylic acid (2-hydroxyethyl)-methyl-amide (351) from 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-cyclopropyl-amide (354) (270 mg, 0.41 mmol). The yield was 150 mg, 67% (white solid)

LC-MS: 538.0 (M+H)

Synthesis of (356)

9-Benzyloxy-2-cyclopropyl-6-(1-naphthalen-1-yl-cyclopentylmethyl)-3,4-dihydro-2H-pyrazino[1,2-c]pyrimidine-1,8-dione To a solution of 5-benzyloxy-6-hydroxy-2-(1-naphthalen-1-yl-cyclopentylmethyl)-pyrimidine-4-carboxylic acid cyclopropyl-(2-hydroxyethyl)-amide (355) (120 mg, 0.22 mmol) and diisopropyl azodicarboxylate (0.22 mL, 1.12 mmol) in dichloromethane (30 mL) was added triphenyl phosphine (351 mg, 1.34 mmol) at room temperature and the reaction mixture was stirred for 15 min at the same temperature. The yellow color disappeared (silica TLC 5% methanol in ethyl acetate, Rf=0.2). The dichloromethane was removed in vacuo and the crude mass was purified by silica gel (normal, 100-200 mesh) column chromatography using a gradient eluent mixture of 1% to 5% methanol in dichloromethane to get pure 9-benzyloxy-2-cyclopropyl-6-(1-naphthalen-1-yl-cyclopentylmethyl)-3,4-dihydro-2H-pyrazino[1,2-c]pyrimidine-1,8-dione (356) (106 mg, 92%) as a white solid.

LC-MS: 519.9 (M+H)

326

Synthesis of (357): (16271)

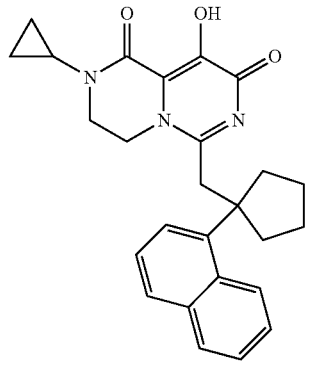 [SMILES: O=C1c2c(O)c(=O)nc(CC3(c4cccc5ccccc45)CCCC3)n2CCN1C1CC1]

2-Cyclopropyl-9-hydroxy-6-(1-naphthalen-1-yl-cyclopentylmethyl)-3,4-dihydro-2H-pyrazino[1,2-c]pyrimidine-1,8-dione This compound was prepared by following the same method as described for pure 9-hydroxy-6-(1-naphthalen-1-yl-cyclopentylmethyl)-3,4-dihydro-2H-pyrazino[1,2-c]pyrimidine-1,8-dione (349) from 9-benzyloxy-2-cyclopropyl-6-(1-naphthalen-1-yl-cyclopentylmethyl)-3,4-dihydro-2H-pyrazino[1,2-c]pyrimidine-1,8-dione (356) (100 mg, 0.18 mmol). The yield was 40 mg, 52% of a white solid.

LC-MS: 429.8 (M+H)

Example 361

2-Cyclopropylmethyl-9-hydroxy-6-(1-naphthalen-1-yl-cyclopentylmethyl)-3,4-dihydro-2H-pyrazino[1,2-c]pyrimidine-1,8-dione The synthetic procedure used in this preparation is outlined in Schemes 47.

Synthesis of (358)

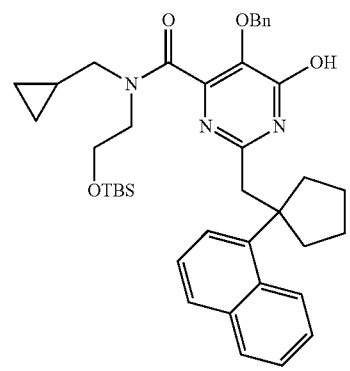 [SMILES: CC(C)(C)[Si](C)(C)OCCN(CC1CC1)C(=O)c1nc(CC2(c3cccc4ccccc34)CCCC2)nc(O)c1OCc1ccccc1]

327

5-Benzyloxy-6-hydroxy-2-(1-naphthalen-1-yl-cyclopentylmethyl)-pyrimidine-4-carboxylic acid [2-(tert-butyl-dimethylsilanyloxy)-ethyl]-cyclopropylmethyl-amide This compound was prepared by following the same method as described for 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-methyl-amide (350) from '5-benzyloxy-6-hydroxy-2-(1-naphthalen-1-yl-cyclopentylmethyl)-pyrimidine-4-carboxylic acid (345) (225 mg, 0.50 mmol) and [2-(tert-butyl-dimethylsilanyloxy)-ethyl]-cyclopropylmethyl-amine (8i) (170 mg, 0.74 mmol). The yield was 307 mg, 93% of a white solid.

LC-MS: 666.0 (M+H)

Synthesis of (359)

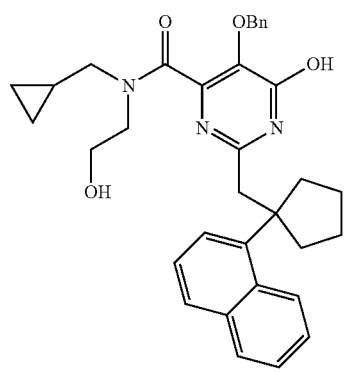 [SMILES: O=C(c1nc(CC2(c3cccc4ccccc34)CCCC2)nc(O)c1OCc1ccccc1)N(CCO)CC1CC1]

5-Benzyloxy-6-hydroxy-2-(1-naphthalen-1-yl-cyclopentylmethyl)-pyrimidine-4-carboxylic acid cyclopropyl methyl-(2-hydroxyethyl)-amide This compound was prepared following the same method as described for 5-benzyloxy-6-hydroxy-2-(1-naphthalen-1-yl-cyclopentylmethyl)-pyrimidine-4-carboxylic acid (2-hydroxyethyl)-methyl-amide (351) from 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-cyclopropylmethyl-amide (358) (350 mg, 0.53 mmol). The yield was 225 mg, 78% of a white solid.

LC-MS: 552.2 (M+H)

328

Synthesis of (360)

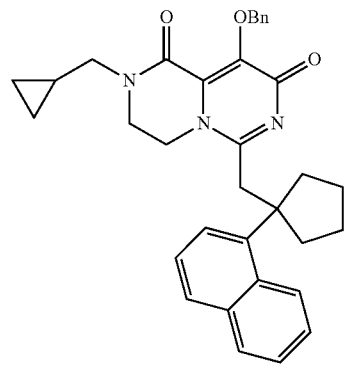 [SMILES: O=C1c2c(OCc3ccccc3)c(=O)nc(CC3(c4cccc5ccccc45)CCCC3)n2CCN1CC1CC1]

9-Benzyloxy-2-cyclopropylmethyl-6-(1-naphthalen-1-yl-cyclopentylmethyl)-3,4-dihydro-2H-pyrazino[1,2-c]pyrimidine-1,8-dione This compound was prepared following the same method as described for 9-benzyloxy-2-methyl-6-(1-naphthalen-1-yl-cyclopentylmethyl)-3,4-dihydro-2H-pyrazino[1,2-c]pyrimidine-1,8-dione (352) from 5-benzyloxy-6-hydroxy-2-(1-naphthalen-1-yl-cyclopentylmethyl)-pyrimidine-4-carboxylic acid cyclopropylmethyl-(2-hydroxyethyl)-amide (359) (150 mg, 0.27 mmol). The yield was 94 mg of a semi pure, white sticky solid.

LC-MS: 534.0 (M+H)

Synthesis of (361): (16250)

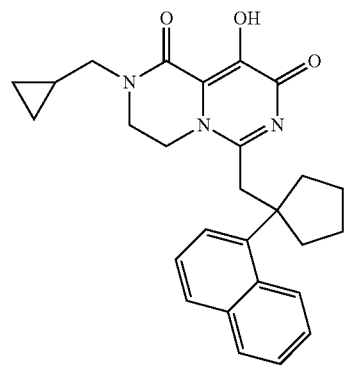 [SMILES: O=C1c2c(O)c(=O)nc(CC3(c4cccc5ccccc45)CCCC3)n2CCN1CC1CC1]

2-Cyclopropylmethyl-9-hydroxy-6-(1-naphthalen-1-yl-cyclopentylmethyl)-3,4-dihydro-2H-pyrazino[1,2-c]pyrimidine-1,8-dione This compound was prepared by following the same method as described for pure 9-hydroxy-6-(1-naphthalen-1-yl-cyclopentylmethyl)-3,4-dihydro-2H-pyrazino[1,2-c]pyrimidine-1,8-dione (349) from 9-benzyloxy-2-cyclopropylmethyl-6-(1-naphthalen-1-yl-cyclopentylmethyl)-3,4-dihydro-2H-pyrazino[1,2-c]pyrimidine-1,8-dione (360) (100 mg, 0.19 mmol). The yield was 42 mg, 51%, of a white solid.

LC-MS: 444.0 (M+H)

Example 365

9-Hydroxy-6-(1-naphthalen-1-yl-cyclopentylmethyl)-2-oxetan-3-yl-3,4-dihydro-2H-pyrazino[1,2-c]pyrimidine-1,8-dione The synthetic procedure used in this preparation is outlined in Schemes 47.

Synthesis of (362)

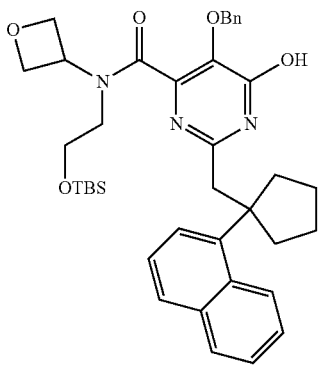 [SMILES: CC(C)(C)[Si](C)(C)OCCN(C(=O)c1nc(CC2(c3cccc4ccccc34)CCCC2)nc(O)c1OCc1ccccc1)C1COC1]

5-Benzyloxy-6-hydroxy-2-(1-naphthalen-1-yl-cyclopentylmethyl)-pyrimidine-4-carboxylic acid [2-(tert-butyl-dimethylsilanyloxy)-ethyl]-oxetan-3-yl-amide This compound was prepared following the same method as described for 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-methyl-amide (350) from 5-benzyloxy-6-hydroxy-2-(1-naphthalen-1-yl-cyclopentylmethyl)-pyrimidine-4-carboxylic acid (345) (325 mg, 0.72 mmol) and [2-(tert-butyl-dimethylsilanyloxy)-ethyl]-oxetan-3-yl-amine (8 g) (248 mg, 1.07 mmol). The yield was 340 mg, 71%, of a colorless sticky mass.

LC-MS: 668.4 (M+H)

Synthesis of (363)

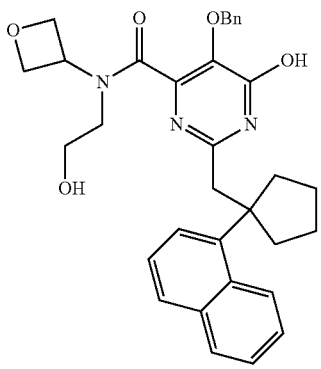 [SMILES: O=C(c1nc(CC2(c3cccc4ccccc34)CCCC2)nc(O)c1OCc1ccccc1)N(CCO)C1COC1]

5-Benzyloxy-6-hydroxy-2-(1-naphthalen-1-yl-cyclopentylmethyl)-pyrimidine-4-carboxylic acid (2-hydroxyethyl)-oxetan-3-yl-amide To a solution of 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-oxetan-3-yl-amide (362) (290 mg, 0.43 mmol) in tetrahydrofuran (10 mL) was added tetrabutylammoniumfluorid (1M in tetrahydrofuran, 1.3 mL, 13 mmol) at 0° C. and the reaction mixture was stirred at room temperature for 1.5 h (silica TLC, ethyl acetate:hexane=1:1/SiO$_2$/UV, Rf=0.3.) The tetrahydrofuran was removed in vacuum and the crude mass was diluted with ethyl acetate (50 mL) and washed with water (25 mL) and brine (25 mL). The organic phase was thereafter dried and concentrated in vacuum to get a crude mass which was purified by CombiFlash using a gradient eluent mixture of ethyl acetate and hexane to obtain pure 5-benzyloxy-6-hydroxy-2-(1-naphthalen-1-yl-cyclopentylmethyl)-pyrimidine-4-carboxylic acid (2-hydroxyethyl)-oxetan-3-yl-amide (363) (175 mg, 73%) as a white solid.

LC-MS: 554.0 (M+H)

Synthesis of (364)

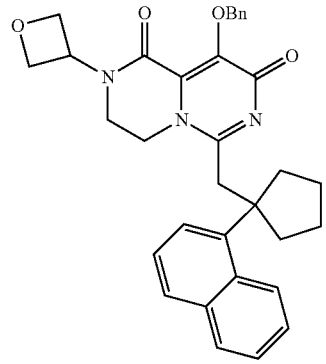 [SMILES: O=C1c2c(OCc3ccccc3)c(=O)nc(CC3(c4cccc5ccccc45)CCCC3)n2CCN1C1COC1]

9-Benzyloxy-6-(1-naphthalen-1-yl-cyclopentylmethyl)-2-oxetan-3-yl-3,4-dihydro-2H-pyrazino[1,2-c]pyrimidine-1,8-dione This compound was prepared following the same method as described for pure 9-benzyloxy-2-cyclopropyl-6-(1-naphthalen-1-yl-cyclopentylmethyl)-3,4-dihydro-2H-pyrazino[1,2-c]pyrimidine-1,8-dione (356) from 5-benzyloxy-6-hydroxy-2-(1-naphthalen-1-yl-cyclopentylmethyl)-pyrimidine-4-carboxylic acid (2-hydroxyethyl)-oxetan-3-yl-amide (363) (140 mg, 0.25 mmol). The yield was 131 mg, 97%, of a white solid.

LC-MS: 536.0 (M+H)

Synthesis of (365): (16272)

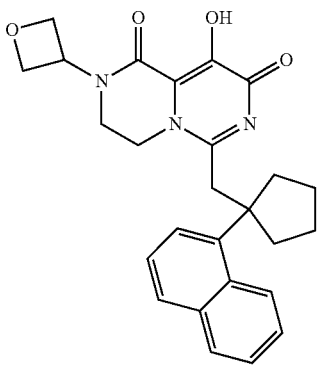 [SMILES: O=C1c2c(O)c(=O)nc(CC3(c4cccc5ccccc45)CCCC3)n2CCN1C1COC1]

9-Hydroxy-6-(1-naphthalen-1-yl-cyclopentylmethyl)-2-oxetan-3-yl-3,4-dihydro-2H-pyrazino[1,2-c]pyrimidine-1,8-dione A solution of 9-benzyloxy-6-(1-naphthalen-1-yl-cyclopentylmethyl)-2-oxetan-3-yl-3,4-dihydro-2H-pyrazino[1,2-c]pyrimidine-1,8-dione (364) (125 mg, 0.23 mmol) in ethanol (60 mL) was degassed under nitrogen, followed by the addition of Pd—C (10%) (40 mg) and again degassed under nitrogen. The reaction mixture was then stirred under a hydrogen atmosphere of balloon pressure for 25 min at room temperature. The reaction mixture was the filtered through a celite bed and the filtrate was concentrated in vacuo to get a crude sticky mass which was purified by preparative TLC plate using as developing solvent 3% methanol in dichloromethane to get pure 9-hydroxy-6-(1-naphthalen-1-yl-cyclopentylmethyl)-2-oxetan-3-yl-3,4-dihydro-2H-pyrazino[1,2-c]pyrimidine-1,8-dione (365) (32 mg, 31%) as an off-white solid.

LC-MS: 446.2 (M+H)

Example 369

9-Hydroxy-6-(1-naphthalen-1-yl-cyclopentylmethyl)-2-(tetrahydro-pyran-4-yl)-3,4-dihydro-2H-pyrazino[1,2-c]pyrimidine-1,8-dione The synthetic procedure used in this preparation is outlined in Schemes 47.

Synthesis of (366)

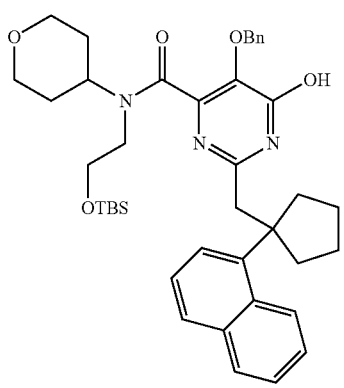 [SMILES: CC(C)(C)[Si](C)(C)OCCN(C(=O)c1nc(CC2(c3cccc4ccccc34)CCCC2)nc(O)c1OCc1ccccc1)C1CCOCC1]

5-Benzyloxy-6-hydroxy-2-(1-naphthalen-1-yl-cyclopentylmethyl)-pyrimidine-4-carboxylic acid [2-(tert-butyl-dimethylsilanyloxy)-ethyl]-(tetrahydro-pyran-4-yl)-amide This compound was prepared following the same method as described for 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-methyl-amide (350) from 5-benzyloxy-6-hydroxy-2-(1-naphthalen-1-yl-cyclopentylmethyl)-pyrimidine-4-carboxylic acid (345) (300 mg, 0.66 mmol) and [2-(tert-butyl-dimethylsilanyloxy)-ethyl]-(tetrahydro-pyran-4-yl)-amine (8j) (257 mg, 0.99 mmol). The yield was 320 mg, 70%, of a colorless sticky mass.

LC-MS: 696.2 (M+H)

Synthesis of (367)

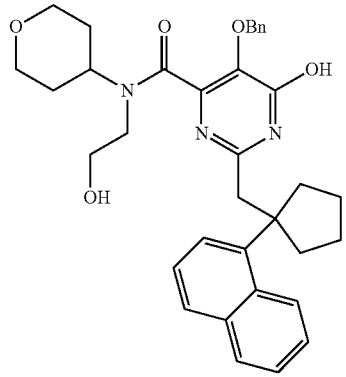 [SMILES: O=C(c1nc(CC2(c3cccc4ccccc34)CCCC2)nc(O)c1OCc1ccccc1)N(CCO)C1CCOCC1]

5-Benzyloxy-6-hydroxy-2-(1-naphthalen-1-yl-cyclopentylmethyl)-pyrimidine-4-carboxylic acid (2-hydroxyethyl)-(tetrahydro-pyran-4-yl)-amide This compound was prepared following the same method as described for 5-benzyloxy-6-hydroxy-2-(1-naphthalen-1-yl-cyclopentylmethyl)-pyrimidine-4-carboxylic acid (2-hydroxyethyl)-methyl-amide (351) from 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-(tetrahydro-pyran-4-yl)-amide (366) (300 mg, 0.43 mmol). The yield was 140 mg, 56%, of a white solid.

LC-MS: 582.2 (M+H)

Synthesis of (368)

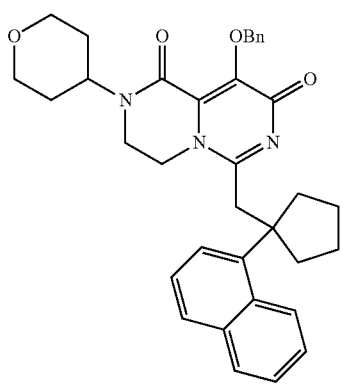 [SMILES: O=C1c2c(OCc3ccccc3)c(=O)nc(CC3(c4cccc5ccccc45)CCCC3)n2CCN1C1CCOCC1]

9-Benzyloxy-6-(1-naphthalen-1-yl-cyclopentylmethyl)-2-(tetrahydro-pyran-4-yl)-3,4-dihydro-2H-pyrazino[1,2-c]pyrimidine-1,8-dione This compound was prepared following the same method as described for pure 9-benzyloxy-2-cyclopropyl-6-(1-naphthalen-1-yl-cyclopentylmethyl)-3,4-dihydro-2H-pyrazino[1,2-c]pyrimidine-1,8-dione (356) from 5-benzyloxy-6-hydroxy-2-(1-naphthalen-1-yl-cyclopentylmethyl)-pyrimidine-4-carboxylic acid (2-hydroxyethyl)-(tetrahydro-pyran-4-yl)-amide (367) (110 mg, 0.2 mmol). Purification was done on silica gel (normal, 100-200 mesh) using 1% to 5% methanol in dichloromethane as gradient eluent. The yield was 96 mg, 90%, of a white solid.
LC-MS: 534.0 (M+H)

Synthesis of (369): (16261)

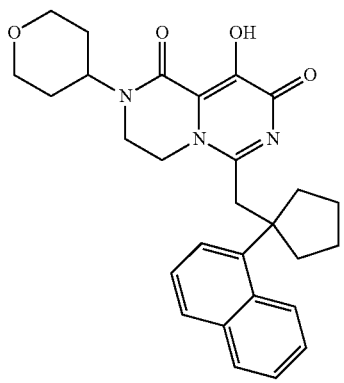 [SMILES: O=C1c2c(O)c(=O)nc(CC3(c4cccc5ccccc45)CCCC3)n2CCN1C1CCOCC1]

9-Hydroxy-6-(1-naphthalen-1-yl-cyclopentylmethyl)-2-(tetrahydro-pyran-4-yl)-3,4-dihydro-2H-pyrazino[1,2-c]pyrimidine-1,8-dione This compound was prepared by following the same method as described for pure 9-hydroxy-6-(1-naphthalen-1-yl-cyclopentylmethyl)-3,4-dihydro-2H-pyrazino[1,2-c]pyrimidine-1,8-dione (349) from 9-benzyloxy-6-(1-naphthalen-1-yl-cyclopentylmethyl)-2-(tetrahydro-pyran-4-yl)-3,4-dihydro-2H-pyrazino[1,2-c]pyrimidine-1,8-dione (368) (85 mg, 0.15 mmol). The yield was 55 mg, 77%, of a white solid.
LC-MS: 473.8 (M+H)

Example 373

2-Benzyl-9-hydroxy-6-(1-naphthalen-1-yl-cyclopentylmethyl)-3,4-dihydro-2H-pyrazino[1,2-c]pyrimidine-1,8-dione The synthetic procedure used in this preparation is outlined in Schemes 47.

Synthesis of (370)

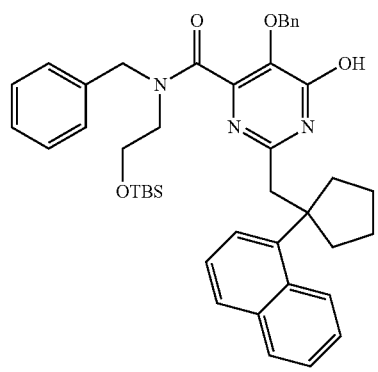 [SMILES: CC(C)(C)[Si](C)(C)OCCN(Cc1ccccc1)C(=O)c1nc(CC2(c3cccc4ccccc34)CCCC2)nc(O)c1OCc1ccccc1]

5-Benzyloxy-6-hydroxy-2-(1-naphthalen-1-yl-cyclopentylmethyl)-pyrimidine-4-carboxylic acid benzyl-[2-(tert-butyl-dimethylsilanyloxy)-ethyl]-amide This compound was prepared by following the same method as described for 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-methyl-amide (350) from 5-benzyloxy-6-hydroxy-2-(1-naphthalen-1-yl-cyclopentylmethyl)-pyrimidine-4-carboxylic acid (345) (250 mg, 0.55 mmol) and benzyl-[2-(tert-butyl-dimethylsilanyloxy)-ethyl]-amine (8I) (219 mg, 0.83 mmol). The yield was 358 mg, 93%, of a colorless sticky mass.
LC-MS: 702.4 (M+H)

Synthesis of (371)

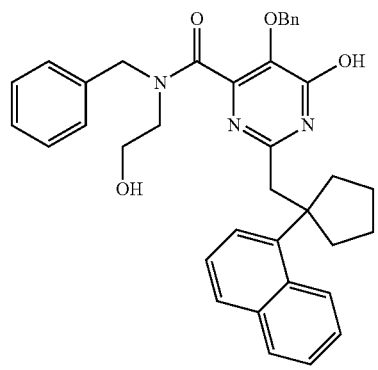 [SMILES: O=C(c1nc(CC2(c3cccc4ccccc34)CCCC2)nc(O)c1OCc1ccccc1)N(CCO)Cc1ccccc1]

335

5-Benzyloxy-6-hydroxy-2-(1-naphthalen-1-yl-cyclopentylmethyl)-pyrimidine-4-carboxylic acid benzyl-(2-hydroxyethyl)-amide This compound was prepared following the same method as described for 5-benzyloxy-6-hydroxy-2-(1-naphthalen-1-yl-cyclopentylmethyl)-pyrimidine-4-carboxylic acid (2-hydroxyethyl)-methyl-amide (351) from 5-benzyloxy-6-hydroxy-2-(1-naphthalen-1-yl-cyclopentylmethyl)-pyrimidine-4-carboxylic acid benzyl-[2-(tert-butyl-dimethylsilanyloxy)-ethyl]-amide (370) (380 mg, 0.54 mmol). The yield was 190 mg, 60%, of a white solid.

LC-MS: 588.0 (M+H)

Synthesis of (372)

2-Benzyl-9-benzyloxy-6-(1-naphthalen-1-yl-cyclopentylmethyl)-3,4-dihydro-2H-pyrazino[1,2-c]pyrimidine-1,8-dione This compound was prepared following the same method as described for pure 9-benzyloxy-6-(1-naphthalen-1-yl-cyclopentylmethyl)-2-(tetrahydro-pyran-4-yl)-3,4-dihydro-2H-pyrazino[1,2-c]pyrimidine-1,8-dione (368) from 5-benzyloxy-6-hydroxy-2-(1-naphthalen-1-yl-cyclopentylmethyl)-pyrimidine-4-carboxylic acid benzyl-(2-hydroxyethyl)-amide (371) (155 mg, 0.26 mmol). The yield was 122 mg of a mixture of a white sticky solid.

LC-MS: 570 (M+H)

336

Synthesis of (373): (16279)

2-Benzyl-9-hydroxy-6-(1-naphthalen-1-yl-cyclopentylmethyl)-3,4-dihydro-2H-pyrazino[1,2-c]pyrimidine-1,8-dione This compound was prepared following the same method as described for pure 9-hydroxy-6-(1-naphthalen-1-yl-cyclopentylmethyl)-3,4-dihydro-2H-pyrazino[1,2-c]pyrimidine-1,8-dione (349) from 2-benzyl-9-benzyloxy-6-(1-naphthalen-1-yl-cyclopentylmethyl)-3,4-dihydro-2H-pyrazino[1,2-c]pyrimidine-1,8-dione (372) (110 mg, 0.19 mmol). The yield was 35 mg, 47%, of a light brown solid.

LC-MS: 479.9 (M+H)

General Procedure for Examples 374 to 390

The synthetic procedures are outlined in Scheme 48.

General Synthetic Route for 382, 384, 386, 388, 390

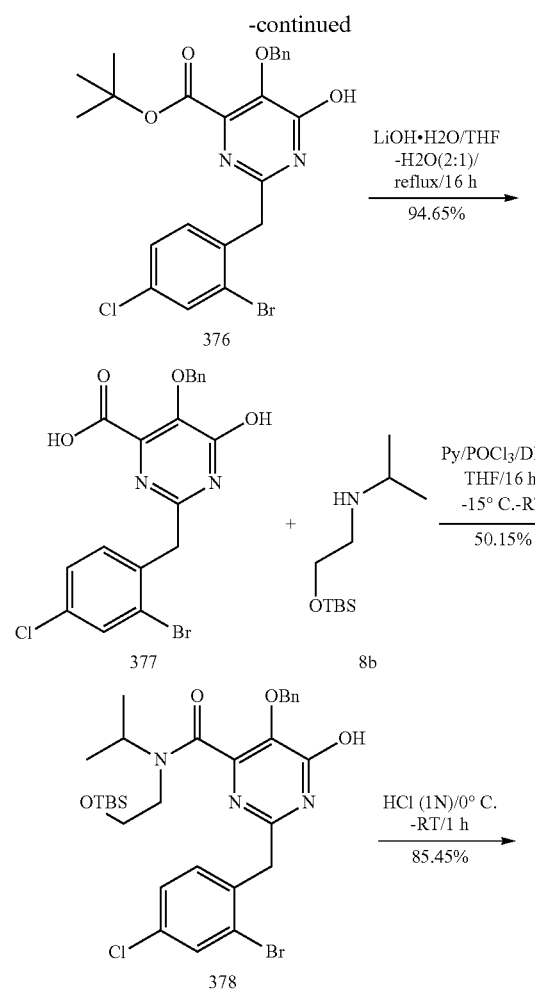

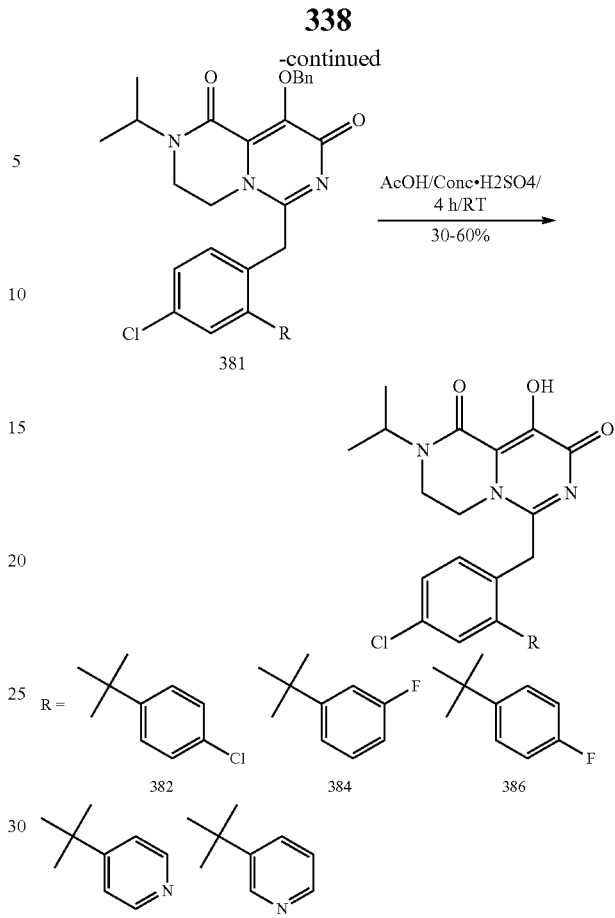

Preparation of (375)

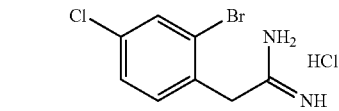 [SMILES: N=C(N)Cc1ccc(Cl)cc1Br ; Cl]

2-(2-Bromo-4-chlorophenyl)-acetamidine hydrochloride

To a stirred suspension of NH$_4$Cl (9.241 g, 169.565 mmol) in dry toluene (120 mL) was added tri-methyl aluminum (2M) (45.23 mL, 90.435 mmol) at 5° C. the reaction mixture was warmed to room temperature and the reaction mixture was stirred for 2 h. A solution of (2-bromo-4-chlorophenyl)-acetonitrile (374) (13 g, 56.522 mmol) in toluene (30 mL) was added to the above reaction mixture and the reaction mixture was stirred for 14 h at 80° C. while silica thin layer chromatography was performed (10% methanol in dichloromethane; Rf=0.2). After completion of the reaction, the reaction mixture was quenched with a suspension of silica gel (20 g) in chloroform (200 mL) and the reaction mixture was stirred for half an hour at room temperature and filtered. The silica gel was washed with methanol (100 mL) and the combined filtrate was concentrated under reduced pressure to get 2-(2-bromo-4-chlorophenyl)-acetamidine hydrochloride (375) (14.0 g, 87.68%) as a white solid.

LC-MS: 248.8 (M+H)

Preparation of (376)

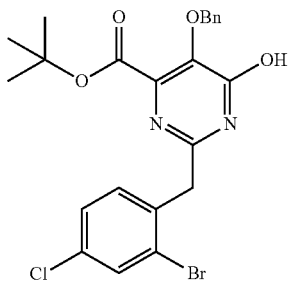 [SMILES: CC(C)(C)OC(=O)c1nc(Cc2ccc(Cl)cc2Br)nc(O)c1OCc1ccccc1]

5-Benzyloxy-2-(2-bromo-4-chlorobenzyl)-6-hydroxypyrimidine-4-carboxylic acid tert-butyl ester To a stirred solution of 2-(2-bromo-4-chlorophenyl)-acetamidine hydrochloride (375) (7 g, 24.823 mmol) and 2-benzyloxy-3-hydroxy-but-2-enedioic acid 4-tert-butyl ester 1-methyl ester (4) (11.47 g, 37.23 mmol) in methanol (100 mL) was dropwise added sodium methoxide (16.1 mL) (25% in methanol) at 0° C. The reaction mixture was allowed to warm to room temperature and stirred for 16 h while silica thin layer chromatography was performed (50% ethyl acetate in hexane; Rf=0.5). The reaction mixture was quenched with 1N HCl (5 mL) and the methanol was removed under reduced pressure to yield a residue which was diluted with water (200 mL) and extracted with ethyl acetate (2×250 mL). The combined organic parts were dried and concentrated. The obtained crude product was purified by normal silica (100-200 mesh) column to get 5-benzyloxy-2-(2-bromo-4-chlorobenzyl)-6-hydroxypyrimidine-4-carboxylic acid tert-butyl ester (376) (6.02 g, 47.95%) as a white solid.

LC-MS: 507.2 (M+H).

Preparation of (377)

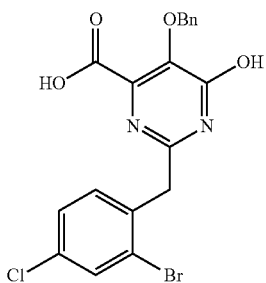 [SMILES: O=C(O)c1nc(Cc2ccc(Cl)cc2Br)nc(O)c1OCc1ccccc1]

5-Benzyloxy-2-(2-bromo-4-chlorobenzyl)-6-hydroxypyrimidine-4-carboxylic acid To a stirred solution of 5-benzyloxy-2-(2-bromo-4-chlorobenzyl)-6-hydroxypyrimidine-4-carboxylic acid tert-butyl ester (376) (14 g, 27.723 mmol) in tetrahydrofuran-water (15:7, 220 mL) was added LiOH.H$_2$O (11.644 g, 277.228 mmol). The reaction mixture was refluxed for 16 h while silica thin layer chromatography was performed (50% ethyl acetate in hexane; Rf=0.1). After completion of the reaction, all volatiles were removed and the residue was diluted with water (50 mL) and neutralized to pH 7 with 1N HCl. The mixture was filtered and the resulting solid was dried to get 5-benzyloxy-2-(2-bromo-4-chlorobenzyl)-6-hydroxypyrimidine-4-carboxylic acid (377) (11.8 g, 94.65%) as a white solid.

LC-MS: 451.2 (M+H)

Preparation of (378)

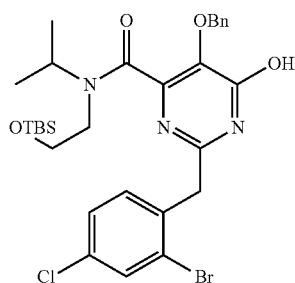 [SMILES: CC(C)N(CCO[Si](C)(C)C(C)(C)C)C(=O)c1nc(Cc2ccc(Cl)cc2Br)nc(O)c1OCc1ccccc1]

5-Benzyloxy-2-(2-bromo-4-chlorobenzyl)-6-hydroxypyrimidine-4-carboxylic acid [2-(tert-butyl-dimethylsilanyloxy)-ethyl]-isopropylamide To a stirred solution of 5-benzyloxy-2-(2-bromo-4-chlorobenzyl)-6-hydroxypyrimidine-4-carboxylic acid (377) (4.0 g, 8.9 mmol) in tetrahydrofuran (150 mL) was added [2-(tert-butyl-dimethylsilanyloxy)-ethyl]-isopropyl-amine (8b) (5.8 g, 26.73 mmol). To the reaction mixture, pyridine (2.159 mL, 26.726 mmol) was added, followed very slow addition of POCl$_3$ (2.454 mL, 26.726 mmol) at −15° C. the resulting reaction mixture was stirred for 2 h at same temperature. 2 drops of dimethylformamide were added to the reaction mixture which was thereafter allowed to stir at room temperature for 16 h while silica thin layer chromatography was performed (50% ethyl acetate in hexane; Rf=0.5). After completion of the reaction, the reaction mixture was quenched with ice cold water (150 mL) and extracted with ethyl acetate (2×250 mL). The combined organic parts were dried and concentrated and the resulting crude residue was purified on a column (normal silica 100-200 mesh) to get 5-benzyloxy-2-(2-bromo-4-chlorobenzyl)-6-hydroxypyrimidine-4-carboxylic acid [2-(tert-butyl-dimethylsilanyloxy)-ethyl]-isopropylamide (378) (2.9 g, 50.15%) as a colorless gummy liquid.

LC-MS: 648.2 (M+H).

Preparation of (379)

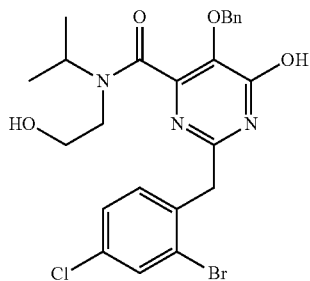 [SMILES: CC(C)N(CCO)C(=O)c1nc(Cc2ccc(Cl)cc2Br)nc(O)c1OCc1ccccc1]

5-Benzyloxy-2-(2-bromo-4-chlorobenzyl)-6-hydroxypyrimidine-4-carboxylicacid(2-hydroxyethyl)-isopropylamide To a stirred solution of 5-benzyloxy-2-(2-bromo-4-chlorobenzyl)-6-hydroxypyrimidine-4-carboxylic acid [2-(tert-butyl-dimethylsilanyloxy)-ethyl]-isopropylamide (378) (5.7 g, 8.80 mmol) in tetrahydrofuran (50 mL), 1N HCl (15 mL) was added and the reaction mixture was stirred for 1 h at room temperature while silica thin layer chromatography was performed (70% ethyl acetate in hexane; Rf=0.2). After completion of the reaction, volatiles were removed and the residue was diluted with water (30 mL) and adjusted to pH 8 using NaHCO₃. The aqueous mixture was extracted with ethyl acetate (2×150 mL) and the combined extracts were dried and concentrated. The resulting residue was purified by column over normal silica gel (100-200) to get 5-benzyloxy-2-(2-bromo-4-chlorobenzyl)-6-hydroxypyrimidine-4-carboxylicacid(2-hydroxyethyl)-isopropylamide (379) (4.02 g, 85.45%) as a white solid.
LC-MS: 533.8 (M+H).

Preparation of (380): (16291)

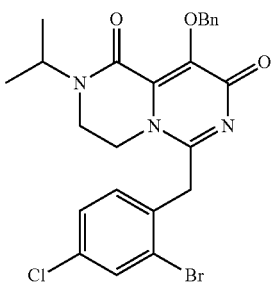 [SMILES: CC(C)N1CCn2c(Cc3ccc(Cl)cc3Br)nc(=O)c(OCc3ccccc3)c2C1=O]

9-Benzyloxy-6-(2-bromo-4-chlorobenzyl)-2-isopropyl-3,4-dihydro-2H-pyrazino[1,2-c]pyrimidine-1,8-dione To a stirred solution of 5-benzyloxy-2-(2-bromo-4-chlorobenzyl)-6-hydroxypyrimidine-4-carboxylicacid(2-hydroxyethyl)-isopropylamide (379) (1.0 g, 1.873 mmol) and triphenyl phosphine (1.717 g, 6.554 mmol) in dichloromethane (120 mL), diisopropyl azodicarboxylate (1.114, 5.618 mmol) was added over 10 h (dilution 0.19 M; rate 3 ml/h) at 0° C. The reaction was monitored by silica thin layer chromatography (3% methanol in dichloromethane; Rf=0.4). After completion of the reaction, 50 mL water were added and the mixture was extracted with dichloromethane (2×100 mL). The organic part was dried over sodium sulphate and concentrated. The resulting crude product was column purified (using amine bound silica) to get 9-benzyloxy-6-(2-bromo-4-chlorobenzyl)-2-isopropyl-3,4-dihydro-2H-pyrazino[1,2-c]pyrimidine-1,8-dione (380) (0.406 g, 41.95%) as a white solid.
LC-MS: 517.8 (M+H).

Example 382

6-(5,4'-Dichloro-biphenyl-2-ylmethyl)-9-hydroxy-2-isopropyl-3,4-dihydro-2H-pyrazino[1,2-c]pyrimidine-1,8-dione The synthetic procedure used in this preparation is outlined in Schemes 48.

Preparation of (381)

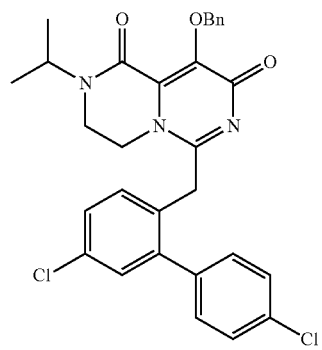 [SMILES: CC(C)N1CCn2c(Cc3ccc(Cl)cc3-c3ccc(Cl)cc3)nc(=O)c(OCc3ccccc3)c2C1=O]

9-Benzyloxy-6-(5,4'-dichloro-biphenyl-2-ylmethyl)-2-isopropyl-3,4-dihydro-2H-pyrazino[1,2-c]pyrimidine-1,8-dione In a sealed tube was placed a stirred solution of 9-benzyloxy-6-(2-bromo-4-chlorobenzyl)-2-isopropyl-3,4-dihydro-2H-pyrazino[1,2-c]pyrimidine-1,8-dione (380) (80 mg, 0.155 mmol) in dioxane (3 mL). 4-Chlorophenyl boronic acid (24.248 mg, 0.155 mmol) and a 1N solution of K₂CO₃ [(64.279 mg, 0.465 mmol) dissolved in 0.7 mL water] were added at room temperature and the reaction was degassed for 30 min under argon. To the reaction mixture, Pd(triphenyl phosphine)₄ (17.916 mg, 0.016 mmol) was added, followed by 2-dicyclohexylphosphino-2',6'-dimethoxybiphenyl (12.729 mg, 0.031 mmol) and the reaction was further degassed for another 10 min. The reaction mixture was heated at 80° C. for 20 min (reaction was monitored by LC-MS). After completion of the reaction, the mixture was filtered and the filtrate was diluted with water (5 mL). After extraction with ethyl acetate (2×20 mL), the organic part was dried over sodium sulphate and concentrated. The resulting crude product was purified by column chromatography (using amine bound silica gel as stationary phase) to get 9-benzyloxy-6-(5,4'-dichloro-biphenyl-2-ylmethyl)-2-isopropyl-3,4-dihydro-2H-pyrazino[1,2-c]pyrimidine-1,8-dione (381) (42 mg, 49.39%) as a white solid.
LC-MS: 548.0 (M+H).

Preparation of (382): (16243)

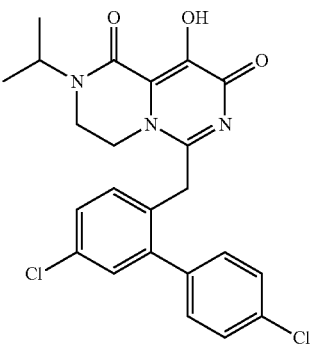 [SMILES: CC(C)N1CCn2c(Cc3ccc(Cl)cc3-c3ccc(Cl)cc3)nc(=O)c(O)c2C1=O]

6-(5,4'-Dichloro-biphenyl-2-ylmethyl)-9-hydroxy-2-isopropyl-3,4-dihydro-2H-pyrazino[1,2-c]pyrimidine-1,8-dione To a stirred solution of 9-benzyloxy-6-(5,4'-dichloro-biphenyl-2-ylmethyl)-2-isopropyl-3,4-dihydro-2H-pyrazino [1,2-c]pyrimidine-1,8-dione (10a) (35 mg, 0.064 mmol) in acetic acid (1 mL), concentrated $H_2SO_4$ (0.001 mL, 0.013 mmol) was added and the reaction mixture was stirred for 4 h at room temperature (reaction was monitored by LC/MS). Volatiles were removed from the reaction mixture and the residue was quenched with ice cold water (5 mL). The pH of this mixture was adjusted to pH 8 using $NaHCO_3$. After extraction with ethyl acetate (2×15 mL), the organic part was dried and concentrated. The resulting crude product was purified by prep HPLC to get 6-(5,4'-dichloro-biphenyl-2-ylmethyl)-9-hydroxy-2-isopropyl-3,4-dihydro-2H-pyrazino[1,2-c]pyrimidine-1,8-dione (P046-03-EB-01) (18.1 mg, 61.72%) as an off-white solid.
LC-MS: 457.8 (M+H).

Example 384

6-(5-Chloro-3'-fluoro-biphenyl-2-ylmethyl)-9-hydroxy-2-isopropyl-3,4-dihydro-2H-pyrazino[1,2-c]pyrimidine-1,8-dione The synthetic procedure used in this preparation is outlined in Schemes 48.

Preparation of (383)

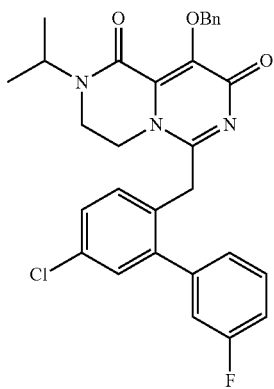 [SMILES: CC(C)N1CCn2c(Cc3ccc(Cl)cc3-c3cccc(F)c3)nc(=O)c(OCc3ccccc3)c2C1=O]

9-Benzyloxy-6-(5-chloro-3'-fluoro-biphenyl-2-ylmethyl)-2-isopropyl-3,4-dihydro-2H-pyrazino[1,2-c]pyrimidine-1,8-dione In a sealed tube was placed a stirred solution of 9-benzyloxy-6-(2-bromo-4-chlorobenzyl)-2-isopropyl-3,4-dihydro-2H-pyrazino[1,2-c]pyrimidine-1,8-dione (380) (100 mg, 0.194 mmol) in dioxane (3 mL), 3-fluorophenyl boronicacid (27.132 mg, 0.194 mmol), and a 1N solution of potassium carbonate [(80.349 mg, 0.581 mmol) dissolved in 1.06 mL water] was added at room temperature. The reaction mixture was de-gassed with argon by purging for 30 min. Pd(triphenyl phosphine)$_4$ (22.395 mg, 0.019 mmol) and 2-dicyclohexylphosphino-2',6'-dimethoxybiphenyl (15.911 mg, 0.039 mmol) were added and the reaction mixture was further degassed for another 10 min. The reaction mixture was heated for 30 min at 80° C. (while progress of the reaction was monitored by LC-MS). The reaction was filtered and diluted with water (5 mL) and extract with ethyl acetate (2×20 mL). The combined extracts were dried and concentrated. The resulting crude product was purified by column (using amine bound silica gel) to get 9-benzyloxy-6-(5-chloro-3'-fluoro-biphenyl-2-ylmethyl)-2-isopropyl-3,4-dihydro-2H-pyrazino[1,2-c]pyrimidine-1,8-dione (383) (65 mg, 63.04%) as an off-white solid.
LC-MS: 532.0 (M+H).

Preparation of (384): (16262)

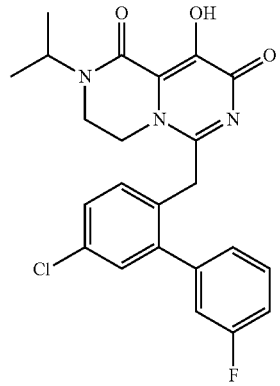 [SMILES: CC(C)N1CCn2c(Cc3ccc(Cl)cc3-c3cccc(F)c3)nc(=O)c(O)c2C1=O]

6-(5-Chloro-3'-fluoro-biphenyl-2-ylmethyl)-9-hydroxy-2-isopropyl-3,4-dihydro-2H-pyrazino[1,2-c]pyrimidine-1,8-dione To a stirred solution of 9-benzyloxy-6-(5-chloro-3'-fluoro-biphenyl-2-ylmethyl)-2-isopropyl-3,4-dihydro-2H-pyrazino[1,2-c]pyrimidine-1,8-dione (383) (60 mg, 0.113 mmol) in acetic acid (1 mL), concentrated sulfuric acid (0.001 mL, 0.023 mmol) was added. The reaction mixture was stirred for 4 h, at room temperature (monitored by LC-MS). Volatiles were removed from the reaction and the residue was quenched with ice cold water (5 mL). Aqueous saturated $NaHCO_3$ was added to adjust the pH to 8. The quenched mass was extracted with ethyl acetate (2×15 mL) and the combined organic part was dried, concentrated and purified by preparative HPLC to get 6-(5-chloro-3% fluoro-biphenyl-2-ylmethyl)-9-hydroxy-2-isopropyl-3,4-dihydro-2H-pyrazino[1,2-c]pyrimidine-1,8-dione (384) (20.0 mg, 40.06%) as an off-white solid.
LC-MS: 441.8 (M+H).

Example 386

6-(5-Chloro-3'-fluoro-biphenyl-2-ylmethyl)-9-hydroxy-2-isopropyl-3,4-dihydro-2H-pyrazino[1,2-c]pyrimidine-1,8-dione The synthetic procedure used in this preparation is outlined in Schemes 48.

Preparation of (385)

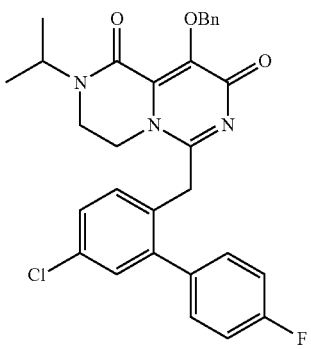 [SMILES: CC(C)N1CCn2c(Cc3ccc(Cl)cc3-c3ccc(F)cc3)nc(=O)c(OCc3ccccc3)c2C1=O]

9-Benzyloxy-6-(5-chloro-4'-fluoro-biphenyl-2-ylmethyl)-2-isopropyl-3,4-dihydro-2H-pyrazino[1,2-c]pyrimidine-1,8-dione Into a sealed tube was placed a stirred solution of 9-benzyloxy-6-(2-bromo-4-chlorobenzyl)-2-isopropyl-3,4-dihydro-2H-pyrazino[1,2-c]pyrimidine-1,8-dione (380) (70 mg, 0.136 mmol) in dioxane (3 mL). 4-Fluorophenyl boronic acid (18.99 mg, 0.14 mmol) and a 1N solution of potassium carbonate [(56.244 mg, 0.407 mmol) in 0.82 mL water] were added at room temperature and the reaction mixture was purged for 30 min with argon. To the reaction Pd(triphenyl phosphine)$_4$ (15.676 mg, 0.014 mmol) was added under argon, followed by 2-dicyclohexylphosphino-2',6'-dimethoxybiphenyl (11.138 mg, 0.027 mmol). The reaction mixture was further degassed for another 10 min, then heated to 80° C. for 30 min (monitored by LC-MS). The reaction mixture was filtered through a pad of celite. The filtrate was diluted with water (5 mL) and extracted with ethyl acetate (2×20 mL). The combined extracts were dried and concentrated. The resulting crude product was purified by column chromatography (using amine bound silica gel) to get 9-benzyloxy-6-(5-chloro-4'-fluoro-biphenyl-2-ylmethyl)-2-isopropyl-3,4-dihydro-2H-pyrazino[1,2-c]pyrimidine-1,8-dione (385) (32 mg, 44.34%) as an off-white solid.

LC-MS: 532.2 (M+H).

Preparation of (386): (16242)

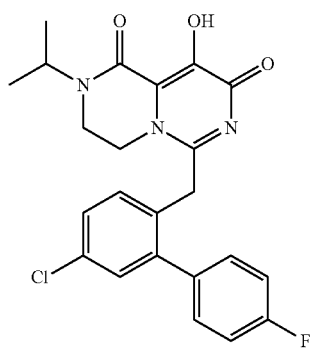 [SMILES: CC(C)N1CCn2c(Cc3ccc(Cl)cc3-c3ccc(F)cc3)nc(=O)c(O)c2C1=O]

6-(5-Chloro-4'-fluoro-biphenyl-2-ylmethyl)-9-hydroxy-2-isopropyl-3,4-dihydro-2H-pyrazino[1,2-c]pyrimidine-1,8-dione To a stirred solution of 9-benzyloxy-6-(5-chloro-4'-fluoro-biphenyl-2-ylmethyl)-2-isopropyl-3,4-dihydro-2H-pyrazino[1,2-c]pyrimidine-1,8-dione (385) (30 mg, 0.056 mmol) in acetic acid (1 mL), concentrated H$_2$SO$_4$ (0.001 mL, 0.011 mmol) was added and the reaction mixture was stirred for 4 h at room temperature (monitored by LC-MS). From the reaction, volatiles was removed and the residue was quenched with ice cold water (5 mL). Aqueous saturated NaHCO$_3$ was added to adjust the pH up to 8. The quenched mass was extracted with ethyl acetate (2×15 mL). The combined organic part was dried, concentrated and purified by preparative HPLC to get 6-(5-chloro-4'-fluoro-biphenyl-2-ylmethyl)-9-hydroxy-2-isopropyl-3,4-dihydro-2H-pyrazino[1,2-c]pyrimidine-1,8-diol (386) (11.2 mg, 44.86 mmol) as an off-white solid.

LC-MS: 441.8 (M+H).

Example 388

6-(4-Chloro-2-pyridin-4-yl-benzyl)-9-hydroxy-2-isopropyl-3,4-dihydro-2H-pyrazino[1,2-c]pyrimidine-1,8-dione The synthetic procedure used in this preparation is outlined in Schemes 48

Preparation of (387)

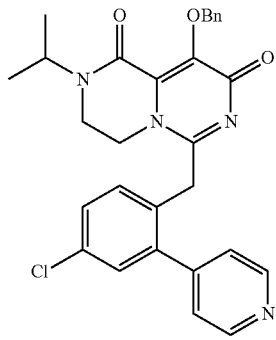 [SMILES: CC(C)N1CCn2c(Cc3ccc(Cl)cc3-c3ccncc3)nc(=O)c(OCc3ccccc3)c2C1=O]

6-(4-Chloro-2-pyridin-4-yl-benzyl)-9-hydroxy-2-isopropyl-3,4-dihydro-2H-pyrazino[1,2-c]pyrimidine-1,8-dione In a sealed tube was placed a stirred solution of 9-benzyloxy-6-(2-bromo-4-chlorobenzyl)-2-isopropyl-3,4-dihydro-2H-pyrazino[1,2-c]pyrimidine-1,8-dione (380) (100 mg, 0.194 mmol) in dioxane (4 mL). Pyridine 4-boronic acid (23.822 mg, 0.194 mmol), and a 1N solution of potassium carbonate [(80.349 mg, 0.581 mmol) in 0.82 mL water] were added at room temperature and the reaction mixture was purged for 30 min with argon. Pd(triphenyl phosphine)$_4$ (22.395 mg, 0.019 mmol) and 2-dicyclohexylphosphino-2',6'-dimethoxybiphenyl (15.911 mg, 0.039 mmol) were added to the reaction under argon. The reaction mixture was further degassed for another 10 min and thereafter heated at 80° C. for 4 h (monitored by LC-MS). The reaction mixture was filtered through a pad of celite and the filtrate was diluted with water (5 mL) and extracted with ethyl acetate (2×20 mL). The combined extracts were dried and concentrated. The resulting crude product was purified by column (using amine bound silica gel) to get 9-benzyloxy-6-(4-chloro-2-pyridin-4-yl-benzyl)-2-isopropyl-3,4-dihydro-2H-pyrazino[1,2-c]pyrimidine-1,8-dione (387) (51 mg, 51.1%) as an off-white solid.
LC-MS: 515.0 (M+H).

Preparation of (388): (16274)

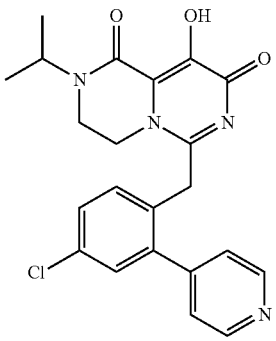 [SMILES: CC(C)N1CCn2c(Cc3ccc(Cl)cc3-c3ccncc3)nc(=O)c(O)c2C1=O]

6-(4-Chloro-2-pyridin-4-yl-benzyl)-9-hydroxy-2-isopropyl-3,4-dihydro-2H-pyrazino[1,2-c]pyrimidine-1,8-dione To a stirred solution of 9-benzyloxy-6-(4-chloro-2-pyridin-4-yl-benzyl)-2-isopropyl-3,4-dihydro-2H-pyrazino[1,2-c]pyrimidine-1,8-dione (387) (50 mg, 0.097 mmol) in acetic acid (2 mL), concentrated H$_2$SO$_4$ (0.001 mL, 0.019 mmol) was added and the reaction mixture was stirred for 4 h at room temperature (monitored by LC-MS). From the reaction, volatiles were removed and the residue was quenched with ice cold water (5 mL). Aqueous saturated NaHCO$_3$ was added to adjust the pH up to 8. The quenched mass was extracted with ethyl acetate (2×15 mL). The combined organic part was dried and concentrated and the resulting residue was purified by preparative HPLC to get 6-(4-chloro-2-pyridin-4-yl-benzyl)-9-hydroxy-2-isopropyl-3,4-dihydro-2H-pyrazino[1,2-c]pyrimidine-1,8-dione (388) (14.3 mg, 31.45%) as an off-white solid.
LC-MS: 424.8 (M+H).

Example 390

6-(4-Chloro-2-pyridin-3-yl-benzyl)-9-hydroxy-2-isopropyl-3,4-dihydro-2H-pyrazino[1,2-c]pyrimidine-1,8-dione The synthetic procedure used in this preparation is outlined in Schemes 48

Preparation of (389)

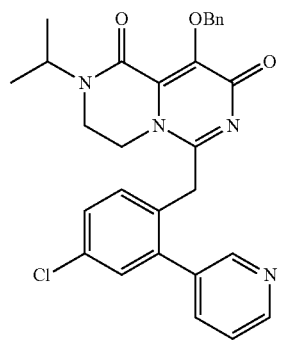 [SMILES: CC(C)N1CCn2c(Cc3ccc(Cl)cc3-c3cccnc3)nc(=O)c(OCc3ccccc3)c2C1=O]

9-Benzyloxy-6-(4-chloro-2-pyridin-3-yl-benzyl)-2-isopropyl-3,4-dihydro-2H-pyrazino[1,2-c]pyrimidine-1,8-dione In a sealed tube was placed a stirred solution of 9-benzyloxy-6-(2-bromo-4-chlorobenzyl)-2-isopropyl-3,4-dihydro-2H-pyrazino[1,2-c]pyrimidine-1,8-dione (380) (100 mg, 0.194 mmol) in dioxane (3 mL). Pyridine 3-boronic acid (23.822 mg, 0.194 mmol), and a 1N solution of potassium carbonate [(80.349 mg, 0.581 mmol) dissolved in 1.25 mL water] were added at room temperature, and the reaction mixture was purged with argon for 30 min. Then, Pd(triphenyl phosphine)$_4$ (22.395 mg, 0.019 mmol) and 2-dicyclohexylphosphino-2',6'-dimethoxybiphenyl (15.911 mg, 0.039 mmol) were added and the reaction mixture was further degassed for another 10 min. The reaction mixture was heated at 80° C. for 4 h (monitored by LC-MS). The reaction mixture was filtered through a pad of cellite and the filtrate was diluted with water (5 mL) and extracted with ethyl acetate (2×20 mL). The combined extracts were dried and concentrated. The resulting crude product was purified by column (using amine bound silica gel) to get 9-benzyloxy-6-(4-chloro-2-pyridin-3-yl-benzyl)-2-isopropyl-3,4-dihydro-2H-pyrazino[1,2-c]pyrimidine-1,8-dione (389) (50 mg, 50.1%) as an off-white solid.
LC-MS: 515.0 (M+H).

349

Preparation of (390): (16273)

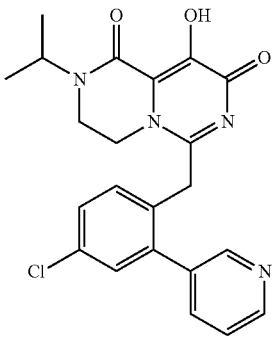 [SMILES: CC(C)N1CCn2c(Cc3ccc(Cl)cc3-c3cccnc3)nc(=O)c(O)c2C1=O]

6-(4-Chloro-2-pyridin-3-yl-benzyl)-9-hydroxy-2-isopropyl-3,4-dihydro-2H-pyrazino[1,2-c]pyrimidine-1,8-dione To a stirred solution of 9-benzyloxy-6-(4-chloro-2-pyridin-3-yl-benzyl)-2-isopropyl-3,4-dihydro-2H-pyrazino[1,2-c]pyrimidine-1,8-dione (389) (45 mg, 0.088 mmol) in acetic acid (2 mL), concentrated H₂SO₄ (0.001 mL, 0.018 mmol) was added and the reaction mixture was stirred for 4 h at room temperature (monitored by LC-MS). From the reaction, volatiles were removed and the residue was quenched with ice cold water (5 mL). Aqueous saturated NaHCO₃ was added to adjust the pH up to 8. The quenched mass was extracted with ethyl acetate (2×15 mL), the combined organic part was dried, concentrated and purified by preparative HPLC to get 6-(4-chloro-2-pyridin-3-yl-benzyl)-9-hydroxy-2-isopropyl-3,4-dihydro-2H-pyrazino[1,2-c]pyrimidine-1,8-dione (390) (12.0 mg, 32.26%) as an off-white solid.

LC-MS: 424.8 (M+H).

General Procedure for Examples 391 to 428

The synthetic procedures are outlined in Scheme 49.

General Synthetic Route for 408, 412, 416, 420, 424, 428

Scheme 49

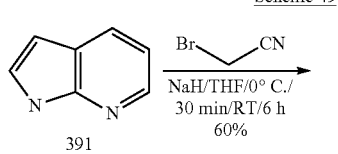

391

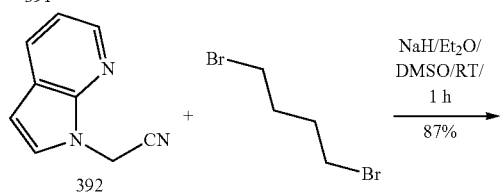

392

350

-continued

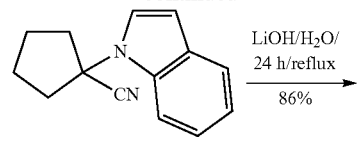

393

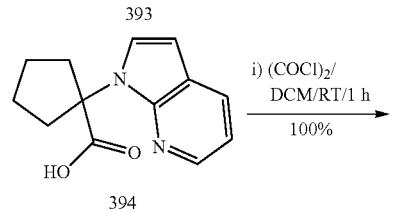

394

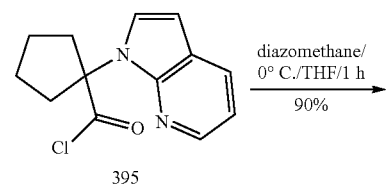

395

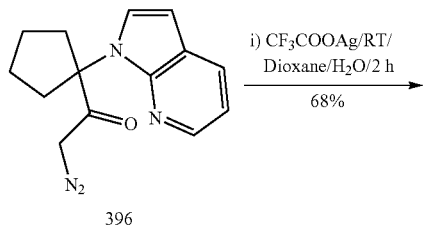

396

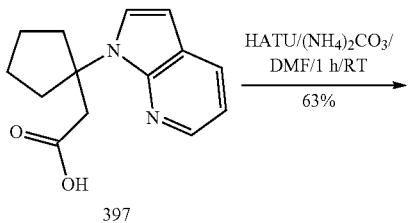

397

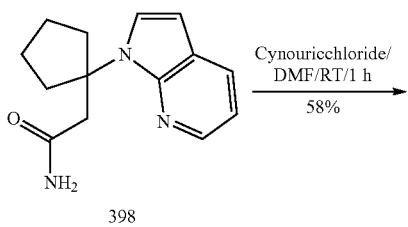

398

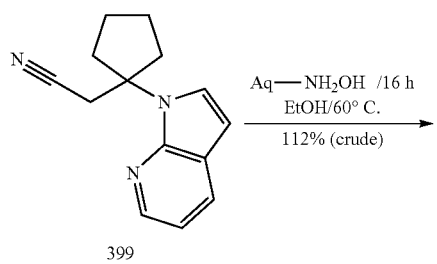

399

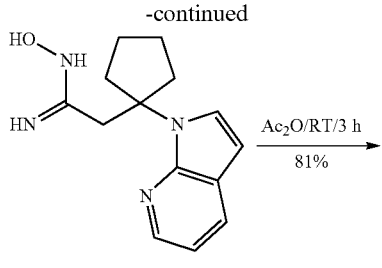
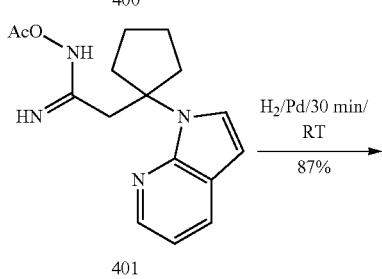
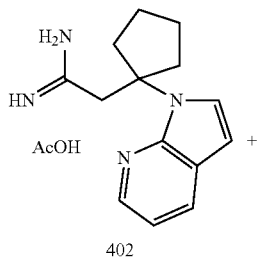
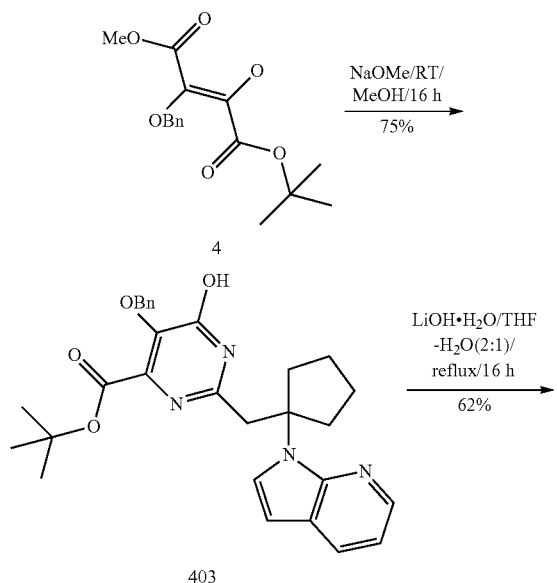
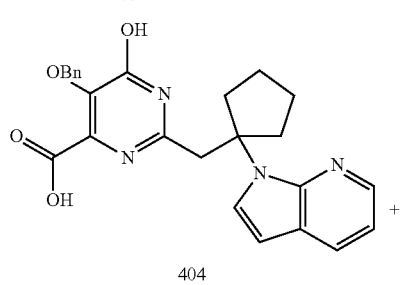
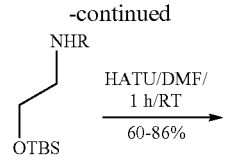
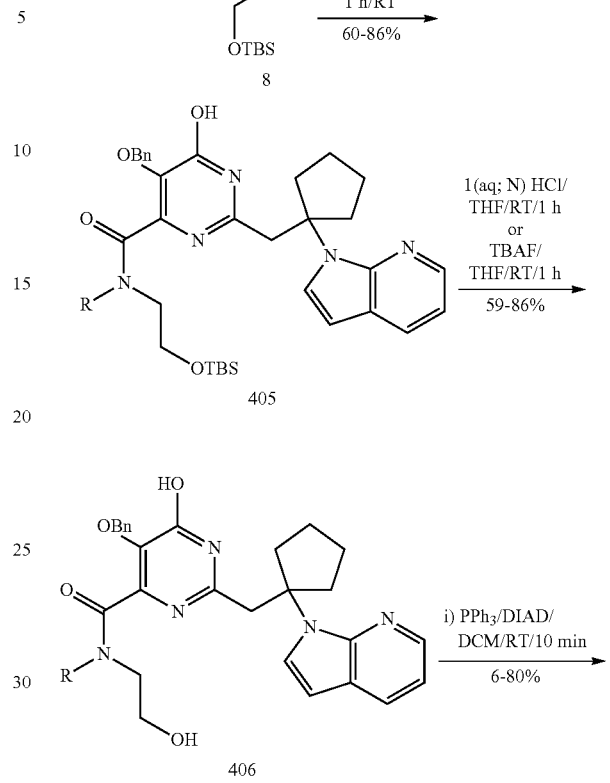
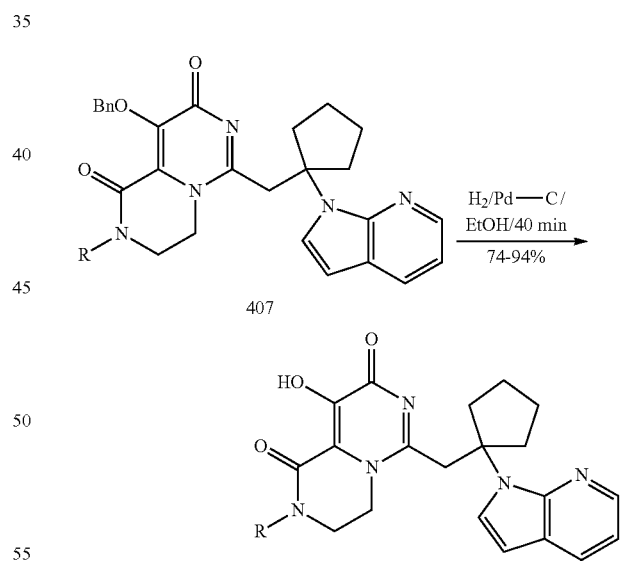
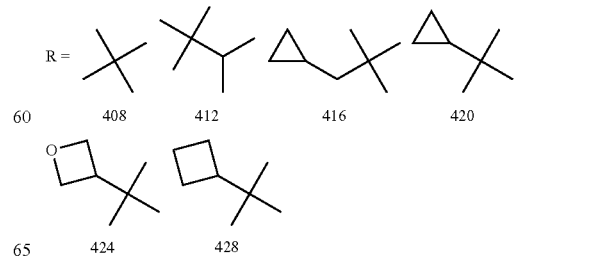

Synthesis of (392)

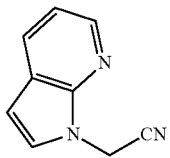 [SMILES: N#CCn1ccc2cccnc21]

Pyrrolo[2,3-b]pyridin-1-yl-acetonitrile

To a suspension of sodium hydride (60%) (3.7 g, 93.12 mmol) in tetrahydrofuran (60 mL) was added dropwise a mixture of 1H-pyrrolo[2,3-b]pyridine (391=(5 g, 42.33 mmol) and bromoacetonitrile (10 g, 84.65 mmol) dissolved in tetrahydrofuran (40 mL) at 0° C. and the reaction mixture was stirred for 30 min at same temperature, then at room temperature for 6 h (TLC, 40% ethyl acetate in hexane, $R_f$=0.5). After completion of the reaction, the reaction mixture was quenched with saturated ammonium chloride solution (100 mL). The tetrahydrofuran was removed, water (100 mL) was added, and the mixture was extracted with ethyl acetate (3×100 mL). The separated organic part was washed with brine (100 mL) and dried and concentrated to get a crude mass which was purified by Combi-Flash (eluted at 20% ethyl acetate in hexane) to afford pyrrolo[2,3-b]pyridin-1-yl-acetonitrile (3) (4 g, 60%) as a light brown solid.

LC-MS: 158.2 (M+H).

Synthesis of (393)

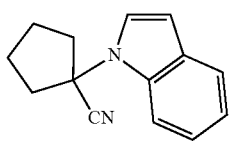 [SMILES: N#CC1(n2ccc3ccccc32)CCCC1]

1-Pyrrolo[2,3-b]pyridin-1-yl-cyclopentanecarbonitrile

To a suspension of sodium hydride (60%) (8.6 g, 215.79 mmol) in dimethyl sulfoxide (90 mL) was added dropwise a mixture of pyrrolo[2,3-b]pyridin-1-yl-acetonitrile (392) (15.4 g, 98.09 mmol) and 1,4-dibromo-butane (31.7 g, 147.13 mmol) dissolved in dimethyl sulfoxide: ether (180 mL, 1:1) at 0° C. and the reaction mixture was stirred for 30 min at same temperature, then stirred at room temperature for 24 h. (TLC, 40% ethyl acetate in hexane, $R_f$=0.6). After completion of the reaction, the reaction mixture was quenched with 1N HCl (100 mL). Water (100 mL) was added and the mixture was extracted with ethyl acetate (3×100 mL). The separated organic part was washed with water (3×100 mL) and brine (2×100 mL) and dried and concentrated to get a crude product which was purified by Combi-Flash column (eluted at 10-20% ethyl acetate in hexane) to afford 1-pyrrolo[2,3-b]pyridin-1-yl-cyclopentanecarbonitrile (393) (18 g, 87%) as a light yellow crystalline solid.

LC-MS: 212.0 (M+H)

Synthesis of (394)

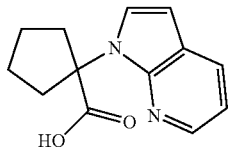 [SMILES: O=C(O)C1(n2ccc3cccnc32)CCCC1]

1-Pyrrolo[2,3-b]pyridin-1-yl-cyclopentanecarboxylic acid

To a stirred suspension of 1-pyrrolo[2,3-b]pyridin-1-yl-cyclopentanecarbonitrile (393) (6.2 g, 29.35 mmol) in water (90 mL) was added LiOH.H$_2$O (14 g, 334.56 mmol). The reaction mixture was refluxed for 24 h (TLC, 30% ethyl acetate in hexane, $R_f$=0.3). It was thereafter cooled to 0° C. and the aqueous part was acidified with HCl (6N) to pH 3 and extracted with ethyl acetate (3×50 mL). The organic phase was thereafter dried and concentrated to get 1-pyrrolo[2,3-b]pyridin-1-yl-cyclopentanecarboxylic acid (394) (5.8 g, 86%) as an off-white solid.

LC-MS: 231.0 (M+H)

Synthesis of (395)

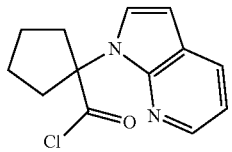 [SMILES: O=C(Cl)C1(n2ccc3cccnc32)CCCC1]

1-Pyrrolo[2,3-b]pyridin-1-yl-cyclopentanecarbonyl chloride

To a stirred solution of 1-pyrrolo[2,3-b]pyridin-1-yl-cyclopentanecarboxylic acid (394) (1.2 g, 5.21 mmol) in dichloromethane (80 mL) was dropwise added oxalyl chloride (1 mL, 11.47 mmol) at 0° C., followed by dimethyl formamide (0.1 mL). The reaction mixture was stirred for 1 h at room temperature. After completion, the reaction mixture is concentrated under argon atmosphere to get 1-pyrrolo[2,3-b]pyridin-1-yl-cyclopentanecarbonyl chloride (395) (1.3 g, 100%, crude) as a yellow solid which was directly used for the next step without analysis.

Synthesis of (396)

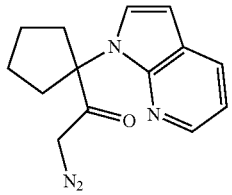

2-Diazo-1-(1-pyrrolo[2,3-b]pyridin-1-yl-cyclopentyl)-ethanone

To a solution of 1-pyrrolo[2,3-b]pyridin-1-yl-cyclopentanecarbonyl chloride (395) (1.2 g, 8.83 mmol) in tetrahydrofuran (80 mL) was dropwise added a solution of diazomethane [which was freshly synthesized following the standard procedure, starting from methylurea via formation of NMU and followed by KOH treatment] in ether (80 mL) at −5° C., while stirring very slowly. The reaction mixture was left standing for 1 h at 0° C. (TLC, 30% ethyl acetate in hexane, $R_f$=0.6). Volatiles were removed to get the crude product which was purified by Combi-Flash column (eluted at 20-30% ethyl acetate in hexane) to get 2-diazo-1-(1-pyrrolo[2,3-b]pyridin-1-yl-cyclopentyl)-ethanone (396) (1.1 g, 90%) as a yellow sticky solid.

LC-MS: 254.8 (M+H).

Synthesis of (397)

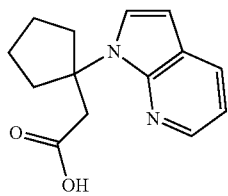 [SMILES: O=C(O)CC1(n2ccc3cccnc32)CCCC1]

(1-Pyrrolo[2,3-b]pyridin-1-yl-cyclopentyl)-acetic acid

To a stirred solution of 2-diazo-1-(1-pyrrolo[2,3-b]pyridin-1-yl-cyclopentyl)-ethanone (396) (0.95 g, 3.82 mmol) in dioxane:water (10:1) (27.5 mL) was added silveracetate (319 mg, 1.91 mmol) and stirring was continued for 2 h at room temperature (TLC, 30% ethyl acetate in hexane, $R_f$=0.2). The mixture was filtered over a celite bed, washed with ethyl acetate (3×20 mL) and concentrated. The crude product was purified by Combi-Flash column (eluted at 30% ethyl acetate in hexane) to get (1-pyrrolo[2,3-b]pyridin-1-yl-cyclopentyl)-acetic acid (397) (0.5 g, 54%) as a brown solid.

LC-MS: 245.2 (M+H)

Synthesis of (398)

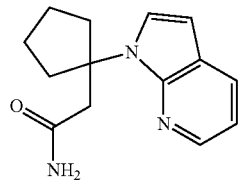 [SMILES: NC(=O)CC1(n2ccc3cccnc32)CCCC1]

2-(1-Pyrrolo[2,3-b]pyridin-1-yl-cyclopentyl)-acetamide

To a stirred solution of (1-pyrrolo[2,3-b]pyridin-1-yl-cyclopentyl)-acetic acid (397) (2.7 g, 11.05 mmol) in dimethylformamide (60 mL) was added N,N-diisopropylethylamine (5.8 mL, 33.16 mmol) followed by $(NH_4)_2CO_3$ (5.2 g, 33.16 mmol) and HATU (6.3 g, 16.58 mmol) and stirring was continued for 1 h at room temperature (TLC, 50% ethyl acetate in hexane, $R_f$=0.5), Water (200 mL) was added and the mixture was extracted with ethyl acetate (2×200 mL), organic part was washed with water (2×100 mL) and brine (2×100 mL). The organic phase was thereafter dried and concentrated. The crude product was purified by Combi-Flash column chromatography (eluted at 30-40% ethyl acetate in hexane) to get 2-(1-pyrrolo[2,3-b]pyridin-1-yl-cyclopentyl)acetamide (398) (1.7 g, 63%) as a yellow solid.

LC-MS: 244.1 (M+H)

Synthesis of (399)

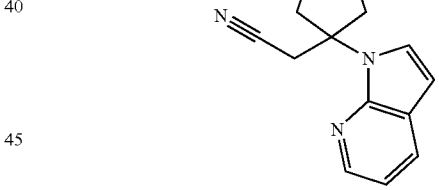

(1-Pyrrolo[2,3-b]pyridin-1-yl-cyclopentyl)-acetonitrile

To a stirred solution of 2-(1-pyrrolo[2,3-b]pyridin-1-yl-cyclopentyl)-acetamide (398) (1.6 g, 6.58 mmol) in dimethylformamide (25 mL) was added cyanuric chloride (728 mg, 3.95 mmol) at room temperature. The reaction mixture was stirred for 30 min at room temperature (TLC, 30% ethyl acetate in hexane, $R_f$=0.8). Cold water was added and the mixture was extracted with ethyl acetate (2×50 mL) and washed with water (2×50 mL) and brine (50 mL). The organic phase was thereafter dried and concentrated to get a crude product. The crude product was purified by Combi-Flash column (eluted at 10-20% ethyl acetate in hexane) to get (1-pyrrolo[2,3-b]pyridin-1-yl-cyclopentyl)-acetonitrile (399) (861 mg, 58%) as a light yellow thick oil.

LC-MS: 225.9 (M+H)

357
Synthesis of (400)

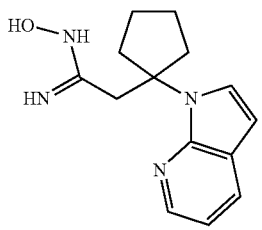 [SMILES: N=C(CC1(n2ccc3cccnc32)CCCC1)NO]

N-Hydroxy-2-(1-pyrrolo[2,3-b]pyridin-1-yl-cyclopentyl)-acetamidine

To a stirred solution of (1-pyrrolo[2,3-b]pyridin-1-yl-cyclopentyl)-acetonitrile (399) (1.4 g, 6.21 mmol) in ethanol (50 mL) was added 50% aq. $NH_2OH$ (4 mL, 62.15 mmol) and the reaction mixture was heated at 60° C. for 16 h (TLC, 30% ethyl acetate in hexane, $R_f$=0.1). Ethanol was evaporated, water (50 mL) was added and the mixture was extracted with etylacetate (3×50 mL). The organic phase was thereafter dried and concentrated to get crude N-hydroxy-2-(1-pyrrolo[2,3-b]pyridin-1-yl-cyclopentyl)-acetamidine (400) (1.8 g, 112%) as an off-white sticky liquid.

LC-MS: 258.9 (M+H)

Synthesis of (401)

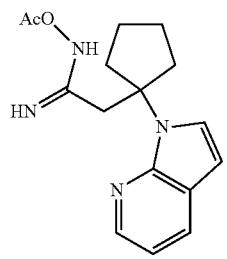 [SMILES: CC(=O)ONC(=N)CC1(n2ccc3cccnc32)CCCC1]

2-(1-{1H-pyrrolo[2,3-b]pyridin-1-yl}cyclopentyl) ethanimidamido acetate

Acetic anhydride (11.2 mL, 118.61 mmol) was added to N-hydroxy-2-(1-pyrrolo[2,3-b]pyridin-1-yl-cyclopentyl)-acetamidine (400) (1.8 g, 6.98 mmol) and stirring was continued for 3 h at room temperature (TLC, ethyl acetate, $R_f$=0.5). Water (50 mL) was added, and the mixture was basified to pH 8 by solid $NaHCO_3$ and extracted with ethyl acetate (3×50 mL). The organic phase was thereafter dried and concentrated. The crude product was purified by Combi-Flash column (eluted at 20-30% ethyl acetate in hexane) to get 2-(1-{1H-pyrrolo[2,3-b]pyridin-1-yl}cyclopentyl)ethanimidamido acetate (401) (1.7 g, 81%) as an off-white solid.

LC-MS: 300.8 (M+H)

358
Synthesis of (402)

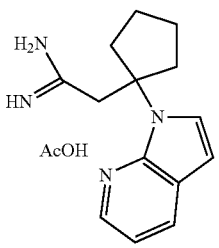 [SMILES: "AcOH" ; N=C(N)CC1(n2ccc3cccnc32)CCCC1]

2-(1-Pyrrolo[2,3-b]pyridin-1-yl-cyclopentyl)-acetamidine; compound with acetic acid

To a stirred degassed solution of 2-(1-{1H-pyrrolo[2,3-b]pyridin-1-yl}cyclopentyl)ethanimidamido acetate (401) (500 mg, 1.67 mmol) in ethanol (20 mL) was added 10% Pd—C (50 mg) and stirring was continued 30 min under $H_2$ (hydrogen-bludder) at room temperature (TLC, 50% ethyl acetate in hexane, $R_f$=0.1), The reaction mixture was filtered through a celite bed and washed with 10% methanol in dichloromethane (5×50 mL). The organic phase was thereafter dried and concentrated to get 2-(1-pyrrolo[2,3-b]pyridin-1-yl-cyclopentyl)-acetamidine; compound with acetic acid (402) (437 mg, 87%) as an off-white solid.

LC-MS: 243.0 (M+H)

Synthesis of (403)

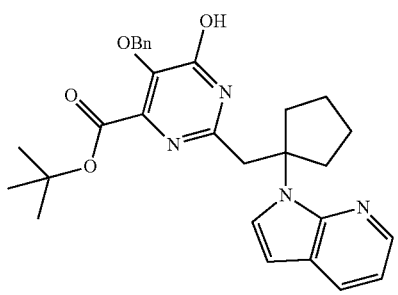 [SMILES: CC(C)(C)OC(=O)c1nc(CC2(n3ccc4cccnc43)CCCC2)nc(O)c1OCc1ccccc1]

5-Benzyloxy-6-hydroxy-2-(1-pyrrolo[2,3-b]pyridin-1-yl-cyclopentylmethyl)-pyrimidine-4-carboxylic acid tert-butyl ester

To a stirred solution of 2-(1-pyrrolo[2,3-b]pyridin-1-yl-cyclopentyl)-acetamidine; compound with acetic acid (402) (800 mg, 2.65 mmol) and (E)-3-benzyloxy-2-hydroxy-4-oxo-pent-2-enoic acid tert-butyl ester (4) (978 mg, 3.18 mmol) in methanol (80 mL) was added sodium methoxide solution (25% in methanol) (1.7 mL, 7.94 mmol) at 0° C. The reaction mixture was allowed to warm slowly to room temperature and was stirred for 16 h (TLC, ethyl acetate, $R_f$=0.3). After completion of the reaction, methanol was evaporated to get a crude product which was purified by Combi-Flash column (eluted at 60-70% ethyl acetate in hexane) to get 5-benzyloxy-6-hydroxy-2-(1-pyrrolo[2,3-b]pyridin-1-yl-cyclopentylmethyl)-pyrimidine-4-carboxylic acid tert-butyl ester (403) (1 g, 75%) as a light yellow solid.

LC-MS: 501.2 (M+H).

Synthesis of (404)

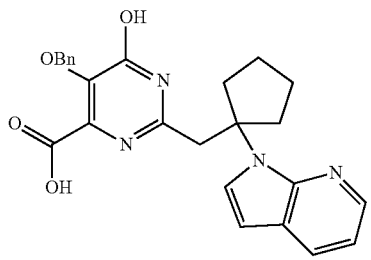 [SMILES: O=C(O)c1nc(CC2(n3ccc4cccnc43)CCCC2)nc(O)c1OCc1ccccc1]

5-Benzyloxy-6-hydroxy-2-(1-pyrrolo[2,3-b]pyridin-1-yl-cyclopentylmethyl)-pyrimidine-4-carboxylic acid To a stirred solution of 5-benzyloxy-6-hydroxy-2-(1-pyrrolo[2,3-b]pyridin-1-yl-cyclopentylmethyl)-pyrimidine-4-carboxylic acid tert-butyl ester (403) (900 mg. 1.8 mmol) in a mixture of tetrahydrofuran:water (2:1) (30 mL) was added lithium hydroxide monohydrate (756 g, 18.0 mmol) and the mixture was refluxed for 24 h (TLC, ethyl acetate, $R_f$=0.1). After completion of reaction, volatiles were evaporated and the aqueous part was washed with ethyl acetate (3×30 mL). The aqueous layer was acidified with HCl (6N) to pH 3 and extracted with ethyl acetate (3×50 mL). The organic phase was thereafter dried and concentrated to get 5-benzyloxy-6-hydroxy-2-(1-pyrrolo[2,3-b]pyridin-1-yl-cyclopentyl methyl)-pyrimidine-4-carboxylic acid (404) (500 mg, 62%) as an off-white sticky solid.

LC-MS: 445.0 (M+H).

Example 408

9-Hydroxy-2-methyl-6-(1-pyrrolo[2,3-b]pyridin-1-yl-cyclopentylmethyl)-3,4-dihydro-2H-pyrazino[1,2-c]pyrimidine-1,8-dione The synthetic procedure used in this preparation is outlined in Scheme 49.

Synthesis of (405)

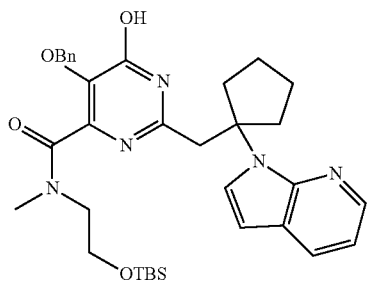 [SMILES: CN(CCO[Si](C)(C)C(C)(C)C)C(=O)c1nc(CC2(n3ccc4cccnc43)CCCC2)nc(O)c1OCc1ccccc1]

5-Benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-methylamide To a stirred solution of 5-benzyloxy-6-hydroxy-2-(1-pyrrolo[2,3-b]pyridin-1-yl-cyclopentylmethyl)-pyrimidine-4-carboxylic acid (404) (250 mg, 0.56 mmol) in dimethylformamide (5 mL) was added N,N-diisopropylethylamine (0.3 mL, 1.69 mmol) followed by [2-(tert-butyl-dimethylsilanyloxy)-ethyl]methyl-amine (8a) (320 mg, 1.69 mmol) and HATU (320 mg, 0.84 mmol) and stirring was continued for 1 h (TLC, ethyl acetate, $R_f$=0.5). Water (30 mL) was added and the mixture was extracted with ethyl acetate (2×20 mL). The organic part was washed with water (2×100 mL) and brine (2×50 mL). The organic phase was thereafter dried and concentrated. The crude product was purified by Combi-Flash column (eluted at 30-40% ethyl acetate in hexane) to get 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-methyl-amide (405) (300 mg, 87%) as a light yellow sticky solid.

LC-MS: 616.4 (M+H).

Synthesis of (406)

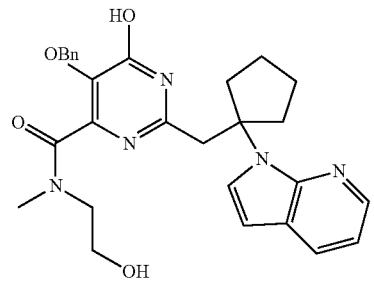 [SMILES: CN(CCO)C(=O)c1nc(CC2(n3ccc4cccnc43)CCCC2)nc(O)c1OCc1ccccc1]

5-Benzyloxy-6-hydroxy-2-(1-pyrrolo[2,3-b]pyridin-1-yl-cyclopentylmethyl)-pyrimidine-4-carboxylic acid (2-hydroxyethyl)-methyl-amide To a stirred solution of 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-methyl-amide (405) (300 mg, 0.49 mmol) in tetrahydrofuran (10 mL) was added 1N HCl (2.4 mL) and stirring was continued for 1 h at room temperature. After completion of the reaction, the tetrahydrofuran was removed and the reaction mixture was basified with solid NaHCO₃ (to pH 8), extracted with ethyl acetate (3×20 mL) and the organic part was dried and concentrated to yield a crude product which was purified by prep TLC (mobile phase ethyl acetate) to get 5-benzyloxy-6-hydroxy-2-(1-pyrrolo[2,3-b]pyridin-1-yl-cyclopentylmethyl)-pyrimidine-4-carboxylic acid (2-hydroxyethyl)-methyl-amide (406) (210 mg, 86%) as a light yellow sticky solid.

LC-MS: 502.1 (M+H).

Synthesis of (407)

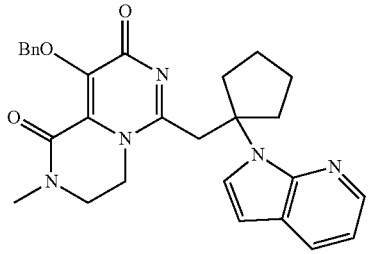 [SMILES: CN1CCn2c(CC3(n4ccc5cccnc54)CCCC3)nc(=O)c(OCc3ccccc3)c2C1=O]

9-Benzyloxy-2-methyl-6-(1-pyrrolo[2,3-b]pyridin-1-yl-cyclopentylmethyl)-3,4-dihydro-2H-pyrazino[1,2-c]pyrimidine-1,8-dione To a stirred solution of 5-benzyloxy-6-hydroxy-2-(1-pyrrolo[2,3-b]pyridin-1-yl-cyclopentylmethyl)-pyrimidine-4-carboxylic acid (2-hydroxyethyl)-methyl-amide (406) (210 mg, 0.42 mmol) in dichloromethane (30 mL) was added triphenyl phosphine (550 mg, 2.09 mmol) followed by diisopropyl azodicarboxylate (0.2 mL, 1.26 mmol) at room temperature and stirring was continued for 10 min (TLC, 5% methanol in ethyl acetate, $R_f$=0.2). The reaction mixture was concentrated under reduced pressure to get a crude product, which was purified by Prep-TLC plate (mobile phase 5% methanol in ethyl acetate) to get 9-benzyloxy-2-methyl-6-(1-pyrrolo[2,3-b]pyridin-1-yl-cyclopentylmethyl)-3,4-dihydro-2H-pyrazino[1,2-c]pyrimidine-1,8-dione (407) (60 mg, 30%) as a white solid.

LC-MS: 484.1 (M+H).

Synthesis of (408): (16281)

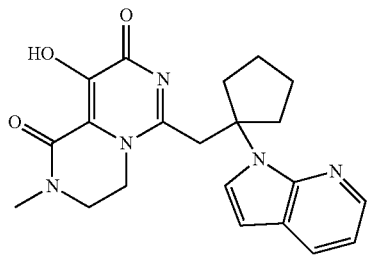 [SMILES: CN1CCn2c(CC3(n4ccc5cccnc54)CCCC3)nc(=O)c(O)c2C1=O]

9-Hydroxy-2-methyl-6-(1-pyrrolo[2,3-b]pyridin-1-yl-cyclopentylmethyl)-3,4-dihydro-2H-pyrazino[1,2-c]pyrimidine-1,8-dione A solution of 9-benzyloxy-2-methyl-6-(1-pyrrolo[2,3-b]pyridin-1-yl-cyclopentylmethyl)-3,4-dihydro-2H-pyrazino[1,2-c]pyrimidine-1,8-dione (407) (60 mg, 0.12 mmol) in ethanol (10 mL) was degassed, Pd—C (10%) (6 mg) added and hydrogenated for 40 min (hydrogen bludder) (TLC, 5% methanol in dichloromethane, $R_f$=0.2). The catalyst was filtered of and washed with 10% dichloromethane in ethanol (3×20 mL). The combined solvents were concentrated and the resulting sticky solid was washed with pentane to get pure 9-hydroxy-2-methyl-6-(1-pyrrolo[2,3-b]pyridin-1-yl-cyclopentylmethyl)-3,4-dihydro-2H-pyrazino[1,2-c]pyrimidine-1,8-dione (408) (38 mg, 78%) as an off-white solid.

LC-MS: 394.2 (M+H).

Example 412

9-Hydroxy-2-isopropyl-6-(1-pyrrolo[2,3-b]pyridin-1-yl-cyclopentylmethyl)-3,4-dihydro-2H-pyrazino[1,2-c]pyrimidine-1,8-dione The synthetic procedure used in this preparation is outlined in Scheme 49.

Synthesis of (409)

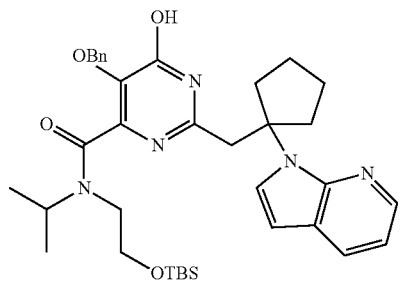 [SMILES: CC(C)N(CCO[Si](C)(C)C(C)(C)C)C(=O)c1nc(CC2(n3ccc4cccnc43)CCCC2)nc(O)c1OCc1ccccc1]

5-Benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]isopropylamide 5-Benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-isopropylamide (409) was prepared following the same method as described for 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-methyl-amide (405) from 5-benzyloxy-6-hydroxy-2-(1-pyrrolo[2,3-b]pyridin-1-yl-cyclopentylmethyl)-pyrimidine-4-carboxylic acid (404) (250 mg, 0.56 mmol) and [2-(tert-tutyl-dimethylsilanyloxy)-ethyl]-isopropyl-amine (367 mg, 1.69 mmol) (8b) to get an off-white sticky solid (220 mg, 61%).

LC-MS: 644.5 (M+H).

Synthesis of (410)

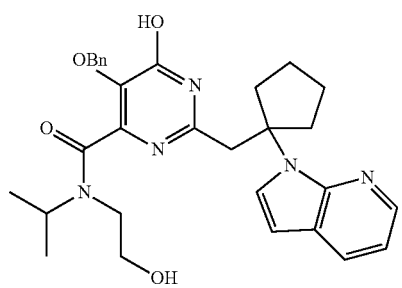 [SMILES: CC(C)N(CCO)C(=O)c1nc(CC2(n3ccc4cccnc43)CCCC2)nc(O)c1OCc1ccccc1]

5-Benzyloxy-6-hydroxy-2-(1-pyrrolo[2,3-b]pyridin-1-yl-cyclopentylmethyl)-pyrimidine-4-carboxylic acid (2-hydroxyethyl)-isopropylamide 5-Benzyloxy-6-hydroxy-2-(1-pyrrolo[2,3-b]pyridin-1-yl-cyclopentylmethyl)-pyrimidine-4-carboxylic acid (2-hydroxyethyl)-isopropylamide (410) was prepared following the same method as described for 5-benzyloxy-6-hydroxy-2-(1-pyrrolo[2,3-b]pyridin-1-yl-cyclopentylmethyl)-pyrimidine-4-carboxylic acid (2-hydroxyethyl)-methyl-amide (406) from 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]isopropylamide (409) (220 mg, 0.34 mmol) and was obtained as an off-white sticky solid (110 mg, 61%).

LC-MS: 530.2 (M+H).

Synthesis of (411)

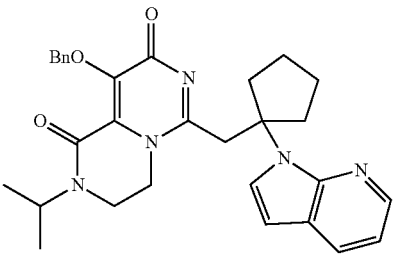 [SMILES: CC(C)N1CCn2c(CC3(n4ccc5cccnc54)CCCC3)nc(=O)c(OCc3ccccc3)c2C1=O]

9-Benzyloxy-2-isopropyl-6-(1-pyrrolo[2,3-b]pyridin-1-yl-cyclopentylmethyl)-3,4-dihydro-2H-pyrazino[1,2-c]pyrimidine-1,8-dione 9-Benzyloxy-2-isopropyl-6-(1-pyrrolo[2,3-b]pyridin-1-yl-cyclopentylmethyl)-3,4-dihydro-2H-pyrazino[1,2-c]pyrimidine-1,8-dione (411) was prepared following the same method as described for 9-benzyloxy-2-methyl-6-(1-pyrrolo[2,3-b]pyridin-1-yl-cyclopentylmethyl)-3,4-dihydro-2H-pyrazino[1,2-c]pyrimidine-1,8-dione (407) from 5-benzyloxy-6-hydroxy-2-(1-pyrrolo[2,3-b]pyridin-1-yl-cyclopentylmethyl)-pyrimidine-4-carboxylic acid (2-hydroxyethyl)-isopropylamide (410) (110 mg, 0.21 mmol) and was obtained as an off-white solid (40 mg, 38%).

LC-MS: 512.1 (M+H).

Synthesis of (412): (16282)

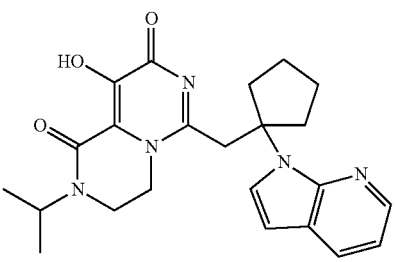 [SMILES: CC(C)N1CCn2c(CC3(n4ccc5cccnc54)CCCC3)nc(=O)c(O)c2C1=O]

9-Hydroxy-2-isopropyl-6-(1-pyrrolo[2,3-b]pyridin-1-yl-cyclopentylmethyl)-3,4-dihydro-2H-pyrazino[1,2-c]pyrimidine-1,8-dione 9-Hydroxy-2-isopropyl-6-(1-pyrrolo[2,3-b]pyridin-1-yl-cyclopentylmethyl)-3,4-dihydro-2H-pyrazino[1,2-c]pyrimidine-1,8-dione (412) was prepared following the same method as described for 9-hydroxy-2-methyl-6-(1-pyrrolo[2,3-b]pyridin-1-yl-cyclopentylmethyl)-3,4-dihydro-2H-pyrazino[1,2-c]pyrimidine-1,8-dione (408) from 9-benzyloxy-2-isopropyl-6-(1-pyrrolo[2,3-b]pyridin-1-yl-cyclopentylmethyl)-3,4-dihydro-2H-pyrazino[1,2-c]pyrimidine-1,8-dione (411) (40 mg, 0.08 mmol) and was obtained as an off-white solid (30 mg, 91%).

LC-MS: 422.1 (M+H).

Example 416

2-Cyclopropylmethyl-9-hydroxy-6-(1-pyrrolo[2,3-b]pyridin-1-yl-cyclopentylmethyl)-3,4-dihydro-2H-pyrazino[1,2-c]pyrimidine-1,8-dione The synthetic procedure used in this preparation is outlined in Scheme 49.

Synthesis of (413)

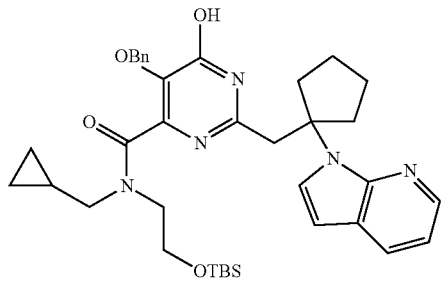 [SMILES: CC(C)(C)[Si](C)(C)OCCN(CC1CC1)C(=O)c1nc(CC2(n3ccc4cccnc43)CCCC2)nc(O)c1OCc1ccccc1]

5-Benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-cyclopropylmethyl-amide 5-Benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-cyclopropylmethyl-amide (413) was prepared following the same method as described for 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-methyl-amide (405) from 5-benzyloxy-6-hydroxy-2-(1-pyrrolo[2,3-b]pyridin-1-yl-cyclopentylmethyl)-pyrimidine-4-carboxylic acid (404) (200 mg, 0.45 mmol) and [2-(tert-butyl-dimethylsilanyloxy)-ethyl]-cyclopropylmethyl-amine (134 mg, 0.58 mmol) (8i) to get an off-white sticky solid (180 mg, 61%).

LC-MS: 656.0 (M+H).

Synthesis of (414)

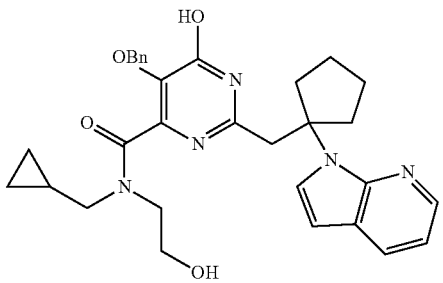 [SMILES: O=C(c1nc(CC2(n3ccc4cccnc43)CCCC2)nc(O)c1OCc1ccccc1)N(CCO)CC1CC1]

5-Benzyloxy-6-hydroxy-2-(1-pyrrolo[2,3-b]pyridin-1-yl-cyclopentylmethyl)-pyrimidine-4-carboxylic acid cyclopropylmethyl-(2-hydroxyethyl)-amide 5-Benzyloxy-6-hydroxy-2-(1-pyrrolo[2,3-b]pyridin-1-yl-cyclopentylmethyl)-pyrimidine-4-carboxylic acid cyclopropylmethyl-(2-hydroxyethyl)-amide (414) was prepared following the same method as described for 5-benzyloxy-6-hydroxy-2-(1-pyrrolo[2,3-b]pyridin-1-yl-cyclopentylmethyl)-pyrimidine-4-carboxylic acid (2-hydroxyethyl)-methyl-amide (406) from 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-cyclopropylmethyl-amide (413) (170 mg, 0.26 mmol) and the product was obtained as white sticky solid (140 mg, crude).

LC-MS: 542.0 (M+H).

Synthesis of (415)

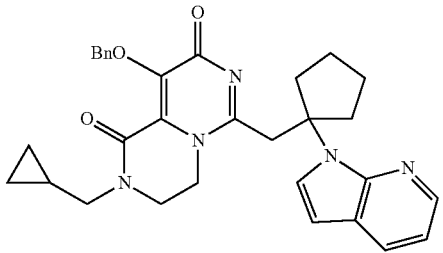 [SMILES: O=C1c2c(OCc3ccccc3)c(=O)nc(CC3(n4ccc5cccnc54)CCCC3)n2CCN1CC1CC1]

9-Benzyloxy-2-cyclopropylmethyl-6-(1-pyrrolo[2,3-b]pyridin-1-yl-cyclopentylmethyl)-3,4-dihydro-2H-pyrazino[1,2-c]pyrimidine-1,8-dione 9-Benzyloxy-2-cyclopropylmethyl-6-(1-pyrrolo[2,3-b]pyridin-1-yl-cyclopentylmethyl)-3,4-dihydro-2H-pyrazino[1,2-c]pyrimidine-1,8-dione (415) was prepared following the same method as described for 9-benzyloxy-2-methyl-6-(1-pyrrolo[2,3-b]pyridin-1-yl-cyclopentylmethyl)-3,4-dihydro-2H-pyrazino[1,2-c]pyrimidine-1,8-dione (407) from 5-benzyloxy-6-hydroxy-2-(1-pyrrolo[2,3-b]pyridin-1-yl-cyclopentylmethyl)-pyrimidine-4-carboxylic acid cyclopropylmethyl-(2-hydroxyethyl)-amide (414) (130 mg, 0.24 mmol) and was obtained as white solid (56 mg, 46%).

LC-MS: 524.4 (M+H).

Synthesis of (416): (16289)

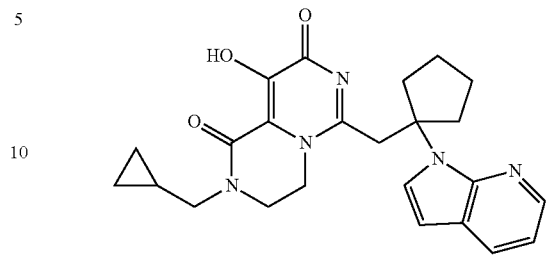

2-Cyclopropylmethyl-9-hydroxy-6-(1-pyrrolo[2,3-b]pyridin-1-yl-cyclopentylmethyl)-3,4-dihydro-2H-pyrazino[1,2-c]pyrimidine-1,8-dione 2-Cyclopropylmethyl-9-hydroxy-6-(1-pyrrolo[2,3-b]pyridin-1-yl-cyclopentylmethyl)-3,4-dihydro-2H-pyrazino[1,2-c]pyrimidine-1,8-dione (416) was prepared following the same method as described for 9-hydroxy-2-methyl-6-(1-pyrrolo[2,3-b]pyridin-1-yl-cyclopentylmethyl)-3,4-dihydro-2H-pyrazino[1,2-c]pyrimidine-1,8-dione (408) from 9-benzyloxy-2-cyclopropylmethyl-6-(1-pyrrolo[2,3-b]pyridin-1-yl-cyclopentyl methyl)-3,4-dihydro-2H-pyrazino[1,2-c]pyrimidine-1,8-dione (415) (50 mg, 0.09 mmol) and was obtained as an off-white solid (36 mg, 85%).

LC-MS: 434.3 (M+H).

Example 420

2-Cyclopropyl-9-hydroxy-6-(1-pyrrolo[2,3-b]pyridin-1-yl-cyclopentylmethyl)-3,4-dihydro-2H-pyrazino[1,2-c]pyrimidine-1,8-dione The synthetic procedure used in this preparation is outlined in Scheme 49.

Synthesis of (417)

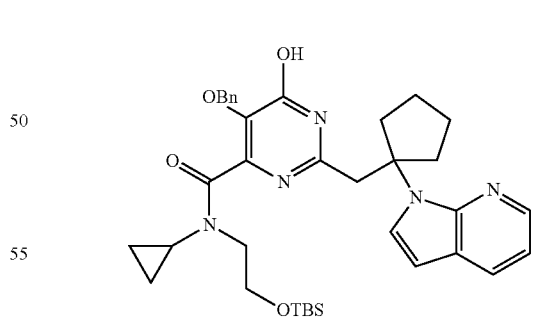

5-Benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-cyclopropyl-amide 5-Benzyloxy-6-hydroxy-2-(1-pyrrolo[2,3-b]pyridin-1-yl-cyclopentylmethyl)-pyrimidine-4-carboxylic acid [2-(tertbutyl-dimethylsilanyloxy)-ethyl]-cyclopropyl-amide (417) was prepared following the same method as described for 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-methyl-amide (405) from 5-benzyloxy-6-hydroxy-2-(1-pyrrolo[2,3-b]pyridin-1-yl-cyclopentylmethyl)-pyrimidine-4-carboxylic acid (404) (150 mg, 0.34 mmol) and [2-(tert-butyl-dimethylsilanyloxy)-ethyl]-cyclopropyl-amine (94 mg, 0.44 mmol) (8d) to get a white sticky solid (96 mg, 44%).

LC-MS: 642.1 (M+H).

Synthesis of (418)

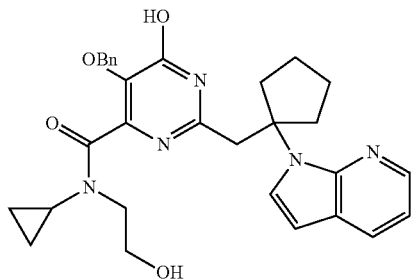 [SMILES: O=C(c1nc(CC2(n3ccc4cccnc43)CCCC2)nc(O)c1OCc1ccccc1)N(CCO)C1CC1]

5-Benzyloxy-6-hydroxy-2-(1-pyrrolo[2,3-b]pyridin-1-yl-cyclopentylmethyl)-pyrimidine-4-carboxylic acid cyclopropyl-(2-hydroxyethyl)-amide To a stirred solution of 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-cyclopropyl-amide (417) (96 mg, 0.15 mmol) in tetrahydrofuran (3 mL) was added tetrabutylammoniumfluoride 1M in tetrahydrofuran (0.7 mL, 0.75 mmol) at room temperature and stirring was continued for 1 h. The tetrahydrofuran was removed from the reaction mixture, diluted with ethyl acetate (50 mL) and washed with water (2×30 mL) and brine (30 mL). The organic phase was thereafter dried and concentrated to get 5-benzyloxy-6-hydroxy-2-(1-pyrrolo[2,3-b]pyridin-1-yl-cyclopentylmethyl)-pyrimidine-4-carboxylic acid cyclopropyl-(2-hydroxyethyl)-amide (418) (60 mg, crude) as an off-white sticky solid.

LC-MS: 528.2 (M+H).

Synthesis of (419)

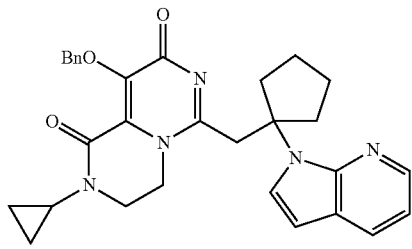 [SMILES: O=C1c2c(OCc3ccccc3)c(=O)nc(CC3(n4ccc5cccnc54)CCCC3)n2CCN1C1CC1]

9-Benzyloxy-2-cyclopropyl-6-(1-pyrrolo[2,3-b]pyridin-1-yl-cyclopentylmethyl)-3,4-dihydro-2H-pyrazino[1,2-c]pyrimidine-1,8-dione 9-Benzyloxy-2-cyclopropyl-6-(1-pyrrolo[2,3-b]pyridin-1-yl-cyclopentylmethyl)-3,4-dihydro-2H-pyrazino[1,2-c]pyrimidine-1,8-dione (419) was prepared following the same method as described for 9-benzyloxy-2-methyl-6-(1-pyrrolo[2,3-b]pyridin-1-yl-cyclopentylmethyl)-3,4-dihydro-2H-pyrazino[1,2-c]pyrimidine-1,8-dione (407) from 5-benzyloxy-6-hydroxy-2-(1-pyrrolo[2,3-b]pyridin-1-yl-cyclopentylmethyl)-pyrimidine-4-carboxylic acid cyclopropyl-(2-hydroxyethyl)-amide (418) (60 mg, 0.11 mmol) and was obtained as white sticky solid (45 mg, 80%).

LC-MS: 510.5 (M+H).

Synthesis of (420): (16303)

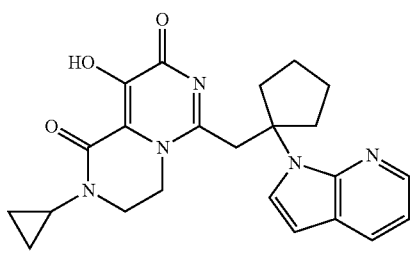 [SMILES: O=C1c2c(O)c(=O)nc(CC3(n4ccc5cccnc54)CCCC3)n2CCN1C1CC1]

2-Cyclopropyl-9-hydroxy-6-(1-pyrrolo[2,3-b]pyridin-1-yl-cyclopentylmethyl)-3,4-dihydro-2H-pyrazino[1,2-c]pyrimidine-1,8-dione 2-Cyclopropyl-9-hydroxy-6-(1-pyrrolo[2,3-b]pyridin-1-yl-cyclopentylmethyl)-3,4-dihydro-2H-pyrazino[1,2-c]pyrimidine-1,8-dione (420) was prepared following the same method as described for 9-hydroxy-2-methyl-6-(1-pyrrolo[2,3-b]pyridin-1-yl-cyclopentylmethyl)-3,4-dihydro-2H-pyrazino[1,2-c]pyrimidine-1,8-dione (408) from 9-Benzyloxy-2-cyclopropyl-6-(1-pyrrolo[2,3-b]pyridin-1-yl-cyclopentylmethyl)-3,4-dihydro-2H-pyrazino[1,2-c]pyrimidine-1,8-dione (419) (45 mg, 0.09 mmol) and was obtained as an off-white solid (35 mg, 94%).

LC-MS: 420.0 (M+H).

Example 424

9-Hydroxy-2-oxetan-3-yl-6-(1-pyrrolo[2,3-b]pyridin-1-yl-cyclopentylmethyl)-3,4-dihydro-2H-pyrazino[1,2-c]pyrimidine-1,8-dione The synthetic procedure used in this preparation is outlined in Scheme 49.

Synthesis of (421)

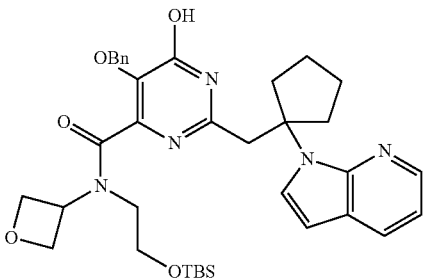 [SMILES: CC(C)(C)[Si](C)(C)OCCN(C(=O)c1nc(CC2(n3ccc4cccnc43)CCCC2)nc(O)c1OCc1ccccc1)C1COC1]

5-Benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]oxetan-3-yl-amide 5-Benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]oxetan-3-yl-amide (421) was prepared following the same method as described for 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-methyl-amide (405) from 5-benzyloxy-6-hydroxy-2-(1-pyrrolo[2,3-b]pyridin-1-yl-cyclopentylmethyl)-pyrimidine-4-carboxylic acid (404) (125 mg, 0.28 mmol) and [2-(tert-butyl-dimethylsilanyloxy)-ethyl]-oxetan-3-yl-amine (98 mg, 0.42 mmol) (8 g) to get a white sticky solid (180 mg, 97%, mixture).

LC-MS: 658.1 (M+H).

Synthesis of (422)

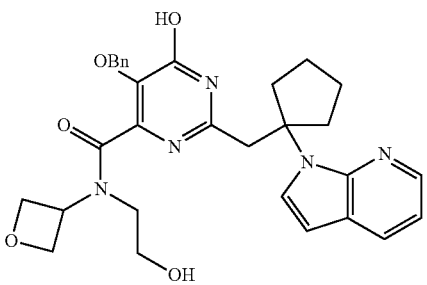 [SMILES: O=C(c1nc(CC2(n3ccc4cccnc43)CCCC2)nc(O)c1OCc1ccccc1)N(CCO)C1COC1]

5-Benzyloxy-6-hydroxy-2-(1-pyrrolo[2,3-b]pyridin-1-yl-cyclopentylmethyl)-pyrimidine-4-carboxylic acid (2-hydroxyethyl)-oxetan-3-yl-amide 5-Benzyloxy-6-hydroxy-2-(1-pyrrolo[2,3-b]pyridin-1-yl-cyclopentylmethyl)-pyrimidine-4-carboxylic acid (2-hydroxyethyl)-oxetan-3-yl-amide (422) was prepared following the same method as described for 5-benzyloxy-6-hydroxy-2-(1-pyrrolo[2,3-b]pyridin-1-yl-cyclopentylmethyl)-pyrimidine-4-carboxylic acid cyclopropyl-(2-hydroxyethyl)-amide (418) from 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-oxetan-3-yl-amide (421) (180 mg, 0.27 mmol) and was obtained as light brown sticky solid (220 mg, crude).

LC-MS: 544.0 (M+H).

Synthesis of (423)

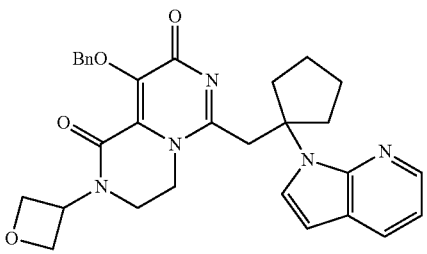 [SMILES: O=C1c2c(OCc3ccccc3)c(=O)nc(CC3(n4ccc5cccnc54)CCCC3)n2CCN1C1COC1]

9-Benzyloxy-2-oxetan-3-yl-6-(1-pyrrolo[2,3-b]pyridin-1-yl-cyclopentylmethyl)-3,4-dihydro-2H-pyrazino[1,2-c]pyrimidine-1,8-dione 9-Benzyloxy-2-oxetan-3-yl-6-(1-pyrrolo[2,3-b]pyridin-1-yl-cyclopentylmethyl)-3,4-dihydro-2H-pyrazino[1,2-c]pyrimidine-1,8-dione (423) was prepared following the same method as described for 9-benzyloxy-2-methyl-6-(1-pyrrolo[2,3-b]pyridin-1-yl-cyclopentylmethyl)-3,4-dihydro-2H-pyrazino[1,2-c]pyrimidine-1,8-dione (407) from 5-benzyloxy-6-hydroxy-2-(1-pyrrolo[2,3-b]pyridin-1-yl-cyclopentylmethyl)-pyrimidine-4-carboxylic acid (2-hydroxyethyl)-oxetan-3-yl-amide (422) (200 mg, 0.40 mmol) and was obtained as white sticky solid (13 mg, 6%).

LC-MS: 526.3 (M+H)

Synthesis of (424): (16297)

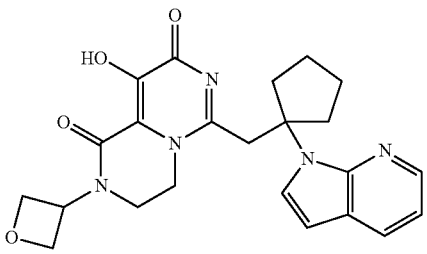 [SMILES: O=C1c2c(O)c(=O)nc(CC3(n4ccc5cccnc54)CCCC3)n2CCN1C1COC1]

9-Hydroxy-2-oxetan-3-yl-6-(1-pyrrolo[2,3-b]pyridin-1-yl-cyclopentylmethyl)-3,4-dihydro-2H-pyrazino[1,2-c]pyrimidine-1,8-dione 9-Hydroxy-2-oxetan-3-yl-6-(1-pyrrolo[2,3-b]pyridin-1-yl-cyclopentylmethyl)-3,4-dihydro-2H-pyrazino[1,2-c]pyrimidine-1,8-dione (424) was prepared following the same method as described for 9-hydroxy-2-methyl-6-(1-pyrrolo[2,3-b]pyridin-1-yl-cyclopentylmethyl)-3,4-dihydro-2H-pyrazino[1,2-c]pyrimidine-1,8-dione (408) from 9-Benzyloxy-2-oxetan-3-yl-6-(1-pyrrolo[2,3-b]pyridin-1-yl-cyclopentylmethyl)-3,4-dihydro-2H-pyrazino[1,2-c]pyrimidine-1,8-dione (423) (13 mg, 0.03 mmol) and was obtained as an off-white solid (8 mg, 74%).

LC-MS: 436.1 (M+H).

Example 428

2-Cyclobutyl-9-hydroxy-6-(1-pyrrolo[2,3-b]pyridin-1-yl-cyclopentylmethyl)-3,4-dihydro-2H-pyrazino[1,2-c]pyrimidine-1,8-dione The synthetic procedure used in this preparation is outlined in Scheme 49.

Synthesis of (425)

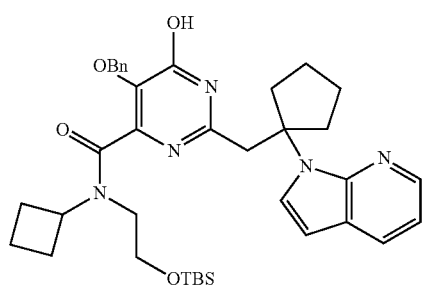 [SMILES: CC(C)(C)[Si](C)(C)OCCN(C(=O)c1nc(CC2(n3ccc4cccnc43)CCCC2)nc(O)c1OCc1ccccc1)C1CCC1]

5-Benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-cyclobutyl-amide 5-Benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-cyclobutyl-amide (425) was prepared following the same method as described for 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-methyl-amide (405) from 5-benzyloxy-6-hydroxy-2-(1-pyrrolo[2,3-b]pyridin-1-yl-cyclopentylmethyl)-pyrimidine-4-carboxylic acid (8f) (140 mg, 0.32 mmol) and [2-(tert-butyl-dimethylsilanyloxy)-ethyl]-cyclobutyl-amine (108 mg, 0.47 mmol) to get a white sticky solid (200 mg, 97%, impure).

LC-MS: 656.1 (M+H).

Synthesis of (426)

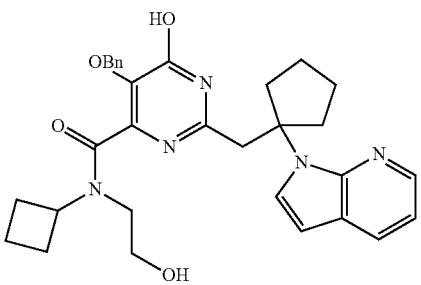 [SMILES: O=C(c1nc(CC2(n3ccc4cccnc43)CCCC2)nc(O)c1OCc1ccccc1)N(CCO)C1CCC1]

5-Benzyloxy-6-hydroxy-2-(1-pyrrolo[2,3-b]pyridin-1-yl-cyclopentylmethyl)-pyrimidine-4-carboxylic acid cyclobutyl-(2-hydroxyethyl)-amide 5-Benzyloxy-6-hydroxy-2-(1-pyrrolo[2,3-b]pyridin-1-yl-cyclopentylmethyl)-pyrimidine-4-carboxylic acid cyclobutyl-(2-hydroxyethyl)-amide (426) was prepared following the same method as described for 5-benzyloxy-6-hydroxy-2-(1-pyrrolo[2,3-b]pyridin-1-yl-cyclopentylmethyl)-pyrimidine-4-carboxylic acid cyclopropyl-(2-hydroxyethyl)-amide (418) from 5-benzyloxy-6-hydroxy-2-(1-pyrrolo[2,3-b]pyridin-1-yl-cyclopentylmethyl)-pyrimidine-4-carboxylic acid [2-(tert-butyl-dimethylsilanyloxy)-ethyl]-cyclobutyl-amide (425) (200 mg, 0.30 mmol) and was obtained as white solid (100 mg, 59%).

LC-MS: 542.4 (M+H).

Synthesis of (427)

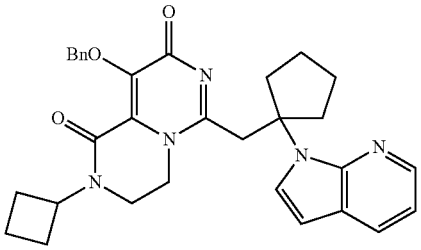 [SMILES: O=C1c2c(OCc3ccccc3)c(=O)nc(CC3(n4ccc5cccnc54)CCCC3)n2CCN1C1CCC1]

9-Benzyloxy-2-cyclobutyl-6-(1-pyrrolo[2,3-b]pyridin-1-yl-cyclopentylmethyl)-3,4-dihydro-2H-pyrazino[1,2-c]pyrimidine-1,8-dione 9-Benzyloxy-2-cyclobutyl-6-(1-pyrrolo[2,3-b]pyridin-1-yl-cyclopentylmethyl)-3,4-dihydro-2H-pyrazino[1,2-c]pyrimidine-1,8-dione (427) was prepared following the same method as described for 9-benzyloxy-2-methyl-6-(1-pyrrolo[2,3-b]pyridin-1-yl-cyclopentylmethyl)-3,4-dihydro-2H-pyrazino[1,2-c]pyrimidine-1,8-dione (407) from 5-benzyloxy-6-hydroxy-2-(1-pyrrolo[2,3-b]pyridin-1-yl-cyclopentylmethyl)-pyrimidine-4-carboxylic acid cyclobutyl-(2-hydroxyethyl)-amide (426) (90 mg, 0.17 mmol) and was obtained as an off-white solid (65 mg, 75%).

LC-MS: 524.4 (M+H).

Synthesis of (428): (16300)

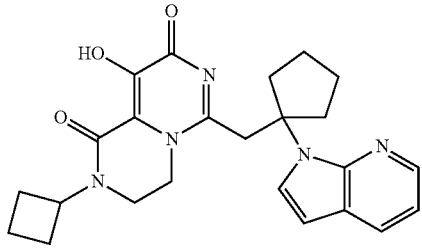 [SMILES: O=C1c2c(O)c(=O)nc(CC3(n4ccc5cccnc54)CCCC3)n2CCN1C1CCC1]

2-Cyclobutyl-9-hydroxy-6-(1-pyrrolo[2,3-b]pyridin-1-yl-cyclopentylmethyl)-3,4-dihydro-2H-pyrazino[1,2-c]pyrimidine-1,8-dione 2-Cyclobutyl-9-hydroxy-6-(1-pyrrolo[2,3-b]pyridin-1-yl-cyclopentylmethyl)-3,4-dihydro-2H-pyrazino[1,2-c]pyrimidine-1,8-dione (428) was prepared following the same method as described for 9-hydroxy-2-methyl-6-(1-pyrrolo[2,3-b]pyridin-1-yl-cyclopentylmethyl)-3,4-dihydro-2H-pyrazino[1,2-c]pyrimidine-1,8-dione (408) from 9-benzyloxy-2-cyclobutyl-6-(1-pyrrolo[2,3-b]pyridin-1-yl-cyclopentylmethyl)-3,4-dihydro-2H-pyrazino[1,2-c]pyrimidine-1,8-dione (427) (55 mg, 0.10 mmol) and was obtained as an off-white solid (37 mg, 81%).

LC-MS: 434.2 (M+H).

General Procedure for Examples 429 to 453

The synthetic procedures are outlined in Scheme 50.

General Synthetic Route for 441, 445, 449, 453

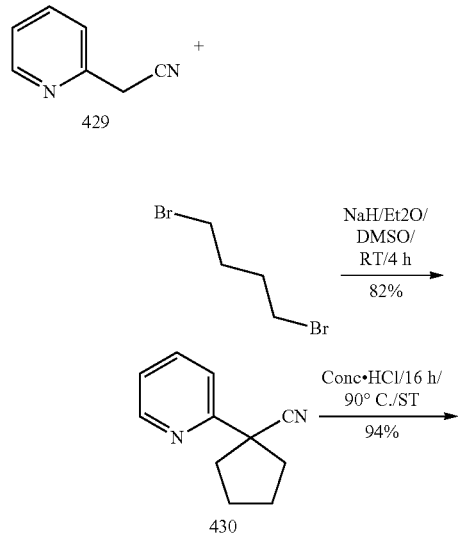

Scheme 50

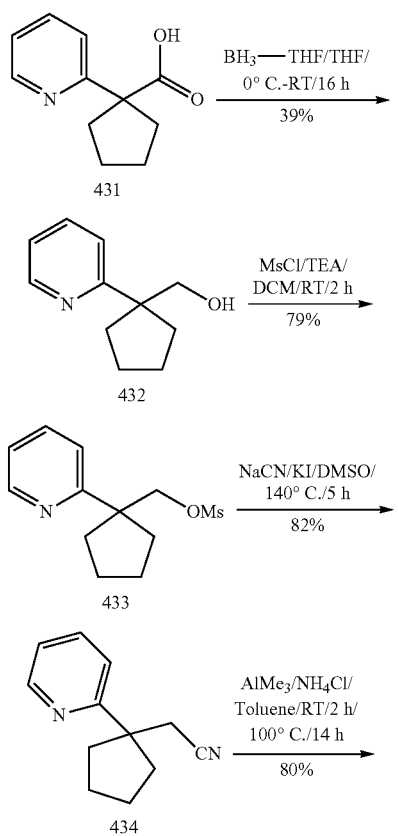

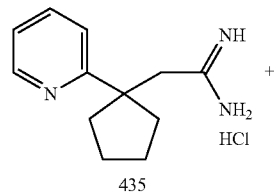

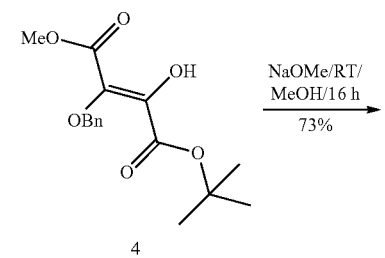

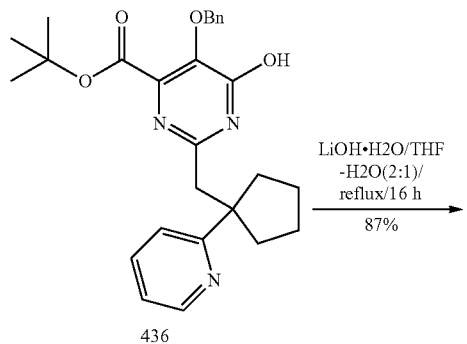

-continued

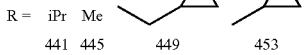

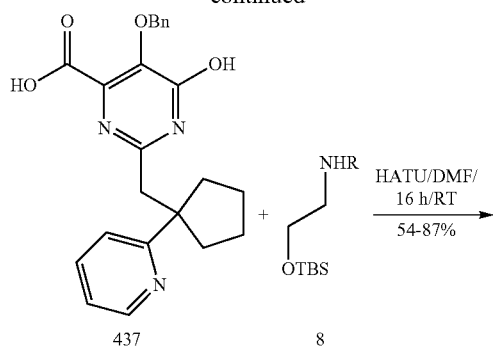

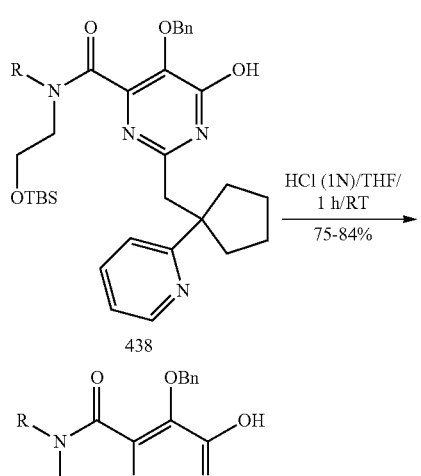

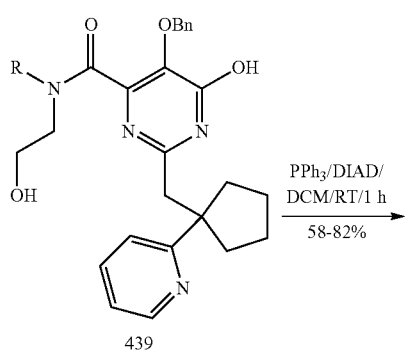

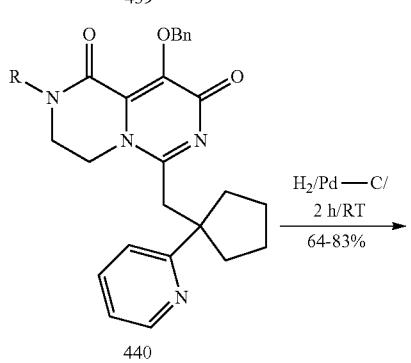

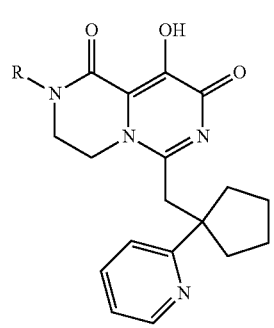

Preparation of (430)

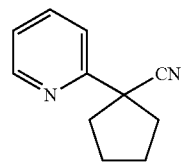 [SMILES: N#CC1(c2ccccn2)CCCC1]

1-Pyridin-2-yl-cyclopentanecarbonitrile

To a suspension of sodium hydride (60%) (0.745 g, 18.644 mmol) in dimethyl sulfoxide (10 mL) was dropwise added a mixture of pyridin-2-yl-acetonitrile (429) (1 g, 8.475 mmol) and 1,4-dibromo-butane (1.831 g, 8.475 mmol) dissolved in dimethyl sulfoxide-ether (10 mL, 1:1) at 0° C. and the reaction mixture was stirred for 30 min at the same temperature and then stirred at room temperature for 4 h. After completion of the reaction (monitored by silica TLC, Rf=0.4, in 10% ethyl acetate/hexane) the mixture was quenched with HCl (1N, 10 mL). The reaction mixture was diluted water (20 mL) and extracted with ethyl acetate (2×50 mL) combined extracts were washed with water (20 mL) and brine (2×20 mL). The organic phase was thereafter dried and concentrated in vacuo to get a crude mass which was purified by combi-flash to get 1-pyridin-2-yl-cyclopentanecarbonitrile (430) (1.2 g, 82%) as a color less liquid.

LC-MS: 173.0 (M+H)

Preparation of (431)

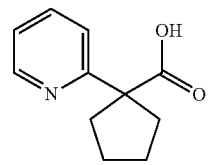 [SMILES: O=C(O)C1(c2ccccn2)CCCC1]

1-Pyridin-2-yl-cyclopentanecarboxylic acid

In a sealed tube 1-pyridin-2-yl-cyclopentanecarbonitrile (3) (10 g, 58.14 mmol) and HCl (12N; 70 mL) were added at room temperature and the reaction mixture was stirred at 90° C. for 16 h while silica thin layer chromatography was performed (20% ethyl acetate/Hexane; Rf=0.1). The reaction mixture was concentrated; an azeotropically distilled with toluene and the residue was triturated with ether to get 1-pyridin-2-yl-cyclopentanecarboxylic acid (431) (10.5 g, 94%) as a white solid.

LC-MS: 191.8 (M+H).

Preparation of (432)

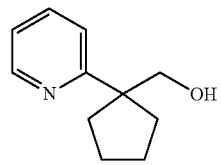 [SMILES: OCC1(c2ccccn2)CCCC1]

(1-Pyridin-2-yl-cyclopentyl)-methanol

To a stirred solution of 1-pyridin-2-yl-cyclopentanecarboxylic acid (431) (5 g, 26.178 mmol) in tetrahydrofuran was added BH$_3$.tetrahydrofuran (1M) (52.36 mL) at 0° C. and stirring was continued for 1 h, then this reaction mixture was allowed to stir at room temperature for 5 h while silica thin layer chromatography was performed (50% ethyl acetate in Hexane; Rf=0.5).

The reaction was quenched with saturated NH$_4$Cl (30 mL) at 0° C. and the reaction mixture was diluted with water (50 mL) and extracted with 10% methanol in dichloromethane (2×200 mL). The combined organic parts were dried and concentrated. The resulting crude product was purified by normal silica gel (100-200 mesh) column chromatography using 30% ethyl acetate in hexane as eluent to get (1-pyridin-2-yl-cyclopentyl)-methanol (432) (1.8 g, 39%) as a colorless liquid.

LC-MS: 177.8 (M+H).

Preparation of (433)

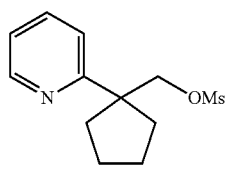 [SMILES: CS(=O)(=O)OCC1(c2ccccn2)CCCC1]

Methanesulfonic acid
1-pyridin-2-yl-cyclopentylmethyl ester

To a stirred solution of (1-pyridin-2-yl-cyclopentyl)-methanol (432) (1.8 g, 10.169 mmol) in dichloromethane (20 mL), triethylamine (2.827 mL, 20.339 mmol) and mesylchloride (0.94 mL, 12.203 mmol) were added at 0° C. The reaction mixture was allowed to stir for 2 h at room temperature while silica thin layer chromatography was performed (50% ethyl acetate in hexane; Rf=0.6) The reaction was quenched with water (30 mL) and extracted with dichloromethane (2×70 mL). The organic part was dried and concentrated. The resulting crude product was purified by normal silica gel (100-200 mesh) column chromatography using 25% ethyl acetate in hexane as eluent to get methanesulfonic acid 1-pyridin-2-yl-cyclopentylmethyl ester (433) (2.05 g, 79%) as a white solid.

LC-MS: 255.6 (M+H).

Preparation of (434)

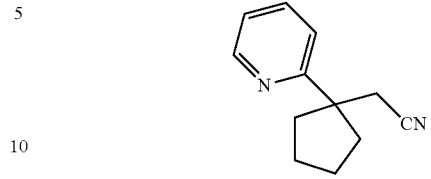

(1-Pyridin-2-yl-cyclopentyl)-acetonitrile

To a stirred solution of methanesulfonic acid 1-pyridin-2-yl-cyclopentylmethyl ester (433) (2 g, 7.843 mmol) in dimethyl sulfoxide (15 mL), KI (0.13 g, 0.784 mmol), NaCN (0.769 g, 15.686 mmol) were added and the reaction was subjected to heating at 140° C. for 5 h. The reaction mixture was quenched with ice cold water (50 mL) and extracted with ethyl acetate (2×70 mL). The combined extracts were washed with brine, dried and concentrated. The resulting crude product was purified by normal silica gel (100-200 mesh) column chromatography using 15% ethyl acetate in hexane as eluent to get (1-pyridin-2-yl-cyclopentyl)-acetonitrile (434) (1.2 g, 82%) as a colorless liquid.

LC-MS: 186.8 (M+H).

Preparation of (435)

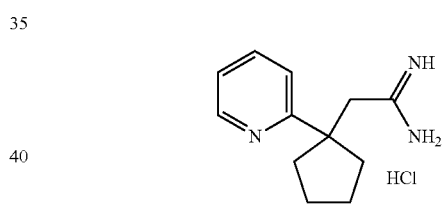

2-(1-Pyridin-2-yl-cyclopentyl)-acetamidine
hydrochloride

To a stirred suspension of NH$_4$Cl (1.05 g, 19.355 mmol) in dry toluene (15 mL) was added tri-methyl aluminum (2M) (5.2 mL, 10.323 mmol) at 5° C. The reaction mixture was warmed to room temperature and the reaction mixture was stirred for 2 h. A solution of (1-pyridin-2-yl-cyclopentyl)-acetonitrile (434) (1.2 g, 6.45 mmol) in toluene (5 mL) was added to above reaction mixture and the reaction mixture was stirred for 14 h at 100° C. After completion of the reaction, the reaction mixture was quenched with a suspension of silica gel (5 g) in chloroform (30 mL) and reaction mixture was stirred for half an hour at room temperature. It was filtered through a sintered funnel and the residue (silica gel) was washed with methanol (30 mL). The combined filtrate was concentrated and the resulting crude mass was stirred with 10% methanol in dichloromethane (100 mL). The thus generated suspension was filtered and the filtrate was concentrated under reduced pressure to get 2-(1-pyridin-2-yl-cyclopentyl)-acetamidine hydrochloride (435) (1.05 g, 80%) as a white solid.

LC-MS: 203.9 (M+H).

Preparation of (436)

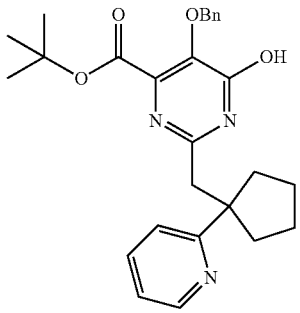 [SMILES: CC(C)(C)OC(=O)c1nc(CC2(c3ccccn3)CCCC2)nc(O)c1OCc1ccccc1]

5-Benzyloxy-6-hydroxy-2-(1-pyridin-2-yl-cyclopentylmethyl)-pyrimidine-4-carboxylic acid tert-butyl ester To a stirred solution of 2-(1-pyridin-2-yl-cyclopentyl)-acetamidine hydrochloride (435) (1 g, 3.55 mmol) and 2-benzyloxy-3-hydroxy-but-2-enedioic acid 4-tert-butyl ester 1-methyl ester (4) (1.638 g, 5.319 mmol) in methanol (15 mL), sodium methoxide (25% in methanol) (2.3 mL, 10.638 mmol) was dropwise added at 0° C. Then reaction mixture was allowed to stir at room temperature for 16 h. Then reaction mixture was quenched with aqueous HCl (1N; 5 mL) and the methanol was removed under reduced pressure. The residue was diluted with water (20 mL) and extracted with ethyl acetate (2×50 mL). The combined organic part was dried, concentrated and the residue was purified by normal silica gel (100-200 mesh) column chromatography using 30% ethyl acetate in hexane as eluent to obtain 5-benzyloxy-6-hydroxy-2-(1-pyridin-2-yl-cyclopentylmethyl)-pyrimidine-4-carboxylic acid tert-butyl ester (436) (1.2 g, 73%) as a yellow sticky liquid.

LC-MS: 461.9 (M+H).

Preparation of (437)

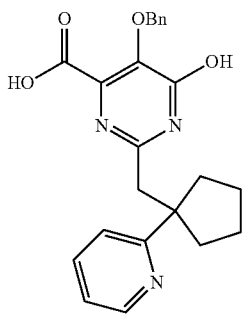 [SMILES: O=C(O)c1nc(CC2(c3ccccn3)CCCC2)nc(O)c1OCc1ccccc1]

5-Benzyloxy-6-hydroxy-2-(1-pyridin-2-yl-cyclopentylmethyl)-pyrimidine-4-carboxylic acid To a stirred solution of 5-benzyloxy-6-hydroxy-2-(1-pyridin-2-yl-cyclopentylmethyl)-pyrimidine-4-carboxylic acid tert-butyl ester (436) (1.2 g, 2.60 mmol) in tetrahydrofuran-water (2:1; 24 mL), LiOH.H$_2$O (1.09 g, 26.03 mmol) was added, refluxed for 16 h while silica thin layer chromatography was performed (50% ethyl acetate in hexane, Rf=0.1). From the reaction mixture volatiles were removed and the residue was diluted with water (20 mL). Thereafter, the pH of this mixture was adjusted to 7 with 1N aqueous HCl. The resulting precipitate was filtered and dried. The obtained solid was triturated with ether to get 5-benzyloxy-6-hydroxy-2-(1-pyridin-2-yl-cyclopentylmethyl)-pyrimidine-4-carboxylic acid (437) (920 mg, 87%) as a white solid.

LC-MS: 406.1 (M+H).

Example 441

9-Hydroxy-2-isopropyl-6-(1-pyridin-2-yl-cyclopentylmethyl)-3,4-dihydro-2H-pyrazino[1,2-c]pyrimidine-1,8-dione The synthetic procedure used in this preparation is outlined in Scheme 50.

Preparation of (438)

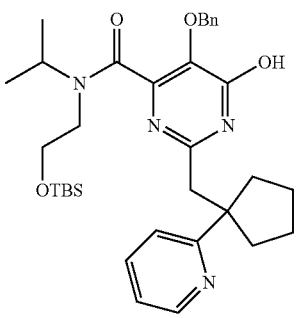 [SMILES: CC(C)N(CCO[Si](C)(C)C(C)(C)C)C(=O)c1nc(CC2(c3ccccn3)CCCC2)nc(O)c1OCc1ccccc1]

5-Benzyloxy-6-hydroxy-2-(1-pyridin-2-yl-cyclopentylmethyl)-pyrimidine-4-carboxylicacid[2-(tert-butyl-dimethylsilanyloxy)-ethyl]-isopropylamide To a stirred solution of 5-benzyloxy-6-hydroxy-2-(1-pyridin-2-yl-cyclopentylmethyl)-pyrimidine-4-carboxylic acid (437) (180 mg, 0.44 mmol) in dimethylformamide (5 mL), N,N-diisopropylethylamine (0.22 mL, 1.33 mmol), HATU (253.5 mg, 0.667 mmol), and [2-(tert-Butyl-dimethylsilanyloxy)-ethyl]-isopropyl-amine (8b) were added, then this reaction mixture was allowed to stir for 16 h at room temperature while silica thin layer chromatography was performed (50% ethyl acetate in hexane; Rf=0.5). The reaction was quenched with ice cold water (20 mL) and extracted with ethyl acetate (2×30 mL). The combined extracts were dried, concentrated under vacuo and the resulting crude product was purified by normal silica gel (100-200 mesh) column chromatography using 30-40% ethyl acetate in hexane as gradient polarity mobile phase to get 5-benzyloxy-6-hydroxy-2-(1-pyridin-2-yl-cyclopentylmethyl)-pyrimidine-4-carboxylicacid[2-(tert-butyl-dimethylsilanyloxy)-ethyl]-isopropylamide (438) (160 mg, 60%) as a yellow gummy liquid.

LC-MS: 605.1 (M+H).

Preparation of (439)

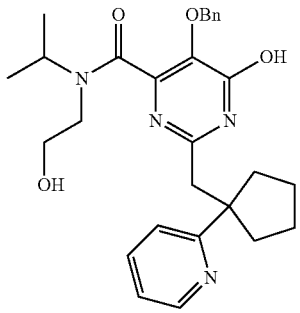 [SMILES: CC(C)N(CCO)C(=O)c1nc(CC2(c3ccccn3)CCCC2)nc(O)c1OCc1ccccc1]

5-Benzyloxy-6-hydroxy-2-(1-pyridin-2-yl-cyclopentylmethyl)-pyrimidine-4-carboxylicacid (2-hydroxyethyl)-isopropylamide To a stirred solution 5-benzyloxy-6-hydroxy-2-(1-pyridin-2-yl-cyclopentylmethyl)-pyrimidine-4-carboxylicacid[2-(tert-butyl-dimethylsilanyloxy)-ethyl]-isopropylamide (438) (150 mg, 0.248 mmol) of in tetrahydrofuran (4 mL), was added 1N HCl (1 mL), then this reaction mixture was stirred for 1 h, at room temperature, After completion of the reaction, volatile substances were removed the from the reaction, then dilute with water (10 mL) and adjust with NaHCO3 to pH8, then extract with ethyl acetate (2×30 mL), then organic part was dried over sodium sulfate, then concentrated, resulting crude product was purified by normal silica gel (100-200 mesh) column chromatography using 50-60% ethyl acetate in hexane as gradient polarity mobile phase to get 5-benzyloxy-6-hydroxy-2-(1-pyridin-2-yl-cyclopentylmethyl)-pyrimidine-4-carboxylicacid (2-hydroxyethyl)-isopropylamide (439) (100 mg, 82%) as white sticky liquid.

LC-MS: 491.2 (M+H).

Preparation of (440)

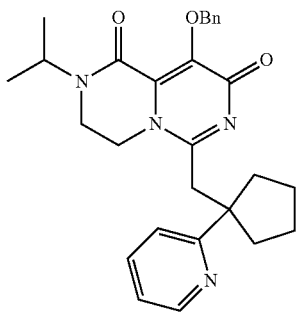 [SMILES: CC(C)N1CCn2c(CC3(c4ccccn4)CCCC3)nc(=O)c(OCc3ccccc3)c2C1=O]

9-Benzyloxy-2-isopropyl-6-(1-pyridin-2-yl-cyclopentylmethyl)-3,4-dihydro-2H-pyrazino[1,2-c]pyrimidine-1,8-dione To a stirred solution of 5-benzyloxy-6-hydroxy-2-(1-pyridin-2-yl-cyclopentylmethyl)-pyrimidine-4-carboxylicacid (2-hydroxyethyl)-isopropylamide (439) (70 mg, 0.143 mmol), in dichloromethane (10 mL), TPP (131 mg, 0.5 mmol) diisopropyl azodicarboxylate (0.084 mL, 0.429 mmol) were added and stirring was continued for 1 h at room temperature while silica thin layer chromatography was performed (100% ethyl acetate, Rf=0.2). After completion of the reaction, water (10 mL) was added and the mixture was extracted with dichloromethane (2×30 mL). The organic part was dried over sodium sulfate, then concentrated and the resulting crude product was purified by normal silica gel (100-200 mesh) column chromatography using 70-80% ethyl acetate in hexane as gradient polarity mobile phase to get 9-benzyloxy-2-isopropyl-6-(1-pyridin-2-yl-cyclopentylmethyl)-3,4-dihydro-2H-pyrazino[1,2-c]pyrimidine-1,8-dione (440) (60.0 mg, 90.2%) as a white sticky liquid.

LC-MS: 473.1 (M+H).

Preparation of (441)

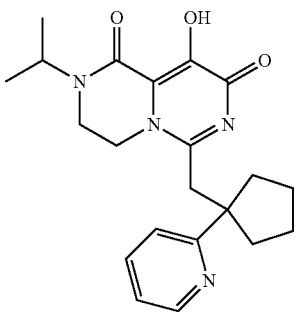 [SMILES: CC(C)N1CCn2c(CC3(c4ccccn4)CCCC3)nc(=O)c(O)c2C1=O]

9-Hydroxy-2-isopropyl-6-(1-pyridin-2-yl-cyclopentylmethyl)-3,4-dihydro-2H-pyrazino[1,2-c]pyrimidine-1,8-dione To a stirred solution of 9-benzyloxy-2-isopropyl-6-(1-pyridin-2-yl-cyclopentylmethyl)-3,4-dihydro-2H-pyrazino[1,2-c]pyrimidine-1,8-dione (440) (50 mg, 0.106 mmol) in ethanol (5 mL), Pd—C (10% w/w, 10 mg) was added and the reaction mixture was allowed to stir for 1 h in a hydrogen atmosphere at balloon pressure while silica thin layer chromatography was performed (10% methanol in dichloromethane; Rf=0.3). After completion of the reaction, the reaction mixture was filtered through a celite bed and concentrated to obtain a crude product which was purified by normal silica gel (100-200 mesh) column chromatography using 2-5% methanol in dichloromethane as a gradient polarity mobile phase to get 9-hydroxy-2-isopropyl-6-(1-pyridin-2-yl-cyclopentylmethyl)-3,4-dihydro-2H-pyrazino[1,2-c]pyrimidine-1,8-dione (441) (26 mg, 64%) as an off-white solid.

LC-MS: 383.0 (M+H).

Example 445

9-Hydroxy-2-methyl-6-(1-pyridin-2-yl-cyclopentylmethyl)-3,4-dihydro-2H-pyrazino[1,2-c]pyrimidine-1,8-dione

The synthetic procedure used in this preparation is outlined in Scheme 50.

Preparation of (442)

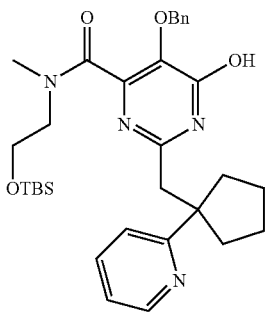 [SMILES: CN(CCO[Si](C)(C)C(C)(C)C)C(=O)c1nc(CC2(c3ccccn3)CCCC2)nc(O)c1OCc1ccccc1]

5-Benzyloxy-6-hydroxy-2-(1-pyridin-2-yl-cyclopentylmethyl)-pyrimidine-4-carboxylic acid [2-(tert-butyl-dimethylsilanyloxy)-ethyl]-methyl-amide

To a stirred solution of 5-benzyloxy-6-hydroxy-2-(1-pyridin-2-yl-cyclopentylmethyl)-pyrimidine-4-carboxylic acid (437) (200 mg, 0.494 mmol) in dimethylformamide (7 mL), N,N-diisopropylethylamine (0.245 mL, 1.481 mmol), HATU (281.7 mg, 0.741 mmol). and [2-(tert-butyl-dimethylsilanyloxy)-ethyl]-methyl-amine (8a) were added. This reaction mixture was allowed to stir for 16 h at room temperature while silica thin layer chromatography was performed (70% ethyl acetate in hexane, Rf=0.5). The reaction mixture was quenched with ice cold water (20 mL) and extracted with ethyl acetate (2×50 mL). The organic part was dried and concentrated. The resulting crude product was purified by normal silica gel (100-200 mesh) column chromatography using 30-40% ethyl acetate in hexane as gradient polarity mobile phase to get 5-benzyloxy-6-hydroxy-2-(1-pyridin-2-yl-cyclopentylmethyl)-pyrimidine-4-carboxylic acid [2-(tert-butyl-dimethylsilanyloxy)-ethyl]-methyl-amide (442) (220 mg, 77%) as a yellow gummy liquid.

LC-MS: 577.1 (M+H).

Preparation of (443)

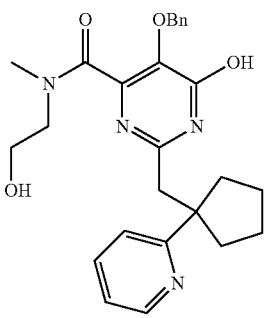 [SMILES: CN(CCO)C(=O)c1nc(CC2(c3ccccn3)CCCC2)nc(O)c1OCc1ccccc1]

5-Benzyloxy-6-hydroxy-2-(1-pyridin-2-yl-cyclopentylmethyl)-pyrimidine-4-carboxylicacid (2-hydroxyethyl)-methyl-amide

To a stirred solution 5-benzyloxy-6-hydroxy-2-(1-pyridin-2-yl-cyclopentylmethyl)-pyrimidine-4-carboxylic acid [2-(tert-butyl-dimethylsilanyloxy)-ethyl]-methyl-amide (442) (180 mg, 0.313 mmol) of in tetrahydrofuran (10 mL), was added 1N HCl (2 mL), then this reaction mixture was stirred for 1 h, at room temperature, After completion of the reaction, volatiles were removed from the reaction mixture and the residue was diluted with water (10 mL) and pH was adjusted with NaHCO₃ to 8. The quenched mass was extracted with ethyl acetate (2×50 mL). The combined extracts were dried and concentrated. The resulting crude product was purified by normal silica gel (100-200 mesh) column chromatography using 50-60% ethyl acetate in hexane as a gradient polarity mobile phase to get 5-benzyloxy-6-hydroxy-2-(1-pyridin-2-yl-cyclopentylmethyl)-pyrimidine-4-carboxylic acid (2-hydroxyethyl)-methyl-amide (443).

LC-MS: 463.0 (M+H).

Preparation of (444)

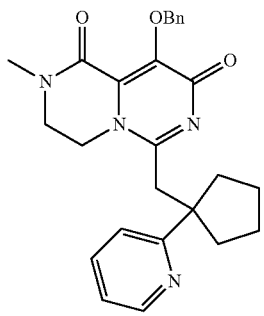 [SMILES: CN1CCn2c(CC3(c4ccccn4)CCCC3)nc(=O)c(OCc3ccccc3)c2C1=O]

9-Benzyloxy-2-methyl-6-(1-pyridin-2-yl-cyclopentylmethyl)-3,4-dihydro-2H-pyrazino[1,2-c]pyrimidine-1,8-dione

To a stirred solution of 5-benzyloxy-6-hydroxy-2-(1-pyridin-2-yl-cyclopentylmethyl)-pyrimidine-4-carboxylic acid (2-hydroxyethyl)-methyl-amide (443) (90 mg, 0.195 mmol), in dichloromethane (10 mL), TPP (178.64 mg, 0.682 mmol) and diisopropyl azodicarboxylate (0.115 mL, 0.584 mmol) were added and stirring was continued for 1 h at room temperature while silica thin layer chromatography was performed (3% methanol in ethyl acetate; Rf=0.2). After completion of the reaction, water (5 mL) was added and the mixture was extracted with dichloromethane (2×30 mL). The organic part was dried and concentrated. The resulting crude product was purified by normal silica gel (100-200 mesh) column chromatography using 60-70% ethyl acetate in hexane as gradient polarity mobile phase to get 9-benzyloxy-2-methyl-6-(1-pyridin-2-yl-cyclopentylmethyl)-3,4-dihydro-2H-pyrazino[1,2-c]pyrimidine-1,8-dione (444) (71 mg, 82%) as a white solid.

LC-MS: 445.0 (M+H).

Preparation of (445)

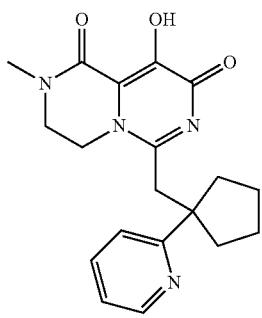 [SMILES: CN1CCn2c(CC3(c4ccccn4)CCCC3)nc(=O)c(O)c2C1=O]

9-Hydroxy-2-methyl-6-(1-pyridin-2-yl-cyclopentylmethyl)-3,4-dihydro-2H-pyrazino[1,2-c]pyrimidine-1,8-dione To a stirred solution of 9-benzyloxy-2-methyl-6-(1-pyridin-2-yl-cyclopentylmethyl)-3,4-dihydro-2H-pyrazino[1,2-c]pyrimidine-1,8-dione (444) (60 mg, 0.135 mmol) in ethanol (5 mL), Pd—C (10%, w/w; 10 mg) was added and the reaction mixture was allowed to stir for 1 h in a hydrogen atmosphere at balloon pressure, while silica thin layer chromatography was performed (10% methanol in dichloromethane, Rf=0.3). After completion of the reaction, the reaction mixture was filtered through a celite bed and concentrated. The resulting crude product was triturated with 70% ethyl acetate in hexane to get 9-hydroxy-2-methyl-6-(1-pyridin-2-yl-cyclopentylmethyl)-3,4-dihydro-2H-pyrazino[1,2-c]pyrimidine-1,8-dione (445) (31 mg, 65%) as a white solid.

LC-MS: 355.0 (M+H).

Example 449

2-Cyclopropylmethyl-9-hydroxy-6-(1-pyridin-2-yl-cyclopentylmethyl)-3,4-dihydro-2H-pyrazino[1,2-c]pyrimidine-1,8-dione The synthetic procedure used in this preparation is outlined in Scheme 50.

Preparation of (446)

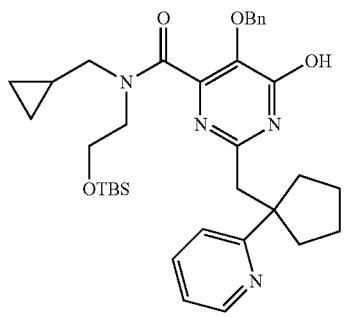 [SMILES: CC(C)(C)[Si](C)(C)OCCN(CC1CC1)C(=O)c1nc(CC2(c3ccccn3)CCCC2)nc(O)c1OCc1ccccc1]

5-Benzyloxy-6-hydroxy-2-(1-pyridin-2-yl-cyclopentylmethyl)-pyrimidine-4-carboxylicacid[2-(tert-butyl-dimethylsilanyloxy)-ethyl]-cyclopropylmethyl-amide To a stirred solution of 5-benzyloxy-6-hydroxy-2-(1-pyridin-2-yl-cyclopentylmethyl)-pyrimidine-4-carboxylic acid (437) (150 mg, 0.37 mmol) in dimethylformamide (5 mL), N,N-diisopropylethylamine (0.184 mL, 1.111 mmol), HATU (211.24 mg, 0.556 mmol), and [2-(tert-butyl-dimethylsilanyloxy)-ethyl]-cyclopropylmethyl-amine (8i) were added, then this reaction mixture was allowed to stir for 16 h at room temperature while silica thin layer chromatography was performed (50% ethyl acetate in hexane; Rf=0.5). The reaction mixture was quenched with ice cold water (25 mL) then extracted with ethyl acetate (2×30 mL). The organic part was dried and concentrated. The resulting crude product was purified by normal silica gel (100-200 mesh) column chromatography using 30-40% ethyl acetate in hexane as gradient polarity mobile phase to get 5-benzyloxy-6-hydroxy-2-(1-pyridin-2-yl-cyclopentylmethyl)-pyrimidine-4-carboxylicacid [2-(tert-butyl-dimethylsilanyloxy)-ethyl]-cyclopropylmethyl-amide (446) (198 mg, 87%) as a colorless gummy liquid.

LC-MS: 617.2 (M+H).

Preparation of (447)

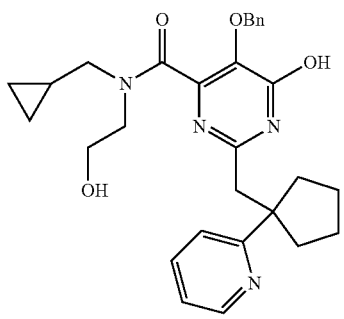 [SMILES: O=C(c1nc(CC2(c3ccccn3)CCCC2)nc(O)c1OCc1ccccc1)N(CCO)CC1CC1]

5-Benzyloxy-6-hydroxy-2-(1-pyridin-2-yl-cyclopentylmethyl)-pyrimidine-4-carboxylicacidcyclopropylmethyl-(2-hydroxyethyl)-amide To a stirred solution 5-benzyloxy-6-hydroxy-2-(1-pyridin-2-yl-cyclopentylmethyl)-pyrimidine-4-carboxylicacid [2-(tert-butyl-dimethylsilanyloxy)-ethyl]-cyclopropylmethyl-amide (446) (200 mg, 0.325 mmol) of in tetrahydrofuran (10 mL) was added (1N) aqueous HCl (2 mL). The mixture was stirred for 1 h at room temperature. After completion of the reaction, volatiles were removed, the residue diluted with water (10 mL) and pH was adjusted to 8 using NaHCO₃. The mixture was extracted with ethyl acetate (2×30 mL), and the organic part was dried and concentrated. The resulting crude product was purified by normal silica gel (100-200 mesh) column chromatography using 50-60% ethyl acetate in hexane as gradient polarity mobile phase to get 5-benzyloxy-6-hydroxy-2-(1-pyridin-2-yl-cyclopentylmethyl)-pyrimidine-4-carboxylic acid cyclopropylmethyl-(2-hydroxyethyl)-amide (447) (123 mg, 75%) as a colorless gummy liquid.

LC-MS: 503.1 (M+H).

Preparation of (448)

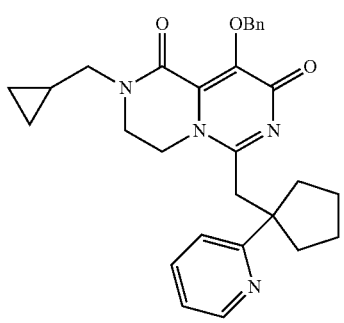 [SMILES: O=C1c2c(OCc3ccccc3)c(=O)nc(CC3(c4ccccn4)CCCC3)n2CCN1CC1CC1]

9-Benzyloxy-2-cyclopropylmethyl-6-(1-pyridin-2-yl-cyclopentylmethyl)-3,4-dihydro-2H-pyrazino[1,2-c]pyrimidine-1,8-dione To a stirred solution of 5-benzyloxy-6-hydroxy-2-(1-pyridin-2-yl-cyclopentylmethyl)-pyrimidine-4-carboxylicacid-cyclopropylmethyl-(2-hydroxyethyl)-amide (447) (80 mg, 0.159 mmol), in dichloromethane (5 mL), TPP (146.13 mg, 0.558 mmol) and diisopropyl azodicarboxylate (0.094 mL, 0.478 mmol) were added and stirring was continued for 1 h at room temperature while silica thin layer chromatography was performed (100% ethyl acetate; Rf=0.2). After completion of the reaction, water (5 mL) was added and the mixture was extracted with dichloromethane (2×30 mL) and the organic phase was dried and concentrated. The resulting crude product was purified by normal silica gel (100-200) column chromatography using 60-70% ethyl acetate in hexane as a gradient polarity mobile phase to get 9-benzyloxy-2-cyclopropylmethyl-6-(1-pyridin-2-yl-cyclopentylmethyl)-3,4-dihydro-2H-pyrazino[1,2-c]pyrimidine-1,8-dione (448) (45.0 mg, 58%) as a white solid.

LC-MS: 485.0 (M+H).

Preparation of (449)

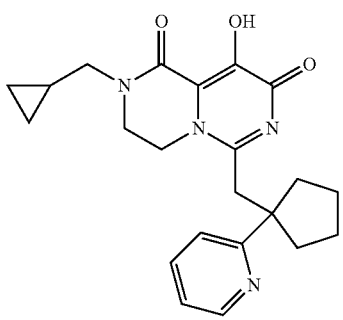 [SMILES: O=C1c2c(O)c(=O)nc(CC3(c4ccccn4)CCCC3)n2CCN1CC1CC1]

2-Cyclopropylmethyl-9-hydroxy-6-(1-pyridin-2-yl-cyclopentylmethyl)-3,4-dihydro-2H-pyrazino[1,2-c]pyrimidine-1,8-dione To a stirred solution of 9-benzyloxy-2-cyclopropylmethyl-6-(1-pyridin-2-yl-cyclopentylmethyl)-3,4-dihydro-2H-pyrazino[1,2-c]pyrimidine-1,8-dione (448) (40 mg, 0.083 mmol) in ethanol (3 mL), Pd—C (10%, w/w, 10 mg) was added. The reaction mixture was allowed stir for 1 h in a hydrogen atmosphere at balloon pressure while silica thin layer chromatography was performed (10% methanol in dichloromethane; Rf=0.3). After completion of the reaction, the reaction mixture was filtered through a celite bed and concentrated. The resulting crude product was triturated with 70% ethyl acetate in hexane to get 9-hydroxy-2-methyl-6-(1-pyridin-2-yl-cyclopentylmethyl)-3,4-dihydro-2H-pyrazino[1,2-c]pyrimidine-1,8-dione (449) (27 mg, 83%) as an off-white solid.

LC-MS: 395.0 (M+H).

Example 453

2-Cyclopropyl-9-hydroxy-6-(1-pyridin-2-yl-cyclopentylmethyl)-3,4-dihydro-2H-pyrazino[1,2-c]pyrimidine-1,8-dione The synthetic procedure used in this preparation is outlined in Scheme 50.

Preparation of (450)

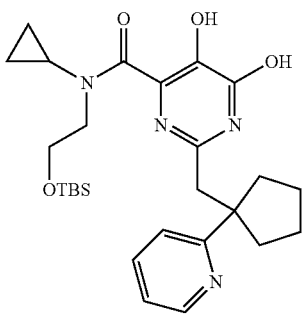 [SMILES: CC(C)(C)[Si](C)(C)OCCN(C(=O)c1nc(CC2(c3ccccn3)CCCC2)nc(O)c1O)C1CC1]

5-Benzyloxy-6-hydroxy-2-(1-pyridin-2-yl-cyclopentylmethyl)-pyrimidine-4-carboxylic acid [2-(tert-butyl-dimethylsilanyloxy)-ethyl]-cyclopropyl-amide To a stirred solution of 5-benzyloxy-6-hydroxy-2-(1-pyridin-2-yl-cyclopentylmethyl)-pyrimidine-4-carboxylic acid (437) (150 mg, 0.494 mmol) in dimethylformamide (5 mL), N,N-diisopropylethylamine (0.184 mL, 1.111 mmol), HATU (211.24 mg, 0.556 mmol) and [2-(tert-Butyl-dimethylsilanyloxy)-ethyl]-cyclopropyl-amine (crude) (8d) (239 mg) were added. This reaction mixture was allowed to stir for 16 h at room temperature while silica thin layer chromatography was performed (50% ethyl acetate in hexane; Rf=0.5) The reaction was quenched with ice cold water (25 mL) and extracted with ethyl acetate (2×30 mL). The organic part was dried, then concentrated and the crude product was purified by normal silica gel (100-200 mesh) column chromatography using 30-40% ethyl acetate in hexane as gradient polarity mobile phase to get 5-benzyloxy-6-hydroxy-2-(1-pyridin-2-yl-cyclopentylmethyl)-pyrimidine-4-carboxylicacid[2-(tert-butyl-dimethylsilanyloxy)-ethyl]-cyclopropyl-amide (450) (120 mg, 54%) as a yellow sticky liquid.

LC-MS: 603.0 (M+H).

Preparation of (451)

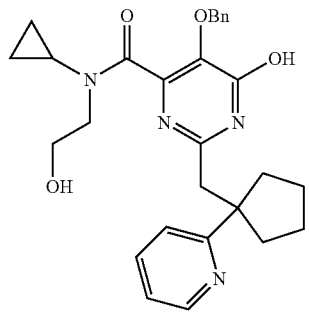 [SMILES: O=C(c1nc(CC2(c3ccccn3)CCCC2)nc(O)c1OCc1ccccc1)N(CCO)C1CC1]

5-Benzyloxy-6-hydroxy-2-(1-pyridin-2-yl-cyclopentylmethyl)-pyrimidine-4-carboxylicacidcyclopropyl-(2-hydroxyethyl)-amide To a stirred solution 5-benzyloxy-6-hydroxy-2-(1-pyridin-2-yl-cyclopentylmethyl)-pyrimidine-4-carboxylic acid [2-(tert-butyl-dimethylsilanyloxy)-ethyl]-cyclopropyl-amide (450) (120 mg, 0.199 mmol) of in tetrahydrofuran (6 mL), was added 1N aqueous HCl (1.5 mL) and stirring was continued for 1 h at room temperature. After completion of the reaction, volatiles were removed and the residue was diluted with water (10 mL) and the pH was adjusted to pH 8 by using NaHCO₃ and the mixture extracted with ethyl acetate (2×30 mL). The combined extracts were dried and concentrated. The resulting crude product was purified by normal silica gel (100-200 mesh) column chromatography using 50-60% ethyl acetate in hexane as gradient polarity mobile phase to get 5-benzyloxy-6-hydroxy-2-(1-pyridin-2-yl-cyclopentylmethyl)-pyrimidine-4-carboxylicacidcyclopropyl-(2-hydroxyethyl)-amide (451) (80 mg, 82%) as a colorless gummy liquid.

LC-MS: 489.1 (M+H).

Preparation of (452)

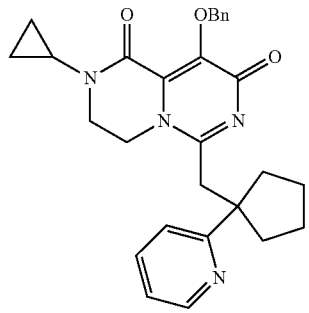 [SMILES: O=C1c2c(OCc3ccccc3)c(=O)nc(CC3(c4ccccn4)CCCC3)n2CCN1C1CC1]

9-Benzyloxy-2-cyclopropyl-6-(1-pyridin-2-yl-cyclopentylmethyl)-3,4-dihydro-2H-pyrazino[1,2-c]pyrimidine-1,8-dione To a stirred solution of 5-benzyloxy-6-hydroxy-2-(1-pyridin-2-yl-cyclopentylmethyl)-pyrimidine-4-carboxylicacidcyclopropyl-(2-hydroxyethyl)-amide (451) (80 mg, 0.164 mmol), in dichloromethane (6 mL), TPP (150.33 mg, 0.574 mmol) and diisopropyl azodicarboxylate (0.097 mL, 0.492 mmol) were added and stirring was continued for 1 h at room temperature while silica thin layer chromatography was performed (100% ethyl acetate, Rf=0.2). After completion of the reaction, water (5 mL) was added and the mixture was extracted with dichloromethane (2×25 mL). The combined extracts were dried and concentrated to get crude 9-benzyloxy-2-cyclopropyl-6-(1-pyridin-2-yl-cyclopentylmethyl)-3,4-dihydro-2H-pyrazino[1,2-c]pyrimidine-1,8-dione (452) (270 mg, Crude) as a yellow gummy liquid.

LC-MS: 471.0 (M+H).

Preparation of (453)

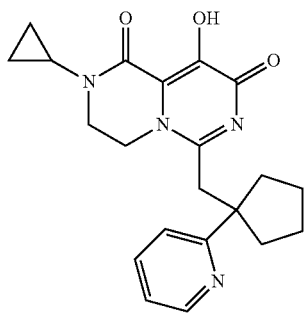 [SMILES: O=C1c2c(O)c(=O)nc(CC3(c4ccccn4)CCCC3)n2CCN1C1CC1]

2-Cyclopropyl-9-hydroxy-6-(1-pyridin-2-yl-cyclopentylmethyl)-3,4-dihydro-2H-pyrazino[1,2-c]pyrimidine-1,8-dione To a stirred solution of 9-benzyloxy-2-cyclopropyl-6-(1-pyridin-2-yl-cyclopentylmethyl)-3,4-dihydro-2H-pyrazino[1,2-c]pyrimidine-1,8-dione (452) (250 mg, crude) in acetic acid (4 mL), concentrated $H_2SO_4$ (0.001 mL) was added and the reaction mixture was stirred for 2 h at room temperature (monitored by LC-MS). Volatiles were removed from the reaction mixture ant the residue was quenched with ice water (10 mL). The pH of the mixture was adjusted to 8 using $NaHCO_3$ and extracted with 10% methanol in dichloromethane (2×40 mL). The crude product obtained after drying and concentrating the organic part was purified by preparative HPLC to get 2-cyclopropyl-9-hydroxy-6-(1-pyridin-2-yl-cyclopentylmethyl)-3,4-dihydro-2H-pyrazino[1,2-c]pyrimidine-1,8-dione (453) (17.3 mg, 30% 2 steps) as an off-white solid.

LC-MS: 380.9 (M+H).

General Procedure for Examples 454 to 505

The synthetic procedures are outlined in Scheme 51.

General Synthetic Route for 466, 479, 492, 505

Scheme 51

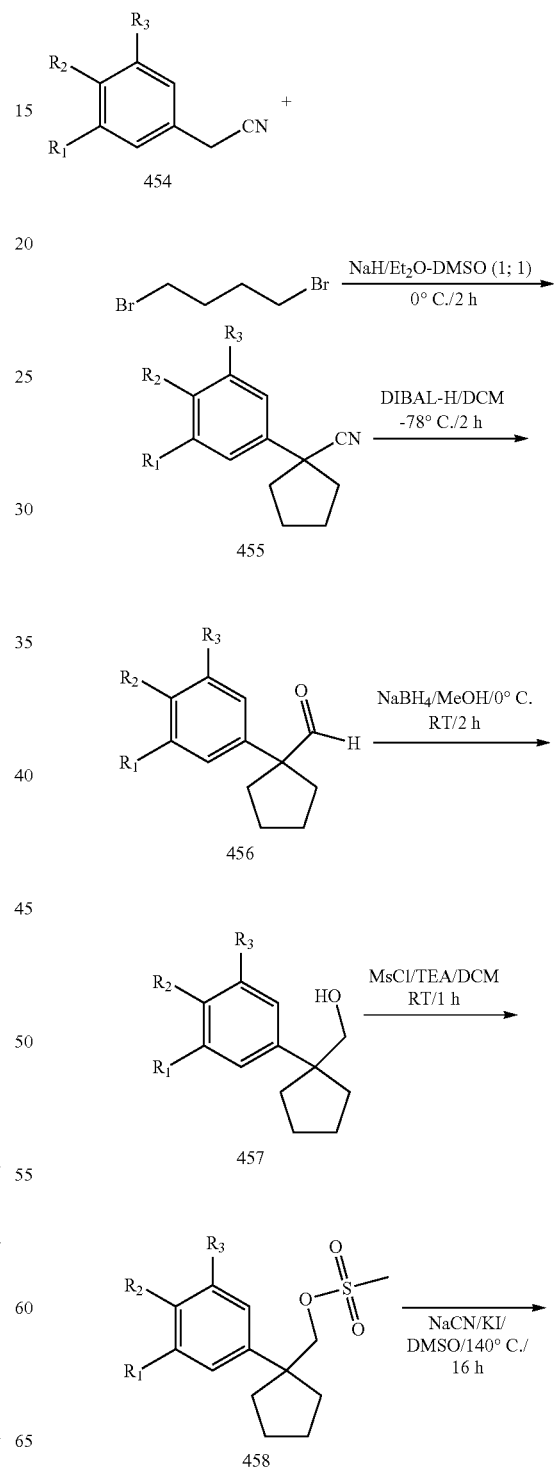

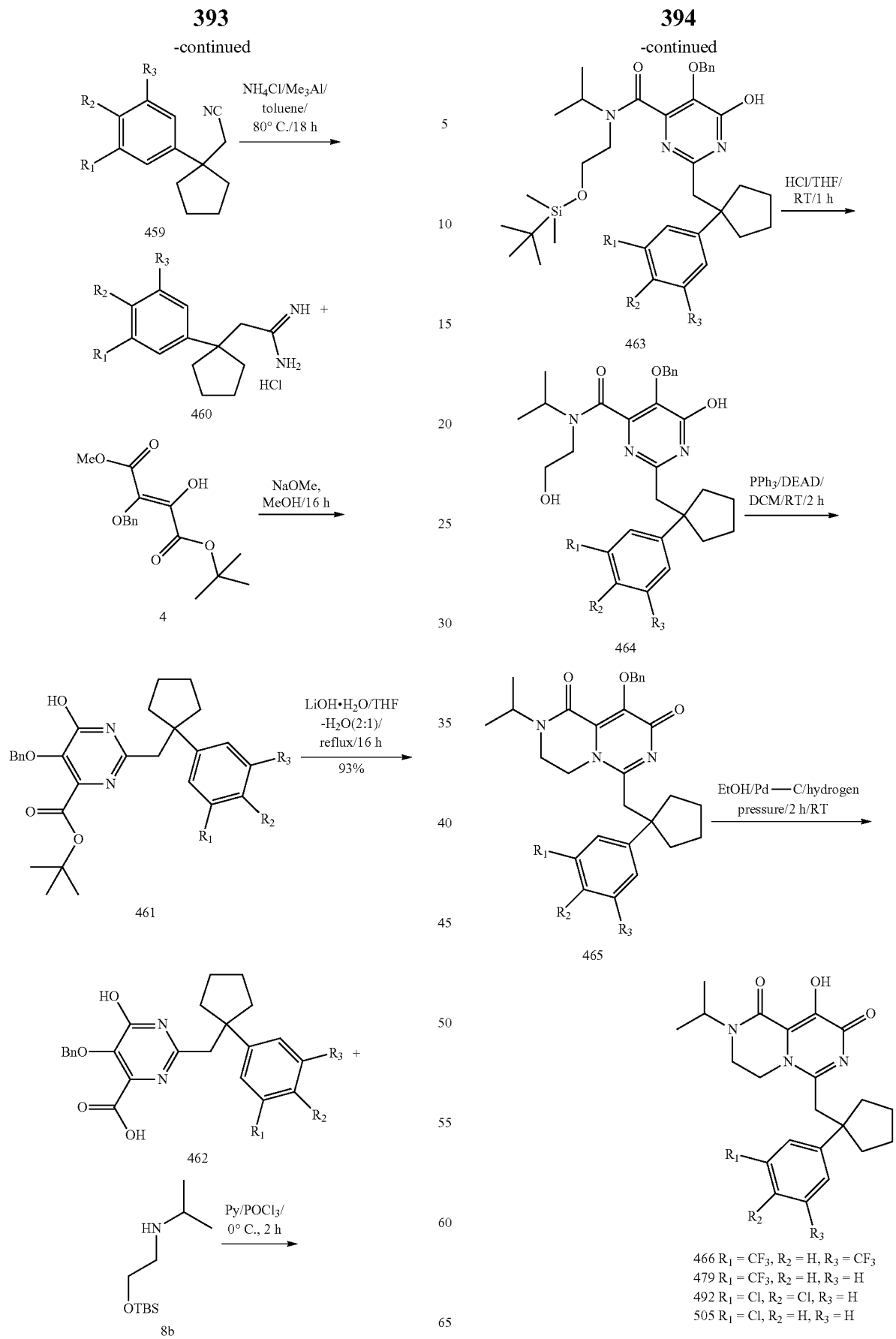

Example 466

6-((1-(3,5-bis(trifluoromethyl)phenyl)cyclopentyl)methyl)-9-hydroxy-2-isopropyl-3,4-dihydro-1H-pyrazino[1,2-c]pyrimidine-1,8(2H)-dione The synthetic procedure used in this preparation is outlined in Scheme 51.

Preparation of (455)

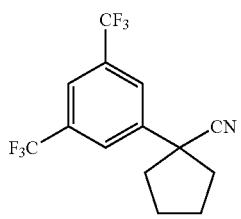 [SMILES: N#CC1(c2cc(C(F)(F)F)cc(C(F)(F)F)c2)CCCC1]

Step:1 1-(3,5-bis(trifluoromethyl)phenyl)cyclopentanecarbonitrile 1-(3,5-bis(trifluoromethyl)phenyl)cyclopentanecarbonitrile (455) was synthesized from 2-(3,5-bis(trifluoromethyl)phenyl)acetonitrile (454) and 1,4-dibromobutane following the procedure described for 1-(4-trifluoromethyl-phenyl)-cyclopentanecarbonitrile (237).

Preparation of (456)

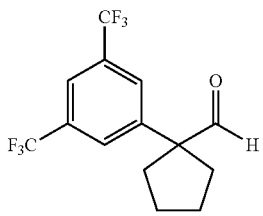 [SMILES: O=CC1(c2cc(C(F)(F)F)cc(C(F)(F)F)c2)CCCC1]

Step 2: 1-(3,5-bis(trifluoromethyl)phenyl)cyclopentanecarbaldehyde 1-(3,5-bis(trifluoromethyl)phenyl)cyclopentanecarbaldehyde (456) was synthesized as a colourless liquid from 1-(3,5-bis(trifluoromethyl)phenyl)cyclopentanecarbonitrile (455) following the procedure described for 1-(4-trifluoromethyl-phenyl)-cyclopentanecarbaldehyde (238).

Preparation of (457)

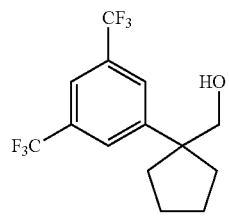 [SMILES: OCC1(c2cc(C(F)(F)F)cc(C(F)(F)F)c2)CCCC1]

Step 3: ((1-(3,5-bis(trifluoromethyl)phenyl)cyclopentyl)methanol (1-(3,5-bis(trifluoromethyl)phenyl)cyclopentyl)methanol (457) was synthesized as a colourless liquid from 1-(3,5-bis(trifluoromethyl)phenyl)cyclopentanecarbaldehyde (456) following the procedure described for 1-(4-trifluoromethyl-phenyl)-cyclopentane-methanol (239).

Preparation of (458)

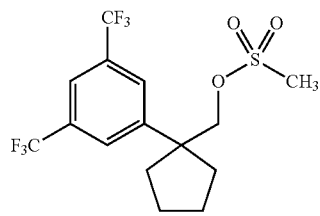 [SMILES: CS(=O)(=O)OCC1(c2cc(C(F)(F)F)cc(C(F)(F)F)c2)CCCC1]

Step 4: (1-(3,5-bis(trifluoromethyl)phenyl)cyclopentyl)methyl methanesulfonate (1-(3,5-bis(trifluoromethyl)phenyl)cyclopentyl)methyl methanesulfonate (458) was synthesized from ((1-(3,5-bis(trifluoromethyl)phenyl)cyclopentyl)methanol (457) following the procedure described for methanesulfonic acid 1-(4-trifluoromethyl-phenyl)-cyclopentylmethyl ester (240).

Preparation of (459)

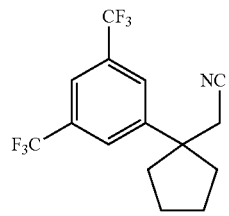 [SMILES: N#CCC1(c2cc(C(F)(F)F)cc(C(F)(F)F)c2)CCCC1]

Step 5: 2-(1-(3,5-bis(trifluoromethyl)phenyl)cyclopentyl)acetonitrile 2-(1-(3,5-bis(trifluoromethyl)phenyl)cyclopentyl)acetonitrile (459) was synthesized as a brown solid from (1-(3,5- bis(trifluoromethyl)phenyl)cyclopentyl)methyl methanesulfonate (458) following the procedure described for [1-(4-trifluoromethyl-phenyl)-cyclopentyl]-acetonitrile (241).

Preparation of (460)

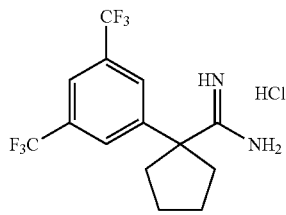 [SMILES: N=C(N)C1(c2cc(C(F)(F)F)cc(C(F)(F)F)c2)CCCC1 ; Cl]

Step 6: 2-(1-(3,5-bis(trifluoromethyl)phenyl-cyclopentyl)-acetamidine hydrochloride 2-(1-(3,5-bis(trifluoromethyl)phenyl-cyclopentyl)-acetamidine hydrochloride (460) was synthesized as a white solid from 2-(1-(3,5-bis(trifluoromethyl)phenyl)cyclopentyl)acetonitrile (459) following the procedure described for HCl-salt of 2-[1-(4-trifluoromethyl-phenyl)-cyclopentyl]-acetamidine hydrochloride (242).

Preparation of (461)

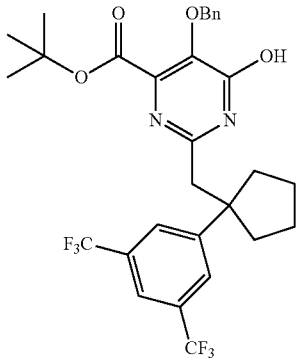 [SMILES: CC(C)(C)OC(=O)c1nc(CC2(c3cc(C(F)(F)F)cc(C(F)(F)F)c3)CCCC2)nc(O)c1OCc1ccccc1]

tert-butyl 5-(benzyloxy)-2-((1-(3,5-bis(trifluoromethyl)phenyl)cyclopentyl)methyl)-6-hydroxypyrimidine-4-carboxylate tert-butyl 5-(benzyloxy)-2-((1-(3,5-bis(trifluoromethyl)phenyl)cyclopentyl)methyl)-6-hydroxypyrimidine-4-carboxylate (461) was synthesized as a white solid from 2-(1-(3,5-bis(trifluoromethyl)phenyl-cyclopentyl)-acetamidine hydrochloride (460) following the procedure described for 5-benzyloxy-2-[1-(4-trifluoromethyl-phenyl)-cyclopentyl-methyl]-6-hydroxypyrimidine-4-carboxylic acid tert-butyl ester (243).

Preparation of (462)

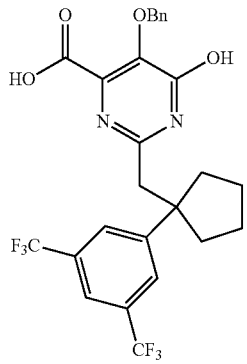 [SMILES: O=C(O)c1nc(CC2(c3cc(C(F)(F)F)cc(C(F)(F)F)c3)CCCC2)nc(O)c1OCc1ccccc1]

5-(benzyloxy)-2-((1-(3,5-bis(trifluoromethyl)phenyl)cyclopentyl)methyl)-6-hydroxypyrimidine-4-carboxylic acid 5-(benzyloxy)-2-((1-(3,5-bis(trifluoromethyl)phenyl)cyclopentyl)methyl)-6-hydroxypyrimidine-4-carboxylic acid (462) was synthesized as a white solid from tert-butyl 5-(benzyloxy)-2-((1-(3,5-bis(trifluoromethyl)phenyl)cyclopentyl)methyl)-6-hydroxypyrimidine-4-carboxylate (461) following the procedure described for 5-benzyloxy-2-[1-(4-trifluoromethyl-phenyl)-cyclopentylmethyl]-6-hydroxypyrimidine-4-carboxylic acid (244).

Preparation of (463)

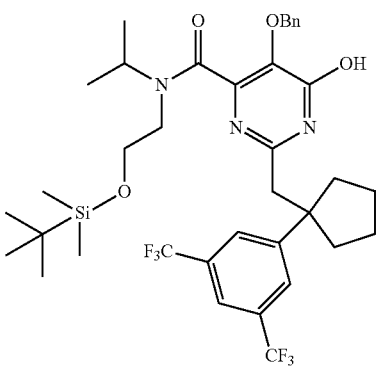 [SMILES: CC(C)N(CCO[Si](C)(C)C(C)(C)C)C(=O)c1nc(CC2(c3cc(C(F)(F)F)cc(C(F)(F)F)c3)CCCC2)nc(O)c1OCc1ccccc1]

5-(Benzyloxy)-2-((1-(3,5-bis(trifluoromethyl)phenyl)cyclopentyl)methyl)-N-(2-((tert-butyl-dimethylsilyl)oxy)ethyl)-6-hydroxy-N-isopropylpyrimidine-4-carboxamide 5-(Benzyloxy)-2-((1-(3,5-bis(trifluoromethyl)phenyl)cyclopentyl)methyl)-N-(2-((tert-butyl-dimethylsilyl)oxy)ethyl)-6-hydroxy-N-isopropylpyrimidine-4-carboxamide (463) was synthesized from 5-(benzyloxy)-2-((1-(3,5-bis(trifluoromethyl)phenyl)cyclopentyl)methyl)-6-hydroxypyrimidine-4-carboxylic acid (462) and [2-(tert-butyl-dimethyl-silanyloxy)-ethyl]-isopropyl-amine (8b) following the procedure described for 5-benzyloxy-2-[1-(4-trifluoromethyl-phenyl)-cyclopentylmethyl]-6-hydroxypyrimidine-4-carboxylic acid [2-(tert-butyl-dimethylsilanyloxy)-ethyl]-isopropylamide (245).

Preparation of (464)

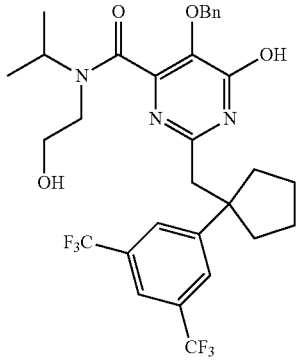 [SMILES: CC(C)N(CCO)C(=O)c1nc(CC2(c3cc(C(F)(F)F)cc(C(F)(F)F)c3)CCCC2)nc(O)c1OCc1ccccc1]

5-(Benzyloxy)-2-((1-(3,5-bis(trifluoromethyl)phenyl)cyclopentyl)methyl)-6-hydroxy-N-(2-hydroxyethyl)-N-isopropylpyrimidine-4-carboxamide 5-(Benzyloxy)-2-((1-(3,5-bis(trifluoromethyl)phenyl)cyclopentyl)methyl)-6-hydroxy-N-(2-hydroxyethyl)-N-isopropylpyrimidine-4-carboxamide (464) was synthesized form 5-(benzyloxy)-2-((1-(3,5-bis(trifluoromethyl)phenyl)cyclopentyl)methyl)-N-(2-((tert-butyldimethylsilyl)oxy)ethyl)-6-hydroxy-N-isopropylpyrimidine-4-carboxamide (463) following the procedure described 5-benzyloxy-2-[1-(4-trifluoromethyl-phenyl)-cyclopentylmethyl]-6-hydroxypyrimidine-4-carboxylic acid (2-hydroxyethyl)-isopropylamide (246).

Preparation of (465)

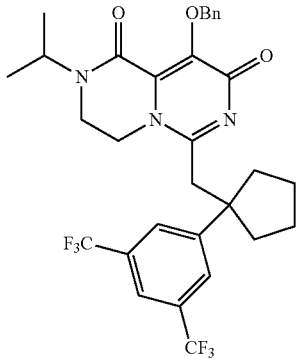 [SMILES: CC(C)N1CCn2c(CC3(c4cc(C(F)(F)F)cc(C(F)(F)F)c4)CCCC3)nc(=O)c(OCc3ccccc3)c2C1=O]

9-(Benzyloxy)-6-((1-(3,5-bis(trifluoromethyl)phenyl)cyclopentyl)methyl)-2-isopropyl-3,4-dihydro-1H-pyrazino[1,2-c]pyrimidine-1,8(2H)-dione 9-(Benzyloxy)-6-((1-(3,5-bis(trifluoromethyl)phenyl)cyclopentyl)methyl)-2-isopropyl-3,4-dihydro-1H-pyrazino[1,2-c]pyrimidine-1,8(2H)-dione (465) was synthesized as a white solid from 5-(benzyloxy)-2-((1-(3,5-bis(trifluoromethyl)phenyl)cyclopentyl)methyl)-6-hydroxy-N-(2-hydroxyethyl)-N-isopropylpyrimidine-4-carboxamide (464) following the procedure described for 9-benzyloxy-6-[1-(4-trifluoromethyl-phenyl)-cyclopentylmethyl]-2-isopropyl-3,4-dihydro-2H-pyrazino[1,2-c]pyrimidine-1,8-dione (247).

Preparation of (466)

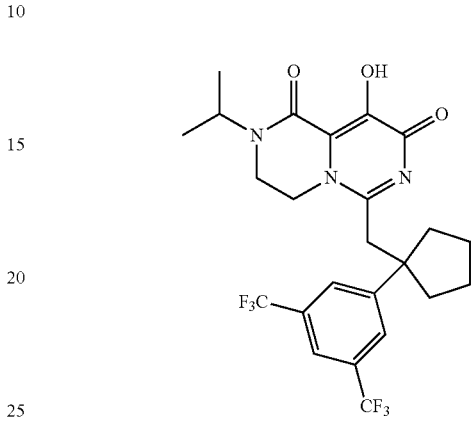

6-((1-(3,5-Bis(trifluoromethyl)phenyl)cyclopentyl)methyl)-9-hydroxy-2-isopropyl-3,4-dihydro-1H-pyrazino[1,2-c]pyrimidine-1,8(2H)-dione 6-((1-(3,5-Bis(trifluoromethyl)phenyl)cyclopentyl)methyl)-9-hydroxy-2-isopropyl-3,4-dihydro-1H-pyrazino[1,2-c]pyrimidine-1,8(2H)-dione (466) was synthesized as a white solid from 9-(benzyloxy)-6-((1-(3,5-bis(trifluoromethyl)phenyl)cyclopentyl)methyl)-2-isopropyl-3,4-dihydro-1H-pyrazino[1,2-c]pyrimidine-1,8(2H)-dione (465) following the procedure described for 6-[1-(4-trifluoromethyl-phenyl)-cyclopentylmethyl]-9-hydroxy-2-isopropyl-3,4-dihydro-2H-pyrazino[1,2-c]pyrimidine-1,8-dione (248).

Example 479

9-hydroxy-2-isopropyl-6-((1-(3-(trifluoromethyl)phenyl)cyclopentyl)methyl)-3,4-dihydro-1H-pyrazino[1,2-c]pyrimidine-1,8(2H)-dione The synthetic procedure used in this preparation is outlined in Scheme 51.

Preparation of (468)

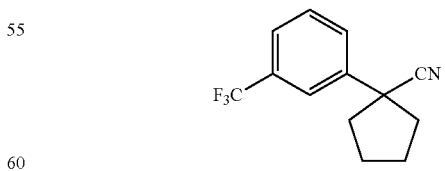

Step:1 1-(3-(trifluoromethyl)phenyl)cyclopentanecarbonitrile 1-(3-(Trifluoromethyl)phenyl)cyclopentanecarbonitrile (468) was synthesized from 2-(3-(trifluoromethyl)phenyl)acetonitrile (467) and 1,4-dibromobutane following the procedure described for 1-(4-trifluoromethyl-phenyl)-cyclopentanecarbonitrile (237).

Preparation of (469)

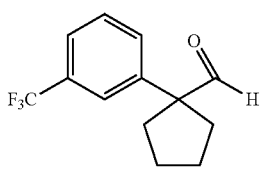 [SMILES: O=CC1(c2cccc(C(F)(F)F)c2)CCCC1]

Step 2: 1-(3-(trifluoromethyl)phenyl)cyclopentanecarbaldehyde 1-(3-(Trifluoromethyl)phenyl)cyclopentanecarbaldehyde (469) was synthesized from 1-(3-(trifluoromethyl)phenyl)cyclopentanecarbonitrile (468) following the procedure described for 1-(4-trifluoromethyl-phenyl)-cyclopentanecarbaldehyde (238).

Preparation of (470)

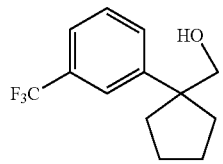 [SMILES: OCC1(c2cccc(C(F)(F)F)c2)CCCC1]

Step 3: ((1-(3-(trifluoromethyl)phenyl)cyclopentyl)methanol (1-(3-(Trifluoromethyl)phenyl)cyclopentyl)methanol (470) was synthesized from 1-(3-(trifluoromethyl)phenyl)cyclopentanecarbaldehyde (469) following the procedure described for 1-(4-trifluoromethyl-phenyl)-cyclopentanemethanol (239).

Preparation of (471)

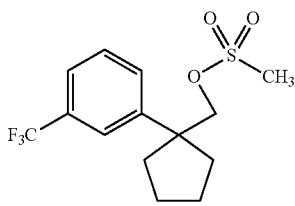 [SMILES: CS(=O)(=O)OCC1(c2cccc(C(F)(F)F)c2)CCCC1]

Step 4: 1-(3-(trifluoromethyl)phenyl)cyclopentyl)methyl methanesulfonate (1-(3-(Trifluoromethyl)phenyl)cyclopentyl)methyl methanesulfonate (471) was synthesized from ((1-(3-(trifluoromethyl)phenyl)cyclopentyl)methanol (470) following the procedure described for methanesulfonic acid 1-(4-trifluoromethyl-phenyl)-cyclopentylmethyl ester (240).

Preparation of (472)

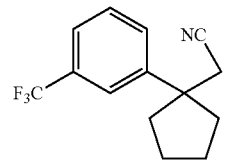 [SMILES: N#CCC1(c2cccc(C(F)(F)F)c2)CCCC1]

Step 5: 2-(1-(3-(trifluoromethyl)phenyl)cyclopentyl)acetonitrile 2-(1-(3-(Trifluoromethyl)phenyl)cyclopentyl)acetonitrile (471) was synthesized from (1-(3-(trifluoromethyl)phenyl)cyclopentyl)methyl methanesulfonate (470) following the procedure described for [1-(4-trifluoromethyl-phenyl)-cyclopentyl]-acetonitrile (241).

Preparation of (473)

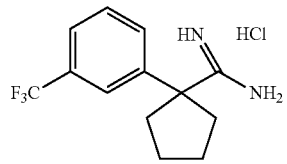 [SMILES: N=C(N)C1(c2cccc(C(F)(F)F)c2)CCCC1 ; Cl]

Step 6: 2-(1-(3-(trifluoromethyl)phenyl-cyclopentyl)-acetamidine hydrochloride 2-(1-(3-(Trifluoromethyl)phenyl-cyclopentyl)-acetamidine hydrochloride (473) was synthesized from 2-(1-(3-(trifluoromethyl)phenyl)cyclopentyl)acetonitrile (472) following the procedure described for the HCl-salt of 2-[1-(4-trifluoromethyl-phenyl)-cyclopentyl]-acetamidine hydrochloride (242).

Preparation of (474)

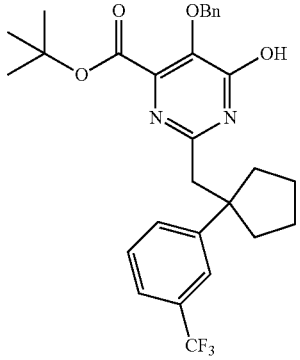 [SMILES: CC(C)(C)OC(=O)c1nc(CC2(c3cccc(C(F)(F)F)c3)CCCC2)nc(O)c1OCc1ccccc1]

tert-Butyl 5-(benzyloxy)-6-hydroxy-2-((1-(3-(trifluoromethyl)phenyl)cyclo-pentyl)methyl)pyrimidine-4-carboxylate tert-Butyl 5-(benzyloxy)-6-hydroxy-2-((1-(3-(trifluoromethyl)phenyl)cyclo-pentyl)methyl)pyrimidine-4-carboxylate (474) was synthesized as a white solid from 2-(1-(3-(trifluoromethyl)phenyl-cyclopentyl)-acetamidine hydrochloride (473) following the procedure described for 5-benzyloxy-2-[1-(4-trifluoromethyl-phenyl)-cyclopentylmethyl]-6-hydroxypyrimidine-4-carboxylic acid tert-butyl ester (243)

Preparation of (475)

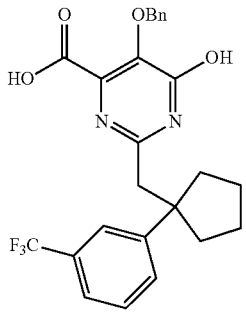 [SMILES: O=C(O)c1nc(CC2(c3cccc(C(F)(F)F)c3)CCCC2)nc(O)c1OCc1ccccc1]

5-(Benzyloxy)-6-hydroxy-2-((1-(3-(trifluoromethyl)phenyl)cyclopentyl)methyl)pyrimidine-4-carboxylic acid 5-(Benzyloxy)-6-hydroxy-2-((1-(3-(trifluoromethyl)phenyl)cyclopentyl)methyl)pyrimidine-4-carboxylic acid (475) was synthesized as a white solid from tert-butyl 5-(benzyloxy)-6-hydroxy-2-((1-(3-(trifluoromethyl)phenyl)cyclopentyl)methyl)pyrimidine-4-carboxylate (474) following the procedure described for 5-benzyloxy-2-[1-(4-trifluoromethyl-phenyl)-cyclopentylmethyl]-6-hydroxypyrimidine-4-carboxylic acid (244).

Preparation of (476)

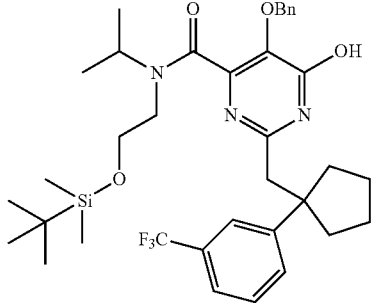 [SMILES: CC(C)N(CCO[Si](C)(C)C(C)(C)C)C(=O)c1nc(CC2(c3cccc(C(F)(F)F)c3)CCCC2)nc(O)c1OCc1ccccc1]

5-(Benzyloxy)-N-(2-((tert-butyldimethylsilyl)oxy)ethyl)-6-hydroxy-N-isopropyl-2-((1-(3-(trifluoromethyl)phenyl)cyclopentyl)methyl)pyrimidine-4-carboxamide 5-(Benzyloxy)-N-(2-((tert-butyldimethylsilyl)oxy)ethyl)-6-hydroxy-N-isopropyl-2-((1-(3-(trifluoromethyl)phenyl)cyclopentyl)methyl)pyrimidine-4-carboxamide (476) was synthesized from 5-(benzyloxy)-6-hydroxy-2-((1-(3-(trifluoromethyl)phenyl)cyclopentyl)methyl)pyrimidine-4-carboxylic acid (475) and [2-(tert-butyl-dimethylsilanyloxy)-ethyl]-isopropyl-amine (8b) following the procedure described for 5-benzyloxy-2-[1-(4-trifluoromethyl-phenyl)-cyclopentylmethyl]-6-hydroxypyrimidine-4-carboxylic acid [2-(tert-butyl-dimethylsilanyloxy)-ethyl]-isopropylamide (245).

Preparation of (477)

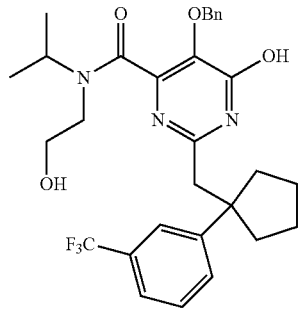 [SMILES: CC(C)N(CCO)C(=O)c1nc(CC2(c3cccc(C(F)(F)F)c3)CCCC2)nc(O)c1OCc1ccccc1]

5-(Benzyloxy)-6-hydroxy-N-(2-hydroxyethyl)-N-isopropyl-2-((1-(3-(trifluoromethyl)phenyl)cyclopentyl)methyl)pyrimidine-4-carboxamide 5-(Benzyloxy)-6-hydroxy-N-(2-hydroxyethyl)-N-isopropyl-2-((1-(3-(trifluoromethyl)phenyl)cyclo-pentyl)methyl)pyrimidine-4-carboxamide (477) was synthesized from 5-(benzyloxy)-N-(2-((tert-butyldimethylsilyl)oxy)ethyl)-6-hydroxy-N-isopropyl-2-((1-(3-(trifluoromethyl)phenyl)cyclo-pentyl)methyl)pyrimidine-4-carboxamide (476) following the procedure described for 5-benzyloxy-2-[1-(4-trifluoromethyl-phenyl)-cyclopentylmethyl]-6-hydroxypyrimidine-4-carboxylic acid (2-hydroxyethyl)-isopropylamide (246).

Preparation of (478)

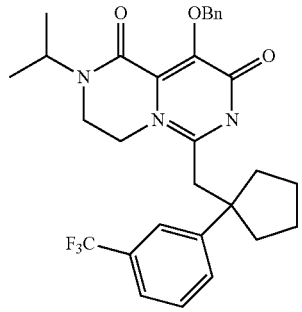

9-(Benzyloxy)-2-isopropyl-6-((1-(3-(trifluoromethyl)phenyl)cyclopentyl)methyl)-3,4-dihydro-1H-pyrazino[1,2-c]pyrimidine-1,8(2H)-dione 9-(Benzyloxy)-2-isopropyl-6-((1-(3-(trifluoromethyl)phenyl)cyclopentyl)methyl)-3,4-dihydro-1H-pyrazino[1,2- c]pyrimidine-1,8(2H)-dione (478) was synthesized as a white solid from 5-(benzyloxy)-6-hydroxy-N-(2-hydroxyethyl)-N-isopropyl-2-((1-(3-(trifluoromethyl)phenyl)cyclo-pentyl)methyl)pyrimidine-4-carboxamide (477) following the procedure described for 9-benzyloxy-6-[1-(4-trifluoromethyl-phenyl)-cyclopentylmethyl]-2-isopropyl-3,4-dihydro-2H-pyrazino[1,2-c]pyrimidine-1,8-dione (247).

Preparation of (479)

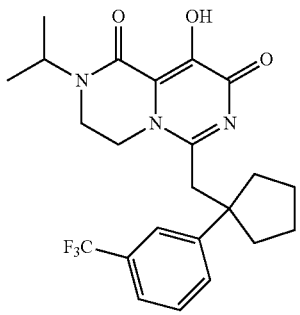 [SMILES: CC(C)N1CCn2c(CC3(c4cccc(C(F)(F)F)c4)CCCC3)nc(=O)c(O)c2C1=O]

9-Hydroxy-2-isopropyl-6-((1-(3-(trifluoromethyl)phenyl)cyclopentyl)methyl)-3,4-dihydro-1H-pyrazino[1,2-c]pyrimidine-1,8(2H)-dione 9-Hydroxy-2-isopropyl-6-((1-(3-(trifluoromethyl)phenyl)cyclopentyl)methyl)-3,4-dihydro-1H-pyrazino[1,2-c]pyrimidine-1,8(2H)-dione (479) was synthesized as a white solid from 9-(benzyloxy)-2-isopropyl-6-((1-(3-(trifluoromethyl)phenyl)cyclopentyl)methyl)-3,4-dihydro-1H-pyrazino[1,2-c]pyrimidine-1,8(2H)-dione (478) following the procedure described for 6-[1-(4-trifluoromethyl-phenyl)-cyclopentylmethyl]-9-hydroxy-2-isopropyl-3,4-dihydro-2H-pyrazino[1,2-c]pyrimidine-1,8-dione (248).

Example 492

6-((1-(3,4-dichlorophenyl)cyclopentyl)methyl)-9-hydroxy-2-isopropyl-3,4-dihydro-1H-pyrazino[1,2-c]pyrimidine-1,8(2H)-dione The synthetic procedure used in this preparation is outlined in Scheme 51.

Preparation of (481)

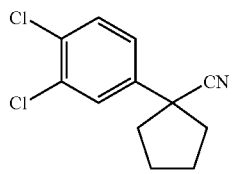 [SMILES: N#CC1(c2ccc(Cl)c(Cl)c2)CCCC1]

Step:1
1-(3,4-dichlorophenyl)cyclopentanecarbonitrile 1-(3,4-dichlorophenyl)cyclopentanecarbonitrile (481) was synthesized from 2-(3,4-dichlorophenyl)acetonitrile (480) and 1,4-dibromobutane following the procedure described for 1-(4-trifluoromethyl-phenyl)-cyclopentanecarbonitrile (237).

Preparation of (482)

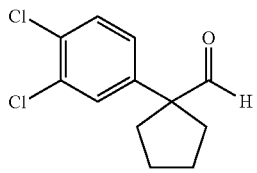 [SMILES: O=CC1(c2ccc(Cl)c(Cl)c2)CCCC1]

Step 2:
1-(3,4-Dichlorophenyl)cyclopentanecarbaldehyde 1-(3,4-Dichlorophenyl)cyclopentanecarbaldehyde (482) was synthesized from 1-(3,4-dichlorophenyl)cyclopentanecarbonitrile (481) following the procedure described for 1-(4-trifluoromethyl-phenyl)-cyclopentanecarbaldehyde (238).

Preparation of (483)

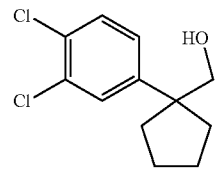 [SMILES: OCC1(c2ccc(Cl)c(Cl)c2)CCCC1]

Step 3: (1-(3,4-dichlorophenyl)cyclopentyl)methanol (1-(3,4-Dichlorophenyl)cyclopentyl)methanol (483) was synthesized from 1-(3,4-dichlorophenyl)phenyl)cyclopentanecarbaldehyde (482) following the procedure described for 1-(4-trifluoromethyl-phenyl)-cyclopentane-methanol (239).

Preparation of (484)

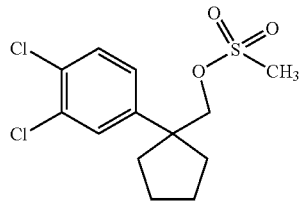 [SMILES: CS(=O)(=O)OCC1(c2ccc(Cl)c(Cl)c2)CCCC1]

Step 4: 1-(3,4-dichlorophenyl)cyclopentyl)methyl methanesulfonate (1-(3,4-Dichlorophenyl)cyclopentyl)methyl methanesulfonate (484) was synthesized from (1-(3,4-dichlorophenyl)cyclopentyl)methanol (483) following the procedure

Preparation of (485)

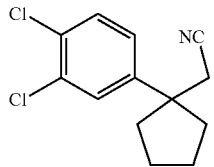 [SMILES: N#CCC1(c2ccc(Cl)c(Cl)c2)CCCC1]

Step 5:
2-(1-(3,4-dichlorophenyl)cyclopentyl)acetonitrile 2-(1-(3,4-Dichlorophenyl)cyclopentyl)acetonitrile (485) was synthesized from (1-(3,4-dichlorophenyl)cyclopentyl) methyl methanesulfonate (484) following the procedure described for [1-(4-trifluoromethyl-phenyl)cyclopentyl]-acetonitrile (241).

Preparation of (486)

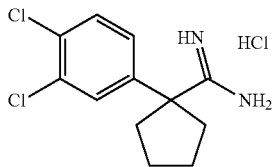 [SMILES: N=C(N)C1(c2ccc(Cl)c(Cl)c2)CCCC1 ; Cl]

Step 6:
2-(1-(3,4-dichlorophenyl)-cyclopentyl)-acetamidine hydrochloride 2-(1-(3,4-Dichlorophenyl)-cyclopentyl)-acetamidine hydrochloride (486) was synthesized from 2-(1-(3,4-dichlorophenyl)cyclopentyl)acetonitrile (485) following the procedure described for the HCl-salt of 2-[1-(4-trifluoromethyl-phenyl)-cyclopentyl]-acetamidine hydrochloride (242).

Preparation of (487)

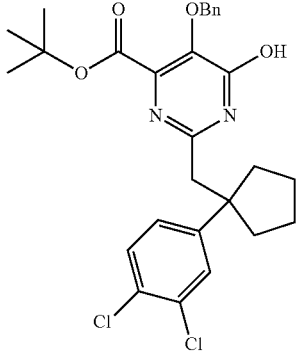 [SMILES: CC(C)(C)OC(=O)c1nc(CC2(c3ccc(Cl)c(Cl)c3)CCCC2)nc(O)c1OCc1ccccc1]

tert-Butyl 5-(benzyloxy)-2-((1-(3,4-dichlorophenyl)cyclopentyl)methyl)-6-hydroxypyrimidine-4-carboxylate tert-Butyl 5-(benzyloxy)-2-((1-(3,4-dichlorophenyl)cyclopentyl)methyl)-6-hydroxypyrimidine-4-carboxylate (487) was synthesized as a white solid from 2-(1-(3,4-dichlorophenyl)-cyclopentyl)-acetamidine hydrochloride (486) following the procedure described for 5-benzyloxy-2-[1-(4-trifluoromethyl-phenyl)-cyclopentylmethyl]-6-hydroxypyrimidine-4-carboxylic acid tert-butyl ester (243)

Preparation of (488)

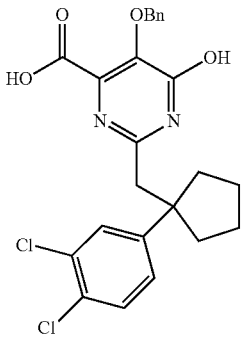 [SMILES: O=C(O)c1nc(CC2(c3ccc(Cl)c(Cl)c3)CCCC2)nc(O)c1OCc1ccccc1]

5-(Benzyloxy)-2-((1-(3,4-dichlorophenyl)cyclopentyl)methyl)-6-hydroxypyrimidine-4-carboxylic acid 5-(Benzyloxy)-2-((1-(3,4-dichlorophenyl)cyclopentyl)methyl)-6-hydroxypyrimidine-4-carboxylic acid (488) was synthesized as a white solid from tert-butyl 5-(benzyloxy)-2-((1-(3,4-dichlorophenyl)cyclopentyl)methyl)-6-hydroxypyrimidine-4-carboxylate (487) following the procedure described for 5-benzyloxy-2-[1-(4-trifluoromethyl-phenyl)-cyclopentylmethyl]-6-hydroxypyrimidine-4-carboxylic acid (244).

Preparation of (489)

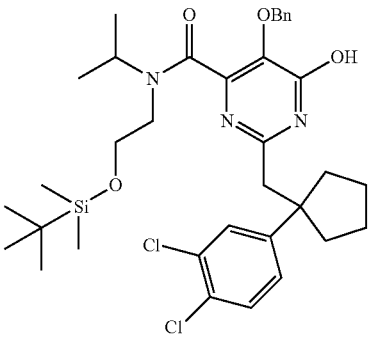 [SMILES: CC(C)N(CCO[Si](C)(C)C(C)(C)C)C(=O)c1nc(CC2(c3ccc(Cl)c(Cl)c3)CCCC2)nc(O)c1OCc1ccccc1]

5-(Benzyloxy)-N-(2-((tert-butyldimethylsilyl)oxy)ethyl)-2-((1-(3,4-dichlorophenyl)cyclo-pentyl)methyl)-6-hydroxy-N-isopropylpyrimidine-4-carboxamide 5-(Benzyloxy)-N-(2-((tert-butyldimethylsilyl)oxy)ethyl)-2-((1-(3,4-dichlorophenyl)cyclo-pentyl)methyl)-6-hydroxy- N-isopropylpyrimidine-4-carboxamide (489) was synthesized from 5-(benzyloxy)-2-((1-(3,4-dichlorophenyl)cyclopentyl)methyl)-6-hydroxypyrimidine-4-carboxylic acid (488) and [2-(tert-butyl-dimethylsilanyloxy)-ethyl]-isopropyl-amine (8b) following the procedure described for 5-benzyloxy-2-[1-(4-trifluoromethyl-phenyl)-cyclopentylmethyl]-6-hydroxypyrimidine-4-carboxylic acid [2-(tert-butyl-dimethylsilanyloxy)-ethyl]isopropylamide (245).

Preparation of (490)

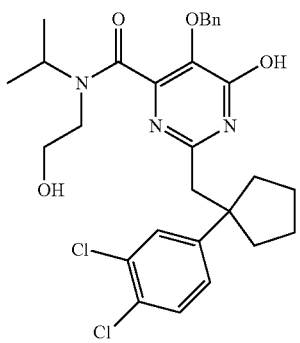 [SMILES: CC(C)N(CCO)C(=O)c1nc(CC2(c3ccc(Cl)c(Cl)c3)CCCC2)nc(O)c1OCc1ccccc1]

5-(Benzyloxy)-2-((1-(3,4-dichlorophenyl)cyclopentyl)methyl)-6-hydroxy-N-(2-hydroxyethyl)-N-isopropylpyrimidine-4-carboxamide 5-(Benzyloxy)-2-((1-(3,4-dichlorophenyl)cyclopentyl)methyl)-6-hydroxy-N-(2-hydroxyethyl)-N-isopropylpyrimidine-4-carboxamide (490) was synthesized from 5-(benzyloxy)-N-(2-((tert-butyldimethylsilyl)oxy)ethyl)-2-((1-(3,4-dichlorophenyl)cyclopentyl)methyl)-6-hydroxy-N-isopropylpyrimidine-4-carboxamide (489) following the procedure described for 5-benzyloxy-2-[1-(4-trifluoromethyl-phenyl)-cyclopentylmethyl]-6-hydroxypyrimidine-4-carboxylic acid (2-hydroxyethyl)-isopropylamide (246).

Preparation of (491)

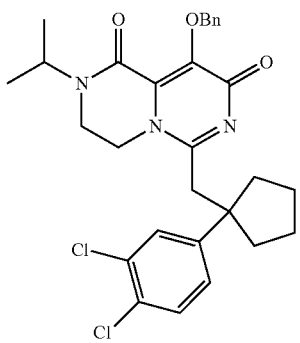 [SMILES: CC(C)N1CCn2c(CC3(c4ccc(Cl)c(Cl)c4)CCCC3)nc(=O)c(OCc3ccccc3)c2C1=O]

9-(Benzyloxy)-6-((1-(3,4-dichlorophenyl)cyclopentyl)methyl)-2-isopropyl-3,4-dihydro-1H-pyrazino[1,2-c]pyrimidine-1,8(2H)-dione 9-(Benzyloxy)-6-((1-(3,4-dichlorophenyl)cyclopentyl)methyl)-2-isopropyl-3,4-dihydro-1H-pyrazino[1,2-c]pyrimidine-1,8(2H)-dione (491) was synthesized as a white solid from 5-(benzyloxy)-2-((1-(3,4-dichlorophenyl)cyclopentyl)methyl)-6-hydroxy-N-(2-hydroxyethyl)-N-isopropylpyrimidine-4-carboxamide (490) following the procedure described for 9-benzyloxy-6-[1-(4-trifluoromethyl-phenyl)-cyclopentylmethyl]-2-isopropyl-3,4-dihydro-2H-pyrazino[1,2-c]pyrimidine-1,8-dione (247).

Preparation of (492)

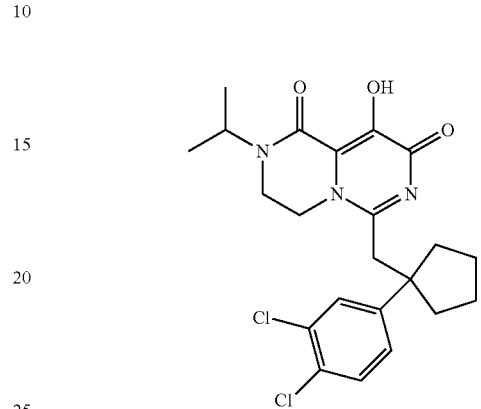

6-((1-(3,4-Dichlorophenyl)cyclopentyl)methyl)-9-hydroxy-2-isopropyl-3,4-dihydro-1H-pyrazino[1,2-c]pyrimidine-1,8(2H)-dione 6-((1-(3,4-Dichlorophenyl)cyclopentyl)methyl)-9-hydroxy-2-isopropyl-3,4-dihydro-1H-pyrazino[1,2-c]pyrimidine-1,8(2H)-dione (492) was synthesized as a white solid from 9-(benzyloxy)-6-((1-(3,4-dichlorophenyl)cyclopentyl)methyl)-2-isopropyl-3,4-dihydro-1H-pyrazino[1,2-c]pyrimidine-1,8(2H)-dione (491) following the procedure described for 6-[1-(4-trifluoromethyl-phenyl)-cyclopentylmethyl]-9-hydroxy-2-isopropyl-3,4-dihydro-2H-pyrazino[1,2-c]pyrimidine-1,8-dione (248).

LC/HR-MS: (M+H)$^+$=450.1358

Example 505

6-((1-(3-Chlorophenyl)cyclopentyl)methyl)-9-hydroxy-2-isopropyl-3,4-dihydro-1H-pyrazino[1,2-c]pyrimidine-1,8(2H)-dione The synthetic procedure used in this preparation is outlined in Scheme 51.

Preparation of (494)

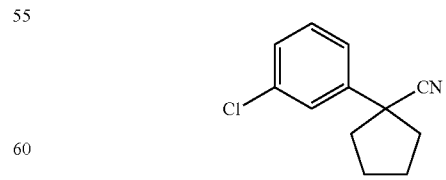

Step:1 1-(3-chlorophenyl)cyclopentanecarbonitrile 1-(3-Chlorophenyl)cyclopentanecarbonitrile (494) was synthesized from 2-(3-chlorophenyl)acetonitrile (493) and 1,4-dibromobutane following the procedure described for 1-(4-trifluoromethyl-phenyl)-cyclopentanecarbonitrile (237).

Preparation of (495)

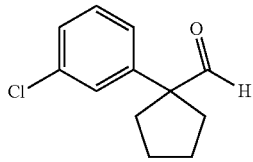 [SMILES: O=CC1(c2cccc(Cl)c2)CCCC1]

Step 2: 1-(3-chlorophenyl)cyclopentanecarbaldehyde 1-(3-Chlorophenyl)cyclopentanecarbaldehyde (495) was synthesized from 1-(3-chlorophenyl)cyclopentanecarbonitrile (494) following the procedure described for 1-(4-trifluoromethyl-phenyl)-cyclopentanecarbaldehyde (238).

Preparation of (496)

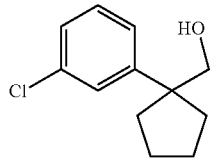 [SMILES: OCC1(c2cccc(Cl)c2)CCCC1]

Step 3: (1-(3-chlorophenyl)cyclopentyl)methanol (1-(3-Chlorophenyl)cyclopentyl)methanol (496) was synthesized from 1-(3-chlorophenyl)phenyl)cyclopentanecarbaldehyde (495) following the procedure described for 1-(4-trifluoromethyl-phenyl)-cyclopentane-methanol (239).

Preparation of (497)

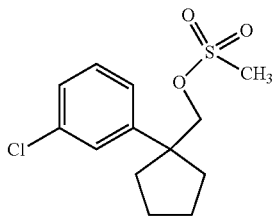 [SMILES: CS(=O)(=O)OCC1(c2cccc(Cl)c2)CCCC1]

Step 4: 1-(3-chlorophenyl)cyclopentyl)methyl methanesulfonate (1-(3-Chlorophenyl)cyclopentyl)methyl methanesulfonate (497) was synthesized from (1-(3-chlorophenyl)cyclopentyl)methanol (496) following the procedure described for Methanesulfonic acid 1-(4-trifluoromethyl-phenyl)-cyclopentylmethyl ester (240).

Preparation of (498)

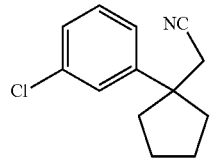 [SMILES: N#CCC1(c2cccc(Cl)c2)CCCC1]

Step 5: 2-(1-(3-chlorophenyl)cyclopentyl)acetonitrile 2-(1-(3-Chlorophenyl)cyclopentyl)acetonitrile (498) was synthesized from (1-(3-chlorophenyl)cyclopentyl)methyl methanesulfonate (497) following the procedure described for [1-(4-trifluoromethyl-phenyl)-cyclopentyl]-acetonitrile (241).

Preparation of (499)

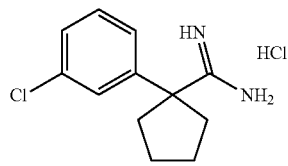 [SMILES: N=C(N)C1(c2cccc(Cl)c2)CCCC1 ; Cl]

Step 6: 2-(1-(3-chlorophenyl)-cyclopentyl)-acetamidine hydrochloride 2-(1-(3-Chlorophenyl)-cyclopentyl)-acetamidine hydrochloride (499) was synthesized from 2-(1-(3-chlorophenyl)cyclopentyl)acetonitrile (498) following the procedure described for HCl-salt of 2-[1-(4-trifluoromethyl-phenyl)-cyclopentyl]-acetamidine hydrochloride (242).

Preparation of (500)

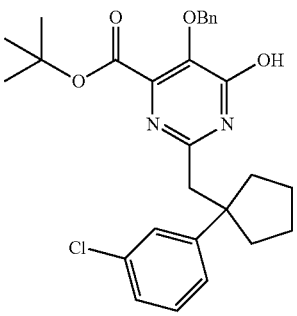 [SMILES: CC(C)(C)OC(=O)c1nc(CC2(c3cccc(Cl)c3)CCCC2)nc(O)c1OCc1ccccc1]

tert-butyl 5-(benzyloxy)-2-((1-(3-chlorophenyl)cyclopentyl)methyl)-6-hydroxypyrimidine-4-carboxylate tert-butyl 5-(benzyloxy)-2-((1-(3-chlorophenyl)cyclopentyl)methyl)-6-hydroxypyrimidine-4-carboxylate (500) was synthesized as a white solid from 2-(1-(3-chlorophenyl)-cyclopentyl)-acetamidine hydrochloride (499) following the procedure described for 5-benzyloxy-2-[1-(4-trifluoromethyl-phenyl)-cyclopentylmethyl]-6-hydroxypyrimidine-4-carboxylic acid tert-butyl ester (243).

Preparation of (501)

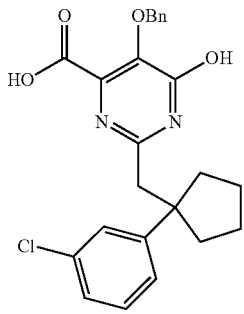 [SMILES: O=C(O)c1nc(CC2(c3cccc(Cl)c3)CCCC2)nc(O)c1OCc1ccccc1]

5-(Benzyloxy)-2-((1-(3-chlorophenyl)cyclopentyl)methyl)-6-hydroxypyrimidine-4-carboxylic acid 5-(Benzyloxy)-2-((1-(3-chlorophenyl)cyclopentyl)methyl)-6-hydroxypyrimidine-4-carboxylic acid (501) was synthesized as a white solid from tert-butyl 5-(benzyloxy)-2-((1-(3-chlorophenyl)cyclopentyl)methyl)-6-hydroxypyrimidine-4-carboxylate (500) following the procedure described for 5-benzyloxy-2-[1-(4-trifluoromethyl-phenyl)-cyclopentylmethyl]-6-hydroxypyrimidine-4-carboxylic acid (244).

Preparation of (502)

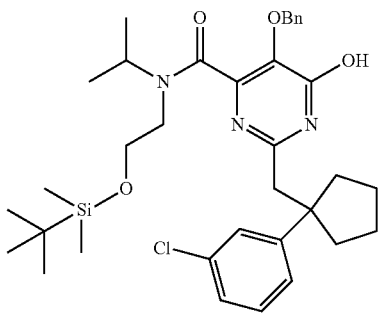 [SMILES: CC(C)N(CCO[Si](C)(C)C(C)(C)C)C(=O)c1nc(CC2(c3cccc(Cl)c3)CCCC2)nc(O)c1OCc1ccccc1]

5-(benzyloxy)-N-(2-((tert-butyldimethylsilyl)oxy)ethyl)-2-((1-(3-chlorophenyl)cyclo-pentyl)methyl)-6-hydroxy-N-isopropylpyrimidine-4-carboxamide 5-(benzyloxy)-N-(2-((tert-butyldimethylsilyl)oxy)ethyl)-2-((1-(3-chlorophenyl)cyclo-pentyl)methyl)-6-hydroxy-N-isopropylpyrimidine-4-carboxamide (502) was synthesized from 5-(benzyloxy)-2-((1-(3-chlorophenyl)cyclopentyl)methyl)-6-hydroxypyrimidine-4-carboxylic acid (501) and [2-(tert-butyl-dimethylsilanyloxy)-ethyl]-isopropyl-amine (8b) following the procedure described for 5-benzyloxy-2-[1-(4-trifluoromethyl-phenyl)-cyclopentylmethyl]-6-hydroxypyrimidine-4-carboxylic acid [2-(tert-butyl-dimethylsilanyloxy)-ethyl]isopropylamide (245).

Preparation of (503)

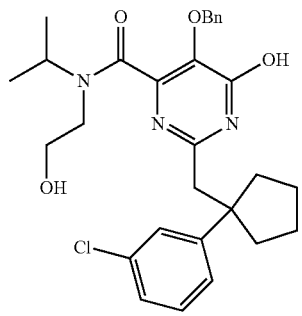 [SMILES: CC(C)N(CCO)C(=O)c1nc(CC2(c3cccc(Cl)c3)CCCC2)nc(O)c1OCc1ccccc1]

5-(Benzyloxy)-2-((1-(3-chlorophenyl)cyclopentyl)methyl)-6-hydroxy-N-(2-hydroxyethyl)-N-isopropylpyrimidine-4-carboxamide 5-(Benzyloxy)-2-((1-(3-chlorophenyl)cyclopentyl)methyl)-6-hydroxy-N-(2-hydroxyethyl)-N-isopropylpyrimidine-4-carboxamide (503) was synthesized from 5-(benzyloxy)-N-(2-((tert-butyldimethylsilyl)oxy)ethyl)-2-((1-(3-chlorophenyl)cyclopentyl)methyl)-6-hydroxy-N-isopropylpyrimidine-4-carboxamide (502) following the procedure described 5-benzyloxy-2-[1-(4-trifluoromethyl-phenyl)-cyclopentylmethyl]-6-hydroxypyrimidine-4-carboxylic acid (2-hydroxyethyl)-isopropylamide (246).

Preparation of (504)

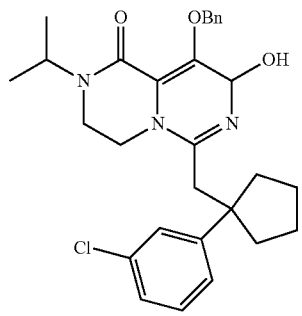 [SMILES: CC(C)N1CCN2C(CC3(c4cccc(Cl)c4)CCCC3)=NC(O)C(OCc3ccccc3)=C2C1=O]

9-(Benzyloxy)-6-((1-(3-chlorophenyl)cyclopentyl)methyl)-2-isopropyl-3,4-dihydro-1H-pyrazino[1,2-c]pyrimidine-1,8(2H)-dione 9-(Benzyloxy)-6-((1-(3-chlorophenyl)cyclopentyl)methyl)-2-isopropyl-3,4-dihydro-1H-pyrazino[1,2-c]pyrimidine-1,8(2H)-dione (504) was synthesized as a white solid from 5-(benzyloxy)-2-((1-(3-)cyclopentyl)methyl)-6-hydroxy-N-(2-hydroxyethyl)-N-isopropylpyrimidine-4-carboxamide (503) following the procedure described for 9-benzyloxy-6-[1-(4-trifluoromethyl-phenyl)- cyclopentylmethyl]-2-isopropyl-3,4-dihydro-2H-pyrazino[1,2-c]pyrimidine-1,8-dione (247).

Preparation of (505)

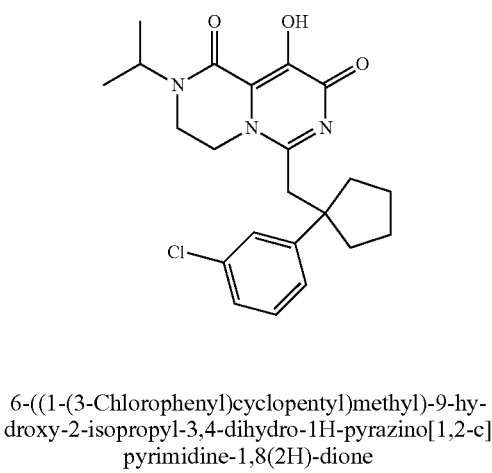

6-((1-(3-Chlorophenyl)cyclopentyl)methyl)-9-hydroxy-2-isopropyl-3,4-dihydro-1H-pyrazino[1,2-c]pyrimidine-1,8(2H)-dione 6-((1-(3-Chlorophenyl)cyclopentyl)methyl)-9-hydroxy-2-isopropyl-3,4-dihydro-1H-pyrazino[1,2-c]pyrimidine-1,8 (2H)-dione (505) was synthesized as a white solid from 9-(benzyloxy)-6-((1-(3-chlorophenyl)cyclopentyl)methyl)-2-isopropyl-3,4-dihydro-1H-pyrazino[1,2-c]pyrimidine-1,8 (2H)-dione (504) following the procedure described for 6-[1-(4-trifluoromethyl-phenyl)-cyclopentylmethyl]-9-hydroxy-2-isopropyl-3,4-dihydro-2H-pyrazino[1,2-c]pyrimidine-1,8-dione (248).

LC/HR-MS: (M+H)$^+$=416.1740

Example 509

2-Benzyl-6-((1-(4-chlorophenyl)cyclopentyl)methyl)-9-hydroxy-3,4-dihydro-1H-pyrazino[1,2-c]pyrimidine-1,8(2H)-dione The synthetic procedure used in this preparation is outlined in Scheme 52.

Synthetic Route for 509

Scheme 52

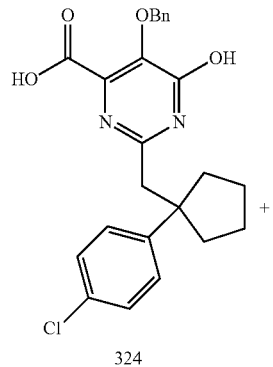

324

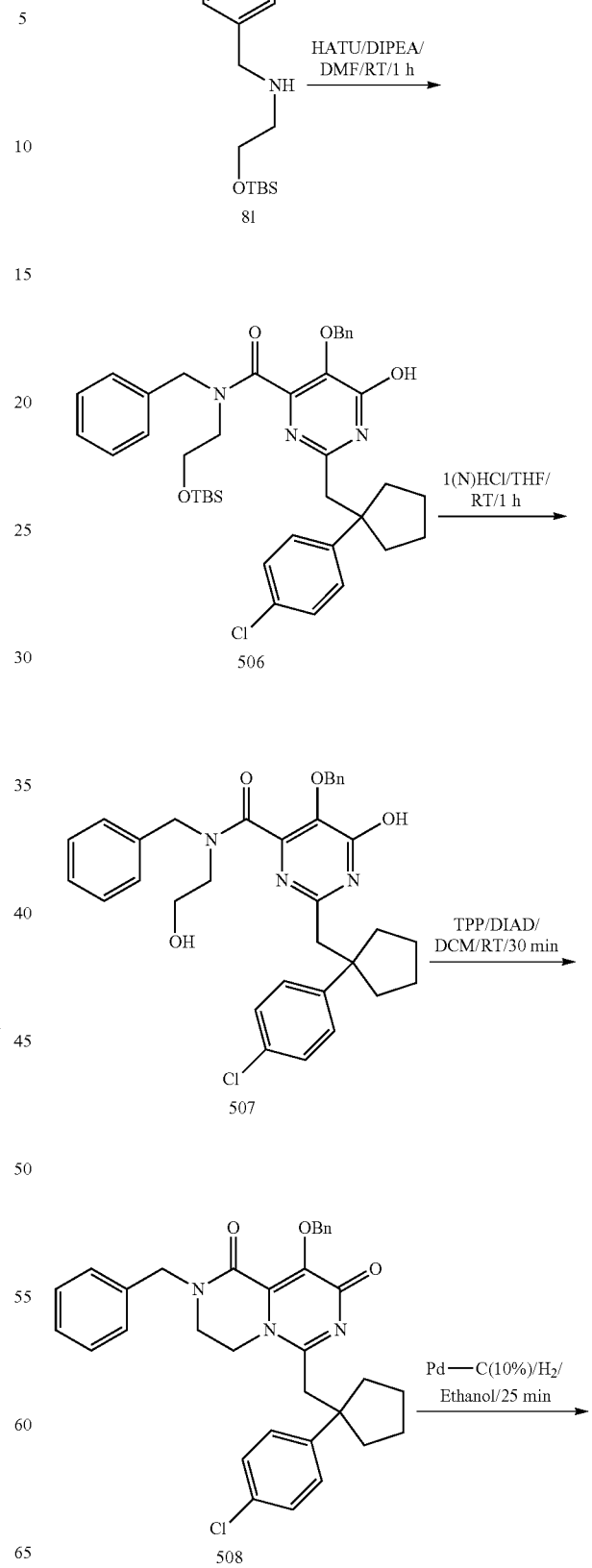

-continued

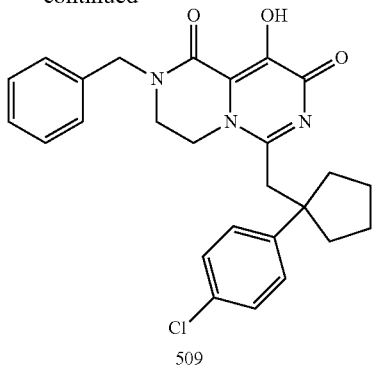

509

Synthesis of (506)

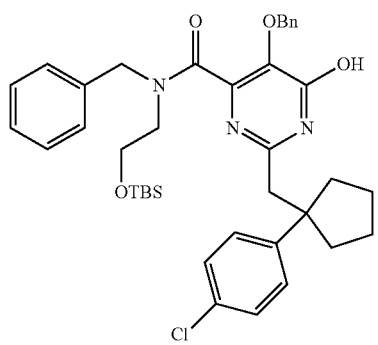 [SMILES: CC(C)(C)[Si](C)(C)OCCN(Cc1ccccc1)C(=O)c1nc(CC2(c3ccc(Cl)cc3)CCCC2)nc(O)c1OCc1ccccc1]

N-Benzyl-5-(benzyloxy)-N-(2-((tert-butyldimethyl-silyl)oxy)ethyl)-2-((1-(4-chlorophenyl)cyclo-pentyl)methyl)-6-hydroxypyrimidine-4-carboxamide This compound was prepared by following the same method as described for 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-methyl-amide (350) from 5-Benzyloxy-2-[1-(4-chlorophenyl)-cyclopentyl-methyl]-6-hydroxypyrimidine-4-carboxylic acid (324) and benzyl-[2-(tert-butyl-dimethylsilanyloxy)-ethyl]-amine (8I).

Synthesis of (507)

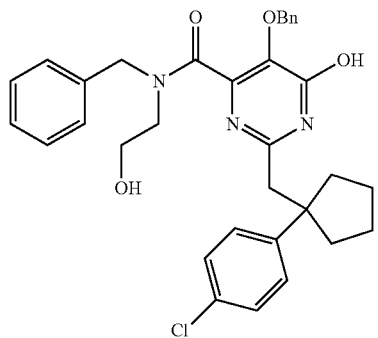 [SMILES: O=C(c1nc(CC2(c3ccc(Cl)cc3)CCCC2)nc(O)c1OCc1ccccc1)N(CCO)Cc1ccccc1]

N-Benzyl-5-(benzyloxy)-2-((1-(4-chlorophenyl)cy-clopentyl)methyl)-6-hydroxy-N-(2-hydroxyethyl) pyrimidine-4-carboxamide This compound was prepared following the same method as described for 5-benzyloxy-6-hydroxy-2-(1-naphthalen-1-yl-cyclopentylmethyl)-pyrimidine-4-carboxylic acid (2-hydroxyethyl)-methyl-amide (351) from N-benzyl-5-(benzyloxy)-N-(2-((tert-butyldimethylsilyl)oxy)ethyl)-2-((1-(4-chlorophenyl)cyclopentyl)methyl)-6-hydroxypyrimidine-4-carboxamide (506).

Synthesis of (508)

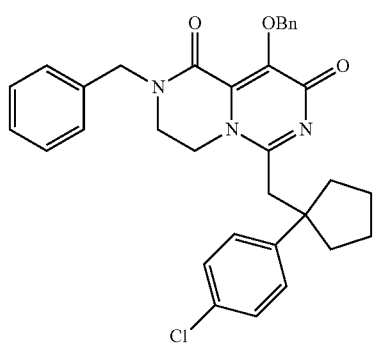 [SMILES: O=C1c2c(OCc3ccccc3)c(=O)nc(CC3(c4ccc(Cl)cc4)CCCC3)n2CCN1Cc1ccccc1]

2-Benzyl-9-(benzyloxy)-6-((1-(4-chlorophenyl)cy-clopentyl)methyl)-3,4-dihydro-1H-pyrazino[1,2-c] pyrimidine-1,8(2H)-dione This compound was prepared following the same method as described for pure 9-Benzyloxy-6-(1-naphthalen-1-yl-cyclopentylmethyl)-3,4-dihydro-2H-pyrazino[1,2-c]pyrimidine-1,8-dione (348) from N-benzyl-5-(benzyloxy)-2-((1-(4-chlorophenyl)cyclopentyl)methyl)-6-hydroxy-N-(2-hydroxyethyl)pyrimidine-4-carboxamide (507).

Synthesis of (509): (16048)

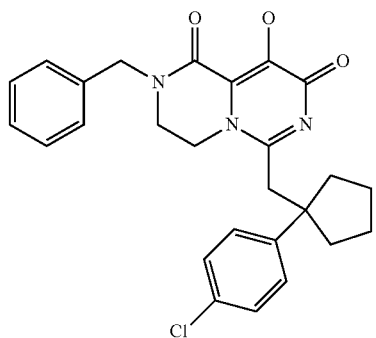 [SMILES: O=C1c2c(O)c(=O)nc(CC3(c4ccc(Cl)cc4)CCCC3)n2CCN1Cc1ccccc1]

2-Benzyl-6-((1-(4-chlorophenyl)cyclopentyl)me-thyl)-9-hydroxy-3,4-dihydro-1H-pyrazino[1,2-c] pyrimidine-1,8(2H)-dione This compound was prepared following the same method as described for pure 9-hydroxy-6-(1-naphthalen-1-yl-cyclopentylmethyl)-3,4-dihydro-2H-pyrazino[1,2-c]pyrimidine-1,8-dione (349) from 2-benzyl-9-(benzyloxy)-6-((1-(4-chlorophenyl)cyclopentyl)methyl)-3,4-dihydro-1H-pyrazino[1,2-c]pyrimidine-1,8(2H)-dione (508).

¹H NMR (400 MHz, dimethyl sulfoxide-d₆) δ ppm 1.62 (d, J=5.52 Hz, 2H) 1.72-1.90 (m, 4H) 2.23-2.37 (m, 4H) 2.69 (d, J=1.76 Hz, 1H) 2.89 (s, 2H) 3.09 (d, J=5.27 Hz, 2H) 3.31 (s, 8 H) 3.52 (d, J=6.02 Hz, 2H) 4.63 (s, 2H) 7.17-7.47 (m, 9H)

LC/HR-MS: (M+H)⁺=464.1743

Example 513

9-Hydroxy-2-isopropyl-6-((1-(naphthalen-1-yl)cyclopentyl)methyl)-3,4-dihydro-1H-pyrazino[1,2-c]pyrimidine-1,8(2H)-dione The synthetic procedure used in this preparation is outlined in Scheme 53.

Synthetic Route for 513

Scheme 53

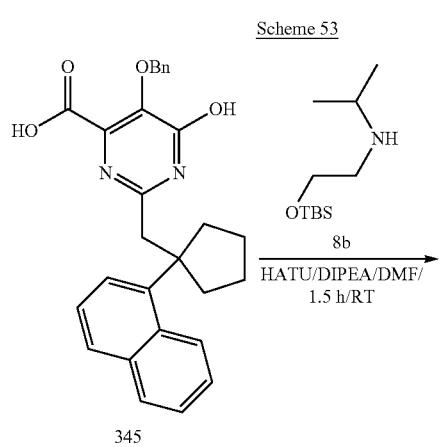

345

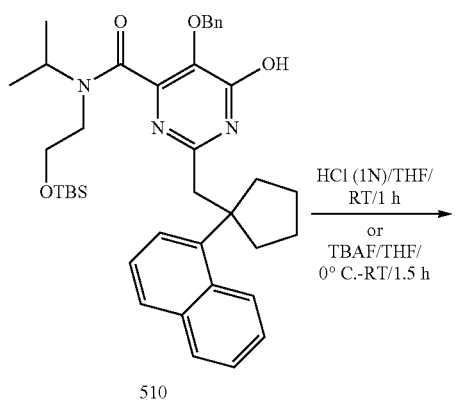

510

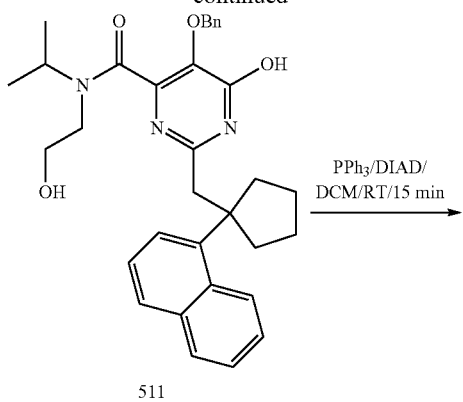

511

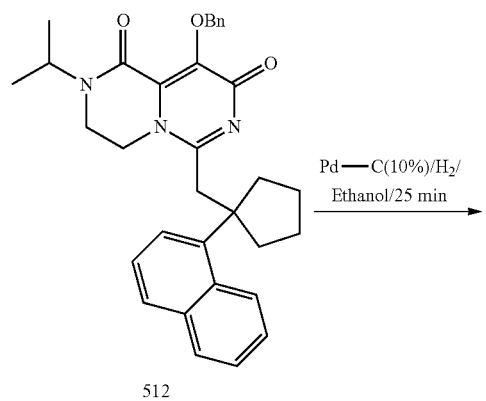

512

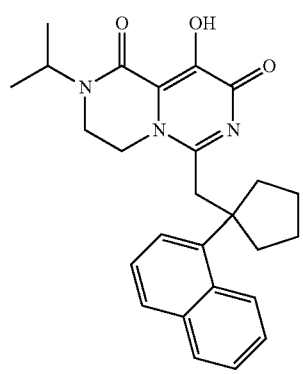

513

Synthesis of (510)

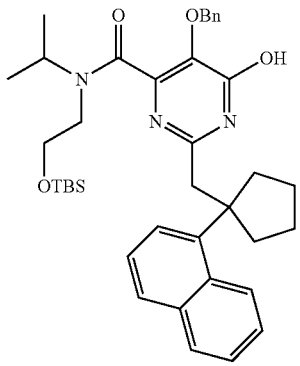 [SMILES: CC(C)N(CCO[Si](C)(C)C(C)(C)C)C(=O)c1nc(CC2(c3cccc4ccccc34)CCCC2)nc(O)c1OCc1ccccc1]

5-(Benzyloxy)-N-(2-((tert-butyldimethylsilyl)oxy)ethyl)-6-hydroxy-N-isopropyl-2-((1-(naphthalen-1-yl)cyclopentyl)methyl)pyrimidine-4-carboxamide This compound was prepared by following the same method as described for 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-methyl-amide (350) from 5-benzyloxy-6-hydroxy-2-(1-naphthalen-1-yl-cyclopentylmethyl)-pyrimidine-4-carboxylic acid (345) and [2-(tert-butyl-dimethylsilanyloxy)-ethyl]-isopropyl-amine (8b).

Synthesis of (511)

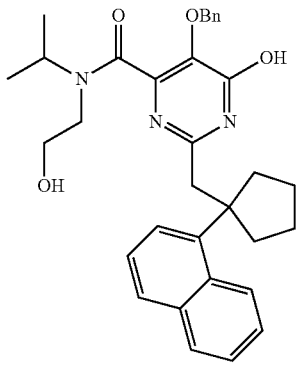 [SMILES: CC(C)N(CCO)C(=O)c1nc(CC2(c3cccc4ccccc34)CCCC2)nc(O)c1OCc1ccccc1]

5-(Benzyloxy)-6-hydroxy-N-(2-hydroxyethyl)-N-isopropyl-2-((1-(naphthalen-1-yl)cyclopentyl)methyl)pyrimidine-4-carboxamide This compound was prepared following the same method as described for 5-benzyloxy-6-hydroxy-2-(1-naphthalen-1-yl-cyclopentylmethyl)-pyrimidine-4-carboxylic acid (2-hydroxyethyl)-methyl-amide (351) from 5-(benzyloxy)-N-(2-((tert-butyldimethylsilyl)oxy)ethyl)-6-hydroxy-N-isopropyl-2-((1-(naphthalen-1-yl)cyclopentyl)methyl)pyrimidine-4-carboxamide (510).

Synthesis of (512)

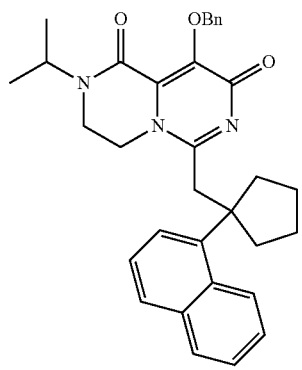 [SMILES: CC(C)N1CCn2c(CC3(c4cccc5ccccc45)CCCC3)nc(=O)c(OCc3ccccc3)c2C1=O]

9-(Benzyloxy)-2-isopropyl-6-((1-(naphthalen-1-yl)cyclopentyl)methyl)-3,4-dihydro-1H-pyrazino[1,2-c]pyrimidine-1,8(2H)-dione This compound was prepared following the same method as described for pure 9-Benzyloxy-2-methyl-6-(1-naphthalen-1-yl-cyclopentylmethyl)-3,4-dihydro-2H-pyrazino[1,2-c]pyrimidine-1,8-dione (352) from 5-(benzyloxy)-6-hydroxy-N-(2-hydroxyethyl)-N-isopropyl-2-((1-(naphthalen-1-yl)cyclopentyl)methyl)pyrimidine-4-carboxamide (511).

Synthesis of (513)

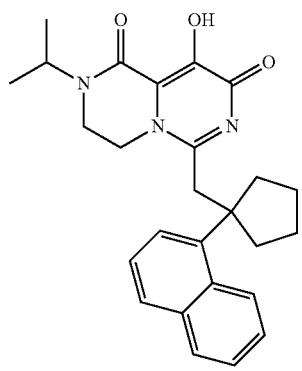 [SMILES: CC(C)N1CCn2c(CC3(c4cccc5ccccc45)CCCC3)nc(=O)c(O)c2C1=O]

9-Hydroxy-2-isopropyl-6-((1-(naphthalen-1-yl)cyclopentyl)methyl)-3,4-dihydro-1H-pyrazino[1,2-c]pyrimidine-1,8(2H)-dione This compound was prepared following the same method as described for pure 9-hydroxy-6-(1-naphthalen-1-yl-cyclopentylmethyl)-3,4-dihydro-2H-pyrazino[1,2-c]pyrimidine-1,8-dione (349) from 9-(benzyloxy)-2-isopropyl-6-((1-(naphthalen-1-yl)cyclopentyl)methyl)-3,4-dihydro-1H-pyrazino[1,2-c]pyrimidine-1,8(2H)-dione (512)

Orange foam: LC/MS: $(M+H)^+=432$.

Example 517

6-((1-(4-Chlorophenyl)cyclopentyl)methyl)-9-hydroxy-3,4-dihydro-1H-pyrazino[1,2-c]pyrimidine-1,8(2H)-dione The synthetic procedure used in this preparation is outlined in Scheme 53.

Synthetic Route for 517

Scheme 53

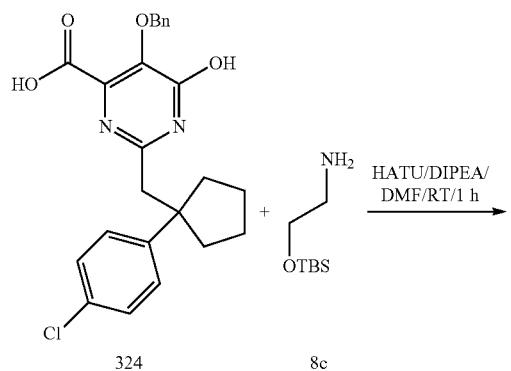

324    8c

HATU/DIPEA/
DMF/RT/1 h

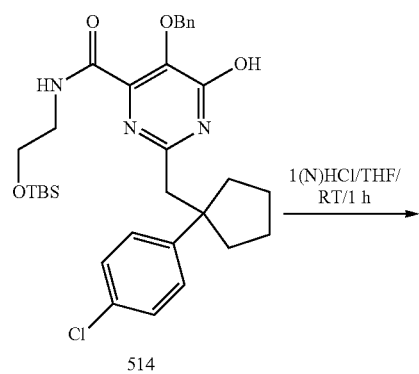

514

1(N)HCl/THF/
RT/1 h

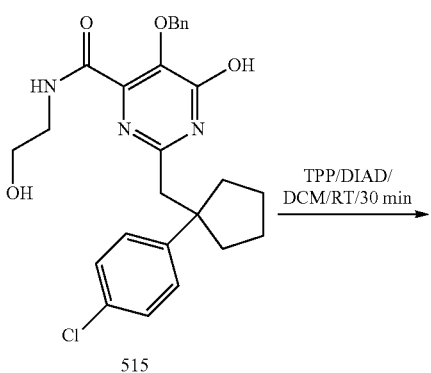

515

TPP/DIAD/
DCM/RT/30 min

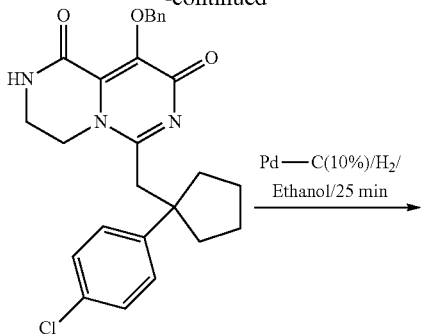

516

Pd—C(10%)/H$_2$/
Ethanol/25 min

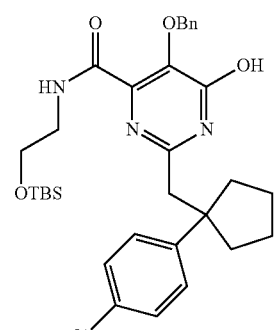

517

Synthesis of (514)

5-(Benzyloxy)-N-(2-((tert-butyldimethylsilyl)oxy)ethyl)-2-((1-(4-chlorophenyl)cyclopentyl)methyl)-6-hydroxypyrimidine-4-carboxamide This compound was prepared by following the same method as described for 5-benzyloxy-6-hydroxy-2-(1-naphthalen-1-yl-cyclopentylmethyl)-pyrimidine-4-carboxylic acid [2-(tert-butyl-dimethylsilanyloxy)-ethyl]-amide (346) from 5-benzyloxy-2-[1-(4-chlorophenyl)-cyclopentylm-

425 ethyl]-6-hydroxypyrimidine-4-carboxylic acid (324) and 2-(tert-butyl-dimethylsilanyloxy)-ethylamine (8c).

Synthesis of (515)

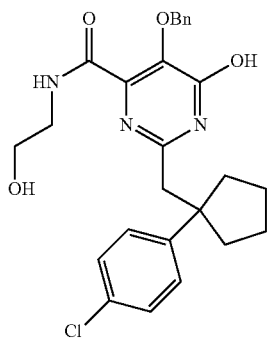 [SMILES: O=C(NCCO)c1nc(CC2(c3ccc(Cl)cc3)CCCC2)nc(O)c1OCc1ccccc1]

5-(Benzyloxy)-2-((1-(4-chlorophenyl)cyclopentyl) methyl)-6-hydroxy-N-(2-hydroxyethyl)pyrimidine-4-carboxamide This compound was prepared following the same method as described for 5-benzyloxy-6-hydroxy-2-(1-naphthalen-1-yl-cyclopentylmethyl)-pyrimidine-4-carboxylic acid (2-hydroxyethyl)-amide (347) from 5-(benzyloxy)-N-(2-((tert-butyldimethylsilyl)oxy)ethyl)-2-((1-(4-chlorophenyl) cyclopentyl)methyl)-6-hydroxypyrimidine-4-carboxamide (514).

Synthesis of (516)

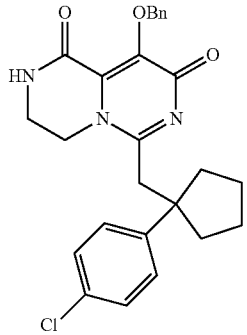 [SMILES: O=C1NCCn2c(CC3(c4ccc(Cl)cc4)CCCC3)nc(=O)c(OCc3ccccc3)c21]

9-(Benzyloxy)-6-((1-(4-chlorophenyl)cyclopentyl) methyl)-3,4-dihydro-1H-pyrazino[1,2-c]pyrimidine-1,8(2H)-dione This compound was prepared following the same method as described for pure 9-benzyloxy-6-(1-naphthalen-1-yl-cyclopentylmethyl)-3,4-dihydro-2H-pyrazino[1,2-c]pyrimidine-1,8-dione (348) from 5-(benzyloxy)-2-((1-(4-chlo-

426 rophenyl)cyclopentyl)methyl)-6-hydroxy-N-(2-hydroxyethyl)pyrimidine-4-carboxamide (515).

Synthesis of (517): (16246)

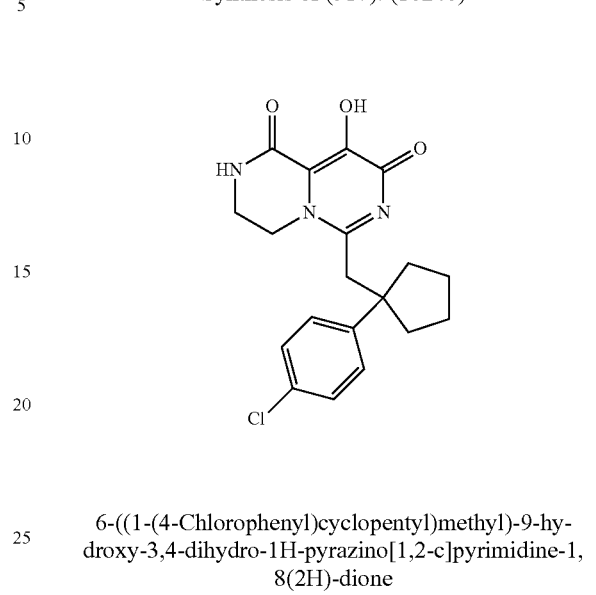

6-((1-(4-Chlorophenyl)cyclopentyl)methyl)-9-hydroxy-3,4-dihydro-1H-pyrazino[1,2-c]pyrimidine-1,8(2H)-dione This compound was prepared following the same method as described for pure 9-hydroxy-6-(1-naphthalen-1-yl-cyclopentylmethyl)-3,4-dihydro-2H-pyrazino[1,2-c]pyrimidine-1,8-dione (349) from 9-(benzyloxy)-6-((1-(4-chlorophenyl) cyclopentyl)methyl)-3,4-dihydro-1H-pyrazino[1,2-c] pyrimidine-1,8(2H)-dione (517).

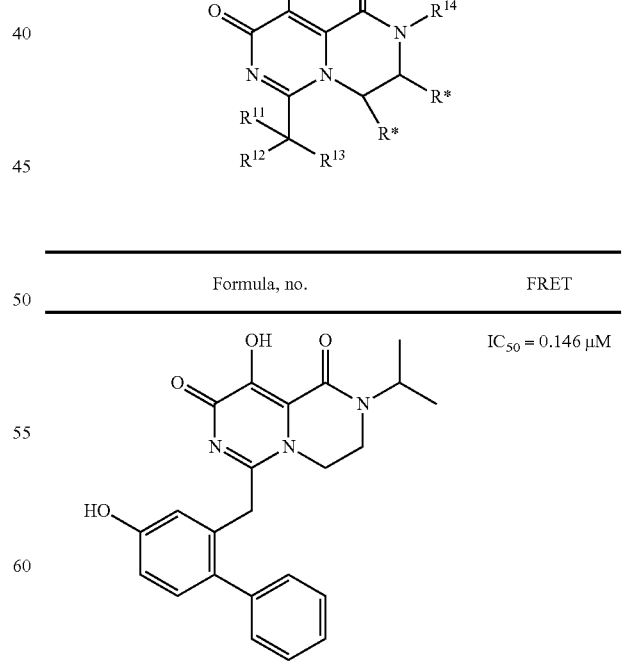

| Formula, no. | FRET |
|---|---|
| 145 | $IC_{50} = 0.146\ \mu M$ |

-continued

| Formula, no. | FRET |
|---|---|
| 172 | IC$_{50}$ = 0.122 μM |
| 157 | IC$_{50}$ = 0.114 μM |
| 154 | IC$_{50}$ = 0.094 μM |
| 173 | IC$_{50}$ = 0.38 μM |

-continued

| Formula, no. | FRET |
|---|---|
| 168 | IC$_{50}$ = 0.38 μM |
| 171 | IC$_{50}$ = 1.06 μM |
| 175 | IC$_{50}$ = 0.70 μM |
| 177 | IC$_{50}$ = 1.55 μM |

| Formula, no. | FRET |
|---|---|
| 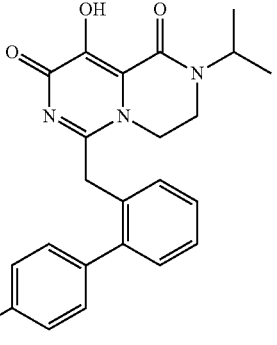 179 | IC$_{50}$ = 0.30 μM |
| 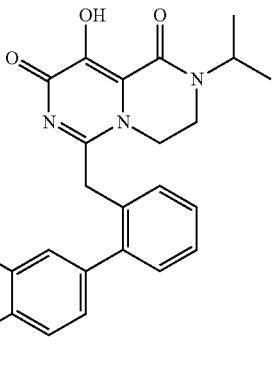 181 | IC$_{50}$ = 0.38 μM |
| 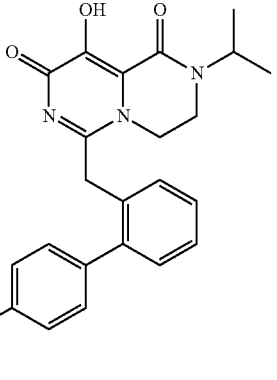 183 | IC$_{50}$ = 0.32 μM |
| Formula, no. | FRET |
|---|---|
| 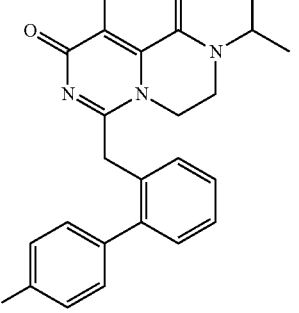 185 | IC$_{50}$ = 0.55 μM |
| 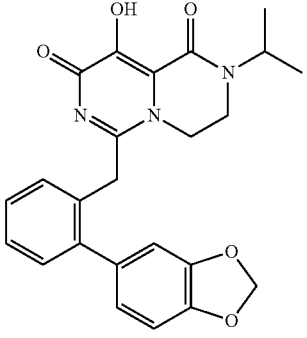 187 | IC$_{50}$ = 0.229 μM |
| 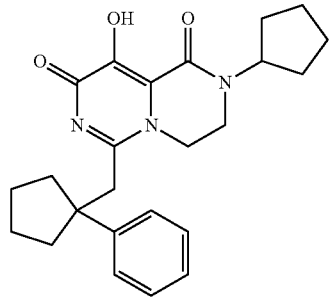 291 | IC$_{50}$ = 0.521 μM |
| 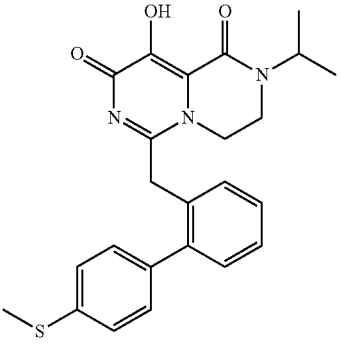 189 | IC$_{50}$ = 0.116 μM |

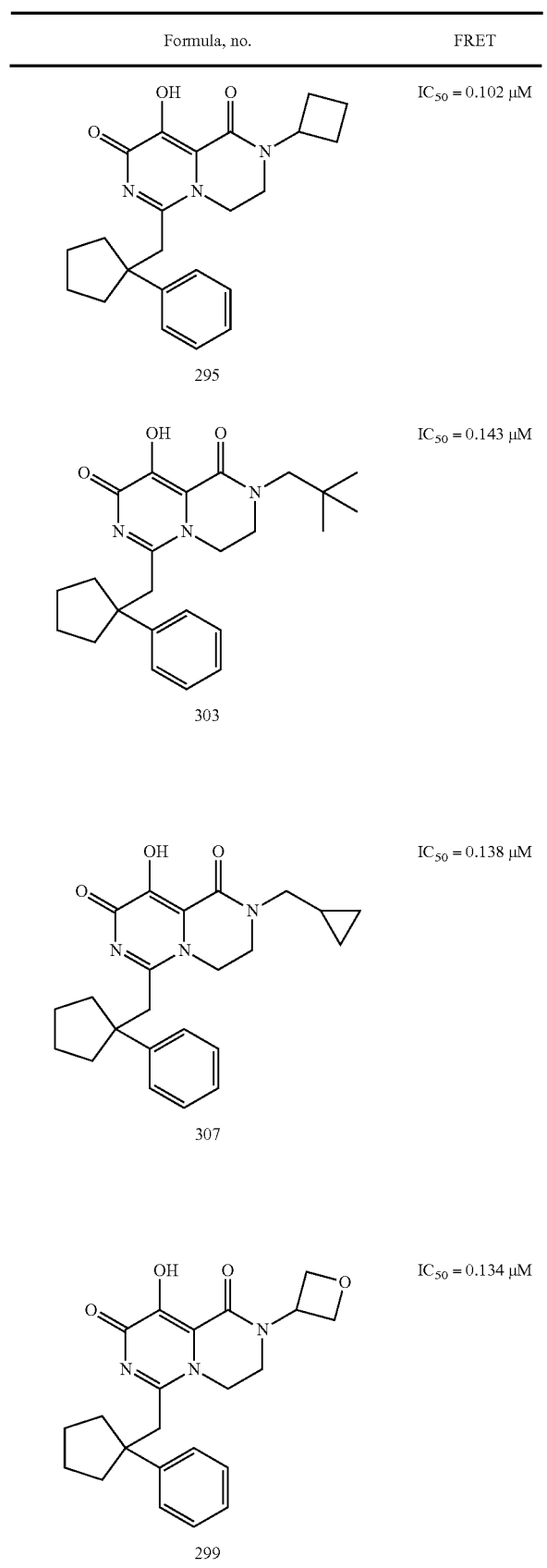
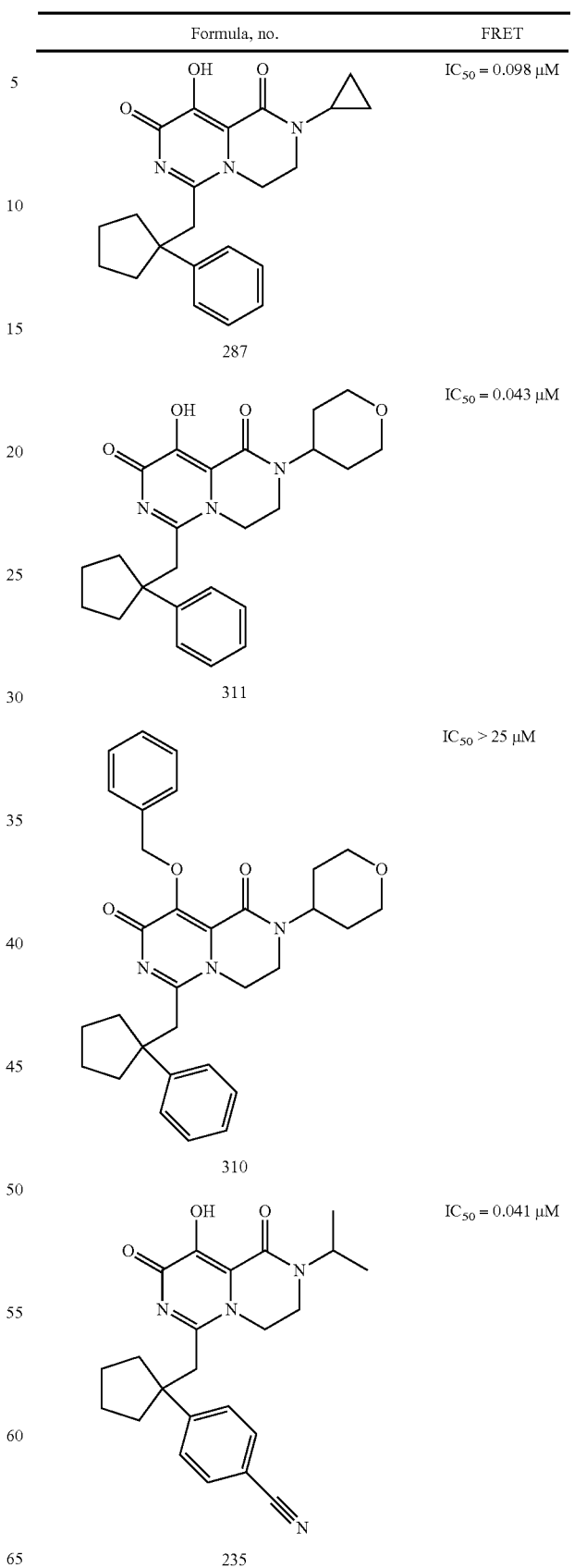

| Formula, no. | FRET |
|---|---|
| 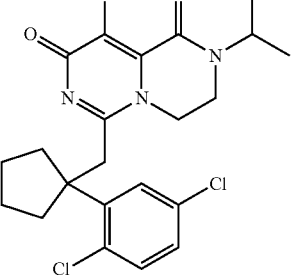 209 | IC$_{50}$ = 0.295 μM |
| 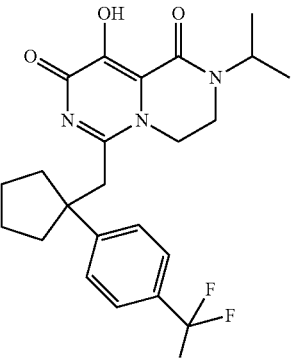 248 | IC$_{50}$ = 0.262 μM |
| 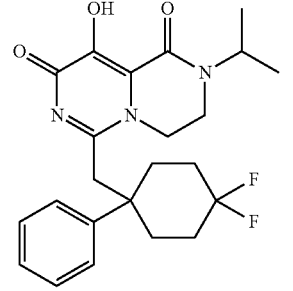 275 | IC$_{50}$ = 0.084 μM |
| 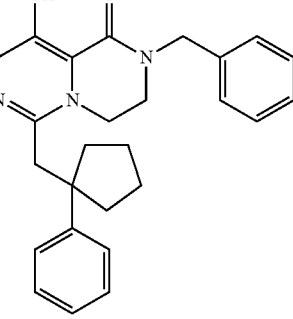 315 | IC$_{50}$ = 0.422 μM |
| Formula, no. | FRET |
|---|---|
| 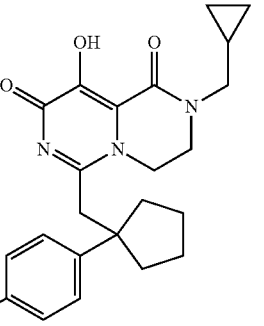 332 | IC$_{50}$ = 0.205 μM |
| 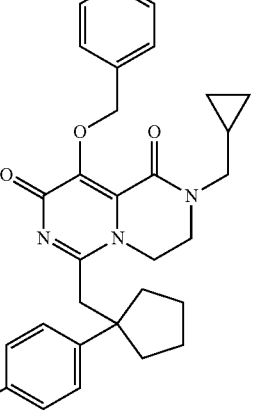 331 | IC$_{50}$ > 25 μM |
| 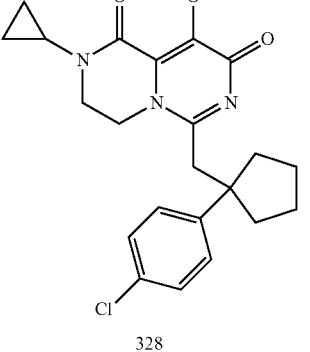 328 | IC$_{50}$ = 0.73 μM |

-continued
| Formula, no. | FRET |
|---|---|
| 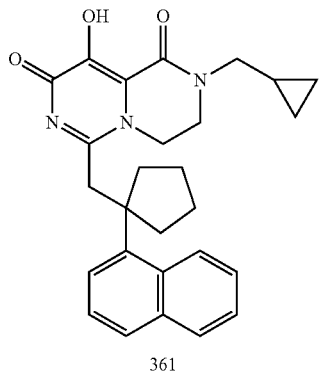 [SMILES: O=C1c2c(O)c(=O)nc(CC3(c4cccc5ccccc45)CCCC3)n2CCN1CC1CC1] 361 | IC$_{50}$ = 0.14 μM |
| 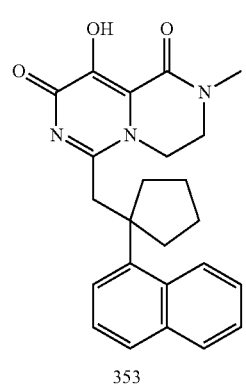 [SMILES: CN1CCn2c(CC3(c4cccc5ccccc45)CCCC3)nc(=O)c(O)c2C1=O] 353 | IC$_{50}$ = 0.11 μM |
| 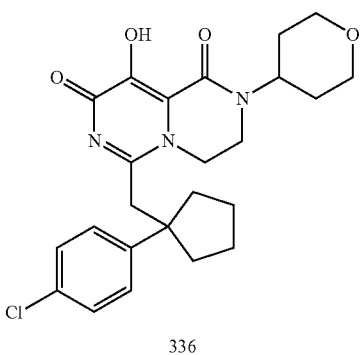 [SMILES: O=C1c2c(O)c(=O)nc(CC3(c4ccc(Cl)cc4)CCCC3)n2CCN1C1CCOCC1] 336 | IC$_{50}$ = 0.06 μM |
| 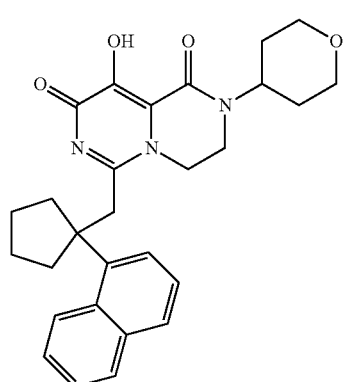 369 | IC$_{50}$ = 0.11 μM |
-continued
| Formula, no. | FRET |
|---|---|
| 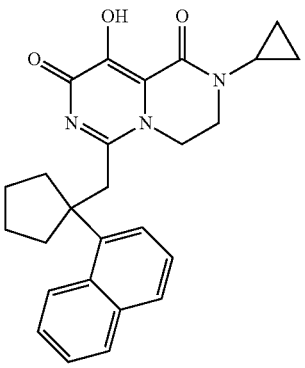 357 | IC$_{50}$ = 0.104 μM |
| 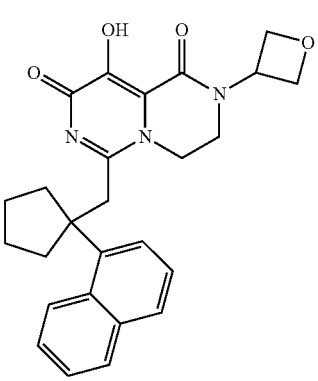 365 | IC$_{50}$ > 25 μM |
| 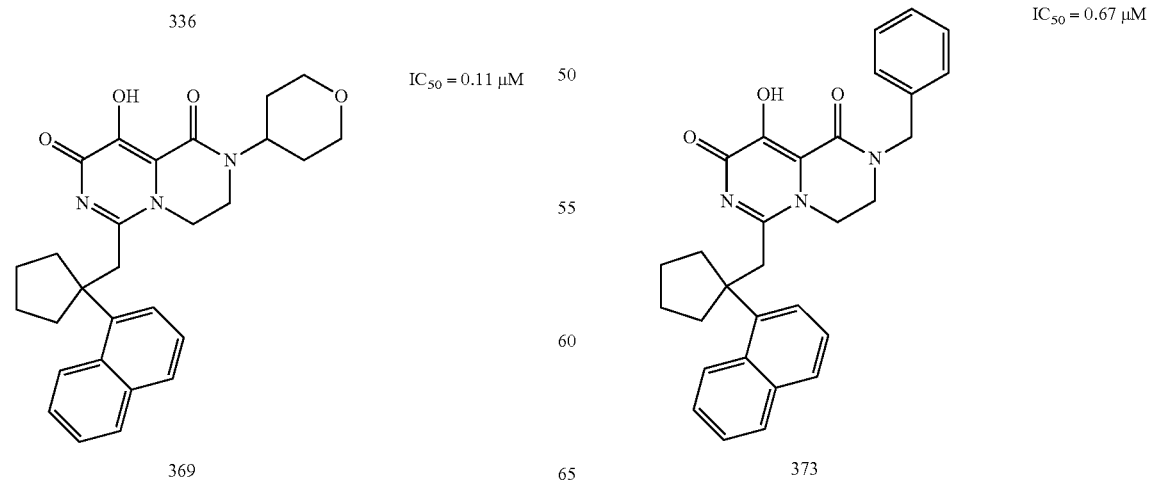 373 | IC$_{50}$ = 0.67 μM |

437
-continued
| Formula, no. | FRET |
|---|---|
| 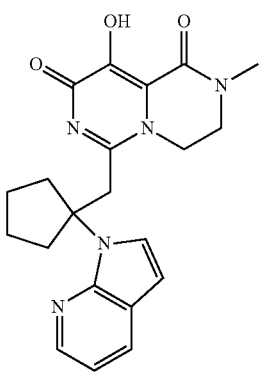 408 | IC$_{50}$ = 0.08 µM |
| 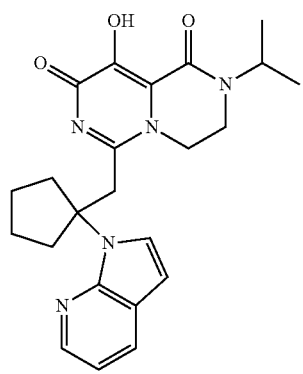 412 | IC$_{50}$ = 0.02 µM |
| 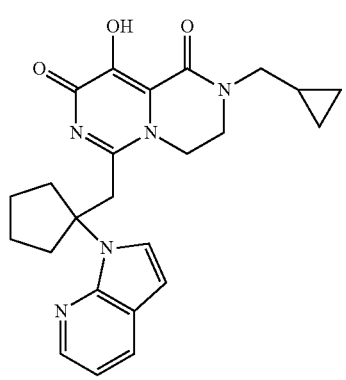 416 | IC$_{50}$ = 0.141 µM |
438
-continued
| Formula, no. | FRET |
|---|---|
| 415 | IC$_{50}$ > 25 µM |
| 349 | IC$_{50}$ = 0.162 µM |
| 424 | IC$_{50}$ = 0.108 µM |

| Formula, no. | FRET |
|---|---|
| 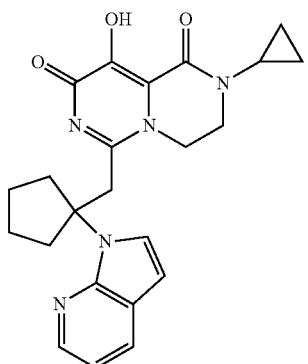 420 | IC$_{50}$ = 0.092 µM |
| 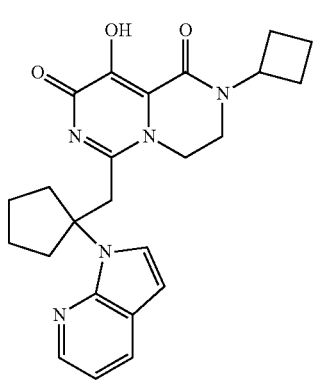 428 | IC$_{50}$ = 0.173 µM |
| 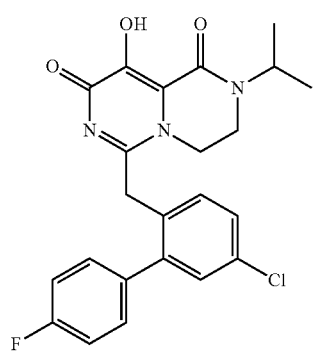 386 | IC$_{50}$ = 0.436 µM |
| 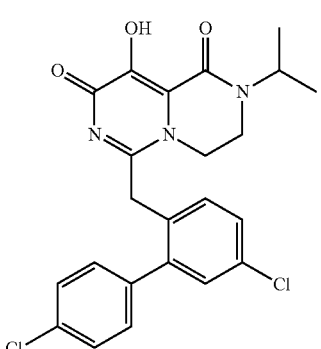 382 | IC$_{50}$ = 0.266 µM |
| Formula, no. | FRET |
|---|---|
| 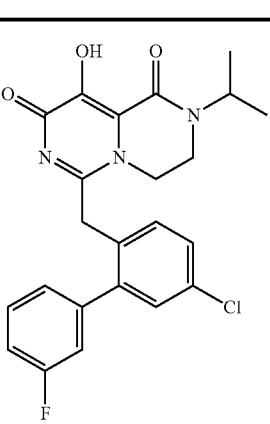 384 | IC$_{50}$ = 0.058 µM |
| 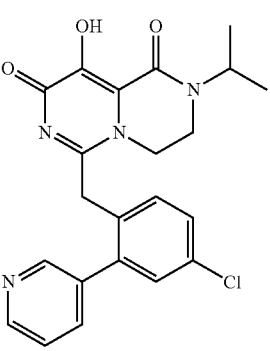 390 | IC$_{50}$ = 0.081 µM |
| 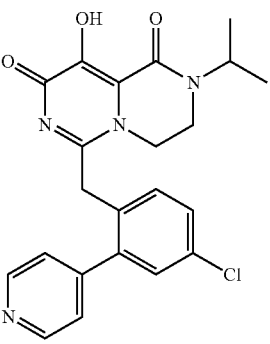 388 | IC$_{50}$ = 0.110 µM |

-continued
| Formula, no. | FRET |
|---|---|
| 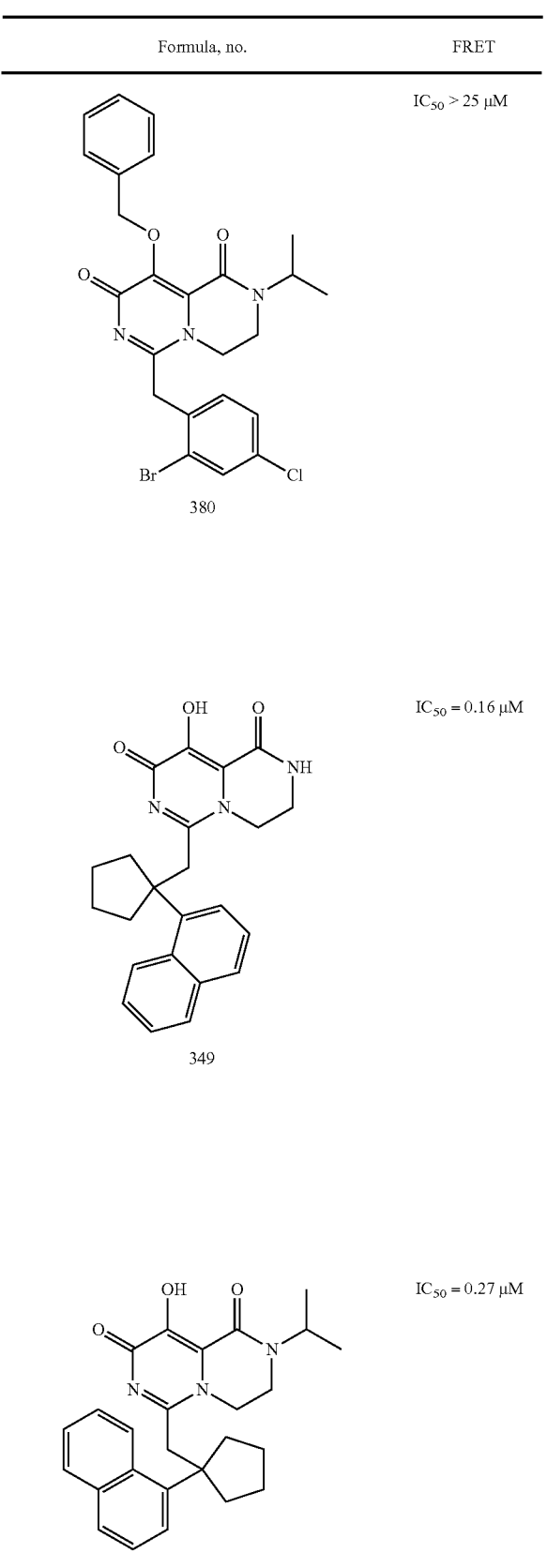 380 | IC$_{50}$ > 25 µM |
| 349 | IC$_{50}$ = 0.16 µM |
| 513 | IC$_{50}$ = 0.27 µM |
-continued
| Formula, no. | FRET |
|---|---|
| 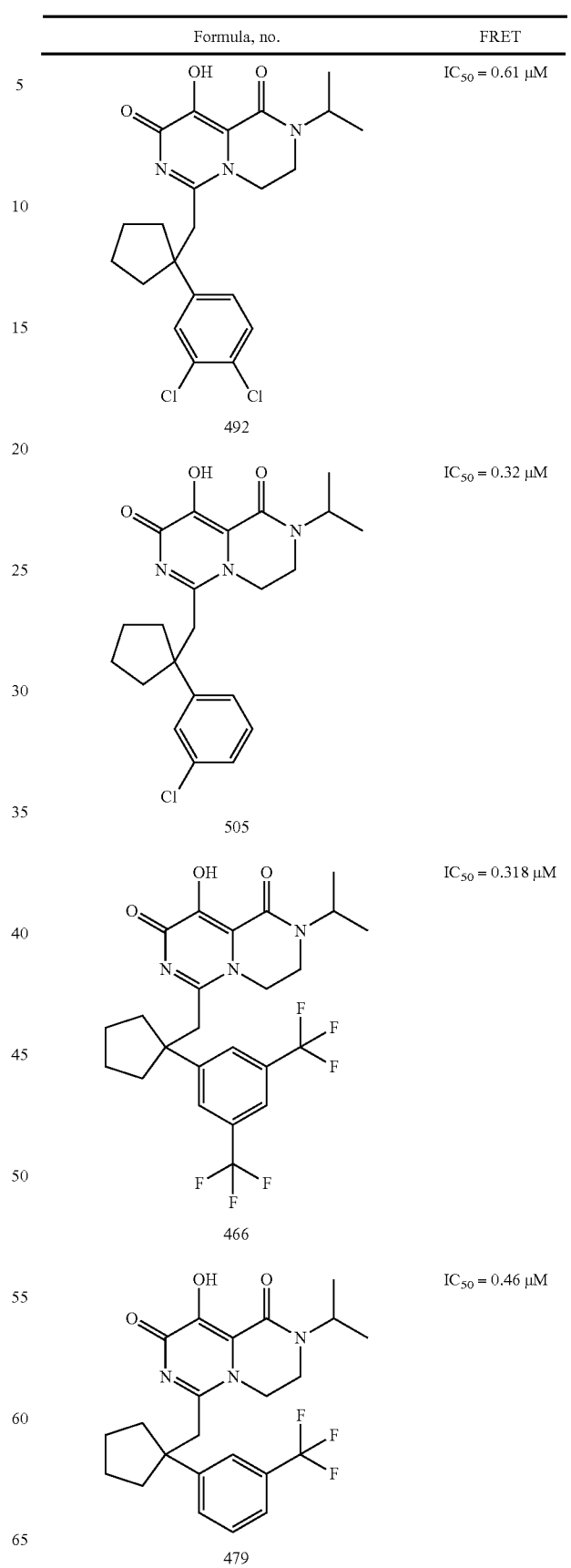 492 | IC$_{50}$ = 0.61 µM |
| 505 | IC$_{50}$ = 0.32 µM |
| 466 | IC$_{50}$ = 0.318 µM |
| 479 | IC$_{50}$ = 0.46 µM |

| Formula, no. | FRET | | Formula, no. | FRET |
|---|---|---|---|---|
| 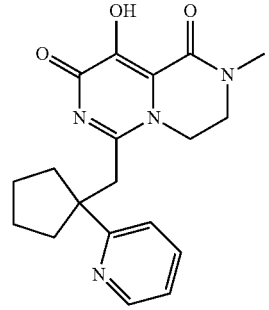 196 | IC$_{50}$ = 1.89 µM | | 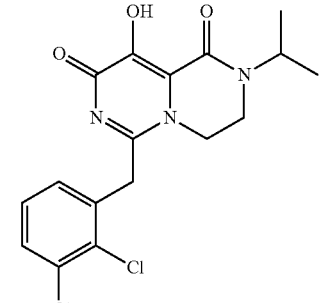 445 | IC$_{50}$ = 0.063 µM |
| 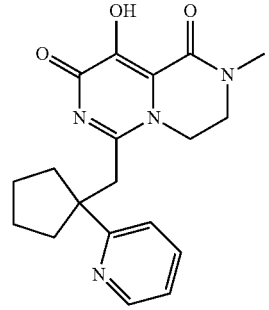 509 | IC$_{50}$ = 0.99 µM | | 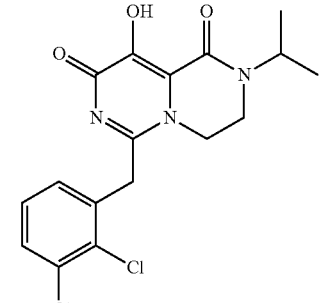 135 | IC$_{50}$ = 0.35 µM |
| 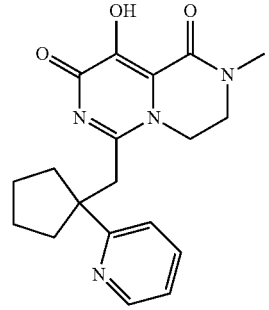 517 | IC$_{50}$ = 1.27 µM | | 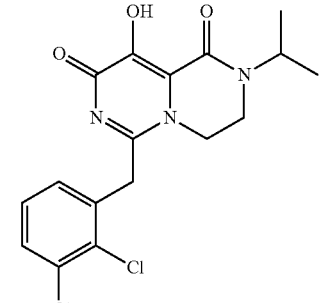 144 | IC$_{50}$ = 0.43 µM |
| 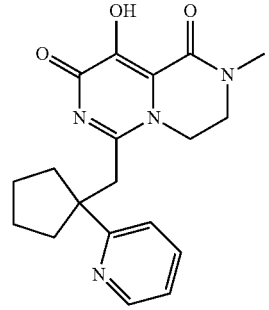 441 | IC$_{50}$ = 0.097 µM | | 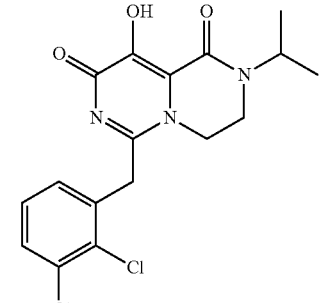 222 | IC$_{50}$ = 0.11 µM |

-continued

| Formula, no. | | FRET |
|---|---|---|
| 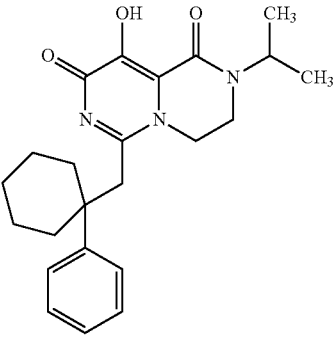<br>260 | | IC$_{50}$ = 0.12 μM |

The invention claimed is:

1. A compound having the formula (I),

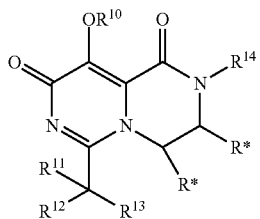
(I)

wherein
$X^{10}$ is $NR^{15}$, $N(R^{15})C(O)$, $C(O)NR^{15}$, O, C(O), C(O)O, OC(O); $N(R^{15})SO_2$, $SO_2N(R^{15})$, S, SO, or $SO_2$;
$R^{10}$ is —H, a —$C_{1-6}$ alkyl group or a —C(O)—$C_{1-6}$ alkyl group;
$R^{11}$ is —H, a —$C_{1-6}$ alkyl group, or a —$C_{1-6}$ alkyl group which is substituted by one or more halogen atoms;
$R^{12}$ is —H, a —$C_{1-6}$ alkyl group, or a —$C_{1-6}$ alkyl group which is substituted by one or more halogen atoms;
or wherein $R^{11}$ and $R^{12}$ can be joined together to form a 3- to 7-membered carbo- or heterocyclic ring;
$R^{13}$ is —$R^{16}$, or —$X^{10}$—$R^{16}$;
$R^{14}$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl);
$R^{15}$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl);
$R^{16}$ is -(optionally substituted hydrocarbon group which contains from 5 to 20 carbon atoms and optionally 1 to 4 heteroatoms selected from O, N and S and which contains at least one ring);
$R^{17}$ is —H, —$C_{1-6}$ alkyl, or —$(CH_2CH_2O)_rH$;
$R^{18}$ is —H, or —$C_{1-6}$ alkyl;
R is independently selected from —$C_{1-6}$ alkyl, —C(O)—$C_{1-6}$ alkyl, -Hal, —$CF_3$, —CN, —$COOR^{17}$, —$OR^{17}$, —$(CH_2)_qNR^{17}R^{18}$, —C(O)—$NR^{17}R^{18}$, and —$NR^{17}$—C(O)—$C_{1-6}$ alkyl;

R* is independently selected from —H, —$C_{1-6}$ alkyl, and —$C_{3-7}$ cycloalkyl;
q is 0 to 4; and
r is 1 to 3;
wherein the alkyl group, aryl group, hydrocarbon group and/or cycloalkyl group can be optionally substituted with one or more substituents R;
or a pharmaceutically acceptable salt, solvate, tautomer, racemate, enantiomer, or diastereomer or mixture thereof,
with the proviso that the compound is not:

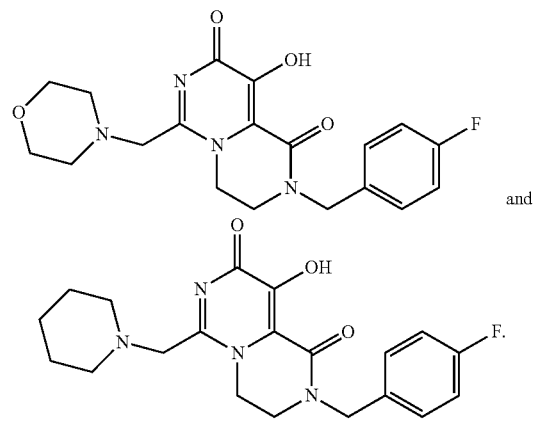 and

2. The compound according to claim 1, wherein $R^{13}$ is —$R^{16}$.

3. The compound according to claim 1, wherein $R^{13}$ is —$X^{10}$—$R^{16}$ and $X^{10}$ is $N(R^{15})SO_2$.

4. The compound according to claim 1, wherein $R^{11}$ and $R^{12}$ are —H.

5. The compound according to claim 1, wherein $R^{10}$ is —H, or -(optionally substituted $C_{1-6}$ alkyl).

6. The compound according to claim 1, wherein $R^{14}$ is —H, -(optionally substituted $C_{1-6}$ alkyl), or -(optionally substituted aryl).

7. The compound according to claim 1, wherein $R^{16}$ is selected from the group consisting of

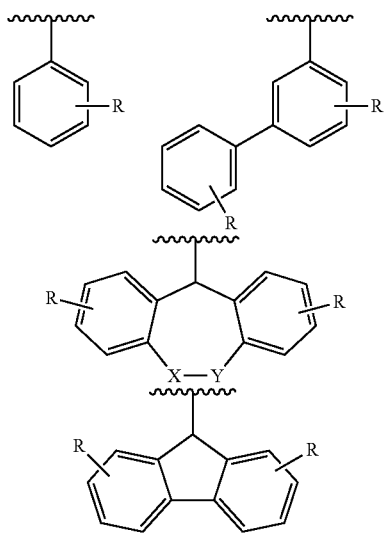

-continued

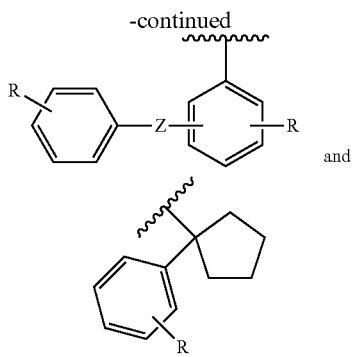

and wherein

X is absent, CH$_2$, NH, C(O)NH, S or O;

Y is CH$_2$;

Z is O or S; and

R is independently selected from —H, —C$_{1-6}$ alkyl, —CF$_3$, -halogen, —CN, —OH, and —O—C$_{1-6}$ alkyl.

8. A pharmaceutical composition comprising:

a compound according to claim 1, and one or more pharmaceutically acceptable excipient(s) and/or carrier(s);

with the proviso that the compound is not:

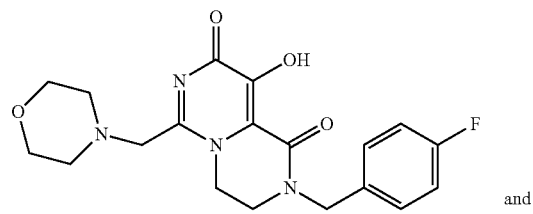

and

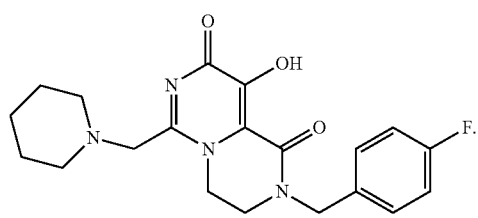

9. The pharmaceutical composition according to claim 8, which additionally comprises a further medicament selected from the group consisting of a polymerase inhibitor which is different from the compound having the general formula (I); a M2 channel inhibitor; an alpha glucosidase inhibitor; a ligand of another influenza target; an antibiotic, an anti-inflammatory agent, a lipoxygenase inhibitor, an EP ligand, a bradykinin ligand, a cannabinoid ligand, and combinations thereof.

10. A method of treating or ameliorating influenza; the method comprising administering to a patient in need thereof an effective amount of a compound having the formula (I):

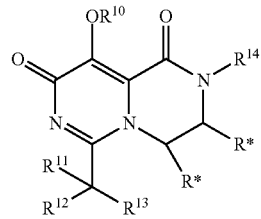

(I)

wherein

X$^{10}$ is NR$^{15}$, N(R$^{15}$)C(O), C(O)NR$^{15}$, O, C(O), C(O)O, OC(O); N(R$^{15}$)SO$_2$, SO$_2$N(R$^{15}$), S, SO, or SO$_2$;

R$^{10}$ is —H, a —C$_{1-6}$ alkyl group or a —C(O)—C$_{1-6}$ alkyl group;

R$^{11}$ is —H, a —C$_{1-6}$ alkyl group, or a —C$_{1-6}$ alkyl group which is substituted by one or more halogen atoms;

R$^{12}$ is —H, a —C$_{1-6}$ alkyl group, or a —C$_{1-6}$ alkyl group which is substituted by one or more halogen atoms; or wherein R$^{11}$ and R$^{12}$ can be joined together to form a 3- to 7-membered carbo- or heterocyclic ring;

R$^{13}$ is —R$^{16}$, or —X$^{10}$—R$^{16}$;

R$^{14}$ is —H, -(optionally substituted C$_{1-6}$ alkyl), -(optionally substituted C$_{3-7}$ cycloalkyl), -(optionally substituted aryl), —C$_{1-4}$ alkyl-(optionally substituted C$_{3-7}$ cycloalkyl), or —C$_{1-4}$ alkyl-(optionally substituted aryl);

R$^{15}$ is —H, -(optionally substituted C$_{1-6}$ alkyl), -(optionally substituted C$_{3-7}$ cycloalkyl), -(optionally substituted aryl), —C$_{1-4}$ alkyl-(optionally substituted C$_{3-7}$ cycloalkyl), or —C$_{1-4}$ alkyl-(optionally substituted aryl);

R$^{16}$ is -(optionally substituted hydrocarbon group which contains from 5 to 20 carbon atoms and optionally 1 to 4 heteroatoms selected from O, N and S and which contains at least one ring);

R$^{17}$ is —H, —C$_{1-6}$ alkyl, or —(CH$_2$CH$_2$O)$_r$H;

R$^{18}$ is —H, or —C$_{1-6}$ alkyl;

R is independently selected from —C$_{1-6}$ alkyl, —C(O)—C$_{1-6}$ alkyl, -Hal, —CF$_3$, —CN, —COOR$^{17}$, —OR$^{17}$, —(CH$_2$)$_q$NR$^{17}$R$^{18}$, —C(O)—NR$^{17}$R$^{18}$, and —NR$^{17}$—C(O)—C$_{1-6}$ alkyl;

R* is independently selected from —H, —C$_{1-6}$ alkyl, and —C$_{3-7}$ cycloalkyl;

q is 0 to 4; and r is 1 to 3;

wherein the alkyl group, aryl group, hydrocarbon group and/or cycloalkyl group can be optionally substituted with one or more substituents R;

or a pharmaceutically acceptable salt, solvate, tautomer, racemate, enantiomer, or diastereomer or mixture thereof.

11. The method according to claim 10 further comprising administering an effective amount of a further medicament selected from the group consisting of a polymerase inhibitor which is different from the compound having the general formula (I); a neuramidase inhibitor; a M2 channel inhibitor; an alpha glucosidase inhibitor; a ligand of another influenza target; an antibiotic, an anti-inflammatory agent, a lipoxygenase inhibitor, an EP ligand, a bradykinin ligand, a cannabinoid ligand, and combinations thereof.

12. The compound according to claim 1, which exhibits an IC$_{50}$ of less than about 40 μM in a FRET endonuclease activity assay.

13. The method according to claim 11, wherein the further medicament is administered concurrently with, sequentially with or separately from the compound having the formula (I).

\* \* \* \* \*